US011193171B2

(12) United States Patent
Ounzain et al.

(10) Patent No.: US 11,193,171 B2
(45) Date of Patent: Dec. 7, 2021

(54) DIAGNOSTIC, PROGNOSTIC AND THERAPEUTIC USES OF LONG NONCODING RNAS FOR HEART DISEASE AND REGENERATIVE MEDICINE

(71) Applicant: UNIVERSITÉ DE LAUSANNE, Lausanne (CH)

(72) Inventors: Samir Ounzain, Lausanne (CH); Thierry Pedrazzini, Le Mont-sur-Lausanne (CH)

(73) Assignee: UNIVERSITÉ DE LAUSANNE, Lausanne (CH)

( * ) Notice: Subject to any disclaimer, the term of this patent is extended or adjusted under 35 U.S.C. 154(b) by 975 days.

(21) Appl. No.: 15/105,319

(22) PCT Filed: Dec. 19, 2014

(86) PCT No.: PCT/EP2014/078868
§ 371 (c)(1),
(2) Date: Jun. 16, 2016

(87) PCT Pub. No.: WO2015/092020
PCT Pub. Date: Jun. 25, 2015

(65) Prior Publication Data

US 2016/0312283 A1 Oct. 27, 2016

Related U.S. Application Data

(60) Provisional application No. 61/964,591, filed on Dec. 20, 2013.

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 5,045,694 A 9/1991 Beavis et al.
5,118,937 A 6/1992 Hillenkamp et al.
5,510,270 A 4/1996 Fodor et al.
5,539,083 A 7/1996 Cook et al.
5,545,522 A 8/1996 Van Gelder et al.
5,556,752 A 9/1996 Lockhart et al.
5,578,832 A 11/1996 Trulson et al.
5,716,785 A 2/1998 Van Gelder et al.
5,719,060 A 2/1998 Hutchens et al.
5,891,636 A 4/1999 Van Gelder et al.
6,028,189 A 2/2000 Blanchard
6,225,047 B1 5/2001 Hutchens et al.
7,312,035 B2 * 12/2007 Makeev ............... C12Q 1/6895 435/287.2
2005/0048542 A1 3/2005 Baker et al.
2016/0319361 A1 * 11/2016 Spetzler ............... C12Q 1/6886

FOREIGN PATENT DOCUMENTS

WO WO-0105935 A2 1/2001
WO 2011005793 A1 1/2011

OTHER PUBLICATIONS

Handbook of Chemistry and Physics, 49th Edition, 1968, Weast (ed.), The Chemical Rubber Co., Cleveland, Ohio, p. A-245.*
Guttman et al., Nature 477: 295 (2011).*
Scheuermann et al., EMBO J. 32 (13), 1805 (2013).*
Agrawal S., Antisense oligonucleotides as antiviral agents. Trends in Biotechnology 10(5) : 152 (Year: 1992).*
Agrawal et al. Site-specific excision from RNA by RNase H and mixed-phosphate-backbone oligodeoxynucleotides. PNAS 87: 1401 (Year: 1990).*
Cramer et al., Nucleotides LXIV[1]: synthesis hybridization and enzymatic degradation studies of 2'-O- methyioligoriboeucleotides and 2'-0-methyl/deoxy gapmers. A (Year: 2000).*
Modarresi et al., Natural Antisense Inhibition Results in Transcriptional De-Repression and Gene Upregulation. Nature Biotechnology 10(5) :152 (Year: 2014).*
Varela et al.Epigenetics and ncRNAs in Brain Function and Disease* Mechanisms and Prospects for Therapy. Neurotherapeutics 10:621 (Year: 2013).*
Database EMBL [Online] Nov. 11, 2009, "Sequence 262 from Patent EP2113572.", retrieved from EBI Accession No. EM_PAT:HC054269.
Database Geneseq [Online] May 26, 2011, "Human SCN10A (SCN10A Sodium Channel Subunit) DNA with SNP SEQ ID: 2379.", Retrieved from EBI Accession No. GSN:AZH12782.
Grote et al., "The Tissue-Specific lncRNA Fendrr is an Essential Regulator of Heart and Body Wall Development in the Mouse", Developmental Cell vol. 24 No. 2, Jan. 28, 2013, pp. 206-214.
International Search Report and Written Opinion Issued in PCT/EP2014/078868 filed Dec. 19, 2014 dated Aug. 7, 2015.
Klattenhoff et al., "Braveheart, a Long Noncoding RNA Required for Cardiovascular Lineage Commitment", Cell vol. 152 No. 3, Jan. 1, 2013, pp. 570-583.
Li et al., "Transcriptome Analysis Reveals Distinct Patterns of Long Noncoding RNAs in Heart and Plasma of Mice with Heart Failure", Plos One vol. 8 No. 10, Oct. 29, 2013, p. e77938.
Ounzain et al., "Functional Importance of Cardiac Enhancer-Associated Noncoding RNAs in Heart Development and Disease", Journal of Molecular and Cellular Cardiology vol. 76, Aug. 19, 2014, pp. 55-70.

(Continued)

*Primary Examiner* — Ethan C Whisenant
(74) *Attorney, Agent, or Firm* — Harness Dickey & Pierce P.L.C.

(57) ABSTRACT

This invention generally relates to lncRNAs and methods for diagnosing cardiac pathologies in a subject. The invention also provides methods for treating a cardiac pathology in a subject comprising administering to said subject an effective amount of a modulator of one or more lncRNAs of the invention.

9 Claims, 27 Drawing Sheets

Specification includes a Sequence Listing.

(56) References Cited

OTHER PUBLICATIONS

Ounzain et al., "Genome-Wide Profiling of the Cardiac Transcriptome after Myocardial Infarction Identifies Novel Heart-Specific Long Non-Coding RNAs", European Heart Journal vol. 36 No. 6, Apr. 30, 2014, pp. 353-368.
Ounzain et al., "Small and Long Non-coding RNAs in Cardiac Homeostasis and Regeneration", Biochimica Et Biophysica Acta (BBA)—Molecular Cell Research vol. 1833 No. 4, Apr. 1, 2013, pp. 923-933.
Schonrock et al., "Long Noncoding RNAs in Cardiac Development and Pathophysiology", Circulation Research vol. 111 No. 10, Oct. 25, 2012, pp. 1349-1362.
Song et al., "Integrated Analysis of Dysregulated IncRNA Expression in Fetal Cardiac Tissues with Ventricular Septal Defect", PLOS ONE vol. 8 No. 10, Oct. 16, 2013, p. e77492.
Communication pursuant to Article 94(3) EPC for European Application No. 14 828 456.5 dated Jan. 24, 2019.

* cited by examiner

Figure 1A *(cont'd)*
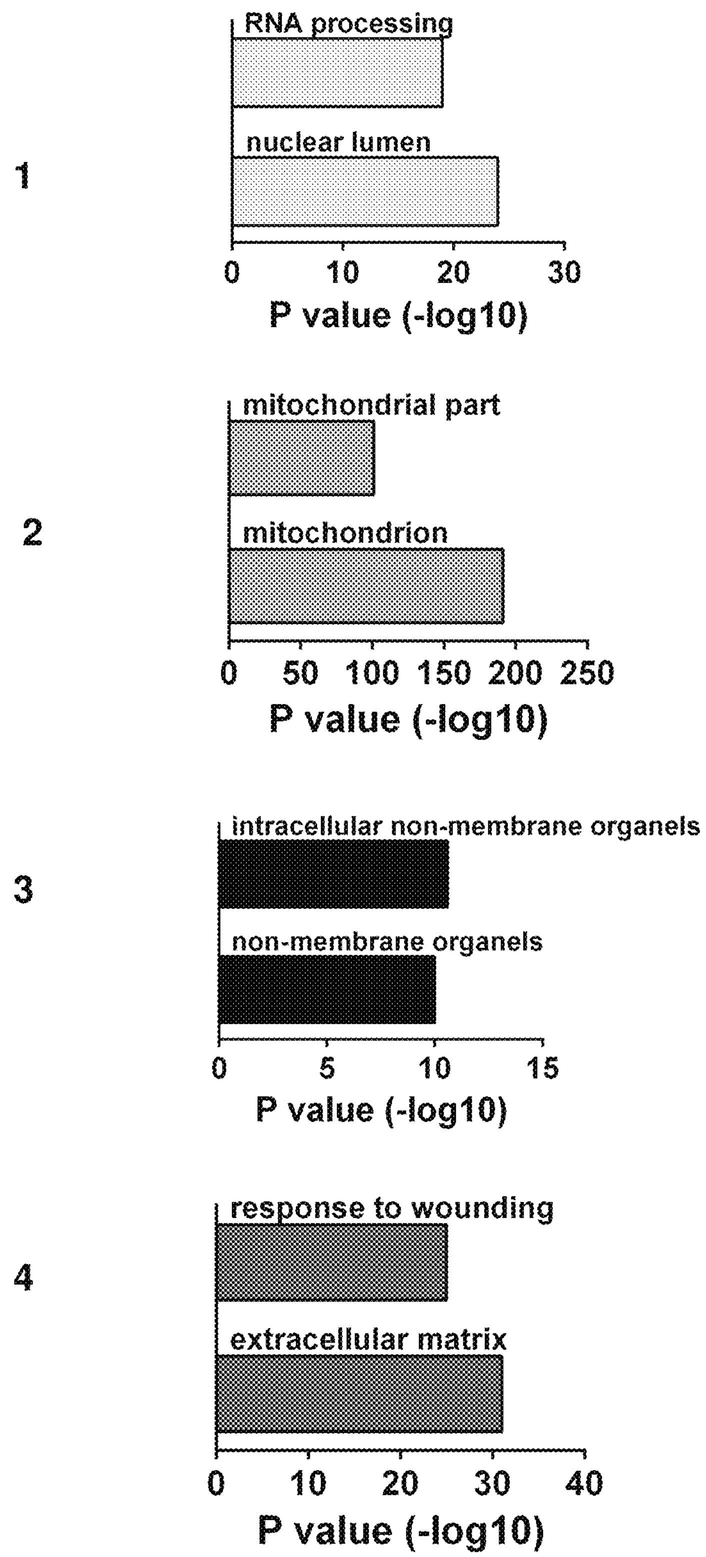

Figure 1B *(cont'd)*
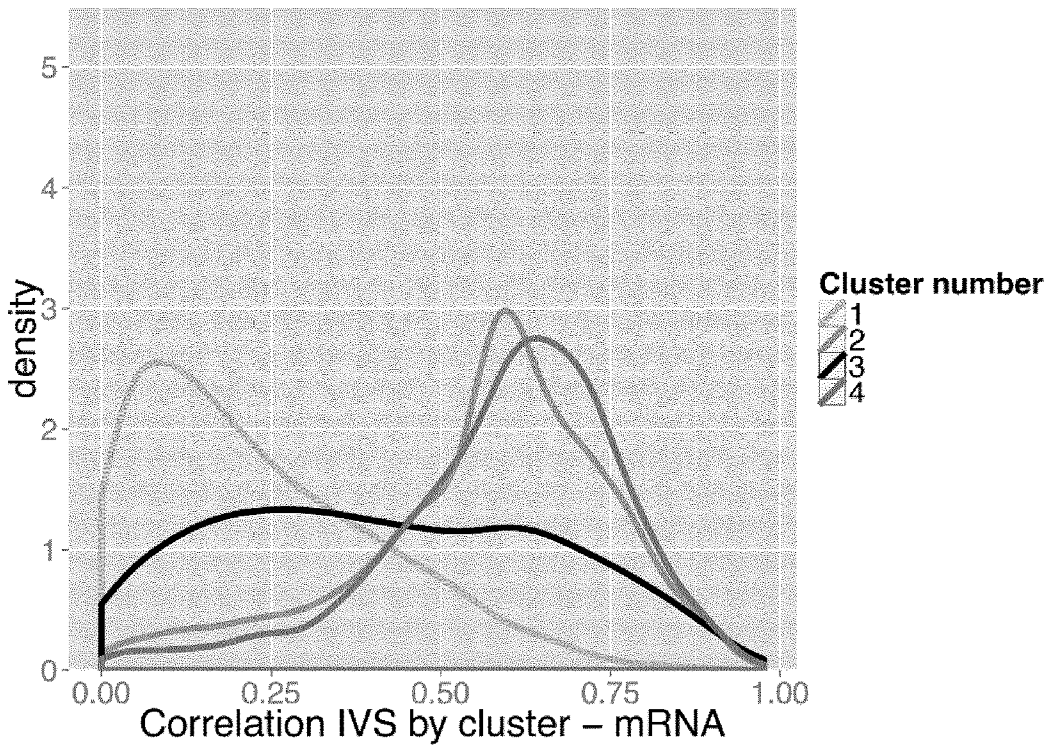
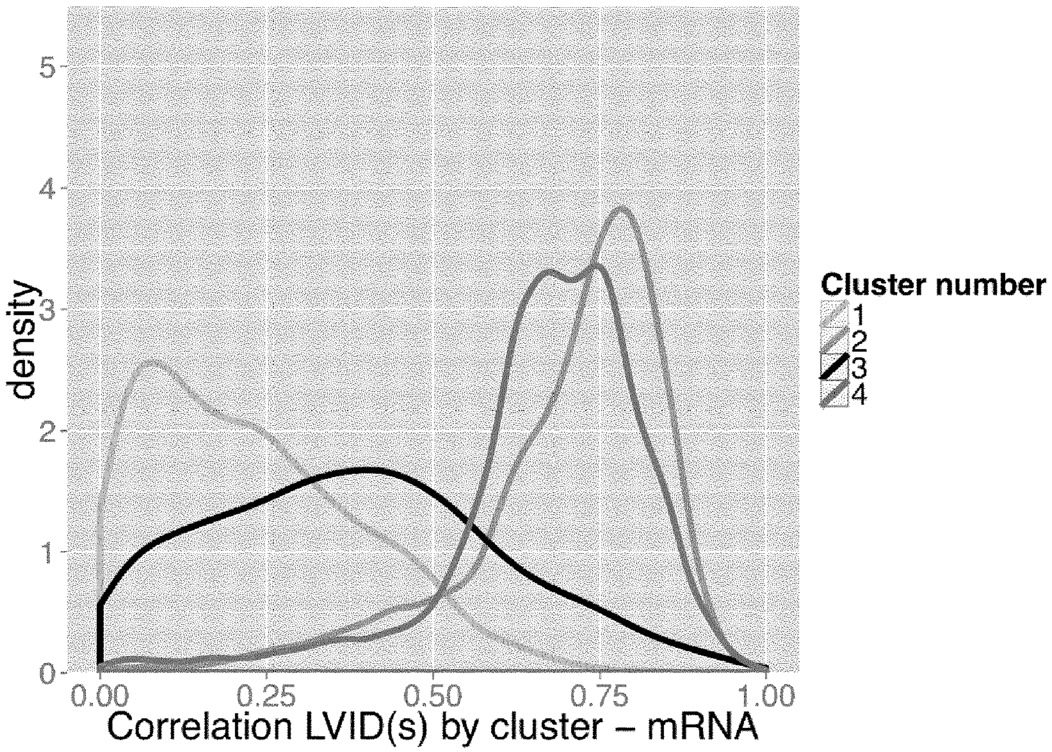

Figure 1C *(cont'd)*
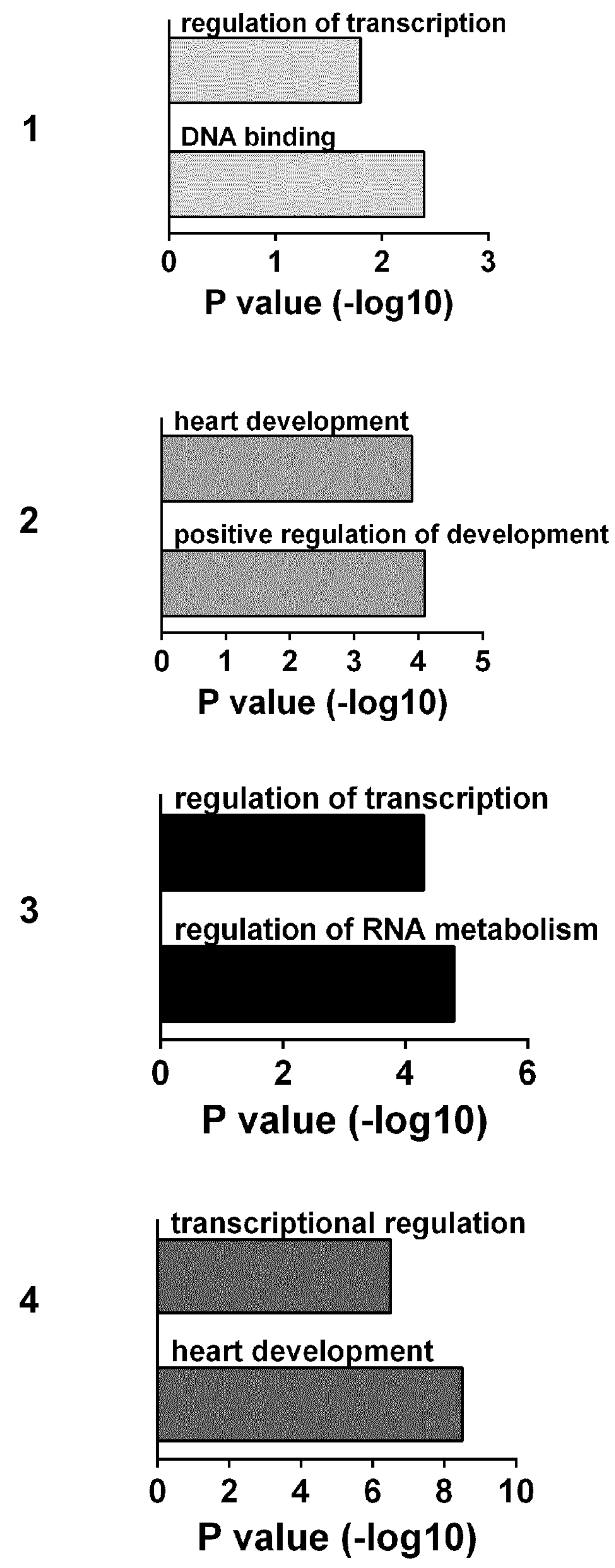

Figure 1D *(cont'd)*
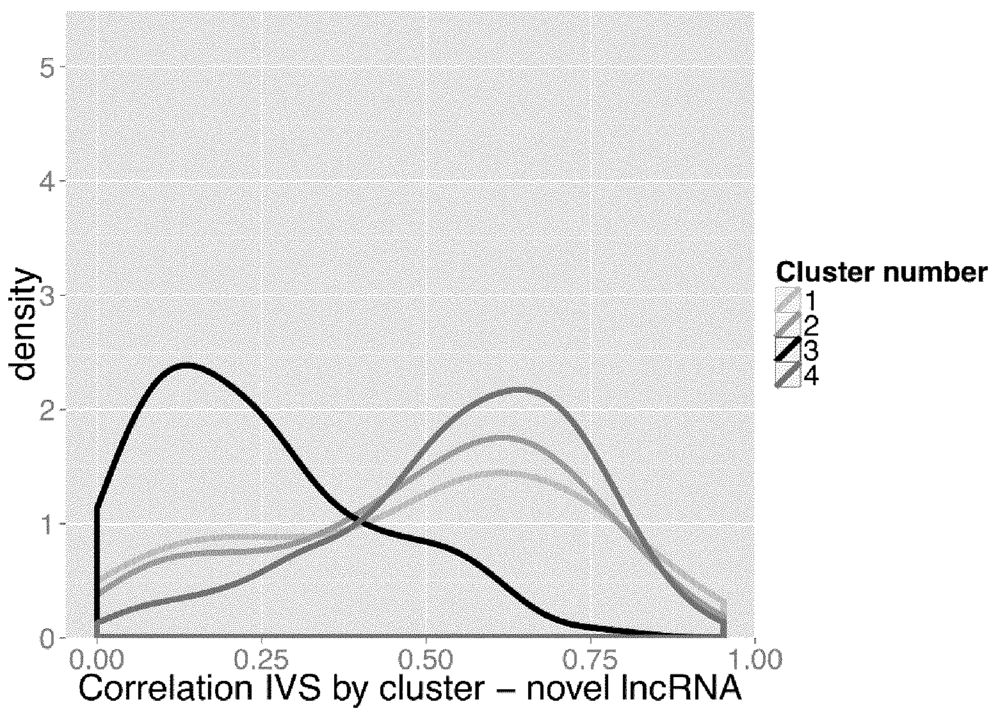
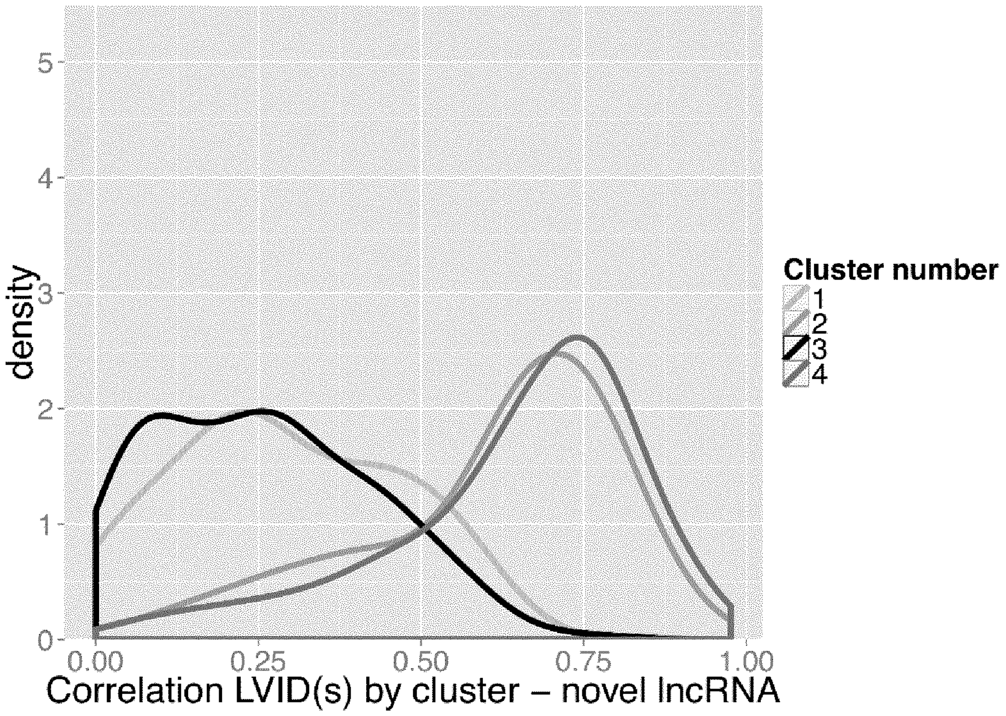

Log2 FC
CM vs FB

Nuc vs Cyto
Ratio

Figure 3C *(Cont'd)*
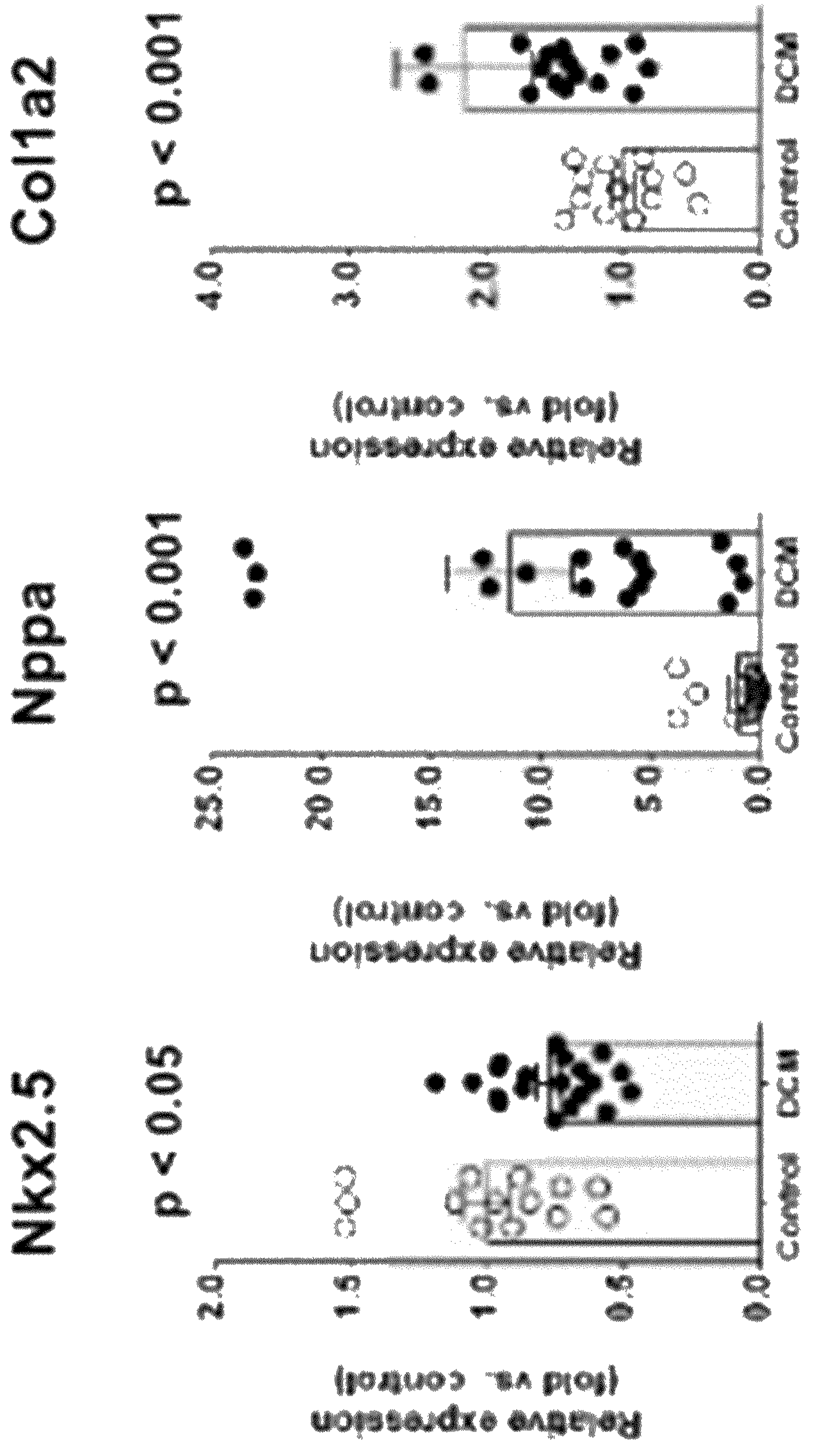

Figure 5B *(cont'd)*
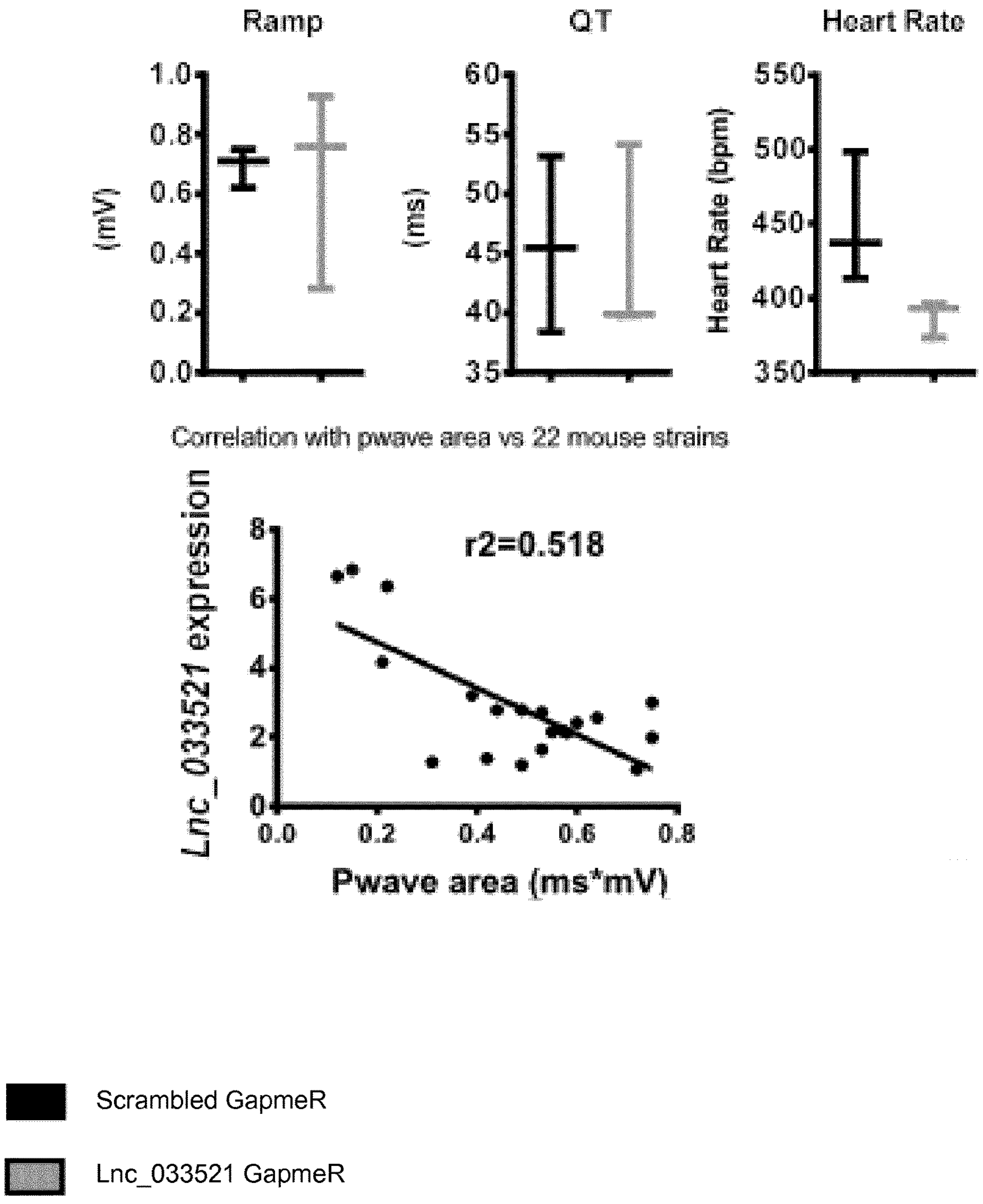

DIAGNOSTIC, PROGNOSTIC AND THERAPEUTIC USES OF LONG NONCODING RNAS FOR HEART DISEASE AND REGENERATIVE MEDICINE

CROSS-REFERENCE TO RELATED APPLICATIONS

This patent application is a U.S. national stage filing under 35 U.S.C. § 371 of International Application No. PCT/EP2014/078868 filed on of 19 Dec. 2014, which claims the benefit of U.S. Provisional Patent Application No. 61/964,591 filed on 20 Dec. 2013. The entire disclosures of each of the above recited applications are incorporated herein by reference.

REFERENCE TO A SEQUENCE LISTING

This application contains references to amino acid sequences and/or nucleic acid sequences which have been submitted concurrently herewith as the sequence listing text file "61766929_1.txt," file size 516 KiloBytes (KB), created on 15 Jun. 2016. The aforementioned sequence listing is hereby incorporated by reference in its entirety pursuant to 37 C.F.R. § 1.52(e)(5).

FIELD OF THE INVENTION

This invention generally relates to lncRNAs and methods for diagnosing cardiac pathologies in a subject. The invention also provides methods for treating a cardiac pathology in a subject comprising administering to said subject an effective amount of a modulator of one or more lncRNAs of the invention.

BACKGROUND OF THE INVENTION

The recent statistics on heart disease from the American Heart Association reports that one in nine death certificates in the United States mentioned heart failure as the cause of death in 2010. The burden of cardiovascular disease remains particularly high, with an overall rate of death attributable to cardiovascular disease of 235 per 100,000. Coronary artery disease is the most frequent cardiovascular disorder and typically leads to acute myocardial infarction and ultimately heart failure (HF). Despite continued advances, no approach currently exists to reverse the loss of functional myocardium, and HF is thus rapidly evolving into a major global epidemic requiring novel therapeutic approaches. In light of this, the elucidation of novel pathways and mechanisms involved in HF pathogenesis holds the promise of identifying new avenues and targets for this prevalent and deadly disease. In the adult heart, stress-dependant pathological hemodynamic and neurohormonal signals induce a maladaptive remodeling response, a process characterized by increased cardiomyocyte size (cellular hypertrophy), interstitial fibrosis and ultimately cellular dysfunction resulting in contractile and functional failure. At the molecular level, these signals activate a network of interacting cardiac signal transduction cascades that converge on a defined set of evolutionary conserved cardiac transcription factors (TFs). These core cardiac TFs (SRF, Nkx2.5, Mef2c, Gata4, TBox) interact in a combinatorial manner to elicit specific temporal and spatial gene expression programs. This integrated modulation of protein coding gene expression is ultimately responsible for cellular fate and is integral to the pathological remodeling process.

The notion of gene regulatory networks (GRNs) being primarily protein-based regulatory systems has been somewhat premature. A number of recent studies have demonstrated that GRN activity is under the control of a myriad of interleaved networks of non-coding RNAs (ncRNAs). Non-coding RNAs control every aspect of GRN activity including transcriptional control, post-transcriptional processing and epigenetic targeting (Ounzain et al., 2013). The best-characterized ncRNAs in the heart are the small microRNAs (miRNAs). Cardiovascular miRNAs adjust entire functional networks of mRNAs via post-transcriptional gene silencing, implicating miRNAs as important stress-dependant modulators. In addition to small ncRNAs, global transcriptional screens have identified other functional classes of transcripts, which are larger than 200 nucleotides, collectively known as long non-coding RNAs (lncRNAs). The functions of most lncRNAs remain unknown, however many have been shown to exert non-redundant roles in a diverse array of biological processes including X inactivation, imprinting, splicing and transcriptional regulation. In particular lncRNAs appear to be important for the global modulation of cell-specific epigenomic states via directing chromatin modification complexes to their sites of action (Furthermore, mammalian lncRNAs appear to be expressed in a highly cell-type and context-specific manner. Considering the functionality of these transcripts, this raises the possibility that lncRNAs are an important class of regulatory mediators of cardiogenic lineage-specific developmental or specialized cellular functions. The majority of lncRNAs functionally characterized to date regulate developmental processes. However, their potential role controlling mature tissue homeostasis and adaptation to stress remains largely unexplored.

Identification of novel regulatory molecules and/or pathways that participate in the adaptation of the heart to stress is an important step towards the development of new therapeutic strategies aimed at preventing the progression to heart failure. Importantly, the hallmark of pathological remodeling in the adult heart is a global transcriptional reprogramming, resulting in the reactivation of a "fetal" cardiac gene program. The intrinsic -cis and -trans activating and epigenomic orchestrating properties of lncRNAs warrants the need to explore and generate catalogues of cardiac-specific lncRNAs in diseased adult tissues.

SUMMARY OF THE INVENTION

The Invention relates to a method for diagnosing a cardiac pathology in a subject, the method comprising: a) measuring the level of a plurality of biomarkers in a biological sample derived from the subject, wherein the plurality of biomarkers comprises one or more lncRNAs selected from the group comprising one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of the biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology.

A further object of the present invention is to provide a method for treating a cardiac pathology in a subject comprising administering to said subject an effective amount of a modulator of one or more lncRNAs of the invention, fragments thereof, isoforms thereof and variants sharing at least 80% nucleotide sequence identity thereto.

The invention also contemplates a composition comprising a modulator of one or more lncRNAs of the invention wherein the modulator is selected from the group comprising a chemical agent, an antibody, an engineered protease, a CRISPR based technology and enzymatically active RNA.

A further object of the invention is to provide a method for modulating one or more lncRNAs of the invention wherein the modulator is selected from the group comprising a miRNA, a siRNA, a piRNA, a snRNA and an antisense oligonucleotide.

Another object of the invention is to provide a pharmaceutical composition comprising an effective amount of a modulator of one or more lncRNAs wherein the modulator is selected from the group comprising a chemical agent, an antibody, an engineered protease, and enzymatically active RNA, optionally in combination with pharmaceutically acceptable carriers, diluents and/or adjuvants.

Also comtemplated is a kit comprising the compositions of the invention.

Other objects of the invention concern a method for diagnosing a cardiac pathology in a subject, a method for monitoring the effects of a treatment on cardiac tissue in a subject, a method for monitoring the efficacy of surgical and/or pharmacological cardiac therapies in a subject, a method for measuring cardiac tissue regeneration in a subject, a method for monitoring in vitro cardiogenic cell differentiation, a method for monitoring in vivo cardiogenic cell differentiation, and a method for monitoring efficacy of agents and/or small molecules that can induce cardiac reprogramming.

The invention also concerns a microarray comprising a plurality of probes that hybridize to one or more lncRNAs of the invention, fragments thereof, isoforms thereof and variants sharing at least 80% nucleotide sequence identity thereto.

BRIEF DESCRIPTION OF THE FIGURES

FIG. 1A shows that mRNAs are highly clustered in their correlations with cardiac physiological traits and that such clusters are associated with genes implicated in expected processes. FIG. 1B shows that for specific traits, each cluster globally either correlates or does not correlate with each individual trait. FIG. 1C shows that novel lncRNAs are highly clustered in their correlations with physiological traits and that the closest coding genes to lncRNAs in each cluster are associated with specific biological processes. FIG. 1D shows that identified novel lncRNA clusters correlate specifically with individual physiological traits. FIG. 1E shows the heart specificity of mRNAs in clusters 1 to 4. FIG. 1F shows the heart specificity of novel lncRNAs in clusters 1 to 4.

FIG. 2B (left) shows the relative expression of candidate novel lncRNAs in isolated mouse cardiomyocytes and fibroblasts. FIG. 2C (right) shows the nuclear and cytoplasmic enrichment of candidate novel lncRNAs in cardiomyoctes and fibroblasts. FIG. 2D shows the correlation of candidate novel lncRNAs with physiological traits. FIG. 2E shows the expression of candidate lncRNAs in mouse embryonic stem cells undergoing cardiogenic differentiation. FIG. 2F shows the chromatin state patterns observed at novel lncRNA promoters during cardiogenic differentiation of mouse embryonic stem cells. FIG. 2G shows that modified antisense oligonucleotide mediated knock-down of specific novel lncRNA (Novlnc6) results in specific modulation of a key cardiac transcription factor, Nkx2-5 in isolated mouse cardiomyocytes.

FIG. 3A shows an example of a transmapped human lncRNA orthogous sequence (Novlnc6). FIG. 3B shows the expression of novel orthologous human lncRNAs in patients suffering with dilated cardiomyopathy (DCM) or aortic stenosis (AOS). FIG. 3C shows expression of validated cardiac biomarkers, ANF and Col 1a2, in DCM and AOS patients. FIG. 3D shows ejection fraction percentage (EF %), wall thickness, left ventricular (LV) mass index, and end-diastolic dimension (EDD). FIG. 3E shows the relative expression of Hs NovInc6, Hs NovInc23, Hs NovInc44, Nkx2.5, Nppa, and Col 1a2.

FIG. 4 show in vitro cell-specific lncRNA expression, and effects of lncRNA downregulation in cardiac fibroblasts and cardiomyocytes.

FIG. 5 show in vivo LncRNAs downregulation in 12 weeks old BL6/C7 mice that received one intraperitoneal injection of GapmeR (20 mg/kg). FIG. 5A shows lnc-019010 loss-of-function impact on cardiac functional parameters as assessed by echocardiography in vivo.

DETAILED DESCRIPTION OF THE INVENTION

Figure 1A:
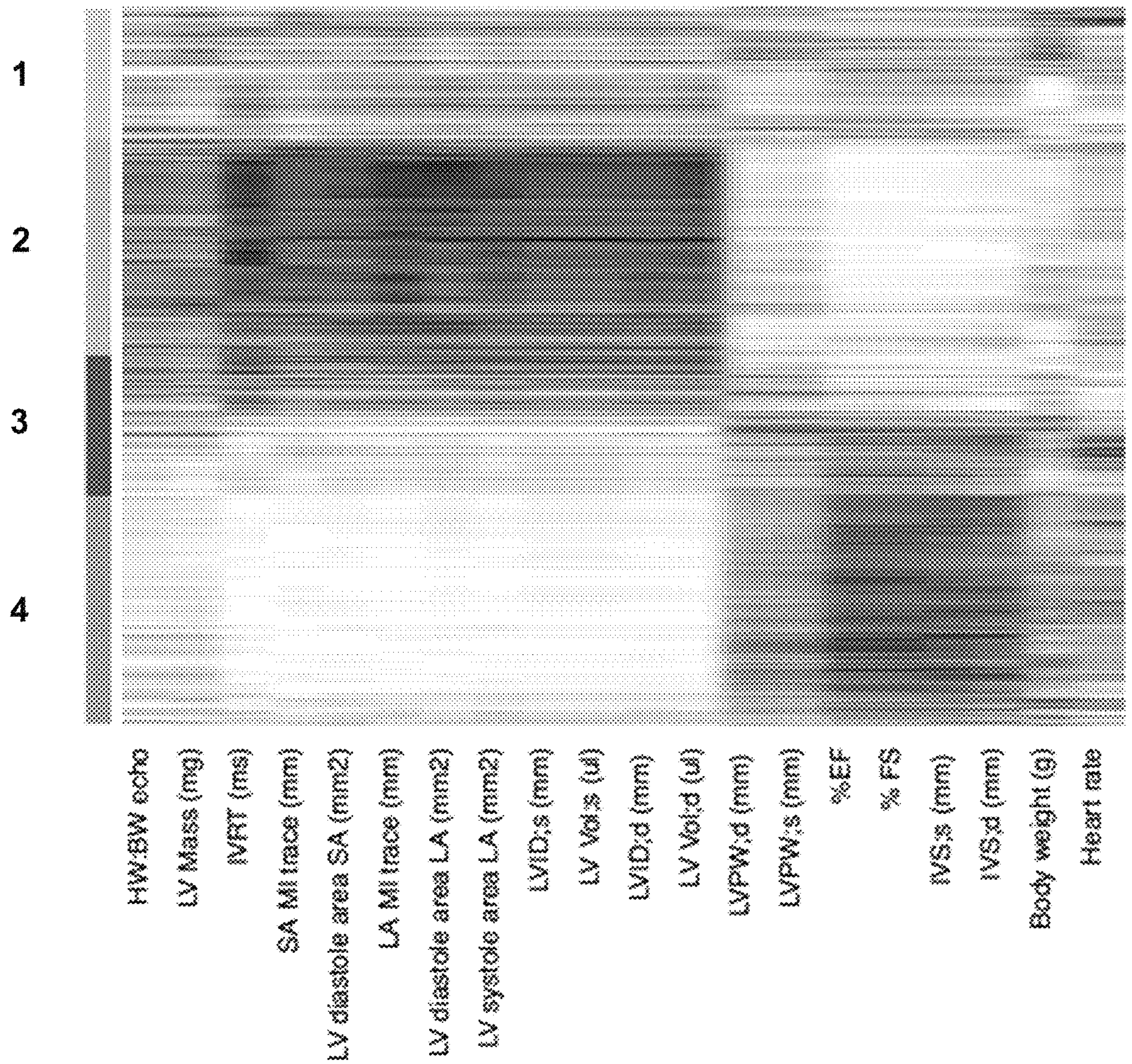
FIGS. 1A-F show that the cardiac coding and noncoding transcriptome is highly correlated with cardiac physiological traits.
Figure 1A:
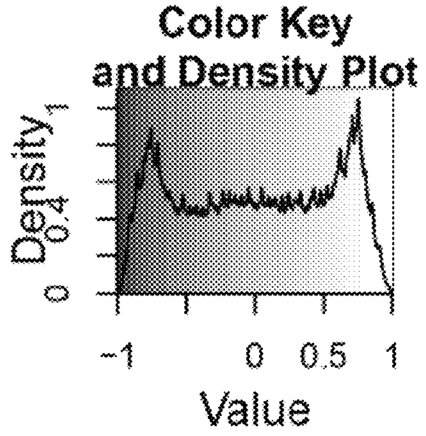

The Inventors set out to characterize the cardiac long non-coding transcriptome and in particular the dynamically modulated fraction post myocardial infarction. The Inventors coupled deep RNA-sequencing with ab initio transcript reconstruction, and integrated genome-wide data sets to systematically identify and annotate novel heart-specific lncRNAs.

Surprisingly, they showed that the lncRNAs of the invention are highly cardiac and context specific, correlating with cardiac physiology, suggesting a role as modulators of the pathological response and critical for physiological homeostasis. Using functional inference based on developmental chromatin state transitions, the Inventors functionally annotated these novel lncRNAs demonstrating that they are predominantly implicated with cardiac developmental, structural and functional gene programs. In particular, novel lncRNAs are predominantly associated with active enhancer states. The Inventors validated several novel lncRNAs in developmental and pathological models in vitro and in vivo and identified hundreds of predicted human orthologs and validated their expression in human samples. A number of these validated human orthologs were differentially expressed in human pathological cardiac states, supporting conserved roles in cardiac remodeling. Collectively, the Inventors have described a novel class of mammalian heart-specific lncRNAs with unique regulatory and functional characteristics, relevant to maladaptive pathological remodeling, cardiac function and potentially regeneration.

Accordingly, the present invention relates to a method for diagnosing a cardiac pathology in a subject, the method comprising:

a) measuring, directly or indirectly, the level of a plurality of biomarkers in a biological sample derived from the subject, wherein the plurality of biomarkers comprises one or more lncRNA having a cDNA sequence selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, iso forms thereof and variants sharing at least 80% nucleotide sequence identity thereto; and
b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology.

Preferably, the biological sample derived from the subject is selected from the group comprising whole blood, serum, plasma, semen, saliva, tears, urine, fecal material, sweat, buccal smears, skin, cardiac tissue, liver, brain tissue, amniotic fluid, nerve tissue and hair. More preferably, the biological sample is cardiac tissue.

Usually, the cardiac pathology is selected from the group comprising Interventricular Septal Thickness (IVS), heart failure, EF, LVID, MI, HFrEF, viral myocarditis, brachycardia, arrhythmia, congenital heart defects, diabetic cardiomyopathy, idiopathic and dilated cardiomyopathy, pathologies characterized by malformation such as congenital heart disease and inherited heart disease; by tissue remodeling such as hypertrophic cardiomyopathies, dilated cardiomyopathies, hypertensive cardiomyopathies, ischemic heart disease, coronary heart disease, myocardial infarction and cardiac fibrosis; by affected function such as systolic dysfunction, diastolic dysfunction, heart failure with reduced ejection fraction and heart failure with preserved ejection fraction; by disorders of the right heart such as right ventricular heart failure, pulmonary hypertension and pulmonary embolism; by arrhythmias such as cardiac arrhythmias, fibrillation, channelopathies, syncope and sudden death; by valvular dysfunction such as valvular heart disease, valvular stenosis and valvular regurgitation; by inflammation such as viral, bacterial, protozoal and metazoal infection of the heart, myocarditis, pericarditis, endocarditis, cardiac disease associated to HIV infection, Chagas' disease and restrictive infiltrative cardiomyopathies; by intoxication such as toxin-induced cardiac disease, drug-induced cardiac disease, alcohol-induced cardiac disease, pharmaceutical-induced cardiac disease, chemical-induced cardiac disease, cardiac disease following exposure to heavy metals and cardiac complications of anti-cancer therapies; by cancer such as neoplastic infiltrative cardiomyopathies, carcinoid heart disease and primary tumors of the heart; by neurologic disorders such as muscular dystrophies; by autonomic disorders; by emotional stress such as cardiac disease associated to acute and chronic psychological stress; by metabolic disease such as diabetic cardiomyopathy, heart disease associated to endocrine disorders and mitochondrial disorders; by trauma such as traumatic heart disease, consequences of cardiac surgery and angioplasty; by a change in hemodynamic such as renal disease, thrombosis and rheumatic disease. Most preferably, the heart failure is heart failure with preserved or reduced ejection fraction.

The present invention also relates to a method for treating a cardiac pathology in a subject comprising administering to said subject an effective amount of a modulator of one or more lncRNAs having a cDNA sequence selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, iso forms thereof and variants sharing at least 80% nucleotide sequence identity thereto.

Usually, the modulator of one or more lncRNAs is selected from the group comprising a chemical agent, a RNA mimic, an antibody, an engineered protease, a CRISPR based technology and enzymatically active RNA.

Most preferably, the enzymatically active RNA is selected from the group comprising a miRNA, a siRNA, a piRNA, a hnRNA, a snRNA, esiRNA, shRNA, decoys, RNA aptamers and an antisense oligonucleotide. One will appreciate that any compound with different formulations capable to inhibit one or more physiological actions effected by lncRNA is encompassed by the present invention.

The siRNA of the invention may, e.g., comprise a nucleotide sequence as set forth in SEQ ID No 105, fragments thereof, iso forms thereof and variants sharing at least 80% nucleotide sequence identity thereto.

Another aspect of the present invention relates to a composition comprising a modulator of one or more lncRNAs wherein the modulator is selected from the group comprising a chemical agent, an antibody, an engineered protease, and enzymatically active RNA.

A method for modulating one or more lncRNAs wherein the modulator is selected from the group comprising the modulator of one or more lncRNAs is selected from the group comprising a chemical agent, a RNA mimic, an antibody, an engineered protease, and enzymatically active RNA is also part of the invention.

Preferably, the modulator modulates cardiac fibrosis, myopathy, hypertrophy, apoptosis, inflammation, extracellular remodeling, cardiac regeneration, CM and CF cell cycle and activation of endogenous CPCs, direct reprogramming of CF, ECs, in vitro reprogramming and differention of cell types for generation of cardiac cells for cell therapy, Cardiac epigenomic targeting of ubiquitous chromatin remodeling complexes, cardiac physiology and heart rate.

A further aspect of the present invention relates to a pharmaceutical composition comprising an effective amount of a modulator of one or more lncRNAs wherein the modulator is selected from the group comprising the modulator of one or more lncRNAs is selected from the group comprising a chemical agent, a RNA mimic, an antibody, an engineered protease, and enzymatically active RNA, optionally in combination with pharmaceutically acceptable carriers, diluents and/or adjuvants.

Another aspect of the invention relates to a kit comprising i) a composition comprising a modulator of one or more lncRNAs wherein the modulator is selected from the group comprising a chemical agent, a RNA mimic, an antibody, an engineered protease, and enzymatically active RNA or ii) a pharmaceutical composition comprising an effective amount of a modulator of one or more lncRNAs wherein the modulator is selected from the group comprising the modulator of one or more lncRNAs is selected from the group comprising a chemical agent, a RNA mimic, an antibody, an engineered protease, and enzymatically active RNA, optionally in combination with pharmaceutically acceptable carriers, diluents and/or adjuvants.

Also encompassed in the present invention is a method for diagnosing a cardiac pathology in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject indicates that the subject has a cardiac pathology and/or a cardiac pathology thereby alleviating the need to execute echocardiography.

This invention also concerns a method for monitoring the effects of a treatment on cardiac tissue in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on the effects of a treatment on cardiac tissue.

Further encompassed is a method for monitoring the efficacy of surgical and/or pharmacological cardiac therapies in a subject, the method comprising:

a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on the efficacy of surgical and/or pharmacological cardiac therapies.

Also comprised in the present invention is a method for measuring cardiac tissue regeneration in a subject, the method comprising: a) measuring, directly or indirectly, the level of a plurality of biomarkers in a biological sample derived from the subject, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiac tissue regeneration.

The present invention also comprises a method for monitoring in vitro cardiogenic cell differentiation, the method comprising:

a) measuring, directly or indirectly, the level of a plurality of biomarkers in a biological sample derived from a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiogenic cell differentiation.

Another aspect of the invention concerns a method for monitoring in vitro cardiogenic cell differentiation, the method comprising:

a) measuring, directly or indirectly, the level of a plurality of biomarkers in a biological sample derived from a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on cardiogenic cell differentiation.

Another aspect of the invention concerns a method for monitoring efficacy of agents and/or small molecules that can induce cell reprogramming, the method comprising:

a) measuring, directly or indirectly, the level of a plurality of biomarkers in a biological sample derived from a subject or a cell in culture, wherein the plurality of biomarkers comprises one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto; and b) analyzing the levels of said biomarkers, fragments thereof, isoforms thereof and variants sharing at least 80% nucleotide sequence identity thereto, in conjunction with respective reference value ranges for said plurality of biomarkers, wherein differential expression of one or more biomarkers in the biological sample compared to one or more biomarkers in a control sample from a normal subject gives an indication on efficacy of agents and/or small molecules that can induce cardiac reprogramming.

Another aspect of the invention concerns a microarray comprising a plurality of probes that hybridize to one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto.

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a lncRNA" includes a mixture of two or more lncRNAs, and the like.

The term "about," particularly in reference to a given quantity, is meant to encompass deviations of plus or minus ten percent.

The terms "microRNA," "miRNA," and MiR" are interchangeable and refer to endogenous or artificial non-coding RNAs that are capable of regulating gene expression. It is believed that miRNAs function via RNA interference. The terms "siRNA" and "short interfering RNA" are interchangeable and refer to single-stranded or double-stranded RNA molecules that are capable of inducing RNA interference. SiRNA molecules typically have a duplex region that is between 18 and 30 base pairs in length.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against one or more lncRNAs.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Vials, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918.

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

"Administering", as it applies in the present invention, refers to contact of an effective amount of a modulator of one or more lncRNAs of the invention, to the subject.

Administering a nucleic acid, such as a microRNA, siRNA, piRNA, snRNA, antisense nucleic acid, or lncRNA to a cell comprises transducing, transfecting, electroporating, translocating, fusing, phagocytosing, shooting or ballistic methods, etc., i.e., any means by which a nucleic acid can be transported across a cell membrane.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

An "effective amount" of modulator of one or more lncRNAs of the invention (e.g., microRNA, siRNA, piRNA, snRNA, antisense nucleic acid, ribozyme, or small molecule inhibitor, CRISPRs etc.) is an amount sufficient to effect beneficial or desired results, such as an amount that inhibits the activity of a lncRNA, for example by interfering with transcription. An effective amount can be administered in one or more administrations, applications, or dosages.

By "therapeutically effective dose or amount" of a modulator of one or more lncRNAs of the invention is intended an amount that, when administered as described herein, brings about a positive therapeutic response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Alternatively, homology can be determined by readily available computer programs or by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of a biomarker, i.e. one or more lncRNAs. In general, the term "variant" refers to molecules having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

Alternatively, the term "variant" also refers to post-transcriptionaly modified lncRNAs of the invention, i.e methylation, phosphorylation, etc.

A "biomarker" in the context of the present invention refers to an lncRNA which is differentially expressed in a biological sample (e.g., a biopsy taken from a subject having a cardiac pathology or a cardiac tissue undergoing regeneration or a stem cell undergoing cardiac differentiation or a cardiac tissue undergoing surgical and/or pharmacological therapies) as compared to a control sample (e.g., a comparable sample taken from a person with a negative diagnosis, a normal or healthy subject, or normal, untreated tissue or cells). The biomarker can be an lncRNA that can be detected and/or quantified.

One will appreciate that the control sample can vary depending on the situation. For example, the control sample can include a cell or sample of cells that provide a reference expression level of the same gene. Alternatively, the control sample can be healthy cells from the same source tissue as the target cell(s).

As used herein, an "isoform" of an lncRNA results from alternative splicing of the gene encoding said lncRNA.

As used herein, a "fragment" one or more lncRNAs refers to a sequence containing less amino acids in length than the respective one or more lncRNA. Preferably, this sequence contains less than 90%, preferably less than 60%, in particular less than 30% amino acids in length than the respective one or more lncRNA.

Biomarkers are one or more lncRNAs selected from the group comprising the cDNA sequences: SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, and SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, isoforms thereof and variants sharing at least 80% nucleotide sequence identity thereto. Most preferably, the one or more lncRNAs is selected from the group comprising the cDNA sequences SEQ ID No 25, SEQ ID No 28, SEQ ID No 48, SEQ ID No 52, SEQ ID No 53, SEQ ID No 82, SEQ ID No 84, SEQ ID No 88, SEQ ID No 96, SEQ ID No 97, SEQ ID No 98, SEQ ID No 99, SEQ ID No 100, SEQ ID No 101, SEQ ID No 103, and SEQ ID No 104, fragments thereof, isoforms thereof and variants sharing at least 80% nucleotide sequence identity thereto.

TABLE 1

| XLOC_ID | SEQ ID No. | Physiology Cluster | Lnc |
|---|---|---|---|
| XLOC_007900 | 1 | 1 | Lnc7900 |
| XLOC_008052 | 2 | 1 | Lnc8052 |
| XLOC_006224 | 3 | 1 | Lnc6224 |
| XLOC_013471 | 4 | 1 | Lnc13471 |
| XLOC_002075 | 5 | 1 | Lnc2075 |
| XLOC_023749 | 6 | 1 | Lnc23749 |
| XLOC_008063 | 7 | 1 | Lnc8063 |
| XLOC_024203 | 8 | 1 | Lnc24203 |
| XLOC_019889 | 9 | 1 | Lnc19889 |
| XLOC_008229 | 10 | 1 | Lnc8229 |
| XLOC_014116 | 11 | 1 | Lnc14116/NovInc11 |
| XLOC_003166 | 12 | 1 | Lnc3166 |
| XLOC_010335 | 13 | 1 | Lnc10335 |
| XLOC_021863 | 14 | 1 | Lnc21863 |
| XLOC_012367 | 15 | 1 | Lnc12367 |
| XLOC_007833 | 16 | 1 | Lnc7833 |
| XLOC_023850 | 17 | 2 | Lnc23850 |
| XLOC_029624 | 18 | 2 | Lnc-TEAD1 |
| XLOC_022865 | 19 | 2 | Lnc-SE-22865 |
| XLOC_018239 | 20 | 2 | Lnc18239 |
| XLOC_022715 | 21 | 2 | Lnc-COL16A1 |
| XLOC_013413 | 22 | 2 | Lnc13413 |
| XLOC_005390 | 23 | 2 | Lnc-MEOX1 |
| XLOC_010961 | 24 | 2 | Lnc-WISP1 |
| XLOC_000709 | 25 | 2 | Lnc-TGFB2/NovInc11 |
| XLOC_013407 | 26 | 2 | Lnc-SLC8A1 |
| XLOC_020214 | 27 | 2 | Lnc-CYR61 |
| XLOC_012723 | 28 | 2 | Lnc-SE-12723/NovInc174 |
| XLOC_022262 | 29 | 2 | Lnc22262 |
| XLOC_000719 | 30 | 2 | Lnc00719 |
| XLOC_004951 | 31 | 2 | Lnc4951 |
| XLOC_026589 | 32 | 2 | Lnc26589 |
| XLOC_019010 | 33 | 2 | Lnc19010 |
| XLOC_022236 | 34 | 2 | Lnc22236 |
| XLOC_011236 | 35 | 3 | Lnc-SLC38A2 |
| XLOC_012015 | 36 | 3 | Lnc-KCNJ6 |
| XLOC_012884 | 37 | 3 | Lnc-NKX2.5 |
| XLOC_004797 | 38 | 3 | Lnc4797 |
| XLOC_003851 | 39 | 3 | Lnc-SPNB2 |
| XLOC_011237 | 40 | 3 | Lnc-SLC38A2 |
| XLOC_014898 | 41 | 3 | Lnc-SE-14989 |
| XLOC_030839 | 42 | 3 | Lnc-CDH13 |
| XLOC_012194 | 43 | 3 | Lnc-ACAP2 |
| XLOC_031308 | 44 | 3 | Lnc-IRX3 |
| XLOC_026621 | 45 | 3 | Lnc-ATOH8 |
| XLOC_002721 | 46 | 3 | Lnc-TXLNB |
| XLOC_003170 | 47 | 3 | Lnc-KITLG |
| XLOC_002849 | 48 | 4 | Lnc-NovInc6 |
| XLOC_016279 | 49 | 4 | Lnc-NovInc25 |

TABLE 1-continued

| XLOC_ID | SEQ ID No. | Physiology Cluster | Lnc |
|---|---|---|---|
| XLOC_024141 | 50 | 4 | Lnc-CARD11 |
| XLOC_021524 | 51 | 4 | Lnc-NFIB |
| XLOC_021715 | 52 | 4 | Lnc-FOXO6 |
| XLOC_020321 | 53 | 4 | Lnc-ANX5A |
| XLOC_006274 | 54 | 4 | Lnc-MAX |
| XLOC_021416 | 55 | 4 | Lnc21416 |
| XLOC_003767 | 56 | 4 | Lnc-LIF |
| XLOC_014118 | 57 | 4 | Lnc-LCLAT1 |
| XLOC_004833 | 58 | 4 | Lnc4833 |
| XLOC_009582 | 59 | 4 | Lnc-PPIF |
| XLOC_024449 | 60 | 4 | Lnc24449 |
| XLOC_006146 | 61 | 4 | Lnc6146 |
| XLOC_033521 | 62 | 4 | Lnc-Dedbt (Lnc033521) |
| XLOC_025643 | 63 | 4 | Lnc25643 |
| XLOC_004910 | 64 | 4 | Lnc-SPARC |
| XLOC_010967 | 65 | 4 | Lnc-miR30b |
| XLOC_002503 | 66 | 4 | Lnc-SOCS2 |
| XLOC_017764 | 67 | 4 | Lnc-ID1 |
| XLOC_020119 | 68 | 4 | Lnc20119 |
| XLOC_001065 | 69 | 4 | Lnc-GPC1 |
| XLOC_009131 | 70 | 4 | Lnc-OTX2 |
| XLOC_000264 | 71 | 4 | Lnc-FAM124B |
| XLOC_032325 | 72 | 4 | Lnc-TALIN1 |
| XLOC_002546 | 73 | 4 | Lnc-KRR1 |
| XLOC_006241 | 74 | 4 | Lnc-DACT1 |
| XLOC_029781 | 75 | 4 | Lnc29781 |
| XLOC_030722 | 76 | 4 | Lnc-SE-30722 |
| XLOC_032031 | 77 | 4 | Lnc-KCNJ |
| XLOC_020634 | 78 | 4 | Lnc-SE-20634 |
| XLOC_031524 | 79 | 4 | Lnc-IRF2BP2 |
| XLOC_020212 | 80 | 4 | Lnc-CYR61 |
| XLOC_000336 | 81 | 4 | Lnc-HDAC4 |
| XLOC_015960 | 82 | 4 | Lnc-ITPRIP |
| XLOC_004067 | 83 | 4 | Lnc-MYOCD |
| XLOC_015277 | 84 | 4 | Lnc-SMAD7/NovInc23 |
| XLOC_020313 | 85 | 4 | Lnc20313 |
| XLOC_008190 | 86 | 4 | Lnc8190 |
| XLOC_033125 | 87 | 4 | Lnc33125 |
| XLOC_032788 | 88 | 4 | Lnc32788/NovInc90 |
| XLOC_014917 | 89 | 4 | Lnc14917 |
| XLOC_014935 | 90 | 4 | Lnc14935 |
| XLOC_007419 | 91 | 4 | Lnc7419 |
| XLOC_006561 | 92 | 4 | Lnc6561 |
| XLOC_024370 | 93 | 4 | Lnc24370 |
| XLOC_006255 | 94 | 4 | Lnc6255 |
| XLOC_029637 | 95 | 4 | Lnc29637 |
| XLOC_010855 | 96 | 2 | Lnc10855 |
| XLOC_007852 | 97 | 4 | Lnc7852/NovInc15 |
| XLOC_009335 | 98 | 4 | Lnc9335/NovInc32 |
| XLOC_019782 | 99 | 2 | Lnc19782/NovInc35 |
| XLOC_010735 | 100 | 4 | Lnc10735/NovInc44 |
| XLOC_007917 | 101 | 4 | Lnc7917/NovInc61 |
| XLOC_033357 | 102 | 4 | Lnc33357 |
| XLOC_023848 | 103 | 4 | Lnc23848/NovInc49 |
| XLOC_016979 | 104 | 4 | Lnc16979 |

Figure 1B:
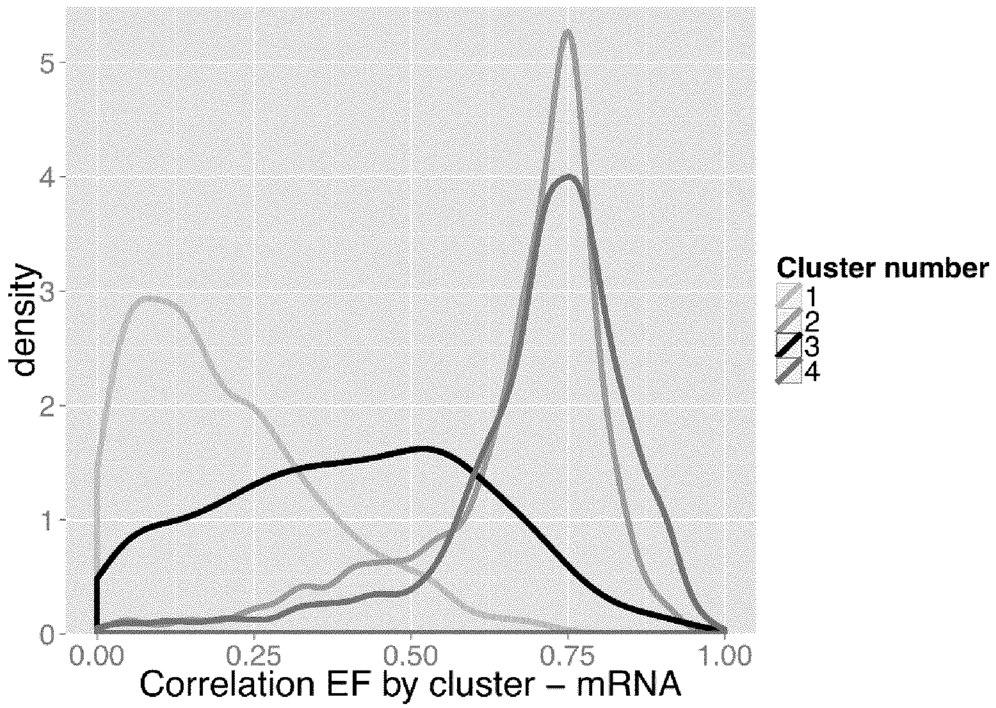
Figure 1B:
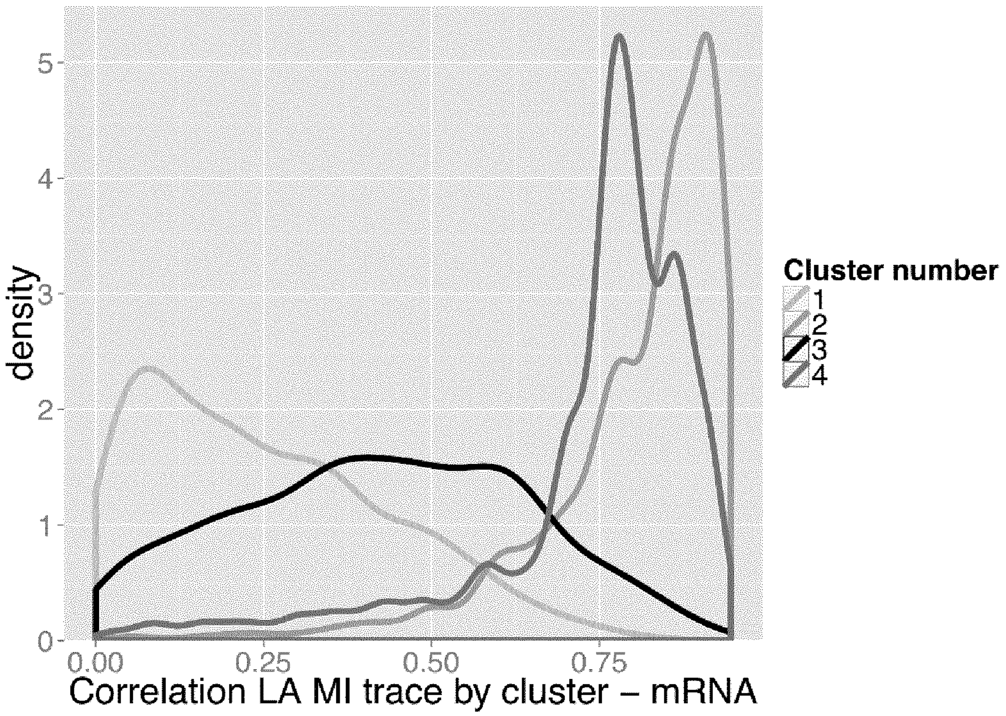
Figure 1C:
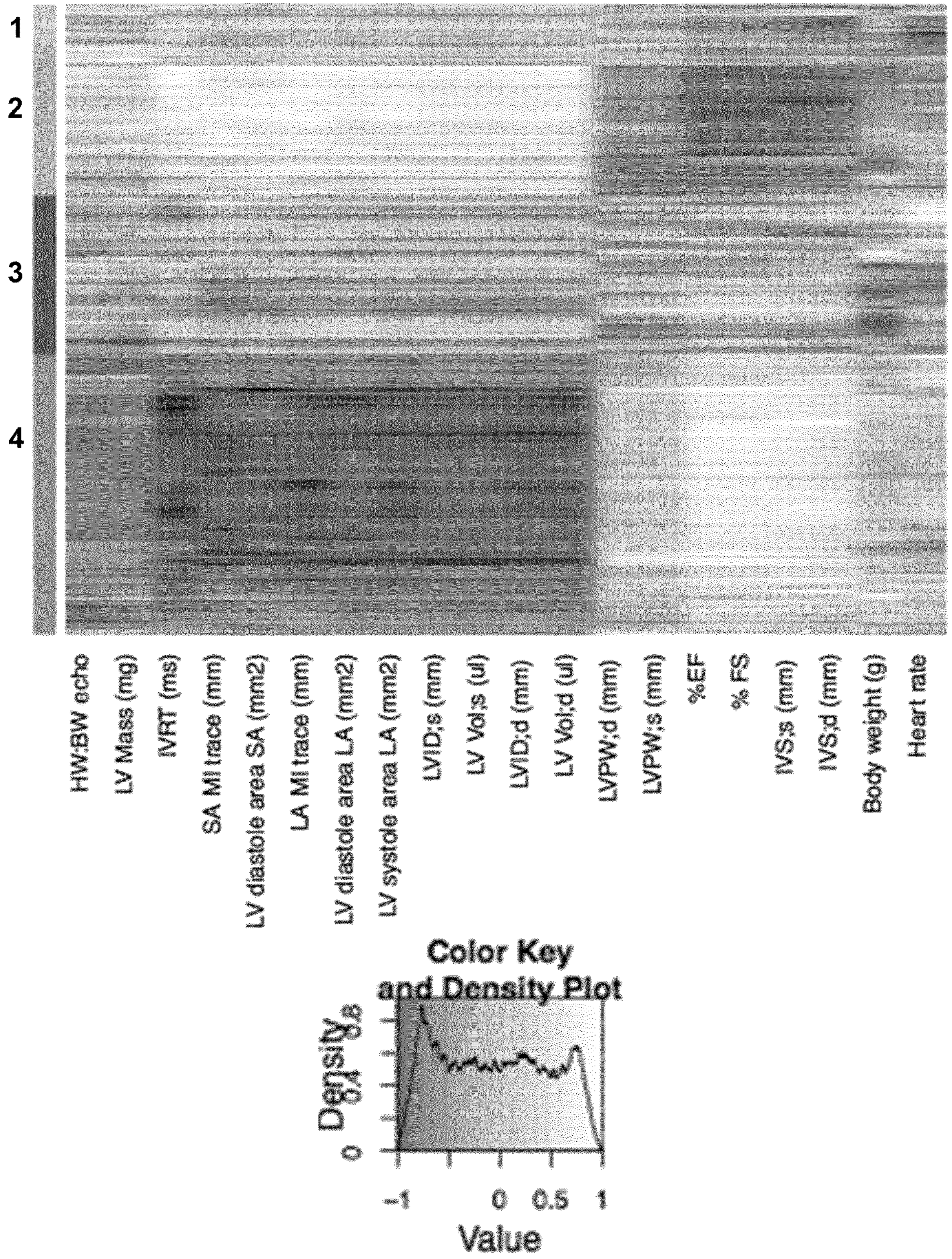

Within the identified transcripts, the Inventors identified four clusters for both coding (FIG. 1A) and novel lncRNA (FIG. 1B) transcripts. In each case, these consisted of one cluster that correlated positively with cardiac function and negatively with remodeling parameters, one cluster with the inverse of these correlations and two clusters with non-specific intermediate correlations. Gene ontology (GO) and heart specificity analysis was executed on individual clusters with GO analysis being executed on the most proximal coding genes with respect to novel lncRNAs. In the coding gene group, the most heart-specific cluster was Cluster 2 (FIG. 1E), which was positively correlated with cardiac functional traits and associated with genes involved in mitochondrial biology (FIG. 1A). The least heart-specific cluster (Cluster 4) was positively correlated with remodeling and associated with genes involved in wound healing and extracellular matrix (FIG. 1A). Within novel lncRNAs, and in particular within the 104 lncRNAs of Table 1, the most heart-specific cluster, i.e. Cluster 4 (FIG. 1F), was again positively correlated with cardiac function associated traits. Proximal coding genes to novel lncRNA in Cluster 4 were enriched with heart development associated processes (FIG. 1C). Since novel lncRNAs that cluster specifically with particular physiological traits were likely to be involved in biological processes associated with those traits, these findings indicated that novel lncRNAs within this cluster could represent a class of cardiac-specific regulators of developmental gene programs, which was reactivated in the damaged myocardium. Finally, the least heart specific clusters were one and two, which was positively correlated with remodeling traits.

Figure 1D:
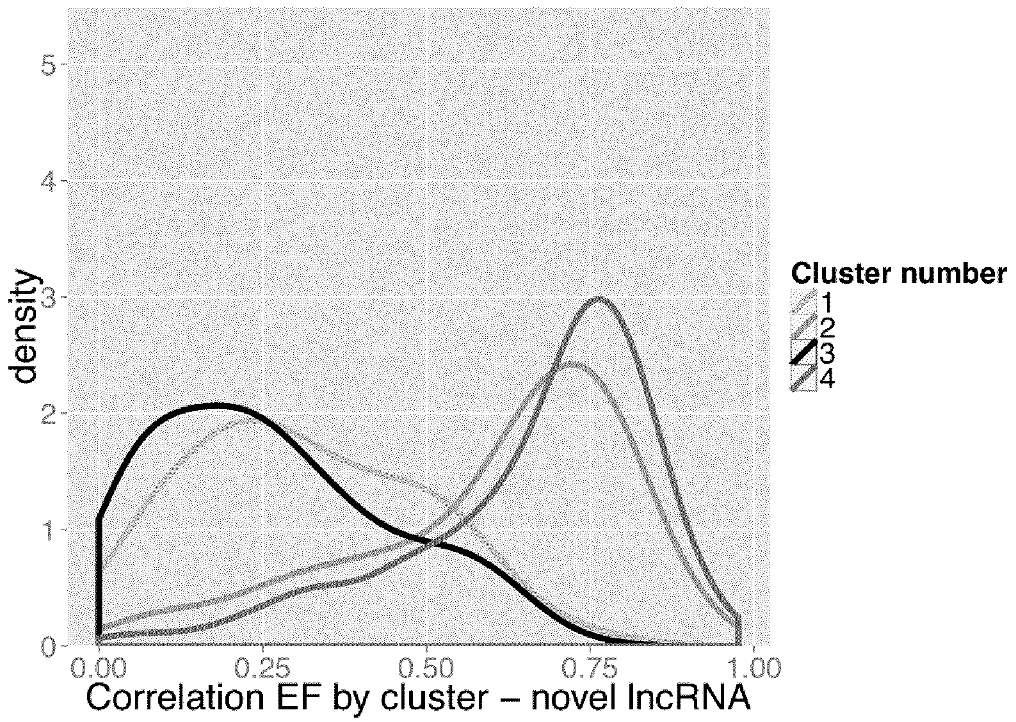
Figure 1D:
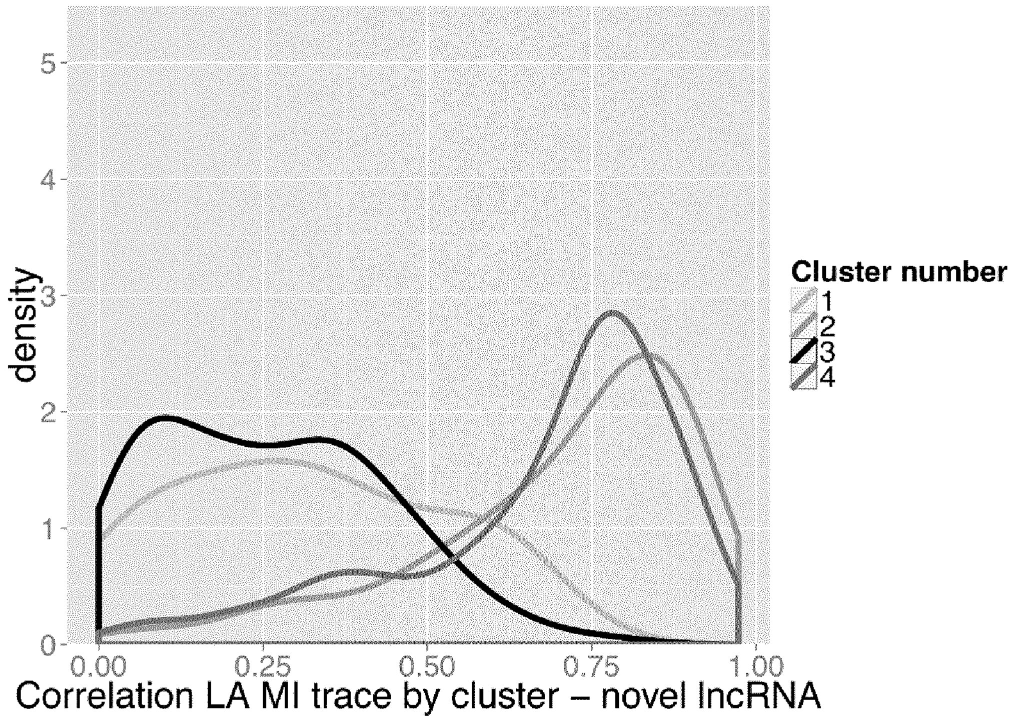
Figure 1E:
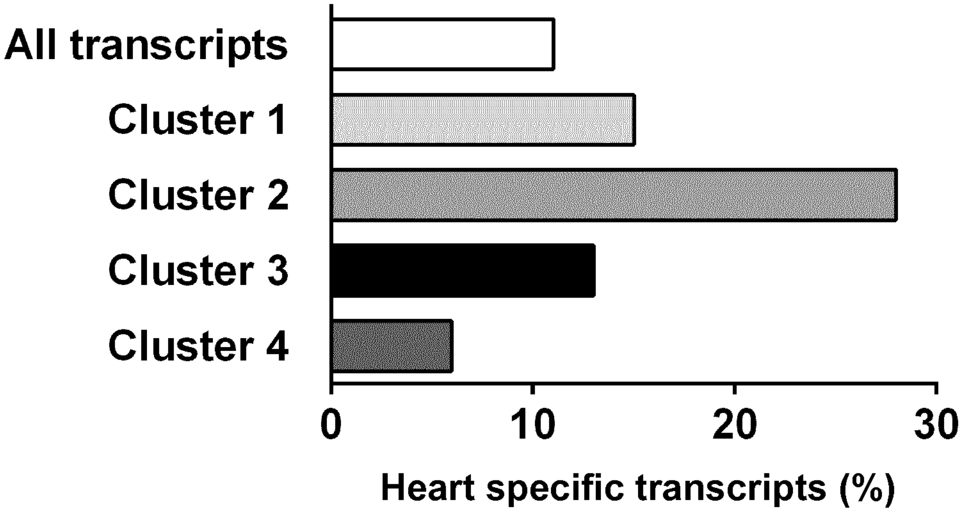
Figure 1F:
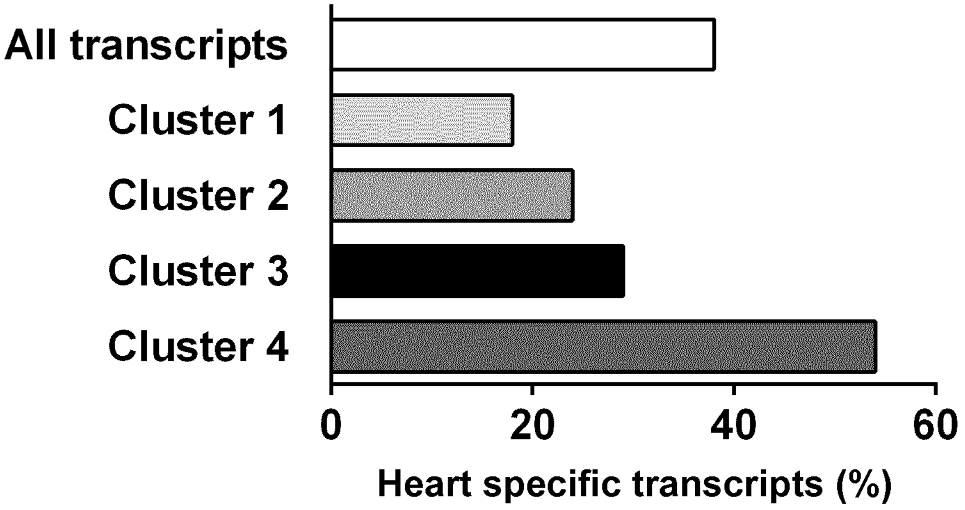

These data demonstrated that unsupervised clustering of transcripts was able to distinguish physiological traits. In addition, it indicated that lncRNAs could represent specific markers of particular physiological traits. To test this, The Inventors compared correlation distributions for each UCSC coding gene and novel lncRNA cluster, with each of the following traits; ejection fraction (EF), interventricular septal thickness at systole (IVS), myocardial infarction trace (MI trace) and left ventricular internal diameter at systole (LVID) (FIGS. 1B and D). UCSC coding gene Clusters 2 and 4 strongly correlated with all these traits when compared to non-specific clusters (Clusters 1 and 3) (FIG. 1B). A similar pattern of correlation was observed with novel lncRNA clusters 2 and 4 (FIG. 1D). However, novel lncRNA Cluster 1 was particularly interesting since it exhibited poor correlation with LVID, EF and MI trace but correlated well with IVS which is typically linked to EF. This unique characteristic is likely a consequence of the exquisite context and cell-type specific expression of lncRNAs, and has intriguing implications for the utilization of novel lncRNAs as biomarkers.

Preferably, in accordance with the method the method for diagnosing a cardiac pathology described herein, an up expression of one or more lncRNA having a cDNA sequence selected from the group comprising SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 96, SEQ ID No 99, fragments thereof, iso forms thereof and variants sharing at least 80% nucleotide sequence identity thereto, in the biological sample compared to the expression levels of one or more of these lnCRNAs in a control sample from a normal subject indicates that the subject suffered from myocardial infarction or is suffering from cardiac pathology associated with maladaptive remodeling of the myocardium.

Preferably also, in accordance with the method for diagnosing a cardiac pathology described herein a down expression of one or more lncRNA having a cDNA sequence selected from the group comprising SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 97, SEQ ID No 98, SEQ ID No 100, SEQ ID No 101, SEQ ID No 102, SEQ ID No103, and SEQ ID No 104, fragments thereof, isoforms thereof and variants sharing at least 80% nucleotide sequence identity thereto, in the biological sample compared to the expression levels of one or more of these lnCRNAs in a control sample from a normal subject indicates that the subject suffered from myocardial infarction.

Also in accordance with the method for diagnosing a cardiac pathology described herein wherein a differential expression of one or more lncRNA having a cDNA sequence selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, fragments thereof, iso forms thereof and variants sharing at least 80% nucleotide sequence identity thereto, in the biological sample compared to the expression levels of one or more of these lnCRNAs in a control sample from a normal subject indicates that the subject suffered from heart failure with preserved ejection fraction.

The phrase "differentially expressed" refers to differences in the quantity and/or the frequency of a biomarker present in a sample taken from patients having, for example, a cardiac pathology or form a cardiac tissue undergoing regeneration or from a stem cell undergoing cardiac differentiation or from a cardiac tissue undergoing surgical and/or pharmacological therapies as compared to a control subject. For example, a biomarker can be a lncRNA which is present at an elevated level or at a decreased level in samples of patients with a cardiac pathology or a cardiac tissue undergoing regeneration or a stem cell undergoing cardiac differentiation or a cardiac tissue undergoing surgical and/or pharmacological therapies compared to samples of control subjects. Alternatively, a biomarker can be a lncRNA which is detected at a higher frequency or at a lower frequency in samples of patients with a cardiac pathology or a cardiac tissue undergoing regeneration or a stem cell undergoing cardiac differentiation or a cardiac tissue undergoing surgical and/or pharmacological therapies compared to samples of control subjects or control tissues. A biomarker can be differentially present in terms of quantity, frequency or both.

A lncRNA is differentially expressed between two samples if the amount of the lncRNA in one sample is statistically significantly different from the amount of the lncRNA in the other sample. For example, an lncRNA is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a lncRNA is differentially expressed in two sets of samples if the frequency of detecting the lncRNA in samples is statistically significantly higher or lower than in the control samples. For example, an lncRNA is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, guinea pigs, and hamsters; rabbits, primates, and transgenic animals.

As used herein, a "biological sample" refers to a sample of tissue or fluid isolated from a subject, including but not limited to, for example, urine, blood, plasma, serum, fecal matter, bone marrow, bile, spinal fluid, lymph fluid, samples of the skin, external secretions of the skin, respiratory, intestinal, and genitourinary tracts, tears, saliva, milk, blood cells, organs, biopsies, and also samples containing cells or tissues derived from the subject and grown in culture, and in vitro cell culture constituents, including but not limited to, conditioned media resulting from the growth of cells and tissues in culture, recombinant cells, stem cells, and cell components.

The terms "quantity," "amount," and "level" are used interchangeably herein and may refer to an absolute quantification of a molecule or an analyte in a sample, or to a relative quantification of a molecule or analyte in a sample, i.e., relative to another value such as relative to a reference value as taught herein, or to a range of values for the biomarker. These values or ranges can be obtained from a single patient or from a group of patients.

"Diagnosis" as used herein generally includes determination as to whether a subject is likely affected by a given disease, disorder or dysfunction of the invention. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

When analyzing the levels of biomarkers in a biological sample, the reference value ranges used for comparison can represent the level of one or more biomarkers found in one or more samples of one or more subjects without cardiac disease (i.e., normal or control samples). Alternatively, the reference values can represent the level of one or more biomarkers found in one or more samples of one or more subjects with cardiac disease. More specifically, the reference value ranges can represent the level of one or more biomarkers at particular stages of disease to facilitate a determination of the stage of disease progression in an individual.

A "control" sample as used herein refers to a biological sample, such as tissue or cells that are not diseased. That is, a control sample is obtained from a normal subject (e.g. an individual known to not have cardiac disease or any condition or symptom associated with).

It is understood that the expression level of the biomarkers in a sample can be determined by any suitable method known in the art. Measurement of the level of a biomarker can be direct or indirect. For example, the abundance levels of lncRNAs can be directly quantitated.

Alternatively, the amount of a biomarker can be determined indirectly by measuring abundance levels of cDNAs, amplified RNAs or DNAs, or by measuring quantities or activities of RNAs, or other molecules that are indicative of the expression level of the biomarker. Preferably, the amount of a biomarker is determined indirectly by measuring abundance levels of cDNAs.

LncRNAs can be detected and quantitated by a variety of methods including, but not limited to, microarray analysis, polymerase chain reaction (PCR), reverse transcriptase polymerase chain reaction (RT-PCR), Northern blot, serial analysis of gene expression (SAGE), immunoassay, and mass spectrometry, any sequencing-based methods known in the art.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., a cardiac pathology).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., Molecular Cloning: A Laboratory Manual (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm2 and 25 cm2; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, lncRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length. The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR Protocols: A Guide To Methods And Applications, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res.

14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., U.S. Pat. No. 5,539,083).

Probes are preferably selected using an algorithm that takes into account binding energies, base composition, sequence complexity, cross-hybridization binding energies, and secondary structure. See International Patent Publication WO 01/05935.

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as known in the art. This method is especially useful for preparing microarrays of cDNA A second method for making microarrays produces high-density oligonucleotide arrays. Techniques are known for producing arrays containing thousands of oligonucleotides complementary to defined sequences, at defined locations on a surface using photolithographic techniques for synthesis in situ (see, U.S. Pat. Nos. 5,578,832; 5,556,752; and 5,510,270; herein incorporated by reference in their entireties) or other methods for rapid synthesis and deposition of defined oligonucleotides. When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking, may also be used. In principle, any type of array known in the art, for example, dot blots on a nylon hybridization membrane could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink jet method are typically of high density, preferably having a density of at least about 2,500 different probes per 1 cm2. The polynucleotide probes are attached to the support covalently at either the 3' or the 5' end of the polynucleotide.

Biomarker polynucleotides which may be measured by microarray analysis can be expressed lncRNAs or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, lncRNA, poly(A)+ messenger RNA (mRNA) or a fraction thereof, cytoplasmic mRNA, or RNA transcribed from cDNA (i.e., cRNA; see, e.g., U.S. Pat. Nos. 5,545,522, 5,891,636, or 5,716,785). Methods for preparing total and poly(A)+ RNA are well known in the art, and are described generally, e.g., in Sambrook, et al., Molecular Cloning: A Laboratory Manual (3rd Edition, 2001). RNA can be extracted from a cell of interest using guanidinium thiocyanate lysis followed by CsCl centrifugation, a silica gel-based column (e.g., RNeasy (Qiagen, Valencia, Calif.) or StrataPrep (Stratagene, La Jolla, Calif.)), or using phenol and chloroform, as known in the art. Poly(A)+ RNA can be selected, e.g., by selection with oligo-dT cellulose or, alternatively, by oligo-dT primed reverse transcription of total cellular RNA. RNA can be fragmented by methods known in the art, e.g., by incubation with ZnCl2, to generate fragments of RNA.

In one embodiment, total RNA, lncRNAs, or nucleic acids derived therefrom (such as cDNA), are isolated from a sample taken from a patient having a cardiac pathology or a cardiac tissue undergoing regeneration or a stem cell undergoing cardiac differentiation or a cardiac tissue undergoing surgical and/or pharmaceological therapies. Biomarker lncRNAs that are poorly expressed in particular cells may be enriched using normalization techniques known in the art.

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise lncRNAs from a normal biological sample (i.e., control sample, e.g., biopsy from a subject not having a cardiac pathology or a cardiac tissue undergoing regeneration or a stem cell undergoing cardiac differentiation or a cardiac tissue undergoing surgical and/or pharmaceological therapies) or from a reference biological sample, (e.g., sample from a subject having a cardiac pathology or cell sample of a cardiac tissue undergoing regeneration or a stem cell undergoing cardiac differentiation or a cardiac tissue undergoing surgical and/or pharmaceological therapies).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., Molecular Cloning: A Laboratory Manual (3rd Edition, 2001). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS). Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously. Arrays can be scanned with a laser fluorescent scanner with a computer controlled X-Y stage and a microscope objective. Sequential excitation of the two fluorophores is achieved with a multiline, mixed gas laser and the emitted light is split by wavelength and detected with two photomultiplier tubes. Fluorescence laser scanning devices are known in the art. Alternatively, a fiber-optic bundle, may be used to monitor mRNA abundance levels at a large number of sites simultaneously.

In one embodiment, the invention includes a microarray comprising a plurality of probes that hybridize to one or more lncRNAs selected from the group comprising SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, and SEQ ID No 95, SEQ ID No 96, SEQ ID No 97, SEQ ID No 98, SEQ ID No 99, SEQ ID No 100, SEQ ID No 101, SEQ ID No 102, SEQ ID No103, and SEQ ID No 104, fragments thereof, iso forms thereof and variants sharing at least 80% nucleotide sequence identity thereto, most preferably from the group comprising SEQ ID No 25, SEQ ID No 28, SEQ ID No 48, SEQ ID No 52, SEQ ID No 53, SEQ ID No 82, SEQ ID No 84, SEQ ID No 88, SEQ ID No 96, SEQ ID No 97, SEQ ID No 98, SEQ ID No 99, SEQ ID No 100, SEQ ID No 101, SEQ ID No 103, and SEQ ID No 104.

Serial Analysis Gene Expression (SAGE), can also be used to determine RNA (e.g., lncRNA) abundances in a cell sample. SAGE analysis does not require a special device for detection, and is one of the preferable analytical methods for simultaneously detecting the expression of a large number of transcription products. First, RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 by away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR.

Mass spectrometry, and particularly SELDI mass spectrometry, is a particularly useful method for detection of the biomarkers of this invention. Laser desorption time-of-flight mass spectrometer can be used in embodiments of the invention. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting the biomarkers of this invention. MALDI-MS is a method of mass spectrometry that involves the use of an energy absorbing molecule, frequently called a matrix, for desorbing proteins intact from a probe surface. MALDI is described, for example, in U.S. Pat. Nos. 5,118,937 and 5,045,694. In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Surface-enhanced laser desorption/ionization mass spectrometry, or SELDI-MS represents an improvement over MALDI for the fractionation and detection of biomolecules, such as lncRNAs, in complex mixtures. SELDI is a method of mass spectrometry in which biomolecules, such as lncRNAs, are captured on the surface of a biochip using capture reagents that are bound there. Typically, non-bound molecules are washed from the probe surface before interrogation. SELDI is described, for example, in: U.S. Pat. No. 5,719,060 and in U.S. Pat. No. 6,225,047.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art in embodiments of the invention.

Biomarkers can also be detected with assays based on the use of antibodies that specifically recognize the lncRNA biomarkers or polynucleotide or oligonucleotide fragments of the biomarkers. Such assays include, but are not limited to, immunohistochemistry (IHC), enzyme-linked immunosorbent assay (ELISA), radioimmunoassays (RIA), "sandwich" immunoassays, fluorescent immunoassays, immunoprecipitation assays, the procedures of which are well known in the art.

Biomarkers can also be detected with any sequencing based technologies know in the art.

In yet another aspect, the invention provides kits for use in diagnosing a cardiac pathology or a cardiac tissue undergoing regeneration or a stem cell undergoing cardiac differentiation or a cardiac tissue undergoing surgical and/or pharmaceological therapies, wherein the kits can be used to detect the lncRNA biomarkers of the present invention. For example, the kits can be used to detect any one or more of the biomarkers described herein, which are differentially expressed in samples of a patient with a cardiac pathology or a cardiac tissue undergoing regeneration or a stem cell undergoing cardiac differentiation or a cardiac tissue undergoing surgical and/or pharmaceological therapies. The kit may include one or more agents for detection of lncRNA biomarkers, a container for holding a biological sample isolated from a human subject; and printed instructions for reacting agents with the biological sample or a portion of the biological sample to detect the presence or amount of at least one lncRNA biomarker in the biological sample. The agents may be packaged in separate containers. The kit may further comprise one or more control reference samples and reagents for performing an immunoassay, a Northern blot, PCR, microarray analysis, or SAGE, DNA/RNA-sequencing.

In certain embodiments, the kit contains at least one probe that selectively hybridizes to a biomarker, or at least one antibody that selectively binds to a biomarker, or at least one set of PCR primers for amplifying a biomarker. In one embodiment, the kit comprises at least one agent for measuring the level of a biomarker.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing a cardiac pathology or monitoring stem cell therapy or regenerative medical treatments.

The kits of the invention have number of applications. For example, the kits can be used for diagnosing a cardiac pathology or monitoring and/or evaluating the efficacy of a treatment for a cardiac pathology, stem cell therapy, or regenerative cardiac medicine. In a further example, the kits can be used to identify compounds that modulate expression of one or more of the biomarkers in in vitro or in vivo animal models to determine the effects of treatment.

By "therapeutically effective dose or amount" of each of the modulator of the invention is intended an amount that when administered in combination brings about a positive therapeutic response with respect to treatment of an individual for a cardiac pathology.

Thus, for example, a "positive therapeutic response" would be an improvement in the disease in association with the combination therapy, and/or an improvement in one or more symptoms of the disease in association with the combination therapy.

The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.50 mg to 5 grams daily, more preferably from about 5 mg to 2 grams daily, even more preferably from about 7 mg to 1.5 grams daily.

In certain embodiments, multiple therapeutically effective doses of each of at least one lncRNA and at least one additional therapeutical agent will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

A lncRNA modulator of the invention can be administered prior to, concurrent with, or subsequent to at least one additional therapeutic agent. If provided at the same time as the additional therapeutic agent, the lncRNA modulator can be provided in the same or in a different composition. Thus, the agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising a lncRNA modulator and at least one therapeutically effective dose of a pharmaceutical composition comprising at least one additional therapeutic agent according to a particular dosing regimen. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In other embodiments of the invention, the pharmaceutical composition of the invention is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition. The pharmaceutical compositions of the invention may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the lncRNA modulator in the bloodstream, is equivalent to that obtained with a therapeutically effective dose that is administered parenterally, for example SC, IP, IM, or IV. In some embodiments of the invention, the pharmaceutical composition comprising the lncRNA modulator is administered by IM or SC injection, particularly by IM or SC injection locally to the region where the therapeutic agent or agents used in the cardiac therapy protocol are administered.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy. Below are examples of specific embodiments for carrying out the present invention. The examples are offered for illustrative purposes only, and are not intended to limit the scope of the present invention in any way.

The present invention also concerns a method for increasing and/or improving cardiac function comprising administrating a pharmaceutical composition comprising an effective amount of a modulator of lnc_019010 wherein the modulator is selected from the group comprising a chemical agent, an antibody, an engineered protease, and enzymatically active RNA, optionally in combination with pharmaceutically acceptable carriers, diluents and/or adjuvants. Preferably, the modulator of lnc_019010 is an enzymatically active RNA consisting in one or more antisense oligonucleotide targeting said lnc_019010. Most preferably, said one or more antisense oligonucleotide targeting said lnc_019010 is a modified antisense oligonucleotide (GapmeR) having a sequence as set forth in SEQ ID No 148.

Also envisioned in the present invention is a method for increasing and/or improving the conduction system in the heart comprising administrating a pharmaceutical composition comprising an effective amount of a modulator of lnc_033521 wherein the modulator is selected from the group comprising a chemical agent, an antibody, an engineered protease, and enzymatically active RNA, optionally in combination with pharmaceutically acceptable carriers, diluents and/or adjuvants.

The present invention further relates to a method of regulating the heart rate comprising administrating a pharmaceutical composition comprising an effective amount of a modulator of lnc_033521 wherein the modulator is selected from the group comprising a chemical agent, an antibody, an engineered protease, and enzymatically active RNA, optionally in combination with pharmaceutically acceptable carriers, diluents and/or adjuvants.

Preferably, the modulator of lnc_033521 is an enzymatically active RNA consisting in one or more antisense oligonucleotide targeting said lnc_033521. Most preferably, said one or more antisense oligonucleotide targeting said inc_033521 is a modified antisense oligonucleotide (GapmeR) having a sequence as set forth in SEQ ID No 147.

The present invention further relates to a method for diagnosing dilated cardiomyopathy (DCM) in a subject, the method comprising:

a) measuring, directly or indirectly, the level of novlnc6 having a cDNA sequence as set forth in SEQ ID No. 48, fragments thereof, isoforms thereof and variants sharing at least 80% nucleotide sequence identity thereto; and b) analyzing the levels of said novlnc6, fragments thereof, iso forms thereof and variants sharing at least 80% nucleotide sequence identity thereto, in conjunction with respective reference value ranges for said novlnc6, wherein a decreased expression level of said novlnc6 in the biological sample compared to a control sample from a normal subject indicates that the subject has a dilated cardiomyopathy.

The present invention further relates to a method for diagnosing aortic stenosis (AOS) in a subject, the method comprising:

a) measuring, directly or indirectly, the level of Novlnc44 having a cDNA sequence as set forth in SEQ ID No. 100, fragments thereof, isoforms thereof and variants sharing at least 80% nucleotide sequence identity thereto; and b) analyzing the levels of said Novlnc44, fragments thereof, isoforms thereof and variants sharing at least 80% nucleotide sequence identity thereto, in conjunction with respective reference value ranges for said Novlnc44, wherein a decreased expression level of Novlnc44 in the biological sample compared to the control sample from a normal subject indicates that the subject has aortic stenosis.

The present invention further relates to a method for diagnosing dilated cardiomyopathy (DCM) in a subject, the method comprising:

a) measuring, directly or indirectly, the level of Novlnc44 having a cDNA sequence as set forth in SEQ ID No. 100, fragments thereof, isoforms thereof and variants sharing at least 80% nucleotide sequence identity thereto; and b) analyzing the levels of said Novlnc44, fragments thereof, isoforms thereof and variants sharing at least 80% nucleotide sequence identity thereto, in conjunction with respective reference value ranges for said Novlnc44, wherein a decreased expression level of Novlnc44 in the biological sample compared to the control sample from a normal subject indicates that the subject has a dilated cardiomyopathy.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Extended Experimental Procedures

Transgenic Mouse Enhancer Assay

Mouse transgenic enhancer assays were previously executed and described in Ounzain S, et al., 2014. Images can be found at http://enhancer.lbl.gov/.

Mice

Animal experiments were approved by the Government Veterinary Office (Lausanne, Switzerland) and performed according to the University of Lausanne Medical School institutional guidelines. Animal experiments were approved by the Government Veterinary Office (Lausanne, Switzerland) and performed according to the University of Lausanne Medical School institutional guidelines.

Cardiac Injury Models—Ligation of the Left Anterior Descending Artery

Myocardial infarction in mice was induced as previously described (Ounzain S, et al., 2014). Mouse was anesthetized by IP injection of a mixture of ketamin/xylazine/acepromazin (65/15/2 mg/kg). Mouse was placed on warming pad for maintenance of body temperature. In the supine position, endotracheal intubation was performed and the mouse was placed on artificial ventilation with a mini-rodent ventilator (tidal volume=0.2 ml, rate=120 breaths/min. The thorax of the animal was shaved and disinfected with Betadine solution. A left thoracotomy was performed. The pectoralis muscle groups were separated transversely, exposing the rib cage. The fourth intercostal space was entered using scissors and blunt dissection. The pericardium was gently opened and a pressure was applied to the right thorax to displace the heart leftward. A 7.0 silk ligature near the insertion of the left auricular appendage was placed and tied around the left descending coronary artery. Occlusion of the artery was verified by the rapid blanching of the left ventricle. For animals undergoing a sham operation, the ligature was placed in an identical location but not tied. The lungs were re-expanded using positive pressure at end expiration and the chest and skin incision were closed respectively with 6-0 and 5-0 silk sutures. The mouse was gradually weaned from the respirator. Once spontaneous respiration resumed, the endotracheal tube was removed, and the animal was replaced in his cage.

Echocardiography

Transthoracic echocardiographies were performed using a 30-MHz probe and the Vevo 770 Ultrasound machine (VisualSonics, Toronto, ON, Canada). Mice were lightly anesthetized with 1% isoflurane, maintaining heart rate at 400-500 beats per minute, and placed in dorsal recumbency on a heated 37'C platform. Hair was removed with a topical depilatory agent. The heart was imaged in the 2D mode in the parasternal long-axis view. From this view, an M-mode curser was positioned perpendicular to the interventricular septum and the posterior wall of the left ventricle (LV) at the level of the papillary muscles. LV free wall thickness in diastole (LVWTD) and in systole (LVWTS) as well as LV diameter in diastole (LVDD) and in systole (LVDS) were measured. All measurements were done from leading edge to leading edge according to the American Society of Echocardiography guidelines. The measurements were taken in 3 separate M mode images and averaged. Ejection fraction (EF) was calculated using the formula % EF=[(LVVD-LVVS)/LVVD]×100, where LVVD and LVVS are LV volume in diastole and systole respectively.

Mouse Tissue Collection and Preparation

Hearts and testes were dissected from sham and MI mice one and seven days post artery ligation. Tissues were rinsed in diethyl pyrocardbonate (DEPC)-treated PBS, snap frozen in liquid nitrogen and stored at −80'C until use. Note, specific care was taken to gently squeeze the hearts with forceps in DEPC-treated PBS to minimize residual blood contamination.

Embryonic Stem Cell Culture and Differentiation

Nkx2.5-EmGFP BAC reporter ES cell line (129/OlaHsd strain, subline E14Tg2A.4) were kindly provided by Edward C Hsiao (Gladstone Institute of Cardiovascular Research, San Francisco) and maintained and cultured as previously described (Ounzain S, et al., 2014). Cells were cultured on mouse embryonic fibroblasts feeders or on gelatinized plates in standard ES cell medium supplemented with 1000 U/ml of LIF. Cardiac differentiation of ES cells was induced by aggregating aliquots containing 1000 cells in hanging drops to form embryoid bodies (Ounzain S, et al., 2014).

Primary Cell Cultures and Transfections

Neonatal C57B6 mice were sacrificed within the first 24 h after birth. Beating hearts were removed, atria and great vessels were carefully dissected away and placed on ice in ADS buffer (H2O, NaCl 116 mM, HEPES 20 mM, NaH2PO4 1 mM, KCl 5.4 mM, MgSO4 0.8 mM, glucose 5.5 mM). The hearts were minced using a sterile and sharp razorblade, and placed in a 1.5 ml tubes (5-6 hearts per tube) containing 1 ml of PIB digestion buffer (ADS buffer+0.05 mg/ml Collagenase type II (Worthington)+1 mg/ml Pancreatin (Sigma). Place the tubes at 37° C. with shaking at 1000 rpm per 15 minutes, collect the supernatants on a tubes containing a volume of complete medium (DMEM 75%, M199 25% ml, Pennicilin/streptavidin lx, L-Glutamine 1×, Horse serum 10%, Fetal Cow Serum 5%) equal to the sum of all supernatants from digestion tubes. Add 1 ml of PIB buffer to undigested tissue fragments still in the tubes and repeat the digestions process other 2 times. After the 3 steps of digestion spin down the cells by centrifugation at 800 rpm for 10 minutes at room temperature. Discard the supernatant and resuspend the pellet in adequate volume of complete medium (2 ml each 5-6 hearts). Plate cells in 10 cm dish for 45 minutes in an incubator 37° C., 10% CO2 (pre-plating 1); after this step the non-myocytes will adhere and the cardiomyocytes will remain in suspension. Transfer the supernatant on a new 10 cm dish to repeat this step another time (pre-plating 2) Add fresh complete medium to the preplating dish to culture the non-myocytes cells. After the second pre-plating collect the supernatant in a new tube, count the cells and seed 300.000 cardiomyocytes on gelatin coated 3.5 cm plates. One day after isolation, a final concentration of 100 nM of LNATM longRNA GapmeRs (Exiqon) was transfected on cardiomyocytes using FuGene 6 (Promega). After 72 hr, RNA was extracted using miRNeasy kit (Qiagen) and the knock down confirmed by qPCR. Gapmer Sequences, Scrambled; TCATACTATATGACAG (SEQ ID No 106), Anti-Novlnc6 TACAACCTGCTTACT (SEQ ID No 105).

Nuclear and Cytoplasmic RNA Fraction Isolations

Nuclear and cytoplasmic RNA fractions were isolated using the Cytoplasmic and Nuclear RNA purification kit (Norgen Biotek Corp, CA, Cat No; 37400) according to the manufacturers instructions.

RNA Isolation, Reverse Transcription, End-Point PCR and Quantitative PCR.

Primer sequences for qRT-PCR are provided below. For TaqMan probe based qRT-PCR expression was analyzed using fluorescent-labeled TaqMan Probes (ABI). Analysis was carried out using an ABI Prism 7500 cycler and relative expression quantified using the ΔΔCt method. For end-point PCR aliquots of PCR mixtures were taken during different cycles for agarose gel analysis to determine linear range of amplification. All reactions were run on a 1.5% agarose gel stained with Ethidium Bromide. Primer sequences were as follows (Fw, Rv).

```
Novlnc6;
                         (SEQ ID No 107, 108)
GTGGGGAGGTCAGCTACAAA;

CGGAAATGGTTTGAAATGCT,

Novlnc11;
                         (SEQ ID No 109, 110)
ACAGACCTGCAGCAGTGAGA;

GCTAGGGAACGCAGAACAAG,

Novlnc15;
                         (SEQ ID No 111, 112)
AAGGCTTCCCAGAGAAGGAG;

ACTGGGTGAGTCTCGCTGTT,

Novlnc23;
                         (SEQ ID No 113, 114)
TGGGACAGCAGAGCTAAGGT;

AGATTCCAGCACGCACTTCT,

Novlnc32;
                         (SEQ ID No 115, 116)
AAAGGGAAGAGGGAAAACGA;

CGTCTAGAACCAGCCCAGAG,
```

-continued

```
Novlnc35;
                         (SEQ ID No 117, 118)
CAGCCCTGCTTTAGTTCCTG;

TTCGTTGGGGATTTTACTGC,

Novlnc44;
                         (SEQ ID No 119, 120)
TTTGGAGATGGAACCTGGAG;

TCTGGTATGGGGGAGACTTG,

Novlnc49;
                         (SEQ ID No 121, 122)
AGCTCTGGGTTGGACTGAGA;

TGCATACATTCTGGCAGAGC,

Novlnc61;
                         (SEQ ID No 123, 124)
GGTTGGGTGCCTATTAAACG;

GGTTCATGAGCCTTTGGAAG,

Novlnc76;
                         (SEQ ID No 125, 126)
TGTTAATTCAGGGGCACACA;

GGTGGAGAGCCACTGAAGAG,

Novlnc86;
                         (SEQ ID No 127, 128)
TCTCTGTCCCTTGTGTGTGC;

CTTGGAGGTGTGGGCATAGT,

Novlnc90;
                         (SEQ ID No 129, 130)
GAGCCAAGTGCACACAGAAA;

TGGTCTGTTCCTGGCCTTAG,

Novlnc95;
                         (SEQ ID No 131, 132)
GTGGACGACAAGGGAGGTTA;

CGGAATGGCTCCTACAACAT,

Novlnc96;
                         (SEQ ID No 133, 134)
GAGGCTCCTGGATCTCTGTG;

TTGGGAGGCAAAGGTAGATG,

Novlnc103;
                         (SEQ ID No 135, 136)
GAAATGAGTGGTGGCAGTGA;

CTTAGGTCTGCGCCTAATGG,

Novlnc174;
                         (SEQ ID No 137, 138)
GCACAGATGCATAGCCTCAA;

GCAGCCTGGACTTTTCTCAC,

Novlnc333;
                         (SEQ ID No 139, 140)
TCACCTCCAAGTGGGTCTTC;

AGCTCGGTCTGTCGTGAGTT,

MmMyocardin;
                         (SEQ ID No 141, 142)
CAAGGCTTAATACCGCCACTG;

AATGTGCATAGTAACCAGGCTG,
```

-continued

```
MmBMP10;
                        (SEQ ID No 143, 144)
ATGGGGTCTCTGGTTCTGC;

CAATACCATCTTGCTCCGTGAA,

MmTbx20;
                        (SEQ ID No 145, 146)
AAGAGATACCGCTATGCCTACC;

GCTGCTCGCCAGTAAAGGG,
```

Col1a1; Mm_00801666_g1, CTGF; Mm_01192931_g1, NPPA; Mm_01255747_g1, TGFb2; Mm_00436955_m1, Nkx2-5; Mm_00657783_m1, GATA4; Mm_00484689_m1, Tbx5; Mm_00803521_m1, Myh6; Mm_00440354_m1, Myh7; Mm_00600555_m1, NPPB; Mm_00435304_g1.

RNA Sequencing and Analysis

Total RNA was isolated from adult mouse hearts using the RNeasy isolation kit (Qiagen). Sequencing libraries were prepared according to Illumina RNA Seq library kit instructions with Poly(A) selection. Libraries were sequenced with the Illumina HiSeq2000 (2×100 bp).

Sequence Analysis of Long RNA Reads

100nt paired-end reads from 8 samples (4 Sham, 4 LAD) were mapped to mm9 reference genome using Tophat software version 2.0.5 (Trapnell et al., 2012) with option "Gene model" G, using mm9 UCSC reference genes GTF (Karolchik et al., 2003). An ab initio transcript reconstruction was performed using Cufflinks, version 2.0.2 (Trapnell et al., 2012). The option "masking" (-G) was used, using mm9 UCSC reference genes GTF. The other parameters were default. The resulting GTFs were merged using Cuffmerge, version 2.0.2, using option -g with mm9 UCSC GTF as reference, allowing distinguishing known and novel transcripts.

Classification of lncRNA

Using the output of Cuffmerge, the transcripts were classified into 3 categories: known mRNAs, known lncRNAs (UCSC as reference) and novel lncRNAs. Novel transcripts were filtered for minimal length of 200 bp and at least 2 exons. Read counts were then calculated per gene from the alignment bam files using HTSeq (v0.5.4p2) with options -m union—stranded no. Genes were then filtered for minimal expression (mean counts >=5 across all conditions). lncRNA genes were classified into several categories by comparing the lncRNA exon and gene coordinates with coordinates of known protein coding genes. The categories were as follows: 'Intergenic Same Strand' was where all exons of the lncRNA gene were between two protein coding genes; 'Intergenic Convergent' was where a protein coding and lncRNA gene are transcribed on opposite strands but pointing towards each other; Intergenic 'Divergent' was where a protein coding and lncRNA gene are transcribed on opposite strands but pointing away from each other; 'Exonic Sense' was where at least one exon of an lncRNA overlapped with an exon of a protein coding gene in the same direction; 'Exonic Antisense' was the same as for 'Exonic Sense' but with lncRNA and protein coding genes on opposite strands; 'Intronic Sense' and 'Intronic Antisense' were where a lncRNA was completely contained within the intron of a protein coding gene on the same, or opposite strand respectively; 'Overlapping Sense' and 'Overlapping Antisense' was where a lncRNA gene's coordinates overlapped with those of a protein coding gene on the same or opposite strand respectively.

Differential Expression Analysis of lncRNAs

Count data was fitted to a statistical model based on the negative binomial distribution using the R package DESeq, which is useful for detecting significant RNA-Seq variation with a low number of biological replicates. To perform the normalization and differential expression analysis, raw read counts per gene were normalized to the relative size of each library. Empirical dispersion (the squared coefficient of variation for each gene) was estimated using the pooled method. Here, samples from all conditions with replicates are used to estimate a single pooled dispersion value, which is applied to all samples. The dispersion-mean relationship was then fitted using the local method and the fitted value only was used in subsequent calculations. The difference between the means of treated vs non-treated samples was then calculated using a negative binomial test and p-values were adjusted for multiple comparisons using the Benjamini-Hochberg method. Genes with an adjusted p-value of <0.01 were considered to be differentially expressed.

LncRNA Analysis

Coding potential—The protein-coding potential of transcripts was evaluated using the program GeneID, version v1.4.4, applied to transcript sequences in FASTA format, with parameters adapted for vertebrates as provided by the authors in file GeneID.human.070123.param, and with options -s and -G.

PhastCons score—PhastCons scores (calculated on a multiple alignments of 30 vertebrate genomes to the mm9 mouse genome) by chromosome were downloaded from the UCSC website. For each gene, scores per base for exons, introns and promoters (defined as 1000 bp upstream from TSS) were summed and divided by the fragment length. This result was used as the score per fragment. 50000 random intergenic regions were generated (size=3400 bp±20%) and the same score was calculated. Log 10 of the scores was plotted by category using R package lattice. The scores of the intergenic regions were added to the 3 plots (exon, intron, promoter) as a comparison.

Chromatin Marker Levels

For the analysis of chromatin marker levels at promoters, we used data published by Wamstad et al. (Wamstad et al., 2012), observed in cell lines representative of successive stages along cardiac differentiation (ESC, MES, CP, CM) (downloaded from data repository of the Cardiovascular Development Consortium (CvDC), part of the NHLBI Bench to Bassinet Program). Levels of five markers (H3K4me1, H3K4me3, H3K27ac, H3K27me3 and RNAP Ser5P) were evaluated within 2 kb regions centered on the TSS of each transcript, using the map command of the BEDTools program, version 2.17.0, with default parameters. These levels were normalized by computing the ratio of ChIP to input WCE DNA within the same region. Based on the resulting profiles, transcripts were distributed among the 31 ChIP clusters identified by Wamstad et al. (Wamstad et al., 2012). Each transcript t was ascribed to the nearest cluster, as measured by a distance d(t, C) based on the Spearman correlation S(t, c) of profiles between the transcript t and the n members c of cluster C:

$$d(t, C) = 1 - \left(\frac{1}{n}\sum_{1}^{n}|S(t, c_n)|\right)$$

Chromatin States

To analyze the presence of chromatin marker peaks at promoters, we used data published by Wamstad et al. (Wamstad et al., 2012), observed on cardiac differentiation cell lines, and data observed in adult tissue (heart, kidney, liver, spleen, testis) published as part of the ENCODE project (The ENCODE Project Consortium, 2011), generated and analyzed in Bing Ren's laboratory at the Ludwig Institute for Cancer Research, UCSC. Four markers were considered: H3K4me1, H3K4me3, H3K27ac and H3K27me3. Depending on presence of these markers, each transcript was ascribed to one of eight distinct chromatin states: H3K4me1, H3K4me3, or H3K27me3 alone, combination of H3K4me3 and H3K27me3, H3K4me3 and H3K27ac, H3K27me3 and H3K4me1, H3K27ac and H3K4me1, or none of these previous combinations. A marker was considered present if a non-empty intersection could be detected between the TSS region and a marker peak, in any of the replicates. The intersections were detected using the window command of the BEDTools program (Quinlan and Hall, 2010), version 2.17.0, with option -w 1000.

Mosaic Plots

Mosaic plots were used to visualize joint frequency distributions (e.g. across ChIP clusters, gene categories or differential expression status). These plots were generated using the cdv R package. In some of these plots, a residual-based shading was applied to visualize the pattern of deviation from independence. Most data processing, statistical analysis and generation of graphics was performed using the R language (R core team, 2013).

Gene Expression Across Tissues—Expression Heatmaps

Expression of the genes (RefSeq+novel lncRNAs) in 18 mouse tissues (Adrenal, Bladder, Colon, Duodenum, Heart, Kidney, Large Intestine, Liver, Lung, Mammary gland, Ovary, Placenta, Subcutaneous Adipose tissue, Small Intestine, Spleen, Stomach, Testis, Thymus) was measured on ENCODE public data (CSHL Long RNA-seq, PI Gingeras, Lab CSHL-m) (The ENCODE Project Consortium, 2011). Counts on plus and minus strands were summed and mean counts were taken for the two replicates per tissue. Expression for the same genes was also measured on the 8 LAD/Sham samples. Between sample normalisation was performed using DESeq (estimateSizeFactors function. Only genes with minimal expression were kept (mean counts >=5 across all conditions). Heart Specificity (HS) score (per gene) was defined as:

$$HS\ \text{score} = \frac{\mu_{cardiac}}{\mu_{non\text{-}cardiac} + 2 * \sigma_{non\text{-}cardiac}}$$

Where µcardiac is the average expression per gene in our 8 samples, µnon-cardiac is the average expression per gene in non-cardiac ENCODE samples, and σ non-cardiac is the standard deviation per gene in non-cardiac ENCODE samples. (adapted from (Anders and Huber, 2010b)). A gene was considered heart specific with HS score >1. Heatmaps were generated using heatmap.2 from the package gplots in R, version 2.11.0. The clustering was performed using hclust, version 1.3.1, using Spearman correlation and euclidean distance, average linkage clustering. A scaling by row was applied. The same sample order was used for all heatmaps to enable comparison. The HS bars were generated using the HS score defined above. The filter for differentially expressed genes is adjusted p-value for differential expression <0.01. P-values for significance of difference between percentages of HS between groups were calculated using Pearson Chi-squared test.

Correlation of Expression between Novel lncRNAs and Closest Coding Genes

The coordinates of the novel lncRNAs were compared to RefSeq coding genes reference. If the coordinates of the lncRNA overlapped with a known gene (at least 1 bp), this gene was considered as the closest overlapping gene. If there was no overlap with a known gene, the closest gene was selected and classified as upstream or downstream depending on its position. For gene expression, the same data as in Expression heatmap was used. The correlation of expression was calculated between the lncRNA and closest coding gene using Pearson correlation. This was done for novel and UCSC lncRNAs. As a comparison, the same method was applied on 2000 non-redundant random pairs of closest coding genes. To generate a set of correlations between random mRNA pairs, a pairwise Pearson correlation matrix was calculated between all genes, and 100 k random pairs were selected from it (excluding redundant ones)

Correlation Gene Expression—Physiological Traits

All heatmaps were generated using the R heatmap.2 function, from package gplots. No scaling was applied. All clustering was performed using the R function hclust. Physiological traits were correlated using the Spearman method, and clustering was using euclidean distance and complete linkage clustering. Correlation between physiological traits and gene expression was calculated using the Spearman method, comparing 2 vectors containing 8 values of gene expression and 8 values of trait measure, respectively. Horizontal and vertical clustering were performed on the expression and traits values, using the Spearman method for the correlation, and average linkage clustering. The density plots of the Heart Specificity by category used the same HS scores as described above and were performed using R package gplots, function ggplot.

TransMap

The GTF file containing the novel lncRNAs to transmap from mouse to human was converted into a psl file using utilities gtfToGenePred and genePredToPsl. pslMap utility was then used with the new psl file and ENCODE chain alignment hg19.mm9.all.chain downloaded from the UCSC website. The orthologs discovered by pslMap were then filtered using pslCDnaFilter with option -globalNearBest=0.005 and -minCover=0.2. The 4 standalone programs used above were downloaded from UCSC utilities.

Visualisation on UCSC

Bigwig files were generated using Bedtools suite, version 2.17.0 from the bam files generated by Tophat. The tool used was genomeCoverageBed, with options -bg, -ibam and -scale. The size factors used to scale were calculated using DESeq (as described above). The bigwig files were then uploaded on an ftp server and the link was uploaded on the UCSC genome browser.

G0 Analysis—Enrichment for Biological Themes

The genes lists were submitted online to the DAVID Functional annotation clustering tool using default parameters and databases.

Human Methods

All human material was obtained during routine sampling used for clinical purposes, stored in a coded way and available for research purposes in accordance with the Declaration of Helsinki and the ethical committee at Maastricht University Medical Center. Right ventricular septal biopsies were obtained during routine clinical sampling from patients with idiopathic dilated cardiomyopathy (DCM) and decreased ejection fraction without cardiac inflammation. Controls (n=6) consisted of patients with unexplained ventricular tachy-arrhythmias but with a normal ejection fraction and the absence of systemic or cardiac inflammation at the time of biopsy. Left ventricular biopsies were obtained from patients with aortic stenosis (AOS) and from control patients undergoing coronary artery bypass grafting (CABG) (Suppl. Table Y). Cardiac biopsies were immediately snap-frozen for total RNA was isolation with the miRVana miRNA isolation kit (Ambion, Austin, Tex.). Total RNA was reverse transcribed using iSCript (Bio-Rad, Hercules, Calif.) and SYBR Green quantitative PCR was performed on a Bio-Rad iCycler.

Statistical Analysis

Data throughout the paper are expressed as mean±SEM. One way ANOVA was used to test significance of data comparisons between experimental groups, with p values <0.05 were considered significant.

Results

Global Identification of lncRNAs Expressed in the Heart and Regulated during Myocardial Infarction The Inventors first set out to characterize global transcriptional regulation during myocardial adaptation to stress for both the coding and non-coding transcriptome alike. The Inventors utilized a well-characterized pathophysiological model of cardiac stress in the mouse, namely myocardial infarction obtained by left anterior descending artery ligation. The Inventors identified lncRNAs expressed in the infarcted adult mouse heart by employing a RNA-Sequencing (PolyA+RNA-Seq) and ab initio transcriptome reconstruction approach. Illumina-based massively parallel sequencing was used to obtain paired-end reads (2×100 bp) of experimental libraries, and Cufflinks ( ) was utilized to perform ab initio transcript assembly on mapped paired-end reads.

This analysis reconstructed 17584 multi-exonic transcripts, of which 15075 (2204 up-regulated and 1338 down-regulated) correspond to University of California Santa Cruz (UCSC) annotated protein coding genes (See Ounzain S, et al., 2014). Our lncRNA annotation pipeline identified 2509 multi-exonic lncRNAs (>200 bp). There were 988 (67up-regulated and 66 down-regulated) UCSC annotated lncRNAs and 1521 (86 up-regulated and 225 down-regulated) novel previously un-annotated lncRNAs, encompassing all known lncRNA locus-types (data now show). To verify the non-coding nature of our novel lncRNA candidates, The Inventors used GeneID coding potential score algorithm and found that these novel transcripts encode minimal protein coding potential comparable to UCSC annotated lncRNAs (see Ounzain S, et al., 2014). Furthermore, novel lncRNAs and UCSC lncRNAs were expressed at significantly lower levels than coding genes (FIG. 1B). UCSC lncRNA exons were less conserved than coding exons although promoters were equally conserved (FIG. 1B).

Novel lncRNAs are Heart Specific and Proximal to Cardiac Developmental Genes

The majority of lncRNAs identified in our analysis represent novel lncRNAs that have previously escaped annotation. The Inventors aligned 17 mouse non-cardiac ENCODE RNA-Seq data sets (Mouse et al., 2012), and found that 16% of UCSC mRNAs and 23% of UCSC lncRNAs were classified as heart specific (see Ounzain S, et al., 2014). By contrast, 38% of the novel lncRNAs were heart-specific, a significant enrichment versus UCSC mRNAs and lncRNAs. Furthermore, differentially expressed novel lncRNAs were significantly more heart-specific than all transcript classes, with 60% of these novel lncRNAs being classified as heart specific (see Ounzain S, et al., 2014). LncRNAs have been shown to regulate coding gene expression both in cis and in trans. If cis-regulation was common, one would expect proximal coding genes to also be more heart-specific. In support of this, The Inventors found that overlapping, proximal upstream or downstream coding genes were significantly more heart-specific than the entire coding gene collection. Furthermore, gene ontology analysis of these proximal coding genes revealed significant enrichment of biological processes associated with heart development, cardiac function and transcriptional regulation. Interestingly differentially expressed novel lncRNAs were more associated with transcriptional control suggesting that modulated expressed novel lncRNAs may be implicated in transcriptional reprogramming observed in the remodeling heart.

The Cardiac Transcriptome is Highly Correlated with Cardiac Physiological Traits The Inventors correlated the cardiac transcriptome with echocardiography derived physiological traits. Both the coding and non-coding transcriptome correlated tightly with cardiac physiology (FIG. 1). Globally, novel lncRNAs were better correlated than UCSC lncRNAs with all physiological traits assessed. To gain a deeper molecular insight and potentially identify molecular pathways associated with physiological traits, The Inventors executed unsupervised clustering and further downstream analysis of UCSC coding genes and novel lncRNAs. The Inventors identified four clusters for both coding (FIG. 1A, -B) and novel lncRNA (FIG. 1C, -D) transcripts. In each case, these consisted of one cluster that correlated positively with cardiac function and negatively with remodeling parameters, one cluster with the inverse of these correlations and two clusters with non-specific intermediate correlations. Gene ontology (GO) and heart specificity analysis was executed on individual clusters with GO analysis being executed on the most proximal coding genes with respect to novel lncRNAs. In the coding gene group, the most heart-specific cluster was Cluster 2 (FIG. 1E), which was positively correlated with cardiac functional traits and associated with genes involved in mitochondrial biology (FIG. 1A). The least heart-specific cluster (Cluster 4) was positively correlated with remodeling and associated with genes involved in wound healing and extracellular matrix (FIG. 1A). Within novel lncRNAs, the most heart-specific cluster, i.e. Cluster 4 (FIG. 1F), was again positively correlated with cardiac function associated traits. Proximal coding genes to novel lncRNA in Cluster 4 were enriched with heart development associated processes (FIG. 1C). Since novel lncRNAs that cluster specifically with particular physiological traits were likely to be involved in biological processes associated with those traits, these findings indicated that novel lncRNAs within this cluster could represent a class of cardiac-specific regulators of developmental gene programs, which was reactivated in the damaged myocardium. Finally, the least heart specific clusters were one and two, which was positively correlated with remodeling traits.

These data demonstrated that unsupervised clustering of transcripts was able to distinguish physiological traits. In addition, it indicated that lncRNAs could represent specific markers of particular physiological traits. To test this, The Inventors compared correlation distributions for each UCSC coding gene and novel lncRNA cluster, with each of the following traits; ejection fraction (EF), interventricular septal thickness at systole (IVS), myocardial infarction trace (MI trace) and left ventricular internal diameter at systole (LVID) (FIGS. 1B and D). UCSC coding gene Clusters 2 and 4 strongly correlated with all these traits when compared to non-specific clusters (Clusters 1 and 3) (FIG. 1B). A similar pattern of correlation was observed with novel lncRNA clusters 2 and 4 (FIG. 1D). However, novel lncRNA Cluster 1 was particularly interesting since it exhibited poor correlation with LVID, EF and MI trace but correlated well with IVS which is typically linked to EF3. This unique characteristic is likely a consequence of the exquisite context and cell-type specific expression of lncRNAs, and has intriguing implications for the utilization of novel lncRNAs as biomarkers.

Inferring Functions for Novel lncRNAs based on Developmental Chromatin State Patterns Pathological cardiac remodeling is associated with the global reactivation of the fetal gene program. The Inventors reasoned that many novel lncRNAs likely represent 'fetal' genes with important roles during cardiogenesis. To investigate this, The Inventors utilized ChIP-Seq data generated in a directed differentiation system that recapitulated the step-wise differentiation of mouse embryonic stem cells (ESCs) to differentiated cardiomyocytes (CMs)(Wamstad et al., 2012).

A previous study demonstrated that co-expressed genes during cardiac differentiation could be functionally grouped based on different chromatin state patterns (Wamstad et al., 2012). Each sub-group of genes appeared to be involved in distinct biological processes, including signaling, metabolism and cardiac muscle contraction. The Inventors reasoned that novel lncRNAs that shared specific chromatin patterns as those described for coding genes were likely to be involved in comparable biological processes, thus providing an unbiased chromatin based proxy to functionally annotate novel lncRNAs. The Inventors mapped the predetermined chromatin patterns (ChIP clusters 1 to 34) to the novel lncRNA promoters (and UCSC annotated genes) during ES cell differentiation. The Inventors classified the novel lncRNAs based on which chromatin pattern they were associated with, and inferred a biological function based on the coding genes and biological processes previously linked to each cluster (see Ounzain S, et al., 2014). For clarity, The Inventors present nine ChIP clusters and inferred biological processes associated with each of our transcript classes. ChIP clusters 1 and 3 are associated with ubiquitous housekeeping and non-cardiac developmental processes (see Ounzain S, et al., 2014). UCSC coding genes and lncRNAs were enriched within these clusters while novel lncRNAs were depleted. On the other hand, novel 1nRNAs were enriched in ChIP-clusters 23, 24, 25 and 26 which are associated with cardiac developmental and functional processes including contractile fiber, z-disk and heart development terms (see Ounzain S, et al., 2014).

The Inventors also identified ChIP-clusters that were enriched or depleted in up and downregulated novel lncRNAs post myocardial infarction, providing a functional insight into the roles of novel lncRNAs in this response (see Ounzain S, et al., 2014). Novel lncRNAs in ChIP-clusters 23 and 24 were enriched in down-regulated lncRNAs post infarction. These clusters are associated with cardiomyocyte maturation and sarcomeric genes (e.g. Myoz2, Myl2). The enrichment of ChIP-cluster 23 and 24 novel lncRNAs in down-regulated lncRNAs could be indicative of the reactivation of the fetal gene program in the border zone post infarction and/or a loss of mature cardiomyocytes. Furthermore, ChIP-clusters enriched in up-regulated novel lncRNAs included cluster 18, which is associated with immune and inflammatory responses (e.g. IL17b), and cluster 28, which is associated with calcium homeostasis and G-protein coupled receptor signaling (e.g. Gnb3), processes that are typically activated in the border zone of the infarcted heart. Finally giving further support to the notion that our novel lncRNAs may be cardiac developmental associated transcripts, The Inventors mapped them to a list of bona fide in vivo validated enhancers active specifically within the E11.5 mouse heart. The Inventors found that seven of our novel lncRNAs map to validated cardiac enhancers including novlnc6 (see below) which maps to mm77, a cardiac enhancer specifically active within the embryonic left ventricle (see Ounzain S, et al., 2014).

Validation of Novel lncRNAs

Figure 2A:
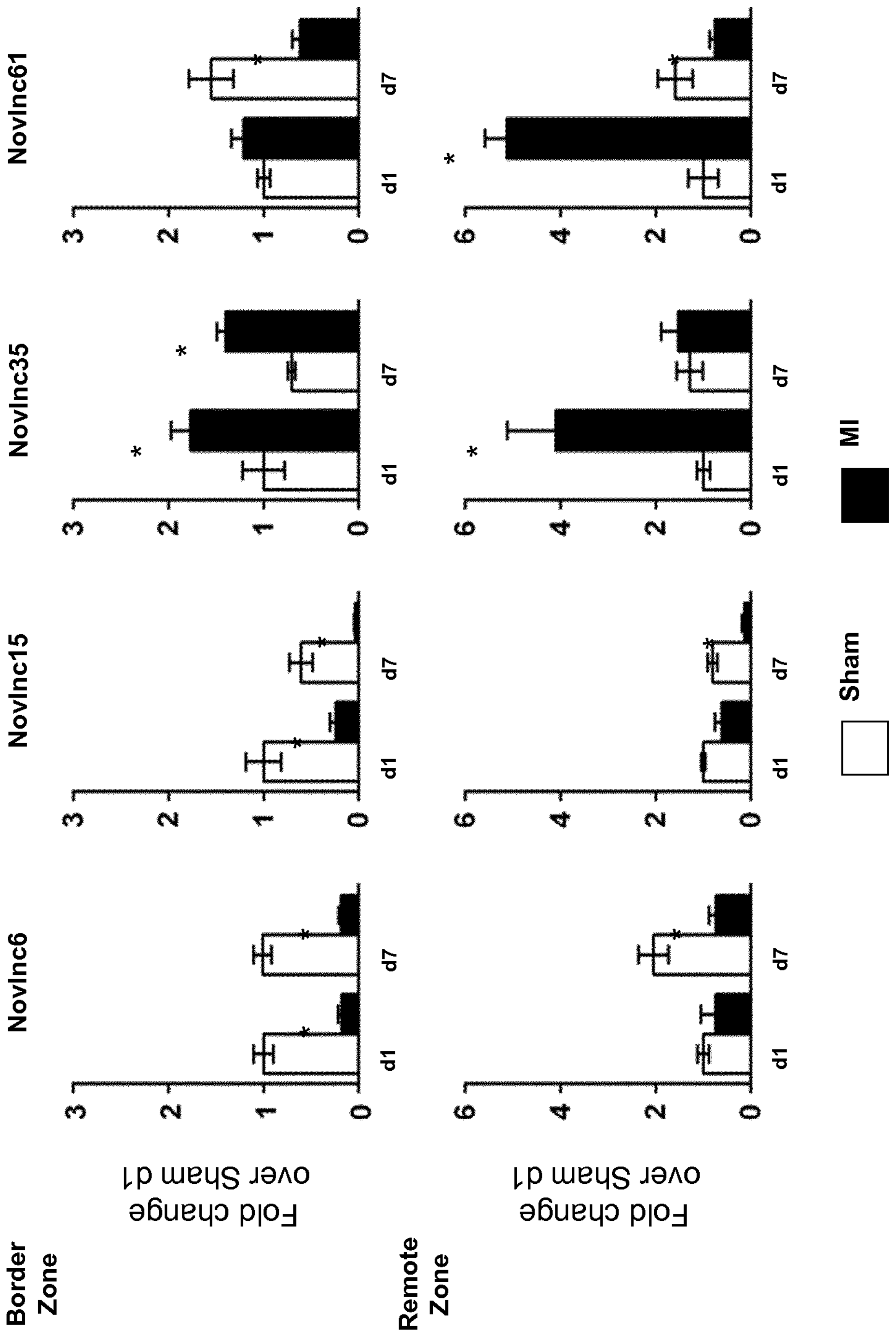
FIGS. 2A-G show the validation and manipulation of selected novel lncRNAs in vivo and in vitro.

To gain confidence in our transcript nominations, The Inventors validated multiple unannotated novel transcripts by quantitative real-time PCR (qPCR). Seventeen high priority novel candidates were selected, and their expression was quantified in the border (BZ) and remote zones (RZ), one and seven days after infarction. The novel lncRNAs exhibited various kinetics of expression in both the BZ and RZ during the acute and chronic phases (FIG. 2A). Many lncRNAs were downregulated; e.g. Novlnc6 (SEQ ID No. 48) and 15 (SEQ ID No 97) some were transiently induced at day 1 in both RZ and BZ (Novlnc35) while others were gradually increased in BZ and RZ (Novlnc74). These distinct kinetic and spatial patterns of expression demonstrate that novel lncRNAs are dynamically regulated in response to myocardial infarction, and suggest that they likely play important roles in the adaptive process.

Figure 2B:
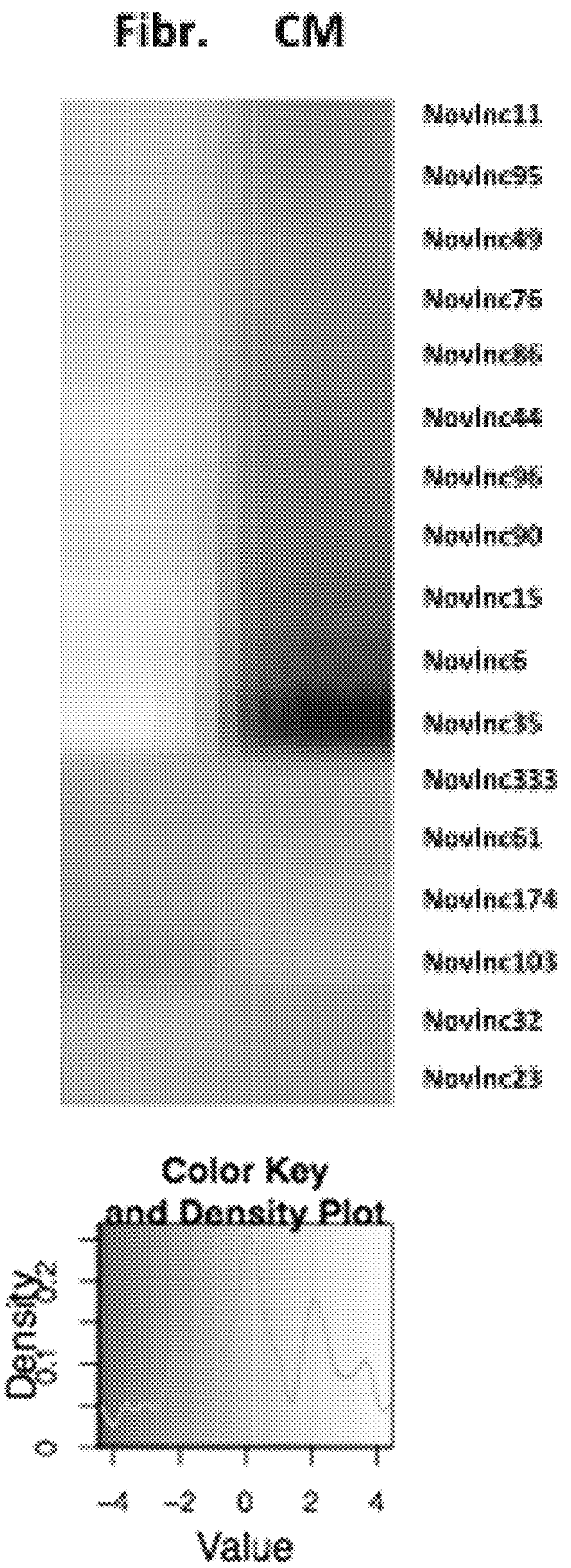
Figure 2C:
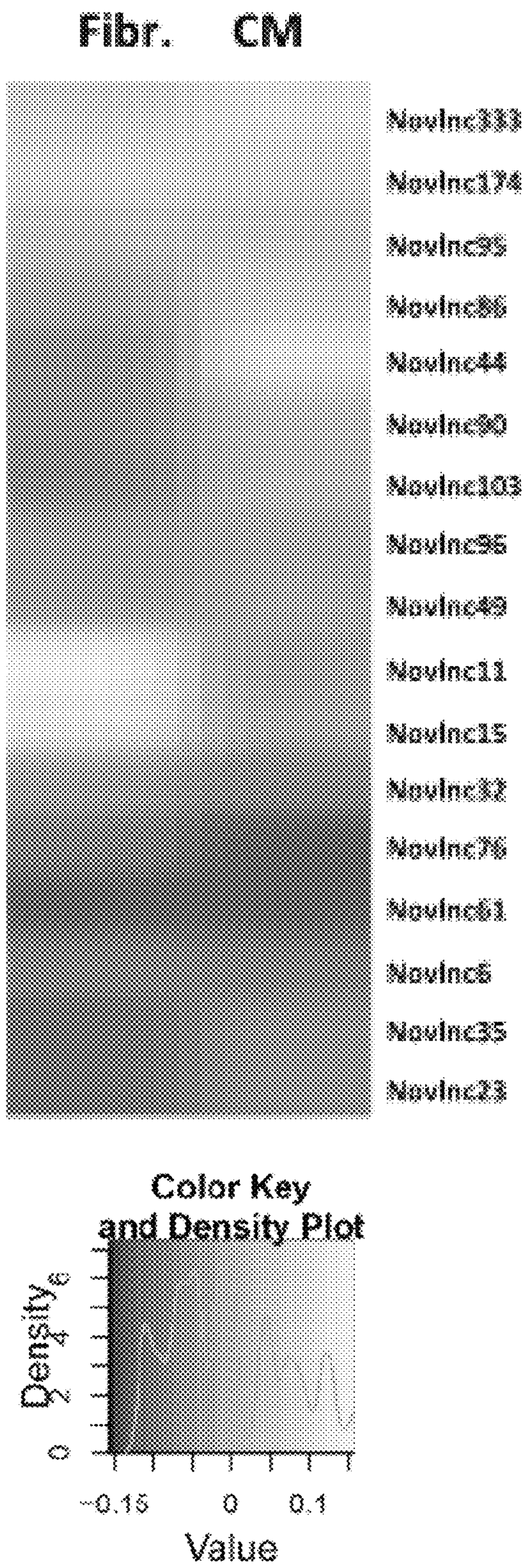
Figure 2D:
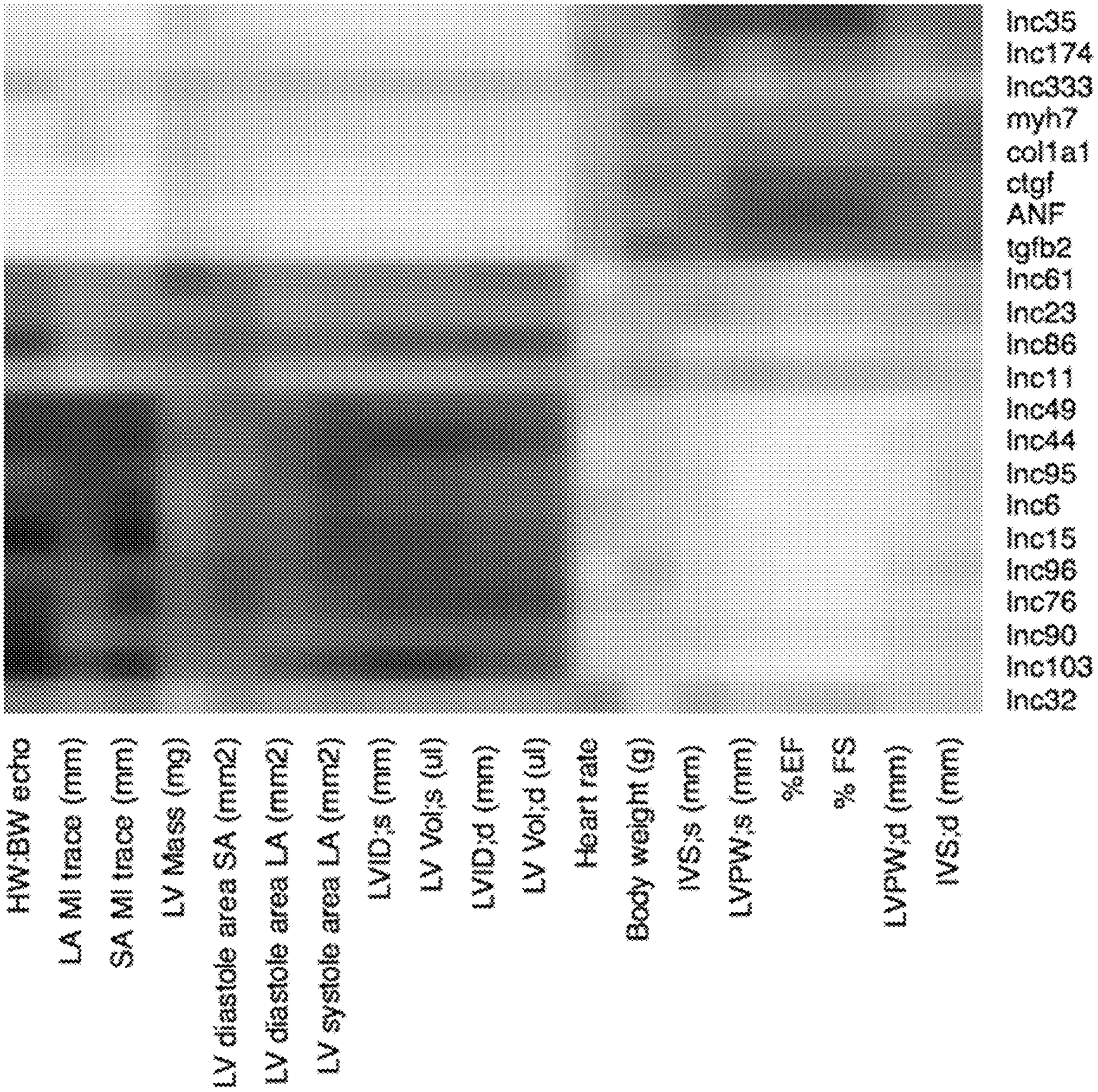
Figure 2D:
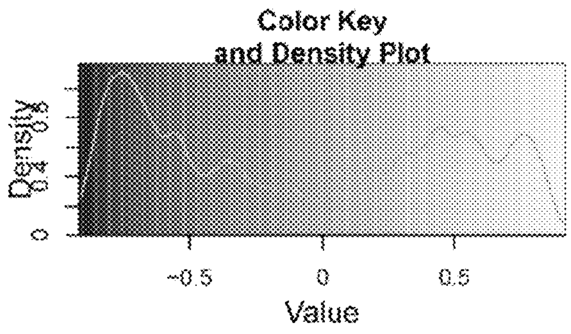

The two major cell types within the adult heart are cardiomyocytes (CMs) and cardiac fibroblasts (FBs) with both being important in maladaptive remodeling. To better characterize the novel lncRNAs, The Inventors quantified their expression in CMs and FBs isolated from the neonatal mouse heart. The selected lncRNAs were either highly CM-specific (Novlnc35; SEQ ID No 99), equally expressed in both cell types (Novlnc61, SEQ ID No 101) or primarily expressed in FBs (FIG. 2B). LncRNA function is also dependant on subcellular localization. Cis-acting lncRNAs (i.e. enhancer-associated RNAs) tend to be more enriched in the nucleus whereas lncRNAs involved in post-transcriptional and translational processes tend to be more cytoplasmic. Therefore, nuclear and cytoplasmic RNA fractions were isolated from neonatal CMs and FBs (FIG. 2C). Validated lncRNAs were either enriched in nuclear (Novlnc174; SEQ ID No 28) or cytoplasmic (Novlnc61; SEQ ID No 101) fractions, in addition to being equally present in both (Novlnc15). Some lncRNAs interestingly displayed differential nuclear versus cytoplasmic enrichment in CMs and FBs (Novlnc90, -49, -11; SEQ ID No 88, SEQ ID No 103, SEQ ID No 25). This may be of functional relevance to roles in these different cell types. The Inventors also correlated the expression of these validated lncRNA with physiological traits in day 1 and day 7 control and MI tissue samples (FIG. 2D). The majority of the lncRNAs correlated well with physiological traits both in border and remote zones. Interestingly, some of our novel lncRNAs were better correlated than stress genes with cardiac function and remodeling.

Figure 2E:
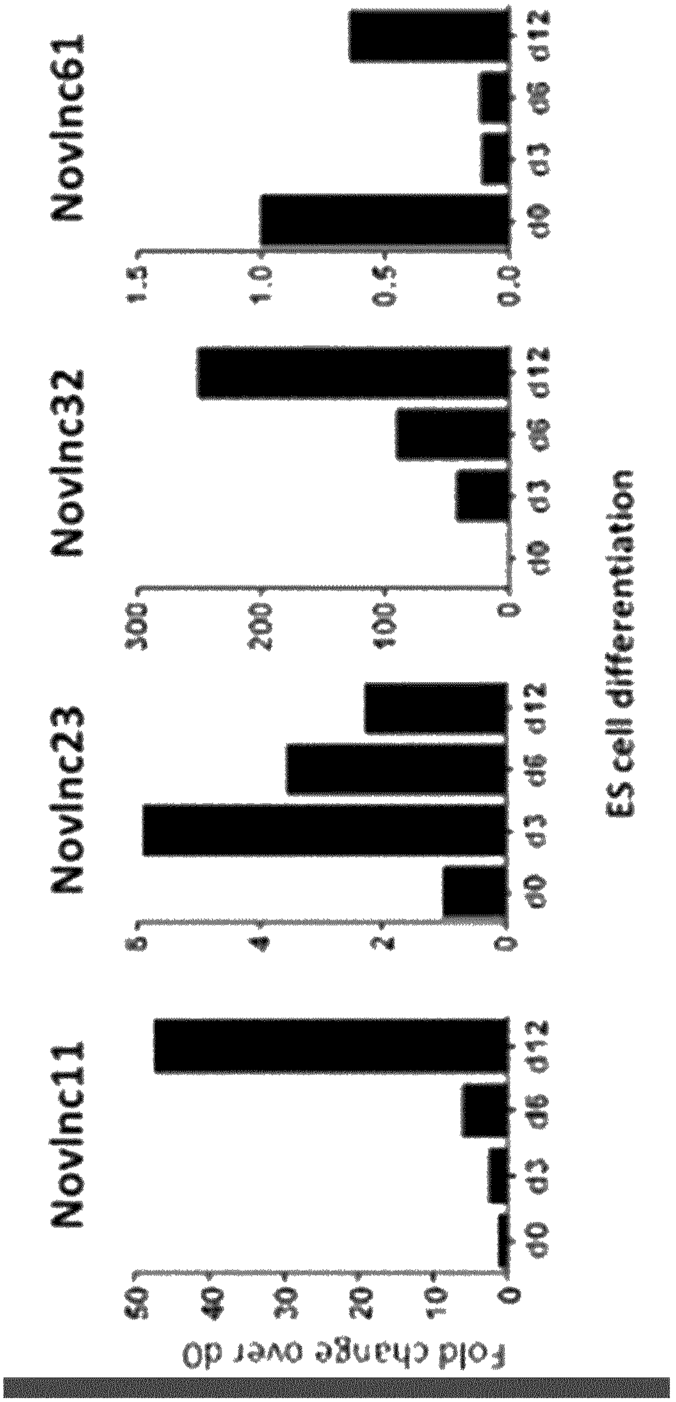
Figure 2F:
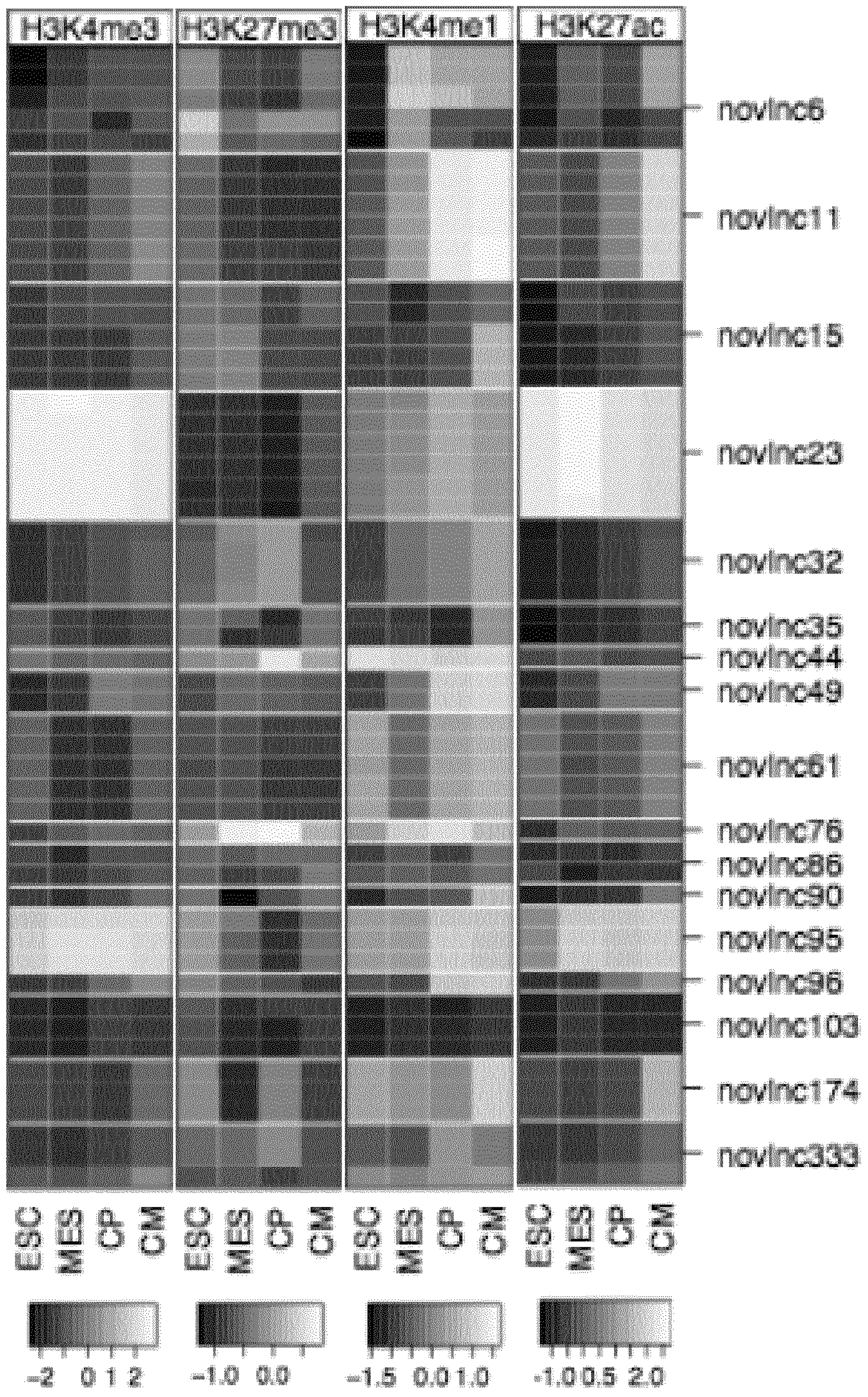

Many of the validated novel lncRNAs were associated with dynamic changes in chromatin states during cardiogenesis in ES cells, suggesting they may have roles as 'fetal' developmental genes (FIG. 2F). To confirm this, mouse ES cells were differentiated through embryoid body (EB) formation using the hanging droplet model recapitulating embryonic cardiac development in vitro. Novel lncRNAs were dynamically expressed during cardiac differentiation with expression correlating with the dynamic changes in chromatin states observed at their promoters (FIGS. 2E and F). Some lncRNAs were induced late during differentiation at the CM stage (Novlnc44, -11, -32; SEQ ID No 100, SEQ ID No 25, SEQ ID No 98, FIGS. 2E and F), and are therefore likely involved in terminal CM differentiation and maturation. Novel lncRNAs exhibiting this profile were mapped to ChIP-clusters 24 and 25, which are predicted to be associated with heart development, z-disk and sarcomere function, cardiac maturation associated processes. Other lncRNAs were maximally expressed at MES and CPC stages (Novlnc49, SEQ ID No 103,) and are likely to be involved in more specific developmental process.

Figure 2G:
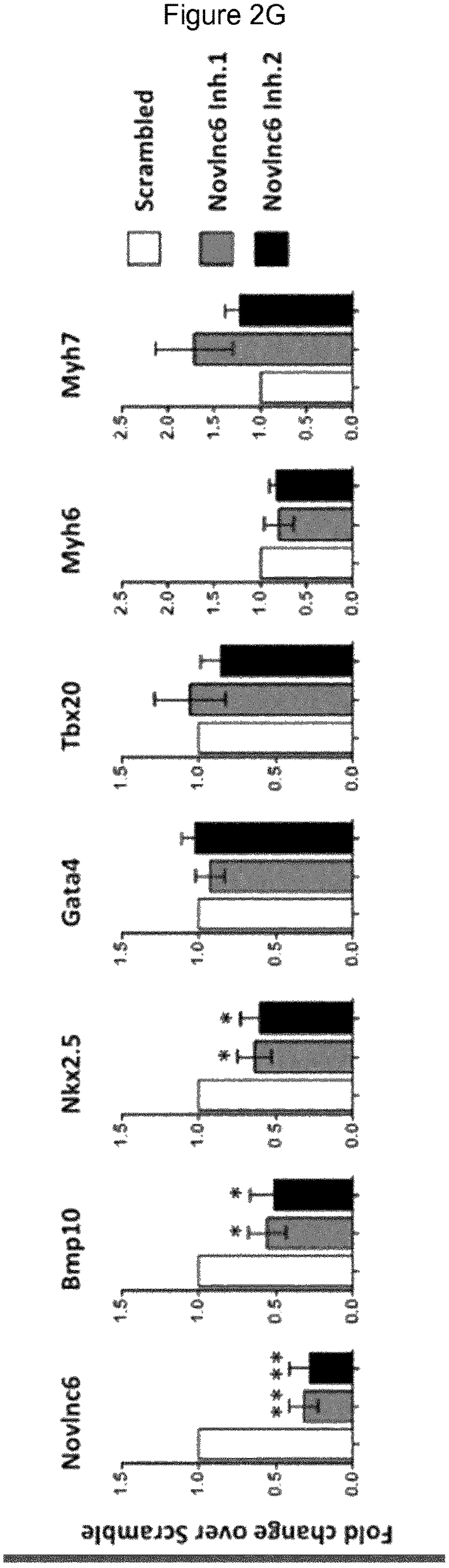

To evaluate whether novel lncRNAs could be associated to specific function involving regulation of cardiac protein coding genes, the Inventors focused on Novlnc6, which fulfills several criteria and unique features prototypical of lncRNAs identified in this study. Furthermore Novlnc6 (SEQ ID No 48) shares a chromatin pattern in differentiated ES cells with the key cardiac signaling ligand BMP10, suggesting Novlnc6 could be involved in similar regulatory pathways. As an experimental model, The Inventors used primary isolated neonatal mouse CMs expressing high levels of Novlnc6. Cells were transfected with modified anti-sense oligonucleotides (Gapmers) targeting Novlnc6 (FIG. 2G). Key cardiac TFs and downstream cardiac target genes involved in stress signaling, contractile apparatus and BMP10 signaling were examined. This screen identified Nkx2.5 mRNA as a potential target of Novlnc6-mediated regulation. Nkx2.5 encodes a core cardiac TF, high in the regulatory hierarchy of the cardiac GRN and critical for the regulation of other cardiac TFs and downstream cardiac differentiation, structural and maturation genes (Bruneau, 2002). Furthermore, Nkx2-5 has been shown to be downstream of BMP10 signaling during cardiac development (Huang et al., 2012). Novlnc6 positively regulated Nkx2.5, supporting the notion that our collection of novel lncRNAs contains functionally important regulatory transcripts.

Dysregulation of Human Orthologs in Cardiac Pathology

Figure 3A:
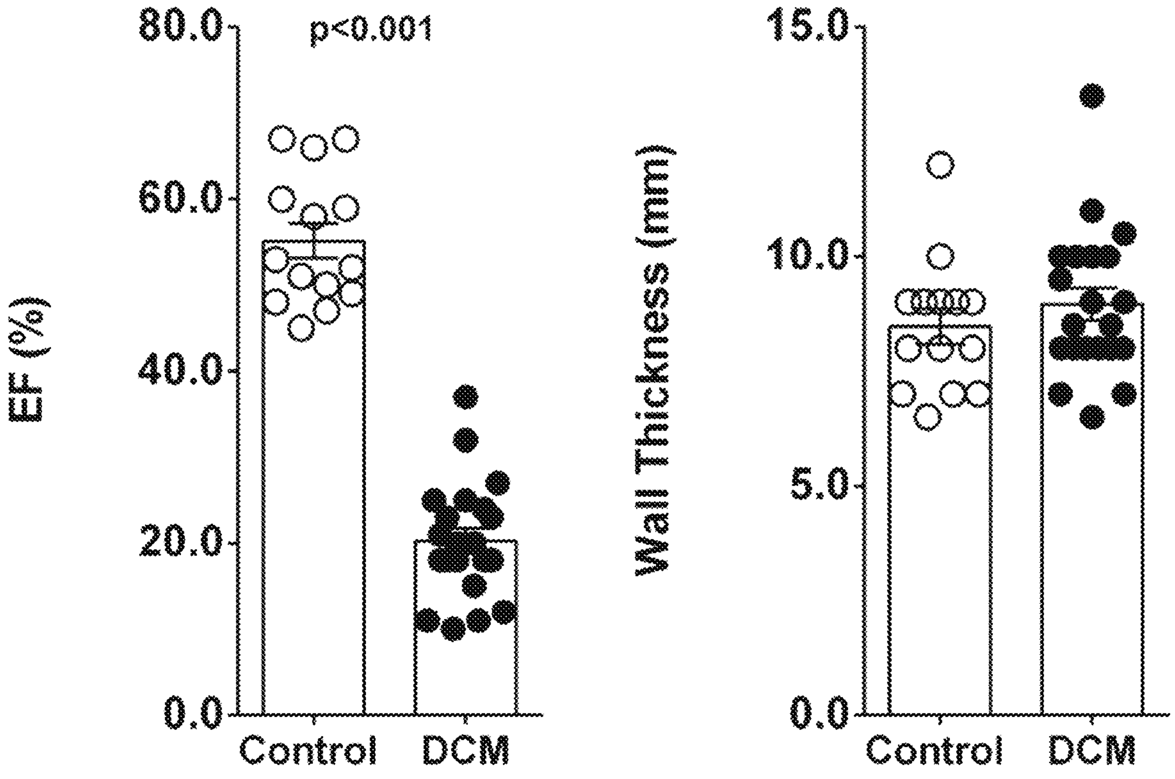
FIGS. 3A-E show the characterisation and validation of human orthologs in cardiac pathology.
Figure 3B:
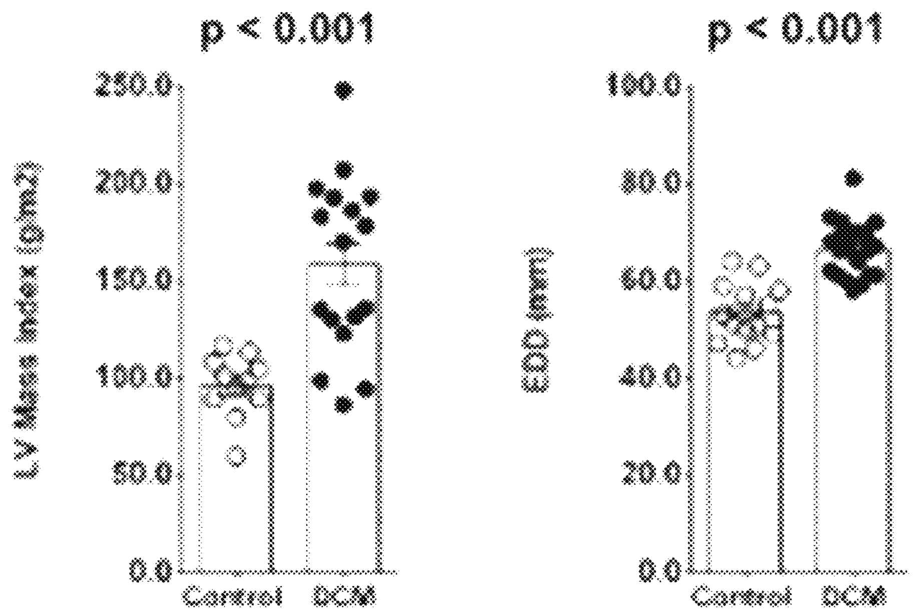
Figure 3C:
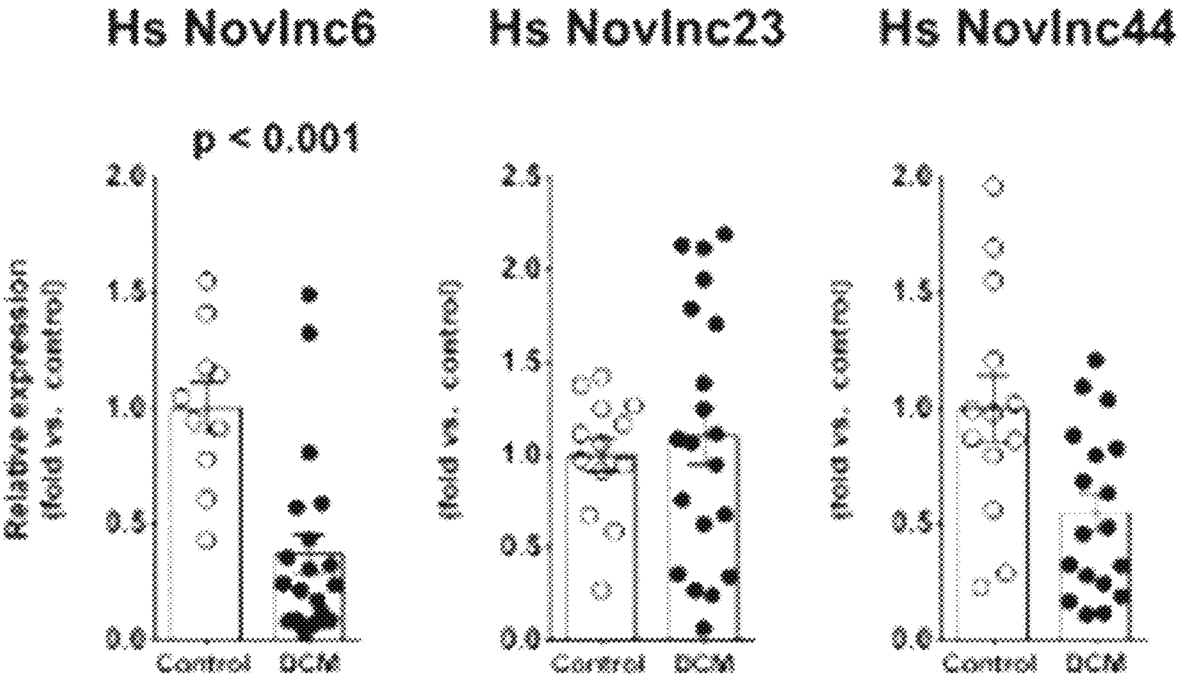
Figure 3D:
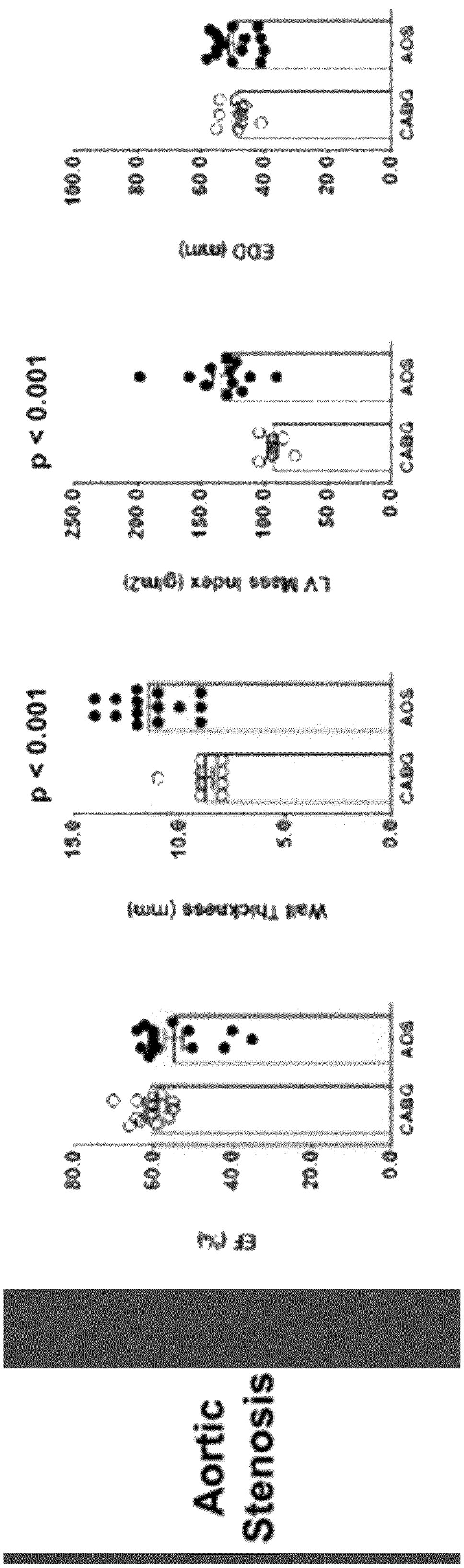
Figure 3E:
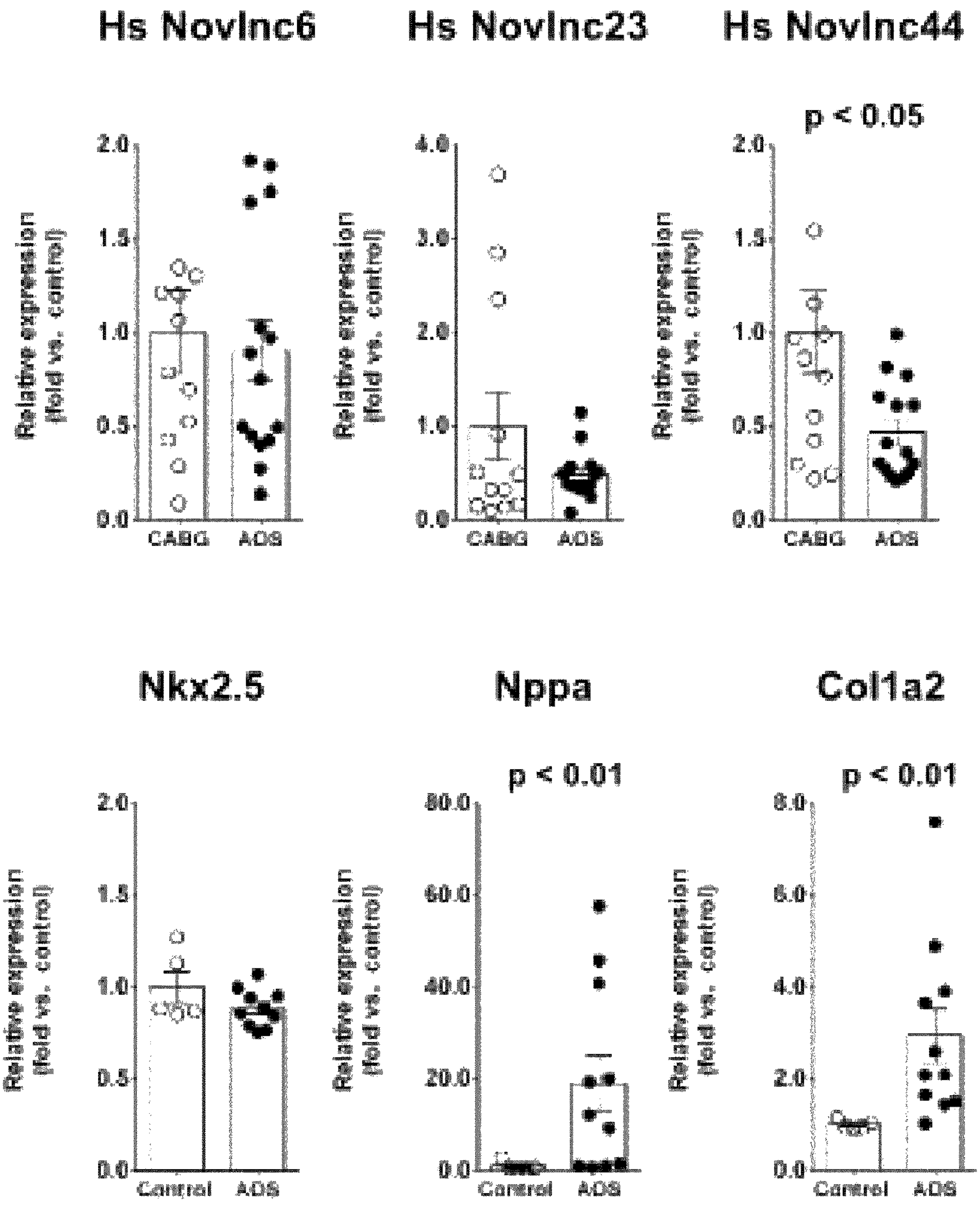

Considering the unique characteristics associated with the novel lncRNAs, The Inventors searched for human orthologs. The Inventors therefore mapped our novel lncRNA catalogue to the human genome using TransMap, a cross species mRNA aligment tool. TransMap maps our novel mouse lncRNAs sequences across the human genome using syntenic BLASTZ alignments that consider conserved gene order and synteny. Of the 311 modulated novel lncRNAs, approximately 72% were confidently mapped to the human genome.To validate and characterize predicted orthologs, The Inventors designed primers encompassed within the putative exons of three human orthologs, corresponding to mouse Novlnc6, -23 and -44 (SEQ ID No 48, 84, 100; FIG. 3A). Quantitative RT-PCR was executed on RNA isolated from the left ventricle of a healthy male. All three putative human orthologs were readily amplified and expressed at relatively high levels (FIG. 3A). To determine the potential roles of these orthologs in cardiac pathology, The Inventors examined their cardiac expression in two independent human heart pathologies. Patients with dilated cardiomyopathy (DCM), and with aortic stenosis (AOS) were assessed. These two cohorts presented with perturbed cardiac functions and associated maladaptive remodeling as expected for such pathologies. Furthermore, cardiac stress marker genes were also differentially expressed (FIG. 3C). In patients with DCM, all three human orthologs were significantly modulated with novlnc6 and -44 downregulated and -23 upregulated (FIG. 3B). Interestingly, the predicted target gene of Novlnc6, i.e. the key cardiac TF Nkx2-5, was also significantly downregulated in patients with DCM. In contrast to DCM, patients with AOS were not associated with differential expression of Novlnc6 or −23, or the predicted target gene of Novlnc6, Nkx2-5. Novlnc44, however, was significantly downregulated (FIG. 3B), comparable to its modulation in DCM.

Example 2

Figure 4A:
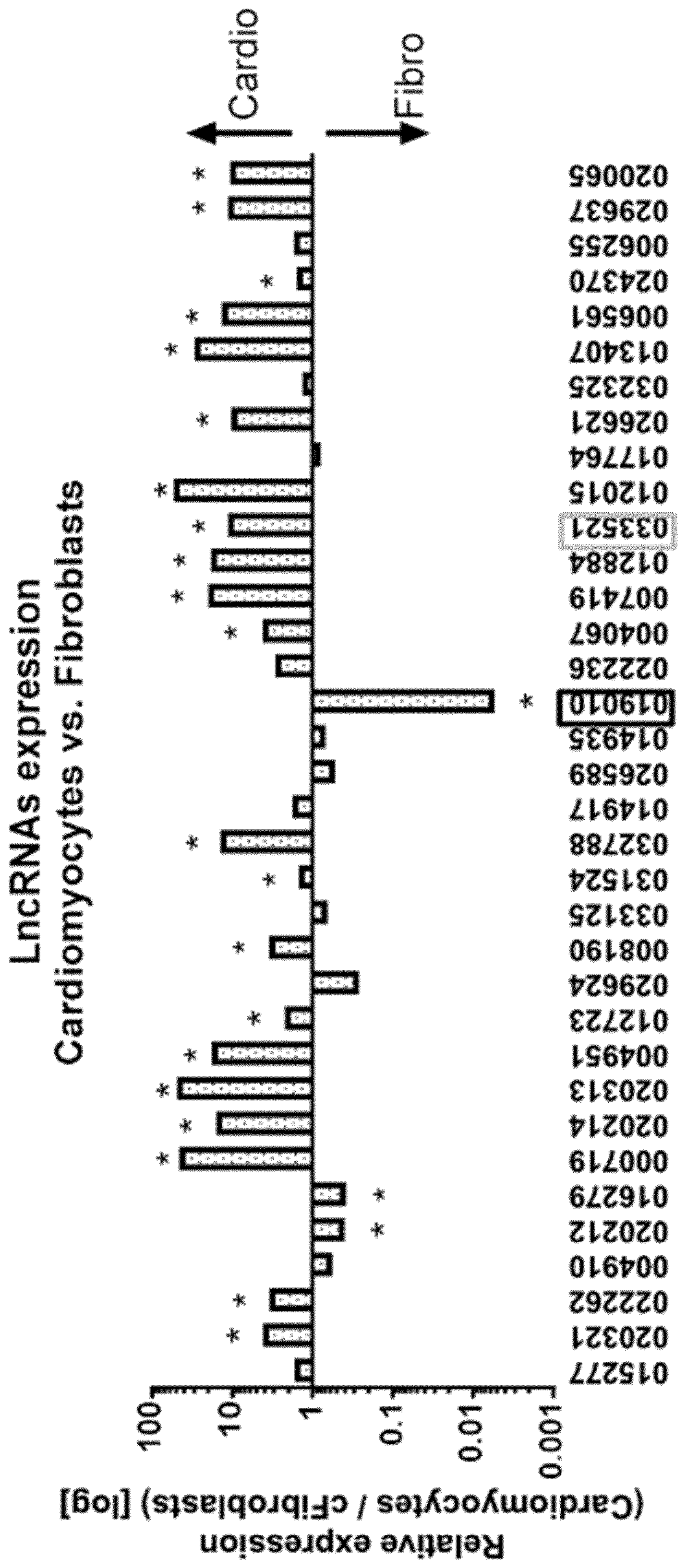
FIG. 4A shows the relative expression of specific lncRNAs in isolated cardiomyocytes versus cardiac fibroblasts.

Cell-Specific lncRNA Expression, and Effects of lncRNA Downregulation in Cardiac Fibroblasts and Cardiomyocytes In Vitro RNA was obtained from cardiomyocytes and cardiac fibroblasts isolated from neonatal mouse hearts. The expression of novel lncRNAs were quantified by RT-PCR in the two cell populations. Ratios in logarithmic scale of cardiomyocyte versus cardiac fibroblast expression of lncRNAs are presented (values below 1 correspond to fibroblast enrichment; values above 1 correspond to cardiomyocyte enrichment). Bars represent mean±SEM (n=3)*p<0.05. The two highlighted lncRNAs: lnc_019010 (fibroblast enriched) and on lnc_033521 (also named Lnc-Dedbt) (cardiomyocyte enriched) have been more extensively studied (FIG. 4A).

Figure 4B:
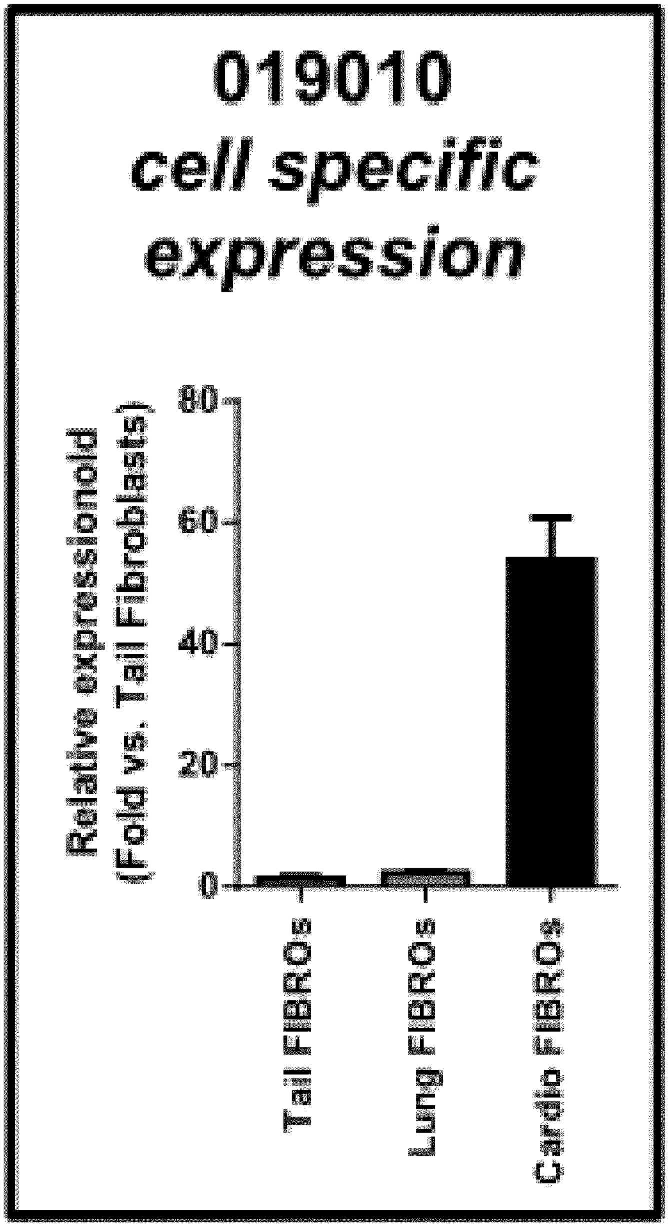
FIG. 4B shows the relative expression of Lnc-019010 in fibroblasts derived form the heart, the lung and the tail.

The expression of novel lncRNAs in fibroblasts isolated from the tail, the lung and the heart of neonatal mice has been quantified by RT-PCR. The expression of lnc_019010 in cardiac fibroblasts is approximately 60 fold enriched compare to the other sources of fibroblasts. This data show the high cell-specificity of this lncRNA (FIG. 4B).

Figure 4C:
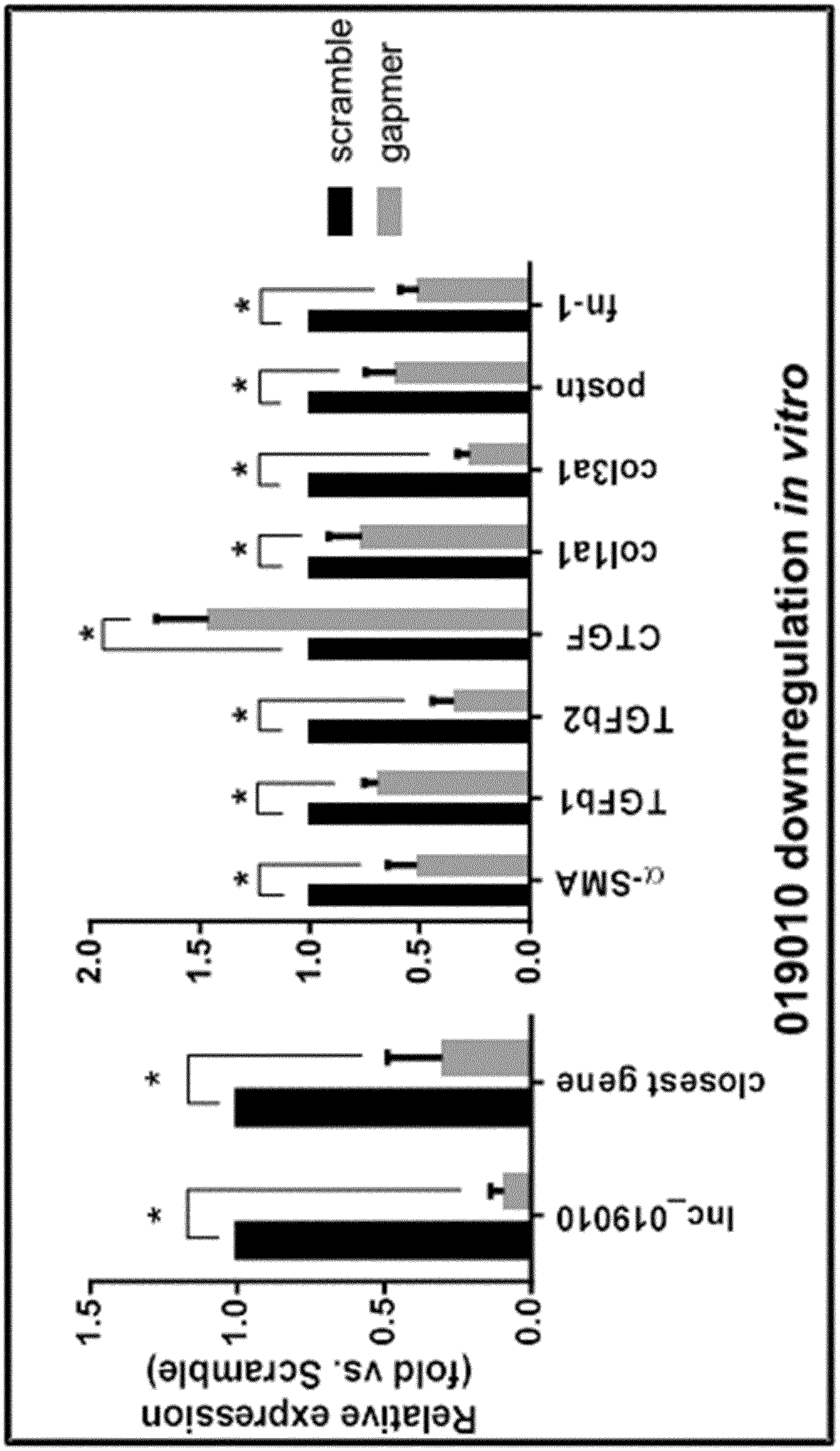
FIG. 4C shows the impact of Lnc-019010 loss-of-function using modified antisense oligonucleotides in cardiac fibroblasts on a panel of coding genes that control the fibrotic response.

Cardiac fibroblasts isolated from neonatal mice were transfected with modified antisense oligonucleotides (GapmeR, 5'-AGGTGTGCGATAGAG-3') targeting lnc_019010 for degradation. GapmeRs were transfected at a concentration of 50 nM and RNA was harvested 24 h after transfection. Compared to control (scrambled) GapmeR transfected cells (black bars), lnc_019010-specific GapmeR cells (grey bars) show a strong reduction of the target lncRNA expression and also of the closest coding gene. Interestingly, the downregulation of this cardiac fibroblast-specific lncRNA impact the expression of important fibroblast coding genes such as α-smooth muscle actin (α-SMA), collagen I and III (Col1a1, Col3a1), fibronectin (Fn1) and periostin (Pstn) and transforming growth factor β1 and β2 (Tgfβ1, Tgfβ2) and connective tissue growth factor (Ctgf). These data, shown in FIG. 4C, suggest that lnc_019010 is involved in cardiac fibroblast differentiation and represents a therapeutic target for limiting fibrosis. Bars represent mean±SEM (n=4) *p<0.05.

Figure 4D:
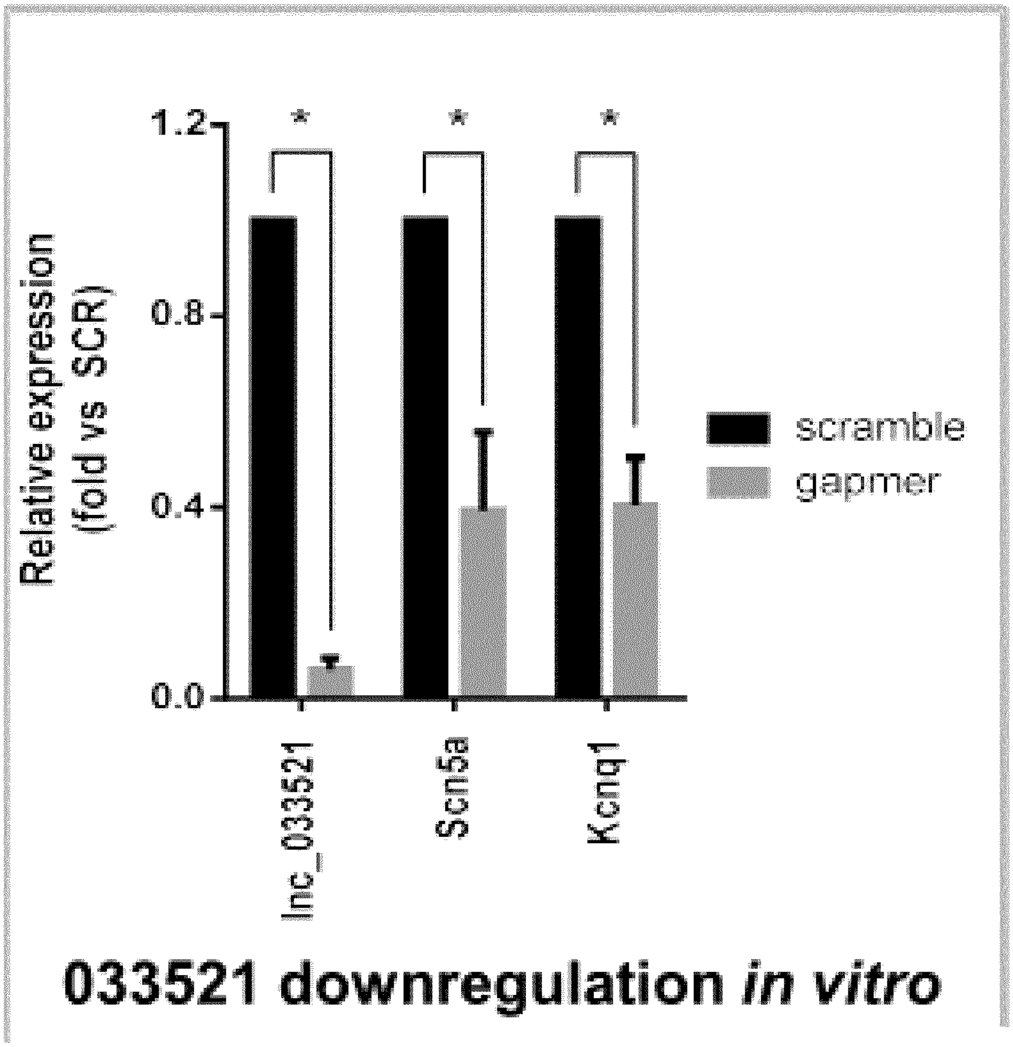
FIG. 4D shows the impact of Lnc-033521 loss-of-function on predicted target genes in isolated cardiomyocytes.

Cardiomyocytes isolated from neonatal mice were transfected with modified antisense oligonucleotides (GapmeR) (SEQ ID No. 147: 5'-TGCTTGCTAGTGTGGT-3') targeting lnc_033521 for degradation. GapmeRs were transfected at a concentration of 50 nM and RNA was harvested 24 h after transfection. Compared to control (scrambled) GapmeR (black bars), lnc_033521-specific GapmeR cells (grey bars) show a strong reduction of the target lncRNA expression. Moreover, the downregulation of this lncRNA has an impact on expression of important gene encoding fundamental cardiac channel such as Scn5a (sodium channel, voltage-gated, type V, alpha subunit) and Kcnq1 (potassium voltage-gated channel). These data shows that lnc_033521 has important function in the conduction system in the heart. FIG. 4D; Bars represent mean±SEM (n=4)*p<0.05.

Figure 5A:
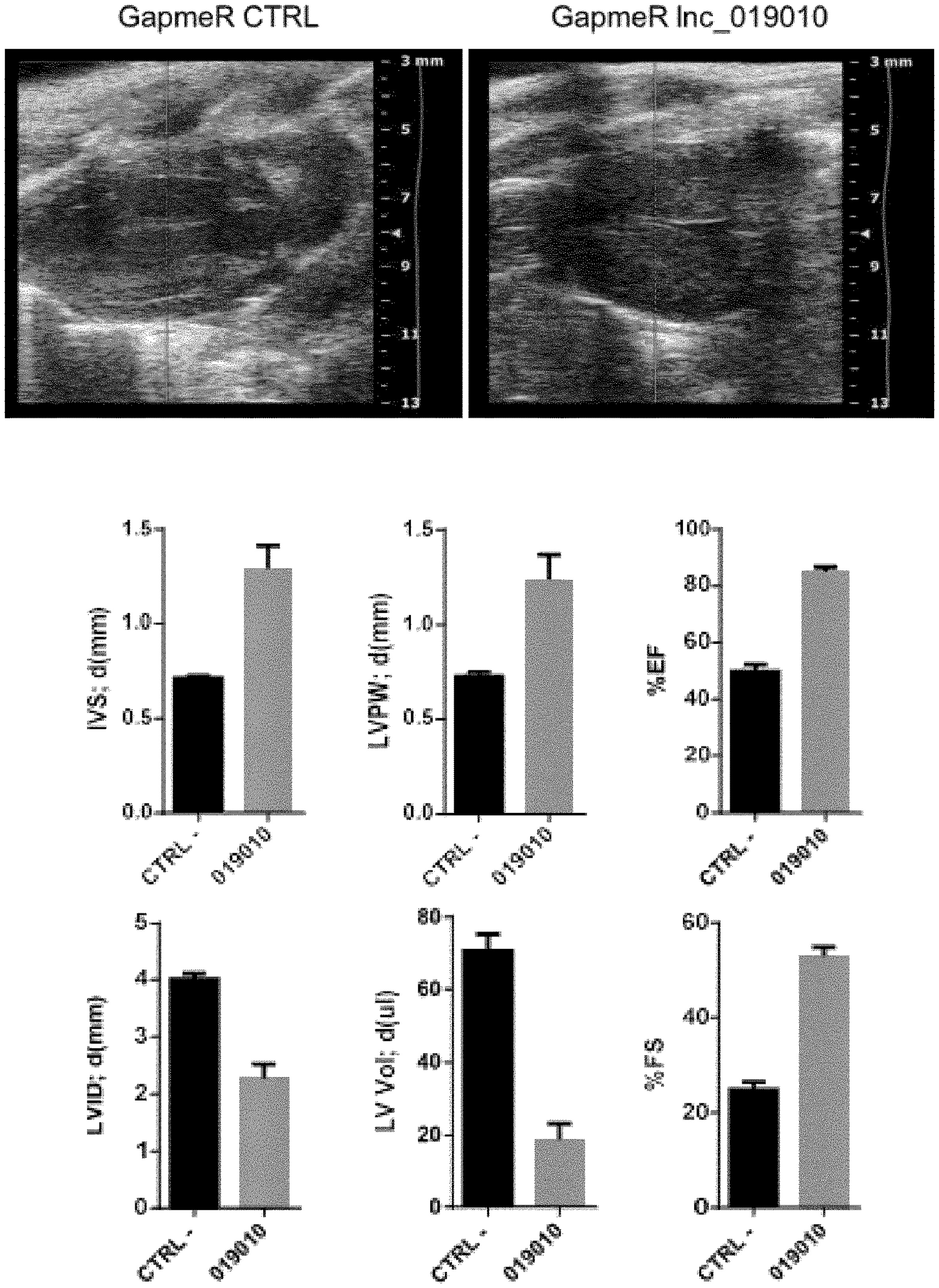
FIG. 5A shows the validation of expression via quantitative RT-PCR of novel lncRNAs in the border and remote zones of infracted hearts one and seven days post myocardial infarction.
Figure 5B:
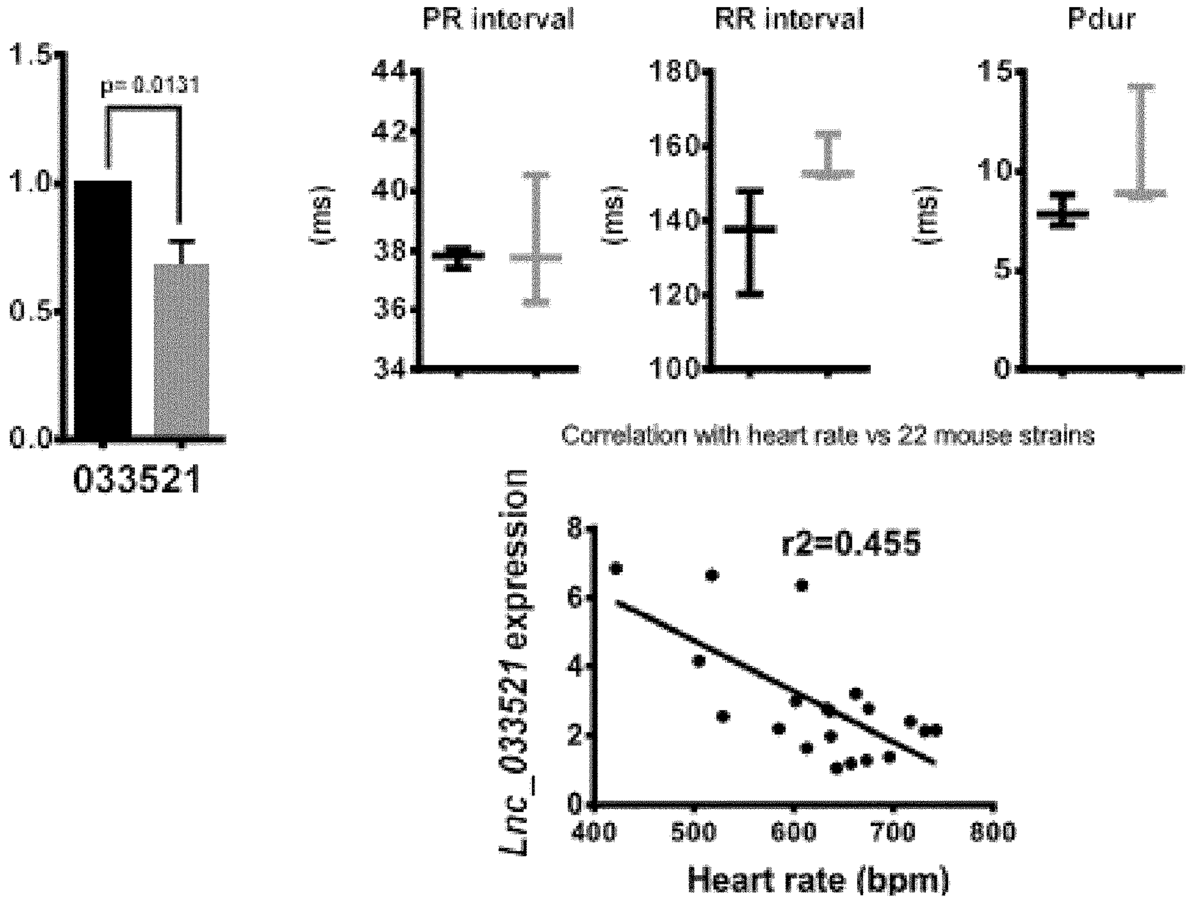
FIG. 5B shows lnc-033521 losss-of-function impact on cardiac conduction parameters as assessed by electrocardiogram in vivo.

LncRNAs Downregulation In Vivo 12 weeks old BL6/C7 mice received one intraperitoneal injection of GapmeR (20 mg/kg). Echocardiographic images (long view axis) of mouse hearts 4 days after GapmeR injection are shown in FIG. 5A. Left panel, heart of a mouse injected with control (scrambled) GapmeR. Right panel, heart of a mouse injected with GapmeR directed against lnc_019010. Bar graph shows a significant increase in IVS (intra ventricular septum) and LVPW (left ventricular posterior wall) thickness, and a significant decrease of LVID (left ventricle internal diameter) and LV vol (left ventricle volume) in mice injected with GapmeR targeting lnc_019010 (SEQ ID No. 148: 5'-AGGTGTGCGATAGAG-3') (grey bars) compared to control (scrambled) GapmeR (black bars). These data show that lnc_019010 depletion in the heart in vivo induced a significant increase of heart mass. Ejection fraction (EF) and fraction of shortening (FS) are increased in mice receiving GapmeR directed against lnc_019010, indicating that cardiac function is increased in this case.

RNA was obtained from the heart of mice injected with GapmeR directed against lnc_033521 or control (scrambled) GapmeR. The graph depicted in FIG. 8B, on the left, shows the downregulation of lnc_033521 expression in mice injected with GapmeR targeting lnc_033521 (grey bar) compare to mice injected with control (scrambled) GapmeR (black bar). Upper panels, electrocardiographic parameters showing the effect of lnc_033521 downregulation on cardiac electrophysiology. Heart rate is reduced following downregulation of lnc_033521. Lower panels, correlation between lnc_033521 expression and electrocardiographic measurements of heart rate (left) and P wave area (right) as measured in 22 different mouse strains. These data show that lnc_33521 plays a role in the regulation of important cardiac electrophysiological parameters.

REFERENCES

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nature protocols 7, 562-578.

Ounzain S, Crippa S, Pedrazzini T. (2013) Small and long non-coding RNAs in cardiac homeostasis and regeneration. Biochim Biophys Acta. 1833(4):923-33

Mouse, E. C., Stamatoyannopoulos, J. A., Snyder, M., Hardison, R., Ren, B., Gingeras, T., Gilbert, D. M., Groudine, M., Bender, M., Kaul, R., et al. (2012). An encyclopedia of mouse DNA elements (Mouse ENCODE). Genome biology 13, 418.

Wamstad, J. A., Alexander, J. M., Truty, R. M., Shrikumar, A., Li, F., Eilertson, K. E., Ding, H., Wylie, J. N., Pico, A. R., Capra, J. A., et al. (2012). Dynamic and coordinated epigenetic regulation of developmental transitions in the cardiac lineage. Cell 151, 206-220.

Bruneau, B. G. (2002). Transcriptional regulation of vertebrate cardiac morphogenesis. Circulation research 90, 509-519.

Huang, J., Elicker, J., Bowens, N., Liu, X., Cheng, L., Cappola, T. P., Zhu, X., and Parmacek, M. S. (2012). Myocardin regulates BMP10 expression and is required for heart development. The Journal of clinical investigation 122, 3678-3691.

Kurreck J, Wyszko E, Gillen C, Erdmann V A. (2002) Design of antisense oligonucleotides stabilized by locked nucleic acids. Nucleic Acids Res.;30(9):1911-8.

Sambrook, et al., Molecular Cloning: A Laboratory Manual (3rd Edition, 2001)

Innis et al., eds., PCR Protocols: A Guide To Methods And Applications, Academic Press Inc., San Diego, Calif. (1990).

Froehler et al., (1986) Nucleic Acid Res. 14:5399-5407

McBride et al., (1983) Tetrahedron Lett. 24:246-248

Ounzain S, Pezzuto I, Micheletti R, Burdet F, Sheta R, Nemir M, Gonzales C, Sarre A, Alexanian M, Blow M J, May D, Johnson R, Dauvillier J, Pennacchio L A, Pedrazzini T. (2014) Functional importance of cardiac enhancer-associated noncoding RNAs in heart development and disease. J Mol Cell Cardiol. November; 76:55-70.

The invention claimed is:

1. A composition comprising a modulator of one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, wherein the modulator is modified antisense GapmeR oligonucleotide which selectively targets said one or more cardiac-specific lncRNAs.

2. A method for modulating one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, comprising administering an effective amount of a modulator to a subject in need thereof, wherein the modulator is a modified antisense GapmeR oligonucleotide which selectively targets said one or more cardiac-specific lncRNAs.

3. The method of claim 2, wherein the modulator modulates cardiac fibrosis, myopathy, hypertrophy, apoptosis, inflammation, extracellular remodeling, cardiac regeneration, CM and CF cell cycle and activation of endogenous CPCs, direct reprogramming of CF, ECs, in vitro reprogramming and differentiation of cells, cardiac epigenomic targeting of ubiquitous chromatin remodeling complexes, cardiac physiology, electrophysiology and/or heart rate.

4. A pharmaceutical composition comprising an effective amount of a modulator of one or more cardiac-specific lncRNAs selected from the group consisting of SEQ ID No 18, SEQ ID No 26, SEQ ID No 27, SEQ ID No 28, SEQ ID No 29, SEQ ID No 30, SEQ ID No 33, SEQ ID No 48, SEQ ID No 62 and SEQ ID No 64, wherein the modulator is a modified antisense GapmeR oligonucleotide which selectively targets said one or more cardiac-specific lncRNAs, optionally in combination with pharmaceutically acceptable carriers, diluents and/or adjuvants.

5. A kit comprising the composition of claim 1.

6. The composition of claim 1, wherein the modulator is selected from the group consisting of a) a modified antisense GapmeR oligonucleotide comprising a sequence as set forth in SEQ ID No. 148 which modulates a lncRNA having a sequence as set forth in SEQ ID No. 33; and b) a modified antisense GapmeR oligonucleotide comprising a sequence as set forth in SEQ ID No. 147 which modulates a lncRNA having a sequence as set forth in SEQ ID No. 62.

7. The method of claim 2, wherein the modulator is selected from the group consisting of a) a modified antisense GapmeR oligonucleotide comprising a sequence as set forth in SEQ ID No. 148 which modulates a lncRNA having a sequence as set forth in SEQ ID No. 33; and b) a modified antisense GapmeR oligonucleotide comprising a sequence as set forth in SEQ ID No. 147 which modulates a lncRNA having a sequence as set forth in SEQ ID No. 62.

8. The pharmaceutical composition of claim 4, wherein the modulator is selected from the group consisting of a) a modified antisense GapmeR oligonucleotide comprising a sequence as set forth in SEQ ID No. 148 which modulates a lncRNA having a sequence as set forth in SEQ ID No. 33; and b) a modified antisense GapmeR oligonucleotide comprising a sequence as set forth in SEQ ID No. 147 which modulates a lncRNA having a sequence as set forth in SEQ ID No. 62.

9. The kit of claim 5, wherein the modulator is selected from the group consisting of a) a modified antisense GapmeR oligonucleotide comprising a sequence as set forth in SEQ ID No. 148 which modulates a lncRNA having a sequence as set forth in SEQ ID No. 33; and b) a modified antisense GapmeR oligonucleotide comprising a sequence as set forth in SEQ ID No. 147 which modulates a lncRNA having a sequence as set forth in SEQ ID No. 62.

* * * * *

SEQUENCE LISTING

```
<160> NUMBER OF SEQ ID NOS: 148

<210> SEQ ID NO 1
<211> LENGTH: 540
<212> TYPE: DNA
<213> ORGANISM: Homo sapiens

<400> SEQUENCE: 1

aataaagcaa accttgaata tattcagcta ggaaataaac cttgaaatta tatggttacc     60

aataacagta aatagagttt caacaaataa ctctgctaaa cattttgttt ttgttaatca    120

cccatgcgtg gcaacatata ttattctttc ttttaggtaa cgcagttgaa ggaccagaac    180

gcattcctaa acaacacctc ccttcggtgt aagttgcagc atctgtgact tagagaacct    240

acagttagaa ttctgttttc cagatattat agttttagtg gaatgcctgt aatcattatt    300

attttttttta gacaaagtag ggaaattgcc ctagtagaaa atgtaattca atataggcaa    360

aatagaatta caaccatttg atcatgtcta tgataaatcc agcattgcaa taaacatttc    420

taggattttc tatttctatc tgcttgcttc ttgtttagac atcttaaaat gcttgttagt    480

gttaagtgat tgcagtgcca ataccgtaag agaaatttat gagaaaaaaa attgagaaaa    540


<210> SEQ ID NO 2
<211> LENGTH: 614
<212> TYPE: DNA
<213> ORGANISM: Homo sapiens
```

<400> SEQUENCE: 2
cttttctata attactgttc tgttttttct gacaggctat caaatattgg ctgccttaag 60
ctctctgtga actgagttat tctcaataat actctgtatt atgaaggcat tatttgagtg 120
gctgtccact gtgatctggt tatttggagc tttacataaa acaggctctt gctatatggt 180
tatgccaaaa ggctttgcaa tagttgtatt tgtttggctc tgtgagatga cccaggcacc 240
ccgattccaa gggccactta ctttgagtgg acatgaggct gatgcccaga accaaagagg 300
aagcagcctc tgatccatga tcctatagtc acagtgctgc tcaatcgtgc cgtttctgct 360
gacccaaatg cctggagttg accctgtttg tctctccaaa cctctttctt gacttagatg 420
atgctttgaa cttgatctgt tgtactatga ctgtaattcc aagagcacag gctttcccgt 480
catgtagagc aatatcaatc ctgcctcaat cgtttgttac cttttgattc tgtgggtttc 540
agtttcttca tctgtcaaag gagaatacac tggcagagct cctttagaaa gcctggttct 600
gtatcatgga cact 614

<210> SEQ ID NO 3
<211> LENGTH: 2884
<212> TYPE: DNA
<213> ORGANISM: Homo sapiens

<400> SEQUENCE: 3
gaaatgctat agttgtaaaa tttaaaatca aatcagagtc cagattttca aaaactgaaa 60
taataagtta aaatgaaaag gtaatggtga tgactataaa ccttgtactt gggaatttta 120
aaatatatca ggatgggagg gtctagtttc acagcctggg ggtttgagtt gtctgcaaag 180
gctcagaatg agctcacaga gagctgttgt gccaagagtg tggctcgccc tccaactgaa 240
gtgttcatct aggatccaga gcacagggca gattccctca agctctgtat ggtcagagct 300
ctgggagcaa gcatcagttt atcccaggac tggttaatgg agcccatcca gaggaagacc 360
gagatgccat ccagggatct gggagtttaa gctggacaag agaagacttg gaggggcctg 420
ataataactg taatacgcgt tgatcattat gtacaaacta tgcctaaacc tggtttcttc 480
caacaataac cgtttgttca cagttctgca gttgggccag ggagctttcc tctgtatggt 540
gtgggctcct atagatctgg ggccagctgg acatctatgg cccatccctt ctcatgttct 600
ttcattcttc tccacaggcc tctcatactc agggaggcag cctagacatg acttctcaag 660
gcagcaagac agtgaaagtg gctgctacag ggctctaaaa gcccgggctc agaatttctg 720
ttgctttcca ctggactgag aaactcacaa gagcagccaa agaagaatgt agaaactgcc 780
aacaaccaca tgactgagct tgcaagcaga tccttcccca gtagccttca gatgacacca 840
gccccagcca gcaggttatg caactgagac catgaggcag aactgccaac taagccccag 900
attcttaacc cacagaactg tgagatcata tttgttgttt taagttgctt agtttaagaa 960
taatttgtag tgattcgtta catagcaaca gaaaaaaaca ctgggttttt ttcttggctt 1020 ttttttttt tctaggcaaa caagaaatcc ctgcatccac atagctagcc aacaaggcct 1080
tgtcctaagg ggtgaaactg gtgaatcaga ataaagaaag cttcccagga ggcctggggc 1140
aagtggcaca agacttagtg atctttccag gcctaaggga gagaattccg tgggctgcta 1200
gaatacacca gcttccttta tagaagttgt ggccagtgca aatgttaacc aaacgtaatg 1260
tatgagcctt ataacaccaa atggaggttc ctctggctgt tctgtaactt aaggggagta 1320
agttgacttc ccatgactct ggcttcccag ttgggatggt tccatatgat gttttcagaa 1380

```
gtaatggtgg aaccttcact cactatgtcc tccccatctg ctcaccccta tattggtcca   1440
gccctgtctg ccccacacac acctccaaat tttgaaaaaa agcatcctac aaatgcataa   1500
gaacatggtc acacgtgctc tttctgacac acttagtcat tggtgggtcc agagctgcag   1560
ggtccttaat gctcatctat gtgccctaag ttgagctctc ttgctgcaga aaacctgtgg   1620
ctagaagcaa aagcttccta aaatcagcta aactaggtaa cgcttttttc ttgaccttga   1680
agtggagact cagagccttt gggaaccttc tgttttaaat atccaacagg aatactgctt   1740
taccatcctt tcagcggggg gacgggacca gacacaccag agaggtagca cccattggac   1800
ctcttaggcc aggtggagac agtgagagct gctaggcatt cctcagcgat gccagtatgc   1860
ttactataca aaacagtgct gagttaattt cacacagctg gggaggactg gaggtgcttt   1920
tggggcctat tgtgtgtgag ccagcaaact catctctcca gctgttcctt ggtagaagta   1980
gaagtagaag aaaacgaaga agttggagcc agaagtcagt ttctgccaac gggaacaatg   2040
ggtgcaattg tgcatctcac atagcagcaa ggagtattaa acagaagtac acactgttac   2100
tacatgagaa ccttgccatg ggaacttccg gatgtacttt tttggaatcc aggggatcta   2160
ggaagaccag tcagggagtg gccagttctt ggatgacctc tccaagcaag agaaaacata   2220
aatgtgtact ttaggagttt caaaagcaat gaagatcttt cttagtgcaa agccctgttt   2280
tccccttaat attaaagata gtcttggtct tatttctggg aagtttccaa ggacagaggc   2340
taaactgtga ccaaactcac aggaaagaga ccctcagagc tgggaaatga tcacttcaaa   2400
tggtttcttg cctgccttga actgcgttca agtgagggac ttctccaaag gaagacgcag   2460
gtggaatccc aaaggcaatg tggtgtgcct cagtctcttg agctgttcac ctcagaagag   2520
tgtttcatct tctcggcaat ggagatgaca cctacctcat ggatttgcag tgaaatttta   2580
acaagagtat gaataaggtt taaacactga aaaaacatct ctgagttgca tttagttgtg   2640
ccggacccac cacattaaca acctaagaga gctctgcccc gtgccccatg ccacacgagc   2700
cctcatcctg ggcctacctg gctggctgga tatggggaca tctcaggtgg cagagcaatt   2760
tgcccagggt ctgcccccag cagtagagtg atgcggagat tttattccct cctcttcctt   2820
ccctctctcc tcaagtgtgg tgcgtgctcc atttctcacg tggccatgtg caagccagga   2880
agaa                                                                2884
```

<210> SEQ ID NO 4
<211> LENGTH: 1851
<212> TYPE: DNA
<213> ORGANISM: Homo sapiens

<400> SEQUENCE: 4

```
cagagggatt agttgtaatt gctaagttct tttgagtaca tttaaccaag tagcagagca     60
cattcttcca tgaattcaga agcctgttaa aacagctgtc taatggggta aaatacactt    120
tctgttgttt ggttgaaaga caagacttca aataaatact aaaatcaggg ttggtcaatt    180
ttcaccagga gcccaggcac ctagggaatc ttgttctttt tcttctgcct ggagttactt    240
cactggaatt gtgagaaaaa ctgatatgat gcaaacacta gtgatctgaa gacttgggtt    300
caaaccattc tttttcgtct tgcaaagtat aagcgtgtgt gtatgccgta atatagggaa    360
aaggtggctc atgtataaaa tcataacaag aatttctatc caaaagtttc ttgggagtat    420
taaaataatt atctgtgaaa tccttagccc attggatatc acatattcag ccctcaataa    480
aggtagttga tgtcaagtca actttcaggt tactttctgc ttattatact gtcactgaag    540
ctagaaaggg acaggatcat gcactcttgt tgactggaac atggctatgg agagcctctc    600
```

attgttcttt gttccatggc aaatagagca atgcctttct attttcccag tgaacattat 660
atataaatat attttaaaaa tcaatctagg ttctctctat tgcaccttct tgtcactgaa 720
gtgttgaata actgttggag tcttggctaa gcaggagcaa tatttgatgg aatctgacat 780
tgctttaata ttctgggttc atacacatat gcagcagaag tacctggatt gcccatttca 840
aggtactctg tggattttta aactttcgtg acagtgtaat aagagaaatt taatctaaat 900
tgacttgaca ttcaaaacca gacatttctg tgctctaaaa taattctatt tgtttctggg 960
cactgttttc aatctctaaa ttataaaagc cctttagctc actggctcat tcttaacctg 1020
attgctgtga cttcgatctg tctcctacat cgtgtccact ttcttcacct ctttttctgt 1080
gggtctcact ctcctgcctc cttactctgt tcatgacgtg ctttaacatg tgtgaatgag 1140
tgacataagc atatgactac accatttatg ttgagttcac agccatttat atcattaagt 1200
agatgataca gagaaaaaga aacacattta attttaatca ggccactata catgatgaat 1260
caagtgcttc agcagtcata agaaactgct cactaaaact ttgattatga tttaatgatt 1320
aaatagagat ttgctatggg ggacagattg ttcatttggt ctttctttaa agactgattt 1380
atactcatct aagtaaataa actattcctg ctctgtgctc tcagacagtc ttttatagcc 1440
aagatgcctg cattccccac agcttagaca ggtttcttcc tgactttagg cttctggtct 1500
cccttttgtt agagcatttg ctttagaaaa cttgtcactg taaattcctc tatccctttg 1560
agatgtaaat ctcccaacct cttgtctgaa tttctggctc caggactact gcctctgtct 1620
cccagtcgct gtgggagaat aggaggagcc taactttgat aagcaaatgc agctggtcta 1680
agcctattgg ccagcctccc cgcaagcctt cctccaagga cgaaagtgtc ttcctttcct 1740
gtttaactct gtcgtgcagt ttttatatgc ggtcttagtg atgaaggttg ttcctgactg 1800
tgagtctatc tgtctcactt cactgtgagt cctgaggtct gggaataggg a 1851

<210> SEQ ID NO 5
<211> LENGTH: 2627
<212> TYPE: DNA
<213> ORGANISM: Homo sapiens

<400> SEQUENCE: 5
gtttgggaag agacaggcta tgagcatgac atgcaggctg tgggggctgc cattcctgtc 60
tcagctcctc cttcttgagt tttgagcagg caaaattgcc tctgtctaat aacacccccc 120
actacttttc tctttctttc tttcattctc ctcctgcccc ctgtatgaca aaataggcaa 180
aatgagtaat cagagggtga gatggagaaa aagaactata gttggagatt ttggacggtc 240
tcttttaggt gggagaaggt aggatagtgg aaacatgatt gcaaagaaga agccatataa 300
ttttttccct ttgactttaa gtcctaagat gggcaggctg gaggcctggg tgaggagagg 360
ctgggagggg acaacgcaag tggtagagct gtctggagag gttttctttg tgaaaaaggc 420
agctgaagtc tcgaaagtga tctggactga gaatcgggag aagtggattc agttcatact 480
cagccacttt ttatgtgacc ttgggactag actattgatg cccagtttct ttatttgtaa 540
agaaaacact gtactttttc ttctgcttta aaatgactgt tagaagttat gaaaattgaa 600
aacagttcac aaaagcccag taacttgctt tcttcatcat tctaagagag aaaagttaag 660
cgaactctcc agttcattgt taaaaaacaa aagaaaagaa aagaaaaagg catcttttct 720
ctttgagaaa caccaaaatt actctgcccc taatagtcgc ctgggcagaa ttttccatct 780
tagcacaaag cagctcgacc ttgtttcaac taatcccttc tctgtattta acaagaggaa 840

```
ctggaagagt cagacagtgt gtgggaagac tgaagaaaat aaggaaggta tagaaactac    900

tagagatgga gataagttaa acattctggc aaattgtcat ggtgtattgc tcatgctgaa    960

ggttaggcag ttgggaaggt agttaagaga atggctttaa atgcttcatc taattgcaag   1020

cagctgttga ttagtggagc ttgaccaact gtttttaatt cagtggtgat gaagagaatg   1080

agacttttaa gggaaactgg cacggttgtg tatacgcatg gagttgctta cactttttct   1140

ggaggtcata gagtgcagta actactaaga gatgttctct gaaaccattg caggctttca   1200

tgataatgac tttcctaaat tttaccagca tttgttgggt ttggcaggag gcaaacttct   1260

ccgttatcca aattctggaa tgattttagg gactgattca tcaatcgcga ggtcttgtgc   1320

caattcagaa gcaactgttc agtggaagca gtaaatctag aatgagagct gataatgcca   1380

ttttagagtc ttcttggaac atttaatttt ttgaaacata ccacttacct gaaacaactg   1440

tcaggttggg tagagaacgt aagtgtctta tgagagttct aggtagagtg ctctgggact   1500

tcaaagaaaa aaagatgcct acctttaaga caaaagtagt aaaattcaaa tgctaaataa   1560

aatgctcagc tccactaatg gaatttttgc gcatgaaaaa aagcaagcta taaaggttaa   1620

gataaccaga ctggctgtat ttctgtccct gctgctgtgg gtggcagaga aagacaaatc   1680

ctaaaaaggt tttcttccca gttagtgttg ggccaggata agacctgttt atgtcaatga   1740

aataactttt taagcagaag atttcagagc caagagaaga acttgcagtc aagacaatct   1800

gccacagtgt gaacgatcca tctgaggaca attgggctga ttgtgcaagc tgatgaagga   1860

acatggcatc ctctggaaac agggaacaac tgtcaatgtt gaaaatgtgt ggaacataag   1920

gaaagcatgc caacttttgg tttcaagata ttgctcaatc agaaatccgg aatttcaaca   1980

catctgaaag taaggcggag ggactctagc agtctgatct ttacgaacta aagactcagc   2040

aaaattccca ctcaatggaa gtgcaaaagt ctctgcagac ttttaaaaaa tgccaatccc   2100

atcagatggg caaacacaaa acaacaaaaa ccctaacacc taacaatacc agagatgata   2160

cggagcaatt ataactcaaa tacattctgg cgggaggcta aatatgtaca acaccttgga   2220

actgtttggc accatctccc caagatgagt ctgtggccca gcaattccac tcctacttta   2280

tacccaagag aaacaaatgc atatgtgcat caaagacata caaaaatgtt cccagcagta   2340

ctattcacac tagccccaaa ctggaaacaa ctcaaatggc catcaacaga ggaatgaata   2400

aaaattgcag tgtattttac agtgaacaaa ctatgacaaa ctacaacatg gatgaatctg   2460

aatcccacaa acagaatgtt gagtgaaata agccagacac cgaataatac atagattaat   2520

gtgccatttc tataaaactt aaaaacaggc aaaactaata catgatttta gaagctgggg   2580

taatgtttcc tttgcagcga ggtagtgagt gggaagggcc atgagag                2627
```

<210> SEQ ID NO 6
<211> LENGTH: 915
<212> TYPE: DNA
<213> ORGANISM: Homo sapiens

<400> SEQUENCE: 6

```
ctcttcctcc tcctcctcct ccccggcaga gctgtaggcc tcacagtggt gacgcggggt     60

catccggggg cccgttacca cctcattctc ataggcgcgc ggaggcggtg cgcgcgggac    120

gactcggcca actgaggagg gagaaagggg aagcggatcg gcgggcgctg gcgctcgagc    180

gggacgcacg gctgcggccg ctgggtcggt cagcgaatta gttccatgat gaccccccggc   240

ctgaggccgc cgccgctcga gcccgggttg ggagggggct ccctctcgcc atagggcggc    300

gggggccggg gagaggcggg gggtgagacc ggctctgccc ctgcccgggg aaagcgcctc    360
```

-continued

```
cgaggggaaa tggtgaaagg gggggagggg agaaaagaaa agaaaagaaa ggggaaaggg    420

gggaaaaata agaaaaagcg agacagaggc gctgccgcgt ccgctcgcgg ggaaggctgg    480

ggagggaggg gaggaggaag aagtgccggc ttcctggctc cgccctcgcg gaccgatttc    540

gcccactcct tgtaaactac gcggacgtct ttcacccttc ctgttcctcc ccgccgcctt    600

cccggtccaa cgaaagtaca gagaagtgcg gccgaaagga gacgggctgg ggaagtcgtt    660

ggcactagga tggaaggagg gaggacgttt tctgtggcta agaaaagccg aagtcttgag    720

actgtagcat ttctgcataa tctattgtaa cataaccatt gttagaccat gaaattgctt    780

ctgattttca ctccaataag aaaattgaag tgtcttctga acacttgagg ataaggtaag    840

gtaaagacaa aaacataatg gtggagaaat atggtgagag gaaccaatct ttatggggca    900

gaaacttccc tcctc                                                     915
```

<210> SEQ ID NO 7
<211> LENGTH: 1001
<212> TYPE: DNA
<213> ORGANISM: Homo sapiens

<400> SEQUENCE: 7

```
gcaggagtct gtagtgccct gaagaatcca agccgtcaca ccagtgattc gaacatttca     60

gagaaacaca acggagggaa ggagcagtgg cttccccggt gggctagggc gtgtcacagg    120

tgtgaaaaat aaattcaaac tcaaattaac tggctatgta tctttgttac aagggctcag    180

tcaggaagaa caaaggttcc tgttggctaa agtgtgtcct gaaaattatc ttcaatcctg    240

catgtactcc tcgtgttcaa agatgagctc acaggaggca actacctgca gggggcagga    300

catccaggga cctccagtgt gggtactggg ctctcatatc tctggcagtg tgtgcctctc    360

ctcaatttct cctttccttc tggaccacct acagacacag cccactgcca gagacgccca    420

gatataaaca caggtgcaaa acacatctgc attactggat ggcagcacgg ccatatggtt    480

ggagtaacag taataccata tccctgctgt agaaccagct ttatttacaa ttttcttatt    540

aaaatatgca aatagcaagt aaatagaaaa ccacagagct ctgttttgct gtaaaattga    600

ttggagacgt ttgactattt taaggacttt tgatatacag atctgaagcc aacataaaag    660

aagatggtta agtccactta aaggcatttg ctaggagcac accatagtac gattaaggtt    720

aaaacaaaag gatgtaaggg gcttccttaa ctaataggtc caatccagga attgctaaaa    780

cagagttgaa acttgcagtc ctgcagaatt tcaaattgtc ctgtaatcct aacagcaaag    840

catggcaatg ctggtggtat ttggtgaaac atctcaatcg tccatttatt gtcaagatgt    900

atcaaatttt gctgattttg tgtctttaag tggccactca gcatattttg aactagacaa    960

ctggacacag gcatctcctc caactctgat gtacattctt a                       1001
```

<210> SEQ ID NO 8
<211> LENGTH: 1203
<212> TYPE: DNA
<213> ORGANISM: Homo sapiens

<400> SEQUENCE: 8

```
ctgctgcaaa atggctgtgg tctgcaaggc tgggaacagt tttgtgggtt tgcagtgata     60

tttgaagttt gatgaatgaa tacaaaatgc atcactggta taatctaaat gatgtgacat    120

aatttatgct ccaactgtta aactccaata aatcccagcc aatgacagga aaatcccaga    180

tgttggccat tctggaaact atcaagccta taacttgata ttaatgcctg atgaatagca    240
```

```
taaagcagca gcattttcca tatgtgtact tagagtaaag ttaatgtaat aaacataatt    300
gcactcatat agcttagtat aagcaattat cactaattac tggtagagtt tctctctctt    360
ttctaatgaa gagtacagtg gaaggatagt ttatctctag atactaattt aatttaaacg    420
ttaataggaa tagttgtttc tgcctaaaag atttgatgaa ttttcattgc atctaactca    480
attccagcaa tgtctttatc cagcctttct tagtctgtca cttggaggat gttctatcct    540
gtcctactgt ccataagacc aagcagctcg gaggactccc ataatcagtg aaaagcacct    600
tgcaccattc tgggaagcag tgggactcag cttctgtgga ttttaaatca gtcagtattt    660
cggagcatcg gtgatcagag gtgtctccta tgtttgtatt cctataagca tccaacacaa    720
tggccagtag gtagttaatg ctgattaaat gtttactgag agaagagaca atgcaggtat    780
ttatgtatat ttgggtttgg gtcattgttt tcttctcttt ttttcctttc tacacatagg    840
ataaagagtc tgtaatacac gactagaata atttgatact taaaaaatgg ttgaaaacaa    900
tgacacatta aactatctac tgtgcaaacc ttcaccacca aagccacctc tggccacagt    960
gcaggactgt tagaagttga ggggaccttt aatttctgcc agaagcccca agtggttgac   1020
aattatatca tttctctatc tcttaatctt aactgatttc ctgtttgtgg acaaaagaaa   1080
gccatgttac agtttgttca gaaaccaaga tggaagcctt ttaattctgt cttcattggt   1140
gaagctattt attgctgtgt tttgtgcttt gaaaaagttg aataaagata caaatacaga   1200
gca                                                                 1203
```

<210> SEQ ID NO 9
<211> LENGTH: 1029
<212> TYPE: DNA
<213> ORGANISM: Homo sapiens

<400> SEQUENCE: 9

```
cacaacaatc ccatgaggta attgctacta tcttcacttt atagatggga aaacaggttc     60
agagatgtgc ggagggctca caggtaatac acagtgcact gcacctacag gatcctgctt    120
gaatagccag tcagaaaggg agaagcaagg aaacggctgg ctgtgtagac agaggaggga    180
tgggcaaaga agaaaagcca gggagaaaat caagacttca gagggaaagg aggcatgtgt    240
tgggtcagag gtcaaaagac tcagcatcac tctccagtgt gggaaggtgg ggcacagaaa    300
cacaggaggc caagtagatc acgcctctgc tcaggtctga gtgtcagagc tggagccaat    360
ccatacccct gagtagtctg tgaaggctgc cagagacatg tacagttacc cgcctggaag    420
ggcatgcaag tgcctcgata tgggccaggt tctgggactg aacacaggga gcagcctgac    480
ctctaacccc cagactcctg ggggagctgg aagagggcct agtacaggat gttggcgtta    540
gaagtgactg agaggaggtg tatgcaggga tcccttctga gccatccacc aagtcatgtc    600
agtgagttag caacactatg gagttcctgg gccccagacc aggtgctgga gagtggagga    660
acccagtgat actacatgca gacagtagcc ccttggagat gagggccgag tggggggaag    720
gggagaggag agatggagct ggatggccag aaattggtgg gtgagagggt gttcaaggaa    780
ggatggatga gcacaatttc cgaacagcaa acatttcact gctgggtgct gagaatacag    840
gagtagacat ccaatcctca aagagcttcc cgtgtactgg ggaaacagaa gcagttacaa    900
tagagcatga tgaattgtaa gggatatcca gaagtgacag gggagatttc taggaaatga    960
catgtagtat aaattgagtc ctgcaagatg aacaaacatt agccaggtga agggtcaggg   1020
aatagcaga                                                           1029
```

<210> SEQ ID NO 10
<211> LENGTH: 1948
<212> TYPE: DNA
<213> ORGANISM: Homo sapiens

<400> SEQUENCE: 10
ggaaattatt tcagcgcatg tttttcttca actcaaggct tttatgaaga aaacatttct 60
taaagctgtt attaaggtat tcaagctgga actcagacga ttctaaaaca ctcctctata 120
ttcttcctca tctaatgtct ttggaagaat tgttagggtc ctggaaaaag aaaaccaaca 180
gatcaggtgg ttgaatatgg cttcctggtg gggcaggagg catctggcag tgcacaaaag 240
ggcaaagctt ccagagagta gcaagtcact gaagaaattc tgttatagag aaaaactgtg 300
tgtgtgtcac atacatacac atatatcttc aaattaggtc atttatgaaa aaatggagaa 360
aaatgcttct ataagatatt cacactgtta actagttttc aaaagttcat caagcttact 420
ctccttttct ttgaatactt ttggaagaga cacaattttc caagccaaaa cacagttcag 480
gcaatagaat agatgaaatt tttacaaaca ggatgaaagc ctggcacata agacactcaa 540
tatgtattga aatatctttg gcgaaataaa actataatgc tctttgcgat atggttttct 600
ctcttaacaa tatattttgg gcctcaccta ttagttacta gaaatcggta gcatcattgt 660
taatcgctgc tttgtattac cttgtagggg tgcactttag gtgcatccaa tttattttct 720
gtcacgacca aagccacaaa gaacatcatt ttgtgttact tttgacatga gtgtaagtcc 780
tgtaggataa acaactacga gggaaaagac tgggtcaaag ggaatttcag gataatccac 840
ttcttcaaaa actttaagtg ggaagtgaga ataagatcag gaactcttct gccttgtcct 900
tttattccaa ctctctactc aacagggctt caccaactgt gttagtttga gcaaatctaa 960
gagcagaccc aggcacaagt gccagtagcg gcaggagatc tgcaggccta caagtagggg 1020
tgtgcagatg agacaggtaa gaaagggtgt tatcatgcca cttctcactg tggacagctg 1080
ggactaatct tgctgggaaa caatgtagta cacacccaga gttaccccag ctgtgggaca 1140
cggaagctat ggtattcatt cacatggcca tatcgaattg ttggatgaga actgaatcag 1200
gggcatcagg tatctgctct tccgcttgtc ccggggagag gtcaagtgct tctgcagctg 1260
gcagagagct gcagtgttgg aaaatcacct ctgctggtag gggtgagtgc agagaggatg 1320
gcagggctac ttagtgatag aaatcagaag tctactctag ataacacatg ccaattttta 1380
gctgcccaga atatcccccct tctttggggg agacttcttt attctgcatg tctttgagag 1440
agagagcccc cttgccaaag cttatactct gcctgctgca tgaggccagg cagtggcaca 1500
aagattcagg tacagtcagt gactatttat ggtggcagta gccaagttca aagtccagca 1560
gcagcacggt gagtgttggg aacagcagaa caggcaacat gtcataataa aatggaattt 1620
gtgttctgga aaatcaaata aaggaaatct ctcacccaca cattacaaaa ggcaaaaaat 1680
atccacaaca accaaaagca aatactaaat ataatgagta caagataaga taataagtag 1740
gtctgggagg tctgataaat aaataacagg agatccttaa ggcaaaagat aactttaaat 1800
gtagaaaaat ttacatttta agaactaaat ggctgcaaat caaattccaa actgcacaaa 1860
aagccccaaa ctcgtcatct cctggtgaaa tttcttaaat ctgagattaa agagaaagtt 1920
caacactttt ccagggagaa agtttact 1948

<210> SEQ ID NO 11
<211> LENGTH: 1075
<212> TYPE: DNA
<213> ORGANISM: Homo sapiens

<400> SEQUENCE: 11

```
tttattaata actgttttct cacttatatg cttatatgta caacctgagt taaaataggt      60
gcttcctatg aaaacacagc ttcatgaccc ctccaaccag agaaattccc ccacctccca     120
agctaaacgc attctcttcc tctgggggtg ttgcctgatg gaggggctaa agggagatgc     180
tgcagggggg gttattgttg atgtcctgca cagagggtgg ggaagcttct cagtgtcact     240
agccaggtgt ggcacattgt catctaggca gccaaggaga cgccaatgct tggagagcta     300
gtttccaggc tgagacttcc aggcactcag aggaaaatgt ctgggctaga ccccgggtgg     360
gcaggatgaa gccttctgcc acttcttccc aggcaatctc tggtgaggct gggatcaaag     420
actgttgcgc cacttttaca cataacagac acactttatg tgtttgtgat tattgccttt     480
caaactccct ccccattttc ccaaatatct aaagtcaaaa tggccttttg gagaagaggg     540
tggggagtaa ggcctccacc agctgttatc tggcctctgg aaaaatcctc tacattggag     600
tgcattgagg gaatacctgg tttctgtccc tactgccttt gaataaatga agaaacagaa     660
acacaagcga atgaagttac ttagagcccc agaaccttag agctgaacga gaccttccaa     720
ataccttgtc ccagtctcct cgttttacag gtgagaagac acctaagaga ttaaatggca     780
tgtccaaggt caccaggcta ttagtggtat agatggaacc taactcttca gactgctggt     840
cagatgttct ttccacttta acactgcagt gcaaaggtca aacacaacct ggactctgta     900
aaccaccaca gtccatcacc aacatttatt gaacatctac tagtcagtga actaaagcct     960
ctgcactccc tccttctccc gtctttgtct ttgggactaa agagttgaat tgcaattctg    1020
cttcaataga atccaggtgt aatcagaatt gccttgcttt ctgacattac ataca         1075
```

<210> SEQ ID NO 12
<211> LENGTH: 1113
<212> TYPE: DNA
<213> ORGANISM: Homo sapiens

<400> SEQUENCE: 12

```
taaagttacc tacagtgaca atgaagttga tcagcactct caatgaccca ctgagatttt      60
ggtggataaa gttgcttctt ctcagtatgc ttagctggag gaaaattatt agtgaccgct     120
attatctgat tggcctttga ttttctttgc cctcaggatg aattcttttc ctgtagactt     180
tcacctttca aataaataat agcctagaat tcctgtccta caagttcttc aagtatgtcc     240
agacataaat atttgccaaa tatattaaga aatatctagc aaacttggga ggactactta     300
tattcagcac agaacaatta actgactctg taataccaat aaatgaatac agtggggaac     360
atatttttga agattaagag atgcacaatt gttagtacca aaaattacag agccctataa     420
aatgaaagga aaccttggaa agggcaggtg ggtttgaggc tgggccacag accatttgga     480
accaggaact caaattatgc catcatgaat gcattgctgc tgctatttct ctgtgtgtta     540
aaaacgtgtt tgccaacagc acttgaattt tgtgtatgac cactttagcc atccggactc     600
tctcagttct atttctaaaa atccccagaa aggactctta ttatccagct tgtgaagcct     660
tagatctgtt acgggttgaa ttacgtcccc ctaaaagatg ctaatgttct aaccgcacct     720
gtgaatgtga tctttctttt tgtagattat caagttgatg gttcattaga gtggttccta     780
atccaataaa actatgagtt tgtaaaaaag gacaatttgg atacagatat agacaggtat     840
acagggagag caccatgtga acgtgaaggt ggagattgga tgaaacttct acaaggcaaa     900
gagtgccgaa gtttcagcaa accactaaaa actaggagag catgaaagat tctccctcaa     960
agcactcaga gggaactacc ttgctgacac cttcctttag ccgctagaaa ctgtgagacc    1020
```

```
cttctattta aaccattcag cttttgagac tttgttgcaa taccctagca aatgaataca   1080

gaaatagtgg cttgggggtg ggattatcag tac                                 1113


<210> SEQ ID NO 13
<211> LENGTH: 614
<212> TYPE: DNA
<213> ORGANISM: Homo sapiens

<400> SEQUENCE: 13

gttcaaatca cctgttcttg tgaatatgct aatttacatg ataaaagaga ctttgcagat     60

atggtcaagt gggatcttca gacaaaaaat ggaaagtgga cttagtgaat aataataaat    120

gtttatgtaa agcttatgcc aagcactgca accacataaa tgtatcaaat catgcaaaac    180

gcaccaactc aatgactcct ctctgtgacg cagatgctgt cattgtgcct attttacaga    240

tggagggact gaggcatttt ccaggctggc acacagtcca acacagctag gaagtggtgg    300

gctggcttca gattctgtgc cctcatgct atgctgcctc tctgaaggaa gtaggggctc    360

tttgggatac ttttgacatt aagaaaggat taaatagtac aatataatga aaacgtttga    420

atactcgttt taaaagtaca aaaagagaga gccacacaca cttttatgtg ggtcaggagt    480

gactgttgtt gcactctttg gcatctgcca agcatgattt ctcaggatgt ggtggttggc    540

cgactgccct tgtggccact ggattccatt ctctctctgg tttttctccc tttcccccctg    600

ccctctgaaa cctt                                                      614


<210> SEQ ID NO 14
<211> LENGTH: 233
<212> TYPE: DNA
<213> ORGANISM: Homo sapiens

<400> SEQUENCE: 14

gtttacccac actttttcca cctactgcaa gctcccaggg gcaagctgat ccctagaaca     60

ctttggctga atgagagaag cctcaagact gcaaatccac cccatctccc caagggcctg    120

ccaagactaa agaagaagaa gatctacatt aaagaggctc tcctaaggtc ttcaggcttg    180

ggatttgtgt gagaaaattc taatttaaga ctttcttgtg attcataggc aaa           233


<210> SEQ ID NO 15
<211> LENGTH: 1618
<212> TYPE: DNA
<213> ORGANISM: Homo sapiens

<400> SEQUENCE: 15

attctggaga gtccagaggt ctctctgctt ggcttgcaga tggccattct tgctgtgtcc     60

tcacatagcc ttttctctgt gcatgctcag gtgtttcttc tttgtgtaac agcagtccta    120

ttcccaccct tatgacctca tttatttatt accttttttaa agacctgtgt ccaaatatag   180

tcagcttcaa catatgactt ttaggaggac cttagagcaa tgaccttcat ccatcaagaa    240

actggaggga tctcactgac catgagatgc tccattggtt gtactctaga ggagaccgac    300

gaggatctgc ctcttcctct tgttccctat ccaggtaggc tgaacatgag gagaagggtc    360

tttttttttc ttagtgggca agttattgga atctttaaaa aaatgatcat ttatgattaa    420

aacttggaaa aggaattatg cccatttttt tcagtttact ctcatggctg tactacaaag    480

cactagtcag taacctcccc ttgaaaagtc tttggataag tgcatcatta ttctagctac    540

cagcacttgg tgaatcccca tgttaaactc aacgtgtttt gaaattaaac ctcagagatg    600
```

-continued

```
ttcccaacct tcttttatgt ccctagagat aagtttacca aatgttaaca aagaaataat    660
tgttctcaga acttatggca gaaagtgatg agatgtaggg ttgctttgac cgaggcacaa    720
atggtgctct gtggcaaacg taaagaaact gttcaataat tactgttttc agcaaagtaa    780
aactctaaac caggggccag caaacttcct gtacagatcc agatagtaaa tattgtcagc    840
tttatgggct acacggtctc tgtccaagct actcagccat tttaccctga aagcagccat    900
agacaataca tatacaaaca ggcatggctg tgttccaaca atactttatt tacaaaaaca    960
ggtggcagat ttgatagttt gccgtcacct cctcaaaccc aggcttgctt tccctctttc   1020
tgtagtaggt ttgaatgcct aatacacaca ttttctctct cctgcctttt aaaacttcat   1080
gcttatgctt tccatatgtt tcaagcatga tcttgtgtca tctttttttgg aggtaaaatg  1140
ttgggttgag tgggttagga aactgacttg tgagtgtgac attggagatg ggtctaatca   1200
tgatgttggc ctggacatat ctcatttctt cccatgggac ccatctgatt tgatttgact   1260
ttaggaataa gagttcagat ttgggattgt gcttggtttg gagctggctt ggtgagcaga   1320
aaatgctctt caggacgtaa gctctgtgtt tcggagttca gggagtgggg cagtcataaa   1380
gagcccccag ggagaaggcc cagggtcctg gcttctccgt gggactgttt cccgggtcac   1440
agaaagggag acccaagtgt cagaggcaga ttgaactgtc cctgccgtta tggggagcct   1500
cttttaaatc tccccatttt atatatggaa gggaggtggg aactattcag tcttggaaaa   1560
ataaagttta aaccccctgtg aatctcaaaa tatcaataaa tgaaaggaca cgtaactg    1618
```

<210> SEQ ID NO 16
<211> LENGTH: 1611
<212> TYPE: DNA
<213> ORGANISM: Homo sapiens

<400> SEQUENCE: 16

```
tcctcctcct gtccagcggc tggctgtagg ccctacgaga gagctggctt ggggcgcagc     60
ccgtacctct gggagaggcc acaaaggggt cggagagcgc ggtcctgtgc acagttaggg    120
ttaagtcagt ctgccctgtg tgccctccga agggtgccca gctttgctca gtgggttgga    180
gaattgcaga attctcggcc cgaatgaaaa gctgtcaaaa atagtgaagt tagtttggcc    240
ttccaaggtt aggtggtgtg gtagattgcg ggaccgaggt tcagaatttc tgggggctgt    300
atccccgagc cccactcctc agaatgcaac tctgtacgac gaaggaactg ggtaatcaga    360
tgactaacca cctaaacggt ccacacaatt atcattgact cctaggtacc gaattggcat    420
ggatttgaca attagcgatt cacggttaag cagactttat ctttaatcca tcaaaggaga    480
atttctgcct gcgtgtttgg agagaaacgc gtggatgtga gttaaacttt gttaaaccca    540
acaagcttta agataaaacg actgatattt aaaatggcaa tttaaataaa aatgttctct    600
gatcagcctt tttgtggtct taaccatgaa atgtctttgc atattcaaaa gtgagtccga    660
aatcttagaa tgcaatgtgt caagaaaact tgttcaagtg cagactccag ttaagatcaa    720
tgtttaaact tttgaatac tttttacata taagtttgtt gcaactgatg tctcaagaac    780
ataactggtg aggacagctg tattgccttt tagaaaattg ttacagttat atttacaaaa    840
aacaatgttg cttcagttaa aatgagtgaa tttagtacag gtaagggtgt ttgtagttag    900
gcttatgtgg taccttccta atgacaaagg ccaaacaaca ttatgctgtg ctctggagat    960
attacaaaat atatagaaaa ctccccccttt tggaagaaat gtgtatcttt ggaacagttt  1020
tttctccatg ttatattgga ggcatttgaa acttcctagt catgatgttt tctgagcttt   1080
tatacaagat tgtatgtatg taactgccac cttttttttc ttttacacct gttttcagga   1140
```

```
aatatgactt attttctttt ctcctgttct ttcatgaatt taaaagtttg ctgcgtgttg   1200
aaaattactt aatagtaaaa aagaaaattt tgattttgac tccagctgct tcggaaattc   1260
tgattcttct aataattata tactagactt ttcaaaaata tgggattttt ttgtttcaaa   1320
aaaagttatt acttgcaatc ttagctcaag gatgccattt ccagtatgct cccaatgtct   1380
atggcaaatg tgggtaattg gctcccacgc tttcctgctg gcttcaagga gcctaagaat   1440
catttactca gcactgtcaa tagagaaggc aagaaaggtg aaccctgttt gccctccttg   1500
gtttctagtt tatgcctaat caaagtccat gattgttttc atctctcagc tggatttgag   1560
tcagcttcag caaaagccaa atatccactt tatataatgc ttatttcttt c            1611

<210> SEQ ID NO 17
<211> LENGTH: 8709
<212> TYPE: DNA
<213> ORGANISM: Homo sapiens

<400> SEQUENCE: 17

gtttttgaa atggttacca cattacaagt tctttgtaca tgctatttcc caattctttc      60
aatcttcttt ttttcagatt ttagatctga ggaaaagaca ttgaattctc acagcaacct    120
tctgagtgcc taccattatc acccccattg tccagatgag aagaggcttt gagaggcaca    180
gattctttca aggtcataca gaggtgggat ttgagtctgt taaccccaga ctgtatgctt    240
ctccatgcct cctttctgct gtcggcagaa gccggcactt gggcatgaaa ggccagcatg    300
cattatccat cttagacaga ctttttgttt ctaagactgg aaaatgctag aaagaagttg    360
gcagcccaaa gccattcctt ttgttttgag tgtttgccct gcatgtctgc atgaagctgg    420
ggtttttcta tcagtgagca tctctggagg ctggggaagc aattgtgttt tcgacattcc    480
tcttcattcg cccaacacct ctctctcatc aagagcctcg tggaatcttg agcgggcaga    540
cgctattcat cagaaagagt tgccagccaa cccgctattt cttgtttcca acagttaagg    600
ggaaaaattt cctagatatt tttacttcgc aattctattt ttgtctcaac ttatctgatc    660
cttaattctg actttatttc cttgtgatgt taaagcccct gaagacccta ttcagggcta    720
agccagatac ccatcagccc ttgtggagtc actcaagtca ctcacttgct tacaaatcct    780
ccgaggattt taaggagttg ggtgacagat agcaactgaa gagaaccatg ctccagggga    840
acaagctttg cagactgagt cccagcttgg gggttcactg ccaatcacta tctgacctca    900
gaaatatcat tggccccacc atggaccagt gacatttgtc attcacccgg ctatgacttt    960
ttctgacaca tagacgaatt ctcagtccca tcttctggtt acccacccat gctcaagcct   1020
tgactatctg ggtaaattac atcatccccc accccatatc tggcattttg agggtatgga   1080
ggagggattg taaagctatt tgctaaactt tctctggacg ttccctccct cctgaccacc   1140
ccaccccact tcctggcaag ccttctggct gtgatttcat ctgaattact ggaatcacac   1200
tgtctcctgt cagcctcccc cggccctcct gctgatgagg ggtcccggca ccacccagcg   1260
catgcactca cgcacgccac tggctcacct cctccatccc atgcctcccc tgtctccagg   1320
tctctgtctc ttactttatt tttctctcca cctccttgtg tctgcctgcc taaagatttc   1380
tgatgcttaa tcctcctctg tctcccttgc tgtctttctc tgtgtcttct gtttctctct   1440
ctttctcctt ttcccttcag aagcatttta ccccaatgtc tctgtatgtt ccttggcatt   1500
ccctctgcag cactgtgagg ctggcctgct tgaatgcaca cctgagctcc ggattcacag   1560
gtaggtgtgt gacctttctt aacttctctg ggcctcagca tactcctttt tacagtggga   1620
```

-continued

```
ataacaatag cacctctcac acgaagttct ggaggtgtgc cactacattt tgggaaattt   1680
attatgcagc catagattac acactcacta tttctttttt ctgatgccat actatatttt   1740
tgtttgctga tttttgtctc tcccactagg cattaattcc ataagggctg actgtgtctg   1800
tccccacagc ctggcatatg gatcactaat aactcaggct gggtaaatgg agatcactca   1860
ttttaggctc agcctaataa atctccctag agagcagtaa aatttgccca ttcttttttct   1920
gtctttctgt attgatttct cactttctgt ggctttctgc tgttttattc ctggctgcct   1980
gacagagggt ggtgcagata aagaggcacc tgtgggagga agggctctgt gtgctttctc   2040
ctttaataag ctgtgtctaa aaaaaaaaaa aaaaaaaaaa tagctcccct ttgcaaaagg   2100
gacgaaaata gccaggattt tccagtttta atggctggga ggctgaagac tgaggcagcc   2160
ctcttctctc tgagcagccc ccaaccccgg ctgatcactt cacacacccc acttgaatta   2220
ttattcattt atccatcttt ccaccaagtc attaattaat tccctttatt tgcttatcta   2280
tttatacatt cattatctat ctttttactt atgaattaat ccatttatcc atactcagct   2340
attcatccat ccatccactc tccatctatc cacccatcta tacatttatc catccattca   2400
cccaccatcc acccatcttt ccattcatcc acccattctt tcatgcatcc atctatccat   2460
ccaccaaccc atccatctac ccatctatcc acatatccat catccatcca ttcacccatt   2520
catccaccat ccatttgtca tccatctatc tatccatcca tccatgcatc catccatcca   2580
tccactcatc catttatcca ctcatctatc cacttatcca tcatccattc attcacccat   2640
ttatccacct atccttccat ccacccatct atccacttat ccatcatcca ttcacccatc   2700
ctgcattcat ccattatcca ttgatatact tttcatttaa tcgcctttat gttaattaat   2760
gaatttattc acttaaccat gtgtctattt atgaataata caaacctgcc ttttaatttt   2820
cactgagctc tgctttgtga tcccagggag attgttactt ctctgagcct ccatttcctc   2880
actataagtg cagcttagaa atacttccaa gcacatgggc agcgtgggtg cctagtaagt   2940
gttggctgtt gtcattcaag aaggatggtg tgagcctgca catgagtcag caggggagag   3000
aaggcaagat tctgcccaga actcaaggaa aatcagatgc agttttcaat tattgagtca   3060
cagtctctcg tggcttggaa ggagatagag gatcctcctc ccaaccaata cctttacgat   3120
gttctttcca cacagctctg tggtttacaa ggcaggctta atcttcaacc tgcacgtatg   3180
agtggggtcc ctccacccct ttttcctcag agcattagaa caagcattct tagagctggt   3240
ccagtccaga gatcttggac tgggcctgca ggctggcgac tctcatctgg tcccaaccag   3300
atcaggaaag caaaactcag tgaagccaca tggctagtgt tgggtcctcg ggtggagccc   3360
aagaagcttg gtgggcactc ttccttcctc acctcaaatc atcttgaact ctgtgcaagt   3420
cccagaatga ccctggctgt cttggccttt gtaaaagttg tcttattcct aaaattccct   3480
tcggtagagg aacaggaggg aagtcaggag cagcaagcag gaaatggaag ctaggctggg   3540
gctgggaaga gcagcccgag tttcatttcc aggtggccca gttcccatcc ttgaccttgg   3600
tgttcacctc aagagttttc agccagtcca ggatttgcgt agaaaagtct ccccatctcg   3660
ttttcccagc caggtctcag atcggttcac atgaggcgaa atatacatca gcgtggattt   3720
ttttcctttt ccatttgcat ttgtttgttt cctgcaggct gacactagcc agccttgaat   3780
ttggtcctgt tctctgcaca gctggactca gggagcccaa cccagatgtg ctagaacagg   3840
tggcctgcct gggggccttg ggtacataca gcgggtgctg catccctggg atctgtaaga   3900
aaatgggagc aggtccccca aaacaccagc agactgcact cccatcatga cctaatgaga   3960
tttgaccaaa atagcccaat cctactagca acagccaaca cgggaaattg aatgaaccca   4020
```

gggcgcagac caagagacct ggctagctgg ctctttagcc ttgggagcct ttggtttctt 4080
catgtttcat gagttgttgt aaaggttgcc agatttagca aatagaaaca caggatgctc 4140
agttagatgt caatgccaga taaacagtgt aagtatagct tgtgcaatat ttgggacaca 4200
gttatcccag aaatttttct ttgttcctct gaattcaaat ttaatggggc atcctatatt 4260
tgatctggca accctcgatg ttgtaacaat aaagtgaaat ggtgtgtaca catccttcac 4320
ggcgtgcttc accccaggtg atcagagccc agtcaccatt tctgttagac caggaatact 4380
agatatctaa tactaatttt atcaattact atattattaa tgataattaa tattaatcag 4440
cacaaatatt aaaactcatt tactgagtag ctactatgct ccaggcatgt ccttcacatg 4500
actttgtcat cacatcactc aatgatagag gaacactgtt ctgagtgcct tgcaagggct 4560
gcctccttaa atgtcatcaa ctctgtgagt agatactatt gctaaactat tactagatct 4620
ctgttttgca aatggggaaa ctgaagacta agcacgggct catcaatggc tatgaggctt 4680
caaacccagg cagtaggctg cctggctcca tccctcctct aggctgcttt atcagccaca 4740
tgaatagata gaacgagggc aactgtggat gtccctagag ggagagcaca gggctaccag 4800
gctgtggcac attaccagct gtgtcccatt tagccctctc cccctgtaaa caaagacatc 4860
actattccta tttctgatgg tattgaggct tcccctgtat gcagtgaggg tgtcaggaca 4920
aatgttttcc agagctgagc actggagcaa ctcggaaggt caagataggg ttcccaacag 4980
agaagctctg acacttcctg gctgtgtgac cctgggcaag gtctccacct ctctgatctc 5040
gcatctcctg cctgtaaaaa gggactgatg tcaatccatg agagtagtta cggtcatttt 5100
tagggcagag cttgagataa gacttcaggg caggtggttc ctttgggagg tgaactcagg 5160
atgccccagt agaggagtgg gagacaggaa aagaagaacc aatacatgtg tgaatgagca 5220
ggtgactgct gccggcactt ggagcacagt cctgctggga actctggtag gctgcacaga 5280
gcacacctgg gagttgtctc tcccaggggt gagggatggg atatttatcc tccaactccc 5340
ctacatctct ggcctaatcc cttgcacatg cccagtgtac tcagtgggcc agagaaagcc 5400
ctgggcaaag gcagtagaag tgagtgggca tgggaaggca agcaggcatg gtcagggcac 5460
ccactacatc ttgacaaatc tctggaagat ttcagttaaa aagcaacctt ctgctaaaat 5520
aataacaatg acaacaacaa tggcgttgac aacgataata ataattcagg ttgaaaacca 5580
agggatctgt ccccacccac agacccccag accagtgttc tcctggggta accagctgtc 5640
caaagaagca acccagattt ccttcggctc caggaagggc aggctctctg agttctagga 5700
gaggcctggc atcctgcaga ggccgtgccc ataaagcatt ttcagagctc ctgtcaggga 5760
ccagcactca gctttgattt agcgtcagag tagataaaag aaaaaggagg aggaggaagc 5820
cattggtgag cgaaaatact tgctaagtgg ttgggccatg agtgtatctg tcaacctgga 5880
acaagaagag aactactatt tagataacta tttgctgcac ctcccaaatg tctggggctt 5940
tacctggctt gcctcttgtg tccccaaccc agccacttaa gaatattttt atttccattt 6000
cagagatgaa ggagtgaagg ctcagagggg gaaggtgact tgcccagggc tacacagtga 6060
ggaatggtca gagctgggat gaggaagtaa taaagaatga aatcaagtga ctttccctgg 6120
ataccaggcc acgttagctc atggcccggt ttctgggtca gggacagggg tgtgtgatac 6180
tcttatgcaa ggcatttggc ggcagagaaa ctctagttcc taaagattat tattttaact 6240
aacccagtgt tgacgtgtcc aaaggcagcg ggaggctctg aagggttttc caagaaagcg 6300
tgtgtttctt ggggttattt tttcagtcaa gttcagggag ggggctgttt tgctcaactc 6360

```
atgtttctgg aaaaacaggc acttggaaag agtcaggatg tggatggaga gctgtgggcc   6420
tgcggggagg ggacggagga ggcagccagg gccggcaccc tttgctcagt ctcttcttga   6480
gctggggagc ctggaaggaa gaggctgaag atgaaagctg aagtctctgt gcctcactct   6540
tgagaaatat gatcacttgg cctctggagc aggatgacga caggaggtgg ggttgagggt   6600
tgcttctcat ggagtgctgt ctagatatcg ctgactcatt gtgtgcctcg gtttcccctc   6660
tgggctcaag agctttgaat gctttgtgta acccagtccc tgcttgtccc tgcaggttca   6720
ttccacgtca ctctcttctt cacgggcccc cacagaagcc cacggtcctg cagccttgag   6780
gccttccctt ctgcctggaa cccttctgct cctaacctac ctctgtcgtc ttcctggcac   6840
cttgaatatc accttccctg atctcccaaa tgagccaggg cctcccttgt gcattctttt   6900
ccttggagca catttctcta taattccttt tccagtgtct acctctctca ctgactctga   6960
ggcccccttc tcatttactg tggtgcctga cagagcgaat ggaaacacct cccaagcagg   7020
gctacagccg tgggtgtccc aaccaaaggc agagcccagg acaccaggca ggcagacagg   7080
tgatggacag atggcttcta caccttctta agattatgca gaaagccaca ctctaggcca   7140
cccaccttca ttatatggtg atcaccagtc aaaagaggga aattccatcc caacctcttc   7200
cctggccctt tcagaatcct ggggacagag acttcgacag actccccaca gggtctcatg   7260
aggagactct gttctcactt ctcccctgct cctggaggac ccacaactct ttcaagctca   7320
gaggtgagtc atccatgcat cacgtgtctt ggtgaatgtc aagtgtctcc tgctttagag   7380
ccttgagccc tggactttgt tttatggggt ttggctgtct ggggccgccg acgatttcat   7440
ccatcaactc aggatcgctc caacactaat gctgaattta tagaagtggt taaacaaagt   7500
gttgacaata gggaccgcgt gtttctgatt aacacgcaat tccaagggaa gctgccaagt   7560
gtggggaagt cagtaaaaca cagcagcgat ttcccaggct caggggggatt tgacatcacg   7620
ggattaacag atgttgcgca aggaacttgc aaagcggagg ctgctgcaca ggcttatata   7680
caaaccggag ttgttccttc ctgtctttct ttttttttc ctgagagatt aaatctgaat   7740
cctctttcag ccttaagagt ttccatcagg aattgctgtc agcttcagca atgctcccag   7800
aatcctgtcc ttactccttt ctgagagtga acagtaacac tggctaacat ttatcaactt   7860
actgggtacc agatacttct acaaatcatc tcctgtcatc ggggaagcag gtgtgatgat   7920
ctacacttta aaaatgtttt agtctgaaac ggtcgaagac tcacaagaag ttgcaaaatc   7980
agacaaaggg ttctcaggtt cccttccccc agcatcctcc atgataatat cctatatgac   8040
catagtacat tgtcaaagcc aggaaatcag ctttcacaca tcttatgcag ctttatccag   8100
tgtgtactgc atttagaaaa atagcctatg atttttagca catgtttagg ttagcaacca   8160
ccaccgcatg agacgataaa attcccttgg gttaccctag aagtcattga gctgttcccc   8220
atcactataa gttcatttct tcttgctgct ggtcagtatt cctttgtata gatgtaccgt   8280
gctttatcta tccacctgtc gaaggacatc tggtggtttt cagtttgtga ctattgtgga   8340
taaagtgcta cgaacatgca tgtaaaggtt tctgtgatga tctgcaccca gcagatgagg   8400
agatggaggc aagagagggg atgcccaagc tctcatagcc acacttgtaa tgagatttga   8460
acccaggtag tcactccaga ggcttcatgc ttaaccacct ccaagactga aaatcttgta   8520
ggtaagaata acccaccctc tgctctgtct ttcttacaga ggggctatga acaggcatgg   8580
agttaattca tatgcaaaca tactttctcc ctgggctctg gcctccttca ctcgcctggg   8640
acaaccagac ccaagatccc agagtcagcc agtgccattg cagctgcttc tttgtctgca   8700
ggatgcgag                                                           8709
```

<210> SEQ ID NO 18
<211> LENGTH: 5221
<212> TYPE: DNA
<213> ORGANISM: Homo sapiens

<400> SEQUENCE: 18
gtttggctcc agttaattac tttctcctga gggcagacct tgttaagaag aataaaatgc 60
actgggtact tcaaaatggt tcctctcctc tctctgctag cagcacgagg agatttttcc 120
ccaaaatcac tgtgagaccc tgtggattct agcagttaaa acccactaaa gtgtagggtc 180
cctgatgact gggaccccat ggagttttta tctccagcaa tttatcagct cagttcagat 240
ttctgtaccc cagcattggt tctgaggaag tttccgcatg tggtttctgc tgtgatttga 300
tcttttgtaa tttattctag tatatagtgt gaagaaagaa cagggcagtg ccgagtcctg 360
ctctatcatt gatttgagca agggcagggt ctttgccggt gttctgggcc aaagaggctc 420
catgcatttt ttcgggactt tggattgttt gcagtttgcc ccataactcc cacacatttg 480
cttcttcatg tcccaaagct ctggctgctg cagcattccc ataggaatgt ggatgcctgc 540
caagcgacct catgtgcatt ccattcatct ccttggctgg gaggcagcag ggaagcaaat 600
tggctggttg cttaactgtt tgggtcccaa ccctgtgttg gacttttcca ataattgaag 660
aaaaaacaga agagagatat ttatttattc atatgaccat ctggaaaaca gctattttca 720
agtgtagctt aatgaaaatc acatcctttg gtttgtttga aatcatcttc caccagaaag 780
gcattttgaa gcaatgaggc tttgtgaggt gtgattaaaa caatgtgagt agtttttttt 840
aagcaatcac accaaactgt agctactcaa attcaggttg ttgccttcca ataatctcag 900
tgggctgtga cccattccaa gatgctccaa cctgtgtaaa attcctaagg aaattactac 960
actctttgtt ttgctttttg tttatcattc agtcagcaca tatgggccat tcttgtgctt 1020
agctttgact acttctagtc aaagaatggc aaactaaaga aatacaacgg cttcttaagg 1080
cagccctggc aatgtcactg gaatggtgac tgcttgaagc agaaaatgct gatctgattg 1140
gataattctg aatgttttct caaaacatct cattattcta ttcctggaat attgaaccac 1200
cctcaaatgc tacttatttg aaaaatggtg acattttagt ccagacagaa ctgccatgaa 1260
acccctccag gacgtataat acatagacaa atctttcttt cgctggcaga aagagtcaag 1320
gatgcagaga tttcagacag ccactctaga agcagctgtt aagattccca ctctaatttg 1380
ctgccacagc ttgaaacagt gaaatgtatt aaaatgtgcc acatcagtta acatgggttc 1440
agttagatgg aggttgccag tttggaagga gggcaaatgt tccttggtgg ccatctttgt 1500
gatgcccagg ctgtgtgtgg agctcaatca gagagaactt atacatgagg ttctggcaca 1560
atccaggtac aaataagacc cagggattag ctttcctgga tgaataatta tttctgaatc 1620
atgggaaagg cacacgtgga aaggaagatg gaagtctttc taagaagtct ccgctgtcag 1680
aggcaccagt cctcaaatga gctccatgca aatgaaaacc ggtcccaaca gcatcttgag 1740
ccaaagaaaa ttcttggttg gggttgaaaa aaatgccaga taaatagttt cttcttgctt 1800
ctcagcaggg cccagctatc actgcaatcc agatctggcc tctaagcagt tctggcaggt 1860
ttagcttgga ccagctgctg tgatgaaatt gcaataattc caggtttccc tcaaatctgg 1920
actgagccaa aggcagtcta ggcttctagc aaccgctgac ttcattgcct tctttcctgt 1980
ccctcttcaa ctttcaagct tctggttttt attttaactt agatagggtg atagaggaaa 2040
cctgttcagt gcaacccaga agtctggaaa atgtttattt caggtcaatt aagaaaccta 2100

-continued

```
tattgagtac ttagtgagtc tatttaggtg agctgcgtgg tataactact gcatcagtga   2160
tacgccaggc tttgttgctt cctacacaga agatctcatt taatcaacca acagcctatg   2220
aggtaggaat gattatccct gtatacaaaa agtctcttac cttaaaacaa acagctggca   2280
aatggaagta tctggatctg aacccagtgt agcctgaatc tcaggcctct acttgtgctc   2340
gctatgacac tggccataag caaatgagtc cttaattaga ggtgagtaaa agagctcgga   2400
caagaaaaac taaagtgaac aaaggcagaa aaccgtggga gaaagtagaa gtaggcagat   2460
aaagagtgtg gaaaaaacag tagaggctag attcatgctc attctgagcc caacctctga   2520
agaccttgtg ggtcctggag cctagtgggg aggtttcccc agattataaa gaacttccag   2580
ccattaacac aaagactgaa tataagttgt ccaaaactct ttgctcccaa gagaaacgtt   2640
caacatggaa gttttaatgt actctaagag gttcaagatt tcagataagt cccagggcac   2700
tgagacttgc agtgtgacgc atttaaaaca ggctttctag accagatggg tggctcactg   2760
cccctactcc tttatgggca cccaggagaa tgaagtagat ctgtttctag agaataaagc   2820
atctttaacc cagaaaggga aaagaactct gggcagagta cacctcagca acccagcagt   2880
cttggaggat ccagaaccac ctggccaaca atgtcttcca tttttgcctg tggcatctga   2940
gactcttcgg ctcatcccga ggcagaggcc cagagatacc agaggctggt ggtaacaaag   3000
gtgatattca aaatggtgga aatgattcca ggaatgattc accaatggtt ctgacctgag   3060
gaagacttat caaaaagtaa agagagaagc agcatcccac cctcttccct gactgcaaca   3120
ttttaatctg tgaattattt attgggaatt aatcgtgaag ccaagaacca gcagaaaatg   3180
agcagctgcc caactttgca tctcaggtag gggaggggga gcccccactg aatagagtaa   3240
aaagtacaaa gagacagaca aatattgtct tttcacagta acttttgaga cctacatatc   3300
cacatactgg cttcatgata tgttttttat tatactctgg aacatttagt aggataaggg   3360
acatgtagaa tgtgattcac aggaaagtgg tgggccctga gcaaggacct gagtgtgttt   3420
ttggtctgaa actgagtgat ttggggcaag taacctcagt ttcttgtctg ccaaatggaa   3480
taattatcct gaatcttgat agaatgttat atatttccaa aatcccaagc acattatgtg   3540
tgctaattaa atgctaggta ataaggagaa aaatgtagac caaaacatat aaaaaaaccc   3600
acataactaa acaaggagca gaaaaggaga gatgaaatgg atggatgttt ttggaaaacc   3660
atttggggaa agtggtgatc ttctctagaa aggatttcat gccctctccc taccagcttt   3720
gcaaataaca caacccttc ccagtggttc taaagggctg tagagcagag gtgaaagcca   3780
tggagtccct cggacgatga cctacagctc tcgtctatta atagctttta agtccttaga   3840
tgcagcccaa gcccctccca cctcagggac atgagagggt cacaaggctg cctgatacag   3900
ctgcagaaaa ctgtggtccc cagaattctc ccagttagga atcctgttca aggtcacaca   3960
aaggaccttt ggttttaggt ctcaatccgc ctgtctcgtg ctgtaacatt tgtgttccat   4020
cttgaactct gggagacttc tgggccttca acaagaccat taaatccctc aatcatgttg   4080
gaaagaaaag gagactgtgg ggggagcaaa gacacagctg gcctcacact tggactcggg   4140
gtcagaaggc atcgatgtgt gcattgatac aactctggtg gcagggtgtt gctgagcatg   4200
tcagtgtggg ctctgggcgc aggcagggcc cttggcccct tactgcatgg tcacatctga   4260
ttgtatcacc tccaagcctt agagaccttc tgtgatttcc tctgtgcagg acaaagtcag   4320
gtcccatagc tcgatgtcga cccaactcct gtctttcaaa actcattata ttcatagctc   4380
cctcattgta gtcatcctga gaggttcctc ctgcctcctc agtgagccac atcttggatc   4440
acaacattgc tgagtcttgt gtacagagtg tgaatgtgac acatttctac cacctttggg   4500
```

```
gacatccctg gggaggcagg atatttggtt taaatcctgg ccctaaagct gcggcatccc   4560

tgggctggaa tgtagagtaa cagggctgcc ctgaggaatg agcgggaact tgatctgcca   4620

aaggaggggc tcgctgaggg tgtgtgcctc ctccacagag ggcctccctg ggaactacgg   4680

ccctggagta gcagggcata ggacccacgc aggtctggga agcctcataa caatccaaag   4740

accccctctt tcccaaaaag ccagaggaaa tgtgccatcg aagaatgtgg gcgtgggaca   4800

ggggttggat cccacctctg ccacgtgcaa gcagtgcaac cttgagcaac tcacttacaa   4860

cttcttggag ggttttatca tctgtaaaaa cacacctacc tcagagggtg ctgtgatgat   4920

tagagaaaat gcttacatac aaataacatt caaacatgtc agcagtttta atatcagccc   4980

caaaatggag ggaagggggg tcagaggtcc ctggagccag ctttgccatc aagggcaaac   5040

tctctcccct ctgcagtggt ggggctagat gcgattattt ctaagacgct gagcgtccca   5100

cctccaggat tcttctttct cttttctttt agcagtctgg tctcagggag gcaggttctg   5160

agatggagat atgagcaggg gcttactggg gagtgagccc aggaacaaca ccagtgaggg   5220

a                                                                   5221
```

<210> SEQ ID NO 19
<211> LENGTH: 3815
<212> TYPE: DNA
<213> ORGANISM: Homo sapiens

<400> SEQUENCE: 19

```
ttgaatgact ctgagaggag ccactggtgg taaacccaac tcccctgtca ggaattgtca     60

cgctgccacc ataagtacca cagcctgcag cttaggggta gaccccttt tacacatgaa     120

gctcagagac gtaaatgtgc ccagtgtcct gcagagcagg gacgccaacc cagagctgcc    180

tggctccgaa gtctatgcgg ctgctcccaa ggccctgagc tgtgggctgg aatttcccac    240

agggtcgtaa gtgacagccc ccagtgctcg cagaggcaaa gggccagagc ctgatttgca    300

acgtgcgcct cgacagccat ggtgctccag gggggcagcc tttcccatgc cttcctgggg    360

ccacagagtg cagttgagct cagcagcttg gaggaggtgc agggggccgg cctcagcccc    420

tgggtctcca ggtgtgggga cctacatcag gaacagacag tctttgcagt cccagctgct    480

ctgtcccctg gaaccttgtc tggaagctca gtcctcccag gaggggaaga aaccagcctc    540

cgcttgcaga tttcacctcc ctgtgaactc ccaaagggcg ggaggccaag ccgcagctga    600

ggtcagagaa agtagcaggg tgaccgtggg gctccacgtg gccctccctc actctctcac    660

gggccctcca aaacaggctt ctgcccctca gcaacagttt ccccaccacc agacaaaaga    720

tgagctgagc tgcccagggt ggatcagggc tctgaggctc tgctgtgaac tccgcttggg    780

cagggacatt gtatcatttt tacgattaga aaacatggct agtctgcgca gcggagcccc    840

actcacgagc acaactcaag ggattgtgtt cttgacatga ttggccccaa actgggtcca    900

tgggaaagat ggctctgggt ccagcagagg cagcctatgg gtccccatcc cagaatatag    960

acctcggggg tctatatctg ggatggtcca atcctccctt cctacagaga cctcaggcct   1020

gtcagcacca aacgcctccc cagggagaga agaaagttac agatggcagg gacaaagcat   1080

tcgggttttc atttcctcca ggggtgttgg ccacattgga acgtctgtga ctgcgagaac   1140

ggggccaaat gctcccacgt gcttgccaag ctgcgagtac aatcctcctc ctccatctct   1200

ccaggggatg ctcgcttccc aagcagctgc attttttttt tctcctcctc ctggagaagg   1260

ttgatactga gttcccattt tacagaaacc caaactgagt gcagggcctg aagccaggat   1320
```

-continued

```
gggaatgaca gagccagaag gactggctcc cacctcccag aggtgggtcc tccatgtggt   1380
ggacaggatc agaggcctcg ttagggagat ggggtttcaa caacaggagg acaatctacc   1440
aagaagccca agggcgaatc tcagctcatg accttggcgt ggcccctgct atttcctggc   1500
ccgtaacact gcctgcccag ctctcgactc agctcacacc actctcctta cacagtcctg   1560
tcattcggac ctcagccaaa ggccacctcc tctgactgtg ctgaccccac caaagctgcc   1620
ctcaaggatt ccatccacct ggcatttgcc ctgtgggtgg ctgtgcccac atctgtctgc   1680
cccctcctgc cccctctctg ttctcccctc tgtggacgcg caccagccca gtgctcagca   1740
tgccacagcc tggagtgaag ggacatcagg ccacttcttg tgcccgcctg ggtcaccctt   1800
caccccggcc gagcccacgt ggatttgggc cctgcatctt cttggggaac catcgaggat   1860
ctgggctggg caggcagcag cgaggagatt ggcagagaag gcggcaggag gccggggcct   1920
gtgaccaggg tctcgtcctg ctctcctgct gacccaccta gaggtttctg tccatgatgt   1980
ctggtccagt gggctccagt gagtgagggc aaacctttgg ggcaggagcc tggggcatgg   2040
ccattgcact tttccagagg gaggggctct tcccttctcc tgaaggtgga gctgtcccgt   2100
aaggggtggc tcaggttgaa gagaagaagg gttgggggtc acgcctgcag ggccacagat   2160
ggaatgaggc ccccgacaag ggtcccctgt ccctgtcaag ggcagtcgcc agggttgtgt   2220
gaccggccaa gggcattgga gagggaggga aagccctgag cttctgaagt acgagagctc   2280
ctctgtcccg agccctccat cctcagcctc acctgggctg gcagtggggg aagaggcagg   2340
tgacaacccc cccgagaggt gacagccctg ggcgggagc cgccgccacc tgagagtggg   2400
tgaggagcag gttagctggg tgaaaagttc acagtgaggg gagctgtctg ttccctcgct   2460
taatttatcc actatttggc taaccttgct ctgaacccag gcccgagacc cctctccctt   2520
ctcccccgcc tcccactggg cttctgagcc gccaccagac ctcccgccca agcccaggca   2580
gggacgtgct ggccttgaag aggcctgggg cccgggcgcc gggagaggat ggctacatgg   2640
ctgtcagtta tttatgaccg cagtcttccc atcttcagta accaaaataa agtccggttg   2700
ccgcgaggtg caggcccccg aacgccagac atccgccaag cctcggaagg cgccccgccc   2760
gccgccttcg ccaaacacac aactgctcgg gagacagtga cctttccttg ggggccatct   2820
gtcatcctgg tttgggcggg agccagacac atggacccgg cctcggaagg gaggccggcc   2880
tccttccctg gccctggggt ggcctccggg ccttcggtct gcctctgatg gctcagggtc   2940
tgctctgaag acccttcctc acctcggtct ccctttccct tttttcattc tttcattgaa   3000
atctttttgg caactataaa agccatgtgt tggcagcagc cagtggaaca aagatagaca   3060
aagagtgaat catcccagcc cccccatatc tcagtctcca cggtctgcac tcacaaatgc   3120
acacaagcgt gtggacacct gggcgtgtgt gagcagggaa tcgcttgtaa taataggatc   3180
cccaccacac attcctccgc agctgtttac taacctgctt gcttttgtaa tggggtaggc   3240
cccacacaca ttctgaagtg tacagctcag tcagtgtcac gtgtgtggcc acccctcaga   3300
tcatgacacc caacattctg cccccagagg ttttcccccc aaccatagca gccctaaagg   3360
tggccactcg ggttacctcg atctctcttt gaacctcatc atacagaaga cagtcttttg   3420
tatctggctt cctttgctca atgttttgtt tgtgtcaccc gtgttactgc atgtggccgg   3480
gaggtgttca ttttcattgc tgtgtagtgt tccattgtat gagtcctaac tgatgcaaat   3540
ttgcatcgtt ttcttgtttc tttttcaaca caaatgatgc tgccatagca ttggtcctca   3600
ttccccttg tgtgctagca cttttataca tagagactcc atcttcccat gtgttaatga   3660
gaatgaaatt ttttctttaa tacttgtcca gaaagataat gtttcttcca ctctggaaaa   3720
```

tcacccacaa aacttatgga ccctcattgg ctggaccagg tcagaaagag cctatcctgt 3780
gggcaatggg gagccattga aggttctaca cagaa 3815

<210> SEQ ID NO 20
<211> LENGTH: 4291
<212> TYPE: DNA
<213> ORGANISM: Homo sapiens

<400> SEQUENCE: 20
cagctttgca gacacaaagt ctgaaaaagc acttttggtt tttgccatca tcacaacaca 60
agatattatt cacatcctgt aagaaatggc cctgaaaaag tgatgactgt tctcttatct 120
ggagcacaga attcccagtc ccaaacattc cgtttctcag gtacttcaag gccaggggct 180
tttgaacaaa tggcgtctga ggatgaatac attttagatc aatgattctg aactcaagtg 240
aggtgagaaa ggggacaaag gaatgggaat acgggctagg cgtccattga ttcagagaaa 300
ataacaagtg gaatttattg ctctgatttt gaactgaatc ttgtggctgt ttttattgta 360
attcaaggca ctgtttaatc agaagccatt ggagtgaaaa tgttcatgtt gcagatttac 420
tttgtgacaa tgatgtatgg gaagattatt ctgcaagaac cagaaaatat gatacttgtt 480
ggaagaaatt gaaataaaga acatccaatc ccatgtgcta acaaagtggg gattcctttc 540
caaagctttg tactatgcaa aggatacttt tctggtgtgc cgagaagtta tctctgggac 600
tgtcacactt ggaattccag cagattaccc tatcatcaag tcatcagtat gctgctattt 660
gaataaacac agctgttgtt ttccaagaaa tatggctagg agcagcaagg aaaaaagggc 720
aattagtgtt attgaaatga aggggtactc aggatggcat atatatattt atgagcattt 780
tcgtttccga atagctattt accatgctgt gacttaacag tggtgtagga tgcatctttg 840
taaatcataa acatacgtag tgtttttgga gatggcattc actcccccat attgatctac 900
cctacgctga ctctaatcct gtcaatctgc atgtctggca taggagcccc atctcctttt 960
cagactgatt ttataattta tactgtagca acttactctc cctataccca ccagaaacct 1020
cctttcctgt tggctttgta ttataactac tacatctttg gcattcccac aagccctcag 1080
gaacaacctt cagtctgctg taggtcacat acatcagtac ctgggagact ctgtctacaa 1140
atatatcttg aggttcccct tgtgaatgtg aggatcttgg agaactatga gattgtgtgt 1200
gaaaattatc atcaccatca tcatcatcat catcataacc tcaaccattt aattatctat 1260
taaaggagaa tgaggttgtc aaagcaggac cagctgggat tcgttggctg actcccagat 1320
gcgactgtga agaagcggat attgggtgct ctcccacctc gtcaggagca gcgttctcct 1380
gcctgctctt ggcaccccct agcatcctgt gccctgctaa ggtgttaact gacaactgac 1440
agattttact aagagcctac tcttcccagt agtattttca cttcaaaagt tgacttaaaa 1500
acttaaaaaa aaaaacctct gagagtcaag gcataaagtt tttccactac agctcataaa 1560
tagatcacag ctctaccatc ttcaaggcaa ataaacaaat gctccctcga ccctggagat 1620
tccattagct accatcccat gtttatcaat tttcaagcaa aattttcaaa ggaaatttca 1680
ttgtctcttc tactaactgt ccaatcatta caaatgaaat caagcttcat cttctcccct 1740
caattgcgct ctttaagatc accattgtta agatctaatt gccaatctga gggacttttc 1800
ttcaatgtaa ttcagtactc tttgggagag ttgtgttgtt aaatttgtct gtctgtctct 1860
ctccctatct tggaggtgta gttctttatg tctgagtctc tgcctcaacc gtcttcataa 1920
tactgttgtc ttacataatg cttagcccct tacaataatc tgatatctgt tgaaaactaa 1980

-continued

```
atgatttggg agccagtgct ggtcacatag ttgaattgaa taaagaaatg ttagactgag   2040
ggagcaggtt aattcatcta tcagcccttc aatacccacc cactcttaag attggctctg   2100
attgcacaaa ttaggaaaag ctgggcagga actcattgag gtttgattga aagaaaagag   2160
tggcatctac agtataacac tgagtaaagc atggaggtca gagaggagga gagagttatt   2220
ctgacgcaga gcaagaaagt gattctagtt ttaatcagac attataaaag acacagaaat   2280
atgcatagca gtggaagtga agatggcctt taatcacttt taacggcatc tctaagcaag   2340
tgagatagtg ctgaagagat aggtacagga tttcaacttt acacatcagt tttcaaaaca   2400
ctgtagtaaa aaatcctgct tctgaacatt cccccacctc tcaatagttc aaatcctgtt   2460
ttgggggtgc tgggaaggga tagtgcatag gggagaaggg ggcacaccac ccaagggata   2520
aatttgctaa gctgaactac aagtaacttt ccttccattg aacacctcca aaattagaca   2580
gcataatttt acatagagcc tgccctgagt gtaacagaaa tagagtcatt gtaatagaag   2640
tcatcacttc taaacaaaca tcttggctgt gcctctgtgt ttgttttggc ttcagaagct   2700
gagtccttta tcaaacagta ggagactatt atctggtgat aatgtatttt gattctattg   2760
ttatcttaaa actggtttct tctgggccca tccttttgtt taatgacatg tttaaaaatc   2820
tttgtaagag ctgtattaaa atgacagata ttttgtgttg ccaacataaa ccacaatctc   2880
caaggctggt gataaactcc actcctggcc tcagctactg taggctttga agctcttagc   2940
tgcttttcaa atgttggcat cgttgtcaat cattctgtat caaccttata gtttgtgtga   3000
gaagccattt gttaaattgc agcctcctag actcaaagaa catttaccaa atgctttcag   3060
ataaaatgcc atcttattaa tactgggaag ctcgcaaagg aagaaatact tgagggaaat   3120
caaattgcaa cgcattactc tattctccat tgcacttttg taagaactga gaacagcact   3180
tattcccctc tcttctgtgt gtgtttgtgt tattcatttg taaagctctt tggggcaggg   3240
tacacatacc atactggtgg tctaaattat aaaggggcca ccccaccatg gtaactcact   3300
cctgagccaa aggagcatct cttggatttt cctcatattc tataatcctt tcctctgctt   3360
ttgagtgacc ctactcttct ctgaaggtct tctaaattat gggaaaatgt atggcagaga   3420
tggtgaaagg tcagtgaata ttcctttttt tcccaacact atcaccagtc tcctgctcca   3480
aggttgccta gtagctggtc ccatagtcta ttttcataaa tcctttttgt atttacccct   3540
ctcatcctgt tattttagtc aaatatgcaa aagatgcaga ctctgaagtg ccaactcaaa   3600
tgtctaccat tgtcttttaa cttacaggat ctaagctagt ggttctcaac ctacatctgt   3660
acagaaatgg aaattgcaaa tcatcttgca gcagagttct ctcattatag gaagatttaa   3720
gtaattcttc ttaggcaaga aagtgccatt gtgctggggg aatcgcctct tggttttcag   3780
agttagtgtt tggggagaag gatgaagaat taagattctc tcttatctct gagattagga   3840
gtaagggaaa cctacctggg tggacaaagc tagttggtgc taaaggatgc caaagtccta   3900
gagaggctct gactataagt taaatggctg gcaacctcat ctcagtatag attctggtgc   3960
ttttatagga gattagagct agtgtggcat gtgtctgagc caagatgtac ctgcaggtcc   4020
tgccaccctt tggactgaag gtactaggag tcttgtttga ggaactatgg aggtgctgac   4080
aggaaacaat gacaaaggcg tcactgcaca ctacacatgt tccttgtgcc acagggtatt   4140
attgttcagt agcaatacgc caatatggca gtggtcatga accggtggga tttagttctt   4200
tctccacttg gtgtttagaa ggacatggta tattttttcc aagtaagccc aaatattatc   4260
taataggatt catggaaatt ttgtaataga a                                  4291
```

<210> SEQ ID NO 21
<211> LENGTH: 7731
<212> TYPE: DNA
<213> ORGANISM: Homo sapiens

<400> SEQUENCE: 21
ctctccgtga cggtcacggg tccccagctt cctggcgctc gagctctccc ggctgtctgc 60
tgcccggcgc acgcctgccg gggactgccg gccactccgg gtgggggaag agggcggttc 120 caggggggctg ggggcctgcc aggacactaa tggaacacag ctggaccggc ccgccaggga 180
ggaggaggag gagggcctag agggtccagc ggcaccagag gcgctagact gcggggtgca 240
cagccccgcc ccgggtctgg ccgagctccc aggcccgccc ctcctgcctc accgccaggg 300
gaatgggcca taaacctggg gtcatcctcg ggtggagcac ctacagaaca ggccctagga 360
aggagagagc tgccaggttc ggggatcccg accccacccc gccgacagcc acgcctccag 420
cccactctgg ccacgccact ggtctgcctt tggaccacac tcatggccgg gtgccttccc 480
tgactccgcc ctagccctgc ctcctatctg gctccgccca gccctggcca accttagaac 540
ctgtcccaag gtccagaggg cctagatgag ggtagcctg cctctgagag gcatggagcc 600
ctcctcccgc gtggggtcag ggaagaaggg cgtcgagggt ggcgggtgag ggaacggcga 660
acgggaagcc tccaggctgc aggacgtagc tgcgggagtc tgcgaggctg gagtggccga 720
ggccgccccg agcatagaaa cagccctgta tacgtgggcc ccagggaggc gcctgggcag 780
aagtgtctag gacgatgcct gccacggagc cctggagtgg gggcagctga tggctcaaga 840
cacatgagct ctggtgggac cggggtttgg ggaggcccaa gtcaaggtcc atccttctgg 900
gatgaggggc ggaggatggg aggcggagcc cggtctccag gctccaccta gcgggaagct 960
tgggaatcgc ggagtgcaga ggtggggtgc ggaaagcgcc tgggctcctt tttctccttg 1020
tcccactggc gcctacccac caccatcctg cccagtatct cggggattcg ccccagatag 1080
aaaggggagt cattctaaca tctatcttcc atctccaggt cctatccttc ccttcttcct 1140
tgcagttatc cctgagctgc ctctgccggt tccagtccct ggaacacctg acaactgctc 1200
ttcctgccta ccctctcccc catccatttt tcatagccat gcggtgtttc taaacaggaa 1260
tctggttgtg tcactttctt gattagaatc attcaatagc atcttatggt ccaaatagac 1320
tccaaacttg ggacttgagc tcttcaccat cagctccacc tccctcagcc ccagtccctc 1380
ttggggcttt ctgtgtctcc tcatcccttt tacgccctcc ctggcctcat ccttgctgtt 1440
gggaggtagt tagctcccac cacccccagt atgtgcctgc ctctctcaga gcagtcactg 1500
cctgggtctc taatgactta ttcggcagga caattgattg agatattaat tgctttgttc 1560
tcctgttttc ccctcccact tgcaagccaa gccctttgat ttttctagcc tcagggaact 1620
gtgcagggcc aaacgcaaaa gctgcttgaa gtctgatggc ttgtcctgag tttggaaaga 1680
gtaaacttct ggaagcaggc gtgccatgtg ttcccaaggg atggggagaa gaggacagag 1740
aattgagagg cagaagctag ctgcaggggt gcagaagctg gggtcctgg tggtagggac 1800 tgtccttgac aggtgacagg tggggatgtg ggtaacgcac ctggggtggc tggagtgcaa 1860
acacttggga accagcagtg ctccaaagta gcaggggaac agcttagtca ctgagcctca 1920
aggaggacaa tggacatctc tgtgtgacca atgtagacta agacaggagg cacctcttct 1980
gtggtgcagg gagggccagc agctccttgc atgggaaagg tgggagggag cccagtgatg 2040
gttgagatta aattttttgc caactcatag gaaagcgttt agagtgagtc agactggagt 2100
tggtttaaag tgaatacaga aacagggtat ttcttgtgcc aagcttcctc cctactacac 2160

-continued ctgtctgtgt gtctcttagc tgcagagctg agagtatgtg cctcattcag aattgtatcc 2220
tcagcaccca gcgtggtacc tggcatatat tgactgctca aaatgtatcg gttgaattcg 2280
cttttcctcc gtagagtcta aaacccaagt ctgcttccgt ggttcccctc tggccctcag 2340
aataaaatcc aaaccccgat gatatcccac aaagccactg tgatctcacc gccccgtatc 2400
cgcagcccat cctctccagc gaactgcact atttgcaatt ccccaaactt gccaagttgt 2460
ttcatgcctc gtgcctttgc ttatgaggca cctctgcctg gagtgccctt tccccttttct 2520
ctgcctgctg agctttcaat tagtctgagc tcagtgcaag tgtttccttg tcttccctga 2580
caccctcttc tgaaggcaga ggaaacttct cctgctctgc agcctaatgc tcaggcccat 2640
gtctgtctcc tcccaagcct ggtttccggg cttctctagt agagtgagtt ccccatgccc 2700
aacatggtga ataaatgggg ctttagcctt gatcctccaa ggactcatgg tgtgacctca 2760
gcaacctctc cagcctcaga tttcctttct gcacaaggga ggagtggaac tgaatgttct 2820
ctagggccct ttcttccctc attgagcctg gaaatgagag catgtaaaac acaactcacc 2880
tgtgtgcacg caggccagct aagggcagaa catgctcaga cacagagctg cccatagcac 2940
catgcatggc caccgggagc aagcccttgc ccagcagctg cacgtgactc acacaaaagt 3000
gcatgtggcc ctctggacgt ggatgtgctg tcctcccaac ccccatcccc catcaaccac 3060
tggccctgac agtgaaaaat tcagcagcag tcagggatgc cagtctggca gtgagttaat 3120
attcaaggaa ggagccttct gcaatatgca tgccctgagg ctggtgtcct atggggctct 3180
ccccttccca ggcctgcaca ggcaaagccc tccccacccc accacaggca cagacacagt 3240
ctgcctgcgg cagggcactg agaactagac cttcagctct aattgcttcc tggacagccc 3300
cctcccaatg tctcctcatt cattcattca gcaatatcta tgcagttcct atcctgtccc 3360
agcaacagta tgaatgtatg accctgttct gccctcaggg gctcatagtc cagtggggga 3420
gacagactaa atatataaac tcagatcagg agaaatgata ctgtggaaag gattaggtga 3480
tgtgattttt aaaaaatgac tgaagagact ttcaaattga gggcacagca aacacaaagg 3540
ccctgggaag ggagaatcca tgaaatgtgt ttgaggagca gagaggaggc catagctgct 3600
cagacagtga cagcaagtgg caggacattg gacagagcgg caaccagagc atgccgagcc 3660
tcctgtgcca cagtgagagc ctttgtttta gtcaaagagc aatgggaagc ccctggaaac 3720
agtatccatc ccttccccca gctcctccat cttgggagcc ttagagacta tgccttcctc 3780
atctttacgt tgtcagtgcc catcccaagg cccagcatac tgataaataa atgaccaatc 3840
aagttctcct ggctcaaggc ttgattcaat ggctcagagt aggtcaacag ggccagatta 3900
agacatttac atgccatcca gaagagtctg gcactcccat acatattcac aatagaaata 3960
atactaatcc atgacatact tctttatgca catctggaat gaaaaccact tccttttgga 4020
ttttcaattg caaaattctg gattagttca tggaagcaga actttgtgtg cactgttgtt 4080
actgtcttgc tggcatccta aactgaactc agtccgccca ttgatcaccc agtgctagat 4140
ggcagggctt gcccaaccat cccctcaatg acatggtctt ggcttttgga cccagccaag 4200
cctttaaatg gggtctgccc ttaccccagc ccctctttcg ctacccagct gagccctaaa 4260
cctctaagct caatgctccc tcagcctcct ctctgggtcc tagagaggac cacatctcag 4320
gtcccccatg tgacttccac agcatcttgt gctctatgta tggccccgaa gggaattaga 4380
ctcaatgtgg ggctgggaga aaagttgacc tcccctcccc acttcactga cctccttagg 4440
aaactcagac aaagctgatt ctcaggggat tggaagctgg gtggttgagg ggagcacctc 4500
cacacaggcc agtttcccag gccaagtcca ggctgagctc tgcctctact aggctgcacc 4560

```
ccaccccacc cccagtgagt gggaagtgac aaatgagcct gaggaaggag gagggagctg   4620
gcgatcgatg gcattaacat ggtgcccaaa ttaaatattg actttcttgg ttgactctag   4680
ggacacttgg attgatggct gaggctttgc catgccacca caggggatag gcacataaca   4740
gcctggagca ggtccatagg gaagctgagg cctggagagg aggggctcac ctttgcttcc   4800
acctgctcag gaggagtaga agtgagggct tcagggagcc cggatgcctg cttctccacc   4860
ttccccatgg agtccagagt ccccgtcccg aaggtcttgg agtcaggcct tgttgagtgt   4920
ccccccaacc ccattcccac ctccaggaac tgtggctaac ctgaagtgca acaaatgagc   4980
agaatcaatc tctgtgatga taaccattac tggtctcagg acccggcctc aaggcgagtc   5040
tagggctgca ggggtaaggg taagggtgag ggtaagggtg accccttccc ccaggtctcc   5100
tcaggacctt cccctacttc cccacacctc ctccctaccc accagtatcc ccaggatatg   5160
tggagcccag gaaggctttg gacctccctt gtgcgggcac tgtgctggca actttccctc   5220
catggcccca tgaggcaggc tgtgcggaag tacctccttt tcagagggca ctgagtgctc   5280
aaggtcactg cctttgttct gcctaagctg tgctgtgaca tggtagcctc acgggagtac   5340
tgagcagtgt gagactgact tgagatgtgt agcacaatat attgaatgag atatattatt   5400
aaaatgaatt tcacctttc aaactaagac tgtaggagtt gtcattatcc caattttgca   5460
gatgaggaaa tcaatgttca gggaggccaa cacagatgac agcagttctg tgtgatcatg   5520
cagtagtgac agtgcaccaa ggctgtgggg gcccagcgag tgctgactgc tgggccaggg   5580
gttcagggac agcatcacac agggggctac ttaggctgaa ggagagtttc ccctctgtga   5640
ggaggaggga ttcaggcaga aggagaggca tggaggtgag agatgggcca gaggagggag   5700
gcagccacat caccaagggc cttgaactct aggctaattc caggatccac agaaggcatc   5760
tgagcagtgg cctggcagat ctgcattttg gaaagatcac ttgggccatg tggatgaagg   5820
gctggagact ggaggcagag aaaatgaggg caatgatgag aaatttgagt ccaggaaaga   5880
aatgcaggtt gttagatatt agctcaaatg gaagggagat cgagccaact cattttacag   5940
atagggaaac ccatgtcaga cagggtccag tggcctgtcc aaggtcacgc agcaagtcag   6000
tgcctggggg agcagggact gagggcaagg gagggacaaa gccccacccc aggaaagcta   6060
agtggctggt ctcaaagcca gcagaggcct ctgcaggtag ctgtggtttg tgtttgagca   6120
gaatcaacaa ggtaaataca acttccatgc aaagcaagaa tggacagggc agggacgtgc   6180
acatcacacc tcagccccag agggccccag ataagaccag gaaggaggga gagcacagga   6240
caaggcatta agagggcctt taggtgatgg tcagaggaag gaatgtggag taggatctgc   6300
tggtacatgg tcgggctttg tttgtgcaaa ccccctttta ggaacaggcc cccctttctc   6360
agagacctgc tccctccccc atggttcctg atgggactgc caatcacagt gcctggggcc   6420
agccagagct cttccttcct tgggggtttt ctaattggaa ttcaagagag aaagtttctt   6480
cccctctagg ggcaatgctg agtgatggag gaggaagcct ggcaggccca gggggaagag   6540
gccttaaaga atgaagcatg ccaggagagg atgaaacacg gtggcactcg tcccatcacg   6600
aaggccagcc gcacttgccc actgctgtcc ttgcggcagc gcgctcctgg gtgaacaaag   6660
ctcccaggtg cctgctggct ggtatcggat tctgccactc ccagccacaa gtcccagtca   6720
caagctgagc tgtgggagct tgggaaagtc atgtcccctc tccaagcctc gatttactca   6780
tctccaaaat ggggcagtca aatacctacc tagaatcaaa tgaggtagtg cttgagtgaa   6840
ctctgtgtac ttaagtgcta gggaggcgga ggagtgcgca ggctagaagc acagtcctga   6900
```

```
gtggactctg ccctcctctg accaggtctc acagcaggca ggattggaat gagaccagaa   6960

agcctgtgcc aaggcctgca aaatgaagag gcctccgccc ctcctccagc acccctgggc   7020

aggccattat ctgtgatacc ccaccccagc agccagtcac ttctgtcact cccatgctgc   7080

agcacctctc tccagggacc tgtctgtgtc tccgagtccc tgggggccca gaggtgccca   7140

tgttgctaaa tgaccaggca agaaggacct gtgaccctgc tactgctcca gctgctgcct   7200

gactccagaa tatgtttcca gatgtaatcc tgtgcccccct ctttctgggg gcctgaaact   7260

caggcatgta atgaatgcaa ctcagtacaa gcctccagcc ccccagcctg gctcccacac   7320

ccctggcccg gtccaacacc tgcatctcca ccacaaccca gcatctgcgg ctcccctgca   7380

gccatggtca agttccagga agctgagctg aagccccacc tccatcaagc gtgggtttga   7440

agtcccagct ctgcctctga ctgtggcctt gagccgggca ctgcccatct ctgtatccac   7500

aaaatgggca accttccaac agggttgttg tgaggggcca ggggagtgtg tgaagctcct   7560

agcgctaacc cgagatcctg tcccctgata acaaccctgt gtaagcggct ctagcccatg   7620

ccccagtgaa tggcagccac gaccatcaca gccacccagc cataagaggt cccctcccac   7680

actcccaact gcttcccaca gcccagatcg gggaaaggat gaatacccag a             7731
```

<210> SEQ ID NO 22
<211> LENGTH: 5273
<212> TYPE: DNA
<213> ORGANISM: Homo sapiens

<400> SEQUENCE: 22

```
ctttctgcca ccgctgtcag ttgtgctggc agctttggat tttgatagga gagccataac     60

ttctgagatg aatatgccca catgtgttac tgaaacatgc tcatgcaaag accaggtgtg    120

agataaaact ggaggctgca gacgcctctc ttagtctgtg taagggctgg gtagggagga    180

tccaggaaag ctgatcttgt agttagaggg ctgggaattg gtttaggaga gggagaagag    240

tggctggctg gcaaacacat cctggttggg tacagggaga aacccactga ggcagaaccc    300

aggattcatt ccattcaatt aattagatac aatttttga gtacttgcta catgccgagc     360

actcttctag gggctgggga cacggtgaag aaaacaacaa aagttactgt cctcatgggg    420

gcgctatgtt gtggctccat ttgtttgact atgaaacctc atttaggttt caagatccta    480

gcctcatcat tgtgcttggt tgcaaatggc tcaggtagga ttcccttcac tcccttctgt    540

tttcctttac acaaccctgg agttattatc atgtttctca gtggtcagat ccaagactct    600

tcttaagaaa gatcccaagt tctggtatag tgccatctcc agggcttctt gataaaggag    660

agacctttgg atctgaggtc atagacgata cctacctccc atctcccata ttttttctca    720

ctgcttccag ggagactgac tacatgctga aaagcaaaca cgaaggttga atcttaaaag    780

gcagagagaa agacacaaca gactgacaac tgactctcaa gtgaaactat ggactccaga    840

agacagttaa atgaatcttc aaagttagaa taactgccaa ctagaattct gtggaaagaa    900

aaataaaagg aaaatacaga cacttctaga aaaaaaatgt gataaatctc acaccaactg    960

acctgtagca aaggaaatct tcggcagaag gaaaatgaac tcaaatgtaa tctgaaagac   1020

acagaaagaa atgaagagcc tgtcctggtt gcctggttag ggtagatca ggggacagcc    1080

accaggtgcc agctccctcc tcctcccggc gccgctttgt gcagtggctg ctgggccgcc   1140

tctctaggac ctagggctct ccctgtgagc ggagggaggg aactttggcc gcaggaagga   1200

ctggaagcca gctcgaaaaa gcacattcct tggcaggata aaaaactttt tttttttttt   1260

aagtgtaagg acttaacctt tgctaggaaa tggttgcagt attttccttt aaatgaaaag   1320
```

-continued

```
accattgtga ttgaaacttc ggaaaacaca caacatcctg agttccgtgt aggggacaga   1380
ggacctggtc cctgctcagg agaaggcctg agacagaaag ggcttgttgt tgcttacagt   1440
gacctccact caggtcctgc tccataattt gtggggccca gtcaaaatga aaatgtgagc   1500
ccatggttca aaaattaaga gtttcaagac agggcatcaa aagtgcagga tccttctgag   1560
ctgactgccc aggtcgcatg ccaggaagct ggcccagcct ccagtggacc actcttattc   1620
tgctggccag gcctgagttt ctgcagcttc tctctcatgg gtagacacag accccagaga   1680
ttcagggcag gactcaggac ttcccccatc cttggctccc atataccaca actggcaaca   1740
atttcccaac ctggttcttc acttgatttc tcctcatggt ttagagacag tgcttcccgg   1800
ttgtgaaaac attctggttt catctgcgct tgcttgtaac ccgggggtct ggggaacaca   1860
gaacagctgc attgagtgct ggtctacttg gcgctcttca agctctttac aagcctcctc   1920
gtaggcctac tgtaaatagg aaagtacaaa cacatgccga ttttgccgca gattaaaacc   1980
atctcctgcg ctccctggat cgtaacacat aacagtttgt gtttatgcag catttattag   2040
cttgcatgct acttagggac tttcatagtt ctctgctagg cgaggcctta gtatttgggc   2100
tctccagcgt ctgggaggca ccatatggag agttgtaaag cctcatttcg ggtcagcctg   2160
accgcacaag gccagaccag agctgtgctg tgcaacagtg tggccacttg ccacttatgt   2220
ctcttgagca cttgaaatgt gctagtccga atgtagagta catactgaac tttgaaggct   2280
tagtacaaaa aatgtaaagg atcttgtttc tttttccttt tttaaatgca gctactagaa   2340
aattatatgc tggcatctta tttctgttgg atagcgctta aagcctctct ttgttgtata   2400
catacacaca cacacacaca caccatacaa actcctgagg atcttggaaa gaaaaccagg   2460
ccagtgagat catgtgactt aaccccaatc tctaggaaca ttcctcagaa gatcccgtgg   2520
ccacctaata ctagaggctt ttatttgcca atggtaatct gtctgccttg ccttttaaaa   2580
ttaaaaaatt tattgaacac ctatatttgc aagggagtat gacttagtga tttcagagtg   2640
caggctccag acttggattc cttggtcttc tcatctgcaa cgtgggatta tgacatcaag   2700
gacagaatca ggatggtgac ccagtttcta cttcatgggc ttattgtgag tgaatgagat   2760
gaggcacaga acacccttgg cctggagtca ttctgctgta cagccaggcc tgatctggcc   2820
cctggacttt cacagggctc agcagactct gaggaaggga gggaaccatg atcccagaga   2880
gctccaagac agattggaaa gaccctagaa atgtaatgtc aaaagttagg atggaaaggt   2940
tccagtcaca atgtcaagca ggcccagggt ggagggtctg ggtggggcta ggattgattc   3000
gggaagccag aaaatgagtg agaaatagat gctcttagta cctgaactca gagcatcccc   3060
tcactggggc cacaatggcc aaggctgagg aagtgggccc aatcacattc caagtcctac   3120
attgggccta agtaggcaga tctggagtgt tggacccatt tccttgcagt cttgtccctg   3180
taaggcaact gcattagggt aatgcgggtt gatgaaacaa atgaatccca aaatttcagt   3240
ggctgaacca ctatgggtgc tcctggtcgg taggagggct tccacgtggt gagtcaggga   3300
tccaagctct taatgactct accctccctt aggcctgagt cctctgcatc tagagagcag   3360
acaggaaaga gtgggggaga agacacaacc tcttctaacc accttggcct gaatgtaaca   3420
tgtatcatta actttatgtt caatctgtga caactagtct catgcccacc tagatccagg   3480
ctgggaattg ccggctctac acatagaata gagcttccct aaggcatttg ccagtcacca   3540
tgcccaggcc aggctttgaa aggaaaaatc atgaacactt ctaagggaat aatgacacaa   3600
caagcacact caaagagaca gcacacacac catagtctca gcacttcagg catcctgagt   3660
```

-continued

```
ggttccaaag gcctctctca gagccctcaa accataccca ggcactggcc tttgagctca   3720

gtgagccggg accagcaatt gcactggcaa aatcccaagt ccttactggc caggactgga   3780

tcaaagggag aggtgtgtgt ggggtcgagg caggtctcac ttattatcca acacaggcgc   3840

ggtgctttta accagtgctt cttccacacc tgctggcagg gggaggggcg caaagaaaaa   3900

ccagaccact gaacctcagg ttgctcatga ttttgtgaca agatggccag acatctgatg   3960

cagagaatgt catgcctctc aaagagggga agtggtgaat gccagagggg cactcataag   4020

tgaggtctgc agagccacgg agcccagcac cagtggagct agaaagaggc tagcctgctc   4080

cttgtgactc ccatcctgtt ggtggggaat aaattttctc caattccgca gccccatctc   4140

tccctacaaa gaggaatcct cccatgttca ggcctgttgg agacctggtt ctgtgtttag   4200

gaattgctgt tggtgtgtgt gtgtgtggtg tgtgtgtgtg tatgtatgtg tgtgtgtgtg   4260

tctgtgtatg ttgggaggcg atgacaacta actctgaaga ctgggctatg gactttgaag   4320

tccttcctag tgagggctcc aggcacaagc tgcccaagtt tattaggtac aggtttatct   4380

ggggctaatt taccttgtta acataattgt gccagaggat gcagccctga ggccctgcct   4440

cagtaattac ccttctcttg atctgtttca tctctaaggg ctgtgccttc atgcagagct   4500

tgctggcccc cacttctcct tccaaggccc cgggaggggc cctggcaatg ctttcacatt   4560

tttgtaaaat ttgcaaaagt attgtatcaa ccacaatcat tcaaggctgc tgtttctttt   4620

caccctgact tcccctctgt cacatttccc ttctgtcaag ggatatcgga actgtggcat   4680

tttggggatc cagcttaggg aagcttgatt gagggatgca tttaatgtga caaatgggat   4740

gtatttatgt gggatgcaat atatgtatat aatatttcat gagtgtgctc agtcacttcc   4800

atgttcatga caattattgg ggaggattgg tttccaggaa tactcctacc acccatggtg   4860

ttgtggggtg atgcagcatg agaagcatgt aggaagtgga aatgaaacaa gattgaaagc   4920

acacagccag aagctggtct gtggaaagtc cctgtagtct tacagctcat gttagagttt   4980

actcctaatt gacaactgtg tgattaattc tgtgtgtcag cccagatatt ttgggatgtg   5040

tcgtgagagt gtttccagaa gagatttata tttgaattag tagattaaga agactgccct   5100

catgtgggtg gggattcaat ctgttgaggg cccaaataaa acaaaaaggc agaggaacct   5160

agtgctccgg gctttggact tggactgaat tacaccacca gctttcctgg ttctctagct   5220

tgcagatggc agattgaggg agctctgagc ctctgtaatc acataagcca act          5273
```

<210> SEQ ID NO 23
<211> LENGTH: 2775
<212> TYPE: DNA
<213> ORGANISM: Homo sapiens

<400> SEQUENCE: 23

```
gaggtgggaa agtaggtatc tttggggaca gatgaaccag gatgccagga actcttgggt     60

taggtccaag gctcttcagg ccttggagct gctgagcatc tcccttccca cctctctgga    120

agacttagaa acttgttatt tattatctga gaacagagaa tcctagagcc ttggacatga    180

gcatggccaa aaacctgcgg gggaaaaatc caagcacaat gaaaaatgag tgctggacaa    240

ggagattagg ggagacacag tgacgcccac ctggacagcc ccaggcagct caaagttgtc    300

ctgtcccatg tccccacgct gggtgagact gcacacccag gccggaagca agtacagaga    360

gccacaggga gagggagcac tggagtctgg gccaagaata aagaacaggt gcccaagcct    420

agccaaagag gtagcgagca ttctggggaa gaaaaatggg ctaatcccag ctacccctga    480

ggtcaggaaa cctttccctc tctgggcctc aatatcctta actgtaaaat ggctgcaagg    540
```

```
ctattaagcg ttcttttccg agttgtttgt gggcaggaga agccttgaaa ttgcaatgaa    600
cagaggcacc tggctcccca gggacaattt ccgagtccat ctccccacct tgtttatttg    660
taaaatggga acacagacac aactggtgta tgttttcatt aaaccaagta ggagcttgtg    720
gcatttctgt ctgcacttga gacatgttta tactgctgag tccattatga atctgtttaa    780
tatccttcga attctccgag tccttccatc cctgcagcca ggaagtgggt aatgtgcaca    840
cagggaagaa atttccaggc actcagacct ttaggtaaat gaggactctt tttttttctt    900
taaagagggg aaagcctgtt gcaaaaaaat taaattcttc ctgttccagt gatcctttcc    960
ttgtaggaaa ttggttggtc ctagagagat ggtgaaggag caccagctag gggagcctgg   1020
gagtgagaat agcatccctt tgccctggga tggaggcatg gaggtgagtg actatccatc   1080
aggggatctg tagccaggag ctcaaggtca cctgagggct gccttggctg gctcctggga   1140
agccagggaa caggcttccc actggagagc tccctgcttg ctggcagaac agagagatat   1200
tattttaagg agaaaaatga gattcctgtt attgctttat tcctcctgca gaaacgttgg   1260
tgcgtcccag ccagggccaa gatgagaggc aggtggtgcc aaggaaggat gagctcatcg   1320
catgtgggga cgtaggtgat tccagcaagc acagtgtgga aaaaaagctc cattcttggg   1380
atcccaaatc cctgtcaaag cagaaccctg cttccctccc ccacctcctc cccatccatc   1440
taagcccact cccatttaat ctctctctct tcttgcatct tcaaccaaac actcaccact   1500
taccatatga tcttgcagct agatgagaaa gaaaatagga aaatatctag cacatactag   1560
atgttccctt aatatttcct tcctcccttc cttcctgtgg aagcaaaggc tatagtataa   1620
ttaagaaatt gtagcaattg tgagactttg aatctacaaa tgtcaaattc ctgcaggact   1680
ctggaaaata tgggtcacag gttatttctt ggactcatca tcagattcct ggcaatggtc   1740
tagggatgac acaagtcact gtgaatggaa cctggcatga tgaagaaggg ttccagagag   1800
tgggggaact ttcctggtct tggccaagaa agaaatgtca tggccaggag ccaggtcaga   1860
gagggcagga gagtgggttg gagggaagta gcctgaagtt tgcggatcaa gaagctccaa   1920
aaagtggcca tgaaatcgga atagttggaa attctgaaag gtgagagtga tccatggggt   1980
gagtcacctt tggtaggaca cagagcactg gcattcggct gcctcaggca agggtctgaa   2040
acaccaaacc aactttggtt ttccatctag gaatcatagg aggtgttatt aaccacaggc   2100
cttctggaag cttcctatgg aagggccaaa tccctttgtt tctgtgtcat gcaggggtgc   2160
atgtgctgtc aaaatgttaa aaatgtcaca acagtttcac tttcatcact ttccgcaatt   2220
attgttttaa attccatatc ctctaaattt ccagccccct gggcaaagcc caatcacact   2280
gccctgggta atggccatga tggggcgagg tatctctgtg atggaaactt gattgctttc   2340
tgcttcattt cttgggttcc gttgactact ctttgtagtt tacgattttt aaaaatccat   2400
cctgtctcca ttttgctaag gaaaatcaag aaaagggatt tgggtccaca cgttggtgaa   2460
tggggataaa aggtaggcaa ggggtgttag gtgccagagc aggggcgcaa agggatgaca   2520
agtgagggac tgagttgaga taaggctaag atgctggaag aaacaaaaat ataacacaga   2580
agagaatttt atttttctct cactttgacc agggttgggc aggcaaccag gcaaacacca   2640
ggagcttgtg tgaccagatt ccttctgctg tgttactcct catcctggag tgttgtcctt   2700
gtcttcatgg ctgaagctac ctcaccatgt gagcccacat tcagcccaag gcaaggacag   2760
aggaagggag acatg                                                    2775
```

<210> SEQ ID NO 24

<211> LENGTH: 2679
<212> TYPE: DNA
<213> ORGANISM: Homo sapiens

<400> SEQUENCE: 24 gggggg tttt attaaagcaa gatctgacgt cagggtgaag gacaaaccct gcattttcct 60
ctgaaaaaac ttttcctgcc tctctctctt tttttttttt tcttccctct gtccccacct 120
ccagcctagc ttggccagcc tccccgctct gacagttctt aaagggaaag ttacagactt 180
cacacagagc aatccttgaa ctagcgtcat gtatagatca tcttctggat acaactgtcc 240
aaagcctgcc ctctctgttt ctcagatccc tgtggcaagg cactgctggc tgcttctagc 300
caccaagcct gggttttgat tctttaatgc aagctgagct caaggttcca aagtgttcct 360
aggaggagga gagtgtgggt tggaggtttg gcagacttgg tggaagatct gggtgcacgt 420
ggggcttgga ggctgactgg tttgggttgg cagcgagcag gaagtctccc ttttgcacgt 480
gtctgtgttc taatctcttt aatgacacca attataccac ccactgacct tgctttattg 540
catctggtgt cagcagaccc aacagtccat gctggtacag aagggatgca aacatgaaca 600
aagcgacaag ccactgcagg gatcacagga gaaaacctag aaaggtcata gaagggctaa 660
aaggcatata aaggatgaat aggagtccgg tatctgggta aggggatatg aggggactca 720
aattttaggt ggaggaaaaa atgtgcacat tcacaataca atgtagcatt taccaagctg 780
tttgtatgta ccaggtgtta tttaaagcac ctcacacgta gtcattcact aatcttcacc 840
atgaaacaaa acgctttcct tctttcagct ccatttgtat gtagagaaca gagatgcaga 900
gaaatcaaat cacctgcccc aagttccatg gctggaaaat ggcagagtcc actcctcaac 960
tctattctgg tctagctttc tataatgctg atggtgaatc tcccattgtt cactgaacac 1020
ctcctatgtg ccagacactg gaaggagctg ggattacagt gctcaaataa ttacagtctt 1080
ggcccccaag gacattaata cataagcaaa tagtcaagtt caatcctatg ccataggttt 1140
gcagttgagg caagcccaag aattatgaga atacagggag acccttcact cagccagagc 1200
catggggtat gaagccagag gtgggtgaga gttgaagcat agaattaagt taggtggaga 1260
aagcaattgt ggctttccag gcagaaggaa gagtagtggt ccagggcgag aaaaattgcc 1320
acttgattgg gggccaaagg agttcagcct ggctgggcac tctgagataa gagagccccc 1380
aaaaccccta tgaaaaattg tggcatccct ctgggatggc actgaaaggt gtcaacagga 1440
ggctaatgtc agatcttcta gaatattccc tagggctacc ttagggaagg ggcatggtgc 1500
ggagagggtt ggcatctggg agtccaggtg gtttggaagt ggggtgcagc aaggggctgg 1560
ggctcaggga catgagagaa ttagtgaaat agaggctcca ctttgaaaga gacagtgtca 1620
ggacagaggt gacttcatcc tctgggtggt ggagagcgat ggatgaatga agtcatatgc 1680
aggattggat gaatggatgt gtggactagt cgtgttggaa agaaagaaca gaagtgggga 1740
gacagcctct ccgtatccat atttcccagg ataacagcct ggagaggtga cagccctcta 1800
agctgagttg attgacttaa taatctgaat tctgcccatg tgggcaacgc tgcatctgtg 1860
agaaaagttg agtggagagt gagaggaaag atggctctaa ctgtccaaca gtgtgcttgg 1920
tgctgcagca atggcccatg tcctcatgga atgcacgcct ggaggaatga tgggagcaga 1980
gattccgtat tgaaacccaa ggcagagttg gggatagctg ctgctttgaa tgcttttagg 2040
tcttctcatg tccagtgtgt ctcctccata taggtttaag cctctagcca gaggtttctc 2100
tccttttgat tctttggttt tctctgtaca gttcaaatga cagttacaca taataaaata 2160
tacatgtgtc tcatgtatta taatatttgg atgtactgtc aattctatgc gatctgagga 2220

```
ctcattcacc tgtgtccctg tgctgtatgt ctgacctgtg ttcagttaag tgtttacagg   2280

aaggaagagg ggaatggaaa gaggaagaga gtgggcagag aggaaaggag aaaaggaaca   2340

gagagcagca aaaataagta taaaaaaaag aataaattgg gaaaataaat atatggataa   2400

atgaatgaat ggatgatgga tggatggtgg atggatgggt ggatgggtgg atggatgggt   2460

gggtggatat aaggatagat gaatagtgat tacatagatg agtaaatgaa ggaacacata   2520

tctgggaaac tgaaaaagat caaattctga ggtttgtaaa ccaggggatg gcagggcctg   2580

ccctacgtct atgctctggg ggtctcagag aacttggcgc tagtttgagg acccaggctt   2640

agagctcctg actgaattta tgaatatttt tatgagttt                          2679
```

<210> SEQ ID NO 25
<211> LENGTH: 10820
<212> TYPE: DNA
<213> ORGANISM: Homo sapiens

<400> SEQUENCE: 25

```
atccagaaat tctgacaaaa tgtcagtatt ccaaagctcc gcaaagactg cctatataat     60

tattatccct attgtttcat aggcatttgg cttgatagaa agctaatgat gggcacttaa    120

aagtcaaatg acatgagtaa ttaagaatag ccatgaagga tgatgtaaag gcatctccat    180

ttcagactgg ggaaagcaca gaaatgttct acctagtgga tcatagataa aaatagctgc    240

catctgctgg tgccaggtac ttttcatgat ctctcattga atactcacag ccaatttatg    300

agatggtgct atattattcc tatgtaagac atgaggaatc caaggcaagg agaggttttg    360

ccacttgtca aaggttacag tcactggggc tggaactcag tcccacattg atctgatttc    420

aaagcctcat ctcttaacca cttaaccagt gctgagatga gactgtctca gagtgtggat    480

tacccactca aatttatcat cagtaaaata ataacgaaga ggatgactta aataaggaca    540

ggcatttgct tcaaagtggc ggtatggaac ccgatttcac agtggctgag gtcagcctca    600

catggatgac tcacacacat ggctgatcta cataaatagc atgtgctaag attaccatct    660

ggtataacaa tctacatcac aagactccac atttcctgtt acccaggcta aataggtaaa    720

tcttatctct ggcagaaaga gctatatatt agtcagtaac ctggaggata ttacttttgt    780

cttccaagtt atttacatcc agttggcacg gtatccgagt cttcaaaagg ccatccccact    840

gttctaccat gccgactgct ttatagtgat tgggaacata gaaagaccac taaatccatg    900

agtatgagcc ccacgttgca cttaatttgc tgtaaactga attgctttgt aatgtgtagt    960

gatagcagca ttctgtgagt tcatagatgg tagtattggc actacaggaa gttaaggcaa   1020

atctaaatct agagtaaatg tctgttctag taacaacaaa gtgctggtgc tgtctgtaac   1080

ctgatggaat tgatccaaaa tcagcctcca accaggtgcc ttcttaaacc caccaggtag   1140

tggtgcccaa gtgttgttct tgctgttggt aggacagacc cttagagtgg ctaagccaag   1200

tcagccttgc ccatgcataa cttctaccct ttcttttatg cctactttct tcatagagcc   1260

ccttgggcaa ggatgggggt agctggagag agaaactgac tgatgtccat aagacaggtt   1320

atctcataca cctgatcatt agatcctcct ctgcttagac tgctctttgg tgcaaattca   1380

aagaggtcca tcgacaaatc ttttccccag acctcttttt cactaatttt ctaatagggc   1440

tttccctaac cttccagata tactcataga tacagtcaat gagtcactgt acatccatac   1500

tttttccctt tctcctttca agcaaaatga gcaactaggt gcacttgttg aagttctgcc   1560

tgctggtagg ttttttcctt agagtggggc tatagggata tagctatcta cttttgggca   1620
```

-continued ttgaccacac atcatcaaga gcgatctata aaccaggctg aaatcgtttc ttctttagtc 1680
aacatctgtg cctttgcatg tgcaatttac ctttgccttc aatacctgct tcaagctgat 1740
ctcatttata ccattttcct ttaataatgg agcacttcta tcgcacacac tttatgagaa 1800
aaatatgtgt gtcttaaccc ataatcttaa ctattgtgct cacttctgtc ataacaaaca 1860
ggaactagca tatttaacat agaagaaaag gtcaggtgac catcattctt acatcactgt 1920
agcatttatc gtgttagcac ttctaattac gagtataaag cggaattaaa ggaagagcta 1980
tgacttaagc agcttctgag aaaataacaa tagaggaagt ctgatttaca ctcttggaga 2040
taatgacctg tgactggaga aaagatctcc cagattatat ataatttaaa ttctaagtat 2100
cttaagtaaa taagtgtttc acaatttttt ttctgttaat gacacattcc catagtaaaa 2160
gaataaagga tttggtctct tcttgacctt ttatttcttc aggctttcta aaataaaact 2220
ttatacagat gatggtattg ctcaaaaata acatttattc atcaccaacc tcaaaacatt 2280
ctgcatcata ttatgacact tataaacata agcttggttc aggcaggttt gacccctgaa 2340
cttataaata aaaggagaga gaagaaattc cttaacaaaa caaaacaaaa caaaacatgt 2400
tgcaggaaac agagtgcaaa gacctggaaa aagcacagct gtaatgtcca tgttgctact 2460
tcacccatca tggaccaaag gaaggctccc tataagcagc tatcccttga attttccttc 2520
tagtcttctg ggtgactttt acactctggg ttcatgatgg tggctgtgac ctgcaaatct 2580
tggctctatt ccctaagctt ctagtatctt gggatttctc tagtgacata aatgagaaat 2640
gaagataaaa atgcagtcac tgtcaagggt ataaaaaaaa ggaagtgata acaagcataa 2700
tccaagaatt gcagttactg tcaaatgcaa gagaatctaa gaattgcagt taagcgaggg 2760
catgcttagc tttggaatgg atcatcaaat ttagatagcc ttctaatata aataagtctg 2820
agccctgggg atacccacca ttatagttct gagaggccag cctgcatttc acatttttct 2880
tcagttgagg tacaaagtgg acaatccaca taaacaattg tatatgttga gtgttatgcc 2940
agtggggaaa agggaagaag agatgaagca aggaggcaca tttcacatgt agccaggcgt 3000
acagggcctc caatcagatc cgtcattcta tctcccacac tttagatgat gcttacaata 3060
gtcacgggtc acaacacgaa atcctttatt cccatggcaa atagcatttg aaaatgaagc 3120
tccgtgcaat taaggtttgt tgggaatttt ttccctttc acatatggca atatttatct 3180
tcaaagtctt ctcttgggct cacagtctcc tttataaagc agctggtctt gtgtggccta 3240
attgtgagat gatttgtgtg attcagtagc ttatttgtac agcggttcgg tggaatttat 3300
aaactgcata atattgttct agactgtttt cctttttagta agaagccaca ttttctccag 3360
cattcatgac tgggattata attagtggag cactcaagat attttcatcc caacttcctc 3420
tgttaattaa tgacattaaa caagaaactc ttgcaattaa atgaaaagat gtgagcagaa 3480
catggaaaga gaactagagt gatgaatcaa gttgaactca atctttgttt tgcatatgag 3540
agcttgtaac aaatgctcac atgtaactaa tacaagctgt aagttatttc taattagtcc 3600
tagctgttct caggaaaacc gaatcaaata tggagtgttt tagaaaagat ctcttttgct 3660
atttctgtcc ccgagaaacc ctcagcaaat ggtcccagtt acttgtcaca cgttcttcaa 3720
tgatgaaatg tctccagtgc tgccaggcct ataaaaagtt ctaaaagcaa tttgaccttt 3780
cgtttccttt attaaaaaga agctgcatgt gggcattttg gttttttttcc aacagaatgg 3840 gggttaagta atagcagaga acgaaaaagg agaaaattct acctgctagg ctaggctaag 3900
gaaatgcctg tggtaactat aaaatttagc tctgaggcag ccaagataat ctatgcattt 3960
tattcttata atctcattta agaaagtttc ctgtgacatc aggaaagaat tttattaaca 4020

```
gttgactata agagaaatta ttatgtggta ttttatgtgt ggaaccataa ggaacatata   4080
gagatcatat tttaaatttt acccaaaaca gagatgtttc tctggcaacc atttctcatc   4140
ttctctcaat gctgtccaag tgcataatga tttgctttta aaattgaata tatttgtaaa   4200
aacaaactta agtcaccccc acatacgttt tgcaagttca gctcaggtgg tccatgttca   4260
tgttgtacca cgaagatcaa ccacatttag ccacactgca cagcatccaa cacaccacca   4320
cacctagact tgtggatagg cagaagacat agtaagacag tagagaagtt gaggaatttg   4380
aaggcttcat cacaactcca attggttccc ttggtaaagt tttcctttgt tgttttcttt   4440
cagggcttga ccaataactc atggaatgtg tcagctctaa ttgccggtct ggattggcac   4500
aagtcatgcc tcaaaattgg aatgttgtca catataacat agtcctgcag gggataaat    4560
gtggaaaatg ttttatccaa acattcctta aaaacaactg tgttctgcca tgcaagagac   4620
agacaacctt taagaaccag ctgagtgaac tcccaggatg ccaaagtttc aacaggtgtc   4680
aggacaccac tcttccttcc tccaaggaca tcagacaatg gcaattcccc tctggggtgc   4740
tcttagccag ggcagctttc caaaagaagg taattggtga gttgtgagta tagaagaggg   4800
atctatgaac ctgggctggc tttgtgagtg cctcctaatt gatgagcaac ttacacaagt   4860
gttgcctgat ggccaggtaa tagctgtcaa gcaagcatca ttggaagggt ttgaagaaag   4920
catagaagct atctgtaggg ggagatttgc cactaagaaa gatgtcatga ggtaagcata   4980
taagaagaag aatggacacg gacatctgtg gagcacctat tgtgtgctag gcactatgaa   5040
ttttatctca agtacttaca ttctcattca acgtctgttt tcttcagaaa taaactgtgg   5100
caatctggtc ctggcaacca attagtagta aatactgggc tacgcagaca aatcagttct   5160
ttgcttattc attctccttt cctctgcacc aggcagacag gtgctgggga ggaaaacaga   5220
tgcttgaacc aaacactaca acatagtagg gaaaacatca tttcaaatgt agtaagctca   5280
gataatgttc ctcttacctc agaaacattc ctcattaaag gtgcatatgc agataccaaa   5340
acgttgttga acatgtaaaa ataataatta ttattttggc tacctaaaac taatcaactc   5400
attaatttaa tttttggagc agaattgaat tgctcttgag actgagttgg ctgtagcaaa   5460
gccaaaacca ttagttgggg aagtaaaatc aaaagctgcc accagggaag ggctctctac   5520
aagagaaaca ttcaaaaaag ttcccataga aagctcaagc ccacaggaaa tgtctagttg   5580
agatgatgga tcacagactg ccccaatcgc cagacttcca tggcaacctt ttgcaggcac   5640
catcatgtga aggaatcctt tttgtcctag gatacgtctt ttttgggaaa tgacaaaccg   5700
tgatcttcta aacatttcat gtttgatatt tgacattttc ccaaggcctc caaccctgac   5760
cttgccatgc aatagaatgg ggagaaagat gcttctttag agatgggcaa cattgctttt   5820
agagatctgg gcagatatac aaccatctct taacagatgg agttgatatg attgagattc   5880
ctggagaagt gagtatgagt ctgttaccag accacatcat agatcctcat cttctgatag   5940
tagttcaaat atttgcagtt acatgaaaat atctttcatt gaaatggcct catttttgcg   6000
acacttggtt acaaatgcta gcattgtact gcatcagatt tacctggaat atatttctcc   6060
tttactataa aattcccttt ctattccccc aaatggtctc agtaggtttg ggatagactg   6120
aaaatctgta attttagaag ctgtcaaggt gactgttgtg tgccctggtt tgggatcagt   6180
gagtacaggg ggaagtgccc atccaagaaa tgtgcgaggt ttgctctaag tctacaactc   6240
tagacttttt cagaagaccg ggttacagag tgatctaatt gactcaaatt tttccccatt   6300
actggcagaa atatctggcc tttagcaggt tggtaaagcc catttttcat tcagtttatt   6360
```

-continued

```
attccttgaa tttccccaga aataactatt cactctcttc tgcagttcag agttaaattg   6420
ttataggtaa attgtgtcct ctggagtcct gacccctagt acctcagaat atgaccttat   6480
ttggaaatag ggtcagaagc acagactggg aacactcact gatttcctgg gaatggggtc   6540
tgacaatccc aaaaacccag cacaacaggg tggatacaga acaaggagca tttctacaag   6600
cacttctttt aaagactcct gttgaaaaca atggcacagt gagactcctc actgaatctt   6660
ttgcttgaag ttctcagttg accaatttgt tttgtttttc tctctacact tgctgtaatg   6720
gtatatacag gacatcaaac tcgactaaat gtgtggcaca catagtcagt gctcagggtc   6780
ccaactccct ttctggctca actccatttg tccctcctgc ctttctactt ctatcttgcc   6840
ctgaggtatt tcacttttcc aggtcctgga tagagattaa ataaatcaaa atccattcta   6900
gcattcggtt gaaattgttt cctgtgctgc cccattgatg attttaaaac tatatatata   6960
tatatatata tatatatata tatatataat atgaatgtat gtatatgctt gtggaaaaaa   7020
tcctacaaga ataattcctc atggataact ctcagagctg taacaaaggg gtaaattaag   7080
ggggttgctg gacttccttg gggctccttg gtgcctctcc caccagtttc tgcctaaatt   7140
tccctttcag aaatttgaat ggagtcagtg atttcttgga gggccaggtt atgggcaagg   7200
ggaagatgtg cacacgtggt gatgtgaaat ttgatacaca actgccactt gatttaacat   7260
tctcccagtt ttcggtagag tttaattttg gttcaaatga agaaattagt gttacgccca   7320
tgcttgagga caagccaaac tgcatgactt cacatcgctt ttagagcagt attgaattac   7380
ataacttctt agcttgtttg ctcccaacag cctgagcggg attttcagaa ttgagatttg   7440
ggcctgagga gagggtttcc aactccaggg ctggccagac ctcggtgatg tcacctgagg   7500
aacacatgtg tgttctttca gttgggttgg catctatagg agagaaaatc ccatgttgga   7560
gggaaagcct aagagattat attgggcctc ttaccactaa tttttttttc tgtttaatta   7620
tgtctgttct cttaggctga atgattttcc tagttctgat cacacagcag tctctctcag   7680
tacattctgt tccctttaca aggtctctgc ccaattacag gaacacactc atctcttctc   7740
caaatgacca ttacgtgctg aaataaagaa actagctaca aagtatttca gggaaataaa   7800
gactcaatca gggaaaaacc tgaagcaact ctttcaaaaa aaggcaatta aaaagcatta   7860
cctttatata ttgatacaat tacctcatat ttacattaat tatttctcga atctcatcag   7920
atctagtcag gaagacaaag catgtccaac catagaaggc ttattagcaa aaggagcaca   7980
gctcagctta ttccctagaa aagtaatgcc atctcaaggc tagtgactca aggaacagtg   8040
agtttttggc ttttttattc tcccctaaaa atggtagaaa atgttgtcac aggtacatta   8100
atgaagattt taagggcaga aatcatttca tacaatagcc caacttgctt aggggaggtt   8160
gtgctgttcc acttctttgc ttgtacgtaa ccatcagttt cacaagggct ttgccagtgg   8220
ggctgtattt tcattaccac atttttcagt cagcatcacc ttttatgttg aactctacag   8280
aatgtgaata ttcaacaaat tctgacctac aaaaactgca ctttcataag atatgaccta   8340
atattgttca atcatatgta aattacaaaa acaaaggctg gtaatatagc ttatgggaat   8400
accatggttt gtaaacagag ctgctttcaa attatttgcc agattttctg gtaactgtat   8460
taaataagtg aaaaaaaaca ggtaaaatta ataatatact ttatttaatc ccatatattc   8520
aaaatagtat atgtaatcaa tataaaaatc attaataaga cattttacat tttacatttt   8580
tttgtactaa gtcttcaaaa tctggtgtat attttacaca tctggcatat ctcaattcac   8640
attagccatg ttttgattgc tcaatggcca cattggacaa tgaagtcctg gacccttcac   8700
ttacaagctg agtggcaagt aattagcatt ctgagtctgc tcacttccct ttaaaatgga   8760
```

```
gttatattct tttaaaaacc tacatcctag gatatgagat taaataaatc aaaagagaat   8820

actgtagtta gcattatcat gttagggagg tcattcaact agccaatttt cattgcgtaa   8880

ccaaaaggtt aacatataga gttatagaat attctcagga attactgatg tgagataagg   8940

gtctggaggt tttatacatt tagtatcaag atggagaaat atgagcccag gttatagtct   9000

ggagagttgc tgacaaattt gccaaagttg gaaggctgtt aggggctctt ttcatctctc   9060

tgattctata ataccttcta ttcttactca tcaattaaat ataatgtggg ttgggtgata   9120

gctctgggac tagccaggct gcacagaagc atgaactaat gttagagtga caaacttcct   9180

ctctctaaga tcaaacaaga tgagactgca gaaaagggaa ccatttttctc ttctatctca   9240

atactcgaat tgatggtttg tttctatggt gtttagacaa cacaacaggc acacactagt   9300

tctttcacta gacaaagcaa gacaaccaga ttgagtcaca attacttttt ttaatcctat   9360

ttattaagag attggcaact cgtttgagga gtctggtctt gtaggtagca gccaaaaaaa   9420

ttggaggaaa tagggtgggt ttttttgttt gtggtgcagt ggtaccagtg aaactgacag   9480

gagtagctga tcccaaacaa caaccccaga aagcacgtgg ctcttgttat atctggctgg   9540

ctcagcaact atccaagtta tggggctaca ggggatactg tctagaccag ttcttttggc   9600

cctggcgttg gcagaacata gaaccagaaa gccaaagcat ggtgcaaaca tctctctgca   9660

tttttctgg tcggcagtca agctggatgg aaactaaatc tcaaacaatt accaaatagc   9720

aataaataag ggaataaaaa gacggcacag ggtttcttct atccttgatg gatatggcct   9780

gactcttgtg ctttaaagca tgacttctga agtgactgtc cttagggaga aagcacagag   9840

ggcaatcgga agtatgactt ttccagcttg agatagtctt attgcatcac aggtgttcta   9900

gactcgatga tggtactgat aggaaaaaga catccacata tcatcgaaat aatttattta   9960

ccactagagc accacaaaaa cagacataca tcgtgttaaa atacagcgta attggtcatc  10020

aaaatacaaa acagctaatc ttatattcca ttttttaacc atgccaacga tcaaattgta  10080

ctgctgatta acacaaaaaa attgctgccc acttgcatac tagcacttca ccccttcctt  10140

gccacctcca ctcccatggc aatatttact tatgggaaaa aagacctaca gaacccccaa  10200

attaaaaaaa aaaaagattc aagagatctt aaaatagaga tcagtgcatt catgaggaaa  10260

gacaaataat acaaaacaaa atgtcatcct atctgagagg aaaatgtctg cagaaataaa  10320

agtgatttac acataataga aaagtggaag acaaaaaaat aatcaacaca cactcaaatc  10380

tgggattggg ttacatccaa cacaagggct gtttactagc atcccatctc ttgctgtttt  10440

caaacttgca aatccaattc tttaattcag gaaattccaa aaaagaagta gaccatatca  10500

aacaacttca ctttggattc ccgcctcctt atgctgctct ttaggtgaaa ctgcaaatat  10560

tccattgctt tgcctattaa tttttatttt aaagctccag catgaggata cctcttctgc  10620

aatgatggca aattatttaa agcaaggtaa actttagcct cagatataga taactctcac  10680

tcagaggaaa gaaagaattt tttgacatag gaaaaattgg cttgtgcctt ttccccttca  10740

aagaacattt ataaaaacct tataacttca gtgaaataca caaaatgact tatgctgacc  10800

tggattaaga aactgaaggg                                               10820
```

<210> SEQ ID NO 26
<211> LENGTH: 1764
<212> TYPE: DNA
<213> ORGANISM: Homo sapiens

<400> SEQUENCE: 26

```
aaagccaacc taatgcagct cagtgctaga catggtagat gggtgcttac ccaggagcca     60
ttcaataccc tctcttccct tactttttct actttagaag ttcaaaagca aaaccttttt    120
tcctattgtc cctcacacct ggagatgaca aggcaacata atattgtcca aacagatgtc    180
aataggcctg ggtgggactt caggaaagct catatttgtt aaaaaaaggc tcagcttttg    240
cccctctctt ccaccttttt ccttagagag taaacttgaa gcctgaaatt gcagcagagt    300
gggcaaacag aaggacaaag gctacaaggt aaggtaaatg gagcagatgg aaagaactgc    360
agttcttgcc agtattattg agtcactaca gcgagaaaaa taaaacgata attaatacaa    420
aaagtagatt ctacattatg aacccagaaa aaagctctgc tctggatctg actctgttac    480
ttactacctg agtgacattg atcatgtcat agagttctat tccctcctct gtcaagagaa    540
cacttgactt ctttagccta gattatccta tgaaataatg cagttatata tcttcataca    600
ttggaagatg ttgcttattt aacatgccag gtggttgata cataggacac gcagtgactc    660
cacagttaaa tataacagtg cccaggagtc tgctttccgt tcaaagaatt tgcagacact    720
tactttgact ggcttaattt cagacttctt gggaattctg ttctgaagtt aggaacttcc    780
aagcttttaa aagattacaa atattcaatc cttggcaatt taatatttgt cttcctttgt    840
ctatacgagg ggaatcttta aagacttgtt gaggcatatg gcaagttttg aaagaatttg    900
aaggtgaata agtaatgaaa tatattccct cttttaacat taaaaacaat tgtatttaac    960
caataaggaa aaattcaggt aaaaaaattc catgcatatt tttctttttt aatttaattt   1020
ctactaatat tatgactcag aggctgaatc caggataaag gtactatcat cagggctctc   1080
tttcagggca gaaagagaac atataaagac tagaaatgaa aaaaagagat taaacaaggc   1140
ttccacttca tctctggatt ctatccttag catagtgttt tcaaagttca ttcatttgta   1200
tcatgcatca gtacttcatt cctctttgtg gtggaaatgt tgagttatat ggaaactcta   1260
tgtttaatca tttgagaaac tgtcagatta ttttccaaag cagctgcacc attttatact   1320
ccatcagcag tgtaggaggg ttcaatttct ccacatactc accaacactt tgttatcttt   1380
ttgatacttg ctatcctagt gcctttgaag tggcatctat tgtggttttg atttgcattt   1440
ctttaatgac taataatgtt aagtagcttt ttatggctca ttggcctgta cgtctttctt   1500
aggaagtggc tattaagatc cttagctgat ttttaagtta tttgtctttt atgattgagt   1560
catgtcttta tatagtcttg atacaagacc cttatcagat atgtgattta caaatacttt   1620
tttccactct gtggtttttc actttcctga tgctggtctt tgaagaacaa aagtttttca   1680
attttggtga aatccaattt attatttatt tcttttgctc atgcttatat aattatatcc   1740
aacagattat ttgccaaagc taag                                           1764
```

<210> SEQ ID NO 27
<211> LENGTH: 12761
<212> TYPE: DNA
<213> ORGANISM: Homo sapiens

<400> SEQUENCE: 27

```
gtcccggcgg agaaggcgcg gagggcgcgg gcgctgctcg ggggcgctct cgctcgcggt     60
ctgcccaggc gcccggagcc cgccttttat agggccggcg gaggcgccgc gtgttgcagt    120
gacgtggctc tgtctgcgcg ttccagaatt ctcaaacatc tcaggaatgc tggttggcgc    180
gggctgctgc caagcgcctc ccctggctcc attgcacctt ttgtgtctgt ctcccagacc    240
cgtcaagaaa agaaaacagt tcgtttttc caccttaaat tacgacttat gttgggaagg     300
gttctttggg gcgtgatggt ggtgatggta gttggagggt cgtgaggggc gagggggcc     360
```

```
agttcagaac tttgcctgga cgtgggagga cctgagaggg aggaacaaaa gtcgttttgt    420
ttggtgatgc tcacccggga aggcagtgag ctgtttgctt ttttacagcg aaggtgagag    480
gcaagttatc tgttgagagt agaacgggga agaggagtgt gtctctgagt caggaatatt    540
tgtggacttc aaagaggcgt gttcggaaca agtcccaaag ctttggcatg atgtttatta    600
gcaaagttca gtgaattgca aattaatacc cacagtggca tttatgaatg gggggggggg    660
gggaaacttg cccatcgtct ggcaaattcc caggcagagg tctcccccac tccccccttcc   720
ctcttttggg tatgttgtac ttgtttgttt ttggaggttc ccactttagt tccagcccac    780
tgcctgggtt ggaagtccga gaggaaacga acgcggagtt ctccgggagg ctgacttata    840
cttcctcacg gatgcaggag acggggtaag cccttcccgc ctccctccgc gggcaggagg    900
ctatgctaac caagcagcca gccagaagtg caggagacca ccgtggagtg gcctgaaatc    960
atcacctgca aagaccgcaa ggccaaacca gattccagga ccattgtgcc ctatgaatct   1020
ctgggaaaag cagactcctt caagctggac attttgtggg gtttttaact cctttcctag   1080
ggaccactgg aagcctccca ttttaaatga attgcaatgc ctctctccaa gtacagaaaa   1140
gagatttagg atgtaatatt gtaaaaatgt cagcagattt taagatcccg ttctacttgc   1200
aacagtagaa gaccccacca caagacaatt tacttgaaac cattagtgtg attgataaac   1260
taggataact acttatcctt tttaatgttt aaggctattc agacttcata atttagcagt   1320
cttgcttgaa aaggccctta gtgctaatgc tgactttcct gataaggaga atctgtcagg   1380
cacactccag tgaagagaat tcttgcagga aggagttcag ttcattcatt ccaaagtgcc   1440
ctttcataaa tggaagcagc atttgctaga gggagtggga tctctaaagc tctttagggg   1500
tggggacttt tcaagacaat ggattgtcag gtgttatgca aatacagtga ggaaagtgtg   1560
ggcccaacac gtacacaggt taatttatta aaacactgtt tttcctgcct tcatttcatt   1620
gtttccttct taatgaagtg acgggggcg ggaggggggga ggaggggtgc agggacaggg   1680
ttgaactaga gagagaatgg agaggagggt tcctggcttc tgttgtggcg tcttttctat   1740
ttgacttcat ggttgtaagt atttccagat ggtgaatcag acaccagacg taacaatatt   1800
tccatatttg ggtatagcag tagcctgcgt ttttaacatt tttctgcctc tgttatccaa   1860
ccacaaagca ttcttgacag cttcaaatgt tgttaaatat agatttaact tctcttccca   1920
gagcaggaaa ttctttggaa ttccttgttt ttcacgcaat ctgtccatca tgatttaaaa   1980
taaaagcaca gtggatcatc caactggccg tatataccctt aattggaggt tggggggggg  2040
acggcagaga tccagtctgc cgcactgcgt tcaaacacac gccattccag agattccttt   2100
aaaatcacat taaagttttt taacaagggt gtgtgggttt gtttctggac ttcaactggg   2160
gaatcttgag gatgagtttg ccccagaaga gaaatttaga gaaccttacc gtcagctgcc   2220
catttaaagc agggggtgtg ttgtgggagg gggtgggaag ctggagcaac agggccagga   2280
ggtgtgggag cgggagacac tagagtaacc tatgtgcaca gcctctccat atagcctgct   2340
agtaatcaag agaaacagcg gctcctcaag tcctgcccaa agaccgtcca gaaaccccag   2400
cctcccgtcg ccttctcgcc gcctccgctg ggagccgcag atcagtcgtt gacggacagg   2460
aggcgaaatg tgcaaatgtt atgggtaagt gttgcttcgg gtgctaattg tatggctctt   2520
ctccttcacc ctccccatac ccaggaggct tgtttccttt ggattgcaat ccacggagaa   2580
ggggctactt gtcttctgca gctcctggct tgggctgaga gatggggtct caaccgctgc   2640
tgccagggaa ttttaggtta cctaatgaag ggctcactgt ctggcggcaa ccgagaataa   2700
```

-continued

```
taacggtaaa tctggcgact ccagtttcct agcccgaagg ctctcagact agcgtgcatc   2760
cgagtcgcct ggagggctag ttaatgaatg gttctctggg tcccaccccca gagtttctga   2820
ttagttacat tttaacaagt ccccaggtga tgttgatgct gctggtccgg agatcacaca   2880
ctgccctgga cgaccggagt gctaaggtgg cgccccccgta ccatcccatt tctctcctct   2940
ccatttcccc gcccccatgg cttgacagcc aggagagccc caggaagcca ggatcctggt   3000
ggctgcggca ggaactgggt ggccgacgcg cgggtcggga gggagcggag gcaccgggtg   3060
cgggacgcga ggcccggacc tgctaccgcc gccccctgcc ggccccccgc ccgcgcgcca   3120
cagtcccgcg gttgccaaga atcgaggttt ccggcggcgc gcggcgcagg acgtttccag   3180
ccccggccca tatttggtga aagtctttca agactccgtc atctagcttc ggggggggcgg   3240
cggcctgcga cccggcctgg caggcttgcg gccgccgcgt tcctgaaaag tgcgccgcgg   3300
cggcccgcgc ccaggcctcc ctccgcgcgg gaccccggag ccggcggggt cccgagtttg   3360
gccccagtcc tcacccctct gagggccgaa gtccgccctg cgctgcgtgg gaggctggcg   3420
cggagggcgc cgcggcagtt gtgtcacttt tcccgtccgc ccccctgttg actagtcctc   3480
ccagcggggc agcgagttgc cgtgctgtgc cagacgtaga gggtgcgtcc ggcgcaaggg   3540
tgtggggctg tgtgtgggag gatggcgttt gcgtggacac caagcgcacc cgagagcggg   3600
acgtgtagcc agctctgggg aaaagccccg aagggcctgg attccattat ccccagaagg   3660
gacacatggg gctctcggtt tctcctggta acaccatttt ctatctaaat gaagaaatgg   3720
aggcatggaa ggtaatgact ggtcactcac ctagcctgga tttgggccca gatcggtctc   3780
acacttaact actgtctata ctgcctactc tctatctctt acctcagaca ttcaggccca   3840
tcctcttccg taatgtactg gctcttttgt atttaggtct taatgcagat acattagagt   3900
ggtctttaag caccttggca ggctggtggg gaagatgttt aggacctgac acctcataag   3960
ccacattgtt caggcaatcc ctacttctgg aataaggctt ggcctggtag gagttgaatt   4020
tgtcattgag ataaaggttt cagcatcact tacttgaacc catatatttg aggactgtat   4080
ttacccttcc ctgaatccca gatttattca gagcttgtga tgtcatggca tagtgctagg   4140
tactggtgac atgagaaaga ggattttaat attgaacgtc ccccgcagga ctgtaaggca   4200
tattgcagaa gtgggtacat gagttagggg gaacgactaa tctggggctg aaaggatgaa   4260
caggagtttg atagcagggc aggacatttg agaggaaggg aacaaggcct tgactgggca   4320
taacaatcag tctgactgga ccataggatt ccttctgaaa actggcaaga gatcagttgg   4380
gacatggcct tgctgtcatg gcattggaac tttgcagagt ggccatgtga gctttttgcc   4440
taggtttcct tgtctataag ataacaggat tctcctagct cagaggacac acactcaagt   4500
gcctgcagga ttcagccagg taacaccatg ccatgactca ggattagtgc tggctgatat   4560
ttggccttgg ccttgggaac catggggaca tggaaatgag agtgaatggt tactaggtga   4620
aaatgtaggt tcactgtttg catattttct cattttaaaa agagatacta gagatctgat   4680
ttttatgtga agtcttcaaa attttaaaag ttggcaatta attacaatgt taccatctag   4740
actaatcctt ggaaaaccca agaagacaat ctgtgggtgc catttgtgat ctctggactg   4800
aatatctcta agaatctgtc ttgagcattc tataactccc agccacctgt gaaattgtag   4860
ggaacagcac cggctccatt taattgtcaa gttgactaga ctttatttaa gagtcagggc   4920
tgctacttac ctcttggttg taggaattta taacctatta agaaaattgg aaacaaattt   4980
tctacttcat ccactctcca gccactactc tgtctccctc cttccccctg aattgatgat   5040
gtaagcagct ggcattgcct tggcaatatg ataggaaaca cttttttagg gcatccatat   5100
```

cccgtgggaa ccttatctgt ttattttctc cacttggcat ctatccacag gaagccagca 5160
ttcctaactc ccttacctta cagaacttct tgttttgtga taacacagaa acattttatt 5220
ggaaaggact ggaaggcacc tctcccacca caccctgcaa tccatcttct agagatgatt 5280
gagcaatatg aaatataata attgtaagtc attatcaaat ggcttggcac ctctgccttt 5340
cgtgttttat ttctggagat acctgtctct taaccaacca ctaacatcac acgtagcaca 5400
tccagaattt agaaaggatt tgctctgggc acagtagatg agcacacaga ttctacagag 5460
agattgaagt gatttatttg tgacaaattt ttgcaagtct tggggattga gtgtaaggga 5520
gtattcaagc attggactta ctatgtgaaa gaagacataa gacatattta ctgctcagcc 5580
tgatgcctgg cacatagtaa gtgcttaatt acaattattc ctactgccaa gcaccatcat 5640
tatctttact ttcactgcaa taacatagaa tgagctagtc ttattctaga gaatactttc 5700
tattctttag aactctagtt ataaaatcac tttggtatat ggtatataga tgatatgatt 5760
aaaaggatcc atccagccag gtattctggc tgcactggac accagtgact atctaaaaaa 5820
ccactcaaat gggcttacct ctcatggcac tccgcagtgg tgagccatgt gagttttgct 5880
ttggtttcct catctatgag atgataggat tgcaccagct ggagtcactc aagtgcccca 5940
ggaatcagag aggtaaaaaa tgccatgcct gagcgttagt gccggctgac acttggcctt 6000
agcaatagga atagttggaa gcatctatgg ggcctgggct ttgcctccca ttggctaaat 6060
ggttagtata cacaatctca tcagacttta taaacaactc tgtaggatat tttattaaaa 6120
gatgagaaaa tgaagctttg gatgtcagta attggtgcaa gggggcaggg ttgttggtag 6180
agcagaattt tcaaagacca ttcctttcgg ggagagcatg gtatttgtcc ttcatgaaat 6240
ctgccttaaa gttcaggaag ttgcctgcaa cttcttgact ccccttaaca actgaatctg 6300
tcacttaaat attgttctaa atgtgtcttt agcttgtgtt ttcagtaact gtggcccaca 6360
gtttcttaat gagagtctga taataaacaa gttaaaaaag ggttctctcc ttagggccct 6420
tgcctgagct tgtttctatt tcctctggga ggaaaaaaga aagagatgtg tcagaacaga 6480
ggtggaactt ctcagagatt gagagatccg tctactgtaa cttagtcatc accatcaatt 6540
ttgttacctg aggcaggcag agctgctacc tcccacagcc tgtggttatc ctcacaacag 6600
ttactaagca cggagccctc caggcccctg ccaagcgcac cctgcatgtg ccttaggtgt 6660
ccctgagcat tgaatgggtg ggggtgccca aggttatagc aataaagaaa aaacatagtg 6720
ccaggtgctt ctccatttac cccttctttt gtagttaggt tttggctttc aaaagacaaa 6780
aaaaaaaaaa aaaaaaaaaa aagaaaagga caaaggattg tatgcttaaa atttccaagg 6840
ctctggaaaa ttgggagaat tagaaagtgt agacatatgc taaagcattg cagacccagt 6900
tcagttcatt ctaataaaca taacatgtat ggcatgctgc atgctaggca gcaatgcaaa 6960
gaggaataat attggacttt gcttcatggc tctagctgcc taggggagat gcagatgctt 7020
aaacagataa tacaatactg tggattaaag ctctagaagc cgtgcagctt tgggagtaca 7080
gacaagggat gtccaactct gagtctaccc tttaaagatg tgaggtcttg ttagtgtgta 7140
catttttatg gatgagaggg attgggcaca gttattccta acatacacat tccctttgaa 7200
gctgggaact gcaaggaatg tgcacattcc tgagagatta gaaaacatct aaaagtgaaa 7260
ctttcaggtg agcctcttaa aatgcattga ttacagagga ccgacccttt ggattgaaaa 7320
ttcttatcat tatggatcct tcttcagaag ggaaagaga agtgacattt actgggccaa 7380
acgccttaca ggttcatgtt caggagagcc ctctgagatg agctttttga catctttcta 7440

-continued

```
agcttaggga atgaaggctc atgatgctat cttaaaatag cttcttacct aagaataaaa   7500
atggtagtca attctggctt cattatttgg agggattaga agcaactctg tcaaacaggg   7560
tgacccttga tgccatttgc aaattcttct tagaaagaaa ctgcaaaagg aatcattcac   7620
ctactaatcc aacatccaat aaagtttagt tccgtgagct agtatcatca atggcagcaa   7680
aattagaaca gtagccatag aagtctaagt tgaccttcct ttgggtgaca agagtttagt   7740
aatgcccatg gattcattgt ggcaggcagt tctctggtct ccatcattac acctaacatt   7800
ttaattgtgt ctttaatttt aattttaaac gtgactttaa ttttaaatgt gactttctca   7860
gtaagaaccg tgagagagta cttaacacaa tataatacac tagattctta atatatgtaa   7920
gagatcacag taggatatga gggagaagag aacacatgag aaatgaggcc cagagacatt   7980
tagcatcatg tctgtcagct agttagtgat agggtagaac taaagtagac ctaatagttc   8040
tcaagtagtt tttttacaac atctgtattt tttatctctt tggatctagt cctctagcca   8100
tagtatagta atttttataa attatagtta acactcttat agtacttgct attttcctgg   8160
tagtttttaa atgctttcaa tatattaatt catttgatcc tgaggtaggc actattttcc   8220
ctacattaca ggaaactaca ggtatgaagt aacatgctca agtcatgtaa agctaaggtt   8280
ggaacccaga tagtcgtcta tatgtaaacc actaggatac actccctgaa atggaatgac   8340
attatctttt tgttaaagtc gtatgaggaa aagtaaacaa atatttaatg attagaataa   8400
cataatatag attttattac acaaagaaca tatttttaaa aatttcagtt aattttgtgt   8460
taaagatgct cattaatttg tttacaaaaa atgtagaatc aataggaaaa aaaaccaatg   8520
tttatacatt aatattaatt agagacacat taaagattct cattagataa catacacttt   8580
ttcaaaatca gtttcttata agcaataatc agtcagtcag aattgatact tagtttctcc   8640
aaaggattta agccttattc tttttttatt ttctatatac ttccaatgtt aaaatcattc   8700
taatgctact tattttttta attgattgct ctggggtttg taaacttact agtctctctt   8760
caaatagtat tagactactt catatataat gtaagaacct tacaataacc ccactttgtg   8820
ctattgcatc atatatcgta cttctatata tgttacaaac gccatacttc attgtaaata   8880
tttttgcttc aattatcttt taaagaatat ttcatattta ctcacatgtt tatcatacat   8940
tcattattcc tttgtataga tccaaatttc catatgattt ttcttttact agaggaactt   9000
ctttgaacat ttcttatagt tcaggtctgc caacagtgtt ctgtttgctt ttatttttat   9060
tttgccttca tttaggcaga atattttttc tgggttcgga attgtagatt gacaccttcc   9120
cctgagcatg gatgttgttc cattgttttt tgcttacata tttctgacaa aagctgttta   9180
tttcatctct tgtaggtaat tatttctctc tggctgcttt tggtattttc tccttggttt   9240
tcaatgattt gtcttggtgt cattcatttt ttatcctgct gggatttaat tagattcttg   9300
gatctgtggg tttattcttt ttatcaaatt gggaaatttt tcaccataat tttatactcgt  9360
tcgacaagtt tgcatgtgct gcttgcttat tccacaagac aaaaagctct gttcatttca   9420
gtctttttct gtgtgcttca ttttgggtat ctaatttgct atgccctcat gttcactggt   9480
ctttttttctg cagagtcata tctgcttcta cactcatcca gtgaaatctt tattttagat   9540
gttatactct tcatccctag aagttctatt tgattcttta aaaaaagatt ttcacttctc   9600
atcacattat gttttacttt aaatactagt acatagctat aatagttgtt ttagtattac   9660
cttctaattt cattatctcc atcatttcta agtttgcttc tattgatcga ttttttttcct  9720
cttttggatc acattttctt gcttcttggt atgtccagta tttttaactg aaagctgagt   9780
attatggcta ttatgttgtt gagttgggga tttgttgtca ttctttaaat agtattgagc   9840
```

```
tttgtcttgg ggagtaaatt acatgtagat cagtttgacc cattcgaggc ctattttaat   9900
atatttctag ggcaggtcta gaataacttt cactcaagag atagttcagt cctactacta   9960
agatgtgact ctggatgaca ctgaggtctc tactagtcaa agaaaagtca tgcaatttca  10020
aaagaatggt cagagatact tcactgtgaa aatggtcttg cacattaata ctttcttata  10080
cctttcatta ctgagtcagg ggtatgaatt cttttaataa tgatatataa tgtcaaactg  10140
ctttccagtt tatacttcca ctaccagttt agaaaagtgc ctgcttcata ataaccttgt  10200
tagtattgaa tttaataaat tatagtatat cctttgggag gaattatgca gcattaagag  10260
catgattttt gagacttgag aaaaggctct caaaccaatt aattaaacaa aagcagagca  10320
aaaaattcta tgtacatcaa gatcccattt tgacataatg tattctttgg taatagcatt  10380
tatattatga atgattttca tattcttatt ttattttatt ttagtataac ttcaaaagtg  10440
tctgttgttg aattttggct cctgtccaac tttgaacaag atatctggcc tttctacact  10500
tcagtattct catcgaggat ggcacaagca catatcttat aacattgttg taagcattca  10560
attatttaat tgatgcagaa ctcacagaat agtgcatgtc acatagccat acactaagtg  10620
ctcaataaag attagctgtt actgttatat caaattatct catctgtgta gctatttaac  10680
actgtactta acacggagat atagtggtaa atgcaaaaga cagttcctgt cttcactgaa  10740
gagagatttt cccctgaatc tagatgttgg tcttatttct ggtactttta ttctacttta  10800
aaaaattctg tatagaaata cttttctaag ggatactgaa cagtcaaagc atgtttgatc  10860
tctctgactt tccctcattg aaagcattga ttcttgttat acgtggttgg tagatttagg  10920
gagatgtaaa ctctgaaaga aacttgaaat aataaatcct atatctcctt tatgattact  10980
ccttttttc taccccttaa acaacacaca cacacacacc tttagctgtg cggacacatt  11040
atctaattcc acgtgcgcaa attctgcatc tagataatgt tgtcttgtgg tatctacctc  11100
attaagcagt ccttctagaa tgctttgatg actaaaaata cagatgacgt gtccttcgta  11160
caccgctttc tcacccgcat gtaggaacat gtgctttggg tacattttca agcaaggact  11220
tgtggtgatc tacctcatac attaatccta gctgtagtaa tactttggga aaggaatatg  11280
atcccaaaat aaccaccagg agaagagtgt catgaaaggt catggcaatg gggcagagga  11340
tgttggacag gagtgttcta aaaatagaga gtaagagatc aaagaaccag cagtaatgag  11400
gaactttttt ggctttggtt cccagggaag gaggaggagg aggcggcggc ggtggcactc  11460
cccagcctgt tcgtccgcca ctcatatctg tgttgcagaa gtagggaggg gttagcacat  11520
tttcctgtcc tgggtgctga ctgcctttaa attatttatt tatataatgc ttaaaaacat  11580
gtcaaaataa gaagcatgga gattttacct tactgccata ttgctactat tgcaaggaag  11640
cctaaacatt ttggatcaag aatcctcaat ttcagctttc tggaccagac cttttttac  11700
cagttcaaat tgacttttg tcatcttcct aaactatacc tgatgattaa gagtgtttgc  11760
agagccaagc actgagtttt gtgcattcat gagaagttgg gtcgatcagc cactctgagg  11820
tgtgggcata tctggccgag tgaagaaata tatcttagat atgctgttca atccctcccc  11880
tgaaatatag ctttgacaat aatgaggcga gtagatgagg acatgttaaa atcacaggcc  11940
tcttgaagga atttttggca gatgattgtg tgtatgtgtt tgtgttcatg tatgcacaca  12000
atatagtaat tccatacagt agggaattaa aaaatctggg atgaatcccg taaccttcct  12060
aaggacaatt tactcaatag tgaactaaac ttattgacac ttggctgaca gacgataaat  12120
gtatggaagt gcttccaact atacaatgct gtacaaatgt tccttaaatc ctgtggttgt  12180
```

cagagaacca gtctatatgt tcaagtcgaa tccactatct cctattcaag gaggtttctt 12240
tctttttgtt cattccaaaa cttttactgt gccactccag tgtgcaaggc actatgccag 12300
gcaccaagaa gcatttaaag atgaatcata cccagatcct gcctcaaaga acttaggata 12360
taaggaggca gataaactac tgaaaaatgc tctgcttggt ctctaattta gcttcaaatg 12420
atgtcataac tgagcataat atgacattta aaaagggact gcacttctta aatatttaaa 12480
taacaatgta catgttaatt agtatgcatt tgcctgttaa tagacttatt aacatgtatg 12540
ctagtagtca agagtactga gaaatgcctg tgcaggcaaa ggtgttcagg acaggcaatg 12600
tgaggtactg tagtgattag caatgactga cagtgcacta atcacagccc ttgttgagca 12660
atcagtcttc attaggctcc ccaaaccaaa actgacccaa aaacaattga ttcttctggc 12720
tttaaagcca atttctccat ttgttttgat ttgaggcttt t 12761

<210> SEQ ID NO 28
<211> LENGTH: 10907
<212> TYPE: DNA
<213> ORGANISM: Homo sapiens

<400> SEQUENCE: 28
gaccaaaggg caggtgcatt ttgagtgcgc caagctgctg gtttgacggc agcgtacagg 60
caggaagaga gagggagccc ttgaaatgga ggaagggcca tggggcaggg tgagaagggg 120
cagaggggac taacccatct ctgtttttat agctgtctag agtttgttag tgcctatgtc 180
tacacagaaa tatatgttat ttttataata cagtgagatc atatatatta ccgcgtactt 240
ttctcctgac tgcgtcatta ggattttcca tagggataaa tttaaaagta gtaaacttag 300
aaattttcac attgataact ttaaaattta atgcatgcta ataaaaatat ggatataaat 360
taattttgac tgtttttgat tttatgaaat tattcagtca tttttattat ggaacatgca 420
ttcttttgct gggcttctct caccaaattt taggattttg agatttctat gttattgcat 480
gtgcctataa tatatgttta ttgcaatata gattctattg acagataaat cttttcacat 540
atcaatgatt atttgctcag cacaaatttg aagaagtaga attgataggc caaatagaga 600
aacattgata gatatatgta gttactctcc caaaaggata cacttactct tccactaatg 660
tgcaggagtg tgtctaatac tcacccacgg cctgcagtga gtatgaactt tatttttgca 720
cctgtgccaa tctgagagac aataaaacat attgttttat aactcctctt agaacatttt 780
gttagtaatt tgcacaaatg cataaaacat ttataaatct tttactatta acatttttct 840
ttgtctctaa atccacaact gtgtcaccat tttaaattaa tgcatcataa tctataaatat 900 ggatatgcca aaatttactt tctgagaggt cactgtataa aagacattgc tttttttttag 960 tgaactcact gtcataattt cccttaatcc tcaagaaaat cccatgaact gtggtctctg 1020
aatatatgca ttttaacaac aaggaaattg aggcacagaa agattggaga ataactcgcc 1080
taagattaaa cagctagtga gatttggaaa caaaatttga acctagtcag gtctggtttt 1140
aacagcgata attttaatac cctcaaaaac tctcttcact aattatcata cttttctctc 1200
cttcaaaaca aaaggtggtt tattcccact gcattttcat agcctcttgt agattgtaat 1260
tgcccgataa atgcagcttc ctttatactt catttttttta tgtcttaagt tttatactat 1320
gaatttttat tggtccaaag aacaattcta atatacttct agattttagt ttctacatag 1380
gacaaacttc ttaaactcag cccggtaaag tggaagagtt tatgcattgt ccagataaca 1440
gaataattct tgacagtttc tccagaatta gcagataact ggcttactcc tcattacatt 1500
tgtagctctg gaaattgaca taggataaaa ggtaatagaa ggattattgt attagggtta 1560

-continued

```
ttaaaaattc cagatacacg aaaaagtgta cgtaaaaacc acccacacaa ttcaactgtt   1620
aactgtgggt taaaaacagt gtgttcagcc aacctctttc aacagtagtc acctaaattg   1680
ctgtttttaa aagctagtgc cttccctgcg aagcccaata gccgtcacat gattaatgtg   1740
ctagtgtctt attaactgct ctgttccaga agctgaccaa ttcacagcca ccctttctgc   1800
agagaccttt ttgtaaaaac ctagttgaaa tcatggtgtt ctgactgcag gctactgcat   1860
cccccaccaa aacatcataa agagcaaaga attactgttt ccagtaatcc aggccataaa   1920
tcaacctgct gtgagcacag gaaaaaaaaa aaaatcacga gcacttcctg cattcatatt   1980
ccaaagccta gcggtaccag caggttctgg aacacgccag ccccgtgtgt gtggtgtttg   2040
tatgtgtgtg cttgtaagca gacgtggggg agggcaaaag aaatcccagt aacataattc   2100
caaatgcttt gatcttatca cgaccttcct tgctgtaaca atattttaag attgttaaaa   2160
attgccacct tatctgtctg gggtatcac ccactgctta acttatctgg gcccagttgt   2220
ttgagagaaa tgcagtatgg catgaccttg gtttcttagc acctgacttt aatatctaat   2280
cagttgtgtg tctcggtgaa gccatccaga catgtcacac aggcgcctct ggcacccagc   2340
aattctaatg atgtttactt cattcacccc ttttagagag cttccagcag cagactcaac   2400
caccccaccc ttccaatctg ggctccaggt ccttccaggc ctagagcgta tttttaaatc   2460
ttggatgccc tttccattga aaataatttg gatgccttga ggtcagtcgc aaaaattttc   2520
tgagatcata tagagacttc tgaagagaag cctcaatttg gatcaagaaa aacattaaac   2580
ctcatggctg ttgtagtttt caaaacacaa acccttcccc tccagcaacg tcaagtctta   2640
aggtcataca atacaatgtg gagaacacac atgcacagct tcgttaattt taaaaaggtt   2700
tcttagaaag gtcccaaata ttttggcccc agatcgaagt aaagtcttaa aatctagaaa   2760
tgagagaaaa gatgtcagtt attagagtac catataataa aagtgacata aaaggagttg   2820
attttctctc tctcagtgac ttaggaatca aatttccttc gttgagaaag caatagagtt   2880
cctgccagcc tggcgggctc aacctggaac ctagctgttt tctttctggt tctgacgctg   2940
tcaccaggaa taaatgttct accatcgcga tgctgctggg gcaggagggc accctggtta   3000
ctctcttttc tttattatag cattcattga catgacctgc tacactgtag tgaactcttt   3060
tggactaatt ctggagaatg attttctgca aaataagcag tgatattctt ctacacttaa   3120
gagaccaacc aagaccctgt gttttcttgc ctcctcccta ataaagctgg acactggggc   3180
cccagatgct ctcccggttg agggggctgt gaggacatcc ctgaaactta ttttaattga   3240
cctgcttgtc cctccccaga tcacacagcc tgtccagatg tccgaggtag ggtatccatg   3300
agacgaggca ggtctgtgct gggggcacct gcagtgcttc attggggaag gcgtgggctt   3360
cctgggagag agtctcctaa cccctgccct ggtgagctcg aggtcagact gtggcaccca   3420
ggggatcagt gcccggcgcc caaggtggct tagtccatcc ctgtctgtgc tccatctgct   3480
gtgcaggcag ctctgaaacc cttcagcaac ttctcattgg ctcccagctg ggtgcccctg   3540
cgtggttcac aaccaggctc caccgaactg gccttcaaag cacactaaac ctgcacagct   3600
ttttattatt ttaattgaca aaaataatta cgtattcaca gggttcaatg tgatgttttg   3660
gtctagtata caatgtcgag tgattaaatc aaacttatta acatatccac cactcttatt   3720
gtccatggtg ggacacgtga aatgtactcc cttagcaatt tagaaacatg caacgcatta   3780
ttaacgatgg tcaggaggtc agccacggat ctcaagagct ctgagcctga gaatccgcct   3840
ctgggggagg ggggcctgac gagagaggct tacactgaag agcacttggc tttgcggccc   3900
```

-continued

```
ttgccatacc cttgcacttg gaatccaggt ttgtgtctct ctccaacaag aggcctgtga   3960
cgctcgccct gcttgttctg ttgaatgtta ctttgcgagc gcgtttacac aactgtcact   4020
tgaggtttgt ttttagcgga attgtccttc tcctgaattc ctctcacctc ccccacttat   4080
ctcccggtaa actaaagcca ccgagctggg tgggaagacg gttcacatgc tgacattttt   4140
ttgtgtttag aggctggtct tcaaaaatcc tcacatgtac aacaaggccc cagatttgag   4200
gaggaaaata actctgcagc ccagtcagcc gttccagcca cctgtcccac tcgcttctgg   4260
taggtgtgtg gctgtgaggg cccggttgga gctccaggct aaataaagct gcaggaacag   4320
agataaacaa gtgctcccaa ctcaaatgcc tgcacacaat atcctttatc tgggcaagga   4380
gagtggccgc cccccataga cggacccaca ggcgcccccc gaattaattg ggacatattg   4440
ttaaagggaa ggcccctcag aatagatgcc aaactccaag gacacaatgt caaattccag   4500
aaggacagcg gcatgggcca atgggaaaaa ccccagccgt tccgcgctga atcggatccc   4560
atagagcccg cctgcttcac atgctaacgt gatgatgaac gtatccaagt atcagcatca   4620
aatccttgag gactatattt gcaatgtcat gtaaaccgtt tcagggagca aactgtcctg   4680
ctgtgacttt atattaatct ctggcttctg gctggtcaca gggtgtcaca tgtactataa   4740
ttagattttg gaagtgtgta cagggaggag gtggtgtaat taaggtaacc tatcagatgc   4800
ccaactgcat ccttcagaaa ggagctgaaa cgcccgccct cccagctttc acactgccct   4860
tcaagggcag aggcaccaga acctattctc cacaccagaa tcaatccggt gaggttgtta   4920
gctcgtggtg catatccggg gaaagccgga gggcacttag actttgactt tgcatttgta   4980
caaagtccca gatgggggac tataagggag ttggatgcgg ggcacttaaa tagttccaac   5040
aagtgcacgg gggctctaga agctgatttg gccaaggtga gctacagcga gcaacaccct   5100
gcacctttct gcatcttcca ctcaaggatt ggcgcttcac accaggcagc tagctcctaa   5160
cacccacctc taagagcaag aagagaagga actgacagaa agtctaaccc agctgtccaa   5220
gtccaacccc cgggtattga gctctgccca cctaggactt agtgatcagg cctcagtggt   5280
caaaggaagc atgtgggttc gaatcccagt tcctcctcac ctgggctggg ttacttcagt   5340
caagttactc aacctcccag gccacccgcg cctcttcttc acctccctga ctacctcccc   5400
ttcccactgc ctctggtgtt ggctagagga tcactttggc cactgggatg atgaggagtg   5460
acatggctga gatctgggag tacctgctca ccgccatgtg ctcccctggt aaccctctca   5520
ccatatttgg aggagccaag gccaccaggc tggaggaagc aggaaaaggc cagtggccct   5580
gtcatccacc gagctctaca cccccgcagg agccattctg gccgaccctg aagcctgaat   5640
cagcccagcc tcacccgggc aaaatcaaca gtggttgttt gaagccactg aattttggga   5700
aggtggttaa cagcaattga agactgacat agttcctaag cctccatttc ctcatttcca   5760
gaatgaggac aatgaaagtc attccctgaa gggcagtcgc caggacaagg gaggggcacc   5820
ccagccctga gcctgggcaa acccagaagc ttttccaaat ttctaagttt taaaaacaac   5880
agttgggcat gtaagaaata caagctctac cttttttttt tttttgtcag agcaaataaa   5940
agaatggcag tgagcttgca tcatttctcc caccttttca tccccagtga ctgaaatgat   6000
agagcagcac tcacggcaca gggcaggttt tgtagccccc aaagctgaaa acggagggtg   6060
agagagggct ggtgccaggt gccccagaag cttatgtatc ctcctcaaca gcagctccca   6120
gccctgcaca cgttggagac accaaaagtt tttctccctc ctggtcttca gacaaagcgt   6180
gggaaaggca gggctaatta atggggcacc agaaggcatt tgccatagtc tccaaaaatc   6240
aaggaaaagg agaaagttgc tttctgaaaa aagccctcta ctttattctg tcaataagag   6300
```

-continued

```
ctaaattaca cacaagtgtg taaggagtgg aacgtagaag agagggagga gaggggcccg   6360
ccgtgcaccc ccccaggtgc agcccaggag cggagaggag ccgggttgga gccttcctga   6420
ctccagcgtc aggattcttc ctgctcctcc atgccagcca gcagagtgcc tgattcaggg   6480
ctgggagaaa cgcagcgcac ccaggatgaa gctggggctg cagggattac ctctgtggaa   6540
ttaagggaag ctgataagat tcattattac aagagcgatt ggtaaggtct gttatttggg   6600
cgtgtgactg gagcttctgt tggaatgaca tttttattca ttcaggaagc atttattaaa   6660
cactgaaaga atagctcgcg gaaacaggag agcgagcttc ccgatgttgg gtagatgaca   6720
cgcgagggag ggggcatgag tgcccacatg ttcgtgaagg aggcaggcct ggagctcgct   6780
ggaacagccc actcagggtc aggagatagg aaggagctta gcggaaccgt cgctgggatt   6840
taaaggggac acattggggc ccctgaaggc tgctgtggac tttcccagag aaagtcccag   6900
gtatctgtga aggtgatgtt ggtcaatctc agtgttaaag taaaaagaat caggtttctt   6960
gacgataaaa ataattgcca atcctgcgca ttttgtcagg tccaagtgaa ttagaattag   7020
ggtggccaaa tttagtaaat aacaacagag tgcccagtta aattgaatac tttagcagca   7080
tgtcccaaac atggccaggg tgtcgtattt tgtctggaaa ctctacttgc aagcaggagg   7140
caggaaagaa ttctggtggg acttgcattg cattgaacaa gagagcagca tgaccacagt   7200
gccgggggcc taacaggaat tccccattct ttgtcatatt caaagtcttt gaaggaattg   7260
aatacgtttt tggagtagag agtatttctg taatggactc ggggaaagaa agcggtttga   7320
acagtaagac tgcaaagtcc tgaaagaatc ctgaaagcac ctatctggaa gctttgctga   7380
gaggccccgt tcctctccgg ctctgtggga aactgaaggg tgtgttttga cccagaatcc   7440
gcagggagag ttgaatttta caaatcactt caggatgcag cgttgagacg gggattggag   7500
aattaatttt ttcctcctga gtaaagcagc tcttcctaaa gctgagaatc ttagcagaat   7560
gaataaacaa tggcagcagt ccggtaagca ctgtatgacc ctaatcattc tgaccattac   7620
cacgttttac aggattaaat aggagagaat ccacgtgaca tggtgctcct gagaacaaag   7680
ctaaagtatg ccaatcaaac catgtgccct ggaggaaaaa cttgggcact ctcttctagc   7740
agctaataaa aaataggaca acacttgaat tctacacgga gaactgtttc ttacatttag   7800
ttgatacagt aagaagtaac cagctacaga gaaatcacaa gactggatta gaccagaaca   7860
tttgtttatt aaaatgtaat ttaagtaatc agaaccttgt gaatgtttca aacggaaacc   7920
ctagaaaatc taagttttct catgagatat tttctagtaa acacttccat tgccgtcaca   7980
cctataaagt gagtatgcac ctgtgtatga tcccataaga gcacttttaa agtaaaaaac   8040
cactataata tgaatatgat aatttccttt tgattttatg agaagcgctt gatcccaaaa   8100
ctgtatgaca gctcactctt ctacatagaa tcaatacttt attgcctata aatctaagat   8160
gcatataatt cttaagtctt cttttcaaac actgctaact gttaaagtat gtccattaaa   8220
actaaggaaa aatcattttt ataaaatatg gatgaaccta tgtctaaacg aagatattca   8280
taaagatagc acaaaaaaaa tgaataaaaa agaatattaa gaaatagctt tgaaacagaa   8340
gccttagaaa aaataaatgc ccatggtcaa acaagtttag gaaaaactct ttgtacaaaa   8400
tgttttcata ttaaaggcac tgagaagttc tgcaacaaag aatcatgttt aattgtattt   8460
aatccaccat ttccaaaatt tgaaatgaga aaaccccact gctcatacct tttattaacc   8520
aaaagaatca tttcttagga aattctaatt tgagaaacaa tagatcgttt aaagagatct   8580
gtatttgcct ttcttaccaa actttcaaaa ggaaaggaag tgtattgaaa aaataatttg   8640
```

-continued

```
aggttttatt gactcatgct gtcagtcgaa gctttctgtc catttttttac gaattgggta   8700
tattccagcc tcctggtctc cagccttggg gagtgacctt cgtttccagg ggaaatacag   8760
gtgcccagaa cttccagcag ggggctctgt ccgctagcac tgactgtgaa ggactcaaag   8820
ctggttcaag gttaagatgg ctcaacaagt gacgagccag aaatgtcatc tggccactag   8880
gacgccgcat tatgaaagtg tgatcatggt tcaagaacgt tgccatgagg aaaatctgtg   8940
acggaattct attattaggt tttatcgtgt gtgcattttc aaacatagta agacagccca   9000
aaagggaaaa agtagaacaa gccaaaaagt attttaaaaa aataattatc caattatagg   9060
gctcctgttg aaaatattaa aagacttaaa agtttcccta catggttgac aactcaagta   9120
tgcccacttt ctatcaaaaa taatgcagaa aatacaaaat gcgagagaaa agttgaaaat   9180
aaatggaaat aaactacttc cattgaaacg acaaatataa ctcttcagaa ataatgtctg   9240
caaatgagag aagcacattg ttttgaggaa gctgtatttt gatacccccta taatctggat   9300
tattttttct taaactcttt cttccatatc cccaacatcc accttctcca gccaaagcaa   9360
aaacgtgcta tttacaaatt aaattgtaaa gaatggaaaa tacttgattt aaggtgaaag   9420
ccgcaccact ttagccagaa gagttggaaa gaaataaagt ggccaagcaa gatcaaaggt   9480
gcaaaataga caatggacac acacagcttt ctgcccttcc tttattgcca gggatggtgg   9540
cttattgaag gcattagtat tcccactggg agagaaattg cagcatgaca ggtgcaagtg   9600
gctagtaaat tacggcattt gcaggagaga ggaacacttt attccctccc aagccttagg   9660
agagtgtata cataacacac ccctcatggg taagacaatc aaacgtggcc attctcttgt   9720
tgaaatgcca caactatctc tataaataaa gcaaatagac cacacactga ttttcatgta   9780
ctcatgtgtt gcttctgaga acatgatttg ttttgatctt actaaggatc aatgttatat   9840
aaaggtgtta tttccacata gccagtactt ttatgtactt ttcattttcc cggaatgggt   9900
acatgatgta cactgtaaag ttttggcagg aggcagaatt gcaggggata caatgtaatg   9960
tacgtaaatg ataataccaa gcatttgcgc ttagattggg tctcgtcttt tcattggaaa  10020
tgtgacttca gggaagagaa gctgaagaat gtccattcct ctgggcatac ctcatgcaag  10080
caaggccatg tggtgactat ttctagcagc taatgatgag gatctggaat aacagctctg  10140
actaaagggg agaggcagcc ccaagacgca ttcacagagc cacttgccac tcacccatcc  10200
ctagctgacc aagccccgcc tggagggctt tgagacaaaa tgtaattctc tggagtttat  10260
gtcactgtag tggaaactaa gagctaaaag caaacaattg ctccatagaa tcagaccagc  10320
atggaatttt cagagtatcc taaatatcag cccaacagaa gtgttggcaa actttgagaa  10380
cctctacagt aaaggacagg gaggcactgc tgaggactag atggggtggg ggagggcaga  10440
agaacagcag gagcctccag agctgtcctt aacccctggc ctgtgttctc aaaaccgatg  10500
cttggaagcc acctccatct ggggcttcta tcctcttgtc tcttagtgcc atgtaaaaat  10560
gaaatttctt cttatgccca taagttataa agctctatgt ggccatatga acttcaaagc  10620
atttaaattt cttatggatc ttatgtgatt aaatgtgtgg catcctgaat aatgaatatg  10680
agggtaacaa aagtggtact gttgagaaag acatttataa tggtctaaga tacagtatca  10740
aacacttagt ctggacaata agatcttgat aatatgtttc ttttttttaag ttttaaccaa  10800
gggtcaccaa tgacagaaaa atttataata aaccacttcc aaacaatgaa tatcttagat  10860
gaacaaagct gaaaaatttc agattccaat tcatcttttt acgattc                10907
```

<210> SEQ ID NO 29
<211> LENGTH: 3962

<212> TYPE: DNA
<213> ORGANISM: Homo sapiens

<400> SEQUENCE: 29
atctcagaag caaggaaggc tctttggagc accagagcat agtctgggaa caaatgagtg 60
acaggctgaa aggtgttcca aagaatattt tatttcaagg ctgctttgca caaatgagga 120
agatgagacc tcacattccc aacgctaggc cactgcagaa cttcattcca acctaacact 180
cctgaccctc atcctccgcc tgcacatgag gtcatagaca aaaagaactt aggtaacctg 240
ccttgagtca caaaacaagc aggtgaggaa tttaaacctg attctactca gacccatatt 300
cttgagccac ctgctcatta tatgcagaag aatgttcaga agttaacggt tggggggtat 360
atatgcactc agaaaattct agaaggaatg ccatccttga agcagccttt tctgactata 420
ctaaaagagc cctcccacct tgttgttatc tctttaacct gcttggttgt ctcatgacac 480
ttatgtaaca tatactggat ctatttattc tctagcttcc ctctagaatg aggaggagga 540
caatgcctag acattgttga tttgaaaaga acttaaaatg gtctttaaag tgcaaaaagg 600
taatctcccc cttcctggac agagcttctc tagagcagaa agttcttttg attgcaaaag 660
agaagaccat tggaaatctg cttagataaa cttgctttga gtcaaaagtg aatcattaat 720
gtttcaactg ctaatccact tagcgtccta ttcacccaga tggcttttga gcactcacat 780
catgcttttt gaaagataaa atttccagtc accagaattc aattgagaag acaattgatg 840
gtagatgaag agattgaagt ttctgagatg agtgaacaca cttatctggt caatgtgaaa 900
tgaatgaaac atttgaaatg aactgatatg agttggttgg gttttatccc tataataaac 960
tctttccctc caaaaaggat taggtcttct gcgaatagag ttataaccaa ctcatctctg 1020
tcctcaagcc atatggcctt gacctttctt agtgacgcct agtcacttta aacctgttgg 1080
agatttttct tgtttgcgtc cttctgaagg gtgactttcc cagcttcagg agccatctaa 1140
aagccaggag caatgcatcc ctgcattccc tgaggctgct ctggctggct tcctccctct 1200
tccccgaaca gaaccaagct cctatagaaa attcataaat tcttggcagg aaagaaatcc 1260
tcccattgga aggaacagat gttgtacgag taactttgcc attatgctat tcctaatatc 1320
atagttttaa agtgtggggg gatgttaact tttttacaaa tgtcaacatg ttctgggcag 1380
tttttccatc tccatctgtg gcatgcacat accaatcctt ctgctgattt tccagggagt 1440
agttggaaat tggaaatata ttaaaaagtg aaggcggaaa ttcaacaata tgctaatgta 1500
tagtaatatg ctaaatgtca gaaatattct ttctcgtcgc ctagaacttg gatggtgtac 1560
agacttctaa caaagtaatt aactgtggga aaatcagtgg agctagctgg ggtcccctcc 1620
ctggggacag cgatgcccgc tgccagagcg cccgctggct gtggccgggc ccagaacacg 1680
cctgatcgct tttgggttca aagtcagaat cgggggtctg ggtgggatgg ggtggagtgg 1740
gaatcgctgc gcagaagcag aggaaggtga ccgggggcgg ggcgaggaag cagcggagcc 1800
agatttaagt gcgccgccgg atcgtcccgc agtttccgct caggccaggt ttccctccgc 1860
caggtcgtac aaaccagtcc ccagatccgt gtggggcccg gaagcacccc agaacgttct 1920
tgtccgtgct caagtggagg tgaaatggga gcgcgtgggg cgcggctcgg gggagagccg 1980
atcacccagt cccagtgggc ccctgtgcgg cccccgcatc cgggaggccc gagggccgga 2040
gctagaggcg ggcgcagcgc ggtctgcagt gccccccacc ggacggcccg gcacaggacg 2100
gctgctggag ggagtcactg cctggcttcc agctcccggg gactgacttc taggcttccc 2160
tttggctaac gaatagacgg aggtcatgta accattttct acctttccgt agaaaaggaa 2220
cctgagcacc cagctggggt ccagtcatct atggctgtgg cctcagctgt ctccttttttg 2280 aacctaatat tctcattgca aaatgggagt aatcatatcc acccacagag tgagaaatga 2340
aggaccctta ttcggggcat cagctggcgg gtcccagacc acctgtactg tagcacgtag 2400
caggtgcagt gcataacttg accctactca caggcggcgg gtcctttttt gaaacacata 2460
gtaggtactc aatgtgtggg aggttttaac tgttgggatt cttcttcctt ctctcccctt 2520
gacacccctt ccacaaatgc ctgggatcct ttctgaattg gtgatgttag aaactttaag 2580
tgagaaaaaa aaaatacaga aaaccagtgt tcaatattta catggcctca ccagtcacag 2640
tgcacttctg tgtacattat atccatttaa ccattttcca gatgaacctc aaagaggtag 2700
agcgactttg gacacagtgc tcatctctac aacacagagt cttctctcaa ttcagcctta 2760
tctctatgct gttagacaaa gatgctgctt tcctaggtat caaagtggga cttttcaccg 2820
gccatctgag caagcgttct ttgagactct ttggaaatga taggacacaa actttattaa 2880
tacagaacat tgaacaaatt agagagtgtt tacatattat gacaaggcat gcagcagctg 2940
ttactttacc aaaactattc attatgggcc gtttgtttaa aggttgccct ggtggcttgg 3000
agacagtgcc ttttgctctc tgactcaagg aagcaaaaat aagttactat caggtgatga 3060
gcatacttag aagccaaact aaaaatgaga gggtttatca tcctctggcg taaagcagtc 3120
ggctccactt tcaaactggt aaatgccagg cagttgaaaa ccatgttatt gaatgtggct 3180
ttaattcata cttctgtgta gtattccact gtgtgaatag aaatcttatt tatttgttgg 3240
tcattatgct tatttgtagt ttttttttt tgaccattat ttacaattct gctatgaaca 3300
ttcttatatc tccagggctt tatctaggta gatctcaaga agtttattgc tggatggtaa 3360
gataatgaga tgtatcttgg cctggcattc agaggtatcc gtgacctggc ctaggatacc 3420
ccccacctgg ctcccacatc cctagccaag cactcccctg tgtgccattt ccggattcac 3480
cctgcacttc catgtctcta ggactttaac catgctctag tctcctgcct gtgcccctct 3540
tccctctcct cctcttttaa agtctggctc aaagcccctc ctccctgcct gatagtctct 3600
tctgtgcctt tgcactttgt gtttggggag gaaagatcca gttaagcccc ggctttatta 3660
tctcctggca ttgtgactct agagtgttta atctctctga cctcaggtcc acatgccaca 3720
tgtagaaggg aaatgctgca acttattgta ctgaggctgg gcttactttt tttttagcat 3780
ccctcaatta ataaaatgag gtgtcacact gtggttaaga tcatatgctt tgggattaga 3840
tcatcctggg cttgaggatt aaatgagaca acgtatataa atgatttagc actgcctgcc 3900
cacagaaaat ttccagtaat ttctggctgt tattatactc atacccttct acaggagtca 3960
ct 3962

<210> SEQ ID NO 30
<211> LENGTH: 1533
<212> TYPE: DNA
<213> ORGANISM: Homo sapiens

<400> SEQUENCE: 30
tgaaggttaa gtgtaaaaat tattgaattg tgaaaattac gctgcatccc tctgggagaa 60
gcatttgcag cctaggaagg gggtggtgct cataataaaa actcgagaag ccaaaatcct 120
aggcctgatt ttcctttggt ttgaaatgca tactgttgca agggcaagta ttgacgaaat 180
cttgaacatt tctttcacag tctgttgctg catgcctgac cgagcaaatc ctgcttaatt 240
cctctgctcc ctagaggaac tcaggaccac ctggaaaaag tgaatgatcg attaatgatg 300
aattggccaa cttgccaata acgataaatt gctttgttca tccccaagga tgccacctgt 360

```
gcctagagac aaaggatggg aactcttcaa ttaacataga tgagctttca gacctatact    420

gcacaatgac aacatctcgt ttttgaccaa cttaaaatgt ttcacaagcc ttatgatcag    480

atatttatat ttgcagaaga aatacaatgg agcagtcaaa attgttacag caggcttctt    540

tttttatttg ggtggatgtg agtgtcgtgg atgaacatgc aattttaatg tgtataaaac    600

tctctgaaga aaaccactag aagatccact aggaatctgc agccccttga gaaaataaaa    660

tctgcacatg aaacaacaaa ataaatacaa acgacagtca acaaggacaa attaccaaac    720

agtcactttt tatttagtat ttttgaaatc atggaatgaa tttatgtttc aagatataca    780

agaactttaa aatgctcctt aaatataaaa tcatttctaa gccattagta acaagtagta    840

agttagccag attatagaat ttgaagtatc ctgggagttg acagattgag actctgagtt    900

catagtagtc ccctttagtc agtgactcat ataaactgat atttatccag taactacact    960

ggctgcagac aagctgaggc tatcaggttt agcatgttat gaaaaactct taattataca   1020

aacttctcag tggaaagtga tctctagatt tagttttgtt tttgtatttt gtttgaatgg   1080

attagagcaa tcttagcttt ctctgtgcct tgggtgcatt ttgtttaata cttcccagtt   1140

tacctactag gatttttgta tgttaatata tatggaaaca ctttgaaata aaacaaaaga   1200

tattattagc taaggacttt tattatacaa cctcataaaa taatttggaa aatgaattaa   1260

gattccatgc agagtcaagt agctgactgg cgtttggaag tatgtgggaa atattttttg   1320

tagatatacg tttgtataaa tgaaaaactg agcatcttta aagagataca tcactaaaaa   1380

catattatta aaaagaagac agttattctg tatacagcct aatgttgtct ttttatgatc   1440

gtatttgaat ttgcattcag gcatctgatg ctgcttgggg caagaactat gattagttat   1500

aacccatctt tggtgcctgg gacagcgtct gac                                1533


<210> SEQ ID NO 31
<211> LENGTH: 77
<212> TYPE: DNA
<213> ORGANISM: Homo sapiens

<400> SEQUENCE: 31

gtggctgctg tgtcacattt gtgttattag gtggcagaga gaagagaggc tatgtctatg     60

ctcagtgttc tgcccca                                                    77


<210> SEQ ID NO 32
<211> LENGTH: 298
<212> TYPE: DNA
<213> ORGANISM: Homo sapiens

<400> SEQUENCE: 32

aaagaagaga taagacaagc aagtacatag tttatttgga ggtgatattc aaaaactgga     60

gtagggaaaa gtaacacaaa aaaggaggaa atgccaggac gcggtgtgtt tcctaagcag    120

cagggcctca gctcctggga acatgacaga atgcccccgt ctgaagaact aaggctgggt    180

catttgcccc tggccccaat ccctactggt tgaggggtgc tcctgggatg ttaggctaca    240

cctgcacaaa ggtgagcttc tttcagcttt ggagaaagcc caggagcaga aagtgaag     298


<210> SEQ ID NO 33
<211> LENGTH: 598
<212> TYPE: DNA
<213> ORGANISM: Homo sapiens

<400> SEQUENCE: 33
```

-continued

```
agagactttg gtccattgaa tgtggtggaa gtgaccttgt gctagttctg agtgagccca     60

aaaagaatgc agtccttgca gtctctctct ctctctctct cccaccctct gctccccacc    120

ttcccccacc cccctggacc cacccccgcc cctcctcccc atgatcactt taagtcacaa    180

acatggtctc aactcaaatt taaaatgtcc agtcaagcta ttaatccaaa ctcccaattg    240

gatctatgtc ctgtccttct ctggacctcc tcccctcccc cacaagtggg ggctgtggag    300

atagtaaggg gaggggaagg gtctcacttg agctgccgcc atcctgctgg cttccagctg    360

acagtgtcac agatgtccca cagatggcca tctgcagggc tccctcactc ttgaccctgg    420

gggggatgca cttctccttc tggaggtccc ttgcaagtcc ttccttcagg aatctccaac    480

tccagcttct ttccaccctc caggaggccc tagggaacaa gacacccctg cccccacccc    540

agcccacaac gaatccccaa acccttccat gtcccctgcc tggcatctgg aggggcag      598
```

<210> SEQ ID NO 34
<211> LENGTH: 5448
<212> TYPE: DNA
<213> ORGANISM: Homo sapiens

<400> SEQUENCE: 34

```
cgtggagacc gagagcagca tcagcagaca ccagcactgc ccgttcctcc tgcaagatgt     60

ggagggagaa aagacagccg ctgagctcca cagcccagga aggctggaat cagtgatttc    120

cttatatgat ggacaaggag actgaggctc agagaggtgg agcgatgtcc caaagtccca    180

agctgcactg agctcctaga tgctgtgacc caccctgcac gcctgacacg gaccgacttg    240

aatgcccagg agtggacctg cggggccata agggatacat acaacgtaac tgatgatacc    300

caattcactg gaatctaaaa atgaagtttc ccaaagcaca cttctcatct aatgactgga    360

aatagactcg tgttaaggtt gttgatttgc acctatttct cctgggaaat tcaagaaggg    420

ctctcagttt gcagcttgtc cctgaactca ggcagatgaa gaacagggag ggtctcaggc    480

ctgggagctg aagtgggggc caaatggtcc cctgtgggtg tgggagggat ggggcaggaa    540

gccaagcaag acattttacc tcctgccaga cagtgttttt agggcttaag tgatttcctt    600

ccattcaatg ttaagttgta gaaatagcca agaggaagct tcgtgtcata cccaagctga    660

tctaaattgt ttaccaccgt tcagtgtaat ctgtgagatt gggatgtgtg aagactgggg    720

atcttatgtc ccaactctta cagaactgga ctaaattaat aggctgtcca ttttcccata    780

atctacccaa tgtccctgat aactcaatat ccaaaagcat tctccatact gtctcaagca    840

gctggaaggg cacaaaaatc tgtggaaatc atctaaaact tggtttctga agaagttacc    900

aagaattagt gcatgtcatt ctagacctca gtttattcac tacatgggta caatgcctcc    960

cttgtgtcta caggaggtag ttagagcttg catatcatct gattaatgtg cagaaaaagt   1020

agatttaact agctaactag aatagaattt actagaataa ctaaagagat agctgccttt   1080

gggataacca agagaaaata atgactgttt agcccacaac taccttccaa ggaggacttt   1140

tgttctgctg agcatcttga tgtgtttatg caaagaaggc tgagacaaca ttggttcaac   1200

ataagagaaa atgatggatt tgaaaatctg acaatccaag aggaaaagaa aaaggaggga   1260

gaatgtatca gacaccttgt gccctgcaac atctgtccag atcccctcca tcttgtcatt   1320

tatgtgcagg gtggctgtct tccactgcca gcacctgcat cccttcacct gagcgctttc   1380

tctggccctg gagcctgctc tgcccacaag cacagtagat gtatttttct cccttcctct   1440

tccagatgca ctgtgcgtaa tttataaggc atctcagaag atggtcacac aatgcttgca   1500

gctattgcct cttatgggct cttcctccta ccctcccttt ccttttcact tctgctctct   1560
```

```
aagatcacac tccctacata gaggcacaca agacttgcct cagatgctac tatctgaata   1620
acccaggatg agacagggga gcttatctct cagcttctga cctattcatg catctaacag   1680
agtatctaag gcaattgtcc cttcctgctc actatcttca gtcagcatga tgtcaccagt   1740
ataagggacc agcaggatag tggcatgttc ttatggacta tattataaca aagagctgtt   1800
atgatactcc tggggcaaaa cagtgaaata tactactgta tctgccatgt aaaagtgaac   1860
tggttttctt ccttgtgatt ccacttgcca ggtcactctg catcccacca ccaaaggcta   1920
tgttggtata ttccagtaaa gataccgtat ttgcatggca gctgcaatgg atgctaccat   1980
ctggccaagt ttatggaaat ccactatcat ctgccactat caatttggct ttcgcagggg   2040
ccttaccata ccctcatcat ttaagtcatg ataggggttc taacccctgc aatactttct   2100
gagaggtgat ttgcttctga tctactgcct tgaagtggag gaaaagtttc aaggacttcc   2160
acttgacttt tcctacacaa gtcaagttgc taatgtaagg gttctgccag aagctaagac   2220
tatctatgta tttgagatca ggccgggtgg tttcctacaa ccagtaatca gttaaggaaa   2280
gaacccagtt gcttcacaca tgagcctgtg tgatatgtca gtgctaatga gctgttgctg   2340
cattgcagcc ttctcaaggg tggccgcaaa ggactcctcc cagggggtag aactatgagt   2400
ggggcactgg tcaaactctt tgaaagagag agaagtagta ttatgtagat gcctgagcag   2460
tgggccttcg atgttggcca gaggcctgaa agacaagatt ggatgatctg ggacaggaga   2520
tctagggaag cataatgtag attgacctac agaaatgagc agtctttgta tctcaatgct   2580
cacgagaaac catccaccac agaggagatt caacagccag gatcctgtgg atgtcagcca   2640
gtctctctcc ttgcccagaa gcatgggccc catccctcta aagcagatat agctgctgac   2700
attgatgaat gcccagcctg ccagctgaaa agactgacac ggagccctct atggcacccc   2760
tccgagaggc cagccaaccc tttggtgata agttgattga gtatgttttc ctcttcagca   2820
tcagtacaat ggaaatgggt ttgccctccc tgaccaaata cttgggtctg gaaaccaagg   2880
agtagtggtg gaattcagtc cttttcctct cccagtgatc cactgaaact aagctctggt   2940
ggggtagggt gctagtgttc agcagaactc ctccaaaaga acaataaggc cactaacttg   3000
aagttgtgac cactaggtca ccttgagctc ctcatgccag tgggcaagca ggcaaaaaaa   3060
gagtgactgc ataagtgggg ctattgagcc ctgatggcca ccgggagcca cagtagcagc   3120
tactttatgg ggcagagaag atatatttac aaagggaatg tcctggtgta tttctggtac   3180
atgcatatcc tgtaatgata gcaaatgggc acatgagcaa tcaaggcagc tgagaggtca   3240
gacccttaaa ggataaaggt ctaggtcacc tcactaggct agcaagccag atcatccaaa   3300
gtatggactg agaataaagg aaatcagact gggtggggga ggagggatat ggcactagct   3360
acagctgagg gtttggcttg tttcactctc ctgcttctca gagatctaag ttggttatga   3420
tcttgaaagg gattctgact actggactcg tacccctctt cttagaaaat aaggagaaca   3480
tcatattctt tcaaaattga aggtcctata tgatagcata cacatctcta accatttcaa   3540
attctctgaa tttcctgcct ccaagtggtc attcattcca gccacagcca ttgctgcaga   3600
gatcaactca ccatccaatc aattacgggt aaaactggca gtgccttcat ttttgataac   3660
tctcacctca tacttaggga cttcattaat cctgagacat gagatgctgt agggttcatt   3720
tagtgcccac acataagcaa cttggaaatg cgaaggaaat aatatgtggc cagctttgaa   3780
caatgagaga tggaaaccag tggatgacta tttctccctc cctatcacac atcagccctg   3840
agcagcagct tctcaaaaaa acacaaggag gacagacctg ttatttgctc ttacttcttc   3900
```

-continued

```
cctgcttctt ttccccctcc aagtttgccc gacacacgaa tgctataaaa atggactttt   3960

gtggtatcaa ctgagacatt aatacaacgt cttggtcaat agaacagaac aagcacacat   4020

tgatgagtta taaccagaac ttagaaacaa gagctcagca tcagaggtga acataagaag   4080

ataagcttct gggaatgtgc ttaaatattg aaaatggctg tgggcttcca aaaaccacag   4140

aatagggga gatagaggcc attcccaagg gacaaagaag tccccatcca acatctgaca   4200

aatgagcaat ataaagtatc caaaatcaga caacaggggt ttaaatccag agactgttct   4260

ttaccagctg gaatatccag agatcttcaa gcctagctcc actcatgccc agagagaaga   4320

aggggattgc ccagggccac tgtcaatcca atgtcctgac tcctatccaa tgctcttttc   4380

tctgctcagt ttccccacat tcggggtcaa gaccactaca aataagaact ggaaatgcat   4440

atccatgttt atcatgtgtc tcaagtctct gcatgctctg ctaagcactg ccctagaggg   4500

tgtcactcca ccaaacaaca ttggtcagcc acggttgact ggttttttta cctgtggccc   4560

gcctgcatca gaatcatttt gtggaaagca tgttaaaagt acagatttct agtctctaca   4620

caatcaaatc agaatgtcta tagcgggctc gagaattgca attaagaagc tccctggtct   4680

tcttatgcac ggccattgac ctaaagtcac acttcggcac ctgttcctga attctatctt   4740

ggaatttctt gcatgggggt agccccaggt atttaatact gtctccacga tgatgcattt   4800

gaacttttta gctcagacaa actgccaaga cctctcttag atggattttc ccatttgccc   4860

acccttggaa aagcaagaaa aaaatgtatt ctgttgagtt aaggccttta ggatccaaga   4920

aagcagccaa gagctagaag ggaccttgta cctgatccca agcccaatag aggctctgct   4980

gtacaaattt atttaataaa gaaataagac aactaaggaa tcttctaggt accatttgac   5040

cacagcctgt caaagagttt gtgggcaaaa cgccacacgt ttgggctgct tgccttccat   5100

tctacccagc tccctcatca gtgcacagac aatgactgcc gcttccacag tactgtaaag   5160

aagatggggc aaatgtaaaa acactacatt taactgctat ttttgtctca aggatgaggg   5220

ttgataaatg tgtccttgag ataagccaga gacggggaca aaaatctgtc caaagagata   5280

gatgttccca aatggcaggg ccacacctta ctcttgagag tggccagtga cagactttct   5340

ctgttcccct ttatctgcct cactgcctcc tgcccataac tgttagaaac agctctgctg   5400

gacatgactg tgaagtggtc actcggagct gccacaggtt gtggcttc               5448
```

<210> SEQ ID NO 35
<211> LENGTH: 6087
<212> TYPE: DNA
<213> ORGANISM: Homo sapiens

<400> SEQUENCE: 35

```
cctctctagt tacctcaaca ttcctcataa ataatatttg acagaaaaaa aataactcat     60

agtacagcta taaaaaaaat cttcaaatat gcacatctaa tgtttgctac atgatttcat    120

catccaataa agggagaaaa atgccttaac atatcaatta ccagtatctg ccttgatcaa    180

aatagccaga tagttaccaa aatcttaatc tcacatagag ttacgtggat aagtaaagta    240

atgacagtat ttaacaccac cacaaatgaa atttccatat tatcaacaaa catcaattga    300

ggaatcactc tattagacta gaatattgtg ctatagtgac acaggtacca accacaaaag    360

cctagccagc cactttttta ctccactctg gaaagtctaa agactgaaga gtagaatcgt    420

cctttagaat gaaggagact gagaattaaa gtcagcagag caggatttga attgtggtac    480

aagccgtctg gtcagacagg ccttgaaatc atttaatatc ctgagccctt aattttctca    540

cttaaaacag aaacaaaata tctcttcttt atttcaagag gttgggatgc ttgaatggaa    600
```

-continued ccataggaaa gaattttatg aaatattatg tgaatatgaa gctgaaacga actgaagtcc 660
tgtgtcacat tcaaacgttc ttcactctga ctctatttaa tggtatgatt caataaattg 720
taggttcatc ttaatctcct caaaatactc ttggcctttg caaagtgggg gaaggaatta 780
gtaactaaaa tagcaagaga agcttgctgt cagttagtct cctggaaaag tactatactg 840
aagattcaat aagcaatact gtaacttact aagatatatg tgcagataaa atgattgctt 900
agctggagaa ctcaagagaa tcagctgaaa aactattaca aatagtgaaa gaatccagca 960
tggggcccag gtaagaaatt atggaaaaat caatactatt cttacatttc cacaaccaga 1020
agacataata gaaggaatca ttctattcac aaagagggca aaaagataaa aaattccaag 1080
agacaaactt aacagtaatt tttttaaaga ctgaagcaaa ttgaattatg tttttcattt 1140
taaagacttg gcatcttaag atgttgattc tttcagagct attttataaa tactctattg 1200
tgaatcacat ccccaaaatt attagtagga ttttcaaatt aaacaagttc ctacgtaaat 1260
ctaaaaaagc aataagagcc aggaaaaagc atctagggaa aaataagatg aatgaggaag 1320
gactgataat accaattaaa aattggagag gagaaggaac aaagagaggg agggaaggag 1380
ggaaaggaga aaaaaagaaa ccctaccttt tatataaatg agcaattata aatggaataa 1440
atgaacaact aacaagtagc ttttaatctt aaattaagca caattttaat aaaataggaa 1500
atataaaatc tactaaaatc cttaatataa tccctggcac atagaggcat atttgttgaa 1560
taaatagtaa gtagtagaga tatttggtaa attgtctttt ggagtcctaa tgccatgaga 1620
tttagacatt atgctaatat gtgtttttta aaggttaatt agtattattt ttaactcaat 1680
tttgaaaagc tgaaattata ggaatcagga ccaaaagttt caattcaaaa gtaacgaaaa 1740
aaggaaataa attttatatt tttaagtaaa tatagcaaaa atttctaatt gttctcctgt 1800
gcttggtcat acaaaatccc caatcattgt agcattataa ttatagcagc aaaactaaat 1860
atccatcaat ggaggacaga ttcgaacaaa tcctggtaca tttatgcaat ggaataccat 1920
ttagttattt taaaaaataa agtagatcct agcacttgat ttgtttcttc caaaatatta 1980
tgaagcataa acaatgtctc aacttggact gtctcttttt ttgtgtctct cttggttaag 2040
ctacgagctt agagaggtca ggaactacac taaccccagt gtcagaacac aataagaaga 2100
gtcaataaac tgaggtgaac tgaaactttg gaccagttca ctgaacttta gtacctattg 2160
tgctattctt tagcaaattg ggtaacagat aatatggaag gatttaaaat gctgaaacta 2220
aaccactaaa ataaaatact agattacttc tcttgagtat ggagaaaatg agccttgctt 2280
ttaagaagct taccacatta gcaaaagtct ggaaatacaa agcacactca aaattaataa 2340
agttaagatt ttcacgctgc catttgtgca ggctttatct gacttctacc tgttattttt 2400
ttattctcta attctatatt gatttctgtg atgatggagg tgaagagcct gtcactggca 2460
acatagcacc atcctcgttt agagtaaata aaactattta aagcaaattg gaaactgaat 2520
gacagaaagt gccacagatg gaccacactg ggaacaggag tggaatgccg cgttgttcat 2580
catccccacc atccaagaat gaagaaatgt ttccccttaa cttgagtcat tattgctcat 2640
ttcctctttc ttttcatgtc ttcttttctc tttggagatg tctctagaat ggaaatacat 2700
ggaactcatc caattgacac ttaactgtaa cctctatgat acaaagttac ttcgtttacc 2760
ataaagctta agcgccccaa tgcagctctt tattaaagtc atgataattc agaaacttaa 2820
ataaaagtat tgctaaaagc atcatgaatg gcaaaagtct gaggacttct ttcagggtga 2880
aaggaccaaa ggttaacact ttgctgccta ccttagaaaa ttgcttattc ttttaaagac 2940

-continued

```
caagtattcc tttgtcctgt tcaatccagg aagacatcag aggagaatga aagaagaaag   3000
gtttatgaga accgagcagt gctcagacaa gaactctacc cactgaagtc aactgggtaa   3060
tttacattac ctatgcagta gtaggtctac ccagccttgc tctaaatgtg tacaatctcc   3120
caaactgatg tatgacctat aattgatctt acctcctgct ttccctataa ccactattca   3180
ttgctccgag cctggaagat cagatattca aatttaccag ctcaggctcc atgttcctac   3240
cggaactctt gacctggtta caggaaggaa aaatagtgac acacttttca ctgcctaaat   3300
gtttcagtct ttctgatttg agagcccact gaaatccatt atcttggtta agcttaaaaa   3360
aaaaaaaaaa aaaaaaaaag aagaagatac ctgtggctgg gaatagcggg gtatactggc   3420
tcaagatggg agaaataatt ggtaaaatat atatcttcag tttctttctg tatttttctg   3480
ctcttttacc cttttttttcc ctttccaccc ctcacaccct atgcttctgt caatgactgc   3540
aaagatacca caattggtaa agttatttct gttcccttct ccttttcatt cgtcaggtag   3600
tggcaaaggt ttaatccaag ttagtgtaga ctaaccaact tatctaagtg ctctgatatt   3660
tactgagtag tgctctgtac tagatgcagt gaaagcgaag aggaggacct tcatccttgc   3720
ctgcaagaag tctacactcc aaagggggga aacaagcatg ccaactaaaa caagagatag   3780
gaaacagagg gaaaagcaac taaatgccaa tgaggagata gtttcactaa tccctaccag   3840
gaaattatac tacagaaaga acacttagga agaccaaagt gcaaattaag tttcactgga   3900
tgtcatgcaa ggaatcctca agctcaaaga gcatctctcc tctcaagttt ttgcacaggg   3960
tggggaattg cacagtacaa atgcttacaa ttccaatcac gtctactctg tgttatgttt   4020
ccacctgtgg tgactctatt ttgagaacag aacttatttt gccaaaaatg gtacaaacga   4080
agctgcaaat tgactagggt tgcacaaaca agctaagcat ccaggtctat aaacattaaa   4140
ggagtagata tctgactggt aagttacccc tctttccttt tttttgttat ccagggaatt   4200
aagcaagttc agagaaggta attacccaat taaacattct ccctgatgca tggaaaggac   4260
aacacgcagg aatgcagaag gagacaagtg ccaagaggcc cttgctataa ataattgctt   4320
ttcccacgtc cttgtcacct cttcctaaaa ttagaattag cttcctggcc tgaaggctaa   4380
acctcactcc cacaccctcc tttctcacaa agcaatattc cctaatgcaa taaggtggtg   4440
ggatttcaac aacagcaaga gtttaggagt caggtaactc tttgctcaac cctgcttttc   4500
atttcaagct ttattaatct gtgcaccaag cttatctgaa aaatgggatg aggatgatga   4560
tggtaacagc tagtaatcgt aaaacaagca ctgtgcaagt gctttacatg cattatttat   4620
gtaatgggca gtattcatga ttattactag caattgagtc ctcctttaca gatgaagaaa   4680
ctgaaattct agaggagtta tgccaactct tgaccctttc tactactata ataataactg   4740
ctaaacaagg attgaaaggg ttaacattaa catatatgga cacaccaatt aatgctattg   4800
tcatcgcttt tgatgttgct gagcatgata ctgtttttgt tgcttttctc tctccccaga   4860
tactagcagt tctaagatca aataagcaca gaccatccac ccatatactg gcaagtgtaa   4920
accaatgtct gggaacattt ttgagcacca aataacaaag ctgatattag atctttcatt   4980
attaaaatat ttctgatgaa tgagagagga agagaaaaag aaatgggatt cagtactaac   5040
taaaatgatc ccccatgcct aagtttttaa aaattcagaa taacaaatga aaggtacact   5100
gttcttacat gtgtcactta gatttcttaa aataaaatta tgtatcatat gctaattttt   5160
gactattcaa actgcacttt gcttcattct tatcttttaa ttcacttttc attgtaatga   5220
aataactgta atacatgttt aaacctctaa cacgctaaaa tgccaatcag ttaaacacaa   5280
tagcaagcat ttggcataca cctggagact ttcctaaata aaataaaatt attattacat   5340
```

ttcatcactt cctttcttat tgccaactaa tgtccccgtg tctgaaaggg tcattttcaa 5400
ctacacatct atttataata gtgtgttcat tgtcttcctt cctctggtgc attatctatg 5460
accttgacca tttcaggatg gataaaatgg tgccataaac atatgtttat gaagctccag 5520
acatcttgta agagatttcg tggttattaa aagcagcaaa gagtgacaag gacagttcta 5580
tactataata tgcctgtcaa gagaaaaatg tcacccttac cataaagtac ccagaggcat 5640
aattaagaag tggcaaagga atgatttcct gggcacagta ataacagggc tgagatgaaa 5700
tccagcagca atggaagctg cctctccaat gtgcctgagt ggagcccgtc cacaccaagg 5760
gtccagggca tagtcatgct cccacgtcca aaatgtaaca tcaaggaatg cccaggacag 5820
ccacactcag aagaggtggc aacaagaatt tctgggagga tgtttctgac tttcctaatt 5880
gcatcattat gaacctcctg ggcaccaact aagaacatta aagaaattga aacttcacag 5940
ttcctaatgc tccataccca taaacacaga tccatacagt ccccacagaa ctataaataa 6000
atcctgcctg aaggtctcct tcctgttcac gtttctccat aaaacttggt agtatctctt 6060
tccttttatc taacttttat ccttgtg 6087

<210> SEQ ID NO 36
<211> LENGTH: 2007
<212> TYPE: DNA
<213> ORGANISM: Homo sapiens

<400> SEQUENCE: 36
ggaaggattt gcggacgcac gctcttgaac gtgcgtgttc tcagaactct gatatgtgtg 60
tctcggcagc tgacaccacg tgccacatct atctttgcag actgccccat ccagcttagt 120
gaacagctga gccagaactt ttgcaaacat ctgccgtggt tgagttgggg atggaaaact 180
gcggagcctg atggttctgt ggagatggac caacaatggc accacaggta agaagggtta 240
tcttcttcct ggcagaaggt ggcaggctga tgctgtcgtc gttcctgtgt gtctgacaaa 300
tcacaaatat gtcagatcgt cacagctgag tcaaggattt ccatgagccc tgctggggtc 360
agcttgcagc gccaggcacc agtgtgactc gcctgtggaa gccggggctg ctcagtgggg 420
ctgagaggag ggggagagag aggcccatca acaaacagtg caaacgccgc agctgccacc 480
accgagttcc agtccctatg agacgtttta tctttcactc aagaggactg aggctcagga 540
ggtttgaatc caggtcattc tgacccagga gttcagactt tttcccagcc cagcctttcc 600
actcgaccaa ttagcacagt caggtgccaa agactttgct tgcgggatcc atttgaaatg 660
gtttttttagg caaaggagac tagatgaacg tggaggagag ggaaagtata ggcgcgaact 720
acagaacagg cttattccag tgcactccaa acccaggcgt ggtgttcttc cttctcgctt 780
actggtatca cctgttgtcc tctgggcacc tgaagctcag catttcccag gttgcttttc 840
cctgcatagc cctggcaagg ctactctgtc ctcactttac cccagccaca tttcccatgt 900
ctttgggatt tccttgagac tgatctgccc aagcctcctt gggggatggg atgatttcag 960
gattttgaga gaaaataaac atggagctgt gatttaggaa aactgtaatc aagcagctgt 1020
tgggaagacc caaagtgggg aagaaagatc atattatatt attcgtgctg gctaaggaca 1080
gctgccataa aatatacaca tatattttat gtgggagaca cgtgctgcat gctttcgtct 1140
tgtccgtgca cagacatact tggattgagt aaagggagtt acaaaaggac caaaaattgc 1200
tgaatcattt caaagtgctt gacagttgtg taaagacctt ttggttttgt ccagtgaaaa 1260
ttatttttta attcaatcta aagacttcag agcctttaag atgcaatgat gggtttatca 1320

-continued aaatactgtt catgctattc gtttcttagc ttagaagtct ctataaatta gcaccagttt 1380
tccaaatgca tttttatcaa atcctatgat cctaggctgg tctaggtacc atcccccaat 1440
cttaccttgt gtgtttctgt tttaagaccc tctcccatgc tggcatgcct ttgcttttgg 1500
ctctctcttt ttaaagcctg cccaaaccta agcaatgtca gggcatgtcc ctttcttcct 1560
catgaggcca tttcttactg cttacgcaga aactgatcta ctttctttac attccagcaa 1620
atttgttgtg cctgtccctc ttcgtttagg tatttctaaa actagactca gttacttcac 1680
gtgtgaagtg ggaagcagta ttttctcaca gggttttgtg tggtcactta gtaagggctg 1740
gcagccacag gcttgttgag gacagtgggg gatgttactt tttctcagag tcttcatagt 1800
aacttgtcaa ggacatcact cactgtactg caagtgttca tcatggccag cactcaggaa 1860
ctttcagaat attttgagtg gagttttgtc ctgttttagt tgcctgttgg gatccctgag 1920
tataaaaata agtgtgtgcc tgctcccagc attgacgagc ttcatgaacc ttgaaaatgg 1980
aaactttatt tctctgtagg atgtgag 2007

<210> SEQ ID NO 37
<211> LENGTH: 16213
<212> TYPE: DNA
<213> ORGANISM: Homo sapiens

<400> SEQUENCE: 37
ctctggatgt gtccgggcag caggtagcgc tgagcacaag gggcaggaga ggcgggacca 60
ggccagagga gggggactca gcctgccatt gggccagggg cctcgatgac aggagcgatg 120
agcagtttcg tgtcacctaa tatagtcata cggaaaaaaa aaaaaagccc tgcccagctt 180
ttttaaaggg gccacgacgc atttggaagg gtctcctgct cctgcagtgc gtttgctccc 240
tgtgagcctg aaaagcctac cagaggcatg cagagtcagg cctctgggca gggctggatg 300
ggtgtgggtt tgaagaaata ttcctcgcac ccaaaccagc atgggagaga gaaggatggg 360
gtgggaagcg ggggaggaga gtgatttgag gaaggcttta ttactgaagt gggatgaggg 420
agagtctgaa taggaagaga agcctggagg acagggctgc tttggggata gcagcagggc 480
gagattctgg acaattcggg ggtttggttt ggcttggcct acagggtcag tcatgccgca 540
ggctctgggt gcttctgggc cgaaagtaag ggcaaggtga gtgatggtgg ggtaggagtt 600
gctgcctcct acagacaact ccagggggcc cagtaccctc ccagggaaaa ggaatcccag 660
ctggtaagct cagcttccca ggagacacct gtcttgtgga gtgcccacct tgtttcccct 720
ggatcccacc tccctccttc ccgtgccctc ccaggccctc atcagggtcc tagcccaggt 780
ttagctcgct cctccaggat ttctctgggc ctctacttcg tggggcagcg gctcggtcag 840
gcgcgtgggg gaacattttt agcccagggt cagtagagta ggaaatctgc cagagtttca 900
ggagcccaga tcctgcccgg gtgcatttct ctgggtctga tgaaagcttg gggtctccca 960
gacactgcag agaggagttt tattttgctt acaattcagg aggggcaggc agagcgggcc 1020
caggttaagc cttctagagc tggggatgac aggatttgtc agtggaaaag cgttggcttc 1080
tcacgcggag tgcgggttgg caagaggcgc ttggagtaga ataaaggcgg cgcagggcca 1140
aaaactacct aaagacacag ctcccgaggc gcgcccaagg tgcggaggaa acgctccatg 1200
tatggggaca aaatagtgtc tgtccagaac gtacatcttg ggtgctcaaa cccgacagcc 1260
gtctgagacg cagtgaagtc agcattggcc tgatttggga cttttcctgt ccctcatcaa 1320
agccacactc ccaggacctg gggcctccat gctgggggag aggtgagccc cgccccagga 1380
ggcgcgcaac gcccgcttct aggcgccagc cgtcagtaac aggcctgggc gccacgccga 1440
aatcacgccc cagggactac tgggggtctg gaattgttag tctgccttgc ggcccttcct 1500
cgcctggact tttggccacg ttaccgttat ggctgtaaat taacctagct tgggggcccg 1560
ccttgcttga agattgtttt gtgtcgttgg agaggatgcc tatcgccgag gcggtgacgt 1620
ctggcaaacg agccacatcc gattcaatta aatgtctcgc tgaaaagagc tcggaacgag 1680
ggtcctggga gcgctgttaa gtgaatctgc tggccaggcg gctcgcgatg acagtttgaa 1740
agattagtgt gagcggacgc ctgaaatatt accgtttaat gggggacatc gaggctacat 1800
ccgggatccc tgtttttagt ttttttttga gagctctgga gaaagaacat tgcccttgca 1860
aatcaaggtg gcaaggattt atttcctttt tcgggtaagg gggcttccag aactgtcagt 1920
cctgtgggtc aggtgttaca aaaagggaag aaaactctcc ctatttgaac aagatcagtg 1980
actgttacac ctctatgctc tttgtgaatc ggctcttggc ttcctcttgg gagaggagat 2040
ggggcaaaaa cggacaaata tgcaaaatag aattggggcg acccatgctg gtctccttag 2100
aggaaagtcc agagccattt gcagcttttc ttcagtcctc actgtttccg agtgagttaa 2160
aaaaaaaata gaaattgcaa tagttggggg tgggtgggag gaaacttgat tctctgcccc 2220
aacaggacca catctttttt cccaagggcc gctgacccaa cctggccgcc tctctgaaac 2280
aaacagcctt cagccgaaag gcagagagag acaaaaggag agagaagaga tcgaaaattc 2340
tgtgtatttc cttgactttt aaagagttgg tgctttaaga taatccaaat tccagggtgg 2400
ctcgagcgca ttctccgtga ataaattatt attaattgaa aagcgatcgg cgcagccgga 2460
gcggcccccc tttcgtgcaa tcagccgcaa aaggtatata tgattaattg aaagataagc 2520
tggaactatc accgggaatg tcattaatgc gctggggaga cgtccattgg agacaggcgg 2580
cgttatccgc ggctttatct tcaacaacgc ctcgctctcg gcccgcgcgg gggaaacaga 2640
tgggagtttc tgtctgggac gctcgcccca tgtttatatt ttgggaagaa tcgcaactcg 2700
tgggagtccc cggctggccc cctgataaat gaacattagc actttttcgg actactgtat 2760
caacaaaggg gctgcggcgc tgcaataatt ggcgagaaag caaacagagg gccgagagcg 2820
cgactctgct cttcgtccgg ctgatggatg agcagcgcgc cggactcccg gcctggcccc 2880
tgcttccttc ctgcgggggg cgaagggccg ccgagctccg gaacaggcgg cctccgcggc 2940
ttcaggtgct cagctgttca gtgcccacgg cgctctcacg gatctcgtca cggatcctct 3000
tatccgactg caggcctagg agaatgaggt tcagagagga gtaagttgct cagggtcact 3060
ggaggaaagc aagaccccca ccatcacccc ccaccccgca gccaggggag aggaccaggc 3120
tgttggattt gagaatagac aagggcataa agtgagaaag agagggggag agaggaattt 3180
aacatgcgtt cacctcgctc tcccactttt cctttctttt gataacactt tatcgagata 3240
taattcgcat accatactcc acagacaatt ttagaacatt ttcaccccaa aaacctttag 3300
ccatcaactc caatcccccc ttcccagccc taggcactgc taatctattt tctgccccta 3360
tagatttgcc tgttctggac atttcataca aatggaatca tacaatatgt ggctgtttgt 3420
gtctcgcagc gttcacttaa cataatgttt gttcgtccat gctgtagcac tatcagcatg 3480
gctgaacaat attccattgt atgtctatgc caccttcgtc cattcatcac ttggtaaaca 3540
tttgggtatt tccacatttt gctattatga atactctacc ttacagtctg agaaagcttc 3600
cccctcctcc cctattggca tctgagtctc acagggtggt ttaatgttcc gctgttctgt 3660
cttaaaactc ttcataagtt tttaagcaga gtctccacat ttctattttg cgctgagccc 3720
acaaactatg tagtcaatcc tgctttctgg gctgtctggc agagcactgg aatactaact 3780

-continued

```
ctctattgcc tagctgggtt ttggctcccc tccccagtgc tagagctagg acagacagaa   3840
agtctccaag ctgctttaag agcgaaactt gctcagccat aggaagggct agagcccaca   3900
gaaggaaaga gcagatccac atggctaggt gtgtgtgtgt gtgtgtgtgg ctggagaggc   3960
cgtagctttc acccagctgc caaggactcc acagcttggt cactgttgga ttcttggcct   4020
gattttctcc atcccttcac ctacattgag tggatccact ttattgaggt ctaatgtacc   4080
tagaacaaaa gtgtacagtt cgatgagtct tgacacttgg atgtgcaccc ccataactaa   4140
tcaagataca aaaacattta acctcaaaaa tgcttccttc tccccttctc agcccaagct   4200
gccactggtt ttaaaaatat atcctcttag agttttttttt gcaaatttaa aacatattat   4260
aggatgtata tatatttttc tttacgtttc acaaactcct ttgcattttg tccttgtcag   4320
ttttgttttg ttgtcagttt tcttaggctc tggggagtat gtttcccaac ccgaatttgt   4380
cctggattag tggatatgat cgattccgag gatccgaggg agtcgctttc agacttccgg   4440
tgtcctttcg cttaatttcg tcctcttttc ttctctgggc tgggtggtgg ctgccacatc   4500
ccaccccttc tgccccgacg gctgcaaacc gcttcagcca aaacgggcgg agaggcggag   4560
agatcgagac gctgtcagtt cctcggagtc ccgtcgctgg aggtcacagc tgggaaaatc   4620
aggtgacatt cgagttggac aacgactcag ggttgtcctg gggctctgcc cggcgggttg   4680
aagcccgggg aagcgacttt ggaagaacct tcggcttggc ggttcaggtt tgggaaaaga   4740
gagctggcgg ccgcctgttt ttgtgcccgc ggaccagccg ggccgacggc agcgctgcgg   4800
ggggtcgtca gaggtgaaga gtcgcaccta ccaccgggtg gccgaaaccc ggccgcagct   4860
ccgggagccc ccagccctgt gctgctgcgg ccggctcagt gctgaattga tgctggaaac   4920
ggctggccag cgggcctagg gtcgccgcct ttccctcctc gcctcttcct tccttccggg   4980
tcgtgccctc caacctgctg tgcgttaccg cagccaagtt tccaccgccc ggcggagcgc   5040
attgtgaaca gcagctgaca aattgtcaca ccaaaaaaac ccaagtctcg tataattcgg   5100
aagcggtgtc tgtggagagc ctcccggggt ggcacggggg acccggaggc caacccgcct   5160
ttcgcggagg gcgttctgcg cgcaaattgg cgaaatgcgg gacgagcgcg ctagagggtc   5220
gtgttgacac atcccatact ttaagtgtac acatgacagt tgcagacatt caagcccctta   5280
aaaggagcag tgggtgcccc tcgccgcgtc cctgccgcac tctagctgct ctgggaacac   5340
acacgtttgt gcactctaag cggccgaatt gtgcgtcgcc tgtgcagacc ctccgttgtg   5400
tggccttgtg tctttaggca gggaacatct tttgtctctc cgcaagaagc tttcctccag   5460
gaaagataaa gtaatcgata gggtctttta aatagctccg cgtttcctgt cgggagagga   5520
gtatcagcgc gcgcaccaaa tctgctctgg tatgtcacct tatctctcgt ccccgctgtt   5580
gtccccaaac gccgcctgtc aaaggagacg ccacccgcat taggacctag actggggccc   5640
ttccgctcgg ggtcaggcgc agcgccctcg gctccgccgc ccttaggggt ccgggagggt   5700
ggagagaagg ggcgggagcc aggatgaggg tcctagaacc cgaggctggt aggagagcaa   5760
actctcactg aaaccgggcg catgtgggct tccttttaac cacgaaaata gggaacaggc   5820
tagtagcgaa tcctcctttg tccgcgtgga ggaaaatcag gtttattctt cagagagggc   5880
attggacttt aggaagtgcc tgccgggtcc aagtttacct tccggactgc gacgaggtga   5940
ggtttcgcca ccgtcctgcc tctgtcctct ccccaacctg cgtcagctct gactccggcg   6000
gggccggagt gcagggcaga ggggaaagaa ggtgccgcca aggctggtcc ttcagtccgc   6060
taggccctgg gcccccttcag acgtccaagc gctgttatgc aaatctcctc atttttttttc   6120
tgtattcagt cggctgtatc cagtttttta aaaataaaaa taaaccctct cagctgcctt   6180
```

-continued

```
ccatgcacaa accctcaatg acctctataa acatagtcag cctctttcca gcctcacaat   6240
tacccacggg gtcttgagaa gctgtaggga aatacctctt ggcttcaaca cagacttgct   6300
cccttccgat tgcccgggat cactctggat tactccaact gctgacggag gaccacccac   6360
caaaacacag cctggccttg ggaaagcgtg ggttctcatt tatcagggtt tatttatcca   6420
aaataaaaat tactgtagaa aagtaaagga gggaaaaaca tcttcctccc ttaggaggct   6480
tttttgactc tttaggcctt cctattccct gtggtccttt gacattatct cagccttaag   6540
tgaatttgat tattatcagt aaccaaaggt tgctggtgga actagctgtg ttttcttatg   6600
atggttcatt tgcaccgtgt gctatgctgg aaccagaaga acatgaactg gacagcccaa   6660
tgcttgaatg cccttgtctc tggcctcttt ggttactctg gtgactagtt actcagtcct   6720
gggtagccct ggagatggct gcctctccca ctcaggcggg gccctcaagc agggctttgt   6780
tagaaggagc cctgggagag tttcttttct tctaacaaga ggtgggagat gaggaagtga   6840
caggcatcgc cctctcccta gatgtgacag tcatcgccta gggacccagg ctcttttcct   6900
aacagaagct gtactgcccg ttcattagaa gtgggagagg ggaggtggga ccaggtggca   6960
ctgctctggt ctagtgacat acttctgacc ttgaggttgt agcactgcta gtctacatct   7020
agggtatctg tggctgggat attttcttgt ctggactacc aggcctgcca acatggtaaa   7080
atcttgaaga cagaatccag ggctggttct gcttgttttt ctcatagtta ctaaagcttt   7140
gtctatttta atgacccatt aaatgggacc ctttgctgaa ttcattatca tgcatccctt   7200
tttaatgggt cagatcttac agagcaatgc aaccgagtgt aaattctttg agtttggaaa   7260
catgcacagt gtaaagaagg agagctgagg ccttgattgc tgctgttcag gaagagaaca   7320
tgagtgaaat gtgggtataa ttttgaacaa tccttctgca atttgggaat tttcaaaaaa   7380
tctttacaaa atacaaggtg aaaatagcat aaaattagtt ttagttattt taatcagtgt   7440
tttaaacccg tttgtatttt tctttttata tcttaacaat tggggtatta tctgttttca   7500
tctttgatct ttgagatctt aggaaccctt tgtcatttta ttttgtgctg caaatatttt   7560
tgccattctc ccgtttgtct tttcaaaacg ttcattttag ttgaagacac ttgataatgt   7620
acgaaggggc cactcaaaca cggtggggtt ttgattccca gttgggactg gtcaagagca   7680
atgtcagggc cagctggccc ggtggggatt ccagaggaca gaggcctatc ccactctacc   7740
ttgggcttca gagactgggg aaacctggtt ccttgaagct tccatcctgg gccccaggct   7800
ggagggagtg ccactggcta ctcccaggga agaaggaaat tgagagcaaa tccaacagaa   7860
agaagtgagg aagacttgag tttgggctgg tgggtggagg ggacttgggg aggatccaga   7920
agaaaggaga acatcagcca gggaaatctg atgggcagac tcaggctctg gagtagggct   7980
gcaacctact gcatggaatt gtttaatctc cctgaacctc agtgttctta tctgtcaaat   8040
gggataatac ttgtactttg tcaaaagatt gtgagaacta aagaagataa cattgtaaat   8100
tcacaagatg aggatctgaa gtcagtccaa gactgtctca aacaaatgct ggaatccagc   8160
ctccagcttc accctttcct tctgtccgac tggtgggcat tggggtagcc ccctgaggct   8220
gggggaaggg cagtgaatga ggagtctcat ttgtgggagg ccctacccca taggagctct   8280
ttgtgtcagc agagggtttg cagaggttga tttcattctt gaccactcgt ggctaactca   8340
gggacaatcg aactgctgtg acctgagggg aaagacccca gatactgtta ccggctcctt   8400
cgggaaacct ccactctctt cccccctcct ttctgtgact aatttctgaa atctctgtaa   8460
ctgagaaggc attggatgag gtttcccact ctgggagggc cctgggtgcc agactggggc   8520
```

-continued

```
aagggggggc tgaggctcct gtgcagtcac atgccatctc tcaagagcag gagcgcaggc   8580
ctccagattg ggtggcagca gctgtggggt attgggataa cctcactgat gactgggtag   8640
atagggctct cttgtgttag cagagtccag aaaacagtgt gctccctgat gaaaaggcca   8700
cggtcactgt cttctgggct ctgcctggct ctgacagttc tcagctgctc cataaatctt   8760
ccatcagttc catctggcca aaaagatgtc atcaccgttt tctcctagcg acgaaaagta   8820
aaaggtcatt aactcctctc tgcctgttca aaccaaagaa gatgatcttc agtttttcag   8880
tggaaggggt tgggttgttt atgtaagtaa tagtttatat ttatatgttg acatgaggat   8940
aaggaggatg attgttttgg gtattattaa cactctgggc acccacatac ttaaaacaca   9000
gaacattaca atctggaagt taaaaggaac attagtgctt atccagttgt tttcgagttt   9060
ttttttaaag caatggaaca ctcatagcaa atgatatgtt tatgcaaaat cccaatacat   9120
caaacagaag gactgagcgt agcagaggcc ccggctcccc ctgacctctg gtggctcctg   9180
tttaacttct ctgtttttag tacctgtgct ggagacggtg gatatttcca actgctgagc   9240
cactttgctt ggactgtgtg gtctgccggg gatctggttc atcttgtttg caccgtgtgg   9300
atgctgtcag gggctgtcac ccctcctccc tcgaaggctg ggagcctgtt cttaccctct   9360
ggtctgatgc ttttccggca cacagggata gccttgggtt ttcatgttct tttctcattt   9420
cttttccccc ataattgcat ttcaggaagc gtcgggttag ttctttttct ttagtttttg   9480
tgtctagagc agaccccagt gtgcagcagg aggatccctg gacttggtta aaagaaaacc   9540
tccaaacctt gacctccctg cagctggggc cccttcacac ttgttttggc ctttgtgaac   9600
tgcgcagaac cagggctgac cctgccgaac tgtggatgtg tggccaagac aggtcccagt   9660
gtcctgcccg ggctgtgcat gtgagggagg cggtgatgca acgtgatggc attgtgacag   9720
ggtgagggaa agattgctgg ctggggcttc aaggggtgat tagattacgg cggagttgcc   9780
tgtttggcgg agatggaaga cttggttctg ttcatttcat aggcagcgga tcccgcagtt   9840
tcagactggc cagagaaatc catttagtag taggcagaaa tgtggagctg agaggctcat   9900
tccacaatgc tcctgagctt ttgcttttta cttcttcact ttttttcctt ctctttgctt   9960
tttattgttt ttctgtatat atattttaca tagttgagat catatatgca attttgttct  10020
gattttctac ctaatttaaa attatacgca tttcctcata tcagcaaata ttctcttcaa  10080
atttgatttt gggagctgag gttcctgtgg tggcccaggg tggcatacaa cttcatggac  10140
cctctttgga caaggtctct attgctggtg agctgatggg actctgaggt gggcaagctg  10200
tccacccatt tgcagcttac aacttggggc tcagagattt gtgcggctta tgttttgctt  10260
tcactggatc tttatgatct tattagaagt tgagagcaca gtgactttca tctgtggttg  10320
actaggaaac atgtttaata aagtgacgtg aaactccaaa caaaaataac attattcata  10380
ataagcgttc tctaatcaga atcagagaac agcctctcag aaaccagtca agagtcctgt  10440
tcatccccac tcctagattg catgtaggtg acacatgttt ctgtttcccc ttccttctgg  10500
tttgttctgg gcggttcctc tctccttttc ccacgtatag taacgccggt tctgtaagga  10560
atcacatatc ttgggtgctc acaggagaat tccttctgag gcccagctcc cacccttcct  10620
ctgggcacct tgcggctctg tcttagggtc ctcacgtcgt agctcagccc aagcggctcc  10680
agtgccggcc actctgtcgg ctctctgcgt ctgagagagg gtgcctcaga agggatctga  10740
gtgcccacag ccttcagaag tgcaactagg aagccaggtc actggtggct ggggatggct  10800
tgtccatcac tagcagccag acaatcgaat agcgccctag gacaggagga gcgcctgagc  10860
cttcacgcca tcccgccagc cctcatttct tgttggagca taatgactga ggacagcaaa  10920
```

```
gcccagtggc ttctcccaga tggctgcgag ctgccttctg gatcccaggg gtaactactc  10980
tgagtggcta gtgcctcaga actgaagtca gaaacctggg gttatggcca cagatcgacc  11040
accctggtgc tcagggccag agtaagacct gaccctccca aactagagga caataatata  11100
ctcatgatga taatacccag aggttaaaaa aacaaccaaa ccccgaactt agatgatccc  11160
atgtatatca tcacgtgtct caacaaagag cagggagacc aggttcttgc tggaagctca  11220
gaattttcat ggtgcctcta gaaaaatcat cccatcccag gccaagctgt gattagaggt  11280
gcttttcatc aggtctcttt cttccagttg ctctccgctc tccagctttg ttctggctta  11340
gactctcagc ccaggccacc caggggcagt ggccgctgaa gggggcagcc ccgcagctgc  11400
ttcctccaaa tgctctggga ttcaaggccg ggtgctgggt gattacaccg ctgttatctg  11460
ggattagcta ttttcactcc ctgtatttat atcatggaag ctgcagcgtg atgctgccag  11520
atgccaatgt gggcaaactt cttccttttg gacccacctg ctgttctgct gacacccggc  11580
aaggtggcag ttggtgggga ccagacctgc caacccctcc tcccacttcc cacatgtcca  11640
gagcagtgaa ctgcgtcatt gtgagagact caggtcagca gcaacaggcg aaggctggaa  11700
cagacttggg ggcgggaggg gtggagggct ggcagcagtc cctgcagaag atgcctgtca  11760
cctccctaat cccctgaagt cttcaagtct aggaaccctc tcgcctgccc cactcctgct  11820
ccaccccgac ccacgtgtat ctccctgttg cagtgaggcc agaaaaggcc aagtgcctga  11880
gagtcccaaa tgtaagtatt aaaaggccct gctgcattta cttgctccat cttcgtttcc  11940
atctcgcctt ccatccctgc ttgtcagctt gtctttcagg aaatggacag gtttttttga  12000
aggtatgttc tatctcactg ggctgcata acttacctca gcaaacttct tagagagcag  12060
agactgtagg tgggatttgc ccccagcccc ggtgcattga gggaggcttc tcccacttgc  12120
ctaggaaggt tgcctgcagg ctcactccct ttccggcaaa aataggcaat gccaggtgtt  12180
atcacatcag gaggaggctt cagatgagcc ccagggattc tgcccagaaa aaaacaatat  12240
gtttggtgtg gccactggct tctcataccc ctgtggagct ctgtccgtct gggcttctct  12300
gccctcatct ctcagggcag aaatctcaag ggtgacaagt tagccctccc aggtatgttt  12360
aaaaatcacc cagccccgtc tatatgggag tgaaagtcac ctggggcaag ctgagcagag  12420
aggccagcca gtgaagtggc tacccgtggc ggtgagagta cttaactcag acttggaata  12480
aggcttcact ttccagaaac ttccacacat tcagatcact aagttcagat gagaaagcaa  12540
ccctttatct ctcataatct ttgacatgga gcccgctccc tgcagcccct gggagacaga  12600
tactcaatct gtgggaagtt ggcctggagc ctggctctgg ctgctgcgta gacaccattc  12660
cgtgatgaag gctggcacag gaggcccctg ggcagggttc aggcttccag acaggcccac  12720
gtgggagtgt tttgaatcca acttgtttgc cgggttattc tcagtgcctg aatgtgctag  12780
aagcgaacag aagccaggat gaggcccaga agagcttgag ttaataaacc tggggaaaaa  12840
aatcaggaag tgttgtgaat acatgacatc agagagtgct ctgaatgcaa ctttcaatat  12900
atacttttat atcttttctc cttttcccac gttctgttaa cgtaagatga tagggaatca  12960
accaggttag ggaggcggca gggcccagct aaatgcctgc gtcctctctg ggctctagag  13020
aggtgctgag tggtgagggg gcctgggtgg acgctgggct tctcctcagc agggaaggag  13080
gcccagggca gaaatagacc tgggggagga tgcatgctgt atgagccaga tttggccaca  13140
tatattagga agacatttct aatcacaaat gtcttaatga aagaacaaaa tgcctcatgg  13200
agcaaggatg ccctttgcag tttaagtgga gattggaagt tctaggggtg ttggtatttt  13260
```

cagccagtgt cactttgagg gttagtaaat ttcctacctt tgctgtcagc tgtgtgaagt 13320
ggcatgcctt tgctttatct ctagaattgt tctttaagtg tcgcgagtag tttggttctg 13380
ttagtctagg ctgggagaag agaggagagg ggagcccccct gggtaggttg aaatccaaag 13440
ctcaatgttg ccttcaagtg agaacatgta ggaactgcag ggtcgggaga tgggtctctg 13500
ccttggatgg ggcatgagtt tgggtgtagg attgagatct ttactggttc agagatggac 13560
ctggggcaat tagatgacga tcaccagata gttgactttc tcgattcatt ttcgattcag 13620
tttttattcc attcagttta tttccttacg aagaagagga agaagaggga gagggagtaa 13680
aaactgctat tcgccagtct tttgctaggt ggtttacata catccatgct aaattttatg 13740
ataatactct tataactact gttttacaaa tgagaaaact gagactcgcg aggtcaagtt 13800
atttgcccaa agtcacccag ctgtcagatg caggaggtcc aaataaagtc tgttgggttc 13860
taatcctgac cattttgcta tagcaggctg atctccgatg aaactgtcag gacgatgcag 13920
atcccagccc aggttgattg gcaaatcttc ggtgactcca tggccctgct attctcaccg 13980
gagctctgcc tctcggcccc actggaagcc ctctatgtca gcgccagggc gctttacaag 14040
cacgcagtac ctcatgcatc ctggttcctc aaggcagccc tggacagtta aatggcgccc 14100
cctgtcctga ggctcagtca agtctcctgc cccagcacta aactgtctcc cttttaaaaa 14160
cattaggtta aaaaaccaag aacgtgaaga aaggaaaagc aaacaaaaaa tcttcccaat 14220
cccaatttcc agatagagag aatacattcc cacggcaaaa cagtcattca aacagcacag 14280
aaagcagaaa aaaaaagtaa actgctgggt ttccttcaag aattttctta agtaatgcat 14340
ctagttacac acatttagaa tccacaaagg ggtggcactc caggcgcgtc cagcacgttg 14400
cttttctccc gggatctttg caaaacccca ttctcgcaga gttgtctggt ttgaaggtgc 14460
cccattggtt gctccagttt cctagagcac tctcagccac gcccccgcca ccccagcggc 14520
gctgcaggaa ccagctgctt acccggcggc ctggctgtgc gcggatgctg cagactgctg 14580
cccccgtgtg gcctggtgcg gggcgtcctc gcgcgtcccg gtaaaccaga acctcagccc 14640
atcaactcac tcgtggggtc tgaggaggag aatctttggt tctcaccgtc atggctcacc 14700
cagtggctga atcctgccgc atccaggcag ctgtggaaac tggttgaaac caggatggtc 14760
agctgctacc ctgtgtttgg gggactatgt gacagtgcct gctgtgtccc tattctggtg 14820
ctaaaaagca ggagctctct tatgctcaca tggaactgtt ggagtcagat aaacttggct 14880
ccaccactta tatgctgagt ctgttcatcc atcatccacc atccatctat tcgttcaccc 14940
tcccatccat ccattcatcc gtccgtccac tcatccaacc acctgtccat ctattcatcc 15000
accacccttc accttgagtg ctgagctcta tgactttgga taagtttgag cctcagtttc 15060
cacatctgca aattgaacat aatgacacct aaattagttg ttggaagact taacaaaata 15120
atgtaggtga aatacatggt acataggatg ctctgtaaat ggcatttata atcttgtaga 15180
agcttatgta ttagttaggg aggcctgacg taggtacatg caattggagt ataaaatatt 15240
gcaagactgt tgtgcacatg tgtgtgcttg cattgtgtgt agcctgtggg ctgaagcagt 15300
gcaaagtgag gggctagagt agtctttaag aaccaggagt gctagagaga agagggtgta 15360
ttcggacagg gactgctcaa gcaaaaatgc ctatcagcca tggaaccaaa caaaacaggt 15420
gggccctgtc cctgtctgag attaaaaaac aacgagagac tttagccaca gattgctaaa 15480
ttcacttagc tcaggagtcc actgtgaacc tagacagaat ttgctagatt gcttgcaggg 15540
gcgggttcaa agattctgta cttgctactt gccaatgatt attaagtgct ggattcctca 15600
catacctata aggtggaatt attacactca ttctcgagga agagactgag ggtcagagag 15660
gataaatgac ctgcccaggg ccacacagac ttttctccta tacctcctct acctttagct 15720
tcaggtaaga actacctgaa gctaattggg tcttccatgt tggcccgagc atctgctctt 15780
cccagggagg acataagtgg ccctcttcat ccagaatgct tgtcaggact ctctctcttt 15840
aaacggtaac cctgaccaca agcactgact tttcagtctc agagtttatt aagaaaggtg 15900
cacctgactc cagtttcata aaaacatact gcaaattcct ctttgtgcat ggaaataatt 15960
acttagttga ttgtgcatca aattatttat gggtacatag gggttgatat ttctctgatt 16020
ttaaaagttt gtgtcatgta ccgtaagtgg ctggcctgcg atgtctactg gtcaaagcgg 16080
gcagtctccc tctggaggaa caccagggat gcggggtgca cccaggctgt ggggtgcaaa 16140
ggcgggaggg gggaagtagc tgtgaggtag accctggctg cgtggggtgg gggccacttc 16200
ctttctacct ctc 16213

<210> SEQ ID NO 38
<211> LENGTH: 2693
<212> TYPE: DNA
<213> ORGANISM: Homo sapiens

<400> SEQUENCE: 38
ctctttctca tcaggtctca cctcaaatgt cactcctccg agaagccctc tgatctctca 60
catcactcag tctcattttc atcacatccc ttatcattac ccaatatctt tctgttcatt 120
catgtacttc cccttgtgag aaggctcaga gcagcagcat ggtctggggt cccataatcc 180
tccaagtccg gatccatctc cagcggcttc cagtccagag ttctaggcac agcaccagcc 240
agcttcttga acgagtgttg gcatttcttt ctcagtggct ttgaaatcag acgtcagccc 300
ccaacctcgt gactcagccg gcagcgtgag aaggctggct tggggacaca aagtccttcg 360
atctttagag agatagcagc cctcctggga acggggccac agatgaaggc tgagcatgaa 420
gcctgggcac tggcctgcca ctggaagctg accctctgct ggaccatgcc aactttgaca 480
tttcccaaac taggcaatgg cccagctttt gaaagccagt atcgcctagc tatggaatcg 540
ccatgcagat agtgctggaa tgaaattaaa tttccctttt cagaacaaag acaaacacac 600
tcctctcacc catcctacga gagctgggcc gggagccctg cctccgtgcc aggattcaaa 660
gcccacgggc tctcctgctt gcttcagcag ttcctggcaa gtgcaacgga gttctcccgc 720
tttaaaatct aattgcctgc cacgcccgtg aatcccatct ccaaaggcaa gaaaaaaaaa 780
aattttaaaa aaaagttggt gggggtggga ggggggggttc tcacacattc agcccagatg 840
agcccattta agcttttgac attatgcctt ttggggaggc cgattcaaaa taaaccagcc 900
cgagaagctc ctgttttaaa cagaaagatc cataaatgca gctctgtcag taatgagaaa 960
atggaaatca caagcaaaac cagaaaactc attcccccag aatcttaatg atctccagaa 1020
taattgtgct ggtctctcaa atcaaggagt ggacggtgac agccctgtga gggtcagatg 1080
ggttcatgtt tttctcattt ctaagcaatg tgcttgtctt aatcccttcc ctgtgcccag 1140
caaaaatgct ttctttgtct ccctcaaaca aatgcagctt ctcaacaggg aaatgagctt 1200
ccctgtcttg caaacagatt tcttatcata gactgatcca ctgtgggtga acttgcattt 1260
ctcttgcata agaaagcaat ttcctgaaga gagaaagggg ggaaaatcaa accgcttacc 1320
tctccttttt tccatattag catccttagc tgaagctcct gaagatatgg gaaagtttat 1380
ttcagaggat gaatatcaat ctttcagata gcagtgggtg tttaggctct aagaggcagc 1440
caggttttcc tgcatttgtt tacaagaagg aacaaattct ttgacaattt caaagtttct 1500

```
ccagacaaac tgctaccttc tgataaaatc taaagttcaa caatgacaaa caaattagaa   1560

aattctgcca ttatagcgga atataaattg gcaggttcat ttaggaggct taaaacaaag   1620

aatgagatct taaaataata aaaaataata atgagctttg ggattaagaa gcaccagtga   1680

tttggcagac agtaaccata gcacacagtc tggggggggcc tcagacctgt cttggccatt   1740

tcacttctct tgtaggttct ggctttcagc ttcgttgcac cagagagggt ggtgagccca   1800

gcacaccagc atgaggatca gcccttgggc tgggggtggg gtcagaaaaa gaggaaagaa   1860

ggagggagga gaagggaagg aagaaactac tgttttaccg ttggttattc aatttgaatg   1920

cttgttgtac cccactatgt gccagctgag gccagaggcc aggagaaaat ggtgagcaaa   1980

gcaggaaccc agctcagccc ttttggagct cctgggatga ctttaaccac gcctgcaaga   2040

agactttgtg agtgtgtgga tggatgtgac gcccttggag gtatggggga gatggggcct   2100

gggaagggga agagacagat tcctggggtc tccatggcat gggaagaaag gggggacatg   2160

agggatagca ttggcagtct ccctgggact ggtatggttt aaactcactg caaggccccc   2220

tctctccagc aggtttgagt tgctggtgaa ataagtgggt caagggaagt tacgatgttt   2280

gggagatgct ggcatctgct accaagagcc taccacctac agccaggcag tacctctgtg   2340

ctgcccatgt gctggctgcc caaggatgct caaggctcag cgagccctgg acactggcaa   2400

ggaggccagc actttcctgg gtcttggaag gcccagggag acagctaggg aagatgcctc   2460

agagggtggc atccaggcgt aggatagaac aacacccaca gcatttctgc agccaccaca   2520

gaagtgcaat attggtttct ttctggcttc tcttgaaaaa ctagaagatt ccatggccct   2580

tccctcttac catggcagtg cctttaagaa cttctgtccc caaggcccac ggcagtggcc   2640

tctgagggca accgtgactt aatttaaatc tggagtttta aacaacgtta agt          2693
```

<210> SEQ ID NO 39
<211> LENGTH: 1861
<212> TYPE: DNA
<213> ORGANISM: Homo sapiens

<400> SEQUENCE: 39

```
ttttatttgt agctggcctt atacttggtt gagataggga gaaaattcta agtaacatct     60

caatgccagg tttctgaggt catctaaact ttaattgtcc atagacatat tgagaagcaa    120

agacttagga aagttgccag gattgctcct cgactagagt cagtcactta agtcagctga    180

cagtgttagg acaatgtttc caaacaatga gagaaataag tcaatatagg gagtttccta    240

aagcacagtt tattcaattt aaaaacgaag tttatatctt ttactttttg gaagttaaat    300

gtcctttatt ttatgacatg atgtgacagt gatgataaaa ttcttccttg gcaaaataaa    360

aataaaatga ttcctcctca tctttttctg gacatttagg gattattgtt tgcattcctc    420

tctttgttta caacaccctt cccctgacat ctcttgctct ctttggcatc ccaatggcat    480

ttactattct ccaaacaatt taaaattcaa ggtcatgctg gaattagtac ccagttacca    540

tgcatgcttt ctgtgataat taccctcagg ttttgtagga aaacagaccc ccagatgcat    600

tcacatatgc aaatatgcac tcagtaagca atgactaaga cagatgagtc ggcagggatt    660

atggagaaat ttccagttta tgtgcataat taccagaata actggtggtg gccgtgggaa    720

aggaatgggc cacttcagat gggggccggg acagctaagg aggaagtgat gtttgaactg    780

agatctgaat gaccaagggg agctgtccat gagactggtg gaagagtgtt ccaggcccag    840

agactgtgca aaggccctaa ggtaggcctt tgcagggata agagtgtgga gggagggaac    900

aaaatcacaa gtgtttactg gccttccgtc tgttgcactc tggggagggc tagtgtccct    960
```

atgcggggag ggcattagag aggccctgct tactcaggct agggattagg gcagagaagg 1020
ggaattctct agagacaaga ggtaggttgt agttgtcaag ggctggaagg aatggggaat 1080
gactggtaat ggatttcttt ttgggttgat gaaaatattc tggaattagc acaacttcat 1140
gaatatatta aaaccactga cttgtgtgtt tcaatgtgtg aattttatgg tgtgttaatt 1200
acatttaaat aaaagaaatg tgaacaaaga aggaatggtg aattttggag caatgctaag 1260
tgctgtcagg accagctgct ctccccaggt atcctgcctg cattcataaa cattttgtgt 1320
catatatttt cataattttc attttgtagt ggattatggt ccactgtgta ccacaattca 1380
caaagagata tctccaagtt ggtcatttag gaatgtttct ttttttgtta taggtgtcaa 1440
caagggcaat agagctcttt cactctgccg caaatcttgg tttttcacaa accttctctg 1500
gaatttatat tcccacacta ctgtgaatat atagttaaat tgtttgctat ttattcttgg 1560 tgccttttc cttttacatg gtctccttca taatcttttc tcaactctgc cagctctctg 1620
cttacctacc tcacccacct catcatgaaa atcaagctct tctgacctca tctgtttcca 1680
ctgctggact tacagcactg ttttgtaatg tatttaccca cctggctcct ttgccagact 1740
gtgagccccc tgaggtcaca cacagtgtct tattaatttc tgactccctg ttgcctttgc 1800
ttgcagaagg aaggtgtaaa atatatgtta attggattta attgaattgc tgaggctgaa 1860
g 1861

<210> SEQ ID NO 40
<211> LENGTH: 2864
<212> TYPE: DNA
<213> ORGANISM: Homo sapiens

<400> SEQUENCE: 40
attagacaga tacaggcata aatacaaaca gatgaagaag agagtctatc ctaagcctta 60
caggatcagt acaaatcaaa agcgtcaaga atctggagtg ggaagagaat agtgaataac 120
gaagccctta tgaaaaaaaa aaaaacacag acaagaagtg caatttggaa gagaagggta 180
taacacgaca ggagtgtgag agggcaaagg cacagagaca aaacggtatg tcctcactgc 240
agggactttg cacttgctgt tcccttgact gagatgcttc cccctagata tgcatatagc 300
tcacccctca ctttctccag gtctttactc aacaccaccc tctcagtggc taccttatcc 360
agtcaatcct aaatttcata ttacctcttc cactttagat tttctcttca gtatttgtca 420
ctacctaatc tactttatat tttaattatt tatctttgtt attttttctt tcttccacta 480
gaatgtaaac tccctaaagc aggaaatttt gtttgtgttt ttactggatt cccaaaacct 540
agaacggtgc ctggcacaga gtaagtaccc agtaaatatt tgtgaaataa ataaatcaag 600
aggacaaagg gattgaagaa gagctattat taaaatatca gttgacagaa atagaaattt 660
tacatgggag aacagattca caaatttgga cagtatggag acaatttgga gagaagctag 720
aatgtcctgc cactcataaa taaaaggctc ctaggagaat ctggggtcac tttgtctacc 780
tctctcattt ctaggcaatt ccacacctaa gccatctcag acaaaacaag atattcagct 840
ttccattgca tgtttcttag agttgaggca aacatcacaa agctcaaatt tctagccttg 900
ccactccatt ttcaaaattt acatctttgt ggagctactg aactccctca gtgtttcagg 960
tgattgggcc aggatactat tggaaagcaa gggtggttta gtgttgctct gaactcaggg 1020
agaaacagct ccctgaaacc tacaagaggc cctggtgcat tggcattcac cctatggttg 1080
tgctcacaag cagaggaaat tctaagcagt tggagcctta aatgacaagt ctacctgttc 1140
gtgtgcccta tcctaaactc tacctgcatt catttctgca tctctcacct gtctatatag 1200
atgggaagga gaggtatata tatttcaaat attctatatg aaaaggaatc agattctagc 1260
cagctgtcac tccataccga aagccacaga gcattcacag gtgcagtatc cattgcaatg 1320
taagtgcact cctaccagca ggaagcatgc gatttagaaa agaaaatgtg taaaaggaaa 1380
tgagaaaaag aagtcagatg gggcagaaac gggagacatc aagtcaatca caaactgcac 1440
aaaatattca cttccttaat tacttgttga aagctgaatt tgttaagaaa catttactcc 1500
tacttagttt aagtgtgcta gaaccaacaa taagctgttg caccaactag caaaaacaag 1560
cttctgactg catgctctga ttgatgagtg aaaaacattc ctaattagca tttaaattca 1620
tgagtaaaat agtcaacaga ctgcaataaa aacaaaataa tttaaacaaa gcaaattacc 1680
ctcttttctt gactctctct ttaaataagg caggaagata actttctgtt tttaaattat 1740
ttttattgca ttttcacatt acatataata cttgcttttc cagaacatca cacagttcat 1800
atttacttta tagcaggaaa ggcatagata ataaggagcc aaagttcagc cacaagctag 1860
tacggaaact ccattaaaca acaacagctc tccaaatctc agtttctccc tgcagtgttt 1920
gcattgcaat tatggaagga aaactgcagg tcctctgata atagctcagg agagaacgct 1980
gcacacttcc tcctccccac cctcagaaga gcgtaggaga gtacagccaa ttcctgatta 2040
tgtgtggtaa ggaggaagga gaaggaagga caacatggac agcccccaaa ccacatttta 2100
tggctacaag cattgtctcc tttaccacag aacttttgcc agaactgaac attagaaacc 2160
aaactggggc ctgcctttcc cccctggctg ccagtccttt ttggtagagg aggttataag 2220
caagtaaagg gcccaaaagc ccaagggaga tggcagggag aatatagcag gaataatcca 2280
cagaaaccag aaaggcagct actcatttct gagggaatca agaattagct acattcttgc 2340
tctctaagca acaactgtca tgtgatcttg ttaaatactg aggtttgatc aatttctaaa 2400
aattattttg atttcccaaa acacatatgt ataatctgct ccatctcaat ggttaaaaat 2460
gtgtactcac cacccttagt catctgattc taatttagaa cacatttcct ggctttcaca 2520
accaaaacta ttcattgcac tgatcataac aattctccta aaacaggcaa taaaaggagc 2580
agaacttcct cctgtggcca gaaactttcc caaagcttag gccttccagc aattacagcc 2640
ttttcactgc agtaccttaa cctattgcta ataaagcctc tttggccagt cagagttgcc 2700
atctttagag acagagggca aaaacaacaa aaaaagtctc agagcggtca tttattcaaa 2760
ctgcccatcc gagaagcctc tattcttggt aaggaggaga ctacataaaa gtacacatca 2820
agagaattct gagaatttta tatcctgaat gattaagaat ggtg 2864

<210> SEQ ID NO 41
<211> LENGTH: 4579
<212> TYPE: DNA
<213> ORGANISM: Homo sapiens

<400> SEQUENCE: 41
ctgcctttga gtcacccatc ccggtgaatg tttcagtggg gctgacccat catagggcac 60
ttttggtaga ggatgcctgt gtgaagttgg gaactggcaa ggcgcagagg atccgctggg 120
agatgacaag tccctgttca cactctccac agaaatttgg ttacttgttt aaactcttaa 180
gtaactgaac taaatggatt ctattacaca atcataattg cttcaaatta aacaataaac 240
gttttactgt ttttctacac cctaggtatt ataaagaaag tgtaaagcat gccagtttaa 300
gcgcctggag ctaaggttcc ttttggggag ttgtcaaata tgcagatgcg agtggtggtt 360
gtttttccct attgtggaag tgtgacaacc caggactgtg gccacaaaga gatggaggag 420

```
aacgaggagc gttaagaatt ggcccaaagt ctggtcttta ttttgccttc ataatttttt    480
ccaaaatgaa caaatgccct gctatagaaa tgccaagcat tttccaaatg acatttcagg    540
tggagtccat tctgcatttc tgaaaaagta cttccgaact tcagagcaga tgtcagcatt    600
ttggaccctc ctgacatgat taaaggtgca ggtggcagct ggcgctgggg agggacaggg    660
cgggagctgg cacaggcagg aggcaacacg gttcatcatt ctcccgttaa ggaagttggg    720
gaaagaagca taaacttgaa aacacacatt tttacttaaa attaggtgtg agcattataa    780
cacaaatgat cccaggctgc cactgctgat gaccctgagc ccatgcccaa atctggatta    840
tgtccaggga tctcagatca ttctctctgg attctgggtc tcagacagag tgtgcagtag    900
cagtctgtca gggttgggaa gaccaagggt cccagcccct ggtgtctctg ctcacatttt    960
caccctggct gcctccatgg gctgtcctat cccctgacag tgctaccggc agggtcctgc   1020
ctggaacaag gggggtagatc ccatttcagg agaaacgtgg cctctcccct aattgtaggg   1080
gggaagcaga aaggcaacca caggcctttt gttggccaac agaaaggctg aagtttggtt   1140
ctccctggtt gcatttcaaa gaagtctaaa aaaaaaggtg gccccagtct catctcaggc   1200
ctgggctcaa agtgagttga ctcactcacc ctcccctgtc tactcagcca tgccatcgga   1260
gcctcccctc ttgaccttga ctcgagctgt catttagaac ttatcatcag cacatagcta   1320
gacttttgat tcctccagtc acatattata tatatttttt atttgaaaag tgctttttca   1380
ggtatgactt ggaagagaaa tttattgcag gaaagttagg aaaccttcca actttaaaca   1440
cacgtgcaca cacacacaca cacatcatga actttttcaa taatagatga ttaaagaagt   1500
ctgtggagag ttcttaatga gctccttcta tgttgtctag gagcaatgat cgttaaaatg   1560
atcgggggga ttgaattata aatttccagg gtgtcccaca cggggctggg gctgatggcc   1620
ttcatccggc ttgttaaaac cagtagttgt gtaagactct gactagttaa tttgaaagct   1680
cccctttggg atcgatatat ttaatttcaa gaccttaatt catgagaatt tattcgaaac   1740
aggcacgggg catgagcaga gcaaaaagtg tccaccaggc ccgctgcacc aacgctgctc   1800
ttggctgggc gcgtcatggc tacgagaaag cgcatgacca cttccctgtt tggtttggtt   1860
tgtgttgtgt gtcagggcgc aggggtttct gctttcactc aagttaattt atttcctttt   1920
ccttggtaat tgtgaaaaaa caaaataaaa cctcctgtga gcctttgaac ttctggaaaa   1980
gccctttgct gtgaaccgct gactctgaga aagctttgag cgggctggaa accatttttc   2040
tgcaaccttt tctttcctgg ggtatgtctg ggtgcacacg gctccccaca aggcaaaggc   2100
tgtccctgga tggttggcaa aatgcgccac accagagtgg gtttgtgttg gcaggaggca   2160
tgagaaaacc tgctgatggc aggggaggac ggcgacacct gggaacaaat cctccttacc   2220
tctaattaca aagaggaaaa agtcactgaa aaaaaaagta aatgtcttaa tatgtcatat   2280
ataatccaaa gctaccaccc cacttcaggg ggatttaaag tggtgatttg gttccaggta   2340
tgcgtcctgc caacctgggt gggtgttccc ttacaaaaaa acaaatgatg gagagttttt   2400
actaggattg gtctgatcag ggtagacaca ctgccagtgt tcttggctct gactccatca   2460
gtggccccca tggataccca gtctccttct ggggctcaaa tcctaatgcc tgtcacgttg   2520
gatgctgccc tagtgggatg ggcagactca ttctctcctc tctgggtctg cttgggccat   2580
ggaaggcatg caaagtcctg tgatgtgagg ccgattatgg ctcagaatct tccagacact   2640
aactctgcat ggctccccga gtgcagaata ccatatcttt agaatcctgt cttttgtttt   2700
tctacattag tacagttgca cagccctcag gagaaggtgg gaggtgagaa agctcttcca   2760
```

tggaagctgt gtgtactaca ggaggacctt gaggttaata aatgtcactc cacatcagca 2820
tggacctcta ggtaggagag atctaagtgg tcccttggcc ctctcatttc aatatctacg 2880
acatcacctt gaccacccca gaactctcat cttctgaagt ctgccttgtc tgttgccata 2940
gctagctgtt gccataggct ggggctacac acacacacac acaatttatt tctcgtgatt 3000
ctggagcctg ggaagtccca atgaggcccc agcagattct gtgtctttgc tctctagtga 3060
cagccaccac cttcttgttg ggtccttaca tggtgtaaag gatgaggctc atgactcaat 3120
cccctcccaa aggctcccct tcctaatacc atccccttgg gggttgaatg tcagcatttg 3180
aagtttgggg agcattcaga ccatggtgcc ccatctgttt tctcatggga ctggcactgt 3240
ctggggactg tcatatcttt ctatggacca tgtcctgccc atttttttgt tgttccctca 3300
ccttctcctc tcaacctcat aagacctggt ccagtcttct gcatacccac ttctagaaag 3360
catttaaggt gattccaaga taaagaaaat agagtgagat gagagaaata attttcagat 3420
taaataaatt ctagttcttt cagatctgag aacctaaaag ttgatgccta caagatgcct 3480
tccacataga aatacacaca tgagaaggtc cagggtctgg cactgcacac ttggttatat 3540
ggagatgctt gtttttctcc agtttcatac atgcatcttt tttcactcgc tggattattt 3600
gcacttagag gaggtgtccc gagctacatt tgcatccatc ataaggcata ccaaaacggg 3660
cctacaggag gtgtgcaatc caacctttgg cctgatggaa gccctgcctt gaaactgaaa 3720
gttgcccaga aaggttagga aatgctataa tgttttcatt actcattccc ttgctgcatg 3780
cccttaagtc ttttagaatg tttgtattat tttatggaat atccaatttc tgcaccagtt 3840
agggatcaga ttacaagcta actctggtga gtttataaag aaagaattta atgggaagat 3900
gtgaggtgcc tgacagcatc tgtgggaggt gttgagagcc acactctgga aataagcagt 3960
aggggagcaa gttcactctg cagggacggt cccgttgtgg gtgtttattt ccataatcgg 4020
gtccttgtcg tagccatcag cactctctca accgtggtgg ggctcacccc ttcaagagtt 4080
aaacctgggg tttcagtcaa tgccttaaga agcaaactta gtttttcctc tcacataaac 4140
tgtccaattc tattataggc agccacctca tcctagaatc cctgaatcct gcttctgtgg 4200
cagactcagc ccagtccccc acctgccctc aataagcact tcaatcctca ggtcataatt 4260
tagctagggc tttagattcc tcctcagcca gataacagtc cagctttccc ctggagttgg 4320
ttatgggcag cccactcaca gttagcaatg tctcttcgct agattgtaaa ctgtggagga 4380
gcttcgtctt attcattagt gtggggccat tggctagaat attgtgagca tgcaataggt 4440
atttgatcaa tgtgtgaata aatgatttga atagcattct gcacagaact atacttagga 4500
ttatttactg gaattctaac cccaggaact ggctgatggt gagaatatta aatgaaacca 4560
aacttcagca aggtggaag 4579

<210> SEQ ID NO 42
<211> LENGTH: 2397
<212> TYPE: DNA
<213> ORGANISM: Homo sapiens

<400> SEQUENCE: 42
ctgggatgta ggtctgagct tttggtgctt ccatctctct gtcaccctca gacatattct 60
ccttccagtt cacagctcca ttttctcgcc tgcatttcta gctaagctct gagtcatcga 120
tctcaacctt taattcaagt ttgtgcctgg atctgaacca aaccatagat agatactcat 180
aaggttgtgc agatgagaat gtgtggttgt tctgcttttg atcagcagca ggctgagatt 240
gcttccagga taacgggagc caagtctatt ttcttaggtt acaatgaagg actcaagtcc 300

```
tgcctggagc tggctgagtg atgaactaaa ttggagaaat gtgccatgtg gctcgccgtg    360
ttgattgagt tcacttgagt cccctttttg cagccaagtg cattcgtaac ttccatagca    420
tggtactata aatctgctga ctatttctgt ggtggttact attccagttt gaagagaggg    480
gtgtggagaa acagtagtga aagcaggaaa aatttagttg tatgtgcaac acacataatt    540
gcaagatgtt tattattcca ttaggcagtg ctggtctaca gttaggagtg gtagaagagg    600
agaaaaggtc atgacaagga gaaccctact atttgccaga cgctaggccc tgccctgtga    660
gcctcttggc agcccaagtt gggaactact tatttatttt actgttttag gtgaagcttc    720
tggagaagaa actgtttgct cagagcccaa cattgaatgt gtcaaatttg gtgtttggac    780
tcagcagttc aatgtcttaa ctattaatta ttgcctttgc caagatgctc aataatgtat    840
gccttgccaa gtgattttga ggattaaatg caatgttgta ggtgaacact tagcttaata    900
agagcctcgt aagtaaggat ggctgctatt aatgtaaaaa taataataat gaggaggaga    960
aagtggagga gatggagaag aagaagaagt agggaggaaa agaaggggag gagtagaagt   1020
ggggaggagg agaaagagga gacaagttat tgccatcacc acaatacgtg ccagggctat   1080
cttgggcact ttacgtacat tatgtaattt aatgctcaca gcaagcctag ccaatactca   1140
cccgcccttt ctgcctctaa ttttttctgg tatgacgtag caaagtccgc ctgacacttg   1200
aatatttact tccacttcac gactcttcat cgtggtctgg gtgcgtagga agcttcagat   1260
ggcaagggag gtgctggcag ggactggcag caaatgagca aacgagatga gagggtggga   1320
cagagcctgc gtttttggct gccctaattt tagcttctga ttcacccaag gaaattttga   1380
gcagtgtccc catccagaaa ctgcgaatac taaggaaggt ctgaccagcg gctgaagata   1440
tcagtgaggg tgggaaagaa aaaagaagaa cgacaatgat acctttaata aggatctaat   1500
tttaaactaa ttaaagccaa ttggaatgga aggtattttt ctttaaggaa ttctagaaac   1560
tgatttcatg caattggcct tgccgcatac gttaattaga ctaaagaatg aagcgggtac   1620
tttaaatcaa aaagccttga gagatgtgag gaaggtggtg tgtgtctacc agggtcctgg   1680
aaacttccaa taatagaatt tatatccgat cctggtcaga cacacaaggg cacaaagtta   1740
gtaagtaaac catccctact actctatgct ttattaaccc aaagcacaga gcttctcact   1800
caaagaccaa gacagatccc catcctccaa aggtggtgga tagcaaggga caacgttttc   1860
cgacttcttg ccaggcccag gtctagctgg atttgaatct tcatgctaac cctctgaagt   1920
attttttacc ctcaatgtat aggtgagatt gaattattct gccaggtcat ttaattacaa   1980
gttggcagag tgcgaatcct aaattacgtt gatctgactc ccacatcctt gctgatctac   2040
cacgtcatgt ggccttctct ttcaattcca catcatgact agagctttct ccacctacac   2100
cggtctggct gctgggacct cccagggtac agagctgatt cacttcaacc ggcatccagg   2160
ggcgtgcctt ggaaagccat ggaggggtag taggaaattg ctcttttgtt aaatgcaact   2220
tgggtttatt tggaaagaaa aagaaaaaaa gaaaaaaaaa cgttctgaaa aagaatcaag   2280
ttgctccatg taatctgtaa attgaaatta gatggttgtc aataattctt actatatata   2340
taaaattcca tatatatgca tatatgtatt tgcttatata gatatatagt ttgggtt      2397
```

<210> SEQ ID NO 43
<211> LENGTH: 5727
<212> TYPE: DNA
<213> ORGANISM: Homo sapiens

<400> SEQUENCE: 43

-continued

```
ctcattctga ttttggggtc tgggtgggct tgagcatggg tgtctctggc tctggactct     60
ccaatagctg gcttgggctc agcttgtcac cacctctccc tgtggctccc gttctgggca    120
cagtgaaagg caggggtttg cagactggca agcacacgat caactgtcaa cctaggagct    180
gcaggcagtg ggaggaggga catcgggctc tagctttggc accgcgtgac cttgggcaag    240
tcacttcccc tctctgggtt tcaggctcct cttccgtcga aaggggcaat gtctgcctcg    300
gtccttgaag atggcgtgaa cgtggccttt gaaaccagtg cagagccgct ggtaggaagc    360
ttcctgagga aggacagcaa aggggtttgg aatgagagct caaagtatca gcctgcgtac    420
aagatgccct cggggggagc cttgtgggcg gtcacactgg gccaggcccc tgctgaggcc    480
cagcactgca caggcacccg gagccctgcc cttctccctc aggcacccca gggcagtacc    540
gccctctggc ccagctgagg gccaggctcc cctggcttcc caagtggagg aggaggaaat    600
ggtgccagca ggccaccacc ctcgaggagg tggggtcttc tttggggctg tgggctagga    660
gtggacggaa gggctcagag gccaagctca gatgttccct atggctgagg tccctgacaa    720
ggatcctcaa acagggagaa tgctggtacc cttccagttt gggcctgggt gtcacttacc    780
tgggacactt gtcacatccc ctttaaatct ctgtccttgc ctggctctgg gattctgaag    840
agcagtaggg tttccagggt tctctcctga agctcgcagt ggcttcaggg taaaacagct    900
ggtaaaaagc catgggtctc tcccttaaac ccaacccagc agatgtctac tctggaggcc    960
cgaaaacacc ttaaactcat cgcacagaaa accgccaggc aataattcaa tgttccagcg   1020
atgtcctttg tgacccattc atttcagttg atttggttct attgcgatcc cttttttca   1080
tttgttcatt cattcattca ttcattcatt cattcattcc agacacatta cagccacaga   1140
ggtgaggagg attcaggtcc tgcccgcaga gacagttgca catacagcca gccacacaag   1200
gggcaagaag tagtctgtgc tgggccacag gggcagctct caggaggctc tcgcccacgc   1260
tgtgctacat tcatcacaaa tctgacagta tgcaacaaaa agcaggccac aaaataatgg   1320
atggtattaa cagcagagtc aagatgtggg aaaatggaat aaaatgagct ctccaggtac   1380
catctatttt tagaaaatgg agaagcttga tggataaatg aagtaggcca gacagggaga   1440
atacaaatag cagcagctcc tgtgggaagc ctgcccacat catccgaagt tggtacgatt   1500
cccattttac agaagaaacc atgacaggaa tgatgtggct ggcttacagt cacagagctg   1560
aactcagtct gtctcactcc agtttctgct tggaaaagat tcctcatttc caccagcttc   1620
cttttaatca aggcagatta gacattcatg cattggctaa tctaggcttt gagtgtagat   1680
gtagtgccta caaagcaaga ttagccatta cacgttttgt cgttctggaa actgactctt   1740
ggcaattccc agcggcttta tctcaacata cttcctgaaa tctcaccatg tgtattttcc   1800
tacagagtgg ctctgaaaat aaagtaggct ggaagtcagg tgactgatgt catcctggac   1860
tcgtaggcga ttaacagtat gaccttggag aagtcacctt cctcgcaaga attaggacta   1920
gaagagctgg gcattcagaa gcatgcccaa gtgctcatgg cagtgccgcc tgtgagcatg   1980
agaaacggga ggccacctgt gagaatggag aataacccgg tgaccatatg tgtctccaag   2040
tcaatccctg tgatctccac ctcctggcat ccccccagtt cctcttccac actgaaccag   2100
ggaagatctg cttgaccaac agcatatggc aggaatggca tggcactccc gggcttagta   2160
aaacctaagc cgcttccatc ttgttttctc tctccctctt gaatcccttg ccctggggaa   2220
gctgcctgtg agcagccctg tagagaggcc cacgtggaag gaattgagtc cttgccaaca   2280
gccatgggcg ttagccatct tatctgtgga tcctttaacc ccaatcaagc tttcagatga   2340
ccacagccct gccagctcag ctgcaacccc acgacaggcc ctgaccagaa ccaccatgag   2400
```

-continued

```
gggctgtttc agggctcctg atctcagaat ctgtgtgaaa taataaattg tttttgtttt   2460
aaagctgcta aatttggggg gtaatttgtt atccagcaat ggataacaaa tacaccccat   2520
actatagatt atggagcaaa gagtggaaca ggtctatgtg tactgataca gaaagatttc   2580
tgagatatgt gttaagacac ccttagaatg tgttgttaga aaataataat tacaaaatat   2640
cttttatgta aaaaccacaa ctcactatat ttatgcattt acatatgcaa gtagatatgt   2700
agcaaattac ccatcatgta gcaatgatga acatcaattt accctcagta agagaaggaa   2760
ggtgcaaagt ggaattttca ttttctattc aatagattat atatataata tatatataat   2820
tttaccatga taatgttgta ttacttatac tcaatttaaa aattctttaa acgaaggcat   2880
ttgagtactt gatcactgag gtctctttca actctggtgt tttatagttc tattaaaatg   2940
tcattggaat gtaaattaaa agaatgggat aacatttatc acgggagggc agggctggcc   3000
tttgaatcca gttatattga ctccaatcta gggcccttcc tgttatttta cctttgtgcc   3060
tatagtttac atgcaggtgt ctgtgttaga ggagcttgtc tctggcctct gttttgctga   3120
ggacaatttc tcatttccca ttacttataa gagacaggct ctgtgagagc ctccaatttg   3180
ccagctgctt ccacttcacc acctctgagc tccgggtcca gcccaactaa cttgactgcc   3240
gagggctttg ctccgtcttg ggatggctgg ggcctccctc acctgacggg tgttcagctg   3300
tgatgattga gcttcgctgt catgaaactt ccccagagtt ggtgccacgc ctccccctcc   3360
ctccagcttg ccacaccact cgggctgaag gatctgcctg cccaaccctg ggttggtctg   3420
cataaagacg gccgggaaag atagcattta tacacagtaa aatgcctctg cattatctcg   3480
cttggagaaa gaaataactg atactggcct gggagctaag aagaggggtt ctctggcttt   3540
gcggagaaac ctgtgctccc ctctccattc tgacggaatg gtctgggggc ttgggcatgg   3600
gtattgtctg aaagtgcctc agatggcttt aataaacagc cagggttgag aacatctgta   3660
ttggagggaa tgtgaaaagg acattgaggt aaatggatgg gattaattat gtttgctaaa   3720
tcaggaaact ctctagagag ggaagtgaca cgcccaccgt tttgcctact gttggaaaat   3780
taaagtttca tcttaacaag ggcggaagag ctttggggtg gtcccaagag gaagaccatg   3840
gggtagtgaa gcggaggagt ctgtcgcaag ggctcactat gggtttttga aaagctgtga   3900
tcttccgtag gaatctccac ctctttgtgg ggggacagtc tcattatact ctcttgggca   3960
gaagcaagct cccatccctg cagctattga agcagagcat gtataacata ctgacaggga   4020
cgtggtgaag gagatccctg aattggatag acaaaacgcc ctttaacggc ccttccaacc   4080
ttgaggtttt atgattctat aattctatgt attgtaaaga acttaacaaa aaaattactt   4140
ccatcctatt caaattatag tgacctgcct tttagcttgc ccaagggaat ggacttaaaa   4200
ctgctgtgca ctcagaatag atgatgtgat tcccacactc tcattccagg tcagttctcc   4260
taagtatggg agtaattatg atggaggaga tgcaccgcgt gctgactgga gagttagctg   4320
cattcgtctc tctagagcag gcatgatgga ccagctaaaa acagagtgtc agtttgacac   4380
atactctttt tgtttgctga tgactttttg aatttttgt tactaagctc acattttcct   4440
tgttgactct gggttttgtt ctctttagag aattttattt agttcttatg tcttagaagt   4500
agctcactaa aggacatagc aagaggaaga agagatgtct tatatgattc tggctccaaa   4560
cgtaccacag atctctgact gatggcagga cacccaattg aatcgtggtt actccatgtg   4620
tcctggaata aaacacagga aataatttct tgacctcatg tggcatctga acatactgag   4680
attaaaatga gaaactattg ataccatcct tggctgtttc taaatagatg ttaaactctg   4740
```

```
atacaggatc cataatctat aggattcttt agccagaata gaatgagaac cttcagcaag   4800

atggaaagaa tcctagcctg agtacaggta ctacaacagc aactgacatt tagccctagt   4860

ttagacctcc acttagactc accatgaagt taaaatatca tgattcttat aagaaatagt   4920

tacttgtgtt taccaaacag gtgggtagat gcagggtaag ttgatctact gtaaagtccc   4980

gggagaaagt agcctctagg aaatgtgcca caaacacctg gataaaatgt aaaaaagtaa   5040

acaatagcca agtgcaagca agaaaagaaa attaccagac accagaaaca aacaggggat   5100

aaacagctac agtggagagt gaatgagttg gcctactctt ggggtaattg tggggagaga   5160

ttgatggtgg cgatggggtg gtggtcatga tggcatcagt ttcagcaacc agggcttggg   5220

ccttcatgct cacataaggt caggaaatga gacctggaga aggaacggag acagaaggag   5280

actctgcaca ccctcaggga aagtagagat tcggggaaaa cccgtccact ggcacagcaa   5340

gatacaaaaa gcatgtctgt ttctgcttgg gcacagagtg aatcagggct ttcatataga   5400

ttacatgtga atttatacta tccagaagtc cggaaactac caaaccaaag cccttaaata   5460

caaggggtcc taggctgctg atacttttga tttgcctaga gaaatacagc aacactttag   5520

agaaactatt ctataatcta ggatgaaagg gtttcactga atacacaagc tacactaaag   5580

atgagaaaaa tatccactaa gtacaagagt ctgatgatat aattaacagg actaaagttc   5640

caggaaattg ggatatagcc agataaagaa aaagaacttg cacataaaca acctatgtac   5700

aagatttctg cagtattgca tgttaaa                                        5727
```

<210> SEQ ID NO 44
<211> LENGTH: 7301
<212> TYPE: DNA
<213> ORGANISM: Homo sapiens

<400> SEQUENCE: 44

```
ttgattcaaa ctctgctttt aagctaaatt gaacactaaa agatggctgg gaaccaattt     60

ggacagccac agcagctttg ggagataaga acctttcttt gcgatttgga taaagcaaac    120

atgatctctc tgcctccttt gtttttagaa attaatagag cttttcaaca gaccgcccct    180

tgccactaat agtgaacagt caaatcatgg cttttattcc cagctcacta cgtcaagtaa    240

atagaagctt acaggataga ccagggaacg ataagcaatt ctcactgcag cgaattctta    300

atatataaat tcatccagca gcagtttagt atctactggc aaaaccagaa acaatgggga    360

acaggcaggc ctggctctga cgaggtcaac catcaaggtt atctatattc aattactggt    420

atctacaaac ttgcatagct gtcagctggt cagggcccaa atgaaaactc accatgcact    480

cagaaagcaa atatagtttc cgaggagagc ctcaaattag ctctgtgaat gacttgactt    540

caaacgcaca ccaagccatc agcctttggg gacgtttctg ccagcagtgc ctcaatgtct    600

aaatttgggc atcatcttat aaatctctgt tcctgaagta ggaaaggact ggaattgctc    660

cttaaccctt ggcgatgata aattatatca cttaacaata gataaactta agacactttt    720

cctgtactgc ggacctattg tgaggtaact gctaatctct ggcatctctt ctctgtggtc    780

ggtaccacta aagacctgtc ggtggtgaag agacacaata atttgttttc taactcctcc    840

tccggaacca tatatcatgt gtggaaacaa agcttcccaa caacagatat gtatctgttt    900

cctttagagt tgcccttccc atcagactca gagaggacat gttttcagtg tgacacttcc    960

ctgccccaga aagggggaca tttccttccc aggccccact ggaagtgggg taaaggttaa   1020

tcacaccccc attcttcctg gcaggtgcct ttcaaccagg accttttggg ggcccaatgg   1080

agatttactc tgcataagtc agggttaatc aatgccaagg taatttctag attagcttgg   1140
```

-continued

```
ggaggccata aattgtggac ctgttaagag ctagatgtct ttgattttct ccttgggtca   1200
gctgaattgt tactctctcc tcatccattc cctgtcacct tcttgataat ccctttccag   1260
gacccccctt ccaattctgc ttgaggctag tatgccagcc atgggctcac tctatttgag   1320
ccacgaaatg aaagactgta cattcatcaa tgcaatctgt ttagattgct tcaggacaga   1380
ggtaaaacca agagtatctt cacaagaaac cgtttgacat gagttcatat gcggagggaa   1440
aggcacatgg agcaaggtca gtcctgactt tcaaccaggc cagtctgggc ccctgggtcc   1500
acccagacag agccgtcata tgtccagctg tgcaggttgt gcactgcaca aggccatatt   1560
taaggggtgc cattcacatc atagcttttg tagatttcta tatttattat gacaactttc   1620
tggacaatga caatatcttg agactgggaa cattttctaa tcaacacaaa gccaccatgg   1680
aggctagggc agtcccgcaa aggaacccac ttcttatccc taaagtcaac tggtcacttt   1740
ctagatcccc tcctacatgt cggggagggt tattgtaatg agatgatcta ttcgtgagtc   1800
tgtctcctcc tttgggatct ccttgtcctt gtttgtatcc cagcatagag cctggctcgt   1860
gaaagtgcct gatccatggt tggctggtcg tttccatcct gcagggcatg tcacaggtct   1920
ccaggagggg tgcttgccaa gggcataagc agccgttaaa gaaaggcagc tgttccctct   1980
tttcattttc cgtttttgtc cgccctcgtc caaaacacca ccctctattc tgtttttctt   2040
catgaatccc acgtggacaa gagaatagat tactgaaggc acacaacaat ccttcctttc   2100
ttctgtctta aagcaaaatt tcaaaaacat gtcttggttt gtttagaagc agcaagatga   2160
ctgctacttt atttttgatg ctgcacacac cgaggcagaa aaacaaaaca gtggactcat   2220
cagccagagc cggtatttat gtgtaagtga tatgagtaac tcaataggtt tcagggctgc   2280
tgccattaag aaaataacac taatacaaga cacatgtggg tgctggccag gacatgtccc   2340
cagagctcat gggcagccca agctggggat caaggctgag agctcaccct agctcacaac   2400
ctttgctgtg atcccaggtc agaacctggt aatgtaattt ggggaatcca tgtgttccca   2460
gtgacccatc aggaggtttt gttttgatct attagacgtg gaatccttga tctttaaagt   2520
ttgagatctt taggttttgc ctgccctttt tcagaggagt agcccagaga agttaagtga   2580
tttacacagt gagcagcgtc aaaaccagca ctttgatatt aatagctatg ttgcagtcag   2640
tgttgccaaa gaaataaggt gaaccacaca ccacttctac ttagcaccat gcttggtttg   2700
ggtaccattc tgagaaattg ttatgagaat gtattccaat gatattattt gggattcctc   2760
aactttgatg gctgcttcct ttgtgagcca tttctctttt attttgctca tgttttgagt   2820
ctcagcttga aggtcaccag tcaggagacc cagtccaaag ttaccttctc cccaccacat   2880
cctagcctgt cacctttctt gtttccttcc cagtaatgat ggtggttatt catctgttta   2940
cttatttatt gtctttttgt tgaattccca gccagtcata cagtaggcac tcagtgttga   3000
atatttgcat gtatgaatga attccactgt ggattcaatt tcttccctaa aacctccatg   3060
ctttgtcttt tacacactta tggcactagc attctgcctg ccccttctac cagattaaag   3120
gcctttgaag gcatctgtgt ttgcacctgc agcagtgctt agaatcacat cctgcccacg   3180
ttggttctaa aattgataca tagatcaaga tttcggagct tttccataaa aaaaccctgg   3240
gctaaaggaa ggcacattta aacgcagagt tcccatcaca actaattaat gttttggtct   3300
ctccctttct cctggacttg aagctgggca cagccaaaat atggtgttaa acaaagatat   3360
cttggaccaa attcttgttt gtgtctcctc aacagctact tccagctggc tttgtttaag   3420
tgatcatggg ataaaatttc atcacaatca ccagtgaaca tgacgaaaga ctgcttcatc   3480
```

-continued

```
tatcaactcc agggctggtg ttcacaatcc cttagcccaa aatgggacat aagacaggga   3540
gggagccatc acccaccctc aggcagccag gttacaacgt gggcaagact gccatgtaga   3600
ggagtgagca gtgtcgttgg aaccagatag atctgcgttc taatcacagg tcttttaacg   3660
ggctggttgg atatcagttt tctcatttgg aaaatgggta taatacatat cttacatatt   3720
tgcacaaaag catggtatag tttagacaaa ggaagctttc caagcagctg agagaactta   3780
agagtgtaac caaaagagag cgtatgttct gggctaatct attgaaagga caggaccttt   3840
tcccactctg gatgttgtta gcatgtttca aaagtcaagt ggtgaaactt cccagccacg   3900
ccctcccacg ccgtccatgg caaccggaac tgagcaaagc caagcaaaca catccttaac   3960
ctcctcccaa cccaaaacca tgagatctgc aattgcaagg gcctcgcctt ggctagaaac   4020
cagcccggca tcatgatcca ggcctcggag gctaaacccc tggggggaaa aaatcctgcc   4080
ctttacaagt tcgttctctc aattttatta accagaaggc tgagagctga ctgtgggttt   4140
gcaataccac ttaccagctg gtggaatcag agagcaaagc cctttctcct ggaaccagcc   4200
tgaaggccac gccaagccac cagatgggca gtaaaatctt ttaaacagct gctgtctatg   4260
gcatgccact acttgtgtgt aagttgattt tatagggatt gtagacaaac agagcccttc   4320
agactaaaaa tttacaaaag ctggttcatc ttcctagcat cttaggattg tagctgctcc   4380
ctggatttag cttggggaac cctaggctct tatactctgg ggccagaatg aggaagtgtt   4440
ggtagtaaga tatgacaacc gtgtaagtag gcaatatttg atccattcaa tagatgggta   4500
tttaggctta gaggtgttaa ggatcagaat tacacacctg gaaattggta gagaaatttg   4560
aatcaaggtt acctttgggt atatttccct acttgagtaa ctccaataaa gaaaagggtc   4620
tatggctcag tgctcagtaa cacatggcta cacagcttct tctgactcca cattccatgt   4680
gctgcctcaa tttccccagc tataaaatga ggatgctaag attatccctt cattgggttg   4740
tgttgagaag tgataagata ataaatgcaa aatgcttagc gtgaagcttg acctatagtt   4800
aagaatccaa taaacgtggc tcttcttatt gtttgtctta ttaccattat ctataaaacg   4860
atatagggca tccctttgtt ctgttccctt aagaccattt cagtcatgtc tgtactggga   4920
agaaaacctc gctttgtttt tagaagccaa actagtcccc tctttctttc accatattgg   4980
tagaaagttc ataacattca aaccagatcc tgtttaacct ttgcccaaca tagctttacc   5040
tacttcaaac ccctttggct ctctgaggcc tggcttcctt caggctcagg ctgtaaatgt   5100
ttgactttga tttgagatac atgacaataa attaggggac atttatcaaa gctgcttttt   5160
gcataaatta ctgcattata caaatacact tagcaggatc ctgcttcttt gatgttggga   5220
ccaaagattt atgtgcaatg gagtttttat ttatctgccc tgttcacctc tacaagagct   5280
ggacatattc ctcaattagt tccatacttc tcgaaatgac atgtatctct tgcaacttga   5340
gtagagggaa caaagacact taaatgcctt ccgagtggct gttaggagag gagaagcttt   5400
atctgacgag agtgtctctg agagcggatt gaaaggcatt caaacctgtt gctctggaat   5460
cctcccccac caaaaagaaa aggaggaagg atttattctt taacattatt tatatcatta   5520
ccacattatt aagagagcca cagaaacata agtgtctatt ttcaacagca agtaggttag   5580
caatacagag atctccttgt catggcttct ggtttctgaa tttcatggag taaggtttgt   5640
gtgacctggg gaatgggcaa gatttttagg ttcattggcc attaaattta ccttttccag   5700
aatgtcatat agaagatata tgtagctttt tcagattggc ttctttcatt ttgccttgtc   5760
tttttgaagc ttgctaattc atttattttt atactgaaaa caataaaact gtggttgaac   5820
gtaccacaat tcacctattg aaggacattg gttgctttca gttttcggta attatgaata   5880
```

aagctactta aacattcgca tgcaggtttt tgtgtatgtg tcttcaagtc agttgggaaa 5940
atccctaggg gttgaattgc tggatcatat agtcagacta ggtttaacct accaaaatgt 6000
cttccaaagg gattgcacct ttgcattccc accagcaatg aataagagtt cctgttgctg 6060
cataaccagc cgttggtatc atcagttttt ggatttactc ctcctcatag atgtgtagtg 6120
gtgtctcatt gttattttaa tttgcaattc cataatgaca catgatgcca agtattcttt 6180 cttacccccta tttgccatct gcatctcttt ttttagtata tttgttcaaa cctttttgctc 6240 atttttaaat tgagtcatta tgctttctac ggttcaattt taagagtgct ttgtgtattt 6300
ttaataaatt attttttctg ggccagctcc actcatgttg tccctacctc cctgcatctg 6360
aagagtttag attcatgttc ccactcagag aattaaaaag gggagctccc cagctgtgac 6420
cacaacttag ctgcctaaga gtcctggatg agccgaaaaa gctcagtcag gagcccaccc 6480
ttttggacat ccccaggacc ccagtaaact tcagaaattg cccatgtacc catcccagag 6540
ctgccccagc aacaatttca aagcaatggc tatatgtttt aagctgcaag gtccttgaag 6600
agctttgttc attttacaaa tgaagttcag ctcatagatg ttactaggtg ttgcaccaga 6660
aaaaggcaaa cagattttga tatatttagg attaatacag ttaaactctt caactccttg 6720
ctattcaaaa tgcaaaatca gcatcacatt ggagcataca aactcttagc ccccagttca 6780
tacctgttga atcagaacct gcatttgaat aagtcccccc tccacagttt atttgaatgt 6840
tcataggaac tttgtaagtc aatggtttct caaatcatta tcgagcatct actacatggc 6900
agacattgtg ccgaggattc atcacaagac atcatacctg atctcatgga gttagtcttg 6960
agtggacacc aacatccaca aattacttct caagtaactg gttccttagc tacatttgtg 7020
atttatacca taatgaaaga gtatttgaga atcagagacc tggagggtac tattaccaag 7080
agttaaataa aggaaggtat gccttcatgc tgaagacttc atctagcaat gtgacaataa 7140
cacgtgtcac tgtcagccca ggccctgctg gcaacacctt gaaaactatg cagaggttta 7200
gaaaataaac agcagtctct ctgattccag tgataaaata ccagtgtaag gagagcctcc 7260
tgagatccat aatctggaat tgtcagggga taagaattgt c 7301

<210> SEQ ID NO 45
<211> LENGTH: 2299
<212> TYPE: DNA
<213> ORGANISM: Homo sapiens

<400> SEQUENCE: 45
ctggctttca gtttgtcctt tgaaaaaagc cgcctttgaa tttgttcttc caaagcctgc 60
cctatgctcg gcctccagaa ggatggacac ttgatcccat ccatggctgg ccaagggcgt 120
ggccttcgga gcagctgcaa ggatagtgtt gactccagat ggaaagtgtc tggagaattc 180
tgacctgaca tcacaccatc acgaactgca caggcagtca gtgatctggg ggtgccctga 240
agctgttccc agcctggctt cttgtcaaaa gctggctttg agttggagtc cagaacaaaa 300
gcgtggccca gggagaggcc agcttctctg agagcagcct ggaggcaaac gggcgtcctt 360
catatattcc ctgtgatgtg agcccagccc tgcactcacg gtactggctg caagcggggc 420
ccggtatggc ctctcttgac tctcctgccc accctggggc cttgccatct ctcccctccc 480
cgctgggcct ccactcccaa aggttctaag tccccacatg tggcctcatg cagctcagcc 540
cctgccctgc tgagccctac ttagccaggt ccagaataaa aatctcaatg caaaaggaga 600
caatagaatt ggggcgaaga gaagctcttg gaaaggaagg gaagtggggt agccttgcca 660

```
gacctgaccc ccagcatgcc tggcccccac tcctgggtga ctgggtctga ggggtctatc    720

ataaacaagt tccttgaggg ccagaccctt ccctttcccc agagatcaat gaacctgcca    780

ctgggtgcca gacctgggct ctggattcct ttgtgaaggt ctctggaaaa agatctgcat    840

ctaacaaaag gaaagaagac aaagtgcagg gaaattgctt tcaaaggaag tattctcacc    900

actgtcattt aatctggaag gaaaaccttt tccagaacct ctccaccaga attcccctat    960

cttggccaaa ctgtgtcaca actggtaaga gcaaatgaga ttaccccttc ccatgggagg   1020

gattgtttag gacaatcctg attcatgatg ggggagccac cttctctgag cacactgcag   1080

ctggatcatg aacaaagaca aattctgtta tcaaaatcat aggaagcaat gattgttggt   1140

ttggccaaga gcagacatta acaatcaatc ttaactctct cacagtcatt acaaatcaaa   1200

aagttggcac atgagataaa gcatatgtat tatctcagtc ttagataatg ggaagtaagg   1260

aagccgtaat tcaaggcatc tttagtgacc cagttatcgt gtcattgtct catggagtgc   1320

ttttaagtcc acaaattctt tgtcctccct acaaaaggtg agctaattcc cctggctcta   1380

gtgattcatt tctaaggaat agaaagtagc agaatgatac tgtatgagtt ttgagagtcc   1440

taaaaggcag gatagctttc accctgctct ttcttggacc acttgctgtg agggagccag   1500

ccaccatgcc atgaggaagc tccagcagtc ctatggagga ggaactgagc agttcgccat   1560

tttggaagtg gatttccagc cccaggcaag ccttctgatg actgtagcac tggctgacat   1620

cttgactgca ccccatgaga caccccgcgc cagaaccccc agctaaacca cttgcaaatt   1680

cccttcccac agaaactccc agatgataaa tgtttgttgt ttgagccacc aaattttggg   1740

taatttgtgc agccagagct cacctagggg aggcaaatgg cacaacataa ggagatgctc   1800

ccttcagggc tatgacagtt cagggtcaca catgaccctg agacggaatg tcttcttaaa   1860

ttctgttccc tgctcctcgc ttgcctcagc cccgcccctg tgtctagcag cagatatacc   1920

tcttctgaac attctccagc ttatgttggg aatctgaaga aattggcttc ccaaggggag   1980

catgtgacta cgccagtctc cattaccctt tggtcagagt gattggatca gtgtggcatg   2040

tggcccagtc ctgtccaatc agagtaggtg gtgaggcttt agcaaggaca aatatgaacc   2100

cacttttctg atggaaactg acttctggca gcctttttgg gacctccaag gggagccagt   2160

tcagggataa aactgatatc aggaaacagg gaaactgggt ccttggtgac attgttcagc   2220

tgttagatta acctgaagcc agcctcatct ctggactttt cacccagcaa ggtaaaaatt   2280

tcccttttaa aatttaaac                                                 2299
```

<210> SEQ ID NO 46
<211> LENGTH: 2685
<212> TYPE: DNA
<213> ORGANISM: Homo sapiens

<400> SEQUENCE: 46

```
ctggctgtgt tcttacaagg agagagaaac ccaatacaca cacacacaca tacacacgca     60

cacacacaca cacacacaca cgcccacagg aggtgggggt agggaaagga acatctatga    120

cacagcaagg ggaaaataca cccaagcttc cctagctgtt gccaggggaa ataccttaga    180

gagagaagca gctggaagat cattagactc tccatgtttt gtcctttcgg aaatttaaac    240

tctgatatat tacccccgaa tgcagtcttt caccattgtt gtccttttgg tagagatcag    300

tttttcttac ttcttgggtt atctccgtgt ggtggaagat tcagcactag cttaattagt    360

gtcaggtttc ttacaggaat cataaaagaa aaacaatggc ataagaacag ggaggtggtg    420

gaaccattaa ttctgatgtc attgtttggt ttgtttgcaa agtttgaaat aaacatgtag    480
```

```
atggtttttg gagctgaact gagtataatc tttgcacgtg tggtgtgacc ggagctccca    540
tctcatctgc tttttcttcc ttgcctgtct attaatttac atccatttgc cttttacttt    600
ctggagcttg tgttcccata cttccaaagc agattcaggc taggcatagc atcccttaga    660
ataatgccac ccaaaagatc tccaacctgt gaatatgttt ctttacatgc aaaagagact    720
tgcagatgtg aggaaggatc ctgaggtagg gagttatctt gaactactgg gtgggttcaa    780
taatcatagg gtctttataa atgagggagg aaggcagagg attggaggag atttgatgac    840
ctcagcatag gtcaggaagc tttagaagct gggaaggcaa ggaaacatta tactctagag    900
cctccagagg gatgcaatcc tgcgacattg atcttagatc aaagaaattc gttttggatt    960
tcgacctcca gaaatataaa atatccaacc ttgtgatgct ttctagaggt aataacataa   1020
aattgtagat atttttgggg ggatttactt tatcattttt aaataaaata cttgcaaaga   1080
gccccacctc ttaagtagcc ttattactct tacattttta tattaacaat ttcatcatga   1140
acttcttata aataatgcag acagattcta ggataggctc ctttatacca attctctgtt   1200
gaattcaaat taatatgaca ttgctgcatg cattctacag gggacatttg gctcatgtca   1260
atatttgctt gaagatcaga ataaggtgtg ttattttgca ggaatattgg acctccccat   1320
ctttgaagag ctcttcctta tcccattgct ggatgtagta gagattcaga agcatagaac   1380
tgcatgttga cttgttcatg cagagtgtcc cctgagggtt tggattttag tggctactat   1440
gggctgcagc aatgacattc cctgttgcaa cccctgcatg caagaggatg tgaaggtcaa   1500
gtgattggtc ctgattaaag tatgtatcat tggcttgttc cggctggccc ctggctgctc   1560
ctggggggag ggattgcctt gttgctgcac atggtaagaa agcccagctg ggtcctgtc    1620
tagagccacc tgatctgtcc taggtagatg acatttgatg aaaaaaaaat ggctctttta   1680
aataagacag tacacttgcc aatagttaag tctccaaaga tgatagatcc atgatgtttt   1740
accatacaag cactgtgact cctttcagag gatacaaata gccttttga ggtttctaa     1800
ctaactaaaa ggtttctctg tctagtatga cagttctttt gattcccctc cctaagggtc   1860
agaagttctt ctctccctta cgtgagtgtc atgaagcccc tcctccccgc tgatcacaaa   1920
gcaatctcag gaagggtctg ttgaacttgt gttgaaagga aagcctgtca ttttgatgtg   1980
ttagaaaact ccttcttgca atgcacttat caaagagcat ggactaattt ttaaattcta   2040
tgtgtggttt tttctctgta acaattttgt ggctttgata ggatgtagaa caacgcaacc   2100
tgggaaagag atggtcaaca ggattgggac tgagtgagca aatgcttaga ccctgctacc   2160
ttgcctcttt attatgtctc ttttttccct ccctttcatg gtgaggggat gcctaggcta   2220
attgtccatt gataggctta aagggagccc attacctgaa cctgtctgcc tttcggcttt   2280
cagagccttt ctgctcctaa tgtatcttat atgactcctt tgtccttaga agagaataac   2340
ttcccttgtg tgttccttat tcaagctcaa ggactacaaa ggacacatct cttctattct   2400
tctttaaact gtttcagggc ccccattctg tataaatttg gaattgtgcc agttaggagc   2460
ccaaactgta gatggatcct ggctgagatg cttgttacct aactccaggg gtcactgttc   2520
aaacaaaata gatgtgggac cccctgagtt tgtggaacat agagttccta gactcaactt   2580
gggaccttga taccagaaac tatggctagg cgaaatcaca aactcctagt tgctttctca   2640
tatataccca agagaggttg caaaattaaa aaatatgaag gaaaa                   2685
```

<210> SEQ ID NO 47
<211> LENGTH: 4757
<212> TYPE: DNA

<213> ORGANISM: Homo sapiens

<400> SEQUENCE: 47
gcatcgtctt atagctatag tcaagtacaa tttaaactta atagtacaat tataatattc 60
aacaactcta gaatttttaa tttgaaattc aaagatacaa taatatgctt gtggcaatta 120
attttgtttt taaaaatatt tataagccag taattcagta ctgtatatat accaactgca 180
atgtgtacat gtgttcacat acctgtgcaa aagtattcat aacagcacca agttccaaac 240
aacccataaa taaattataa gttatacaat ggaatgctat acagcacaag actaaacaaa 300
atctcacaaa cacagtgtta agagtaggaa gccagacaca agtgagtatg cattgtgtga 360
tttatttatg cgttcagaaa gagacaaaat tcatctatgg cattagaagt catgatagtg 420
gctatccgct ggttgggagt ggagggactt aagggccaca ggataatctg agattctgct 480
aattttctac tgggagctgg ttaaatgata tgttcagttt gtggaacttt tacatggtgt 540
atcattagat ctatgcattt ttcaatatat accttgtact ttggtaaaat ttcaagatat 600
atatacataa ttattttaca tatgtaaata ttcctcttag gaaaactggc attactcacc 660
atatggagac caggctatta atagaccaat agcgggaaca gaaattttaa aagattggaa 720
acactgatag caatagtcaa tgaattcttg aagggagccc tttcaaaata aaataataca 780
aaactaaaaa tacaaaatta ggcacacaat gaatatttag aacaagaaaa ttacaaaata 840
taacaatttt attaattacc tgtaacagct ataaaactta ttttctacat gttataatta 900
taaattcttt gtttcttcac atgatatgct taatatttgg tagagagatt ttgtttccct 960
gtatagtatg gtcgatgcaa ttttttagag attttataaa cagacatatt gtttgtattg 1020
ttagtacatg cttgggcttt aaaatcacag gaattctgat aaagtctact tcttgcaatt 1080
ctcgtaaaat gtatgatgct tttttttatt ccttacattt ttaaatataa tccccaaacc 1140
acagaacttc catttgatt ggaaatttta aagaagcgaa tcccatttaa aattatgcat 1200
atctaacaaa caggaagaat tttcaagaga actagtctcc tttccctcca ctacctacat 1260
tcttccaatc tctgtggaag gaacatgttt ataatggaac acctttatgt taagactctg 1320
ggtaagtcta cccaacagca agtaggagta ttcctggttt tcctgaacca ggacagatag 1380
gagaacttaa ttatagacag aagtgacaaa tatatctcgc taaagccaat aaatgtatct 1440
gtaactcagc ttccccactt ggatctcaga aatgcccatg actactctca cactctccac 1500
acaaggcgaa atggaaggct aaggaaagag actgtgatcc caaccaattg ctgttaaaat 1560
attataattt tgaaaatgtt acaaaaacaa atgaccatat gaacccagtg ctagcccctt 1620
gctggtgcct tgaaagatgc cagcgcaagc ttcatttgct tctctataaa ttcactctgc 1680
tgtttttctt gcctcactgg ttgcatacag cttctcctgg aagtgagctc ttcatctcta 1740
attactgtca aaacactaca cgcacctatg gttggctctt atgttgtgat tctccccaca 1800
gtcaacacta ttgaagtttc tccttcagtg actttttata atttcatctg actgcttcat 1860
agacagccct ttttagctta gtggacagta gctggtgagg tatctgggtt ttgttatcga 1920
ccattgttag gagatgacca gctgagcaca gtggggcggc cattaagctt tgttgcagca 1980
gcactggctg tgcttcaagt tcttaatgtt tttctcttgc catctgatgt agatttgata 2040
ccagcacata gggtggagcc tctatggata cacacaacag cagtattatc agtgttcact 2100
ttgattacac ggttcttgat tcaattcatc acttgcccag acaggaactg catttactta 2160
cttgtgctga cacctgactc tgttttacac cttgaaaaag tactcagagc ttttatttcc 2220
tttcacccgt aatgtagatt tgctcagcaa tatgatatac atttgatttt gcaagcactt 2280
agatcagaag aatacttcta taaggaaaat gtttacctaa caaaggaatt tttgcagtct 2340
aatgttattc tgtgttgagc atcttctctt tcacctaaaa aagtagttca ttattctaag 2400
ttaatctaaa gcttttgtat gcagcacaga aatttattta aactggcaaa ttggattaaa 2460
taacatgaat ttatactagc actcagacaa taaccattga aagaagcttt taaatttata 2520
attaaattaa ttatttcttc tttagttgca ctaacagtat ttcacaggta ttatttcatt 2580
taattctcaa agcaaaactg taaggaaagc aatgttagcc ttgttttgag gaaactaaga 2640
tctaatagag caggaagata ggagcctggg tccctcacaa tgtgaagctt ctatccttcc 2700
ctgaaaagcc taccactgga tttgttttac atgaatgaga aataaaccac tatttttcag 2760
atttttattt tctactatcc catatatcca cagcaatctg accataatta tttacaaacc 2820
aggacttttt cactgtatca attgatggtg acatccttca taaatctggg catttttctt 2880
cacttgccaa caaaaaggta gttgtgggta ctacggctcc aatgaagatg agataataca 2940
ggcatcatac attacatgcc ttccggaagt gagatgtgac tctcatacat gtaagccagt 3000
cttctaaaat gatattctgc attttctgga tcactctgcc tgctcatcta ctatcagtgc 3060
agcatcggtc agcaccctac caggatggat ttctggcctc actcagaaac agctggacaa 3120
agagttttac gaactcatca aagatccgta agcaatttat ataggaactt caaattagct 3180
gataagcact tttatttttg gtcctcgttt atttattgcc acttcacact gatcaacttc 3240
aactaaaatg ttgctgtttt gtggcaatct tctaatcatc attgtattct gaagttggag 3300
agttcaatac ttgaatttta catttgagga atgtaaatgg ctaatcaaga gccatccgct 3360
aaattcaagt tagaactgag agccccggct ctcagttcat cgcttttctc tcagctaggc 3420
ttccctagaa ggccattcag attcctttcc tctacttgaa atttaatctt aactcgtagc 3480
atatactcac tcagcattta gactgcagat agtgctcaga atgggttagg tacttactgt 3540
gttcacaaga actctatgtg gtaggcactt ttttacctta acagagaaca gagagaaata 3600
gcttttgcat ttacacagct agtgagtagg agagtgagga cttgaactta tgcattctga 3660
ctctagagtc tatactctaa tcctcttatc acccggtctc acaagtagag tgggtgttcc 3720
aaagaaagca tactcttcct acaaggacca tttccctaca tcttcctttc cagcttccat 3780
ggtaagtgac taaatttttt tattattctg ataatcttta cagaagggac ttaaagaact 3840
gaaaaataaa ccctacaaag gtatcatgca aaataaatga tataacattt tagcataaaa 3900
tttttatcag ataaacatta ttggtccttg actcttaagg aaattggaca tgagacagac 3960
agtaagtcaa gttttgaaat ttggacaaat taaaaagttt gaatctgcta ccatcaaagt 4020
actctatact tacttctgtc ttgccttgcc taattttgaa tatattcatt ttattttaga 4080
ttatatttct ttctttagct caagctgcat atcttaagaa gtattattaa taagcatata 4140
gacatatttc tctcacctga agaaataatc tccaatttta tagtataagt ctagtgggaa 4200
agctgtgtct aatatagaat tttgctttag caattatttt atttacatct tgtttcaaga 4260
cacagccatt gagcttgaca gccaacctct aatttttatt tattgcctgc caactttgtg 4320
ctttttaagc ttctaataaa gaacagttta agcaattttt agtcatccct catgtatggg 4380
cctcatgtaa catgttttgt aatgacatac atcattttat aataaaattt catcttatga 4440
gtctttcaag tattttgatt tctcgcagga taaagttcta catgtatatt atacatgaat 4500
catctgtttt ctttagcaat tcactgatct cataaagcat gcatctgggt aaagaactac 4560
tgaaatttaa acctctttat ttggaaatga aaaattgtta agctaacagt agcaaattcc 4620
atgtttcatc aagcttttct ctaatccatt ggattttaaa acaattcata gttacttaag 4680
agtttactta aatagcctca gacagcagaa ctttctctgg aagcctccct caggaaatag 4740
tcttgtgtgt tctcttc 4757

<210> SEQ ID NO 48
<211> LENGTH: 5297
<212> TYPE: DNA
<213> ORGANISM: Homo sapiens

<400> SEQUENCE: 48 ttttatttg aaagaagtta attaagacat tattagtttg atcattatac tttttcctag 60
aaagtaaaaa tggcatgtct ttgtaaacat gggcagaaca gaagagctcg gtgagatttg 120
tattttggtg tcatctacag gcactgtaca tagtttcttc aactgatttt ttttttctg 180 ttggtgcggt tcatttatct actttatgga actattacaa aatacctacc tttgctggtg 240
taatttaata gtcacattgg tactgctgtt ttatcacttt atactcaatt tttaaagtaa 300
ttcaaaagta tgtaatttgg aaggaggctg tgttttaaga cttggctggc attcacattc 360
tgcccagcta ggcattaaat gttgaaaaat agacttgagc ttgcaacaga gaccatacga 420
cccaaaagcc taaaatattt cctgtctggc cctttgcata tgcttctcca tgctatttct 480
aaagcaggtt attgtaaaac agtgctagcc catgaattct caagagaaaa atgtcatgag 540
aaagatacct aggaaatgta tctatttcct tattatattc ctatttcttc accgcttttg 600
cctgtttatc caatacctat attttgcctg gaaacttcgc ttaatattgg ggatcctggc 660
aataagatag gcaagatagt gttttctctc ataaatattg gggcttaaga gcagtttctg 720
gcctcaaatc tgattttgct acttccacga tgtaaacccg gatacattat tgtgctttag 780
tttccttaac tgacttttgt ttttaaatct gtcaggtgtt tgatgagatg attcctatgc 840
ttttaagccc agacctctaa tgaatactct aaattttcag atatgaattt acaacctgtc 900
attcattcaa ctgtttagca ggaggagttg gagatttggc aatgaatctc aaatagatgc 960
ctccttcctc agagagatta atctgtgatg aagacagata gtaaagaaaa gatagtaaaa 1020
catatagcat atcagatggt atgaattatc tgaagaaaac tgaaagcaag aagttggaag 1080
ggatcttttc gattttcatt gtggttcact atgaagatga gatttgaaaa tttacctagc 1140
tgagatgagg gaggaggcca agcactatct aaaggaagag cgtgtcaggc agacagccat 1200
gacctccagg aggccaacga gagtgaagta agggggaaag ttggagaaga ccaagctgga 1260
aagggaagga ggtagaggtc tagacggtgg ggccttctag gccatgaaag gaaggaattt 1320
agggttttat gtagaggagt gtcacgttct cacttgtttt ctaaaggatc actctggtta 1380
tgttaagaat aggctgtcaa gcctcaaaat ggaagcaggg aaaagcgcaa caattcaggc 1440
tgacagggtt gtgctgtgtc agttaattcc agcaggcctg gaattggcct gagctgtttt 1500
gtcgtaggag atgtatctgg atgacactga tccctagtca aggcatgaaa tatacaggat 1560
aatagtgtta ctttgtaacc atgaggccaa ggcaagtttc agggtggtta ttaccaggtt 1620
ttcagcatta ttttgtttac tggtaacagt gagattgatg atttgtacct ggtttcagtg 1680
agacttccca gggctctgat gctgaggata aataataaga gggtctagaa tgactcccaa 1740
tttctttatc ctgggcaatt ggcatgatac agttaggaaa atgactgaga tgaagcctaa 1800
ttagcattca cttagttaac aaaagaaaag aaagatgagt ttagacaact ctcttgggga 1860
gatctgattt aaacagaagc agagaaagga aaatttgttg gagaatcaca gaactatgaa 1920
gatttaaaga gctggtaatc taggcataaa agggaattat ttcaacttga aaactcattt 1980
gaataaatta tttccttttt ccacactggc tattaaattt tagctaacac aacaaataga 2040
atgcagtaaa catcagtgcc atatttaatt atattatggg ttgtcctata tactatatca 2100
ttctatctct caggtatttt cattccaaag tgatattcca tttaacaaca aaataaaagg 2160
tgattgcaat ctatagcaca ataaaatcag aagctggagc ctagggaaat gtaaaaattg 2220
actcagtttc tatgtggaat attatattta agcaaaatat tattccttgt gattctggac 2280
ccaagattaa tcctagaatt atgtggatat tatatgagcc caagaaaaga atcccattaa 2340
aatgaattaa acctgccatt aatgttgcta tggcctttaa tatttatttt attctgtatt 2400
tacatttcat ctggaagtct tttgtaggaa atctgggatg atttttactt gtttgaaggt 2460
aaaaactttg aaaaccttaa ctgctgtgtt gtgcatgcag aataaatttt gctaaatgga 2520
tgaatgcata cattaatgaa tatatgaaaa agtgagagtt gcatgaatgg ttgacaaatg 2580
aatatatgaa tttagtgtgg catatataat gcaaaaacat tgcacataaa cagagaggaa 2640
gtcatgaatc ctttatgaat ccctttatgc gtgaatagga aaaatattga gagatattag 2700
cagaattcag gcagaaaaga gcattatcat ttatcatctt agaataaacc aggtggatgg 2760
aatatgggca gaatgagggg aaagcgcaag tctaatgcag attacctaca gtagcacaat 2820
ttgatagaaa ttaatcaaag aaatcagctc ttctagccaa gctgccacac tgcccactaa 2880
aaccacaaat ggggattcca ttcaaatagt tgcaaaatat tctttgatac ttcagactct 2940
attaatggta ggattgtttc ttcagcgaaa cagaacaatc ctgccctctg taatgaaaag 3000
aaaattaaat taaatgttaa aagaaggcag tttgttgttt gtctttagac aatagacacc 3060
agacaccagg aggtaatgaa ataaatgcaa agagaaaaga tgtagaattt ccaaagtttt 3120
tcccacggaa taatagtcca gatgctccga gaaaagcgtg ctccatgctg aaagagttct 3180
gcagcgctcc atatgctgcc ctctctaggg gacgcatagt gctcattaaa atagtaaagt 3240
ccccaaaatc ctgaactaaa aagcccattg agtggtgttt ccaaaattta tgagtccaca 3300
cagcttttaa aatataacac acatcaagat cctgcagagt tagtgatatg gaatatgcct 3360
ggggctttcc tatacagaca atgcaaacac atccaaatgt acacagagct aggccctagg 3420
gaaatggaat cacttcgtgg taatcaaagc ctttggtaga aaaacatacc tcttgatggt 3480
cagagcatgg aaaaaaaatt attcaggttg ggaacaatgt actataccac ttagggatat 3540
atggaattag aaaaaatttg aaagaagcca agaaactgga aacaaagctt aataattaaa 3600
tccactagac tgtattttaa attaatcttt ctggtggtac tggacacaac ttttctagga 3660
taaaggatat taatattatg atattgttca ctacaccagt gccttctaac tctgagatac 3720
atttatcttt ggaaaacccc acttcccagg ggttccaatg gggagaataa aaagactcac 3780
aaggcatctt ggacatcaaa ttcctcttat aaaacaataa tttgttgaat taagtgctaa 3840
tgaaacagat ggattacatt tccatcacaa tgtgcacaaa tttaaacatt aaagagtaaa 3900
agcacgtggt aaaaccagct ttgtgttttg ctgattctga aacagttagg aaaatggttt 3960
cagatgccac caggcctgtc tggctccaga caccagcctc attgactgaa atattctatt 4020
aagcaaacag atgggggagt ggtttgttac tgatttctcc ataaaagtga aacatgaaat 4080
gtaatattcc cggaagaata aaaaccttgt gcttcatact ttacaaagct gcattgagat 4140
tcatctctag ggcactctgg aaaaatagaa gctgggaatt tattttttac agagattaat 4200
tgtatcagta tgagataatt gagaaaagga gaaataagta cctaaagaaa acaaagtaaa 4260
aaaatgtggt agcatattgg tagcataaat tgtgaatagc ctgaatttct gcagctatga 4320
atacaattat tgaaatactt cttagaataa catttataga taaaaataag attttgtgtg 4380
tgctttataa aaattaataa actttatttt aagagcagtt ttaggttcac agcaaaactg 4440
agtggaaaat agagtcccta cccaccccca cacaggttgt cctatcaaca tcgctcatca 4500
gagttgtgca tacattactt cagctaaagt ccatacttta cattaggatt cactctatgt 4560
gtgtttttaa caaggcagta acttggttat ggattattta tcttgtcaat aattgacaat 4620
gctatgtaaa gcatattatt cgtggatatt tgaggataaa gaagactgga attaatgctt 4680
tcaaaagaaa taatttaatt acatggttta tttgatttca aaacgaaata aattacagga 4740
aaatgtaagt tttacacact taactttgat gttcatcaag cagataagcc taataaatta 4800
tgaaatacca ttgctaatgt aaaatgtaga aatattattt ccctgatgtg acccattctt 4860
tctttggata gctatctttg gaaagggcac atacaggaaa ttagctttat agcaatgctt 4920
tacatagatt atcgtaagaa caaaacaaag cccatattca tttctcttgc aaatgcttcc 4980
atttcaatat catgctgaga tcttcagtgc atcaattatg tatctcctct ttacagggac 5040
actaagatat attcatggaa tgattttgat gctgagactc taaaggttga actttggttt 5100
tctgagctct ggatcttaat ctattccctg acattaaaat tcctgagaaa gattagaaac 5160
tccacaatca atttagagtg tgaatattcc tgaggccttt tccacacatt tctggcatta 5220
actctcctca gatatattcc tgaagaggat gactgaagca tgcctttggc aacccaaaga 5280
atcctttttg ctcagca 5297

<210> SEQ ID NO 49
<211> LENGTH: 17936
<212> TYPE: DNA
<213> ORGANISM: Homo sapiens

<400> SEQUENCE: 49
atgaatgagt gttgggtcat cctcagaaag aaaagtgtat ttacctttag gattctcctc 60
ctcaactttc tgatcaaaac caaaaatggt tcttttgttc tcagtgcata ggcattccac 120
aacaacagcc ttttccttcc tcttcctctt ctctacattt aaggaaattt caaatataaa 180
tccagctgac tttggttctg gacaaaacta caaatatgga aacctaaaag gggtcctata 240
aacagaaggg cttagggatt tctctgtgta gaacaaaaat aagaaaaaca tgttactatt 300
ttccattaac actggaagac agggcaccag ttagcacatc agcattgtgc agctggaacc 360
ttcaggggag gggtgagaag gcctgccact caagatgtaa gcagctagat ccaaatctgt 420
cttgaagaag agtgacatgt atacagctcc acatgaaagg gagatagaat aaattattca 480
tgcccactaa aaagtaatat taggacatga ggcacatatt tgtgatacat ccaacagacc 540
gctgattgga agagagatgc tggaacacag ctggaagaca gctctcccat gagtcctccg 600
gaagcccacc tgtcagcact tttgcccttt ctgcattcac gtggaatttt gttcctgctt 660
atgtccattt aagagcttat gggcttaagg cttcaagttg aaataaatac tgagaattta 720
tggcaccttg ggcaagacta tggaggagga atatggacat tagttgcccc cagtgaaagc 780
agtggacaaa attttctcca ggttcctcct atgtgtaaca aattagaaac tagtctgaga 840
atccagacca ctggtccctg tctcatgtgt gcctccaacc agatgtgggc aagtctattc 900
tctctgggtc ctggtttgac tggtggtagt aggatctcta gagtcttttt ggctacagct 960
catctgcaat tctaaggaag gcctaaagac cccccatcctc ttgtgatgta tacccaggag 1020
ttcactgttc ccaaggagct ttagatgaag gacactgagg tccccaagct acccctattt 1080
gattttgtca agctcagtac tgtggtgaga gaaagataac ctggtagaca ttagaggcac 1140

```
ccagatatag agccatagtc atttgaaaga ggttgcctcc tgccttgcct tccctgtcct   1200
cctcactgag acacaaatgc cttcactctg cagctcagcc ttagatagtc cctaattata   1260
agttaacatt ttaacaaatt attatttcat caacagcatt atcatcccat tattgagagc   1320
cagttttgtg catgtctctg tgtcagattt acttggtcct ttacaataat tctgcaagga   1380
aattatagcc ctgtgttatt tgggactctg tggtagcttt ttattgtgta catttagaga   1440
agcaaaatta catctttata tgatttggga ttaggtttgg ccacaagaga aatttggatg   1500
agatttggaa gacagaagtg aagcagccat ttccacacca ggcttggtgg cagcttgcac   1560
acatgtcact gatctgctgg ctcccttgtg ggcacgggca gcatccaggc tcccagctcc   1620
tccatctccc actggatttt ctccttcagt ttctctgaag cccgagccag gcatgtgtgc   1680
agcaccatgg ctaagggcat tggcttctcc cacaggtcac tcatgctgcc aaggttggag   1740
gtgttttgtc ctgtattcca gtttgtcctc atgagttcct gcatgggttc tagtttgtct   1800
tactctttcc tgtgcagctt tccttcctgc cagcctggct gatctatagt ggcttaggtc   1860
caacgtcaga agcagaggca acagcctttt gtgtaagatc taaatcctat aataaatccc   1920
ttatcctaca gcatcatagt agttctctga tcatatcctg actgatattt ttgttgcaag   1980
taataaacca ccttcacata gcctaagcct agaaagggta attattttaa ggatgtggga   2040
gtatctcatg gaatccaagt gtggaaaggc aattggtcac agggagggga agttcccata   2100
ttaaaacaac aacacaaaaa cacttccttt atcctctagt ctctacccca tttatgagct   2160
ccccttcaaa tgcaaaaatg gtcacaccct tctgcattcc ctcaactcct gaaaaccgag   2220
ttctaatgcc accaaactag attgtcaaga gcaacgtatg tcttcacact ctcaattacc   2280
tgctcagcac tgctgatgac ttgctgtctg gctggacctg tgactcacca cccagatccc   2340
ccttaggtga ggggctgttg cctcagcgac tgaggataag gagggctgtg cacctgttta   2400
gggatgaccc catccaattt cctccctgac aactgcactt tgctaactta taagcatctc   2460
aaaattgatg tttctaaaac tagacaatgt tctttcttct gaatttgttt ctccccctag   2520
aattgtccaa ttcagtcaac tgtatccacc atggttcagt cagacacctg gctccatcta   2580
tggtcctccc tgtctttcat cccctacgta tcattcagca tgtactgtca ctcatgtcta   2640
gccacagcca tgcagctggt acaaagggtc tgggatttct ttaggtttcc ttcttcctga   2700
ctccactata agaacagtag aagatctgtc tggaggcagg cagatgttga acaattagtc   2760
atgcatacat cttaggtcaa ctcccaaagt gccctttgtg ggctgcttag tttcacaaag   2820
gcacagagag atgcaacagg tctgaggatc ctgaattcat tcttatcatt ttgataaagc   2880
tatattcttt attctagggc attgtccagg aattgttgcc attaatcact tttattaact   2940
gaatatatcc ctatatgtgt gcactttgta ttgatataaa tagcgtacat tcctgttgat   3000
gggggcaggt gttgctttgc tttgtccaca gttcttagtc catggcaatc aagaataggt   3060
aagtattaca gatttgcaac aagaaagcaa gaaaacaaag tagagtgcaa atttctataa   3120
agaacatagt caatcaaata tttactgaat atccacttca taccaggtac cctgctaagt   3180
gctgtgaaag ggctcactga taaataaggc atggatcctg tgattccaca aagccaatat   3240
gtgaacagtt tataataagg aggaatttag tattatgact gtttatacaa agtaatacag   3300
agaaattgta tattggaatt gtttctaaac aatgctttgc aaacaattat aagagtaagg   3360
actgagaagt attaaaagat ccttcaattg ttttgggtcc agtggagtat gtatctaggc   3420
gcacctcagc acctcagcta ttcatttcca cagtaactga aaagtctaag ggagtaatac   3480
```

cattaatact tatcaggga attagaataa taatagcata tgctgaggct aactatgttt 3540
cgggcacagg caatgcactt tgctcatatt atatcattta aatctcacaa caaccctata 3600
aaggagcaac tattgaggct cagagagcat agacagtctc acatcctgta agtggtaaga 3660
gctacttgaa cccaggtctc gcttctaacc agtaagtgag atgtcaggat aggaactttc 3720
ctcatccctg tagctccttc tgagaagaaa gaatgaagaa agacagtgga attatatgga 3780
ggaacaggtt ggctggagac agggaagcag cataaattct ctcaggtaca ttcctccaac 3840
aaacttaagg ggagaaagaa gatttgtagg tgggtgttta cacacagatt gctagaaagt 3900
caacttctca tttgaaaaca ctcctggata tagggctgga gtgtgtccta gaatgtggat 3960
aaagaaagaa acatggaggt tgttattgaa ccttgtaggg agaatgtgta taagggtggt 4020
ctaattttta aagatgagct cacaaattcg agaaataatc cagaaaactg aactttagaa 4080
aaatgagcaa actcttccat aggactccat tattcgtcta gcagaaagtc ttaggaatcc 4140
ctggaaactg gggacttgca ccagcatgga gacctaactg ttaaattatc tggaacttcc 4200
caaacagact gacatcttgg tggttggaaa tcaacacgtt gggaatattt acactatgaa 4260
aatcagtaaa tgtgtaaatc ccccagagac attgttaagt atttaccagc acaccattgc 4320
ctagaagcaa caggggttct ttagtagaac taatgtggtg aaaactgggg gaagagtagg 4380
tgtagagaag gaagatgggg aatacagaaa tggagttaga gcaagtaata aatacagatt 4440
atgattccca catctgtgtt attcttgttt tttagaacct actgtttgaa tgcaagaaaa 4500
tgttgtacca cagatgttga ggacacaaat taaacccaaa gcaaatcaaa ctcccaacca 4560
ttaaaaacct ttgagaccat gtggctgact gtatatatta aacatatata atactggaat 4620
ttcctcaaat taattccatg ttaaatataa tgtttaataa gtgataatga tatgcattaa 4680
aatgcatacg ttacttaaac tcaaagaatg tagactaaga aaagattttg aggggagagg 4740
tatttcatca ctgatatcat ttagtactgc tagcacatag tggtaataaa aagagactga 4800
ttggttctat gattgttctt taaattctca gagaatgcac ccacttgcct gcacctgttg 4860
tactgctctt ggcatgccat gcctggatcc catctcaacc aaaatattaa gaatcttctc 4920
gggggtgagg cccggagtct attttcatga aaagctcttg catgtgattc taatgatcag 4980
ccagttttgg gagctgctga tatgggaaca aaagggacac aaatagctat gattcaaagt 5040
caagggatat ccaaggagct gctcaactct tcaaacccat tctttcactg gtctgggtag 5100
atggacgatc attgaaaaca accctgttaa aggaacctcc agggcaacta taggaagttc 5160
tcctattgtg tcagaaaaat acttagcata gatatttacg tgttaaaaca agaaaacact 5220
tatctgtaat taaaaaaaac atatcaatga gtcttcatcc ttattgattc ctctgctcca 5280
tcttcagacc atttcagaaa agtctatcct caaaaaaggc agaattttg caaaacttag 5340 atgctattcc tttgcctggg ctttccgcct cactcagact aaagaccaac tctggctata 5400
catcctgcca ccaccactct ctctgtgact ctcagtgtct tccagccact tggcctcttg 5460
ctgttccgaa ctcattgagc actcccacct cagggccttt gcactgtctt gcctctgcct 5520
ggaactcttc cctcaggaat tcacaattca agtctgtgtc caaactcttg cctgatataa 5580
aagagcatta tttttcttca ttgcacgtaa caccatctaa catatcaata ttttacttgt 5640
tttttatttc ctctagatta ttgagggcag gattttagat gtttatctag tgttgtattt 5700
ctagaaccta tcttctgcct tgcccatagt tgacacttaa caaatatttg ttgaacaaat 5760
aaatgaatca aaatgcagat gaccaaacat caaataataa agaaataata ataataataa 5820
taatgactta caaaaaatct ctttttcccc aaaccttcta agtcatactt ctggtaacca 5880
cttcttctgc tagttgtcct gagatctcta aatgacatac ttctacttac atttcttgat 5940
ttatcccctg ctatgccaat gtaatcacta tgactatttt tatactttgt tatttgtacc 6000
ttagttatat tctctgtgtt tattttcatg tctttgagac agtgtctact gtctcctcag 6060
ttagataagg accctctttc tttccttcca ccctcccagt gtgactagga tttcaagtct 6120
catcactgaa gtcttcaaaa agatctctag gagtctgtgg ctgttcctaa caacatttca 6180
ctttcccccg atctccattt taaatttgga aaagaagtag tgtagagcaa gatttggaat 6240
gttgtctgga gcatctggag ggcaaaaaat tcttggaagc ttgcctgtaa atgagcaccc 6300
ctatattcct ttgggcattt cttctctgcc cccttggagg ctctagatga atcatatccc 6360
cagcccaaga agcaccctgg agtgagggtt ggttctatgc taattgttca cgagcatctg 6420
actttttccc ttttattaat agaaagtgaa ggagaaataa ggagcttagt gggcaaagat 6480
ggagggagaa agctgcgaac ctcattaaca attttatctc atcgcatgta aattgaagtg 6540
tgtacattaa actttgtaga gttcatctat ggaatggctt cagttcccaa atagtcttac 6600
tgtcactgtt cttataaaaa attatactaa aggcttccct ttaggtatta aggggatagc 6660
ttaagcaagt gagtgcaaaa atttttttc ttattttcct agtgccccga ccatatagag 6720
taaataatga gggcttataa aattgcttcc cttccagggt gtagggataa catttacat 6780
caataaattg aaggaaaaga cattgcccca tataaggcac atagtagggc tcaaggggag 6840
gaagaatcta gatcagcctt ggctgcatgg tggagcacca ggggtacttg aaaaaataat 6900
tccctctaga aattctgatg taattggtta ggtgtggtct gagtgttgac atttttaaaa 6960
gccagaaaaa aaaagaaaca caccctggtt tagagggaaa ctctgggttc ttctctacat 7020
tttccttctg atctttacag ggatgcatat catctttaac tcagccatgg gcttggaggg 7080
tcaagagctg attgtataga aattttatat tattctagat gtggtctact acatgttaca 7140
aagttgagtg tgtgtgccat atgcagcact ttcttgtgag ccctttgaag ctccatgtcc 7200
ttagcagggt tccctacact tagaaatttg gaagccttcc tttaagtttt ctgtccaaat 7260
ccaataatta gtagcataaa tcaacaagca gaatgtagca accagtacag agaggctggc 7320
ctgacagtcc tcaacgatac ttttattttt atatatccct atgctcaaga ttagtttatt 7380
aattctgtag caggttaagg gagtggaggc agctggtaat cgttgattca tttatatttt 7440
cattcaatag ccatctgctg aatgtcttgt tagggttggg gactcaatat tgaatagact 7500
gcacagcccc tgttctcagc ctagtgggag aaaaataagt aaatgagcaa ttgcactctg 7560
tgtgaatgtg cagtaatgcg gggacacagg atgctgagag agacaagttg ggacatccaa 7620
cccagacatg gttggtaggt tagggggtgg ttatgggaaa gtctcttggg aaaaaaataa 7680
accacttgga tttcccttca agaaagaacg tgctgtgctt ctagaaatgc agttatctga 7740
tagcatccag ctgttaggct ctcaggatta gccttagctt tcaagctgac cccacattct 7800
tataggcagg gggaacaagc agagtggaat ggatagtaga aggaaaggga ggagagagag 7860
gtaagcaggg agtttgtagc ccagatcatg ggggaccttg taggccattg taagaacact 7920
ggcttctact caaagtgata tgaggtgaga ggaggggtgg gcactgataa gctaattcat 7980
gtttgatgtt ctcagccttt gactttgctc cagcttccta gtcagtgatc caggggccct 8040
ccagggtact tgcacctagc aaagcaatac accagtgact cctagtctga cagattagag 8100
cagcttctgt gcagtgggag ttctaaagaa gctgaagatt tcatttctaa gttcaagagt 8160
gttatgtcct tatagatgag tatgtgaatt tttgtgccca aaagttgtag aggtcaaggc 8220

```
taggacatgc cagatgacat cccagaaact ttttagggtg acaggtaaaa taaaagaacc   8280
aacatctcta attgtcctcc acgttagact tgccttccct gacttgtgaa acctggttat   8340
cagtgagcct ggcaggggcc gtgaaaaggt cctggttggt gtacaagccc aaatttggag   8400
catgagtgtt tattttctat tctctgtcct ctgaagattt ccatgtagag agttgacctg   8460
ggccttaagg taacaatcca aaaaaaggaa taatttagaa gaaaattaat tcctcccttg   8520
aggaacaatt tctgtttata attttaaaat ttgtgtttta tttcactatt tcctaggatt   8580
tcattcctct agctgaactt aaagctgtct tcagaagacc catacttctc agcttctcat   8640
ccagctgcag aatacacacc aggactgggt gtgcttggaa gtccactttc caatagattt   8700
tgtggcacaa aaacaacttt ttcaaaacca cctggtgcca gggaatgcca gtttcgggga   8760
gagcaaatct gttcctgtct gcatcttttc ttcatctggg tctctgagct acctggcctt   8820
gataattcct ggtcccaagt ccacaatgaa gacagtgaca ccaccatcat tataaaaata   8880
aataaaagag atctgatgat tcacacatgt taatggtgaa taaacacaga aaagtattta   8940
gcatcgcttc aaagaggaag agaagcaatg tagaggcaaa agcaataaag ttaacaacca   9000
aaatggcccc caacaggcaa ttggttaaat ctggatacta tggaatatct ctgttaataa   9060
aagtattggc atcataaaat atcaagaaat caggtcacaa atatgcaaat atgttcttag   9120
ctttcaaaat aaaagcattt aaaaagaata ctctccaaat atcaacaata tttatttttg   9180
gaagtataac tatgaataat tttaattctt ccaaatattt ttctgtaatt tccaattttc   9240
tagaataaac atgaaacagg aaagccaaat caaaataaat tataagaaaa ataaaagaga   9300
tattaaaatc aaatttttcc tatagtataa ttttcacaga aaaaatgttt gagaaaatat   9360
tttcaggaag tcatctaata ttgctgttgg cttttcctca caagaatatg atgtgatggc   9420
aataaaaagt tgttcataaa gttatgattt aaatggttag actggtctca gtgaaattca   9480
gggtcagctc tacagtttaa tcatattgtt tttactggct accaaggcta aagaagtata   9540
agtctgctaa attccttagg ggaagtggca catttaaagg gcgcaaatcc attctcttgc   9600
agccctcttt tcactgcaaa gaatcattta gttaatatga tagaaaagaa ggaagagggg   9660
gcacctttgg aatgcgacac ttgcaagatc ctatgaatga tgatgtaaat ctttccctgt   9720
gttttgtaac ctgaaatttc caagatattc cactgtattc agatatcagc tgcctattgt   9780
gggccatttt ggttgtttac aattgcctgc cctacatcct tcttcctctt tgattattag   9840
tgatgctaaa atatttagat gtttattcac taatatttgt gaatcatcct ttctctgagc   9900
ctgggccctt ctaagttctt ctcccatata attcattctc tctcatagaa catagaaatg   9960
ggtatcatct tctccacttc acaggtgaag aaacgagact cagagaacta acttgcccac  10020
gattatacat tctgtaaaca atgaagctac cttcataact cattctgaaa ttacatgtac  10080
atgtgtttgc atgtgagtgc ccaatgaaca tggctttgtc aaggatgttt cctcatctag  10140
tcaccgagaa gtgagactca atcgtggcca tggagatgag aacacaatcc accaattaac  10200
agtctaaatg aataaagcgt aatttgtgtt ggagtttcac actggggcaa cagctttgag  10260
atggagaggc tttggttgct agcagccatt tgggaaagag agaatcatga aaaacagcag  10320
aaggtatgga agatgatgtc tgtgagaagc tagtctatgg gaaaatttgg ggtgtgttga  10380
caaggagtat catcatccaa ttagcaactc ctcatagtac ccaaggttcc catttttccta  10440
ggatctgggg agtgttctga agggcagatc agagagagcc aagcttgaca ggaaacaact  10500
ggagaacata cagattgggt gcagaccctc tttttctctg gcttccttgg tgatgaatgg  10560
gagtgggatg ttgtacataa catttgccaa tttagcatga gctcagcctg tgctcagagg  10620
```

tgtccttgtt ctgcctgggt ttctatgaaa aggagataat ttaggtaaaa gtgcctggtg 10680
catagtagga actcttaaca tgagacttct tttcctccta ccttcttagt tcattaaaac 10740
acttctgaac cactgctgcg cagcaagcat ggcctaaaaa agaggttaaa atgttcgtaa 10800
ttaattaaac tgaaagacag taaactggga ttagaaatgt acatatgtct atatgtgaaa 10860
aggagctaag aaattgtgag tggcagtagc ctgtaattcc ctagagtgga ggactctgaa 10920
agagggtgat ttatctttga gcatcgctca ggtgcctttt ttatagagtc ctgctgttgc 10980
tatggaaatc gtgtctgtag aaatgtgtgc aaatctagaa tggattgcca gttgcatgaa 11040
tagggaagtg tggggaaggg gcaggcaggc tgacacctgt cagtctccag cactggtcct 11100
gaagagaaag aattagaatg gagagagtgc tgtgggcagg caccaccata gatagctagt 11160
gtctgaggga ctccaagact ccaatctcca ctctaccact tgggtgacct attatgtctg 11220
ttatcttagt gttttgataa ataatccttt cactgtcagt gttacctggt ttagttgacc 11280
gaatagtcac acgatcacta cagaatatag tttctgtcat aaaatgaaaa aagccaactg 11340
aaatgatcct gtacaccttt gacgatattt tgtgcacagg acttaagtta ttttccaggt 11400
aagaactatg tctccctttc tctgcacttc tcccacagct tcaattgaac agctatgctt 11460
ctacccaccc ccaaaaagga acaaatattt ttatcatctc acaaggaaaa actaaagttg 11520
tactgagtca cggaactgga gatctgctcg gctctctcac tagtgaagtg accagctctt 11580
acatatcagc cttccagact acatatttca aatttgcacc acaaggaata aataaatgac 11640
tgcctatagt gaaccccata agggtggacc attcaaagtt tcttgctgtg agcaacttaa 11700
aaaaagtgat gtgttgaaag gatggagaca tacagaatcc ttgcgggagg ctggagaaca 11760
agatttagac agtgacaggc aaaaagtcct gggcagccag accacagcca agatcaatgt 11820
cacagttgtc ccattcagac actaatgcct ctgccggtgg gcattgaact caatcgtata 11880
aagtgctggt gagcagggca agtgctgtgc tgacctgaca atggggagga cttgagcttg 11940
aggccctgtg gcagggacaa caggcaccaa agccgcctaa gagccaagga tgttggttgt 12000
tgcttggaac tgtgaaaatg taaaggtagc ttacctttcc tgcctactgg tccctcctag 12060
ataacacatc taaggccacc caattcacat ttgaaaagga aaaaggtcag tctctgttta 12120
catcccaagc aactgctgtg aggggatgga actgacttaa tcatacaatt gttttgatat 12180
cacacagaca accacagttt ttagtttgga aaaaatatgt gtgcattgac ctgagctgat 12240
ggcagcttca tctcccggtc tcgctgggct ttgctgaaac cagaccctaa aaagtatact 12300
tatgatatta aacttgtatt ttttagtgtt ggaagaatta tcactttcta aacagagctg 12360
gataattgga aaaggacagg gggaagctcc tgaaaaactg tagttgagtt tatgcttcac 12420
tgctcataag cagagactgg catccgcctc ctaacttatt gccactgaac attttatgtg 12480
aagttctgtt tcagggactc aattaaatct atgtttcacc cagctctctc tatatgataa 12540
gtcatggtct accagccttc ttccatggca aaataaaact ccatagtgga ttcaaccatc 12600
attgctactt gaaaatgcct cagagtcatc tttttctatt tctactttta cttaagtttc 12660
ttctttttgg acacattctt aatttttta attaaaactc tatcctttta gggatatatg 12720
tcaacatatc aactgctttg tcatcagaat ttaaaaagct gaagtgagga attgcgtttt 12780
ggaatgaaag ccacgtgagc agtaagggca gccagccaga accttgggga agtgaatgaa 12840
agcagaactg tggtggaaga gtttaaatcc cctttacagt ccgtcatcct cccccatttc 12900
ccagcctcta gggccgactg gaacaaaggt ggtgtcatat tccctgggca cactgcctgc 12960

```
cactgcactt ttgtttttc cagttttttt tttttttttt tttctttaga gcagttttag  13020
gttcacagta aaattgagag gaaggtacag agacttcttt cctatatact cccgtttgga  13080
caaatatatg ataacatgta tcctcctata atattacaca gaatagcttc ttccactgct  13140
cttaaaatcc tctctggtct gcctattcaa ccctctcttc tgacctctga cctccattga  13200
tgttttctgt ctccacagtt ttgccttttt tggaatcatg cagtatggac ccttagattg  13260
gcctttcact tagtcatgag catagtttcc ctgtgtcttt tcatgacttg atagctcatt  13320
tcctgccacc atacttttag tgtaagcacc aagttcattc ttcctgcccc caccttgaca  13380
aagcatacat cttagaatca tttccttgcc accaacttcc tgtgtgggtg agagaaaatc  13440
agattacaca ccaaagtcta aacatctgct tctccactgg tttcctggta cccagtgtcc  13500
tcctgggctt cgagatttcc tgtttgaaaa ccaaatgtgt ttgccacctt gtggtctgta  13560
tttttaaatt tgtttttagc cagatattgt taataaattc attgcctagg gccgtaagtg  13620
taagtgtgtg ccatgtattt gtccttgttt aagatttcca ttccgtttaa caatgatggt  13680
taaagttacg aggctattca tattggacat ttgtacatca gaaatacaga actgtctctc  13740
aaaaccctgc atatcagaat agttagcagc agcatgggaa gaagctattt catttccatg  13800
gcagccagga cccagacgcg aaagctttat agattaaaat caatgcctga attgcattca  13860
gaaagcctga attgcctgtc agacttcagg accagcggct caatgtgata aatgaggcaa  13920
gggagtgcgt gccgcattag ccagcacttt ggatcctttt tcaaggcaaa taccaaatgg  13980
gatgaattac tgggaaacag caaatgaatg tcaagaattt gagatgtggg ggttataatt  14040
tactaattac tgggaaaaga tgaacacagt caatgtgtga aagaatgtgg taggggggaag  14100
gctagatcag ggagacaaag agagtgagct gcacagaagg ctcctgtttt ctgttttgat  14160
aaaaagagat ggattttaga ggcatagata cctggttgaa ctcccagctt ggtcattacc  14220
agactgtgtc ataaattgta attagcatga aaagagtata tgaacaccaa gcctcatacc  14280
tggcacatag tgggcagtca ataattaaat ctgccttttc ccagatccct ttctattctt  14340
ttcttattta gcactcagtt gtacaatgat tcagtgtgag aatgagccta ccttcctccc  14400
atggcaggtc aatattcaaa gacagtgaag caaagatgca gaattgagaa acttgcagaa  14460
atgctgtcac aaagactggg ttcactataa aactgctaca tattatgacg ttttgatgcc  14520
tgtacagatg tgtcacatgg caaaataatg gaccatggtt ttattctccc gtgctcttgc  14580
ctctcttttg tgacactaat gcattctctg agcccagtgg gagctaggca gagtagtctc  14640
aatcacatgc tcccaacagg gctacagctc caagcagcca agacagggac ttcctagggt  14700
ctcctctctg ccaccatgga taggaaggat atcatctgaa gaggaaccac ggagtaattg  14760
agcaagatgt gaaagagcag ccaagagaca cagatgctta tgctggacac ttgccaacca  14820
gttgttgaag gggtcagacc catcatttac tagttcttta agagactgtg taaggaaaat  14880
atacactccc ctccctttct ctagtgccct cgatttttgg ttgtggatat gggtactcag  14940
aatgccgacc acactgacca gtcttccttg cagctgtgcc aagtgatgag gttctggaca  15000
atgatatgaa agcataggta gtatgtgcaa ctccttggaa gtgtcattgg aaaggagagt  15060
gcatatgtcc tctgctgtcc ttccttgttg tgttatgcgt ttgtagtggc tgaaactgga  15120
gcagccatct tggacatgga tgtgaacaat gcaacagaag gagacagggt tcctgaggct  15180
gtctggggcc atgccaaccc tagactatct agatttcttt gtgtaataaa ggaaaaaatg  15240
tcagctattc tgaattttat gttactcaaa attacttaat cttaattaac taatagagat  15300
tttaataaat gttctactaa aatgggtccc ttgggcaaat aaatcctgga aatgttgtgt  15360
```

```
attacagaca ctttttaaag atttgcagtg caatttagcc cattacaggc tagtatccgt  15420
gggctcttgc aactcagagt ataatccctg gaccagcagc tcaatatcac ccaggagctt  15480
gttagaaatg cagactcagg caacccaaac ctactgggtc agaatctaca tttttaacaa  15540
gatcccaggt tatttgtctg caattcgttt gagaagcaca accatagatt acaatagcat  15600
cctatggtct ttgagtctgg aatagaagta gcagctgcca gtgggtatgt ctggagatcc  15660
tggagcacag gaatttttca cagccataga atggccgtgt gctcttcaag cctgaggttg  15720
ctgctatcaa cccatgaatc ctccaaaaat ttcagctctg agttttgagt cattttcagg  15780
accccatctt ggttgtcatt gactgagcta ggtttgtggc agacatcctc ttcctcttct  15840
gtagggatct cggagtgtcc ccctggtgct gcacattttg tgtcctacaa ctgcttttct  15900
tggcaagtta catctagatc tacgggaaag gtgagaaggg gtcttaggaa acctacctgg  15960
tgggctgcaa aacctctgtc agtcattttt attctcacac aactcacata tgggcacctg  16020
ggctagctaa ccagaacatc agttgaacta ggttattttg tgtgtgaaac agtaaccaat  16080
tagatcattt ctttttgctt tctggtttag ctggtgatag tatgtcaaag gcattacttg  16140
ctagtggtga gaatcttctt ctccggagcc tgacttcctg ggtttggctc caggctcacc  16200
atgcgccagc tgcaagactt cagtcaagcc tcagttcctt catctgtaaa gtggggatta  16260
gggtggtatc tacctcccag gttggttgtg catgaaatat atatgaagga cttagacttc  16320
ttccttgcta ataggaaaca ctatataact acaataaaaa tatatatata tatatataca  16380
cacacacaca agtaataagt tgttaccact atgttataat ttaaggggtc aaaatctaaa  16440
tcatgtgaat aaaaatctaa aaatgaggaa tgaaaagaag tacaggtatg aattggcaaa  16500
gttttcaatc tgtctctccc tttcattaac gcaaagcaga caatttgaac atccactgag  16560
tgccaaagtt tgaggtccat gcagggcact gtggaaatgc agtgatgacc ccagtgctgt  16620
gattcagtgg aggagaaaga gagatgcaca cataccgtat taaaagacaa atgtagaaag  16680
tgctatacaa tattctgtga aagaagcaaa gtacctgcag tataaatgac tctcatttta  16740
caaatcaata ggtggagctt caaagatatt aagaaaatag ctaagctctc agacctgata  16800
aagaaagagg tgggattcaa actcaggtct gcctgatgtc agagtccttg ctttctctgc  16860
cacactagat tgactacaaa acttaacagg cacttcatag agaaggtaac atttcaactt  16920
gacctcgaaa gatgagtaaa aagccaaacc aaaccaaaca acccactgta cttataaaca  16980
agtctgcagt gattctggcc ctccaatcac cagttttcat attctgtcca gcagtcgtgt  17040
ccccatgaaa caggggctta aagctggagg caaggagacc aattaggagg ctgtgtgggg  17100
acaacaatga gggtcaggac taagagagtg acagtggggt cagttaagaa ataaaaaaat  17160
tctgtaaatt actaaacagt ggattttaaa tctgctcata tcacttcctt aattatcact  17220
tgccatgggg gcaaagagac gcatcaacta agcattatcc ataggtctgc ttctgaagct  17280
tctaaaattc aaatggatga aattactttc tgtaatcctt gtgatttaac tgcgtgcagc  17340
ctcacagcca gcaagggagg gggcggggag gagtgaggat ggttaaataa aaacagttct  17400
atttctggca tgctttaatg acaaccttgt cttagaaata tttttttttg caatgtcttt  17460
tcagtgtcat tgaaagtgtt tttaatttca aagagaggct gtggcacggg atgttaatca  17520
atgaaattct ggcacgcttt tctatgaaca gggctcgtta tttatattta ccagtgacag  17580
agatgagttc ttcaacccag gcaatattat cattcatgcc tggttaatta aggaagaaat  17640
gccttaggaa actcatcctg atattagagg ggagaaggac ctattttagg tcttgggata  17700
```

tttcatttcc ccaaagccct ccctgtgagt cacaggacag aaattggagg cagaatagca 17760
tagtcgtcca gactaaaaaa tgttttggct gaaagactgg ataggcattt atgtattcct 17820
tgcttgtagg ttctgagtgc tttctgttat gtatgcaggg atgcaatgcc agctttttgt 17880
tcctctgaat tcctgtcgtt ggacactgcc aggatttagg gtagggtcag ccctgg 17936

<210> SEQ ID NO 50
<211> LENGTH: 2563
<212> TYPE: DNA
<213> ORGANISM: Homo sapiens

<400> SEQUENCE: 50
ttcagcttta ttttatagta ttgaacattc ttcaaaacag cccatctcca taaagggaaa 60
ctgggaaatg atgatatgag ccgagttctt cccagttttg agaggcaaga caccgtgcaa 120
gtgcatgatg cctggctact ggcacagtga cgtctcgtcg ctaactctcg ataatcccag 180
atcatgatta aaaacagtcc ctcttggctc ccagggaggc tgataacact tgtcaagggt 240
gggtgggctg attcaggggt actacattcg tgttgtcttg tctgtagtcc cactcctaac 300
ctcagaaagt gagtaaatga agaccctata caccagagaa aacctgtcat tcccgcaacc 360
ttccttttgc cctgcaccct ttcccatccc ccaaagtaca cttgacccct ctctaaagtg 420
gctgaattct acagtactct ggggagaaag tcaagttctt agctatgacg ttggtctttt 480
ttcccctttt gttaaaagaa aaaatgatga gaaatgttcc tttcttcacc atctcctctt 540
tctcttcctc aatttcttag gaacgaaatc acccaagata taaataaaat gttctaaata 600
aagctctgcc taactgcagc gtaagacatg tctgtgtacg tttgtgactg tcagcctccg 660
atggaagtca ttttcatgta attaattatt cttgtcgcag ctgaaagaga caggtgcatt 720
attggtgtac tttggcagac ttctgggtga acttaagaag tctgcatttc aaacacacca 780
aacaactgga gtgcagcttt ggcttttgtt ctgatattgt ttcttgactt ggaaccttta 840
tttctcaatt actgcaaact gaaaaaattg gaaggtaatt tactgataac ttagattttt 900
caatcaaaaa ccttaaattg caaaattaca tattttgggc atgtattagg taacaaaagt 960
aacaaagaat ctttgaactg aacttcctgc tctgaggcag aatgaggatg tgattttttt 1020
tctcttaaag gcaattttgt ttctccagca taaagtcggg tctgtaatcc ctggagccac 1080
gcagggttct gctacctgtt tgtcctgatt gttctcattc agtccaggtg atcagccaag 1140
atatgttttg atgaaaatag caattttgct cacccccaac ccacttgctt ttgtgtcccc 1200
cgtcactacc tcaatttggc cgtaattgta ccgctcccat aacaacagcc aaataactgg 1260
atatttgtgg agggcttata acagggttgt ccacaaagcc actggcaacg ccaaacagac 1320
cctgtatatc agcatctcac aagagagaca gctatccggg ggagcaattc ttggcagctc 1380
ccaatcaaac ttgctgctga ttacctctgc gtttccaatc tgaggccagc accccatatt 1440
tctcccacat ttcctccgta cactcagtct caggaccatc attccctcat ggcctgcctg 1500
ggacattaaa acaatgcaca cacagaggaa aacacacaac aaaaactctt tctctgcatt 1560
gagagcacca aattgcagca aagatcaggg aaccacgcgg tctcagggct gtgcttcagg 1620
ttgtgtgcta gctatcagca ccaagaatca aaacatcttt atgggtatgg atacagattc 1680 ccttttttgct gagccactgt gtgattttgg ggagcacgtt cgctgatcag ggtatgagag 1740
ctggatggag aggaagtcgc ctgttccggc ctgcacgtca tgtcaagcga agttagatat 1800
ttccctaccg acagctattt tgatctctca gtactaaaga gaaccgctgc aggtaccctg 1860
aagttgaatc ccacattctg tctgagttta ggactaggac tttgcaaatt gacagctcac 1920
atacttttgc tggtgtgcgg ccaacacaga gatgggcttc agtcaaattc agagggaggg 1980
agggagaagg caacaggagc aagggatggt gccccgtctt caaacgcaga ctcacagggt 2040
ttggaggtgg ccgcagtgtc acacctggag ctacagatgt aacagcatca gagggaactg 2100
caagcacaga gcccagtcct cccactgaag accacctctg gtgtctctgt gggccagtgg 2160
ggtacctgac acctggcagc aaggtgggcc ctaaggcctg caggcctcag gttgggtcaa 2220
gaaatgggtg tcaaatgtgt ccctttggat gaaaattaag tttttaacct aaacagggat 2280
aacgatgttt cacatttgta ggaactactg ccgtttccaa gcaattgctt tgttttacta 2340
atgatttgat caactccatg cttttggcta tatgtttgct gtctgagtgc caagtgtgga 2400
cccaggccag cagctttggt gtcctccaga gcttgggtag atttggactc caaggccctc 2460
cccagccatc ctgaatcaga acttgcgttt taataagatg cccggccgtg gcagggatga 2520
atcatttccc tgtaagatgt gctttggaat tttgtttaaa agc 2563

<210> SEQ ID NO 51
<211> LENGTH: 8474
<212> TYPE: DNA
<213> ORGANISM: Homo sapiens

<400> SEQUENCE: 51
tttaacgttc aaaaccagtg ccaagctaaa ttagaaacag gagtctacat acctgtaact 60
tacctcatcg gtatataatt tgtaacctga gatcccctca cagagaagta aaaatagcaa 120
ggctctcaag cagacttctg ctctgctgag tgcaagggca gggtgaggga ggcagcactg 180
gggaaagata aaagggccaa ggcagagaat gccaatcatg tggtcttggc aagaacacct 240
tctctcctat accctgtgat ggtatggaga atatagccaa ggaggtgaca tcaggacctt 300
ccaggcagag gagggtgtca ctgaagttct gagcctgcct aatcccaagt taactagtcc 360
aggaaacgcc agtactcagg caggtgcaga acagatgagt ctgttttcaa gttttgtagc 420
tggctcccaa caccctggaa gagatgattt gctgcatagt tgtctcactc tctggataga 480
ggaaagcttt gtccttcctt atcctgctac atggaaaaag tgacaaagta gaaaggagag 540
gaagcttatt ttttaattaa tcacatcaaa aaaatgggca tgtctctgca ttctttgtaa 600
tgattatata ttgaaagcta ttaatataac aaatgcaata ctgagaattt ctaaatcaac 660
accatctttg taaaggaaac cttacttgta ttatttcaaa tatgtttttg tgttaatttg 720
taaaactctg ttcatgtaaa tgggttttgt tcattcgttt tgcaaattca aatattcttc 780
cagttaccat ttgaagagaa ggtatttttg ttctgcctcc tgttcataaa taggttcatc 840
aggtcttatt tattacgaag aatcaagaca gaactgcaag ctcttcactt tcctaaaaga 900
aagcaaccag gaacaacaca acagagtaga aacaaagagg gctatccaaa cctggctttg 960
aatcctggct ttgctctata agaaatgtaa cacctgagag acttaaataa cttttctgag 1020
cctcactcaa ttgcctttcc tataaatggg aacagtagtg cctaccatac tgggttattt 1080
taatgatttg gtaaaatggc atatgtcaaa gcccctagaa agaaactgtc caatagaaat 1140
atcacgcaag ccacatatgt cattttctag tagccacatt ttaaaaaggc aaaaagaaac 1200
tgggaaaatt aattataaca acatattttc tttaatccaa tatattcaaa atattatcat 1260
atcaaaaccc aatcagtaag cttatgttaa tgaaatattt tacattcatt ttttttctat 1320
gaagtcttca aaagccagtg tgtatttcac acatttggac actaaatttt cataggaaat 1380
gcttgatcta tatttagatt tcttaagatt ttcagttgaa aaaacagatt cacataccca 1440

-continued

```
ggttgttcca aaagtactta aagttttcca aaaactgaac caagtatcag tgttttaaat   1500
ttaaaataat caagattaaa caaaatttaa aagtcagttc ctcagccaca ctagccgtgc   1560
atgaatcttg gatgttgttt caaaaggaac catgagccat ttattcttag cctgaaattg   1620
gcaggcttta cattttggag aatttttaat aggactagca gaggaaccaa cattagggat   1680
tattttctca gtgtggggtt agatgtgtaa tgcatatgtt tgccctgagg accccaagcc   1740
acatactgta aaactctgtt aaaatgcctt tctctgctat taacattttc ctgtgcacat   1800
tgttcattta taatagtccc agccaaaagt ttagaaagct atgttccccc atagaccatt   1860
atttttatgc taattaatta gcaaaaccaa tatctcagct atgagatcca agctctagct   1920
actcagtttg gctgaaatct gtttttctaa ttattgacta ctttctgcta ctttaagtcc   1980
gccacctaag ttcttggaca gagctagctt ctgggagcag ggatgtctc caatggcaac    2040
acagttccac actgagtggt ggagtgggag ggagggattg cagctgttgg agtcactgtg   2100
gatttgggag gaagtaagag gaagaaagga ggagatttgt aggacagact taaaaaggaa   2160
aagactaaga cttttgacaa aatttcagtg aggtgcaatt ctctaaagtt gctaatacac   2220
ttcaacactc ttaaagggaa catagtattc atatacaaca aggagaaatg aggactcatc   2280
tggaaaataa ttctgtgtat atattcttgt gttcttaggc tcttgattct ttgattttat   2340
ttctgaattc ctggaactat atttttattt ccaatttgac aggaatttag gcagattgtt   2400
ttctcattat ttcccatatt tacaatttac attgcctgtc tgattgctta catttgggca   2460
tacagatata cagatatgaa tatacacaca tataaataga tacaaataga tataatctct   2520
cactatctga gtttttataa gggtaagagg gaacagagca gctactaata ctctgagcat   2580
aaaccatgcc tcatgggcta tgtgttccat ctattcttaa caaccaaaga agaaagagtg   2640
attatcccta ggtaacagat gagaataatg aagactagag aggttacata tgtgactaag   2700
gtcctagtat tggtagagat aagacttgaa tacagatttg tctagaagaa cactgaggct   2760
ctttctccta aaacatgttt cttggaaaaa gacttgcaca acacgtgttg cctgcagttt   2820
gttcttaaaa ggaaagttct ccttttaatt ccttattatg aacatttatt ttaactccta   2880
agacagtgtg tacaaatgta tcattgtcat aagacatttt tacacctgtc aaatgggaaa   2940
ggtcatttct taagagcagc cagctgtaag tcaggggttt taaaattaaa gaaggaatta   3000
ggcgtgacag gcaataaaga aggggattgt gtgggagaaa caaaacagtt tgaaaaagaa   3060
cagagaccaa agttatggga tattttttgc taagggcatc aggaatctat cccacccttc   3120
aatatttggt gcctttctag gcacacatta agatcagcga ttccctaagt tcacaatata   3180
gctacagaac taattctcca ataatctgat aatttactct gttataataa taaccacaag   3240
gactaaaagc ttaactcctt attttcctca cttccagttc cttagctttc aatagaacct   3300
tgaatgcttt tgtcaggaaa ataattcaac tggcacccct tgaggaatcg tggaggaaat   3360
tttgccatca tttgcatttt gagtatttcc cgaattttaa ttatccttga accactatat   3420
gatttcacca tcttatatta caggtttagt atgtatacta tttttatat tgacccctac    3480
ttttactgat atcattttcc ttagcccttt tcatgtttgg atctctacag ttacaccatt   3540
ctagccatag caaatggcac gtggggaata attaaggaac ccagccaaca aacagaactg   3600
aggccccaga caagttgtcc cagcatcccc agccaagatc cagtaattac ggagcagagg   3660
cgagtgacca atttaccatt ccttaattcc cacaaacttg taagtatagt aaaatggttc   3720
ttggcactgg atttggggag atttattata caaaattaga taccaaaacc aaaaattcat   3780
agggtgacta tttacccatg ttttcccaga acagtcccag tatacacctg tcgtcccaac   3840
```

ataattatga ttagtgctgg tttcattcac ccttaaggca tcccagtttg gatgacagtt 3900
caccttctaa tatgccatgt tctgtactca aattatggtc ttgccaaatg tctagtcttc 3960
tagtatctta aagtttgcat acagagagcc gaatgttgct tgcttctgaa tttggaccac 4020
agttgtgact gagcatacat aaaaattcag aattctttaa gtttgcctga aagaaaatag 4080
atgcttaaaa tatatattta taaaaagatt tctcaaccgg tgacactgaa aagaccacat 4140
accaaaatgt tatttacatt gtggtaccta gtaacagaag aaacaggtgt aaagagaaaa 4200
caaaatttg ttgccatttc aattttcatt gccacacatt attgaaagaa cccaaagcaa 4260
tagtttcaag actatcaggc aaactagtgt tcaaagacga aggaaaatgt tgttcacgtt 4320
tactaaaagc tgttccttct tcaatctata tagcaagcac aattacatgt gttatttaat 4380
tttcatggca ctgtgagata ggtactacta tcaacccatt ttacagatga ggaaatggaa 4440
gcttgcagag ttaagtagtc tgcacaatca atgctgataa atacaagagg caggatttat 4500
acccaggcag tctgattcca gatcctgttc tcttagtctt tagcacttac tctctattca 4560
aatataacat agagaaatta atttgtctgc atcaaatcaa tttgtaagta tcataaatat 4620
aattttgtga agaaaatgat tctgtatttt cttccttctg gtgaatctat ttctcttcta 4680
ttacaatctg atcagtctta caggaaagca aaatcaaata tactgggtac attgtctgca 4740
attttaagat gctaaaccta ccagtattta gcaatattca cttagattat atactaatta 4800
tacctacata ttataggatg tatattattt ataaaagcca ttgttgagtg attagttcta 4860
caagggctgg tccttggctt gatatttgtc aattttttt tttttccttt tacaacttaa 4920
ctgataggat attctcctca tattgtctat gaaagtgata caaaagttat atttgagtaa 4980
aataacagag atagctcaag aaattgcata gttgaaagat atttgtccat atacaaattg 5040
gttaagtata gcccacctca gtggaaggtg gtatgtctag aattactgga aaaagtgctt 5100
attagtaatt tacaggaaga aaaacagcct tcgtgtctct caaagaaaga gttcatcttc 5160
aaaccaaatc agcactcttc ccaagaaaaa gaacaagtat acatcccttt tcattgctgt 5220
aacatgggac aggactcctt ttggccagaa caaaaaggca gaacacagag gacttgcatt 5280
aggagagata atgtcaggct gtgcagatag tagaagccag acattctgta gagtaacacg 5340
aataacaaca gtgatatcct tctatggcca tgaacaggtg cttgctaggt gttaacgatc 5400
ctttctgtcc ccattttata gattaaaaaa agatatggga aagttaagta aattgcctaa 5460
aatcagagag ccaggatttg gtctagatag tctgtgctca taaccacagc attatgctaa 5520
acaaagaaca gagatttctc taggaaagaa caaagctatt attttacctt atataattct 5580
atttaatcca aattcatggg atgaggcata aagaagatgg agggggagat tagaaataaa 5640
tatcaggacc ttagagaacc atatctgtaa tgcttctgta gggttacttt tacgtacaca 5700
atattttgtg tgatccatga tatggaccct tctctctctg tgttctgtat ttcagaagat 5760
tcagaaagac ctctaagtca taatgattcc aagcttaatt caagccaacc atccagtatg 5820
gtttgctttt aagttcagat gggcaaactg tattaagatg atggggagga gaggagaatt 5880
attttattca ttgtcgtgat agatataatt aagttgtaaa taactcagaa gtaccaaggg 5940
agaactgctg caatcctaaa taatgattaa accaagccta aaagagacca aaaagaatca 6000
ggctttctga acagaacaga aggctacaca gaaactgtct ttaaatgtga gagcaaacat 6060
acataatggt gacattcaac ttcaggatga attccttact ccagattttg taaagcacag 6120
aaacagtgac ttcgtatttt taattttta aagaaaaaaa tacatagccg gagtgatttt 6180

-continued

```
aatgcattct ttctctgaga ctgggacttg attagatggc aattcaaggt cctgcaaatg   6240
ctgatcatga tggaacctaa ctcctctgtt ggcaggcact ctgatggtag gcacttccat   6300
tgctccatgg ccattattac aaccccaaca gtgccaagag cagatgtttt tttctgttgt   6360
tgtcggtggc atggagtcct atatcccata aatgtaaact aggtttaatt tggactttta   6420
gttagaaaag aaaaagttgg ttcttaaggg gaaagatttc taaggacctc ttcaatactg   6480
tatagcaaaa acacagaaca tgccatatga acctcacttg ggaaatttaa ataggagctt   6540
tagaaactaa cgtgatttgg caagaacgta attgaatgtg gttgtgaggt cccactagca   6600
acatatgctt ttactaagct gtactattcc tttcagtctg agcttttaaa atgttacttt   6660
atattttcta tgattatcat tcagaaccaa aaccaaagta gttaactctg aataaaacta   6720
tcctattata aaattagagc tcatcctgag gaagagatgt ttaaatgtga ccccttctc    6780
ttctctccac cccttccaaa tacactcata aaaactaaag ggggaggagg aaaagtctgt   6840
ttatgattat gaattgaact ttgaaccatt cctattgttc ctgccaagga tttttgaatg   6900
ctaatgtaaa aagatatata taaagtaaga tctgctaagg tattttaaga gtctacagta   6960
atgcaccaag ctttttttcct tgcttcattg ttaaagataa tatgcctttc taacaaaaat  7020
gctttcaaga tgtaaccata ttttgaaatg aatatcataa tacatccttt gcaagcctgg   7080
aatttggaaa caaagaactt gctttaatct gtttttcttc ttacctgata agcaggatga   7140
cagtgctgct ggaggaggtt tagacctgtc cccagtctca tttgcttttc ttcctctttc   7200
ttcatcgtgt gggccctgac aacctttctt tctgaagcta cataaattaa acagggctaa   7260
gactatcaat ttttgtacca gctccaaaac aagccaagac aagaaagaat cctccagttg   7320
atcgacagac ttccagtatt tctgctaaac tggtagagcg gtgaatctcc atgctttcct   7380
ctctaatgaa ataacatcag aggttggatc cttggctgtc tttaattttt tccctttac    7440
gtagctaaaa gatatttcaa atgatgtaga aagacaatat attctcttta ttgttcattc   7500
cttctatttc acaaatgctt ctagtcttgg ggtatcagct cccctgaaag tcagatctaa   7560
gaacctcagc acacaagccc tgaagtggcc tgaagcacag cagtgaacat gcttcaaact   7620
gatgagttga tttttccttt atgaggtctg atcaacaaaa taacttgtga tttttcagat   7680
aggtacataa aggatggttt ataataggta atcaaaggaa gtatgattca atttgcaaag   7740
taaatgtcag tagagccatc tgattagaag acaaggcaat aacatgaagg atctactagc   7800
tccagaaaag actcagcaga tagaagggtc ccaatatatt ttagttgaaa ctggatctta   7860
gatctgactt tagattgtgg aatttcacaa aaccactgca ttaccagaca attatgcatg   7920
catattgtct aattggctaa ctccaggaac aaaagatgga caactgttac agttatattc   7980
tgatgaattc aggctaaagt ggcttgaatc aaggaatatg gtgaccctaa aattataatg   8040
aaaaacaaag caaaactata tatcttgttc tttcctctca tatctgtgga cattaaaaaa   8100
aaaagcctca gcttttcact agtctgaatg gtataggttg gagaagattt tagacatttt   8160
ggacttaata gacaaaacaa tgcagttaaa tgtattaagc aatttacata aattaccaaa   8220
acattatcaa aactactcta tgaagtaagt gcaaatggta tccccccttta tgaatgagaa  8280
cctgaggctt tgaaaagttg agtgaaccaa tcacttacag ctagtaaatg acagaactgt   8340
ctctgaatca aggttatttt tattgtgttt agacacagtg acttggaaag tgtgtttgta   8400
caaatgaaaa agagagaggg agagattgag agactcaccc ttgcccctct ttgctttctt   8460
attaccatct ataa                                                     8474
```

<210> SEQ ID NO 52
<211> LENGTH: 1938
<212> TYPE: DNA
<213> ORGANISM: Homo sapiens

<400> SEQUENCE: 52
ggggctggtg accagaggag gcctccaggc agaaaggggg agtgtctgca gaagccagag 60
gggatatcag gacagctggg agcgcctcca ggacaggctc aggcctggcc cctgcaggga 120
cagtgacagg gagtgggtgg ggctgagctg aggaggctca gctaggggga cagtgcagca 180
atgcagcccc tataagaaga cccaaggccc cttcggcggc ctgcacagac cacggcctgg 240
gcagagagtt cctggctctg gggaggcagc ttaagcagcg actgcgggtg cccaagaaca 300
tggagcccag gcccaaagga ccttgtacct tccttgtcca ggaggctgta ccaccactgg 360
cagggtagag aatcaatgcc aaagtgagct cctcttacag gcgcacacca tcccattcaa 420
tcctatattc ttatccccta aggttcccca agcactcact aagtgctggc ccctgtggag 480
cacctgacag agaatcagac tcctaggagc aagaactggg cacatctcgt tcactgctgt 540
gtctctgggg cctagagcag aggctgacac agaggagaaa tatctgttga gtgaagggat 600
gtgaaaagaa atcacaacca cctgagaggc agaaagtatt attcccattt tctggatggg 660
gaaagtgagg ctgagagaag ggaagtgagt aacttacttc cctggaactc aaactagagt 720
ctgggtttgc tccttgcata gcagcggggc agggaaaccc ttcagcactg atttagtggc 780
ttttcctgga aggaagtggc atctgccaat tagctccctg tctttcccgg ctagtcatgg 840
ctgggatgca ctcacagccc agagagggtt caggttagga gagtaaggct aagttgttct 900
taaaatgact ggtaaagatt cagtcacagt taacatttac cccaagtact gagcgagaca 960
cagtctcagt tgttcaccaa cctcaggagg aaggtggaat tctcctctat ctcacacatg 1020
gacacagatt ctgtcaagtg aagtgatgtt ctcagtcaca caggtggctc ttggacggga 1080
acgaggcctg tggtcagctg gatgtgagga gttggggagg aagccaatga gggaggaagc 1140
tgtgggcaat gtgatgtctg ggtttcacta ggcacaggga ggggctggga cctggcctca 1200
caaccaccac catgaaggga cggctctgaa gtgacagacc agacacctgg gcaggcagag 1260
gcgttttcat ccagcaggac acctgcagac acgtatcaaa acctgccatc actgtcctta 1320
gtctacgact tagggaaaga gtcatgacaa ggaagggaag aggttgaggg ctgcatgctg 1380
gtatccatgg tggccaagaa gcaacatgag tccacagccc tggagctcag ggtcaagtat 1440
gaaacagata agaaaaccta aaacatgggc tttccaagaa acatgtaaca cagcacatgg 1500
ccccgggggg ttcctggcac acctcgtgat tgtcagatga ggagctgagg cctggaaagg 1560
aagagcgaca tgtgaactaa tgatgaaacc aagacgggtc gcgattgcct accacccaga 1620
gccccagccc ttaggcactt gatgactcct tcctcctgaa cagtgatgtg tcagctacaa 1680
caccacagca gttcagatca tgttcaaagg tagagtctgg acggcactgc tcagcactgg 1740
agccactacg tggagttccc gagcacctga aacgtggcta gtccaaatga gatgttctgt 1800
aagtataaaa acacaccgga tttgaacatt ttgtatgaaa aaaggtttca agtatctcat 1860
gaatgatttt ttgatactga ttacatgctg aaataacatt ttctacattt ggttaagtaa 1920
aatattttta agttaatg 1938

<210> SEQ ID NO 53
<211> LENGTH: 1638
<212> TYPE: DNA
<213> ORGANISM: Homo sapiens

<400> SEQUENCE: 53
agcccagtca gaagagaatt ctacagtgac atgtttataa ttgtgccctc ctcaagcaga 60
aagcaattta aacacaataa agtattgcat aagaaactgt ggtagacata tagaagcata 120
caatgtcagt gaatcctgaa gatggataca atgtttgatg actgtgttcc aaaatacctt 180
cgagaatcca gacatgtttt ataacttaaa ctgatagata tatattttaa tatatttatg 240
tctataaagc caagaagcta ataatgccat tttctcagtg ttaatattag ctgctttgta 300
aaactaagca aaatattaaa ataatgccat attttggata aacagtagac tgattggaac 360
tggcatcttc aaagccacca aagcattcat tcacagctca aactggagaa tttactccct 420
gttttttttt aatgaaacaa ggtaaatttt gagctgcttt cttaattcca ttttctaagt 480
gattatttta acacaaacta ccctgagtct agctggaaag agaagagcaa agggagagaa 540
agtccactat ggaatggcag ggctccaggt cacctgctct tctggaaagg tccccagaaa 600
ttctggcatt gtgttgactc agattcttta acacttgtat tgtacacatt aaaaaggagg 660
aaacctttaa aacactagta ggaggggtca gttgcttacc cagaattcct tctccaggca 720
ggtatagctg gaggagctgt tagagccatt ctcctgctat ctgtcatttt ctcagatgtg 780
ctatcaacag tgcttgccac taaacctgct gagatagtca ctggcccatg agagacaaag 840
cttgtcactt aaccagagca ctttggttgc aagatgtgac caggtggttc catgaacact 900
taggtcctaa cccccagatt cagggaaatt tgagcttctt ctgagtgata tagaaatgct 960
aagactgtgg gactttagcc agtgtttctt tctcttggtg gacactggcc aacatccatc 1020
atcgaaagag ccatctctgc cctgagcttg ccaaccacag aaaactctga gaagaatagg 1080
cttctacaat ctcatggcta atctgtgttt tcccagacgg taaaagatct aaacataaac 1140
acaaattcaa aaaagcctaa caaaccaatc atgaagccaa acaaatgcaa acatggatat 1200
agtttcagga tgaatggatg aatcccatgt gctatttggt atgcagggaa tctaagggaa 1260
tgtatttata gtctatttcc tgagagagta atagcaaatg acatccacag gttcttaaat 1320
tgcatcactg tcatcctgga tgtccttatt tcctctactt ctgaatgcca gatttgggac 1380
tttaattatc aaatgggtgt ccctgttcag atgtctatac ataataaagt cagaagggag 1440
tttaatttga gactttgtga aaatttactt aagaagcatt tctatagcta tatagaaggg 1500
attcttctag attatttaca gtatgagttt acttaatctt ttgagagatt tttaagagaa 1560
agtattttta tggtctctta cagtgaagaa actgcccaag tttccagagg atgacagagc 1620
cggatgcaaa cccgggca 1638

<210> SEQ ID NO 54
<211> LENGTH: 9353
<212> TYPE: DNA
<213> ORGANISM: Homo sapiens

<400> SEQUENCE: 54
aatgtgaaag gccctgagaa accccaaacc acagctttcg atcaaccaca gcatagtggc 60
cctctccagt tctgtcagct cctcgccgac tccagtttgt agaacagtgt ggagaactcc 120
agcatgttaa ttccttatgt ggattgagag cgttttgtgg tcagcacagt ctgaagctgc 180
catgtacttc accaagacag gtgttccggg gtgtcagggg agagaagagc agcgtctgtg 240
aacgagaacc tgggggtcta gagcactcag gtgctctttc taggggtgag tgggcaaaca 300
ccacccacac tgtcatgtaa gtttccacaa tccagttgtc acttccagct gccaatgctg 360
aacttcatgc tcctgtcttc cactttgggc ttggtagaga tagcagcccc tggagcaggc 420

```
tgtcttggct gaatacatct taccctctcc atcactgcca gtcgcgaatg aaaattatgt    480
gaaatatctc acttgataaa tctctaattt atattgtgta aaaaagacca cagggaccag    540
ataaaacatg ttaggacaca ttgctctgtg gctactagtt agtaacccct gaaaaagcct    600
taggcagggc agggcagcgt agttgtggca catggtttgt gttcccaggg gcaacaagag    660
tattccattt cagtttggag atccttgtca aagccagtac attttgctca attgatcatt    720
atttttcttt ggctgagtta agtagcttcg ctctttctaa aggatcaatt ccttgtctca    780
ggagcatttg aagcttctgg atgaggatta gaatgattga aatctactgt gacctgtgga    840
gtgactaggc aagtctcaga tgcctctaac cctctctgtt tttctctcta cagaaacttg    900
cttcaagaag gagtctctac tttaagtgcc aggctaggag cctctttatt ggaccacatt    960
agttccctac agcccaattt tgaattatta ttttattctt tcttattctt taacactcaa   1020
gaaacataaa gcctgtgatg tagttcatgt tgtgagttaa gggaggtaca agaagtgtgt   1080
ctttcaggtt gagaaacaca tgccaagatg gaaggcagag cataaatgca cgggggagaa   1140
tgtatgtgaa ggataagggt ggggagcagg agtggtgggc agcagtgcag gcctggcact   1200
tgctgaaggg aaagagagtt gggtaggaag aatctagact acagcatagc tccaagatat   1260
gggaagccca agaacagagg agttgccact ggggcctggg ttgtgcccag ggaggggagg   1320
cctcagtgtg aaggctgcag ggagcccaaa ggatccatag ttaaggcttc atcctgctac   1380
tcctaaacac tgcttctact gagggaccaa aaaagcttaa aaaccctcct ctgtggctaa   1440
agtggcctca tggcactgat gtattcaatc aactggaagc agaggtcagc tgggaacttt   1500
ggggattgat ttacttttaa aaaaaaaaaa atcggaagtt gctagcctct tctttctgcc   1560
ttgaatgtct agagctggac ctgtcctcct gtgaccctga agacagtaga tgggttcttg   1620
atgacattct gagaacgtca tctatgccta ttctgggctg cttgttgaat gagaaaaata   1680
aacctctctc tacttcttat gtgagaaaaa caaaccactt tgttgaagcc tctgttagct   1740
gagttatgtt attgcaccca aatgcccaaa tatcagtgaa acttagtggt gtgtcagaca   1800
gcccagatgt tgatgatgtc atctggcttc tgaatacaac tgtgcctgag actaaaccca   1860
agccccggac ttttcagcta ttagagaaag agagttctct ttctgcttaa gcagtttagg   1920
ctggattttc tgtggcctgg atggaaagac ccctgatacc aaaaggttag aagcttttac   1980
agttccttgt ttggaaaccg ggtcctagtg tcccttgcgc aggatgcttt tctgactttt   2040
gtggcctgcc accattcgca gtgggtagtg tgactcagct tcccattccc aaaactccag   2100
agccacattg ctgggtccct tcactctgct ttactctcct cccaagagta gcatgggcca   2160
cgtgaattca tccatgtcct gaactaatct ggttgttcta ccaggttact cttaagttca   2220
tgggccatca ccccccttgta cttactgagc tccagggttt tcatctcttc tgagaatcga   2280
ccgtttagtc caatcttagt acagaccagc attaataggc aattaccaca gggagataat   2340
acagagggaa aaatggctaa aaatatacag tgaatcacag aaaattacat ctcttaaaac   2400
ctacagtgta ttcctattgc catagcaacc cttggctagt aaagacagag atgatttatc   2460
acaggctttc cccggagctc ggttctgccg gaagcacctc cagcctgtgg tgagttccag   2520
cgaggagggc aatgcagaca cgggttttct ctcctccatc ccttccagtg gcatttctgc   2580
ggaagaagac ttgagttcct tctataaacc caggtcatct cccggcccct ttctgagatg   2640
aaagtggctg tctctaacct ctgacaacgc ggcgtcctgc cgagccagcg gccttccagg   2700
agggggcagt ggggcgggga catgaggagc tgtaccagac cgtctgaaca aatgaggaga   2760
```

-continued

```
ggagaggagt tctcctcctt tccttttcct ccctacttct cctctcctct ctaccctgct   2820
acttccttgt gaaatggact ggagaggaag tcatgtcctc acttggaaat gagtctggtc   2880
tttaggaaga ttataagtat gtaaataaac atcttgttat ttcgttggaa ctctaaaatt   2940
cactggcata gatctttctc ataatgtaaa aattagattc ttgatcaagg gatgttaaaa   3000
gtgggtaaaa atttgatgag aaacagtgta tttacacaat ctcaaagtag atcctcataa   3060
aacacctatt gatttcaaag gaaaaataat acagtagaga ggactgataa tccccacctg   3120
aatcaaatga tcaaaaacat cgcaagggac aaatgggaca gattgatagc atatctcctg   3180
atgtgtgtgc taaggacatg atatcacctc tgtggttttc ctgccaaaaa ggtacaaccg   3240
gaatctaatt gtgaggaaac atcagactaa ttcaaaagga gggcagtcga taaataaatg   3300
gcttacattc ttcaaaaatg tcagtgtcat gaaagacaaa gctgaagaac tattctaatt   3360
gaagaaacct aaagtcgtga cattgttaag aggttggtgt tggatcaaaa cattttttc   3420
tctttactta taaagaacat tattagaata actggtgaaa ttttagaaag atgtatagtt   3480
tagataatag tgttgtgtca atattaattt cccgagttag ataatggagt tatgaaagag   3540
aatattcatg ttttttagga aacatacact caagtattta gggataaagg gggatcttat   3600
ctgcacctta ctctcaaatg gttcagaaaa cagacatagg gaaggaaaat cagaagcaga   3660
cagggtaaaa ggacacagga attgtctgta ctcttgtatt tttctgtgaa aagtactttg   3720
tgcttttctg taagtctgaa atggtttcaa aagaaaaagt tcccatctgc agactcaaat   3780
ccttttcagt gaattttctt cccagtcttt ctttccctcc ctctgatggt atgctccgtc   3840
ctcacagctc cctttacaaa gcgaattctg tatgggggag tgtgaggaag ggtgtgtgt   3900
gagtgtgtgt gtgtgtgtga atgtgtgggt gtgtggatgt gagagtgtgt gtgtatgtat   3960
gtgtgtgtgt aaatgtgtga gtgtgtgggg gtgtgtgtgt gaatttgtgt gtatgtgtgc   4020
gtgtgtgtgt gtgtgtgtgt gattgtgtat atgtgtgtgt gaatgagtgt gtgtgtatgt   4080
gcaactactc cgatgtcaca gcaaaccata aagccgggat aaagtcagtt gttacgatgc   4140
cgaataaggc caggaatgaa gtcagaagcc ccttggtggt tcttttcagg tttctgtgga   4200
caggagggcg tggtctcggc gggatgcact cccagctcag agagtgtgag aaaaagaccg   4260
agttcctagt ctgcatgctc gcccgctctc actgtctccc cctcccctgc tctctttctc   4320
acacactcct ctctctttcc tcttctgtcc gagagtgcct ttgaatactc tggaaccatt   4380
tctctctggg acagacatct ctccacagca gggttcttcc ctggggccag agagcaaggt   4440
tcagtatgca gagcccgcta actttggtat aatgatagct atgggtttaa tgtatattgt   4500
gttgaggttc attccttcta tacctaattt gttgagtttt catcatgaaa ggatgttgaa   4560
ttttgtcaaa ttgttttcca cacctattga gatgatcaaa tggtttttat cttcattctg   4620
ttaatgcgat atatcacatt tattgatttg catatgttga actatcttgc atccaaatcc   4680
cactgatcat ggtgagtgat tcttttaatg tgtggttgaa tttggtttgc tagttgttct   4740
gttaagggtt tttgcatcta tattcattaa ggatattggc ctgtaatttt cttgttatgt   4800
ccttgtctgg ctttgatatc agggtaatgc tggcctcata aaaagagctt ggaagtctcc   4860
tcttctagtt tttttggaag agtttgtgaa ctgcacctta gatattgaca ctgtcaacaa   4920
ctcttggttg gcctttggtc tttggcgttc tagatttttc tttacttctc ccctcctgat   4980
taagggtcat gtgtctctaa aactccacaa cggacacagt cccttcaggt gctccgcctt   5040
ctcaagctgg ctctccctaa ctggcctaga cagcagcaaa gcccagatat ttccacgtga   5100
ctcatgcaac ccccttgctt ccaatgtttt gcctcctgct ggtgctcaga agctcagagt   5160
```

-continued

```
ggtattaaag gggcaacagg aaagcagcaa gactgccccc accccacttg ctccatctac   5220
ccactgtagg gaagcaactc cagctcctaa ttatttattt tatgaagtgc tgcccttggt   5280
gttaaaatca cctcagggca cagagcacac aattttaaaa caaaagatac aaggcagagg   5340
cttggcaatg acgggcactt tttaaaaatc agcaataaaa tgccagtttg aggctcaccc   5400
cagggctctg aagattctcc aagagggctc tgtcgatggg aggggcaggg agtgagtttc   5460
ctacagctgt ttgctcacga agctgcctct ctactcactt tccttcacac tctctctgag   5520
tttttatgac tcagcttgag gccagaatca actcatttat tttcttcctg tacctggctc   5580
ttggggctgg tgggggtccg tggtgtctgg caagggcaga gtggcaggcc tgctttaaga   5640
gcctggcgtg gggggccagca tggcagctag tgcgtcactg ctgggccttg ccagtagtta   5700
aaaaccaaat aataatattg ataatcacaa taataataat aatatggtga gagctaatct   5760
tgactgaggc ttctgtgagg tgggtatctt ggctcatcat taagggttct tcagctttta   5820
aagatgtgtt tagaatcaga ggggaaaagt ccaaagcaac catgttattg gatgggaaaa   5880
gaaaagtacc atgttgaagt cattttagct tgaaggaagg tcacagccac tggtaacaga   5940
gatactctca tggcagatag gtttacctaa agcacgagca atgaactaaa gctggaatga   6000
tcccagctat aattcccagc ttcagtgcct gcatgacttt ataaatgaat ttctaattct   6060
cagaactcaa acagtcattg ccaaatattt attgaccatc tctttctgcc aggccctgga   6120
gggatctctc aggagaagaa acattctcta atcaccacag gtttctctcc agagacctca   6180
gcccagcacc tctgcaaggg gagagaggag aggcgtcctt cagctcattt atgcctgtat   6240
tgatcgctgc tgcctcaccc tcgatgtcgg tggttaccat ccagtcctgt tcgatctgat   6300
tcccatgcaa ccatgttctg gaattccctg agcactactc cacctgaaga gcagcccctg   6360
tctctcctgg acagtaatga ggtttccttt gcagtctcac actggcttac tatctcatcc   6420
cgccaagcat ccccctgcta cattcatttc tctctatgcc cgggtttatt cagctgtgtt   6480
ctcctctgct ctgtgggcga caggagactg tcacagccca gttggaattc actttatctt   6540
tccctctgcc ctatacgctg agcaaacatg tgcagttggc atttcagcag tggaaattct   6600
ctgacccccct ttgctgttgc ctaaaacaga aacctcagtg gctttgcagg aaaattccac   6660
agtctcctgc aacctaaatt tagctatttg ttgaatatac atgatatgcc ttgctgttgt   6720
gccctcaaga ggcttatgaa gctgttggtg aaataaaaca gacacatgtg aaacaatttg   6780
aaaacagcaa agcacggtat aatcagtatt atcattaggt gccaaaatgc gtgatactaa   6840
aataccatca actagtcata gagctgacac acactgagta cccaggcaca tctcatttca   6900
acctcatgac aagcccatga ggtgggctta ttgtccccat tttatgcatc aacaaactga   6960
gtcacagaga atttaatagc ctaaggtctc ttggctggta agacaaccca gctctgttca   7020
actccaaagt gtgtgcattc tcattctact ctatgctcaa ccactgccct gcttagctcc   7080
ataaaggtgg agtctaggtg ttttgcttgt ggctgtgttc cagagcccag tgctaggaag   7140
catgctgcac ctcttacaga aagatctata ggaaaagcca gaccagctag atcgctttct   7200
cgagtcagat gtgggacaaa tgttgagggg tttggaggat gtccaagttt ggccatccca   7260
gtggtgtagg gtttgcgttt gatcatgaag agtggagaaa gagaaaagga aactaacaca   7320
tacagaaaca cacatacacc gcatgaaaca acacaaaccc cacatacccc aacactgctc   7380
ctctttttga ggttctaaat ccagttcttc ctggcctctt cctgcccctc acctgccttg   7440
gtgggacctg cctgctttta tgcgcttaag tctgaatcac acctggagag cggggcaggc   7500
```

```
ttaatcctat tttttatccc ctgagatggg ttagtccttt gcaggctata tttgttaaaa   7560
tgaattgaaa tcaggagtgt aagacttttt ttttgaattt gtttcttttt cttgtctctt   7620
tttgggaagt agcaatggta gaaaggaaga acagtagaga cactcctcga tagttacaag   7680
gggagatgaa gccttgggtc tgatctgtcc cacattagat tcccatttga aaaaaagaga   7740
aaggaatgaa gctacctccc tcatcaagtt agcctggggg gtctgccgca aagaggattg   7800
aaggggaaat gttcaatttt accgctttgt tctgctgggt tcttctcccc aggacactgt   7860
ttagtgcact gagtgaagta gaaaatgaag agcaggtgag caatcagctg tgaaaagctt   7920
taatgggccc ggcacccctt tgggaatgag gctcggctct tgctagtgct ggggaacaac   7980
atctctttca gttcagtagg ctttgttttt gtaatgggaa tttaactccc tcaggtggtc   8040
ccgggatgga ggaataactg tgctcagcag cagtggcgct gcagcatctt ctaaagggaa   8100
ccaaggccac tgtccccaaa ggggcccctg gctcactggg aggcctttgg aaatctcaga   8160
cttcctgggt gggagaggag gagatcatgt gaccccgtga acagcatgat gctgtgatta   8220
cctggggctt cctagcaagg gcactgggac aggtcctgga ctgagagctg caatggattc   8280
agacccatac attggatccc ctttttatgt ttttgagtag aaaactttat aaattatgtt   8340
tggttttaga actgtcctct aatgtaactc tgtgcagaga ggtttacgtt atctcacata   8400
atccttacaa ttatacacgg taggtggcat tattcttgcc ttacaaatga gaaattgagg   8460
ttcagagagg ttacataact tctcagggtc acacagtgga gctggattcc aaatgtaagt   8520
tcatttgacc tcgtgttctg cagccaaaag agcccacttc aaaccgaatt tctacttccc   8580
aactaaatgc cactggcatt tttaaaagta cttgagatgc acctagaata gactctgatt   8640
tttagtattc ccttttcagt tgaagaaaca gattcgagaa gataagggtc acacaggtag   8700
gaaggtagtg gagagccaag actagaaccc agacccatgc gaggaaaaat agggatggaa   8760
agcccagggg aaagctgcaa aaactggtca agctgactgc ccctttatct cttccttcct   8820
caaattcacc tccctaccct cttccacgtc cctctctttc caagcattgg gccagttcca   8880
tttccacgtc ctgagccagc tgtcataatc cctgcaaggt gttagctgat aacagcctgt   8940
ggaaggattg taaatgttag cccagcggag gatatgaaag gctgtagaag tctaaaagca   9000
aatgtgtgct aagacggtga cagagggcct ggccaccagg cagccttgca agatggcatg   9060
caccttggag tattcactca gcgtctggtc tgtccccagc cttgctagtg cagacactat   9120
cttctcttgc ctcaaatttg actggatgca gggatggtga tttgtagtaa taagctcaga   9180
gagaaatgca aacaaaaaaa ccaatttact aaagtataat aagacataaa acagctaagc   9240
tgactttagc ttgaccagat ctttcctctc acaggacaag aagatacctg gggaatcaag   9300
gtctttcagg gctctggaat cagtgcaggt ggagttagat aggaagacca gag          9353
```

<210> SEQ ID NO 55
<211> LENGTH: 8756
<212> TYPE: DNA
<213> ORGANISM: Homo sapiens

<400> SEQUENCE: 55

```
cagctccccc atcactgtcc ttacacgcca aatagctgtt tctccccagc tgaacagagc     60
agtcctttgg tgttcagaag acatctttct ctatcatata ttcagatgcc tatgttggga    120
atgcagccaa agccctgaga gagaacaagg tgctacagag tgcttgatca ctcatcacat    180
tcccgccttg accattggtc cagagccctg aggctaccgg aatgggtgaa tcactttgga    240
atcccagcat aactctgggg caattctaac agagaagcag ctatatatag ggcccaatct    300
```

```
tccagttttg tcttttacat aaacattagc ttgtttttcc cccttcttag gaatcagctt    360
ttcctctgat ggaggttgtt tcactctgac cttatcctga gaaaactccc tccttatctg    420
tgggcatgtc ttgactctag cagaagtaga cataagtaga gcgggtttgt tcattgactg    480
tggcctttat aagttgcacc atgatagacg aggctgctat ttctgggtgt ccgcccccat    540
cattaccatg cccggggctt tacaaaatag ctgggttgaa tcacactgac agaatctttt    600
agtcactttc aattctgcca aggaaatata ggcatgagct ttcagattct aaattaactt    660
tgattcctac cagatcccag tccctttag gtcacaaagc atctgaaaac tcagttgaac    720
actttcattt aaaaagaaca gataagggat aaataattga agccaataaa ggattaagat    780
ctatgtcaaa taaagatttt atccaaaatg taagaaaaac ggagatccca ataaactatt    840
gagatctgtc caaactttcc aaccctgaat ggaagccaag acagaaatat ccagttaaag    900
gggtcactga aatgtggttg gctctttccc caagagcagc tcatcctggc attagaagct    960
gggctcaagg agccacatgt ggatttgaat ccaaagagcc aaagaagaac atctgatgag   1020
gccacaactg agagaccagg agcaggtgtc aaaagctgaa atatgggagg gatggaggga   1080
aaatattgca atgtatagaa acattaggct cccctaagaa aacaagtgaa attatcacat   1140
atttttatca aatggaaaag aaagtctcca aggcaaagga cagccccaat ttgtgaaggg   1200
tgaagctgga ggacagacac ggccaccaga gagcaggaaa tgcacttgat gccatagaaa   1260
aatctttggg aatcagctgt actggcagcc caggagaact gttgcactca gcagaaacca   1320
agacagcagg gttctctctt aatggctctg ctcttttctg atatggccag ctttccctga   1380
tgtggaagaa atacaagcag gctgtgtcac agacactctg ccttcatggg gctaaggcag   1440
acagagattt gggtgcaagt tttttaacat aaacttcgcc ttgtacaaga tccctcctac   1500
ccatagcatc cttgaatgag gactaccagc cctccagtta aagacttaag gattctagat   1560
tcatccaagt aagacctaag gagaattcac ttgccttaat tttgggcaaa tatggaccat   1620
tcagatataa cacatacaca cacacacaca cacacacaca cacacacaca cacacagaga   1680
ggataaatgt aacactcaga gatagaaaaa ggttgggaga gatgaaataa gagcaaagag   1740
aaacaagaaa tgaaagagag atggataagg tagttaatga aaggaaggac agcactaatt   1800
ttgcagaatt agatctgtaa tgtggaggat aagcctgagg caatctcaga atgcatagca   1860
aaaagacaca gattaaagtg ataaaagaga aagtggaggc cagaaaatga agaaatcatc   1920
atgtgagttg gctgcatact agctctaaat gtttcttcta ctataaaatg gggtgataat   1980
actactctat ggggtgctat aagggttaag aaaataagta attagaaagt gcctagcatt   2040
tagaaagtat caaataaatg gtagttgtta ctactattac tactaatatt attattaaat   2100
aatgagcaca gggtcacaag aaaaaatcaa taccactgac tgtggtcatt ttcctgagac   2160
taagttagtt tgtcagcaag tagatttttt ttaagaacat agctgctata gttccttttt   2220
tttttaaaga atgtctgctt tttatcttct acataaatta taatttaatg aatacaaaat   2280
gtttaggtaa aacttcctaa aagaattttg catacagttt ctcattgtct tctgagatta   2340
aatgttacaa tggagaaatc agagacaagc ttgaggttct tacatggaat ctttatatgg   2400
aataaaaatt gcagatataa cattgtcttc gaagcttagt aactccatat atctttctgt   2460
cttttttttt cctttctgga ttcagttctc ttaacctgcc ttctatgata tccttcaatg   2520
ctgtcttatg tgtttgttct tttccagcaa cattgctatg cttatgttgc ctttatcttc   2580
catgaccatc atttttcttt ctaacaattt atatacatct ttactcttta atttactcaa   2640
```

gcctctcctt ctcttgaaat tattgcacta aagtgacttc tttttctata ttgtagtttt 2700
cagttttttt cctctcactt tttctccttt ggctatctta gaatgagtct ttatctctct 2760
gttttttttt caaaggtgcc atgttctttt taacttctct gcatggctgg ggcaaaggga 2820
tctgagtcct gggtcattct ttctgaatat attcagagat agtctttttt ctaattttca 2880
ttgtttgccc gcagaccacc cacacaggag gtatgtctgg ctcgcagaaa atcctaactc 2940
acaactggag gcccataaat ctggaccatg cctgaaatct ggagggttat gtatcatctc 3000
tcagcattct tttcaaattg attccaaatt caccaatttg gcagatattc tctctagtct 3060
gattggtact tgtagctcta gctatatttc ttcagatgat ttttcttttc tgctttatgt 3120
tccgtggatt attttatagg ttacacactg gagactatag taaacagact ttttaccaga 3180
agtccaatgt agtcttttaa aaataaaaat ctgatgttac cccatcattc tgcttccatc 3240
atctgctttc cacccacatc tccttttctc cttcactctt ctgcctctcc tctgaaagct 3300
gtgccctctc tcctggaagg ctctgccgtt tcttggttct acttgaagct cagtttaagc 3360
atcacttatc gaggatgctt tttctgaaca ctctatatcc tgttccccca cttactatgt 3420
caaatctccc ttcacatctg ttagaaagtc ccataagaac atctcgattt ctctcaatgt 3480
tgtaatcatg tggtttgggc aacaaatact gaattcaaat tttaaattat aatattcaaa 3540
ggaagtttct ctaatctaca ctggacatgt tcgcagcaaa gtacaaatgc attgtgaatt 3600
catttgaagt gttgcatgtt agatattcac actagaacaa gcaaatttaa tgagagtgtt 3660
taataataat gggtgttcca ctgtttcata aagttcacca gggcctaggc tactgcctgg 3720
cacatagaag atgctcaata aatatttgtt aaacaaatga atgattgcta tatccagatt 3780
tatctctcta cctacatagt ccatctacat ccaaataaaa ggtaactagg aggtaggaag 3840
taccattggg gtggaaagag aatagtccct caagataaat cagggtgttg actcaagttg 3900
ttttgtcagc ttgtctcatt ttgttttcct acttcttatt cataggtaac cactttgtaa 3960
acctagatgc aaaatggaaa gcctacagat tccatgctaa cgagctgtgg agacattctc 4020
agcatctctc caggctgtca aagggcttag atcaagcatt cttacacatt gcctaagctc 4080
ttctcagaca tatttgctcc aggcttttat caactgccag gaaatgagca gctgtgagtt 4140
ccaaacctaa caggtatgtg gacggtcagc atgtcccatt ctgatcactc aggagagaga 4200
cattgttttg gggtcaactg tgtctgatac cccttccctc ccagtgacca gcagtttgtg 4260
taagcttggg ctcctgctaa actgggggat ttctgccctc agcctgggga cttctgccaa 4320
gcagcacagc ttcccagatg cacttagctc ccagtgcccg tgttttttga aatgtcacgt 4380
ggattccaag ggcagagata gctccggtaa tgtctgtggc tgtttaaaat gtggttcact 4440
gtgatgctga atttgtttta cctttagaaa gctcagaatt taattatgtt ttcttttcag 4500
cccttaatag tattgaaagc caacggtttt aacagctctc aggttgtact gggtcttagt 4560
ttttgcatgt agtgcctttt tccaactaat tactttttaa atgtagtaag agttcttttt 4620
tgctttaatc tgtcttagat tgatattact gtgttgtctt ttaaatttaa ctattatttg 4680
ggtggcttta ggggttttct aatagaatca tgacttttag agctaggaag gctcctgaca 4740
tattttctaa atctcttctt ttagaagtga agcaactgag gtaaatgtgt taagagactg 4800
gctcaggttc tccaactagt ggtgaagttg ggattaggaa aaccaggttc tctggtgctc 4860
atttcaaagg tatttccact atagatgctt atctagatat tttcactgtg cctcagaacc 4920
accaccacct ttaatgaaaa tacatctgcc aacttgtatg gaaaagaaaa agcagtgaat 4980
gataggtaca gtcaatataa tattgttacc acccaagcaa gaaatgccaa tagctactaa 5040
gtgtttctgt gtgttggtac agcaactgcc gaaatgtaga tgccctgttt cttatgatag 5100
ggtcacagga gatatcagaa agtataataa gcatattgat gatattgatt atttagattt 5160
gcagtggata ttgagggagt tgcttggcat ccagacattt tcaaatgaca catgataggt 5220
taaaagtagc agaaaaagcc tcatgttctt tttcaattag taatactgat agagtacaat 5280
taatttagta aggctttata tttttggtta taataataac aacaataata gttttcatgg 5340
catcttatgg tttgcaaagc tctttcatat ttacaatctc atttaattgt cacaatcaat 5400
attttagata agtatctccc ctttcaaaag atgacattga gactctaaat ctcatagctt 5460
atctgggaga aattagattt taatccagct tctttctatt caaaatctca tgatctttcc 5520
atcgtcattt ctttcttcaa aattgattca acaagaggaa aattattagc ctaatctatc 5580
acattaatag acaaagcagc aaaaactggg ttttgtggct gtattagaac agtggaaaca 5640
gccttctttg gatgagttcg tcctggttca cattttgcca atgagggaaa cctgttccag 5700
aggtgggaat agctcgaact tcctggaacc tgagtagctc agatatatta gcagaccaca 5760
gcgcttctca gcacaagctt ggtcttttta tacatttctg aagactcaga atggatacac 5820
acacacaaac acattataat ctcaatggag aaaccataga agggaaaaaa caggatattg 5880
tagtttttaa tagagattag agatactcta taattagaga tgctcatgaa ttcccataga 5940
aaaggaaaag agaagatcac cttctaaaaa tctaagggaa tcaatcccaa acttaagaag 6000
gtaaacagtt gcagatgtca aattgataca taataaacaa ttcctgcgaa cctgagataa 6060
attgccagaa aatcacacaa catcaaacaa tgtattcatt caacaaatgt ttatgaagag 6120
gctactacat gccaaaccat gttctcagca ctggggttag ggccaagaac aaaatagaca 6180
attctttcta agggagggag acaggcaaag cataagtttg tgtcacacct tgaatctcag 6240
tgcttgggaa caacagagcc aagcaatgag catggatact aagacggtcc agccattgag 6300
aaggtcgcat ctgagtcaag gcctgaaggt cagtgaattc accatgtgga tatttgagaa 6360
aaaagtgttc aaaagacaat tggccagtgc aaagctgtca ggggagcctc cctgtggggt 6420
taaagaaaca tcaaggcagg gagagtccag tggcttctgt gtagatgttg ggctggacga 6480
aggaatatca cacacagtct tggagacctt tgtatgatag gaaggatttg ggctttactc 6540
tgagtgagga gtgaaaacag gtattcacaa taggacttgg atgatcattc tagtggctgt 6600
gttgaagcac atctccactg ccaccccccc tcctctccta acctccatca tcacttacct 6660
caattattgt ggataataga ggcttgggcc aaggtcaggg cgtggaggtg ataaaagagg 6720
acaagttctg gatgtatttt gagggaagag gcaacaagat ttcctggggt ggcatgtgag 6780
aagaaaagga gaatgctcag gatataggcc tgaccaactg gacagatatt taataattaa 6840
ataatagaca catgggaact actggaagaa gatgctaaaa gcttatgata tactactaaa 6900
atgaggactt taatggtctt gttcccctca gagcctagaa caatgcctca acaggcactc 6960
aataaatact tgttgaataa attcataaat taatagtaat tattaaaatc tcctctctga 7020
gctaagttta agttggcagt tctcaaactc tagcatgcaa tgaaatcacc tcattaaaaa 7080
acagattgcc catccccaga gtttctgatt cggtaggtct gggatgtgac ccaagaattt 7140
gcatttgtaa aatttctggg ccatgcagat gccactgctt cagttaacta gaggccaaaa 7200
tccaaatacc cctatagatt ctgacaacaa acagagacat gagaattgga aaggaagagg 7260
taagacaata tatgcagatg gtctgattct atatgtagaa aaaatatcag acccaaaaaa 7320
tgaggagact acactctatt gagaggcatc aaccttgtta caaccaagaa atcctttgtt 7380

```
gattttatgg gggttttgga cgccattttt agaaagcaaa tgtctaccaa ataaacagca   7440
tttatttttt aaaaattcaa catatggaaa tcaatagatt atatggttca tttcaaaagc   7500
aagtaacaaa agtaattagg atatctctgg aaaagaagca agtggagaat ggggctagca   7560
gatattaaaa catgttttaa aggttctatc attaaatgtg tcgtattggc atagcaatag   7620
aactgaatag aaactccaga aatcaaccca gtttcataag aaaatttaat gtatgatgaa   7680
acaaatcagt agtgaaaaat gaggatagcc acatcatgca ctaggataaa ttctaattgg   7740
atcagagatt taaacgtgga gagagggagg gaggggaggg gagggcaggg caggggaggg   7800
gaggggagtt ggggaatggg gaaaggtttt accctatgac tcaaaatcca aaagccataa   7860
aaaaagatcg atagatttga ctatacaaaa attaaaggac acaccaaaaa atagtgaaag   7920
gcaaatgaca agctaagaaa catacttgta tcacagacaa cagggcaatc ctaatatata   7980
aagcacttct aaaaagagag actaaaaaga gcaacaacct atagaaatga gcaagagcta   8040
tgtacagact ggcatagaaa aagaaatgca aatagctctt gatcatatga aaagatgctc   8100
aataacttac aataagggaa acacaaatga ataggacact gagatagcat tccaaaagtt   8160
tgacgactga caagattagt gaaaattgct ggtgggatat aaaatgacat aatatctaca   8220
aaagggaatg gccatatcta tcaaaatcat atacctttga cccagctatc ccacttctag   8280
gaatctatcc caaagacata gtggagaaga gacagggcta ctcactgcag tataattttc   8340
tatatccttt tgtccaataa ttgattgaat aaactatgat gcatttacat agttgagacc   8400
taaaaaggga taaatatgta tgtgtgtgtg tgtgtgtgtg cgcgtgtgtg tttcctaaaa   8460
tatacacaca ctttatacat acacttcgtc ttagctattc tacttctaaa tttatcccat   8520
acaaatgatt gaaaataaat taaagtttga ccgcctggat gttttgtcat atggaacaat   8580
tagaaaaaac ttacatgtcc catagcaggg ggttggttaa agtgtttgta gtgaatacaa   8640
aataattgga gagctccttc tccaagaagg cttccctgat gccccacatt tacacagctc   8700
actgtgagtg cctctctatg gcactcatca cctcatgcct tgcttttgaa tgattt       8756
```

<210> SEQ ID NO 56
<211> LENGTH: 4556
<212> TYPE: DNA
<213> ORGANISM: Homo sapiens

<400> SEQUENCE: 56

```
tcagcaaaac ctcctgcccc ctctccagct gcctggtaaa gttaaccttg gccctttgtc     60
ctaagggcta tgtctttatc catctttcta ttatcagagt ctaattcaat cctgacctga    120
gggcagtcac tcaacccacg catgttctgg gctcccatcg aaaagcccca gtttccagca    180
gtcctcagag tacatgtgtg gtgaatccct actatgtggg gatccaggaa caagagccaa    240
ctggccctcc aagactccac ctcagttccg attcctgcca tccgcaaact gccactgaga    300
tggcagctct gggggcagcc ttccccaccc ggcagacaga ggctggcact catctttgct    360
ctaatgaagc aatgacacag tgatatctgc ctttcctacc tggccaaagc ctccctgggg    420
gcagaaagga ccatcctgct cttgctgtgt cctagggcca cgcttggggg cgcccagagg    480
ccataaagac catgtgcctt agctaagaaa caatttgaca cgtgccaacc cagcctctgg    540
accctgtcag ggcctgctag caagcttcct gagggcaagg ctgtatcttt catatgcctg    600
ttattgccct aacatctggc ctgggcctgc tgcctggagc ataacaggcc tcgtacatat    660
ttgttagatg agtgaaggat gaggtaagtt acaactgctt taagttcact gcctagtaaa    720
tggccttaat ccaaagatcc tttggatctt gagccaaaat tatattgagc caaaatctac    780
```

-continued

```
ttccctccaa tacagattat gtgtaccatg aaagccccat atgcatgtga agatggacat    840
tatactcttc caaaagcctg gatccaagct gaacatagtt cccgtagcat ttctcatcgc    900
agatgcaaga tccttcaccg tgtggccacc tttatcagga caaatgcttt ttttcaagta    960
catcttgaaa tatggttcgt acctgtgaat ataaccttat ttgccggtct ttgtagaatc   1020
aagtcaagat gaggttataa agtgcaatgg ctgatagctg tgtaagggag agatttggag   1080
atagacacat gggaagaaac ctttgtgaag acagaggtag agactggagt gatgggcctg   1140
aagaatcaca ggattgtcaa accactggaa gctaggagag gcatcgaaca gattctccct   1200
cagagcctct agaaggagcc aaccgctgac accttgattt caggccttca gaactgtaaa   1260
agaatacatt ttaatacatt tctgttgttt ttaagccact cagtttgtgg tactttatga   1320
cagcagtcct agggcactaa tatgttggac caccaccccc cttgatcaat atattattct   1380
ttgcaatcac atggttgcct taaaaaatta aagactacta aattaataaa atgatttatg   1440
gctggacaca agataaacac cccaaaatca aggcattcat ctttaccagt aagctattga   1500
aaccataatt caatatccta ttcacagtag cacccaaagc cgtaacacat agcagtaaac   1560
ctatgtggga tctgataaag aacacttttt aaaggtggag aaaataacaa aatcctgaaa   1620
gggaaggaaa ggtccatcca acgagatatt agaacatatt aactcaagag tataaaacag   1680
aaaaacacca taaacaggca gatgctagtt gacgtctgtt acctcctcca gaagcaagct   1740
cagagtgagg tgagatgtgt tgagaattgg ggcacttagg tgcttacaca gactaaaaat   1800
ccttgttcac catttatcat tagcagcaca gaacgtcatt tctacccaga gagatcctgg   1860
cttaaaaccc catcaaccaa attgcttttg gggtggaaag gaagcccctc caccttattt   1920
tgcaatgata tgaaaagctg ttctcgagga gaaagaaagg gggagaggta ggaaagatag   1980
cagcttgtgc tatctactga tcacgcctgc gtttctttgg ctagttctgc cacttgccgt   2040
tctctgagag gggtttggta attaccagga caacttttct cagtccagtc atttgaattt   2100
ccagaacaaa attaggttgg ggaaaccccc tgaatttgca gactcaatat tctctgtttc   2160
atcagaagtt tgctgagcac ctgtggtgtg ccaagctctg tgccagcccc caaaggttcc   2220
tgagggttcc caatacacag ttatttcaac aggatggatt tgcacgaagc tggtacacag   2280
acctgctgag gaaggggcca gccaagcagt catgtgccac tggatccgct tggttttctc   2340
cacctcatta catgagaatg accagatggt ttataaatac aatcattttt attgagtagg   2400
aagtaattaa aatgtttata cctgaggcca ttttaggaag aactttttttg ccatggtata   2460
gtcacagggg ccagatccca gatgctggtg tggggtgaag cgaggatgag gaccagggag   2520
atgatgccca agtgagagga tattgtgcaa ggagctggca aatgtggctc aattttacag   2580
agcagtggag ggagctgcat taggggctgg cctagttcag tggatggtga cctggacaca   2640
cattataatc agctggagag ctttaaaaaa aaaaaagatc tgtgctcaga tcccaggcca   2700
gcccagttaa atccgaacct tgggggagac actcaggcat tcaggtatct gttgttgtgg   2760
atgaatctct acaggtgaca tgtgaaagct ctgagaacag agctccggcc actgcttagt   2820
tatacctgac ctgggcaaat aaaatcacac acacacttac atgcgtatac acatatacaa   2880
gtgtgtaaaa tctggttaat gttctctgtc atttcctttc ctttgactaa agtaattgta   2940
ttgaagatct ctcaggttgc tgagggcatt atacttgtgc ctttttaagg gtttgcctac   3000
agagtgtgga gatggggagc ccacaaggat ttttctagaa gtttctatcc tcagagattt   3060
gctctaacag agggtggtca gttctgaatt aggcatcctc ttgctcatgc ttctgataca   3120
```

```
tttggacttc agagtcctat ccttatgccg ctagtcaccc agtgattccc aaggaagaaa   3180
agcatcataa gatttagaga tggggcttcc ctctctgtga ttaacctagg tccagttcag   3240
aatgaagaaa ctgaaaagag aaaatccaac ccttttcaca tccaacccca ccctgtccct   3300
gggtggccct taccactgga aaagcctgcc caaaaacttt ggtcctaaga aaaaaagaaa   3360
ctggtgcagc tgcttttatg gaaggagcta gaccagagcc aacaagtcag gcctctgtaa   3420
gaatcttcca aggaggtaag gcggggagaa aaaggattcc tcatttacat tgagagtaaa   3480
cttcctgtcc tattaaacaa tgaggcattc aaaatccgcc tgagtaaaag tcccctgatg   3540
caatgagagg gtgagcaatt tcatgtcagg ctgttgttat gggatttata catgtcctag   3600
ctagggcttg aggtgaaagt cagagccaaa aacaatagcc ctaaacccca catgcacaga   3660
aacctcattc cagtggagtt tccttaagag agcacagcag acttttcaca aacaaagtga   3720
cttcaaaggt agccttgcat cactgcctcc tcccttccct tcagcccaga cctggcccct   3780
ctgtttcttg gtttaattta tgaggttctc acacacattg caaagcaatt atctgagctg   3840
ctggccaaca ggaaggtaat tgtaactgag tacttccttt gtcaaacgct gacgctggcc   3900
accgcgaggt gataggaggc gtgccggcag ctcagcaccc agtgacagga tacctttctc   3960
ccccacccac acaatgctgt ctgactgaat tctccaggga ggaggaagcc agtgggtgag   4020
gaatggggga attttcttac atcacttgac gtgcttgctt tcactcgcaa aatcctgagt   4080
catgactgaa gctgtattgc ctcaagctcc ggctgaaacc aggggttata ggtttggaaa   4140
cctgattcca cggctgcctc ttgtccaatt cagaggaaat gtgtattatt tcagttgatc   4200
ctcttcaagt tgaagtgcct ttggattgag gggattacgt gagggaagtg gctctgtagt   4260
ggcttagtaa gccaatgcca tgcgagtgaa caatatttga cattcggtga gtttacagaa   4320
agggcagtct ctctgtttgt ttaaaccaga ttaagtgaaa ggaaaagttt ttctttccca   4380
tcccaagaca aatgtgaaac acatgttttc ccttttgact ttgtaagtac aaggctcaaa   4440
cagttctccc cacccccctcg gccatgagtt tttaaggatt gcagaatgtt tcctctcttt   4500
ggtggccaaa gccaatgtga gcctttatat ttccagacag tggagctgat gatgat       4556
```

<210> SEQ ID NO 57
<211> LENGTH: 3748
<212> TYPE: DNA
<213> ORGANISM: Homo sapiens

<400> SEQUENCE: 57

```
gtatgttcaa gggctaaatt gcttagtagt tgtgcagcta cagggagaga ccagttatag     60
ccacaaagtc cttggaggat aaaaaaatgg tggtggtggc gctgagaatc cttgtgagga    120
gggctaggct ttgttctggg cagtaagaga gcccagggca cagaaaacat gattaaatgt    180
gtgttgaata aatgaatgaa taaacacttc attggaggga aaacaccagt aagacattgg    240
ctgtgtcctc aaggtgctca ttccccgttg gaagacacag gcccattgcg ctaactagaa    300
cacaagcgag aagacagtaa atggaaatgt tgttgagcct tggtagggct tggcaaggtc    360
tcttatggct ctgctcctgt atgctgtctc tccattctgg aagccctttt tgctgcagtg    420
actggctcca tccacctgcc agacagacgc tttcgttccc tcttgaaaag gcttttgctt    480
gatggaggag gaaaccaggg aggaaaagag acgcatctta ttctcctgag aagagtcatc    540
ctgtttgtct ccattggcgg ctggctttat ttggcttcta tttggatggt gaacccattg    600
ccttgaggtg gggagaggag gagattctgg aaggatttca gtattgaggc gcccctaata    660
cctcccagat gaaaaactag gagtgatcct cccaagtgtg cgtgctgaca tttgctcccc    720
```

aatgcactaa gcataagctt gttttattgt gtttacaatt ttgtattcag accgtaatat 780
tgcaaacatg aatgtcctag acagtagaga tgtccaggct tttctctaaa gccagagcta 840
atcctgcacc agagatccag tttgatgaac tcttcagtgt tcccaaacct catgtgctta 900
tgagagatca gatatctgtc ttaagcagct ctaccctact gcctacccag gagaggatct 960
tggcatgtgc ctgcctgaga ttgacctcct gccctgtgac cctgagtata gagcagagga 1020
caggcagtgt tgcaaatatg ctcctcacaa atccagatag gagatatgat ttaacactat 1080
cttctccttg aaccacttga taattttttt ttcaatcgca agaaaactta attcctgttc 1140
cactgtctct agctctctga gggataatgc tctgacaatg tagacaagga ccagatgtgc 1200
agtggatggg tcggctgctc caatctggct gtggagacgt gagggaggat tggggagaca 1260
gttgtatgta gtccatagtc aggataaaag gcctttgcga gttcctaagt atggtttctt 1320
gagtctgcgc agaagggcgt atgtgggaaa cataaacaac acaaaataaa acggtttgat 1380
cagaaattat agttattacc aattccacaa atcattctcc tcctttatcc tagactacaa 1440
agaagcatca caaattattg acaaagatat tctggaaggt taactctgga ttaaatcaga 1500
cttctctctc agcagctggt gcctctcatc taagatcaaa aggatcttga accttccaag 1560
tgaactgctg tcaagcaaac agcaggagaa cctctaatat tatttacata gcattttctt 1620
tttccaatta tgtattggtt tcttcttggt acaagtctag cttataaatg tggaaaccaa 1680
gacacagaaa agaaaacaat gttaaagtta ggtagagagt cagtaagaca ttaacccaca 1740
gataaatgtg tctagatatc acctctactt attcaacaat ccttttcagt tgcctaccaa 1800
aaatatgaag tcatttttgc tgagggtgca gtaaagcatg ccaacttcat tttccaacct 1860
ggagtttctt gggcctatag gaaacggatt agagtctttg aggctttggg gaccttgttt 1920
gcaacgttcc tctaaagtag accttataat gaatggaagc aagagaagag tgccagatta 1980
ttaatgctgt caatatcctg tgtctctgag atgttgccct tatgtcaggt accagtgagg 2040
aggaaaaagc agaaatgtga actctcagtc acctactcag gccaaggtct ctgtctagga 2100
actgctatgt gtgagtcaat ttcctgatga cagtttttcc ataccatgct gagtggaatg 2160
tcttgtttat cagccctcac acctggtact gtggcatcat gacgattgtc atagtctatg 2220
ggaaggtgac aatactgtgt gactcccagt ttcagactca gtcattaagc agaagaaaga 2280
atgggaaggc acagagatca gagggagaag gacaaagaga tacaaggaga gtgacaggaa 2340
agaagaaaaa atgactgaga aactcctaat gcaaagtggg taatgggttt tgaaaataac 2400
agggtgagcc aaagagaaag ggacaaatga tttagcagag agtggaacat atactggtac 2460
ctccacctac tgtaccccaa gccttgtgtt gaacctggac aaacagtctg gcccttccag 2520
ggactcccag cacaacgaaa ctcaaaggaa agaagagcag gaagttggtg ggtttcaggt 2580
gcttggaaag aagtaggctg acatctgact cacctattca actgcaagca ccaacacaca 2640
cagaagcttt cagatgagat catctggtcg tgacttgcaa aagatgattt ggtggcatat 2700
ggggctaggc acttatcaac atttttcttc cagcacagca aaaggtgggt agaattgcag 2760
ctcttttata ataataaata atgttatgga aaggaaaaat gaagtataga gaagggacag 2820
accttaaaaa ggatgctcaa tataagaaaa acaaacacac attgttctcc ttgatccatt 2880
gagaggatat ggtaggacag aaaacacaca gaaagacgta ggcctaagcc tgcttttgcc 2940
acttactgac cttggtatct tacaatggga aaataatacc tactattcag ggttgttgtg 3000
acggctgatg atgagatgtg catttgttag gagatcagta actgtcagcc attattctac 3060
tatctgttag cttcaagcag cagtgtgagg actaacttct ccaggcagct cctccatctc 3120
cccagttatt gttgttttat ggtactttgg aaaggagttt caagttcatt tggttcaagt 3180
cgttcctttt gtggtccaga aaggtgggtg gctgattcga catcaattag tggcaaagct 3240
gggagcagag gatcctaagg ccacaaggga gtgctgagca caagattcag tagaaaacac 3300
atccctcata gcagctctct gggttcaggg ctcctggaag cctttggagg gagacaaatg 3360
tttttcattt aagaaagtga ttatttagtg actcctgcac aacctcttct gcagcccctg 3420
gatctgatta cacagcctgc cccacgaggt gggaggagaa gctggcatgt ggcatgtggt 3480
ttaaacgtag ttgatctttt taaaatccca cattttagcc agtctctcag ctccacatga 3540
tctattctca gaaaatgcta accggccaga aggaaagagc aagagaagaa aaggaaggag 3600
aaagagtaaa agagaaagaa aagagtgaca atgaaaagca agtaagaaaa gtgaagagag 3660
gaaagagaaa gatggaagaa gagcgagctg gagcaaaagg gagagaagta gcgaccctga 3720
aacagtgtga tgagatatgg ccatagta 3748

<210> SEQ ID NO 58
<211> LENGTH: 5013
<212> TYPE: DNA
<213> ORGANISM: Homo sapiens

<400> SEQUENCE: 58
aaatagtgtc ttctggtttt gtctctttgc tgagacagtt gcttgggatg gctttggaaa 60
aacttgttcc tgaggccagg aagggctctg ggaagttttc ctcagctctc gaatacccca 120
cttatgccct caaacaaaaa aatgagttgc ctttaggatg attcatttca attatttctt 180
ctcccttaaa gctgtttggc tctgcagggg tttggggagg caaggaggcc agctataggt 240
gcaaaacagc ttcatcgctg gagggacacc atgcccaagg tgggaatggt aataacgatg 300
aagacccgag aaacatccat tccttggaaa aaccccatgt ggtgatggtc aagtgggcac 360
taccctctag acagtgtcag gaatgagaac ttaagacagc ctaatgaaaa tcagcctaag 420
gatttttgcc agaacaattg agaatgagac tctttagagt cactaaaaca tggataagaa 480
tacttgctgc cttaggtagg tactcaaggt cacagagcta aggtgcagac agcaagcttc 540
aactcaggca gtctgattgt aatgcctatg tgctccctgt gaccttacta agccatttaa 600
tgtcatctcc atgagggagt agagaggagc ctataagcgt taaggtggga gacaaaagga 660
agaagtcaga tgtacatctg gctatggtgg actagaaata gatcaactta cattagggaa 720
cagggtcaag aacctataaa aatttatgtt gttgaaaatg accataaaat tgatttctga 780
atgacagtga aggagctttg tgggcctact acctagtgaa accagtgaaa attatttaaa 840
gcaaacattt acagccttgg gcatataaca aatgaagaaa acctattcat gaaaattcag 900
taagagggta agtggaaatt aaaaaaatata ctcctacaac cagtggatta aaaaagaaaa 960
aggaaaatca gaaaatactt caagatgaat gagattaaga caaaacatac taaaacttat 1020
ggggcagcta aagcaatgtt cagaggaaaa cttatagttg taaaagagaa aaaaaaatctt 1080 aaatctataa cctatcactt taagacacta agaaaaagaa gtacaaacta aacctacaga 1140
aaatagcaga aagataataa taaaaatcac agttgaaatt aataaagtag gaacagaaaa 1200
acaatggaga aaaagtatga tgccaatcta gttgtcttaa aatgtcaatt gacatacttt 1260
tagctaggtt gaccaagaaa acaagaagac tcagtactag aatcagaaat gaaaggatat 1320
caatactcac cttggaaaac aaaaaagatt ataaagaaat atataaatca ttgtatgcca 1380
ataaattaga taacttagat taaatagaga aatttctaga aagactgaaa taactgaaac 1440
ttactcaaga attagtctga ctagacctat aataataaaa aagatcaaat taaaaataat 1500
aaaaactacc acaaagttaa gcccaggtcc aggtggcttt cctactgaat tctactaaac 1560
atttaaagga gaattagtac tatctcttta aaagtttcca aaaagaaatt taagtattta 1620
tttaatgatt ttaaagatca gtattaccct aatatcaaac atacaaagac atcacaacaa 1680
agaaaacaag agatgaatat tcatgaatag gggtgtaaaa ttctcaacta aatactagca 1740
acctgaatct aataacataa aatccaggaa atctaatttt cagtcaaaac aaggctattt 1800
tcaatgcagt tctgcctcca tttctgattc acaaacacac ttcccaggaa agaagcctct 1860
tgtatacatc tcatgctagt gtgcatgcag cttgagaagt cagctgcatg gagaggagct 1920
ggcagaaata aaaatttttc tgaaaaattc agagaaaaca acaactgtaa tgtacatatc 1980
attttgcaca atggcccgaa aattataggg aaagaacata gatgatgtga agaaaaataa 2040
tatgaagaaa attaattttt gttggttttt cagactttct tggaagaaac agtatttctt 2100
tcctcatatc cattcatgtt aagaattcct aggatgtctc aagcacaccc tcaataattt 2160
acaattgtca agccacaatt tgtagacact cacaacttta aattaaaagg aattcctaga 2220
gaaaagttat aataattagt ttgtgttgtt tcagttagga tgtttttgtc cataaataat 2280
agaatatcag atgaacagtg gctgagacaa taaagtcatt tattactcac ctagcaagaa 2340
gcctgcatgt aggcagttcc tgggctgttt catcagctca acaatggcac taaagattta 2400
acatatttct acttatttcg tcatccttaa ctgttggagt tttgcctcat gctcattgcc 2460
ttgttatcat aaaacggaag ctacagccct agacatcaca tctgtgttca aggcaggaag 2520
aaagaagaga taacacaaat aaactcttca ttcattggta tcttttataa aaaacacaac 2580
aaattttttt ccccaaagac tcttggcaga cttcataacg actagactga actgggtctc 2640
acagccatcc ctaaatatga gtaaagctgg agaaaaacct gattagtaaa agtgaaaggc 2700
tgctaagatt ggcttaaaac aaccatgatc tagtaaagta cttccttgaa caaaatcagg 2760
attctattag ggaggaagtt gagaatggct gttggttggg ctcctcacag gtatccacaa 2820
atgccatgta atgttctttt ccctgagcta ttttcccttc tatccaatcc cattcttaga 2880
gtctcccaag gagttagata ggttctgtgt gtcacagatg taaagttaga ctctagtaag 2940
tgagcggctc agatgctctc caaagctttc taaaatattt ctcagaatga aagtaattct 3000
gtggttaaat tcttttgagg aaatactatc tttaaaacat agagcactta agcactctta 3060
taagacagag gtgtgctaga tgccttagat gtattatcca acttaaaagc ctacatttgt 3120
gaaccctggg agagcgggag ctgggtcttg tttatagcta tagctgtttt ctaccagagt 3180
gcctggcaca tggtaagtaa tcagtacata tttaataaat aaataaatac aacttgaaga 3240
caacaaaaaa tactttttga tggcaacatg gataatgaaa gtacaagttt cctcctacta 3300
aggtaatcga tgggatagaa ataatcgcat gtctttttct gatgtttact aatcctcact 3360
taagttcaaa aatacttttc cttggatccc aaatactagt gagagcacag ctggggttct 3420
agacctcact tctgattcta actccttgca ttcaatttac cgtgctacat tacatagagg 3480
ataagcgaag gggccagtt gtatctggaa ttagaatgag gttcttctca ttctaaagaa 3540
atgtgatatt gtataattac ctaagtcata aatgtgttta tgcgtagcta agtttattac 3600
attagcttca aagcctaagc agctccacac aagacaccag acattcacat tcatagggct 3660
ggagggcata attcaacaca ccttgtctgc caaatctttc ctgtgcttga actagagaca 3720
aaatgaggag ctcctaaata gttgacaatt tctaattcat tcttttattt ccagtgcctt 3780

-continued tgtccaaatt gtaatagcat aattctgata aacaagtaca ggtatccttt ccaggtatct 3840
aggtgccaag tgcccatctg cctaatgggc acagggtgga ttgggtagta ttacatgtac 3900
ttttccattc tgcccttgca tgtcctcatt catcctagga tagagtgttc ttctttgcta 3960
cgttatgggg ctacaaaatc caaattgaag ctgagcaaga ggtttaggaa actcaatttg 4020
agaaaagccc tttggtaata ataagtttta attactattt tcaaccttat tttttattta 4080
aggaaacttc ttccatcctc tctcagcccc actacagaaa agacctgtga cccagactgg 4140
ccaatctgtg tactggacca cagtggcttg ttcaaatttt agcgcagaat tagagtcttg 4200
taggattaat atttgaacac aaagagaaaa attctctttc ctttgaggat actttgaagc 4260
tgcagataga tgactcctag taaatatttt gccatttgtt cagatcttat ctgcaaaatg 4320
aggttaacaa acacaagtgg tggtggtgat gacacaagac atttattgag tgttacttat 4380
ataccaataa ctaccctaag tgcattacac atattaactc atttaatctt cacaaactta 4440
taattatgat tactgttata ttattgctat aggcacaatt tgaacccagg cagcctggct 4500
cttgagcctc tgctgcctct aacagtacag gaggaggagg aggacaaaga gaagaacagg 4560
tttccaggat actgtgaagc ccttggatcc agccgtgtct gaacctaggg cacctggatt 4620
cttggttaaa tgacccagta catcacaatt gttatttagc cagtttgagc tgagttccta 4680
ttccttgaaa cttgcctaaa atactctacc accatctctc attctgattg tgccttatca 4740
tactgcttta ccataaaaac attgtagaaa tttggaaaat gcaaaaggat accataaatg 4800
aaaagaaatt gcatatgata cagccaactt gagattatta tttttgtttt cttccagtct 4860
gtttttaaat catgtacata tacacctgta aagttgtata tgtttcttgt ctttcctttt 4920
tctttttata ttaaataata tgtgttcccc tatattaaat attttgagac cataattaat 4980
ggcaatataa tttgtgtgca cacgtgtgtg tgt 5013

<210> SEQ ID NO 59
<211> LENGTH: 1153
<212> TYPE: DNA
<213> ORGANISM: Homo sapiens

<400> SEQUENCE: 59
gggtcttctc accctagaga atctaccatt gctcagctgc agggcgacac ccaacagtac 60
agctgggtaa catagaaaca cacactgact tcatttacac agtccctgcc cagagtcaat 120
agaaaagtcc agtccagatt cgtcctttgc atcataagaa caggagcctg gctggatttg 180
gaccccaatt agtttgctaa tccctggaat aaactaaagg ggcccctgag gcaccttcca 240
gcagaccctt tttcttacca ttagtgaaaa aggtctgtgc ggtgggggca gtgtgtctat 300
gacctcagct tgaccacacc tagacagggg ggaaaaggtg gaattagtcc gtctttccta 360
tatcaggccc aagcctgtct agggcaggct tctgttctga gcgtattttc cattcttccc 420
tccacctttc cactcactca acaaataccc tttcccctta aggtgatcaa aataagcttc 480
tgttgctggc acccaaacct ccctgactga caattacact ggtagtctca cttgtccagc 540
ccagtggatc ttctgagcat gcattcgggg tcaggggccc ccaaagtgct caggattctg 600
ggtccccatc accatcatcc ctgggatggg tgatgtggtc ccagtccctg accatactca 660
gtttgaccct ggagtctctg agtccccagg tggacccagg caactcacgc ctctccttgg 720
agtaacatgg catcggtgca tcaagcacct taggcgtggg tcaaccaaac agtaaggggt 780
tgcatttgtc agatgtttct ccagaggctt aagcagtgcc cggtagagac ccaagtcaaa 840
tgtgtctctg tgaaagggga ttcactggct catgtaactg aggaagacac aggtgtgact 900
gggagctcct tcacctccca tcccagttca ccacaggtgc acactgctac ccaattcctg 960
ccactagtgg tgggtcctca ttgtcatctg gtcagtggta cctctccagc atcagagcct 1020
gcctcccaga cccattccca gcacccactg tcttcgatct ggataggagc agagcatagg 1080
catgctgatt ccatgattta ttgagggagt gatcttggga gactatgagg gaggcaggca 1140
gaacaaggaa ggg 1153

<210> SEQ ID NO 60
<211> LENGTH: 2938
<212> TYPE: DNA
<213> ORGANISM: Homo sapiens

<400> SEQUENCE: 60
gcactggttc tcattgctcc atcaaatact aaactctaat tagtgacacc gtctccagcc 60
attctagtgt ctaaaatatc acaagtcaca gtatgaacga tcgaagttga gccccaagtt 120
agcagaggta tttaagttac atagttgatg aaaatgcaaa tggagacata acaagtatga 180
aattcagtca ccaccaagga actagtctgt gaacacttag gattttcacc aagatatatg 240
cattgttaat gctttttcct tctaattaaa aaagaaaatg gataacagat gaggaaaatt 300
tgatgtgatg gtttttagga aatgcacaaa tgactcatgc actcgatttg acaagggtac 360
tggtttctat ataaagaaac aacttaggcc caaaatagaa gttgtgcaca gcagattgta 420
actgatagag gaactgcaca ttccaagtag tgtgaagtgg tcgcaagagc agtggctctc 480
ctgctctggg gctgagaacc cctctccttt gtttagcctg gagaaagccc cagtgaagtg 540
aaagctgtga gcacaaaggg ctgagaggca agcaggacat tgtgttcaga gtcaggattt 600
cccagctgga aaggtcttta cagtgcatca gttaaggtta gatgcagcag cttggaaccg 660
aagtcttaga ggagcactct caggctgcag gctgggtatg cacaatgttg tcagggtcct 720
ggcttcattt tcctgcacca ccttacctgt ggcccccttt ctagtgatgt tatttggggc 780
aagttgctta atctttctga gactcagttt cctcatctga agaagaagag taattgcaat 840
acccatttca caaggataat gagcagatta attaaaataa tacctgtctt tgcaacagtg 900
atacagcaag ccttggctgt ttttatttgt tttgttcagg acttgtacaa tgccaggcat 960
atagttggag ctcaataaat atttgtgaat tagttattat cattattatt gttgccacaa 1020
aggacccaca agcgacatca agagcccact ccatatagca cctaggaaga gcctaattta 1080
acccaacttt atttccaacc agccaagctg gagtgcaatt gtcaaaaggc agctgatgga 1140
cagcccagcc cacgtcggac cggtggagcc caggactccc aaatgctgtg cctccgccag 1200
accagacgct gctaatggct tttgttcgtc tgccaattct actgcccatc ctcctctggg 1260
aagaaagagc agaccggaca gagtccttca gaggccgacg catgccagag gctgggagac 1320
ttggaagggg agtgaggaga cagtcactgg ggaagacagt tctcagggat tccgcaaggc 1380
cctggaggtg tttctgtctt tgtaccttgg ttgcctctgc gcaggcagcc ttgcttcata 1440
tcacctgcac ttccttgctt ctagagggat tgtggcaaga aagctcgcag aagtcaaaac 1500
aagcctggtg atatgaaaac catatgaaaa cttggcaggg tcccatttca gactaatggg 1560
cctgccagac atcaccggcc cacagacact ggccctttgt gaggtcgggg actggctccc 1620
tcactcccat tctactaaga cagaattaaa aaggaaacaa gcaaggcagc cagtctcttt 1680
tctctcatcc acgtgcttcc aaggttagaa acagagtaac gtcaggtact ttgagtgatg 1740
aacacaggat gttgttggcc aggcccattc acagtgcttt tcagtcctca cttgatcttc 1800

```
atggtagacc catttcaaaa atgaggtcgc tgaggtttct ggggctccca aggttccact   1860
aaaaaatgat ggcccagcca gctggggttc agatgcagac ccatctggcc aaaaaccttg   1920
acctttgttg ttacagagct acctcccaga tgaccttttg attatttcag acaaatttac   1980
caacattcaa aattttgctt ttagctttct gtttcctgtt ctagaaagaa atcgagacat   2040
aacattttt tttcatgacg ttattgaatc tttggacaat actgtaacat gccattgtta   2100
tttatacctg aaattcctgt atttcaaagc ctgttgggtg tggagggaga ctattttcca   2160
gagccatcat tattgcagta ctaaaataag tgctctttta aagcaactta aaaaaatcaa   2220
aaactgagat aagtggctgt gcaagtataa tgacttgttc tttgttccca aagactggaa   2280
aaacaaggtc ggtatgcaaa tacacctgca gattataatc tgtatgtaat ttacaattca   2340
catctcttcg tgacatggct tctgaaaaaa tctgaagata ttttaaagac attttaaaac   2400
ttgataaact tttgtaagtc tggcaagacc caggtgctct gaattcctct cttatggatt   2460
acggggctgg aaattgaacc ctctgctaga agctgcccgg tcacttctgt aaaggccctg   2520
atcattttag aagacacgag gatctgcgcc ctcatgaaga gactcatgaa ggcctctccc   2580
acttagctgc aatgaaggaa aggaaggggg aaggagagtg atcaaaggaa agggagtaaa   2640
accccctaat tgcccatggc aggggtcaat gaatcactcc acgtgcacat ccaacagctg   2700
gtgagaagag ctgaatctgt agggactgat aaggaacaat ctttttatta tgttttattt   2760
acagcacatt tttttaatgc aggccagggt ataatattta cttaagaggt aggaactatt   2820
tagatgagaa aactgcttat acttctagca tctgaaccga agtagagagg ttccaaaaat   2880
ccaaaccata tgcatgtact gcttttaaag aatgcactat tttttctcaa ttgccaag     2938

<210> SEQ ID NO 61
<211> LENGTH: 2081
<212> TYPE: DNA
<213> ORGANISM: Homo sapiens

<400> SEQUENCE: 61

ctcctctaaa acacttatca cttggttctg taatgcttac agtgtgttac agtgaaaaga     60
acatgggctt tggaatcaaa cagcctgtgt gaaagctggc tctgccattc atctgcctga    120
gcttaggtta ggtacttcct ctctctaagt cagagtgcgg ctactgatga ctcccctggt    180
tgttgtaaga attagagaat ggaatgcata tgaaagtacc aaacactgtc agaagcagta    240
agtgctcact aaagattgga tcttctcttc cctagtgaca gtgcgtgact taaagcctgg    300
cccactttat ttattttgtg tatctccaga gcttagcaca agatttggta aatgggcatt    360
atttaaaaac aagaaagtgg ctaagtgctc tatcaagggt gaaagtggaa tttctggtac    420
cttatctgaa gtccccccctg ttgcaggttc tcaacatctg ttgtcaatct tcctattagt    480
taattaaact cctccaaaca ccatccttga ctgttgttgc ttctggcttt ttcccaatga    540
gtcaactctt caaggaaatg aaagagcctt tgcacagaaa ggccagaaaa ccctagttgg    600
ccagcatcct ttgggtctaa gctatagcag cgcaaattag cccagccatt tatatgcaaa    660
agccttgaag attgtttgaa aattgcctac ctaaggagtg taagttaaaa ttgattcaaa    720
aactgtttgg ttgcatctag gaaagtgaat gccaaattgg tcttttcaaa ttcaaatcta    780
agttaacctt caacttaaaa cctacagcgc ctcttcatta tcacttagat tcaggggcag    840
aatctcttcc ggcctgagtc cctaagtgga ccagcctggc tcccacattg catcttagca    900
cttcagctcc tttgttttac taatttccgt gtgtccagga tctggtgctg cactgttgag    960
ttgtgctgaa tcactgttat ttctgggttt aatttctgca gttaggctca gaaatggggt   1020
```

```
aactctgtgt ctcatgggca tggtgaagca ggaggagcac cccttcctca agtgataaat   1080
tgcaatgaag caaccatgtc agaaaaaaat tagggaacca ttgatcctca tacaataata   1140
cacttatgta ttttcattgg aaagagagtt atctgtgctc tgtgaacatt attggctagc   1200
cctggataac caattttatg ttttcacaat aaagttgagc catgttcaga tttttatccc   1260
agggagtttc cctggatatt gacgttgaaa gagcccatgg gggacatttg caattggaac   1320
tatatcccta gatgcctcca caagacacat acaccagagc tgtcaaaagc agagttcttt   1380
ataacctatc acatgatagc tactggcagc ctcgagctaa ccccccatct cagttaaacc   1440
ttcctaacag catccttaca gatgaaaaac tgaagttggt gtgacttaag tatctcgcct   1500
taaggcatcc atccattgaa gttgccttct tggtctaaac ttgagcctgc ccagttcaaa   1560
aggctttctt tcagcctaga tctaccacta cggaggtttt tatatataac gtattttaat   1620
tacttgtgtt cttgttatca tagatgtatt ttaagagaat agaacctgct tttctaaagc   1680
tcaagtactt ttttataaca gccacttaat tggacacaat actcagacat gtcagttttt   1740
atatagctaa aaactgaaat aaaactgcac attaaaaatg tattttgcca attttctgca   1800
atgaaggtgt atcattttta aaattagaga aaggaaagca ttgtttcaaa ataactttgg   1860
attcaatcaa tatggtaaca ttatcagtgc attctgggtg ctgggctgat catgcgtgtg   1920
tattaatctg gtttatttta accgcaactc tgaggtagac gcatttgcct gatattttaa   1980
ataggctgtg gctggaaatg ttaagtaaca tgttcaaaca ggcactatgt gctggagccg   2040
ggacttaaac caggccttct ctctaagtgc agccccctttt c                    2081
```

<210> SEQ ID NO 62
<211> LENGTH: 3911
<212> TYPE: DNA
<213> ORGANISM: Homo sapiens

<400> SEQUENCE: 62

```
cataacacag tcttcagccc ctgccccagc acctggcaca gataaggagt gggaatgttt     60
gcagaagaaa caaacttcag ccaattcact ctgagttccc ctggacctgc tcctccgttt    120
gaacccttct tgtccctcaa gtttcctgcc ccttttctca ccagcagtcc caccttccac    180
tgtttttctg gaaggaggtc agacacagga ccatttgaaa ttcttgccag attggattca    240
cctgtagtca aaatcccgag aatgaatgtc aggcttcctg tcccaaacct ccttgggcca    300
gggccctcag gactttccca gggacagagg taggcagaca ggccagagaa gagtcaagca    360
gagaggatgg tgaggaactt agttcagaaa tgatacttaa aggctggcag ttgccaagct    420
ccatccgagg gcatcccaga gaccccaggg cccttcagga agcgccatcc tcatggtatc    480
ccagccagcc tgagtggcag gggtcggggc caggccagcc tgagcccagc acgtgtaatg    540
accatcctga caagcacttc ctcccatgcc agctcacgga gctggcatcc cgggcagctg    600
ccaggcacct gctgccggag agaaaagccc catcatccca gcctctgtgg acagacaggc    660
cggctcggat tccagaaagg catgcaaggt cagagtggag ccccttcccc ggatgtgggc    720
tgagcagcca gcacagggag aagaggagcc aagcggccag ggtgcagaag ggtgaggaag    780
atgagaggca agggacaacc tctggtcctc cccccaggcc ttcacttcca ctaagcatac    840
tcttcatact cattgtcacc ctcttgattg cgggcagccc tgcccagcct tcccagctac    900
cagcccccac caggactctc ttggcacccc agccacccag tgtcctcctc ccttccaggc    960
cagccaccac ctccatgctg ccctcaccac ccactgctgc aaggccccca tcacagagcc   1020
```

-continued

```
tcaaagccaa tttctctccc agctgaaacc cacccagccc caagcatagc tataaagcca   1080
cacatctgcc ttctgccagc cctacctgcc accctctctc ctgtggacac actgacattt   1140
gaaggatcaa tgaatactga gcagcagggc cagatgagag gctccagaac cagagggtcc   1200
ccttcctcac tcaactccca tcaagtgaga tcagccacat gggaccagct ggggaaaccg   1260
aggcgtctgt ccactctttg tttacaacca gagcatctta tagataaaac cagacaaggt   1320
ccctgtcctc atgtagctca caatcaagtt aggaaaacag gttctaagaa tgaatcccag   1380
gtcccatcca ccagatcctg cctcctacag caggagccta aacaaggcaa gttcctgttg   1440
aggcagcacc cacacgtcgc tggtgatggt gaagacactg gcgtctctgg tactgtgaat   1500
gcagctgttt gaactttccc ttgggcacag agcacaaagg tgccaatttc ttctgttaac   1560
caatcaagaa tttacatgag ggctccctct gtcaactgat gcgcttcctc cagggaccag   1620
ctttgcatac cagagatctc agggagagga ggctttggat ctagtctcaa aacaataaac   1680
caggtggggg accaaggcca ctcattcacc ctacatttac ataactaaga aagctattta   1740
agtggctttc attgaactgt tatttcattt taaactgtct ctgtgacttg tggacacaga   1800
gagtggacgg cacttaaatc ctcctcgttg gtccccagag ccttgaggct tatctggaga   1860
acagacctcc cacagcaccc tatcccagcc tccacacagg ctctgctctg agtgcttttc   1920
ggcagggaaa aggaacacgt ccaggtggaa atcttccaaa tgtgtcttcc ccatcaccct   1980
gtcaccagat tgttctcagc aaaaactttc tcataaattg tctttgcctt tggcttttca   2040
cacacaaagg tcacatagtt gtctgcctct ggtatcacac gtgtagctgc agaagtggtt   2100
tcagaggttc ccacactgga atctccagag gaattttgat caagaaaagg gaaagttcag   2160
caatgctcaa cccgggtttc aagacccgcc acatacagga cccagaccct cccctgccca   2220
agtgaaatca ttaggactca acaggataag ctccacgttt ctgacttgct gcataactcc   2280
aaaacatctc ttgtcactat ttgcaaaacc ctgcaggggc ctcagaaaag aatcaactcc   2340
attattcctg cctctaaaga gttagcaggg cactgggtaa atgcatgaat gaccgaatag   2400
aaagcaaatg aaaataacaa caaccttggg gagttgaggg taaacattag attggaaact   2460
ggaaaatcgt aagttcctag agtttgttgc ttcatcgcgc cgattaaatg gtggactgca   2520
taagctctaa ctggaaagcg ctctgcaaac tgagcacgga tatggctggt tgcaacacat   2580
cacagtctta gaaccacttc caccacctca ggttaacacc ataccccggc tctgtccttc   2640
actgactttc atcagacacc aataatctca caacacgaaa cttgcgtatg tgaagtgggt   2700
tgccatgtaa agtgagtttt ctaccagagg gatcttccat tctgtcttgt tcaatgcttt   2760
taacaaacgc attgaaggct tgtttattca atctgcatct caaagctcgg atgcatagct   2820
aaccatgtca gatggccaaa tcgggatcat caagaatgtg aactccttga agatgggtag   2880
aaactgtaac acgaatccta acagttggca cacataaaac tcacatttgt gctccaaaaa   2940
ttggcctgta agtgcataac gggaaagtga tttgacagca gatcgatcaa aagacctgag   3000
gcagttagtt ggaccgagtt ccacaggaac aatggtatat agtgtgaaaa gtggagcgtc   3060
cctgagagag cggtcaatcc ctggactcag ttcagcacgt cctgaatgct ttgctgtgaa   3120
gggcctggca cctgagcgtg acatgagatg ccacatgtct ttataagctg catatctcaa   3180
aaggacttca ggtgaaagga ggtgccagcc agttctgtat actgattcca acgtcacacc   3240
aaatctacag aatcaaaacc tcaagaagag ttagagaatc tattttttct ttgagtgaaa   3300
atcaaattct ggtaattttc ttttttaaaa ttataataaa atttaaaatt atataagaat   3360
gttcttattc ttaggtaata taagctgaag tattagaaag gtgaagtgtc atgccttaat   3420
```

ttactttttt aaaaaaacag caaattgctt ttaataattt ggaaaaaaga gaaagcaaac 3480
gagacaaaat ttggggggag ggaatcattg cactcttcaa cttttctgta ggcttgaaat 3540
ttctcaaaac aaagtttagg ggattaagct gttagctatt ctgatgtgaa aacatgagac 3600
ccactggaca gataacctct gctattccat ccagcctgag tgcctggctg aggctgactg 3660
agttctttgt ggcttacaga gctgaggcca cagtgacccc tagaggtact tggccccttg 3720
accacagtaa gcccatcccc ccactggcat ggggcctgtg tcaatgcatt ggccctaatg 3780
atgctcccgg aaaaaggaac agatccccga tagacaatct ccagaaggat gaccatccca 3840
gatggaggct aggcgcagga gtttcacacc tgatgtgagc ccagcctgac caaatccatc 3900
agaatgaact a 3911

<210> SEQ ID NO 63
<211> LENGTH: 1009
<212> TYPE: DNA
<213> ORGANISM: Homo sapiens

<400> SEQUENCE: 63
aactgaaaga ttttcaatga atggaaatgg aaatgacact gcaaaatttc taagactagg 60
tcatatatga ttaactgact tctacctggc tttctcgggg tcttttgtcc ttggaaccca 120
gccaccatgt tctgaggaag cccaagccaa acagagtgtc ctggccaaca gacagctaag 180
gcctcaccag agaccaacat caactgatgt tgaatgaccc tcatgtgaat ccagcccctg 240
acattgtggg cccagataag ccatactgct taagccgtct gaatttctga tctgtaaaaa 300
atggttgttt catcccacta agtttttggt tttaattttt catgtggtca ggcccaacaa 360
tcttttgtaa tttcttattt cagttgtaaa cagaaattca tcttgtttct acagaggtga 420
taaatgatct atcctatttt ttgtcaactc aattctaact gaagcattct ctggacactc 480
ggaactaaaa attcacgttg gctcagcaaa atgcaaatga agagctctgg tgcaaatgct 540
attatggagt gggtaaattg agaatgtgtg ataatcgaga tcacatgtcc ccattctcac 600
ttccagttgt cagtttatgc tgcctcagca aaacgagttc tggggcaaat gctgtataag 660
caaatgttat aattacccaa agatagctac gatgaaaaat aagaagaagt caagttgaaa 720
acgccagaac gcatgaagaa ctcagaataa gacaagagag atgggtttgg agacaaaact 780
gtcagaatag agatgagtaa aaggatagta ataatcgttc ctgattattg gaaattattg 840
ccgtatttct ccctgtacag aaaattatgc aaagtttttc acctacatac acacatagaa 900
agaaatctct ctactttcgg gcagaaaaaa atttgttgag gcactttggc ctagcatatc 960
actgattaac ataaatgtta catatgtgct tagaaatgtg ttctccaag 1009

<210> SEQ ID NO 64
<211> LENGTH: 1804
<212> TYPE: DNA
<213> ORGANISM: Homo sapiens

<400> SEQUENCE: 64
tggaagctca caatggcatg gtgtcaaaag gaatgagcct ctaatctgac ctgaaagcat 60
agtgcagacc acagatttct gcctctgaat cggaatattc ctatgtgatc ctggctgaac 120
tgttagacat tctagagctt cggtcctcag cagtcaatag aaaaagaaat ctatcctctt 180
acccttacag tattgttctg aggatcaaat gagctctatt cctcttaccc agatcagtgt 240
tcttattacc acctgatgca tcatattgat ttacctgatt gtttgacttt aaaatgtcag 300

-continued

```
ttccataagt gcgctttgtt ttgctgtaat ctcagtgctt agaacttggc acacacacgc    360

cccaaaaaaa aaaaagcgag gggaggagac aagaaaaaaa taatcagcag acagtgatag    420

cagagtatgg gacagtgaaa gagatttcag tgggccaacc atacaaaaca aaggacagga    480

gaccccatgt tccctgctgc ccatcctcat ctcctggctt ggatgcatta gagcaaagcc    540

tcagtgtaat catgggcatt tggattgttt actcctcgtt aaccaccctc tttgctcact    600

taattggtcc aaagcctgtg gcatgagtaa ctaactgtgc agcgatttgg cacgtggtca    660

gcagcagtag cagccgtaat gtactgcact catactctgg gtgcagttcc cacacggtaa    720

tggagctcag acaggctgcc gctgcctgca gcacctttga tgtcctggca aacacaccca    780

tgggacttgc tcaaccacag gatcttcact cttggcttct tatgggtgcc caactagttc    840

ccaggtccct gctgtctgag catcttacac aagtgggcag agaaattcac acccctggtt    900

taagggaact aaatccaagt tgcgtgcctg gccacctccc ctcacacctc tcctccttgg    960

attgctctgt tacactcacc tcctgcctgc tttcccgtaa aggtcgtgcc tcaggccctt   1020

tgcactagct cttcccccac atcagtactc ttaataaaga atggttaaag aagatttgga   1080

gcttgactgc aagcgtttgc accctagttc tgactctaga aagtttttaa ctgctttcat   1140

ttttaaagtg gagatacagt ggagtcacac taagaattat tgcattaagc tgtgttattg   1200

catgtaatcc caacaacgtg tgagggctca gtgtttattt tcattatcac tctatgtatt   1260

acctccttgt gaggaagccc accttctggt tgaaaagagt tggggcccca gttctatccc   1320

tgtctatctt ctgctgcccc ttcccaaggc aacccttctt tgggatctag ggcttcttga   1380

aacagtttga aatcacttta gcccattctc cttcattcat tgaagagagg gaaatatact   1440

gcttaaggtc acagtcagtc agaggcagag acaggactag aaccttgggt tgtttctgcc   1500

acagttgggg tccccaggtc tccctgctgc ctcaggagat tgtgctgctg ccagaactcc   1560

cagattctgc tccctccctt ctcccagtct cagggataat cctttaatga attaagtgga   1620

gcaattatgg ggggtgggga ggctttggta ctttgtggta accaactggt atctcattta   1680

ctgtcagttg tgtacttagg gataaaccca cttactttcc tctccccttc aagttagcag   1740

tccctaccag gcaaagggga taaagtgtga acatgaactt tctctttttg cctcctctcc   1800

agag                                                                1804
```

<210> SEQ ID NO 65
<211> LENGTH: 14186
<212> TYPE: DNA
<213> ORGANISM: Homo sapiens

<400> SEQUENCE: 65

```
ttctctttca agagcttata attttctgta aaaaccaaac attatccttt gggcacgtgt     60

gttttattct ttctcttgat tctgtgttat aaagtttgat taaaaaggaa agatactttt    120

tgtctcccac acaaagaatg ttcataattg taatttttgg gacttgttgc catacccttg    180

agcctccctt tgtttaaaga gtatttttaa tctataaaga agtatctgtg tgtgtgtgtg    240

tataaaatca aaacggcata cctttttgag aatatttagt gattcctgaa gactatatta    300

tagttgtata aagaattatt tagcaatcta atgtggtagg tgatctggta ttatctgtct    360

ctttggtcac atgaggataa ggctgcccat ctcggttatc catgtcctgg gccttaggaa    420

gaaggcagcc agaatcttag aatttgaact gagaaaattg aacacaagtt agcagcctaa    480

aatataatga ataaaaattg tatgattttc tcatctttat tttgtgcaga caagaaactg    540

aactttgcaa gtattttctg taaagggtga ataagctatc caaagtgagg attttatgta    600
```

```
gaaaacatct ccagctgtgt taaatataaa gctgtcagtt ctttgaatat ctccttgcaa    660
taattaatca tccttctcag ttaacagcac agacagtaca gcacaggtaa gagagtaggc    720
tctgaagcca gtctttgtga ctctgggtac attgctttca tttacaaaaa gaggatgata    780
tagtacctac catagtgttg ggattaaat tagttaatat atataaaaca cttagaacat    840
agatagtaca tgtatttact gtttgttctg tataatacat tttaagtggc tggttttagt    900
taagttctct cagagagttt ggcatttgaa ctggtccttg aaggattttg taaaagtgaa    960
acataaagaa ttaaaaatgg taaaagctat gtgaattaag tagaggaaga tctttgtttc   1020
catttattgc atactagcta tgtgcctgcc tctgagcttt acattatctt attcaatcct   1080
cataataacc ccaagatagg tattttaagt catttaacag atggcaaata gccacagaaa   1140
agtagccact ttttcaaact cacaaagtca aatgtttggc ctagttctgt cagactgtaa   1200
agcccatgct tttaattggt atctaatact gctttcctat agtagactat cagattatca   1260
ttccgagaga ctctggatgt gtgtttgctg gtcatttcaa aggctgaaga gaaacagaca   1320
tgcctgtcct tgccaaatac attgtttccc tatcattctg tcacttggaa gtacttgttt   1380
ctgacctgga ataatggtat tgtggttatt ggcgtttttg ttacctttct tactagaaat   1440
tatgcagatt ccccaattat atccagatgc acaccttata ttccaaattt tgttgcctgg   1500
gattgactga gtaccctttt gagttcctgc atcagagacg tgtttacagt tgtgttccca   1560
gtcttcagca tttatggttt cattttgtca aatttgtttg aagtataaaa acgataatct   1620
taattctgtt actgatcatt ccttatttgt cacatcatct ttttttgaaa cgtttaggga   1680
attaattaat aattttatac tcattctttt tccactcaca tatctcactg gctttgttca   1740
gaattaaata taaacccagt aaaactctct tacaacaata ctcttgtatt cgttctggat   1800
tgtcacatag gagatgtgtt taggtatcta acttggtttc agcattgtac gacagaatct   1860
gtggcaaatg tggcatggca tacattatat atggatattc ataaactgct tttacaaaca   1920
tttccagtta ctgaaccagt agcactgttc cagtcagtat ttttgtctgt acatgtatgc   1980
atgtgtgttt tcccattttt ataaaaatgt gttaaaagta aaatgctaat gctgattata   2040
caaagatagc atttgacaaa attccttcat aactctgaag aaaatattct atgataatgg   2100
gtagagttat ttacaacatt aaacaaaaag tatttgagag caaccgttaa atattatcac   2160
agggtaaatt cagcaactga aatccttttc tcatagtttg tattaggaaa ttaatagtct   2220
ctcagatgta tattggtttt ttcagtagtt attcttgtgt gatatgcatg ctcatgtatg   2280
tatgtatttc ttaaaaatca ctggactttt gtggacttaa ttgttttcat agtttttttca   2340
attttacata ttttaaatta aagcaaatct atggaatgca gatttactta tatcacttag   2400
tctttttcct ttctttcaga aaagtggtgt ggaaacaaaa tggttttagt attgccttat   2460
aaacaaattt aagatcatga gtttctttta ttatcctctt tgttcatttc cttgaactac   2520
atccctaacc taaatcagct ggagacaggg aagaaagtgt tagattctta ctcagtttag   2580
atcctctgcc aggaaaactt gtaactaaat taacgctttt ttaaataaaa ggagtcattt   2640
ttaacaataa cgtcagggca gcaggcatcc atgaaatgta tggtcactga tcattagatt   2700
ctaatgtgtt tactattttg aaactctagg gagaagaaaa cttatttttg catatgttgg   2760
aaaaatgtat cctcatgggg taatatagat aaatttgtaa tgcgtatttt ctaattagat   2820
tatttaggag aaattaccac tttctcttta attattagca ttaactttat catttttgtt   2880
tcaagatgtc acagctattg ttcagcactg aaattatata aattattagc tgaagtgatg   2940
```

-continued

```
actggccatt tattctgtta tttctttcag aaagtctgtt gttgtaaaca tccccgactg   3000
gaagctgtaa gacacagcta agctttcagt cagatgtttg ctgctaccgg ctattcacag   3060
acatcctctt gatattctgt cccggagtgg agttgaggag gctataaaat gtgtgggaaa   3120
cctcagaaat ctttagctgc attcttttac tgcttgctcc taataacagg atatgccgtc   3180
tcgagctgac ttagcgtgct gctgctggcc ttagagaatt tagttaaaaa aagtgttatt   3240
cctgtttctg ccctgtcaat gaaattttag tctttataac ctttccaagt aggctggagt   3300
ttaacatccc aacaattcag gagactgatt ttctccattg taaattctgt gggttcttca   3360
tcactaccac ccagcagtat gcaatctaga aatttcagct ttccctatac ttaatgtgtg   3420
tgcaacattt ttctccgtcc tcttgtgata ttacagctcc taatcagaac tctcctctaa   3480
gactgcaaga ctcaagccac taagcctgtt tacatttgct aatgggtatg catgtctttt   3540
tatattaata tttttcctaa tattttcaga ttgttgcttt gcttccagct gccctgaaag   3600
cagctgtatt gtatctattt tttgtgtttc cccacagatc tgaataatcc agggcttttc   3660
tcacagatga cactcagtgt ggactagtat aattttatag ctttctgagt tttaaaaaat   3720
tgttatttta tttctgttag tctttacatt tctattttat tggcattttt cttttcaata   3780
aagcattgtt ttttaaatca tttattttta ttaaactgct aaacatacta tgttaggttc   3840
catacatgat taaaccaaaa gataaaggtc ttgccaatct aatgttttac atgcttttct   3900
ttgattagat tataagcttt ctgaggtcag agacattaaa tcttgataat tctatttttt   3960
ctgttataaa cagcaagtaa gcaccttgat gtatagtact ttagtaatga ttttataaat   4020
gctcttttgt tagagtagta gtttataaga cttatttggg gatgggggtc agttgcttat   4080
tttcaggctg agttattgct gagctcagaa gtcttccctg ccaaggtaga atgtaatgtg   4140
ttctgtggta ataggattat tttgtttgac caggtgacac tgtttatttc ttataaaatt   4200
ttgatatatg ctttaaaatt tagtaagatg gatgcataat ttatgcagtg aaatttgaaa   4260
ggtttttcaa aatgataagc caaacctaag ctaaatgagg gggattcttt ataataaagc   4320
tgttatactc tgcccagcta ggccagttat ccctagatgc tacagattaa tggcaatctg   4380
ttatgtaaca tttgttctat attattctgc cctaatgagg tgaatcaaag acgatgtcag   4440
ttttaattct ggatgccctt gcttcagtat agttaggtac agccttttttg tagttttcag   4500
atggcttctt tatgttttta tattgaagaa ccactaactt cccattggcc tataaggtta   4560
gcaattgatt atttaggctt gaaagttaga tcatcagtat ttgtcaataa gcctgtaata   4620
acttgtttcc ctagccctta acttagtgtt gaagaaaaaa attgtggtat ggacttagaa   4680
agcacagaaa ttacttatta tttaagattt gttctaccaa ttgatattta aagtaaaaca   4740
tttttagcca ttctgtaaat gacagtattc ctgagtatat ggtttaggga caacttttta   4800
agcaaataac tattacaaaa ttgggtctaa tttatttcat tgtacaaata ttctttagaa   4860
atagtcatat aaatacactt tggacttgtt ctcattgtct ccacacctca gttccttcta   4920
catgagtcat gggcttgagg ttacccagaa aggactgtga acctataacc cagcatgcat   4980
gtggtattgc gtcagcatgt tccccttcta ctcttgttac agctttattc attggatcaa   5040
tgtgcattat ttgctgtgtg tgctcagttt ttgtttcttt tttttagttt gaatatctgg   5100
gcttagttac tttttaaaat aaggctgttt cagatagttt gcctagcctg gttaatgtgg   5160
gtggacccat gctacatgtt ttggcattgc cttttttat ctgtaccata ttacaaactt   5220
cctagtaatt tgacattcac tgctgtcttt gctttagctt tccaacaggt ttggtgaaaa   5280
ttgctgttca atatcagctt gcatcagaat tacggagggc ttattaaaac acagattgct   5340
```

```
gggccccaaa aaaagtttct gattcagtag gtctggggtg gaacataaga atgtgcttta   5400
gttcccaagt tgatgctgct cctctaggcc caagaatcac agagctcatc ttacattctt   5460
ttgatattat gccaaatcct gaagtttgat tataaaaagg cccagagaat tgaatgtgtt   5520
ttcagagaaa agcagaagaa aaaaatacgg ttgtaatagt agttaaaaca gaaaagcagt   5580
atggttgtag agtggggtgg cggggaggta tatgttaatc ttgagaacaa tgcttttgga   5640
aaacaggagg ttcctgaagt cctgggttac ctgtgaaatg ccaaagattt ttagtttgct   5700
ggcagtgtta tatgtagttt tacttccaaa tttgaagacc tcttctttga tgcaagtgtg   5760
ttggtaggaa ctgataatag ttagtggaga tatttgtggg aatatatttt taatcagaaa   5820
gaatgcaaaa agagggggag acatttcttt gagacacctt aatgacactg ggaacagtag   5880
aaggtggaaa tgtgggaaag atgtgcctga gatgaaatta tctgaatgtt gagggggagg   5940
agagggttga tgcatcatac tggtcatcaa gtaagttctt ataaatgcaa gtttgattgt   6000
tttgaaggga aggatatagg aaggctggat aatcagctac atttagatat ggaacactac   6060
aggatgtcgg catttcaact cacttctgcc ttttccttgg attctacact ttctctcagg   6120
atatctttcc gattgagtct tgcctcattt agaatgctgt gcctgttctt tttttcaaca   6180
gagtcttacg taaagaaccg tacaaactta gtaaagagtt taagtcctgc tttaaaccaa   6240
gtttcagttc atgtaaacat cctacactca gctgtaatac atggattggc tgggaggtgg   6300
atgtttactt cagctgactt ggaatgtcaa ccaattaaca ttgataaaag attttaaatg   6360
ctagttatta ttaatgctgt gttgtaggtg ttcagtaaat agttgccata atgcttaaag   6420
cagacacttg tttttattaa taaagatgat gccaactttt tggtttagaa atgctttgaa   6480
tctttgatat tgttgtaata tagtggcaaa gaattttaat cccagcttct ggcgctatgt   6540
tacttgggga agttattaat ctctctgtgc ctcagttctc agtcgactaa attgaattat   6600
aatagtacct gataggattg ttgagttaat ttgaaacttg ccaaattttt acattatttt   6660
ataatttata gtactttaac atattgcaat gcattacaaa gcatataatg taaaggtagt   6720
tttatgaagt gtcaaattaa gcatatttgg gaattgccca tcaatttgtt tttgaacctc   6780
agtggaattt ctttcatatg ctagatgtga aaaaagcata tgcatgtggt ttaggctaca   6840
aaatagcctg taggttaaat tcctaattct agtgtttaat tctttttctt cttgtttaat   6900
ggccatatgt ttatatcttt atattacata cattcctgat tatgtaataa ggtctttgat   6960
catgtgggct atcagatttg cctcacttta agaagctata catgaaacta tgttgtactt   7020
aagtgaaaat ttgattcttg tttgaatgca gtgaaacatt ctacttacag ttagctgtct   7080
cccaccctta caggaaggta catgccttca ttttttacag aatttttttt ctgattaatg   7140
tgtttatcag ttttatgtta tgaaatctgg atatatgtta aaatgtctca gttttcccct   7200
tgtttaccat attgccatta tagataacat aatgtaaaat tggatgtctt tgataatttt   7260
gggatatgtt ctgaaattaa atttgaagat ttggtatctt ataattattt ggtgagcatt   7320
tggcatgaat tatttagctt ctccccttta tgatttattt ctctcatcga tttctatggt   7380
tctaatgtct cctgtagact tcagtaaggg aatctgtaat atataatagt tatcttttag   7440
ttatatttcc acttttttta atgtgttttt tttttagtaa atgtcaaaag tgttactcag   7500
taacatatta tgcaatatta taatcaacta acctcttcat tgataatgac ttcatattga   7560
gaggtttttt aaatctagaa attgttttaa attccaggtt aaaatgtaaa ggtattttta   7620
ttttttaatt cttctcaaag ctactagtca ttataaaaca acaatttcac atttagaatt   7680
```

```
tttatatgta tataaattag attattttta tattagcctt aactttcttt aattttatga   7740
aaaacaacta gtcccaaggg tatttttact atttaatata cattattcct gtgattcaaa   7800
atcttagcag tagaacctgt tgagctactt aacttttctt gggactatcc aggtgcagtt   7860
ataactggtt tcaaagtttt tccttgcttg tttcaaaatc attccttaaa aaatgttcag   7920
tatttttctt ttgtcaaaaa atatgtgggt tgttctgttt tttaaaatag tttgagaaac   7980
ttcctttgcc acttgttttc tgtgcaaatt gtaagagctc aaattccctg ggggtaggga   8040
ggacttttat aaggtttttt tggttgaagg gtataaaagg cacttaaaag gtatacagtt   8100
acttttattt atcccagtca ttttgacatt atgataagct ttccccactt tataggttat   8160
ctgaaaattt ggtggggggc tttatttata cttaatataa caaaattatt ttcctatgtg   8220
tagtcaatag cacatacaaa aatgtttgta gtcagtagca cagtattcac caaaatactg   8280
agttattttc aagtaaaggt ataagtatga atgagttgtc agtccttctt tttcagataa   8340
ctttctaaat taaacttttt taatgttata agtgaccaga ctatgtcact gatacaatgt   8400
catgattaga tgtgcagaag actttacatg gatgataaat gaaacatata gaaattaata   8460
tcagattaaa ctaaaacatt aagcaaagta tgcttgcata catatatatt taatgatatg   8520
tggagaatct ttgtgcttca tagtcactag acctaaagta gaagcagttg tcaagaatgt   8580
ccaactgcta ttcatctttg tggccaaagt aaatttcaga ttttttttt gaatggtttt   8640
ctctttatta acccatcatc atgacaagtc tgtcaagtga cacatgtgaa aagcagatgt   8700
ccttttaagg aggcagtgca atgcaggaga aggaacatta ttagagataa aggaaaaaac   8760
cagaattcca ctcaacactt cctcaccaaa tgtgtgtggg gatttctacc aacaaccaag   8820
ttctttactg cagattctcc agtggatacc agccaggtgt cctctaattc agttcaattc   8880
tattatctac tgggagatag tgtcagatcc cgcaagtgga gggctcagtc ctacaagact   8940
acccctactt cagatgtcag tcacaagcag ttagcggttt gtgattctga ccaactggct   9000
agaggtcccc ctcctcaagt gtgattaatt tgctagagca gctcacagaa ttcagggaaa   9060
cactttacat ttacccattt attataaagg atttatgaag gatacacatg aactgccaga   9120
aagacaagga gcataggcaa gatacaaggg tcacggagct tccaggtgca ccaccctctg   9180
ggaatattca tgtgttcagc tgttcgaagc tcattcgaac cctgtccttc tgagtttctg   9240
gaggcttcat tacggcatga ttgattacat cattggtcgc cggtcctgtc gtgtccctgg   9300
aggttggagg gtggactgaa agcttctcat catgctttga tctttccgat gaccgacccc   9360
accctgaagc tatctacggg tccccagcaa cattcatttc gttaacattc ttacaaagag   9420
attccaaggg ctttaggaaa tggagatgaa gagcaaatat atcaatatca caaacatacc   9480
cttgggaatt agacctctga tctaatctag gctccctcac ttgccatttt tgtgaccttg   9540
aacaagttgt tcatcttttc tagttctctg ttaaaaaaat taaaataaaa aaagctatca   9600
ggttgttagg aggactagat aagagaacta tgtgaaggac ccgcacagtg ctagcaacaa   9660
agttgtttag taagtgctat ttgcttccag tgagctccct cagtgtgtac caccaaatca   9720
catgtatccc agtcaaatct taaagtccac cttgaatctt taaggtgtgt ttttaaaact   9780
gcttttgttt tgatccttgg aagttaaatt ttttacacaa gcattcaact gttagcttca   9840
aactgaacag aaaatatctg tattatttca ttatgtataa aaaatgatta agcctgcctc   9900
aggcagttca gagcaggttc aaggagtaac attagactaa tcagagtgcc taaaaagctt   9960
tatgcggtcc aggttgtaca gggatgttgg aacagtaaat atgaaggttc gagataggta  10020
gaatagagca ggttatatta gagaagtctt tctaaaattg tgttggctag cctgggattt  10080
```

```
gaacttatac cgtgtatgta tgtccatgtg taacaggttg catgcaagaa gcagtgttca  10140
taaaaggtgg caaacttgtt ttacttgttc agtcttttca gatcagtact tataaaacat  10200
atttacagta aatatcttat attaaatatt agctaaccct attaaattgt gtgtccttgt  10260
gctgcatcat ttaatgacta agttggcatg tgatttgaga tagctctaag tgctaatgga  10320
tttgaaggag ttaaaggcaa aaccaggaag agaaaactat ttttaggaaa aagcgatcat  10380
acaacaggcc ttaaatagaa gaaatgagat atcttatctt tactatgtaa cctttaattc  10440
cttacacatt ttgacttcat attttttgta tgtaaatgag aatgttatag tcttgtaaat  10500
tccttttcct ctgtgactac attcagttat tttatgtgtg tttgtgcatg tcggtaagca  10560
cagtatttag tagaatgagt tattggttaa accttgtaag ggccacctgt ctcttaaatt  10620
gtaatgagga tttgattaga taatctagat aaatcactaa gcactcagaa aatatcccat  10680
tcaaaactca gttccagtgt caagtctttg atttggaact ccaaggtagt tggtcctctc  10740
tttgtgccat aaatgtgcct gtactcagta gtgctaaatt gctatcaact agtctaaatg  10800
tacactaatt catctgtgtg tccacttccc ttctttcccc tccctgatgg aagatggtct  10860
gggagcaaag gtgacaggta atcttttttt aaacagctaa aggattggat caatttttca  10920
cttccctttt tcacactttt ttccttttac taagaaaaag tgcaaatgga gaaaactgtc  10980
cactaaatat gaattaaagt gctattatca gaaattgtgt aaaagcaaca taatggcact  11040
ataaaaaggt ttatcttaga atcaaaaacc ttgggtttat attatagcct gctactttct  11100
agtcatatga cagtcaagct atattacctc tttggcttac aaaataggtc atctgcttgt  11160
tatgattgat gtgaaatatt catacaaact accactgtgc ctggtaagta gaagacactc  11220
aaatatgtct tggagttaca gttaatgttt aaatttgaga aaaaccaact ttatcacata  11280
gatacagttg tttactgcta gaaattttat ttaaattagt tgatactctt ggttaggtaa  11340
tgaaaaacaa tggttttatc tccattatgc tgtgataggg aagagtaaca cagttcaaat  11400
ggcatacctg acaattaagc atagttaatc acacaagaaa caagtctcta cttgatacct  11460
ctccatcatt gatactttgt gccatacagt gaaaacagaa ccatctaggt gttcacggat  11520
ttatttttcc ttatgaaagg tagagagaaa attattccca atacaaaatt ggttattagg  11580
tgccttttaa ttaggcgtaa gggcatatga acattaccta tgagaatttt gtcaaaatta  11640
tttcccagtt actgttttaa aacagcctct cttccccact tctaatttct cctttctatt  11700
ctaccaattt tactccatac ctttttgcta aataaacatt ttcttccaac tctgtttggt  11760
gttttttttt tgatctgctc ttcaaagtat cagctagtga ttaggctata gaactctaag  11820
acagtagctt aaacaagatt tttttttaa cccctgacac aaagacaaag ctttttcaga  11880
aactcttatg tttttagctg taagagatca tattgtcact gagcaaagta cttacaattc  11940
gtagtcattt gtcaggaagg gtgaactgac taaataaatt atcctaccac cacaatccca  12000
taactctaaa cttagatgtc aaacaaatat acacacagct aaccacaaaa aaaaggaaat  12060
cccagctgcc agaagtgaaa aaacagccag aatagtgaac tcagcagctg aaggtacact  12120
gacctaggtg gatgatagtg ttggctgtgg gtctcaccaa tggaccctga gactttaaca  12180
gcaagagata tggcctgact atacagggaa gctggactga caaagccaag accttagaag  12240
gtgcagcctc agaaggagga tgagcaaact tctacaaccc agggaagcta caaagttagt  12300
tattttaatt aatattttca tgtatttcct taaatcactt agcttagaac tatggaaagt  12360
cagaaacagg ccttggtagg taaattgccc aagtcgtggt gaattcttaa agacagcatt  12420
```

ctataggaaa tattttagtg ctggcagttt agttatttaa tggtggaaac ttgaaatttg 12480
atctttgaaa tataaaggaa taaagagtac attttagaga catcaagctc tacgttgaga 12540
agacattgag agattacatg agtaacaaga aagagaaact ttctgagaat gcacagctct 12600
tttacaaata acaaagcatt tagttttctt taggcttggg gcaagacatt aaatccaccc 12660
ctggtttata aacagatcac accaagttta gtgtccactg atatctggaa gactttaagg 12720
gtattacatt tttgctatta ggatcttgtt gcctctagca acatttggtc ccaggacaag 12780
aaataggggc gggtgaatgg gagagtcatt aagaaagcat gtagaattga agaaacctga 12840
aaataatgga agattctttc agaactcatc ccaaggtctg ggtaaagcct gtaatgtaac 12900
atacataatt ttgtaaacac accacatcag ataactacag atgttttgga cagcagctga 12960
ttgtttaaaa ctcatttcag agtaccaggt attggaggga gggagatggg ggttgaaaca 13020
gtggggtaga attcagtgga ccaggattct ataccttttta aggcaattcc tgattatatg 13080
tatttataag aatgtgagcc tcagtcacca cattccttca gggttgggta taaaacgaaa 13140
tacttggaag atataaagat tgtagatgac aggttttatg ttcaagcagc attgacattg 13200
ctactgtaaa agtataatag ggagtttatc aatgctgtaa tatggtttta aaggcttttt 13260
tctaactata gatacttata catttttct tttggcaatg atttttaggg agaactaaat 13320
cattcttgta gccagacttt gcaaatgaaa gaaaacaagc caagggaacc tcacttagga 13380
tataagacac tcacaagcat gagtgttgca actccagttg tcgtgttttt aataacacat 13440
ttaaaaagta tagacggtga attcccacta agtgtgtatt ctttgctgtt taccagggtc 13500
agcatgagct gcgaatctgc atgcgtgtct gtcccacatt gtggttacct gtttggcagt 13560
tttgcaacat tttaacccca gattttatta tttttcaaac tcattctcct cctcctgttg 13620
agactctgtc ctgcggggaa tgaaacaaga ctctgtcact caatctgttg aacatctatt 13680
tgagaattag gttcagattc cctggcttaa gccacttaat tatctagcca ggagtttca 13740 aatattttta tagtggaacc tgctctttaa aaagaaatca ttcaccaaag cccaccatgt 13800
aaagcacatg aacgtgaacc cacctgctaa ctgattccct ggttacccct tttagcacct 13860
gaggcacaca ataagaccac tgagttaacc caccttctgt tatccatctc tggaacagac 13920
tctccaatat agccattgta aaccatcctg tttgtaatcc tgtgccttcg tatatccagt 13980
tcttccattg tgaatgcttc atcatccttg atatttagtt gtccttgata taatcttttc 14040
ctagaaatct gccctgatac ccttgtctgt gttcctttgc attcattcct ctatctttgc 14100
tacactgtat ttattagtca gactctccca cactaatagt gttctttttg gaacatgtct 14160
tattcgatat tctgcctcca gggcca 14186

<210> SEQ ID NO 66
<211> LENGTH: 9518
<212> TYPE: DNA
<213> ORGANISM: Homo sapiens

<400> SEQUENCE: 66
tcctgtccaa cccagtaaaa ttagaggata ttgtgtatta aatgtacatt ttgcattaat 60
tcttgtaatt aactcatgta aattaattca gtgccaggca tatatgaagc cataattaat 120
gattgtgttg ttttattatt gttaacaagg ttcctattgc attgcattca aatgatgaag 180
caatttccta ggtaggaaca acacttcttg aaacaattaa aatgcagtca cagagtttct 240
ttaaaatggg gtttaaaaat tccatttcta ggcacctaga gaatacttct ttaagagcac 300
aagggatata tataattaca ttatacatat tacttaccaa tacgtaagca ttctaaaata 360

-continued

```
tgtgtagtga tacctatcca tttcaggata gttattacct ctggacaagg aaaataaagg    420
gaagaaagat ggaacttcag ctgtaactat ggatacatga aagtctatta gagtattttt    480
tctgtgctta attttttggt ctataacatt aaagtgttga cattaacttt tacatgcagt    540
tttattactt agtaaaactc aaatatcacc tcccttggaa accttgctgg aatcttctgg    600
aaatctccct ccttgggttc ccacaggtcc tgttcagttc agtacccttt tgtggcccac    660
atctttatga ctcaggtgta aagtgttagg atctcaattg cagtgactgg tgctaggatg    720
gctgttatta tatgcctaaa aaatacttat aagtaatgaa gccaacttac atattctgta    780
attgctgatg aggtgtgctg atggttgctg ataaaaatga ggaaggaata tgaagaaagg    840
tacagtcatg aaacaatacc cctgataaac ccagttgtta aatcctcagg ctgccacaac    900
aaaataccat aggctgggtg gcttatggaa cagtttctca cagttcatga gcctttgagt    960
ccaagattga ggtgtcagct gattcagttc ctggtgggcc cttcctggct tgcagatggc   1020
tgcggtctct ctgtatcttc acatggcaca gagagagctc tggtgtctct tcctcttctt   1080
atgaggactc tgatcccatc atgagggccc tacccatgtt ctaatctaac cctaattacc   1140
acccaaagga cccacctcca aataccatca tattggaggt taagacttca acatatgaat   1200
ttgggggaga catgaacatt cagtctataa catcagtcca aagttaattc tctacctgtg   1260
atcattttat agaatgagca ggcagggttt ctgctctagg ggatgctacc cctggtcaga   1320
gactcgtgtg gatttggcag ggaggaaact gcagaattgt atggcctctt tcatcggcat   1380
gtttctataa tctcttcaca tacctgaatg cctgaagagt aagtgaattt caacactatg   1440
tgctttgtaa ttctcatcag cttgtcattg attgctctcc cgtcaagatg atggagaatt   1500
ttagcttttg caaacaatta tagaatcttc tgatcaattc acagtctttg aatggtctgc   1560
atatccttat gcaaaagtca tttcaatttt taattatttt agaaagtgat ttgatgcatt   1620
cattctttaa ggtaaaataa aacataagca taagcagtta gaattagata aattattgta   1680
aaagtcaatt caataatcaa ttattacaaa tctaaataac tatgcacatg acggttgggt   1740
atgttagcat aaccagataa ttggttattg atagaccgta gggtacataa ttattcatta   1800
cctggatgca atgctgattt ctcgctgtgc tgatgtatgt cattagctac attttaaaga   1860
agaccttatt cacttgctta aggctccata gaaggtagat cttgtttttt atctctaaac   1920
aaaaaagatt tcttttacat tttttatcat gacataaaat tgtgtacttt cctcatttag   1980
aacttcaagc tcctgggttt gtaagaccaa ctgccaagcc tcctaaagaa gtttctggga   2040
gtccctcctg cttattccat ctccataaac ctcaggattc aaactgatga ctcaccatat   2100
taggtttctg gcaatagact gatgtttctc gccattgctc tctagagcac tgtaatttta   2160
gccttaagat atcatgataa tttctcctac ctgcaaattc acactcatta aactgggtga   2220
taattatgca aggactcact aacaaaaggc caggcaacaa ttccataatt aatgtctagg   2280
ttcttgtttt tccagtgata gattttttttt tctcttttca gcttaaataa agatgacatt   2340
gtcgtgatca ttgtaaaact agccagtaaa aaatacatta gactacagaa aagaaagtcg   2400
ggttctgttt caggactacc ttgtctgttc tccacaactt tttagtctct gtaggccaat   2460
tgcactagga accactctcc catctactat tattactaca aaacacacag caaactgtgt   2520
gcaagcacat acatgtttat tcacctgatg agcttttact ttaactatat ggctgacata   2580
atttgctgct ccgtagaatt caaaaaaaca gtcacttttt aaaggatgca taggtataat   2640
atgactcagt aaatcacaga agaaatacaa tgaccaatac atatttgaaa cactgttcac   2700
```

atctaccagt aatcataaaa tataaacaaa agaaagaaat ccaatcaaag ccagagtagg 2760
actccctcta tggagggctg cattttgtgt ttgacattgg aagacgtctg acacgaataa 2820
cttacagaaa gccctgaaga aaacaagaca aatggcaccc agatgaaagg cactgggttg 2880
tcagagcctg ggtgatgagg acaaggatga aggagaacag taaagccacc tttcgcacaa 2940
taaattatga gataaccctg gaacgacagc aaacagctgt cggtttcctc agagctaaca 3000
gcagccacct ctgctgcttt ttccaccacc agctcctttg acaaccagcc taacagaatt 3060
gatgatcaaa gctctccagt gtggcagcaa agcctttgcc gggggaaagg tctttaaatg 3120
ttactggagc gagaagggaa agtgccaggt aggaataacc ttgacagaat aaagtgaaca 3180
acaaagtgct ggaagcaaac tgttaagagg gtgtggatac agctcgtgag gtggcggctt 3240
tgtggaggtt ttcactggtc cccaacaaaa aaggacaatg tagcaagttt cccttatacc 3300
tttcacttaa aagactgtcc tttattccaa gatttcttct ttcacagttt tgatattaaa 3360
tctccttttg tgaaaagacg atagaagatg gtgttcttcc tctctcttat attcatggtg 3420
aaataaaatg ttggcaacaa aagtatatct caataaagct gttattttaa aatatagaaa 3480
aaaatctaca gagaagatta cagatggttt ttagttcttc tttgtatagg catcctaaat 3540
tctctattac catataatgt tatgttatca gagagttata aatatttcaa aataattatt 3600
tacgacatga ggtttagaga gtgctgtaac acagttgcat acaaggtaca gggtggatga 3660
aaagttctgg tgctatttgg atgtaggggg aaaaaaagct tgagttgagt cttgaaggat 3720
acgtaggggt tctccaggtg gatgaggtag aagggcattc tgggagagaa cagtatgttc 3780
agaggctctg atgtaaagta tcctgacctg cttggtaatt gtgttcgtta ggtatgtctg 3840
gattttaaag cctgttggga ggttgcagtg ggggtagagg gaggccagca agataaggct 3900
gggtgagctg gaggactgag gttcttatgg ctgcattcag cagagaccag acattacctt 3960
aagaagcctt caaggagtac attgttaaga gaaacggcat ctgtgggata aaaagaggca 4020
gaaagatcta agcaatgatc tcaggctgga aagaaccaaa cctttggcag agtctaaaac 4080
ccaggcgctg aggatttgcc gtggtccacc ttgcatggtt actgagcacc cagtatttgc 4140
aggcttaaaa taacaagata gagtatcacc actacctcag ttagtctcat tattgaggga 4200
tttcagatac aggagcaact gaaggtagca aagcaaacaa cacaatgtgc taagagagca 4260
gtttcccttt tacaaaatag taatgatgaa ttattttcac caagtaaaat tcaagctttg 4320
aagggctgga gtggacttgg ttaaagacta agtaactgta cctttatttc aattgcatga 4380
actaaaacta caaaacaagt gaagacatgc actgagaaag tggagtatac tatgacggta 4440
aatagttttt tagcatttta atgacagaga gagattgtgt gtgtatgaca catcaacaac 4500
aaataaataa aagaactggt gaggatagat gagtcactga gaatgtttaa aactatttgg 4560
ctcccccagg agatgaccag atagtcagtg aatgattcag catgggaaat aaccagtaag 4620
agcaaatgcg aatgctaaag ggatatgaaa atctcagaga tggggaaaac agggtcttca 4680
cttgccactg agagttttaa aaagattatc tcaggggata gtaaaaggca gggcttcaac 4740
ctgcttgttc taaaggtagc tcataaggta tagtcgagaa aacaggaaga agcattagtc 4800
actatattta gctattaacc caagattcca gcaatttctg atgcctgcag cattcatctc 4860
tgttctgctc ttataaaacc cttccagagt gacttgggtg agagtattgt cttagtctgt 4920
ttgtgctgct ataacaaaac acctaagaat aattaacaca taatagaatt tttcatagtt 4980
ctggaagctg ggaagtccag gtgagggcct agtctttgct ttcaagatgg accttgactc 5040
ctcatgtggt ggaagggatg gaaggataac aagggaacta gtttcctcca tcccattcat 5100
gaggctttca ctctcatgac ttaattacct cctaaagacc ccacctatga ttaagaccag 5160
gctcatgatt aaatgtcaac ttgtgaattt tagaggatgc atttagacca cagctagtac 5220
ctagagggtc tctatacaca ttttaaatgg catcttacat gttcacccag agacaccata 5280
aagttgctgt cagataagga ttttacaaga agagccagaa atcaagattt ttgtataaaa 5340
ctccagagtt ttaaatgttg gctcaaacta aagaaaattg tgcaggccaa acaaaacata 5400
tctgcaggcc aattttcagc ctcaatctaa gtaagagttg ttgtaagaac aaattaaatg 5460
agtttaaaat aagatcaggc aagtactcac tctgctcgct tcaccacttt ggtgttcata 5520
tgttaactga tttaagtctc agaacttatg agggaggtgt aattactacc ttatgtgata 5580
aagaaagtaa ggaagagaag ttaagaacct tgttctgtca tacagtcaga agaagtgggg 5640
cgggatttga accagaccca ggcaatcgga ttcagatttc acctctctta atcaatgcat 5700
tatgcttgca gtacaagctt ctgatccatg atagacagtc tgtgtaattt cccttccaca 5760
tcccctcagg tgctttgagg caacttcagg gggattttct gatgctaaga aagacagttt 5820
ggtattttaa atacaacaaa agttgtcatt tcaattaggt atctcaaaaa ctactgtgat 5880
gttcagtata atgatggaat ctatatagtc ttgactagga gttggaacag tcacgaggac 5940
gtatatgctc agctcttggt cgccaaagga caaagttgca ctgaagatgg tgaaatgtta 6000
catcttcaga gaagaccacc tctcctcacc tgggctccca agtagtgcag acttggatag 6060
atggatatgg ctggacgaat ggatagatga atgagtgggc ttcccaaagg tatccatcta 6120
tctgcatata ccaggagaca cttttgactc ttccattaca agatgaatta caaaatagag 6180
tgtcaaagtt aaacttatct ggtgtagtta caattgtagt gtttaatcat cttcactaag 6240
cattccctaa aaaagagctt agtgaaggaa ttccatagga ataaatgtcg ctccaatgta 6300
gctccggaca acattgatat tgaggcgatg ggggatgcca tccacccgaa tgtccacaat 6360
agaaaatgat ttaaatttg gtacagccat agaattacta ttagactacc aaaaacattg 6420
tttacaaatt atgtgtaata aatacttatg atccaatatt aaatgagaaa atgatacaag 6480
tttatacagt atatgtaaaa atgtatcatt taagtgattt tttcttaaac aaaaaaagac 6540
atcaggtaag taaatttatt gattacctgc aataaggata caaagtaata gacaaaagaa 6600
aaacaaaacc aagatatttc aaatagttga ggagatgaga agctctcaaa taattagatt 6660
atgaagaaat agatggcaat tgaaacgtga agatatataa cagttgctat aatatccaga 6720
agagagaaat tacctttggc tgtggatcca gggcaggcta ggaggagcat gagctgaacc 6780
agaagttaac tgggatttag gcaggctata gagcattcca ggcaggaatg ggagggatgc 6840
aggttccagg ctgatgcaag tatggaaaca tgcaatatat gtttagtgta atgcaaggga 6900
aaaaacttgg aacctcagtt ggaatcctgg ctccatgatt tctctttaat agggtatggt 6960
aacctctaag gtctcaggat catcagccat atacagggac agtaaggtat ctcataggat 7020
tcctgtgtgg attaaacaag attaaattcc tgtggatatc ccttctttct cttcagcttt 7080
ctttgttgtt catttattca ttaccattca tttagcatgt gatgtagcaa gcaatggttg 7140
gctaggcttg tttgctccga tcctgccctg tgccccaccc ttcctgccct gttgggcccc 7200
agagtctgac ccctatggac tgtgtaaggc tctcttgctc tctggcttcc agttgggctt 7260
ggccaggaaa taattgggag gaggaagaag cggggcaact tacccagtca ccgcttgtcc 7320
cctgcgttgc catggctgtg gtgggtagct cctctcccat agcctccgct cttaccatct 7380
ccaaacacag ctctgcactc ttgccccttc agttctaccg gtggggatag ctttccacag 7440
tggtaggccc tgggtgccgc atcatgtgtt ctcttaaccc tgcccacgtt tctgtacctg 7500
gttcctttct caaattccct tcagttaaac tcctttaaga atgccatctc ttgctggtac 7560
cctgatacaa ccataaacaa ggtagacaac atccttgcct tatggggctt atgttctggt 7620
aaacaaccat attaacataa tagctttgga tacagtgaaa aataaagtaa agtagtgaga 7680
caataatggc tgagaggggc tactcgaggg aatgatattt gagctgggac ctaaggaatc 7740
agagggagcc agcaatccaa agatctggga gacttctatt ttaggcagta gaggcatagt 7800
aaaaaaggct aggacaggat gtggtgttgg gagaatgaaa agcagtgggg ctgagaaagg 7860
gtggtgggag ctggtcagag aggcagtggg gactggtcaa ggatggacac agtgagccat 7920
ggagaaggat ttggacttta agagtgtcag gaagtcttcg aagggcttgg gtggggagta 7980
atttgagcca tatttagtag acaaaggatt acacatcagg cagagtggag ggtactgctc 8040
ctgtccaggc cggagttact ggcatgatct agagtgatgg cagtggaagt ggagagatgt 8100
aaatggatga ggtcaacttg cactgtgatt ctgaactata acaatacttc agtctttccc 8160
aaccagtatc ctaggctcct ggaagattgt gaaaactcta tttttttttt ttacatttat 8220
atgttcattt tgattattac atatttaaat ataaccccat ttaattttat ttctaagacc 8280
tccacagtgc caaataattg cctacaataa cagcatttaa catactgtgg tgtttttatt 8340
cagacatact tagaggaaat acaacattca taggtgcata gttcaataaa ttttcacaaa 8400
ctgaacatct ccatagaagc agcacagttt aggaactcaa catcaccaag actccaggaa 8460
ccctctcctg tcctctccaa gtcactactc ccacacccta gtttagttta gctggttgtt 8520
gaaatttatc agtacctgag aagaggggga aatcaggaga aagcagattg ctaaaaatcc 8580
caccctggga tgtggttagt atgggattcc caccaggaac aggcccacaa tttctgttcc 8640
tgcttattgc acctggtaat gaagaactga gcttgcaacc aggttatccc caaagcataa 8700
gcatatcaca gtgatataat tgtttgcctg atccccatca atggacacgg ccctttgcat 8760
aatgtttgtt gatggctgtg actcttctgc atgccttagg tgagtcatga gaggtcaata 8820
aaacagtgat gccttgactt ttggttttgc caggtccaga ccaaaaggtt ttattaatcg 8880
agaagaaaca cagctgaatc agcttctagt cacatgtact tccctattca ttagactgcc 8940
agggttaaaa gggaagcagc caaagtttgt tttgatgtaa ccctttcatt accccatggc 9000
ctcatgcctc ccacttgtcc ccggagcacg tcactggatg cacacatacc cccgcccatc 9060
attccaattc tgctctctgt tatgtgacag tgggtggtat tgggttaatc agaggaatgc 9120
ccgatgtggt ttggtgggca tttgaaagtt aagaagcctg cttctaggtc aattctttag 9180
gctaactagt ggaaagtgac agaaacttga ctgagcaaga aataaacaga aaccccagta 9240
attaattagc tcctacagag atcagaggtc aggcatggtt gtatgatgtc attatgagag 9300
acttctctcc atctcttggt actgcttccc ttggctctgc ctctggtgac aagatggctg 9360
tcagtctcaa gcttgaatct cacctctcag caaccccaat ggagcacata aacttctctt 9420
tccaatgtcc tgaaatcagg ctttgtctga ttgaagaggc ctagttctca tgctcatcct 9480
gggagtaaag tcagcaccag ccaaaatgct aggaccaa 9518

<210> SEQ ID NO 67
<211> LENGTH: 3021
<212> TYPE: DNA
<213> ORGANISM: Homo sapiens

<400> SEQUENCE: 67
cggggtgccg gcctctcccc ggctggaccc aacgctgccc ggggctgctg caagagcggc 60

-continued

```
cccgcccgtc cgccgcccaa cacccgctct tcctccgcac cgaacacttc gggcttgcag    120
gagacaactg tcacgccctc ttccctttc tctaagacgc tgcacattct tgcccacatc    180
tgctttcttg tgtgcaggcc tcccagggta tgtccgtggg agtgaatcac tggctcatag    240
ggtgtttaaa tgttcacttt tggtgatatt gccaaattga gttccaagtg gtcataccag    300
tttacacacc caccagcact ggatgagtgt tattttccca catgctcacc aacattttgc    360
agggtgacac agcagttgcc tcctgctgac atcccagata tgcaaatgct ggggctagga    420
gcatctgtct cagctggact atcacctcct ccttcaggaa ggccccccag tctaccttag    480
ctgactggca gcttcccata acctcgcgtg ctttcccatc acagcactgg gaacttgagg    540
ggtgactgtc tcacagcgga ctgtgagctc cccaggaaga ggtcaatttg gggccattga    600
acaggctgaa aggaacacaa agttgctaca aatagtactc atctacttga agtaaggagc    660
tttctctaat caaagtacgc ccttgggatg gcagtagcca cctacccacc acacctctgt    720
gtcctcagca tctggataca gcagtagctt ccttttaaac agcacatcgt tgcttttgca    780
tcagccagaa aaaaaaaata ctttttagaa gaaaagtaca ttatcatgag tcatagtatt    840
tgagtacagc tggcctgagg tgaggctgga ggcgccgccc ccggtgactg ggtactcagg    900
gttgggttga gccaggaggg tggtggttgc ctcaggctct gagggatggg cagggagctg    960
ggcggggtcc tgagacattc aacctcagct ggttcctggg ttccgggccc tggagcagtg   1020
agggaagcca gttatatggg aggcaggtga gtcaaaggag ggtcaggctg ggtgccagag   1080
aggagggcca ctgcttctgt gagggggcct ctggggcctt ccgtccatcc ccagtgggca   1140
tatggggaca ccaccgaggc ccagagacct cttgcccagt cccccaccct ctgctgagct   1200
ttgcccaggg tgtagccagt tggcctcagg gccaggctgc cagggtcagg tcagctccca   1260
cgcctccacc ctgggcaggg cccaggcctg cattcatggg tgcgagaggc ctgagccctg   1320
gatgggtgtg gttgtgtgtc cttggggctg gtgttttggc gtgagtaata ctgtatagat   1380
gtaagtgtgt gtagtgtttg caatgttgta gtgtgggtgc atgtgtctgt gtgtcctgtt   1440
tgttgagagg attcattgca tgtggttctg ttaggagtga taatggggtg ttttgagaca   1500
tttcctcctt ggtctctttt ttggtgtgtt ggttatgttg gtgtttcggt atgtgcgctc   1560
agtgtgttgg tgtgcatttg gcaggttgtg tctattggtg tgtggctgtt gggtttgttg   1620
tgtcagtcgt acatccacgt tgggctgggt gtgtgcattt gtatattgct ctgtgggtcc   1680
ctgcaggttt gggagtagat gggagcggcc ctttgtccag ccacaggaaa accccacccc   1740
cctcatcggc aggggacttg ggaggggccc agactggtag gctccagcct cccgtccatt   1800
gttctggggc ctctctggaa aacaggatgg gaggtgaaag gtggacacag gcctggaccc   1860
ccacactccc tgaaacaacc aggggcacag cacagaatcc ttaggaggga gggcctgggg   1920
cccattttgt ggatgagaaa actgaggggt ttcattccta ttaaagggag agagcctgaa   1980
gccccacacc ctttatgtgc ccacccacag cctcctgccg ggtttggggg atggaaaaat   2040
gacaccccag aaggaaacaa aacggtcttt gtggtttcca tttctgaatg cttaccatgt   2100
gctaagtgca gatcataact ctgggttaag ttcatatttt gtacccattt tgcacaggag   2160
tacactgaac cataaggcaa caatttattc ttcaaaggac actatctaaa cattactgta   2220
tttcaagtag tacgctgtgt gaccttgagc aagttgctta ccttctctgg gccccctagt   2280
tcagctccac agcatgacca aaggagccgt ggttcctgct ctcttagagc ccatagcctg   2340
ggcagggagg aggaggcaag gaatggcaaa tacacaagaa aacaaagatc atttctgatg   2400
```

```
gtaaaagaaa gtagcctagg gggatctgag aaggcctctg gggaggcgac atttgacctg   2460
agacttaaga atgaggagct ggcaaagacc tggctgatca gtgttctagg aacaagtaac   2520
agcaagggca agggccctga ggcaggacag agctattaat aggaggcctc tgggctggtg   2580
agagaaaggg aaggggccca gttgggtagt gggcagggga ggagtttgga tcttattctc   2640
cgtgagatgt gctggttctg ggtagtgggg ggggcctgtt ctcctgttac aattgggggt   2700
ggggacagcc agagccaaag gtcttccccc acagctccgg cagtcccagc ccagaggcgc   2760
cggcctggcg gctggaagat tgcactgtgg gcacatctgg ggagcagctg ccgagccagg   2820
gccagagtgg gtcacgtggc acgggcagga ccgtcctgga gcctacaagg ccaagactcc   2880
taggaggggc agtggagaac actctggacg agaacacgtc aacgaggagg aactgtgcac   2940
tgtagacgtc caggcaacgg ccccctgcac cccacacagg gacagaatgc cacctcccag   3000
ctttgtgatc tgaaacaagt c                                              3021
```

<210> SEQ ID NO 68
<211> LENGTH: 2909
<212> TYPE: DNA
<213> ORGANISM: Homo sapiens

<400> SEQUENCE: 68

```
acctttctgg gccctgtttg ttcctctgga tacaatacag atgtaatcag gcttcctggg     60
ccccatgtct gccctggagg tcagttgcct gcattgtcac atgctaaaat cccctatgat    120
tccaaaggct ttgaataaca gtgttggttt ttactgaaga ttcggggggg aggttgggtt    180
atatcaccag caaaacatcc ttaaagattt cttgaaaact tccccgcaaa taccctttt     240
ttttttagtg ttatatagag agagatgagt actttttttgc tctcaaaggg cctctcagct   300
ctatttttaa taattgtatg attttataaa tttaattcat agcaatgtct ccttccaaga    360
cactgataat cattataata agcatttatt atactcacag tgcctcttaa atcctcacaa    420
tccagtaaac tataggtact atttcccttt tctctataaa acatttagat ctgtgacttg    480
ctcaagtcaa acagctgcca ggtggcagat ccaacattga gacctagtcc tgcctgactt    540
tggatgctgt gctttttagc ccctgtgctc actgcaccgc cccgtccctc ctgtcggccc    600
ttacccaaaa gtgtcgtatc tctgggaata ttaacaaagt tagaccattt ttgctctgaa    660
gatttttgcc ctctgctgaa gtacaattgg aatcagtttg aacaaatcat gtttccacca    720
accaacatct atggtgcact tggcactata acaatgctgt tgattcatta tttaaaattt    780
ttaaggttga gataatagaa acccaactta aaaaaaataa ttttgattca gataaacaaa    840
gtctaggtct caacccaatt caaagcctgt agattcagct caaataataa ctcctattcc    900
tcctcttttt tcctggccct gctcttctct tcctgtcttc attctgtatg catcaccaaa    960
agcctcaggt tcacatctcc caactcagca accccaaaga acagagaatg aatgcctctc   1020
tcgatactca tttatctttg attagctctg cccaagtccc atggaccaat cattatggac   1080
tgtgattgat agccccatca atgccatatg gggtagggga gaaattaccc aaagaaccca   1140
aaagagaaga ataggaaagt gtgtgggaga agccaaagaa tagatgcaac catctaccac   1200
ctggtctctg ccatcaaatt agttgaggac atggatacat gaaccaaaag ataatgtgaa   1260
gaagcataca cttgcccaat ggttggcacc ctgtaatgag aagccttctg aagatcgccc   1320
ccagaggcct tctagcctgc agttcttgtt tggcttcctt ctcatcccca cgccaccact   1380
caccagtttc ctgtgagcgt ttcttagtgt caaccccagt aatggtggca ggaacaggag   1440
agaggcccag cagacaaaat ggtaaagctg ggagattccc actcgcatgg cagcaaatga   1500
```

tcttttcatc agagcaagca gagtaaacag gagctggcca tttggtgaaa cacgtagcgt 1560
aagacccaag aaaggaataa gaaagagcca agaggaaagt agagaaaaaa ttaatttgaa 1620
atgaaactag tttttgctgg acatgtagag taatagtaca gcctttcttt aatggaaaaa 1680
ctccattcat tatgcttaga gagtcacttg gcctctcaac atgctttaaa gtcatgggct 1740
taataaagtc cagactcgga gtctcttagt tttcttttta tgtatttcat gtatatttca 1800
tgcctcctgt cagttataat ttttttaaac aaagttttct taaaagactg cctttagtga 1860
gaactcctag aaggatttat aaaccaccag gttttctgtt tctgtcctaa aaacactgga 1920
gtaagtggca acaggtcttt ggggagctgc ccatacattc ttcatatcaa cgtggctaga 1980
gtgatctgat ttgagcaaca gaagtcattg aattcttaga agcatcagtg atttttgtgg 2040
aggctctaac ttggtatcaa tcttgacaat tgtgatttag aatgtcacgg tttttatgaa 2100
tttgttgaca taattaaagt atccaagggc taccacatga atccttgttt tcttagggac 2160
tgaaagaaag agtcgtgatt atataagata tattccagtt ctgaaaagga aacgagtcag 2220
taacaatgga aggatttcct tacttttctg ctactgttct ggagagcggc acagtccaga 2280
tttgtttaac caaacctgtt aactttttca taaatttact ggattgtaaa taggagttaa 2340
tttactccct atccaaatta tatattaaat attttggaat actaaggctc tggctttacc 2400
attgataatt ttgattaaaa aaaaaaagac acaccttgat tttgtttgat gtgctgtgct 2460
tctttgacac tagcagtgga ctatttgctt atcaatggaa ttcaaaagaa aaatgacata 2520
attttatttt tggggaaact cagtcttatt tcctttcttg tgtgattctc caaggaaaaa 2580
tggagaccag aaatttggtt aaaatataac ttataactgg caacccacaa ctcattattt 2640
tccatacttc aggtatgttt tgttctactc ttaaggggaa aaaaacaacc tatgtaaact 2700
aaaattcagt aacccagaat tcatcaagtt ctctgttatc tagaggcact tagcagaatg 2760
gtttaatacc tggaccctgg ggtcaggctg cctgggttca aattctgtct tgccaggcca 2820
ctgcacttca ctgtgcctca gttgtttcat ttgtaaggtt aggattatag ttgtaacatc 2880
tttatagggt tgttttgaag atgaaagag 2909

<210> SEQ ID NO 69
<211> LENGTH: 4306
<212> TYPE: DNA
<213> ORGANISM: Homo sapiens

<400> SEQUENCE: 69
ggatgggggt catgttgctt cacgcaggcc aggatggccc tgagatgcct ctatgggcac 60
cgcctccact ctccagccag tctgcccgct gcactcctac tccgaggtga ggtcccccag 120
tggcatccct cctgctacac ctgtgactcc tcagtgtcca cgtggccctg aagcctttgc 180
ggaggaaacg tgaattgcat caggaatgaa agaaacgttg tcacccactt cacgaatctc 240
ccgagccagc gttggggcca cagggccact gactccagga gaacaagggt ctctgccttg 300
tgtagggggg tcatgctgtc attccccaac ccgtggggca aatagggact ctcaatgggg 360
agacagcacc ccccccttgca aagtggccca ggcctggtga gggccgtggc tgtcccaggt 420
ggacaagtca gggagaaaca cagcactcca ggcacccgag ggtgcttctg gggcctcagg 480
aggagctggg ctgtgggtgg ccgggcccca ggcccatccc gctgagggca gcattccggg 540
taggcccagc aggtgcggcc acagacagct gagcttcccg ggatgcttgt ggcgtgaagt 600
cagctgccca acccggccac tggccgcacc ccggctattt ttggatcctg cagctcagag 660

-continued

```
cctgccttgc tgctcccgcc cctggagctc ctggaagtct ggtcagagtg tggacaatgc    720
ccctcttgtc atacatctgc cccttcccca cagcccccac gggccaccct cctcccccag    780
acacagctgg tcctggctgg gctggggtgg gctgcctggc tggaggaggc tggccttgga    840
ccgggccctg gcatcacggc aaagctggga ctcagggagt cggaggcgag aggctgccag    900
ggttgtcctg ggccgtgtct gtgtcagctc gtgtccctcc aggataagtg gcaaggcaca    960
cctctctctg gcagagaggg ctctggaagg ttttcccagg gtcctcctcc ctcaagtcct   1020
cccatgccct gaggctggtc cctgagggtt ggtcggggac tccagtcctt gctgctcaga   1080
aaagcatgcc cagtgtccct cgccctgccc agtgtacgtc caaggctgct gaaaatggag   1140
aattccttta cttctgcctt cattccttgg acagatatta aaacctggtg tccaggggta   1200
aatcaggtct ggttccaact tcaaacaggc agccctgacc gtgcagcccg accttggact   1260
gggtaccgtg accttggagc aggcagccct gacctggagg catgcagctc ctgcagaacc   1320
agatgtgggt gggggggccc atagtcacct ctttgttggg ctggggaggt gggttcccag   1380
cttcggacca ggtgaatggg ggatgcaagc gtgggtgggg caggtgaagc aggaagggca   1440
gggacaggtc agatgacttt agcatcacgg cggtgggacc cgctgtggtg ttctgagtca   1500
ggaagtttgg ttgcagacaa gggtcaggag agaggtgccg agggcatgaa aggaggtgtg   1560
ggaggttatt agggagacat ttaagtcgat caatcgtgag ccacctgtgc ctggatccta   1620
cctgtcagaa cgcctgagtg gccccacgtt ccagcctaga gacaatgctg aagactctgc   1680
ccgtggagtg gcctgaccct gggcacaagg tgatgggcag agcagccagg gttgcctgtg   1740
cccagcctgt tgtgcagcag tgggggacag agaatgctcg ctgcagggga aacaggcctg   1800
cccccaggct ctgccctggg gcccctgagc ttactctgtc cccaggctct agctcacccg   1860
gctctgcctg tcttggctgt tataacaaaa ccatagacct ggtggtgtag aaacaatgta   1920
tctctctttg gtcgcgaagt ccaagatgaa ggtgctggac tgtgtctggt gagggccgct   1980
ttccatagac agtgcggcct cttttctaag ggcaccagtc ccattcacgg gctccactct   2040
cacaacctaa tcacctccta aaggctcaca atattactgc actgggggac aggtcaacat   2100
gtgcattttg ggggaacaca catttcgacc atcacacctc cgtaacagcc aaccccgagg   2160
tccagcctag gtggctctgg gagttggtgg ccggaggtcc acagagcagc ttggggctgt   2220
gcccagctgg gccccttcca ggcctccagg tgcggccaca cccatgtttc ggaggctggg   2280
gacacagcgg tggctctcca ctctagcaag cgtgcagcac ccgccagcag gatcctctgg   2340
ctgcagaaat gcgtaagaag aggcgtccgc gggacccagg ccggatgccc gtggagaggg   2400
aggagccaag gggctccgc agtggaaagc agtgggagcc tcccatgggt tctctgctgg   2460
gctgcatcac cccaaccctc tcaggagggg aagccctgag ccccccttgg ggttgattgt   2520
ggcagatgtc aggggctgtg accaaaagga tgcctgggcc aggtagagaa acctgggaga   2580
tggccccgtc tgaggcacag cgcacggtgt cttcatcctc ctgtgtggac tctctgggtt   2640
catggaggag ccctgactta gggctggggt taaatgtgcc ccccaacccc tcccttcacc   2700
cctgacccac cttggccttg gggaggagaa gaaacaccct acaggaagat gaggaaaacc   2760
tgtccccaca ggctgctggc tgataccccc gacttaggac gagcctgggt tggggagccg   2820
tcctgccctt cccggctgtc atggaatgtc aggtttctgg gagcctctgc ttcctgctgc   2880
aggctctgcc tctgagttca ggaaggagac aggccccctg gtcatgctgc caggaccaca   2940
tggctcagct tgctgggccc ggggagggta gaggctggcc atctttgctg tttggtacct   3000
ccttgtcagc ccgtggtggg ggcccagggt atggcgaggg tgggaggctt ctaggtcctg   3060
```

ggggtcagga tgaagggagc ccggggagca gctcttggcc ctggtgggtc tgggctccaa 3120
gttgtggtca gaggtgacag ggtgtcctcg ggcctgtggt cagtgccgct gggcctcatg 3180
gaggtggcgt cttggatgac aggagagagc tttttagggc tcagattagc ctgtgagacc 3240
aaaaccaggt tcagtttcca aataacactc aagagacctg ggcttagcat tggcccccca 3300
gctttgcagg agaggggtgg gtgcccacgg ggaatcaagg ccctgcgacc caagcccgcc 3360
aggctcagca ctgaggaggg aggcgggccc caagactgtg cagtctcgag gcgtccaagc 3420
cacagggcgg agcggcggga gcgcagccga gagtgcctcc tttatgcttg ggccaggcgg 3480
ggccacgggc ctgcagccat aaagttgggc tgtggatgtg ccccagatcc tgctggtgga 3540
gcccaagacg ccgctgcccc cacactccgg agcttccgcc cggcccagac atccgtgtgc 3600
agtgtgggag ctgaggaggg gccccccagg atgctgtgtg gggtacacac agcaggaggg 3660
ggcagggcag gacgcagttt cccttcaggt tggggtcctg accaggggac agagccgcac 3720
tgtctcccca ggcctgcttg gggacaaagg ccatggatgg gtcttaggaa gtggcttcag 3780
ggctggactc ctcttttccc gttttcccaa ataaggtgtt cccagttccc tgggagaatg 3840
agtgagggct ggggatggct gactttgtgg tgaaggtgca gagagtagat tggggttctc 3900
tttgatcccc tacaaagaag ggacgcccgt ggtgtgcttg tagtgagatt tggccctccg 3960
ccccaaggca gcagcgcggg agtgcggggc tgggtcctac ccaattaccc accaccaggc 4020
tggcgagccc aggagcctcc agagagcggc gaggtggttc tgtttcgacc gcaggccagc 4080
ttctcctggc tttgctttgg aggcgcccag aggggtggct gaagggggc tggcacagca 4140 ttcttggggt gcctgggggc ttggaggttc tgagcctggg ccgggccgga gactcaagtc 4200
cggctgaggt tatcagcaag gtctctgaaa gctgacagag cagagcaagg atacgcctga 4260
cgctgtgcaa ggtttgcaga gtcgctcagc ctctctgggc ccactt 4306

<210> SEQ ID NO 70
<211> LENGTH: 3237
<212> TYPE: DNA
<213> ORGANISM: Homo sapiens

<400> SEQUENCE: 70
gatccaaacc gaggaagtgg gaggccgcgc acagcctgtg gtttgtgcag caccctctgc 60
cctgttctta aagtaagaaa ctgatgtctc taggagccct ggtcaactgg aattggggac 120
ttggggtttg gttgagcctg ctaggccatc tgaacccaca gcaagctgat gatagactgc 180
aggaaaagct ccgtccttca ccagccccat tccatgacgc actcaacgac cctgcctcca 240
aggaacaagc ttgcagatac taatcagggc tgaggccctg ccactcaata attacccact 300
gtctcatcat aatcccggaa ctaagcccct gcccaatcca tctgggaccc ttttccatct 360
attgcacagc tcaagaatac gtgtgtaagc tattacctct ggttgtgcta tctgtcccct 420
gagtatagat tcatggcagt gaccaattag gttgccgtgt tctttttccc cctttgcttc 480
caattcatcc tgtacttctc agcactggta atgaagcaga ttcatcgggt gcagaaatcc 540
actcacctct aaaagctgtc tcatatgatg cctaatattg taggatactt taaaaagagg 600
caagatcata cctctgtatt ctgaggcttc tttaagccac tctcgacctg ccactgcctt 660
ctgccaggaa caaatcacac atggaggaaa atattcctga ccctaatcca gaaatcaaac 720
agctgagaag tgaagagggc aaatgtgggg ataattgaat cctgcatccc tgaatgagaa 780
cccagtatca tgccaagggt gaaatccaag acacgtatgt ggaaactcag gttctgctgt 840

```
tggccggcca gtccctcaac ctcttaaaga ttccattttt gccctcgcta aaacagcgtc    900
tgcttcagtt gctctgaaag ttaactgaga cattccatgt aaagcactca actttacaaa    960
tgataaaaaa agttagctac ccctaccatt ttctgaattc ctatagccaa aaccaaaaaa   1020
gttagctctt gatcaaattg tgctgactat tttgtgtgta tacaattcat cttccccaaa   1080
aacatataca ttcctgaagg gtaaaattca catcttgttc ttttgtattt cctacaggtg   1140
accatttata aatgcttact cattcctgta tttgaacata agaacacatc ataaacaatt   1200
ttgaaggtga cagggacaag tagttagtta taattctcaa ataaagaaat tagataagga   1260
tgggtttcgt tacagttagt tgtagaattg cagaaactgc atggggccca ctggtcaaga   1320
aaacctacct gaaacggcag gggctgtttt cagtgtacac tgtcagggca caggcccagc   1380
tcttaattag caggacccca tttcagatct ttgctgatac tgacagggtt ttaattagtt   1440
aaatctacaa gttggctctt gttctctggc agagaggaaa atatgctaac atgttccaaa   1500
acaccccttc caggctttga ggaagtaccc tgaagaagga ccaccctttg gaatttatac   1560
cagcagccct gacagctgtt ttgtatttat ttctacggtt gggccatttc aatttggggc   1620
ttttattcat tatataagca aatatttgtt aaaggatcag gcacggatga ggtatgtttg   1680
tcaggattgt aattaaggtg gtgtgtatac cagggttgca agaggacaga ggggttgggt   1740
cttcaaccca ctgtgtgtta ctttgaaaga ctcacagacc tctctgggcc acatctggcc   1800
cacatgctga tgcatgtaca gtcctcattc ctactgtcct aaaaggtaga gagaaataat   1860
taatttggat aaaacatttt aaggccctaa tacattagct tttggcaaat tatttgcctg   1920
cagtgtatac taacgccctt ttatttttca gattgtcctt ttcaaagtga atgatgttat   1980
caatgagtac tttgctgaag acataattat ttctctgaac agtttcctga tttgccagtt   2040
gttgcccccct gaggaaaacc agcctcagaa gtgtggcact cacttctcag ctcccctggg   2100
catcctgcat cccccagcat tacttgtaaa tatttcaaat tcttgccaca cgagaacacg   2160
tagcatattc acacatacag tattgactct cttataggtc aactccttca tttcgtttaa   2220
tagctttcat cttggaaact gtaaaattca tcagttggct cctctcctcc aagtaggatg   2280
tgtctacctt gataaggtgg ggaaactgag gctgtgtagt tacaagtctt tccagggagt   2340
cagcctcttt cttatgagga gttggaatgc ctgaatccca gccaggcccc cacactagag   2400
ttctccatga cctttgcgct ctacatcaaa cacacctgtg gcttctgtaa tgtgaccttc   2460
cccctcctcc tggacctccg actccttaat cctccatcag tttctttcca aatttaagcc   2520
ctccagaact tgctctttct agtgtcctta gtatcatccc tgtatagaac ttggaagctc   2580
cttctccagt ccggcccatg ccctggctct gattcttaga tgtctgtgcc tggaaaaagc   2640
ctatctcctt aagttccata tggccccaaa taagcccatt aatgcctctc cccaggaacg   2700
tatttcctct tccaaacaac agtattttac ttccagcagt ggcgccacac aatttgacac   2760
ttccccttc tctaattgct tactttgtgt gtctgttttg cctcctgact agactgcaaa   2820
tctttgaggg aggaggttcc tggagcagga ggcccccgga gagtccctaa taagtgccaa   2880
atgcaaaaag gttgaagtca ccagttgaga aaatccacat aaaatacact tttggcctgt   2940
ataaaatcag catgatgttt tctcctgaga ggttcacagc atataatttt agttcctatt   3000
ctccccaatg ctcaggttac tccaggaagc aatttggggt gagagaaaag caaggccctg   3060
ctgaattagg gaaaaaatgc tctaaaatat ctccacagga aaacttagtt ccacctgact   3120
gaacattccc aacaggcaag gtggaaatac ctcgttaagg gactgcaaat caagcagtgg   3180
gttcaaatcc aacattagct gcttatggtc tgtgcaccct tgagaaaatc acttaac      3237
```

<210> SEQ ID NO 71
<211> LENGTH: 2130
<212> TYPE: DNA
<213> ORGANISM: Homo sapiens

<400> SEQUENCE: 71
cgcaacagca ggtcctctct ctgtgagaca gctatgtcct cctgaagtat agctttgaca 60
gctgatacct ggcatttgca aggtaaagcc agtgttaatt aatgaggcat attttcaact 120
ctctgttaac taaaagtcat catattcaaa aatggtcatg atgactcgcc aggaggagag 180
ccagaaggta agtttgggca ttttctccct tgaccctgct cctctcatga caaacagcct 240
caagtttgag aaagctggtg aaggttggga gaattatcca cttggtatgg atggaattgt 300
ttttctgggc ttagggaatg gtgccttcat tagcaccaca ttcttgtcaa aagagctaac 360
tctctaccat ctatattaat tttgatttta cagagatact cagaaaagat ttctgtaaat 420
agcctaatca taatatcaac aaacatgctt ttaaaaaaaa tcttagaaac aatagtccat 480
tcgcctagta attagttaac acccaagcat gccttcaaag gaaagcatga caaaatgact 540
actttctaga aaacctatca gccttgtaat ttcagttgtt catttgcttt caggttgaaa 600
tatatatatc ttaaatgtca gtgatatctt ccatagatgc ttacccagtt gaccagatat 660
gcagccatga atgtggaatt cactaagctt gaaatcctgt tttcaggcta cacactagat 720
tttctaggtc ttgacactgt ttcctttcat ctcttttaat catgccctaa attcctccag 780
caccatggga ccagccaaaa tacaggtatc tatccaaaaa ttttaacttt gtgcaaaggg 840
ctctggaaat ttaagttaac ccactgcctc cacttttctc tccaacggaa accagaacca 900
aatactaaca ttctctccag aaaaaataag gaaataaatg tgcaggaagc ttaggataat 960
attgtcacat tgagaatctg tcccattcta gtggggtact cagaaaataa acaaaatgca 1020
tctcatgaag ggaataaaat ctgaatcaga acagagacat atgatggtgc taaagaccag 1080
agccagcata acccatgctt tacgggatct agcattcaaa tcattttggt tagccctgtg 1140
gactgtgcct cccctccccc aaaattcata tgttgaagcc ctgatcctca atgtggttgt 1200
atttggatgg tttctcttct ggtgaacttc aaacaccttc tccttggccc tttccctaaa 1260
cctttctctg ctggaccacc agagcaagct ttctgagttc atactctatc gcattgcagg 1320
cttctattct gtttacagtg aatgctcctt gcatgtatta aatcattgaa acatctcaac 1380
aaaggccata ttcttatcga tttgttaagg tgagccaaag gaagcctcct tatttacctc 1440
tgtgtttctt cttcacccct ctcccacctt cttctccacc tatcacaacc accaccacga 1500
gccttaaaac gttcaggatt cccaccctgg gcctgacacc acacgcccga caggccttcc 1560
atggctggca ggcaggcccc aaagagaaca gatctccagc tgcatccaat tgcttgcagc 1620
ttccccaaca agctgcattc ttctgccttt tcacatgtaa attcctctta aatgtctgtg 1680
cctaaacctc atcgccgctt ggcacctggt gaattccgct ccttcttaga aattcggcat 1740
aagcattgct ccctccaaaa gccttctctg acgcctgtag gcctcaccac attcatatcc 1800
atgttacgga acttagcaca ctgcaacact acccttgaat atctttctcc aaaggggaag 1860
ggctacagtt ctatttatct ttagattccc agtgcctgac acatactagg tttttgaaag 1920
caataaataa atgaagaaca tgaagggcaa acacaagggg acagctgtgg agtgtataat 1980
acccatatta attgggtttt attaactaca gaaatgattc taacttttgt aactccagaa 2040
cctctttagt tatcacattt cttggttata catgtagaca tgcatgtgaa atttttattc 2100
cgtaaaccat acttgattag acaaataatg 2130

<210> SEQ ID NO 72
<211> LENGTH: 4564
<212> TYPE: DNA
<213> ORGANISM: Homo sapiens

<400> SEQUENCE: 72
tggaggtcat ccaggcctgt gcctggtagg accccaacat ttaccactgg tctgggcaaa 60
ttgctgcttc ccagaagtgg ctttaccaag acaagacctc acttaggtcc caagtgaggt 120
tagccctctt tttatcatga cccaagccca ggaagggagg acacagggcc tattacatta 180
tgtctggaaa gttggagggt atccagtcgt gttgcataac ctgtgagagg ccacggccac 240
atcccaagaa ggatcccaaa gatgagcttc acccaccaat gctcctgaga tggccaaagg 300
caggctcttt actccagaaa ccagacagga ggcataggga gagagagatt tgagtattaa 360
atcctgggct gagacggtgg gacctagtgc cagctctccc atggagtgac cttaacaccc 420
cgtttcatgc accaagcctc agcttcctca tggacaatgg acttgcaaac cctgtaaagt 480
ttttgttaag ctccagcaag acaggtatga gaagtgtgca gtgggaagac acaatgcgag 540
ctattgttag tgtctgggag gtggcatgag gagtatgcca ggctggcagg aaatgtgggg 600
gacctggcac ctatgattcc agagagtgtg cccaggagct aggtgtctaa ataagcaaat 660
gcaggcctcc ctgatggaca gtcatgcacc ccgaaggtct gagtgggtag ttatgggcac 720
cccaggtttc tggaccagca gcccttggag ctggaagcag aatagagaca gagtctggtc 780
agggttgggg tgggctgttg tgaagctgca ttgtgcattt gctgtgggaa tgctggcagt 840
cacatgcctt ctattgcctg cccggctggg taaaactgag cttctgtgcc tttaaaattg 900
tttgacatct ttgagattgg aaacagagct ccccagtgga aggccagcag tagctatgga 960
atgctattct aatacaaaac ttactctcgg tgtttaaact gataatccca ctggcaggct 1020
ttggagcgaa atcacctatt atggaaaagg ccccgattct ctgggctgat ctttgcccat 1080
gtgggctagt gagaatagag ctgttttccc tctcaggcta agccccatct cccaccctca 1140
gctgacgaga caaccctgag attctagtcc ggatacagga ctgagagctc agggctggcg 1200
gggagtcccc atggtgtttt gctctaagac actcgctagc ccaacccctt aggggtgcct 1260
gggctggcgg acaggtctcc attccaggct gcctccctcc ccagaccata atgtcaggat 1320
gcgggtttcg cagagcctgg gtactgcagt ttagtcagct cccggttcct tcctcccact 1380
gcggggaccc ttgtgaccgc ctggggactc tccagctaat ccctcctggg cggccctccc 1440
atggtcaagt cctctgttcc aacggagctc tggaggcaga gagagcaggg ttaaatcctg 1500
gtctgcaaga ttacttaggg caagttctta ggcctttctg atctttagtt tcttcccctg 1560
tcaaatgggt atagtaatca cacacatttc aggttaagag aatgaaatga gctagactag 1620
aatcaacagc ctagcacggt ggctctcaaa gtgtggtcca ggagtccgca agaccctttc 1680
agggtagctt tgaggtcaac actgttttca tgaaaataaa gatgttattt gtctttttaa 1740
atcataaaaa catgttactg aaaaacattt tccaaaatta cattgccttg agtcaaaagg 1800
ttagtgatat catcaaaaag tgaacaacta cttagtaatg taaatgaacg ttgacttgtg 1860
cctaagacag tccttggaac gtagaaaatg ccatatgagt tttgggaacc atttgaaatt 1920
ggcatgaagt ctttattcac ctaaacctct gaaaagcact gctctaggag cagagaaaaa 1980
gggggattgt acacatgact gggaaatgcc tgcaatatgg tcactgcaaa ggctgaatat 2040
taaattgtga ttatataaaa gtataggatc tggaaataaa acctggaagt gaaatattga 2100

```
ccaaaagaat tctaatgagg gtttctagat ttaaaagcta agcatcaatc taacttagct   2160
gttatttact aataaatccc tactttactc caagaatcta agaggcttag aagctggttt   2220
gtgcacagct gaggccaatc tgagaggcta cgggcctttg ttcttccatc gcctcaaggg   2280
ccagacctgg aaaaagagag agggtttctc cagtgctggc ctgcctcgga actacctggt   2340
gcttaggaac aagagtggtg actgggccca ctctggcacc tgctgagtca tagtctctgt   2400
ggttgaggtg ccagattcat atttttctga aactccttgg gattcatcag caggttacat   2460
tttgccaggg ttaacaccca tttcctcggg tgaggatgtg gttggggagg agggcatggg   2520
tgctcatcac agccctgtac ctgccgtggg aagatgtgat tagggacaac ctcctgtcca   2580
tccaaagctt cattgtcaaa aacacagcag ttctgagtca ttaatgtgac ttaggtcttc   2640
aaagtttcgt aatcattttg ctggcttggc ccgaaagtgg cacatgttcc tctggtgcca   2700
gtgtttgcta gaaagaaagc tgagggcttt tacatttttc acctgccacg cctccagggg   2760
ctgagggttc ccttatatca gaagccagag caatcactga cccagtccta ttatgtccac   2820
tcttggtgat ggcaaaaatt ctgtgaggtt gaagagagag aattgttctc ccaattaaaa   2880
aacagaaccc ctaacaccct aaatgctctg ctctgttcag tagcccaggc tacctttgag   2940
aatctactcc agccacctcc tcctcagtcc taccctccga cccgccctga ggctggagtc   3000
ctgctggcac ttggcattga gacgggcttc tccagggtct gagatcttgg agggaagaac   3060
cgttgcccat agatcaggga gctgagagga caccagcccc ccgtctccct tcctgctttt   3120
ccaaatgcct ctgcaacacc agggtgctgg gcgcatggga ctgagggcct ccctctgggc   3180
cccttctcac cctgggctac ccaagtcttg gacccctgtg gaacatggtc agccttctga   3240
tgagtccaga agcatttctc caacatagtt gtgagcttaa gggaattaaa cttctctttc   3300
taagctgcag atttcctgag gcccaaacag gcaggaggct ctgaatatgg ccgcaagagc   3360
tcaggctgtt actgcccctc ctaggtgcca gccccaggca gggttttccg cccaccccc    3420
aggtcagcct ggcatagagg gtctgggggc ttctcccctt ggggaaggca gcagaagcaa   3480
ttgtgctctg cttggggtga aggtgttcag ataaaaatgc ctggtggagt atctcggaac   3540
cacagaacta cctgtgaacg ctgtggtgct gtggtctgaa aacagggttt tggagacatc   3600
agtgggaata aatctgtgac tgcatgatac agaacaagct cctcactcag tggtctcaga   3660
atgtcttctt cttcccccag acatgtgcag acttggcctc tcctccccac cagcccctat   3720
gtccctactc gcccaggagc cccagcaca tcccaggttc tgccatatgc acacactgcc    3780
cccagctcct ctccctgtgt ctgcctgctt aatatctatc ccactagcca ggtctgactg   3840
aggttctccc tatgctcttg atttaaaaaa aaaaaaaaag ctttggaaac aaaaatttca   3900
atccctttgc cactcactag ctgatcttaa catagtggtt gggagatccc cgttctgcta   3960
gctgtgtggc cttgggcaag ttacctacct ctctgtgcct cagccttgct ggctgtgagg   4020
attaaataaa ggtgacgtgt ctgtagctaa cttagagatg cgcggctccc ccatcctatc   4080
tggcagcagc ccctcccact acagcatctc ccactgggca gctctgggaa ccgaacatca   4140
tgcattttcc tgatctcctc cctccctgac actcctggct ccggcctcag ggaattgttc   4200
acctccttaa gcaactgcct cttcaaaccc aggccagtgc ggttcctgca gcctggagtg   4260
ccaccccttc tctgctgggg aactcctatt tataggagtc gggcaaatgt cctcctcttg   4320
gaaatccttc ccagcttcag ggctctgccc tttactccca caccccttggg tcaatgtttg  4380
ccctccctgg actgtgacct cctccaggaa ttaggctcgg gccccagagt cctacacaca   4440
```

gcaggggctg gggctctaag ttaaggtcgt agttgatggg tcagcctgat tgagctgcgt 4500
gtgcagagga tctgaactcc tgcagacacc acttctgcat gagtcttggt ttgccgctct 4560
gcaa 4564

<210> SEQ ID NO 73
<211> LENGTH: 3037
<212> TYPE: DNA
<213> ORGANISM: Homo sapiens

<400> SEQUENCE: 73
atcatcaagt ctccacaata ccagttcctt aaaggagaat gtttttgttc caactgaaac 60
caaaatattt tagtgaattt tgtcttcagt attacttcct tcctattcta atactgtggt 120
caaaagtata acttttggca aactctttca tagcggaatc tgcttagttt gcgaatttga 180
agttagctgt tgtctttact ctttatgtag gttggatgtg cctggctagg ttattgctga 240
ggataagaag ctggcactgg aatggtaaag tgccactggc ccttttttggg tatgtggtgc 300 ccagacctga gctgctattt agtctgagag gaaggcacaa agagatcagt gatttataga 360
ccctctgtag gaaaagaaaa aaaagcaaaa caaaaaagtc caataaactt aagatacttt 420
tccatcagca gctggttttg ccggaaatat ttcttgtatt gaatccagct ttagaaattc 480
ctcctgtagt ctgaagacct gtcatcaggt caatggatac tatacccttt ctaggtacta 540
gcatctctag ggttggtact ccccaaactg cctttactgg tgcaaggtca ttctgtgggc 600
aggcttaccc aaaggagttc atgaagtaga tagagctcca caggacgcca cggactggga 660
gtatagagtg tcctttcttc acagcttcac tgtctaattg attatttctt tatgtactct 720
ctatttccag tggggtactt gggattcttg ttctttgtga tcccagactt actgactttt 780
ctagatgagc cagattatat tgacatgctg acaaggacag ctcacagaat gatgggtgaa 840
tatatttccc ttcccacaga gtaaattttc tagatttgcc caaatatatt gtaaaaattt 900
gttctttctc tggtaaagat tctaccacag tctcaaacaa tgcatcaaat aaacacatat 960
tagtattgtc tatagcatat ataaagtata aatcttgtga gaaagttatc agagaaatcg 1020
acattttatt tgtctccata gagtctgtgt tttaatgggg gagtcaggga aagtctaaat 1080
gaaggttttt ttttcaatgt atatgatcct gttttgaatg ttctactgtt gtggggagta 1140
gaaagtctct accaaacttc acagagatct gcaatacttt tactatttca tatttctagg 1200
gcagcatcta cctcatgtga ttttattcta tttaatataa gtgattttta gaatctatac 1260
caatgcaact tggttacgta gtttttcatg caaataaaaa ataaaacaac aacacacctt 1320
tgatggaagt tctggtattt ggttctgaaa aaatgatctt gtggattcag atccctttga 1380
gtttcatggg tttttgaaaa gtattactga gacaaggaag ccagaatagt ttgggcatct 1440
gacagcctct gaggtggtga ggacaatgct ttcctatttg cagtttgtga cctctgtacc 1500
acaaatagtg ggcctgtcag cctttcatct gtcagagtgg atggaggaca acgttccagt 1560
gaccctgcaa ttgtttatcc ccggcccctg cttcctctcc tctctgactg gttaactttc 1620
tcacctgtga cactgaaagc tgggtagtac agggatggag caaggcgtta ttgaattccc 1680
cgccagtcaa agggagatgc aagaaagcct ctgctctatt ttcttttaaa ggagattgaa 1740
gagaacgttt gtgtcatgtg tcatgatgtg aatttggcgt ctaaactgag aagcagagag 1800
ttcattgttc atctttgtgc ttcgggctga caattcttta ggtggttttg ccctttgtct 1860
agaagagtaa tgttacacgt ggagctcaaa ggaattttcc tgcttactat ttaatagtac 1920
aaataataac tttaatgtca tacagaaaag acacttccct ggagtgggag aagagaggat 1980

-continued

```
ggggcagact gagtgtttga atcgctctag atcagagttg cagttttgtg gtttctcctt   2040

tggttcataa gctgtatttg ctacaaaaca ttttagaaat cttagcataa aacatcctct   2100

attgcctcag agtcgtctcg aaataatttc ccttaattag gtctaatgga ctgtctcatg   2160

aatctccatt tggtctgaca gaggtaatta gccatgaaca attgtacttg gccgttttta   2220

attagaccag ttttattttt acagctgcca attgaagaaa cctaaagact ttactgatcg   2280

tatctatttt ttttttttta aaacatctat ttaaatattt tatctctgta gcagacaatt   2340

ttgcttatct aattccagat tcctacagct tcttcttcct gattgccacc tccctctcca   2400

tggaagattc tgacacgtct aagccaattt taatagtttc atttgcttgt tgctgattgg   2460

tttaggaatg gaaatgtgac atagttccag ccagtgggat ctgaggagag ctcacctggg   2520

aagctcctga gatggtttct ttgctgataa aaatgagtta caggaaaaat catccagtaa   2580

tgtctgcgtc tgtgacagac catgtgacag acttaaactc agagtaacca gctgggcacc   2640

ccagggggca gagctgaaag aagaaaataa cctggctcat tgataattgt tgagccccgg   2700

tttacccact tgaagctggt ctgcttcttg caatctgaga tacatgttct ttgtggtctg   2760

gccccactaa gtcaggattt tctgttactt ggatctggaa atgaatacca tctggattat   2820

gttccttaga aaggtaacta ctgccactgt atatccttgg actgtattga gctttaccat   2880

ggggtttcca gcctgagagc cagctgtgag ttagcagatt ctgcctcatc ctcttctaaa   2940

tcatttgcct catgttcttt ggagtaaatt cctatctcag gccagtcatc ttctacaggg   3000

attattggtg ttggcatgtg ggggaaacag actctta                            3037
```

```
<210> SEQ ID NO 74
<211> LENGTH: 2495
<212> TYPE: DNA
<213> ORGANISM: Homo sapiens

<400> SEQUENCE: 74
```

```
agtgagctag ccagcccagg gataaaagcc atgaattaat gaggcttctg agaatcctca     60

gcaattggac tgaccccctg cctagcttcc cagggtggtt ccaagcaagt gtggcctaag    120

tagctgacag caggaggtgc tgataggagt agtggagttt gccagaagag aagctagaag    180

aaagccttgc taccctaaat agtgacagct ggaaatcacg agggagcatt ctgtttggga    240

gtcatgaccc ttcccgtcac atttctgcat ctggcaggct gttggagaga tctgtgtgac    300

agcctcacct ttcagcacct cagtcacacc agggagacag caggagtgag gaggaaagag    360

agaagagagc ttgcgcctgc ttcctaaact ccttctctct gggtcaggac caggttacag    420

aggtcaccag tcatgtggta acatcctgat gataagctgt gtccatgcat gtgcatatgg    480

gatgctgcca actaatttcc caagagccag gcagataaca taaacgtgtc aaatcagctg    540

gatataaggt gaattggaga atgatgagta ttatgctaac ctggagagct tatactttgc    600

ctaaagtatc tcaaagtttc agtaatatgt ggccaaatat aacaatgtag gcaggattta    660

gcttgtgggc caccagctga tttcacagga gaaattgaca attacttcta aattgcaaaa    720

taaactgaac cccaggtctc taggctgtcg aatgggtgaa aagcaaatca ggagaactat    780

tagagtagca atcagagtga aattaacatg aaccacaaga gaaagccagg caggggaaca    840

ggaaaacatc aagcattttg cttaggaatc agatgaccag tgctgttcaa tatgccagtg    900

tttgtatttc tttccttcaa ggctcctgcc cagcagatat gaagacttgc agttcattgt    960

ttaagaacta ctgtatgata acaatatctc ttgtttttaa atttatacat cccttttttt   1020
```

-continued

```
ttttgtctca ctgtgaaatc ttttcaacat acagagaagt atagatgaga taacgaatac   1080
ttcatcattt ggtcatgttt gcttcagcta tttataaaac tcttcatctt gacataattt   1140
tagattttga aaatcaaata ttaacacctt atgtaaccac agcacaatga tcaaaacgag   1200
gacattaatt tgatacaata ctcttaacta acctgcagac cttactcatg tgtcactaat   1260
tgtccctctt tttttctggg ccaagatcct accttgcacc tgggacagtt cctcaatctt   1320
cttttatttt gtatgacggg atatttttga aaaggactgg cccgtgattt tgtggaatgt   1380
ctctcaattt ggatttgtct agtattttct catgtttaaa ttcaagttat gcatttttag   1440
caataccaca gaagtgattt tgtgcctttt cccatatcag gaagtactca atgtcaacat   1500
gttccattac aaagtgatgt tcacttggat cacttggtta aggtttctcc aatgtaaagt   1560
tactcttttc ctctttgtag ttagtaagta ttaataattt atcattcaga aatacttcga   1620
gaatgcaagt atactgtttt ttattataat tttatgtact aattttaata tccattcttg   1680
cctgcaacaa tctttggtgt ttgccaaaag gtgatttttc tatgccttct ctctgatgta   1740
ttcatttagc cagctattta tttatagctt tatgggctaa tggaatttgc tttataagct   1800
ataacccatt gctatcactg ttttgttatt taaggtgttt cagattgggc caatgtcctg   1860
tgttctttct agatgctcct gtgaacactt cttattcaaa ttttttgtt tcccacggtg   1920
gatgttttta ctgtcctgat gtgggaccta tcaaccctat atatatttcc atccatgact   1980
tcatacattg attacatgtc tatgtatcca taaattacag tagggatttt tgcatatttt   2040
atgactctgg gtaaatgaaa tattataaac acatgtaact agactttcac aaattaatat   2100
cactcaaaag ctcattcatt ttaactgctg tgtcacatac cgttgtagga ttaaacaaat   2160
gtatttattt tttcatcact tgaaacattt tgattgcacc caatttttgc ccttataaac   2220
atgttcttgt aagctatctc ctgaactatt atgttacagt ttcattgggt tatatactta   2280
gaagtataat tactaggcct tagtatgtat gtcttcaatt tcattagatc tcgtctccaa   2340
aatggtttta tttgtactcc taccagtgat acgtgaattt ttgtaggagt gaaatggtat   2400
ttgttgtttt tatctgcatt tccttaatta ttggtgaagc tgagcatctt tcatcctttg   2460
tgcatttctc ctctgtaagc tgttcataat ctttt                               2495
```

<210> SEQ ID NO 75
<211> LENGTH: 2248
<212> TYPE: DNA
<213> ORGANISM: Homo sapiens

<400> SEQUENCE: 75

```
gtaaaaattt cagaattgcc ttacaacaat tttcaaataa cacaccctgg ccactccaca     60
caagagtgca aaggacagag cccttaccta gtggctggca tccttgttgc tgattgctaa    120
cctgtatctc ggctccgtct ctgccacagg atccttcata catgtgtatg gacatcacaa    180
agaaatgcct caggggggta cagtgggcgg cccctggtga gggctttggt actacatgct    240
gatggttttc tgagttgagg ctgcaggtaa gggatggagc ggatcatggt ctttagagag    300
atgcgaagtg acgacagaga cttcgaaggg agtggataaa taagaaataa tctggaccgg    360
atacgtcaga ggtgggtggg ctctggtggg agctggcaga gagaaatcct atctgttggg    420
acatgtgtgc tcaggactgc aggaagatct ctgaggcagg ggagttcaga ggaagcttcc    480
agagctttct ctgactttca cgtagtcact ccggcttgtt ccatgttttg ttagttttca    540
tttcatgaac attttgtaaa tagtgtaata tggtaaatat tgtgaacata gacataggtc    600
ttaactcctt acccacacgc ctattataat actaaagaaa gcatttctct ggcttattca    660
```

```
aggccagcag ttgtgcttgg cataacacac aaaaaatctc attgttgctt ccatgaaaat     720

ggagatttat tagatagagg aatgtgtaaa agtatcagca cttaaatgca tggacagtgt     780

ggtgccattg aagcgattgt gaaacatctg catggaaatt tttggaaaac agacttggct     840

tataaaatcc ttgaattcaa tgtacaaatt catttttctc tagacatatc tagattcccc     900

cagtattcca gaaaaagccc atctcttgaa tgggataaca tatgcaagtg ttttgtaaac     960

ttaaagcact gtaaatagat aaatcattgt tattagtaat aaaattccct aatatcatgc    1020

aataatctaa gtgagaagaa tagggggatg tggatgagaa gcagaggaaa ggaattgcct    1080

ctcgacttgc actttgttgg atgcttgcca ggccggatag gccaccccag agacagaagt    1140

tggcttgtat ttatttgtcc cttaattctg aaaacataaa ccatcacatc aatccatatt    1200

ttctttgtga attttctatt attttaccgt ttttacattc attcattgca caaattcatt    1260

ggggtaaaaa gactttattc cctcttatgg aatttatagc ccaaagatgt aaaaaaaaaa    1320

gtcttatttt taaaaattgg cttatttatt tcttatttac tcactggatt atttttatcc    1380

atctggaatt tattttgttc catcatgtgc caataaccta tgtcaggttt tttaaacact    1440

attttccgaa cactttttgc taactatgga aaaatacaag aacttaagac tatattagat    1500

tttcttgtgt tgagtaattt ctttgggaaa cgagcctgga ctatccaggt ggtgtaatca    1560

caggatactt gaaagggaag agggaggcaa agaggcctca gagacatgcc acgtgggagg    1620

actcagctca gcactctggc tttaaagatg gaggaagaga ctaggagtca agtcacacag    1680

gaggtaaagg cagggacgga ttctctcctg cagcctcgag caacgcagcc ctgccaacgc    1740

ctggatgtta gcctggtgag agccatgccg gatttccagt ctgtaaacca tacggtaata    1800

agcgtgttgt ttttggctag tttgtgtaac ttagtacagc agcaatagga aaccgatatg    1860

taagtgaacg tgcagaggag ctgggttggc gttgagtttg tccactctca ctcccacgtg    1920

ggaaagtact ggttcttccc tgggctggcc tggactgtga gtgaattatc tcctcatatg    1980

ctgtctcctt ccttctaacc ctgagttcag tccaagctca gcagctcaac ccacagccac    2040

acacttacaa acttctcaat ccttctggcc cacttctctg tggttcccaa ttaatttcct    2100

gaaaagaaaa aatcagttct aatacgtaga aatgagcatc ccatccaccc tctaagccat    2160

ttaggacatt tagtaaaagt gattcttaca aaatttactc ctaaaattct cgtgtagttc    2220

cagtctcctg cctagcgctt cagtcgat                                        2248
```

```
<210> SEQ ID NO 76
<211> LENGTH: 3309
<212> TYPE: DNA
<213> ORGANISM: Homo sapiens

<400> SEQUENCE: 76

cgcccccggt ccacgctgct gcgggggctg acgtgtctgt ccacccccgg gaatccccca      60

ccctcttcct cggaccttac acccgccagg ggagtagcgg tggaaggaga gagagagcga     120

ggttgcgggg ggagtacgtg tgagactgaa ttctcccttc ctctccctcc cggctcgtcc     180

ttttagcaag taagctagtt atggacacct tctctgccca tgacacccac tcccctaggc     240

tcaggtctag ctagaattta gggggtccta aattcacaca aaatcctttc cactccccat     300

cctggagttg aagattctcc caatgagcct aaccttcagt gtgagggttg gtgtcaccca     360

tgagcccctg ggggccctga gagggctgtt ggggtgacag agttgcagga tgcctgcttg     420

ctggggagga taccccagcc cagaagaggg aagggattaa actcagtccc catcccacct     480
```

-continued

```
cccagcacac caggcagctg ccagcaactg ctaaaaatac ccagccctgg ccctggccat    540
tctgctcctg gactggaagt tgcccagagt tggggaaatc caggccaatg gtgttgaatg    600
ccagcaggag ccagccactt cgagtcgtca aggtctccct tctctctagc tgtaggctga    660
gccagccacc cagggcacat ccagggcctg gaggttcagg cccccaccca aaaggggcat    720
aaacacaggg tgtggtcaag gcatgaggag tgtcttagct ccctgctcat ctctcagggg    780
tctgagggtt gcaggtcagg ctgtgaggta ttttgtgaca gggacctgct atcagacgat    840
tgtgacaagt gtggtggggg tgggagggca tccatttggg gctcaggtga catcacagat    900
ggatggaccc tggtgggctg tggtaggttg tcatggagac ctgggccagg ctctttggtg    960
ctgcatcagt ttccttggca acgcctaaga aggccttgga ttgaggaggc tggctcggta   1020
agattagggc cctcttgtcc ttgaggtctt caaataggca aaagctgggc tgaggggcct   1080
gcccatggtc ctaggggatc ttggaggcct gagcatcccc tgctggttct ggcttcctga   1140
acgaactcca gtgggaagag gaagttatgg gcagagcctc ccgttagcag gcaagtctaa   1200
agagccacca cacacttccc atgaggaatc ctggctggct gcctgtgccc cctccaaccc   1260
catgactgtg ccactggaaa gagcctcctc tgggtgtctg gcagagggcg ggtgggggt    1320
agctgtggcc cttcccagag ggggccatgc aaagaaggag ggctgggttt cccctctggc   1380
aatctgagct cttgacctca gcagtgtttc ttcattgcca agggaactgc aaccacaaag   1440
ggccactcaa gccccaggca ttccgtggct gctccaacag gccagagaca ctcaccacaa   1500
gctagatatg gccaggggcc ccagggatta acaccaggac acaaccttga gacccactcc   1560
caccacctgg ttctcccagc tctcttggct gcccaggagg aataaacaga ttataagaca   1620
aaacaaacat gaaatgcaga ggcagttggc tcaagtcggg cacacagtaa tatctcacta   1680
agagcacgtt tatcatgatc atccttcgtt ggatggggca ggttaggtga atttgtggtc   1740
cctctcctgt ttctgctcca ctctctccag gatggtggtc tgtccaggag tggggcagag   1800
gtctcagagc atctggggtt ccagaaagtt ccctgggcac tggcccagga tgcacagatg   1860
gtgccctgca ggcagccagg ggccaggcac tgatgagtca agagtgacaa gagaacatca   1920
tgtcagcagt ttggtgtccc tcacccccat ggcctggctg ccaggaaggc cagccaaatg   1980
actcaatcac acctgcctcc cttcatccct caacacagac accatggcca cctcagacag   2040
ggactgtccg gcagaggtac acacgtgggg aggccttcag ctcgggaagg agccctcagc   2100
ttcctcatct gtgcgggata cagtgcctag atcatcagag ctaggcctag acccatttaa   2160
atctcccaag ggcagtccca agtggttgcc atgactatcc ccctcacaga tgaagaagct   2220
ctgggcaata ggggctgatg gcttcacctc tctgatctta ggtagccaga tccagcactc   2280
ctcttggtca ttaggtggcg aggccactcc tcctaagagt gagctgagaa taggagttgg   2340
ggttcaggat gggcttagcc ccttctgtag gcaacggcgc cccctgccac tgaggcttct   2400
ctgcccaatc atatctgggc ctcagtaggg atgagtattg ccatcagaga atgagactaa   2460
agcaggaagg atgctccccc tgggaaagtg atcctaacca gctaagccaa agtctgtcca   2520
ggtgaccaaa tgcaatctgg gcatagggcc aaggggaggc agaggcctta gacccgagca   2580
cgtcacttca cagtgctgag cttccctact caacactggg ggtgacacat gcctttggga   2640
gggctgattg agagggtgcc tcaggttccc ttcaacagag aagtctgatg tcactgccct   2700
tatcagggac cagacggcca tcactacagc tggaaaagct ggcatcacac ctactagtgg   2760
gcttataaaa tatataccac tcctgggcca aaaagcgcaa acctggactc actgaggcct   2820
ttagaccaat ttccagttgg caaaggaaca aatcagactg cagaacttga cacattaggg   2880
```

```
aaatccagat atgcctgggt attagatggt gttgaggaac tgttcatttt ctgatcagat   2940

aaatattgtg gctatacagg cttatattga cttaggatgc agtacttcaa agtgaagagt   3000

caagtctctg cagcttactt actgatattt atatatgcac acataaatat ggcccaatat   3060

gtcaactgac tctactggtg gtggtgagca tacaggcaca ttcgtacact actctttcca   3120

ttttgatttt attttacgaa aagttgcaag tacaccaccc tttagaggca cttactacca   3180

ccatcccccc ctcaaactcc aaatgactcc accatgaaag acaccaaggc atgctgggaa   3240

ctgaatataa attaacttta ttacaaaaag caaaatgtta gtttctcatt gtgagtgatt   3300

caagaaaac                                                           3309
```

```
<210> SEQ ID NO 77
<211> LENGTH: 2385
<212> TYPE: DNA
<213> ORGANISM: Homo sapiens

<400> SEQUENCE: 77
```

```
agaagccttc cctgctccat aagagcagcc tgccgccccg gcgatgcctg tgcctctccc     60

ggcgcgcagc agctggagtg gtttattacg ttgcaggcac caagtccatc ctctcctgta    120

aggacagtgc ttagtctcta acatgggggt cctcttgcct cggagaccag cgtacacaca    180

gcccgttgcc cagggagcgg tccggccaga gtgggccagg gggtgattgt taaatgtggc    240

tgcaacaggc cctaacagga aagctctgtg tcccctactc agcttggctt aacactatgg    300

agaaagttct taattcccta attgcctagt tcttgggaga ggcttggctg tgcagttctc    360

aggtccagat aacacacact ataatcatct gctgagccct gaggaggggc tctgtcctgg    420

ggcagcagtt gcttttggat tggtataaag accatgatat tccttttgcc acggggtgga    480

gcaaaatata gctgggaaat actgttttgc aaagattttc tcagtgatgg gaccttggat    540

cggagacaga aaaatttgtg tccaggtctc acctgagaac tgaaaaacgc gaaatttggg    600

gattctagtc ctgacaattg ttgcaacttg gaggagcttt gagaggccca agcctctcaa    660

agagcacaga caacatctga ggatagcaat gcaataaaag aactactcag ggagcgtaca    720

aggtgctaag tatgtctttc attgtctgaa aattgctgag ggcaacagaa aatgtgtatg    780

tattatcact gttaattaga gtacagcctc acttcttctg ttctctttat ctgcttctct    840

taccttcttt catgagcggg agatgggttc acaattaaag atgttctctt tagaatataa    900

gacttgcaga aaattatttt ttctcctatt tatagaagtt atatttgcat taggagcctg    960

gtaatgtctc ataaatattt ccttttagat aaaatattaa ttaaaggagt ttgttgagtt   1020

atactctgaa atcctaacta aatagcttct aaaacaaata ttttaagcat tttttctcat   1080

gtcaggagaa ttcttcatac gtccataaac agcagatatc tatcagtaag gtattttgca   1140

atatttaaca taatactgta gctgctaccc agtttaaaaa aacaaaacca ggcattgcca   1200

acactgccaa atccatgtga gattacctcc tcttccctca agaaccagcc acctgagttt   1260

tttctctttc ccatggcttt taaatgctaa acagacacac acacaaacac acacacacac   1320

ctactatgtt tgagacactt tgataggtgc ttgagagaga ccaaaaggta taatggtggg   1380

ctttgatctc aaatgtctca catctaacag ggaaggtggc atgtctgcgg gggaagtcaa   1440

attaacagca taggttttaa ttcctaggtg ttaattggga gctggtgtgg aattgacagg   1500

aatgctaaca cagctcggag aagaggagct gggactgact tctgacggca aggctacgca   1560

gagtctgaaa ctaaggtttt gatgagaggg agaggactgg aaatcaaggc ttgggcagcc   1620
```

-continued

```
tcgggagaac aggctcagac aagtcaagtc ccctcacact ggcaggaatt tcagacctgc   1680

tagcagaaca gtttttccaa gatcatattt ctaattgtta tgagatgaac ggtgtcccaa   1740

attcagatgt tgaagccctg attcccagtg cttccggtat cctcataaga agaggaacta   1800

ctttgaggac actaggagaa ggcagctgtc tcccagccga gcagaggcct caggagaaac   1860

caactttgtt gaaccttgat cttggactcc taacttccag ggctgtggga aatcaatttc   1920

tcttgagcaa aagagatcga cgatagagta acatcaaagg ttctgtgaac tgcaggtgaa   1980

cagacgatca tcttcaccta cggggctcat cgccgtttca ttcctgtgct tctcgggagg   2040

aaagttaccc ggagcagcct ggtggaaacc caagcgtcct ggctgcagtc tccaactgga   2100

gtgtgaatgc tttccttctg acggcagaca gctgagaacc tgcagggtta agtgcacagt   2160

ccgggaaggt tctgttccca ggacagcgct atcgagtcca ctgggcgctc cacgcggtct   2220

acctaaaggg aacagcctgc ggcgcggcac tattcaaagg gtggggagat gaaaaatacc   2280

gtgctgctta gcattgatga cgcttgcttc agggaaactg actagaatct atttagtctc   2340

gagcatttct gagaggcaag caggcctcag ggcactgcag aggga                   2385
```

<210> SEQ ID NO 78
<211> LENGTH: 2732
<212> TYPE: DNA
<213> ORGANISM: Homo sapiens

<400> SEQUENCE: 78

```
tgcctgcctg gccaactgtg gggtcacac cccgtgtgtc cctggtctca attgcaaagc      60

gctgtggagg tgaagtggca ctgcccactt ctgaaggtca tccaccaatg ctcctgcctc    120

ctgtagatcc agtgaagttc tgggctggtt ctgagccgag ggtgtcttgg gaggtcaagc    180

ccatcatcca aggagccctg atggggggt cctcagggcc tagccgaaga gtcagttccg    240

ctccatagca gcctgatggt tcaggtcagt cccaggccca tgagaaaaac tccagttctg    300

caccaaaaca cagtggcctt tggagtccat cagactccaa gcattaggaa gggccaagct    360

cttctcccat tggtagttct cacacacctg tgggtccaga gggggctacc cgccatgatc    420

ctggagctgt ggtctaaggg atctctgtat acctcagctg cggtttggtg tttttatta    480

gtgaatggct tagctccaac ttctcaaggg aacatgctgt gcccttatct ttgtgtgcct    540

gcatgacagc acacagccag catgcaaacc atgacctcat atgcacttaa cacttgacta    600

tatctctggc gactagactc tctttggaca gggacttctt aattctgtat ttctgaatgg    660

cctagtgctg gctgtgacac agggtagtta tataattgat ggtgttgatt tgaattttga    720

ataaattttc taaatgagtc gacattatga cacaatggat atagatgaga ccattaatgc    780

atttgaaatt tacactagtg gacacatgat ggtagatgct atgatacagg aacccatgca    840

aattccaact ttgagaaact agtaacctat ttcgaaatta tacctttctt catgggcaaa    900

gatgatccaa gcatggagga catgacattt aagccttctt cccagtgtaa gggattggga    960

gtgagaaggg atgaattctt cctggggcag gaagggagga tgaaatcagg aaaggcctcc   1020

cagaggagat gtttgaagga tggacaaatc cagatggaca atagagtatt ctaggctgga   1080

gggtattaac caaagcattt ctttgggagg agaacagtct cctctgctct cactgtagct   1140

ggtggcttga ttgctgacca aggtcagggt gacacctttg gccagggcat ttgcttctaa   1200

gtcagccaag ggctctttct gtctgaaaat agctgcctga attcatttcc ccattagtcc   1260

cagaggccaa agataggagc aggctttctc caccagcagg gcagaaactg cagctagaaa   1320

gccggccctg cagcatgagg aacccctggg gagctggcag gagaccttga ggtctgaccg   1380
```

gctgtgtttg gatggaccct ctctagctct ttcccccatg tgactgaaaa ccttatcata 1440
atgaaagctg taaaaatgcc aaactttaac cttattaaag tcacactgtt ctggtcttgg 1500
caaccataat aggattttac aactcaacct ctactagagt ccttgaacag cccagggtct 1560
gtcagggtcc gtgatgggtg acttatgcct tcagggactg gtgcccaccc acattcccac 1620
cctcccgtgt ccatccacca cccgtgtcac cgtggccttc catatggcct cctgttttgt 1680
tactcataga aatggagaaa tttccactac catggacccc ggaaaaacat atgagcatcc 1740
ctacagcatt accagctgac ggtattttcc tccggattaa tgaagcacag tggaatttta 1800
gcagttctgt aatgattaat atgtcaaatc catattgcag gagagggaaa caggaaagcg 1860
atgtgagaac ctaggagggg ggatagcaaa gccaaagaag gaagggaagg aagagaagaa 1920
caagggaagg tggggagaga ggaacacgcc acaggggtta ggctcgagct aggaaggtgg 1980
gtcaagtcag ttcctgagga gaggtctccg gagcagtgca taaggttcta catgtcggga 2040
ggtcatggac cttaaaggta tggggtttat ccctagaaaa aaaatacaca taaaggggtt 2100
tactaagccc ctaaacctcc atgagaaaac acaaaactgg gttcagctga cggtgtttgg 2160
actgtgtcat ccctgtcagc atcccctctc tgatgccttt cagcaagttt ggaaagatga 2220
caatggcgtc ctctgtcttg ccctgtgaga ccctctcctc aggctgcaga ggatgaggtc 2280
ccttcctcca actctaggca gtccagtgcc acatgaagtg gtgtccatgc tgtgcgtgaa 2340
catgctccgc agtcttgaga cacggctgga caaaggaact ggccaagcca ccaatgggaa 2400
atactttgca atgcaaatga gtcctccaaa gccaagcatt cctctcctgc taattacttt 2460
tacctggttg cattacatat tctgtatagt caggagctgg ctcaatgtta atgtcattgt 2520
ctcctgaaat ccaagagacc tgaatttcct ttctttcttg atctaagcat gtagtcatgg 2580
gccagaatat cacatactat cctctgaaca tatgcttctt taacaggaaa gaaaaaatca 2640
ggttctatat ggccttaaat cgtctgtgat gggaactgta caaaggtcaa caacaaacac 2700
tagtttacat actcagtagg tgaaagagtg ag 2732

<210> SEQ ID NO 79
<211> LENGTH: 2973
<212> TYPE: DNA
<213> ORGANISM: Homo sapiens

<400> SEQUENCE: 79
aatttgaaga cactgagagt gttgcaaaaa aaaaaaaaaa aaacagagag agagggtgtt 60
tcagttgcct gcaccataca tctcgctggt tccgaataat gcaagtctct cttctgttct 120
tgagtttcct gccccttaaa tatcgcttta ccagaaaatg agaaagtctt cacccaaaaa 180
aacagcacag aagtgaagcc aagtgactgt aggtttcata gcctggtcaa cagggaggca 240
gctggcgatc acttcctgcc tcaccctgga ggaaggagct actaaggaaa gggacgtcta 300
agctgaaaca acttcaggtg gttcctgtcc ctctctagag actaaagtct cactgcatgg 360
aatgcccttg atatccagac tgggaaaatc taagcctgtg gacaggaaga aaagtcattc 420
atttacattc gtttatcact cctactactc atgagagtca agtgagggtg tctctgactg 480
cttcacccct tggttcagcc cagtgaaagc tggtcaactc ttaatgctca gatccgtaat 540
agcacaacca ttttagtatc tttctctgaa gactgcaaca cgctgtcatg atattagtca 600
actgacatta ttatagtgga ggctgctcct tgaaagccct tcactgcctc cctggggtgt 660
gggtggagga tgagataagc agctcacaag tgggacagaa ccctggctct gcggaaagcc 720

-continued

```
cgggcttcct gtgtgagcgc atagacagcc ctgtagtccc tcagccctgc ctgccagaaa    780
cccaagcccg aggatgcccc tccagatgtg tgctggaact gagctttctg aaatccttct    840
cctggggcca gacactcatc aaaggccaac tctatcgcag catttgagtc acctgttatg    900
tttgagatcc gccctgtgtt gggagctgaa acctgttggc tggtcttgct ggggtgaagt    960
ctggaagagg actcctgctg tacttctgag gtccatgctg cagctcacag ccagtgtggt   1020
cagccgaatc agctctgggc ggcttattgt gaacaaagga gctcagttgc tggggttcac   1080
tcctatccca tcagaataca agctgcactg gggctagatg tccacggctg tatcctcagc   1140
acctagaaga gagtctggga ccaagtgtga acatctataa accgttggca ggatatttag   1200
tatagcaata tctttggata aacaaacaaa attatgttgt tggaaaccaa acgacaccac   1260
tgatgaatgt acttaggcta cttaatcaag aaatagtcgc aatgattcta cttctgtctt   1320
ctttttaaa aaaaatttaa ttagttgttt tattttagaa tagcattact gattaccttt   1380
cttccctgga aattaacaca tttcgtagag acttaaggat gcatcaatga aatacttaga   1440
attgaaagag gaaaattact tgatttctca ggatgtgtgt gtctattggt gctctagcac   1500
agttatgcca ctgaaaactg atgcaacttt tgtgaagcaa cagctgtagg cctctgtgta   1560
acacttcctt gtgtagaact taggttttag aaaatatcag aaaagacctc tttataggct   1620
taccacataa gtacattgtt ttcatccccc agtagactgc gattggcttt gactggggag   1680
ttcctcattt gtctccgggg ttggggccca cttctgtttt ttgacactga ccagctatgc   1740
tgtcttcata gaaatcaggc agtgggcagt gacctggttc ttactaactc ttgtgatgcc   1800
tcacgcgatg ttatatctgt caccagcacg ctctcctctc ctgagagagt gttagaaaat   1860
tgcgtggtct gggagtgcag gggttaatga acagttcgga gatgcttcct ctccttgtgg   1920
cccagatgtc ttcgggaatg cttgaatcct ctccctttgc atcgtagggt tacctgtcac   1980
atccctttca cttgcaggga ccatgtctgg acaaattagc caaagactat acctatgttt   2040
gaagcaaaat ttaatattcc tccaaaatta tggctttcca attctccatg gctcctctta   2100
gacaacaaat atttctgagc actgccgtgt tccaggcagc tgctgagatc tggatctgat   2160
gggtaaatac acacagaccc cacctctgct ctttcaaagc acgccttaca ctcaatgaga   2220
acaaagagga atcacagtta ttggcatagc tcattttttt tgtcagatcc agttttgcca   2280
tatgacaggg ccaaatctat aaaacattgg gagctttata ggagataaaa tacctctaaa   2340
gagaattttt atagcccaaa ttcctatcca gagtctccag cccctttggg tagacagccc   2400
cctcaagatt ctcagggagc tcatcacatt ccccattggg cagtgtgact agataagggc   2460
caagggcatg agtcagtgtg ggaagtggcc cagctcagct cagccactgt ggcaggcaag   2520
aaggatgcca cgaacacgcc aatggcctca gggaggtggg tgggtgaagt gtggtggggg   2580
tcatgtttgg ttatgtaaat atgactccag gcagagccag tgctgagttt gatgatggag   2640
gaggattgga ggtaaagcta gagctctcag agccttccct gggatagaga ttcctgctga   2700
cactgctggc catgatagtc tgtctgggga gccatctcac cttcagcttg tgcagagaag   2760
ggtggctggg gaggtttgca tagctggtag gtgcattgat gccacttgtt tctccacttg   2820
gcttcagtcc agagccccac tctgggctgg tggctgggta agaccatagg taaacagtag   2880
acttatagta tggtttgggg gctattttgc tatgacacgg gcttaatggc cctggtgtct   2940
tcatgctact ctgtatgctt tgaaacaatg gct                                2973
```

<210> SEQ ID NO 80
<211> LENGTH: 2353

<212> TYPE: DNA
<213> ORGANISM: Homo sapiens

<400> SEQUENCE: 80
attgtcttgc aggaggcccg cgccaggctg gtcaccgggg gccctgctta atcgcaaatg 60
gtgcaaccca gtttttgatg ttctaaacta ttaccataca agagaaaaga aatttagaaa 120
caaacagacg gaatacatta gccacatctt ttttcttaga cccttctgat attggttaaa 180
gctgctttgc tctttacttg gaagtagttt tgactacttt taaagtaaca tttgccaaga 240
gaatgcatgc tttgtcatga ttcctcatgt ttggggaatt tgagatttga gttctgggct 300
gagtggatca ggagcagcta ctcagccttt ccagttggag tagaatgggg acaaggaatg 360
accaatgagg tcaaaggaag aactaagcac tgtccccaaa atgcattctg gaaccattgg 420
gctgggtgct ttacttctct ggatctcccc tggggtcccc agagccttac taaagttagg 480
gtttctctgt agagtgttct gaaaagcaga gaaagtcctt gtccaaatgg aatccccagt 540
ggttaagatt gcttagactc atacccatga atcaaggcaa tggatgatgt cttctaggac 600
agatgtcaaa accagctctg aggaaggtgc ggtgtgagca gggagagggt aggctagatg 660
tctcctagca ttttcaatcc tctaaactga ggtcagaaag gaggaaaaca ctgtcttcac 720
tgttcattgc ctgcacggca gcaggagaaa taagggaata acaccaattt gaaaccatgt 780
gtatgcccat cccgtactcc atatctctcc tgcatcccct ttgttcctgg acatttttat 840
aactgtttcc aaccggaaga agtgcatgaa ttgatacttt ggcatcaggc tagatgtgcc 900
actcgggttt cttctctccc cccctcctgc tgtgtgtgtg tgatgtctaa aggcctcccc 960
atctggacac tcacccacgg cattggacat tttcctttca ggtttatccc acgcagtcct 1020
attccaggaa gcctcctctt ccccacttag tgtgtagaca actcactctg ccaacaataa 1080
gtagtatgac aataaactag tttctaacta ctttatgtgg attaactcac tccccatcca 1140
gttctctgaa gaaggtgtta ttgtctctgt ttacgttgag gaaactgagg cacagagtgg 1200
catggcattt ctcttctgcc tctccactct gtgagcgatc tgcgtttagc agcgcctgcc 1260
acaggggtct ggctcttagt gaatgattgc tcctggatct cccaaactct tcatatactt 1320
tcacatcccc aagattcctc ctgccagctc catctgtgaa acttgtgggc cggtatttga 1380
agaatgacta aagggggaag aggttttatg aacttcagac tgtgaactca aggaagagag 1440
tgagtcaggc ctccacattc ctgaaatact ttcaggaggc tcagtgacct cagacaataa 1500
gaacctgagg cagaatgtcc ttgggaggcc ccccaccagg aagaacgtga gggcagatgc 1560
tctgctgtgc tgccttctgt ggttcctgcg cagtgtgtgg gttaggaaac cactagccag 1620
aggcccaggc ctaccgagag cgctgccttg gttttgccag gctgactcct ctccctggaa 1680
tgcttgaccc caaatgcttg tgagcttgtc atcccagact cagctcatgt gtcacctcct 1740
ctgtctgcta caggtagaag aggctttgtg gttgggacac cacagggaat tgcgcttgct 1800
tctctcactc ctaaacgccc tagaaaaaca ttgctttcaa catgtgtgcc caatacattc 1860
ttcaacctac tgaggttggc aacagctcca aggttgagga gtgagccctg tgccggagat 1920
gtgggtgctg ccttgcttct gaggtacaga gacttttaac ccaggcgcta ttttcagagc 1980
ggagacatag ctattcaata agtttaaata attacaaatc tttctcccca gcttctatct 2040
ccgtccatct ctttcctcac caagcttaaa cccaggtatg aggtgcaacc atccacaaag 2100
ggaaagacag agcaaacgag aggctgacag gtaaagaatg agtctcaccc aagatgaaaa 2160
tgttagaaaa gctgagggag cacattcagt caagctcctc caagctgcac cactttccaa 2220
cagaaacaag ctaactaggc tgtgggttac tgcaagtgaa ttgtaggctc gtctgcctgt 2280
agtgccatct agtgcctctg gtctaaggaa gttggtgggc ttggccgtgt cgtataacct 2340
cccgtgtcac ttc 2353

<210> SEQ ID NO 81
<211> LENGTH: 2251
<212> TYPE: DNA
<213> ORGANISM: Homo sapiens

<400> SEQUENCE: 81
gacccaaatc agatactcgt gagccaggca gtgacttggg ctcgctttga ttggcacaaa 60
taaacagaaa atgtctataa acttctttag ttggaatcag aagtgggctt tacttggatt 120
actcctcccc agggaggggc atgacaacct atttttaaag gctcaagtgg aaaagtcctt 180
ttgcagctgt gaaaacaccc tcagggtcag cccccccacc tccctgcccc ccctgttaac 240
cgcaatgggg atgtggtctc cttgatacgg agggagggag ggaggccgtc ccctgggtgc 300
tgggggaggg agttgtggcc ggcatgatcc tattttacac aggaagaaac agacacccag 360
ccaagaccct catttctgca agtcaaattt agatacaaag aggcacctca tggtgacgaa 420
aagcatctaa agagaatttc ccttgttcct gggcgtgagt gtgaaaatgg gttctgctag 480
cttttgtgcc tgtggttatt ttaatgaata gctgtgtaaa cattattctt tttgcaattt 540
tcttcagcaa gttgtgactg caggctccct cttccctgat gcccagaggg agcacagttc 600
gatttaagga ccgggcaaat ggatgtcatc cgtgtactcc acccattcct gccccaaaag 660
gccaactttc cgttgaccat tattttggat ttctgagttt tggcgcttct ctggcaagtc 720
actgtgtatc tctgagcctc aggctcccct ctgtgacagg gagagtgcca ggttgccccc 780
agggcttaaa tgagctactg acacgcagtg ctcacctcag caggagacag gcacagctgc 840
ctgagtgagg ctaaacatga gccccggggc agcgtggcag agagagcacg agacaggacg 900
catacccaaa tcaaggctcc aaagctttgg gtcagggcat cttgccctgg agccagaggt 960
ctggcaaatg tttatcatgg gggtggggtg tagcatctgc cctgtctctg gtgtaaatat 1020
tcccattgta gcagatgtct gaaagagatg ggaagatgca tttcagcttt tgggaaccca 1080
agtgactcca tgacagcact gaaaaggcat ctgacaccag agctgggccc agggtagagt 1140
ccactaagcc ttcaggaagt caaggacgtg agttttggag tcagatgggt tggtcctaac 1200
ctggctcctc cacctaccat ttgcgtgttt agaccttgtc agctataaaa agaacacatt 1260
gagagaaatg tagagtcatg gattaggtgg aagaaccacc cggtcagaaa cagaacaaag 1320
ccaagcccca ggcgatgacc taagcggata aaacacaagg gagggtgagg gaattggaga 1380
tctgccacgt ttgacagcga agctgggttc cagccaggcc agtccacggg gcgctgcttc 1440
attctgctga ccatccatca ggagctggtg gcaatcacta cccacttcat ccttgggtga 1500
atcacttaaa gcaaaagaaa tacagaaccc cggaatcttc catagtacta tggacccctt 1560
tggctaaagt agcagacaga tacattttag attctactct ctagatcaca agcctcctag 1620
tttcttgttt cgggagccct cgatttcctt gaaggatgct ggcgtttcat aacagtcaga 1680
cttctcgctt tgtgaaatcc cgtcctaatc tccaggtcaa taaagtgact catctttggg 1740
cttaacatcc ttttgtttag ggagaaaata gtttctactg agtgataatc tatttataaa 1800
acgttgcatc tgattagcca ctattttatc ttccaacaat gcttaggctt tcgtgtttta 1860
aggaggaaaa tttagtgggt tttcttggcc aacctcaaag gtgtctgctg ggattggttc 1920
attttccgga atgcctaatg gattgtgaaa catgcccgcc tcccagcaag gtacctcact 1980

```
tggcctattg tgtacgacaa acatcttctg ccctcatgag ctgggctgct gttgatccct   2040
tccagccgaa agcatgcacc agagaagagc aattagtttg tattcctaca aaaattttca   2100
tggattcaaa ttcttcatag aaagaatgaa ccagagagta aactgaacca cagattaaag   2160
ggctcatgtc aggcaattct ttgaacagtt tttttggttt tgaaccatca ttatttgtaa   2220
tattctctga aaagccagca aataattgtt t                                  2251
```

<210> SEQ ID NO 82
<211> LENGTH: 4498
<212> TYPE: DNA
<213> ORGANISM: Homo sapiens

<400> SEQUENCE: 82

```
ccagggaggg gtgggggatc tggggaaacg gtcttgaaag agctgtattt ccaaaatgtc     60
tagaagttgg tccggtggga cacccaaagc agcagaataa acaactccca ttgaagttac    120
aataataaaa tgtttcatga taagttaaaa tattctttat attattttaa tttcttaaaa    180
ttaagaatta ttaataatca ttaagcttat aataaaaaat taaaaaccag actaggaaat    240
gaaccacatg agggtgtgaa ctggtaaatg ggaaaattag ccccttaagt atctgagaca    300
atagaacaat ttgaaaaaga gtatcaaata gttatggtca aaatacagag ataaaatgat    360
aggacatagg actatgaaaa aagaacaggt aaatttgaaa aagtacagct ataatatgta    420
gaaataaaaa gtttagtcat ttacatataa aaaacctcaa tgattgaagt caaaaatcta    480
ataaaaatag ctcattgaaa aggggaaaga aaagtaatat attattgttt ataaatatag    540
aaatttaaaa taatatatta acaaatagaa ttccagcagc ttacatcatt aatagatcaa    600
aagagaaaaa tggaaagatc atcaccatat atgctgaaaa gccatcagaa tttggcatcg    660
acatataaac aaaccctctg taacatgaaa caaagggtaa agttcagccc ccaaaccagt    720
gttagaaata ctagttctaa atgcaagata tgaatgtcct ccttcacccc tattcttttc    780
tgaacagaac tggccacctt tatgtgttta tgtgtgaaga ctctgttaca acatccccca    840
gttttctagt gtatacatgt gtgtatgttc ttcatgatct taagtgctag atgaggcttc    900
acattccata gtgaaaggtg acttgtgaca aagtctgaac caacttcaca ccacatctca    960
cggttaggag cactggaaat tttttaaaga ttaaatacac agggacagat ttcctgttca   1020
ccccatctgt ggttattcca gtatatggaa taaaatgcat gacaatggga gagacaggaa   1080
gcctatacta gtcattaagc atctatggag gggaaagggc acttcccttt caatttccca   1140
ctaccctgat ttcaacttca catggaattt cacaagataa tagcaagtta gtttagagga   1200
tgtttcacag aacaggctgc tttgctgaga cctcagaggt gtcagttgaa caagacgaat   1260
gatttgcatt tggctatttc attcctcaag gtcagtgctg gcacgtccct cctctggctt   1320
tagagattat ttactgacaa aaataagtcc agagaagttg tcaatactca aggtcacatt   1380
gctggttagt gactgaataa tttgtgccat ctgctaggta ttactcttta tacctaccaa   1440
ctcatttaat cctcatatca actcacgtgg taggaatcat tagattttat ttatttatta   1500
ttagtgggaa taggttgtat ggagccaatc tggtccaccg attgacttgt gcacgtcctt   1560
accagtcctg taggacatca aactgcaacc ttggtgtctt gggcaagaag caccaactga   1620
atgatctagc ctaaccagtc atacccaaaa gtaatctgtg tgggagaaga cagctgcttt   1680
taagccaata aaattcaagg caggtaagac gacttagtta tgacactgct gtctccttct   1740
cctggtaaaa atgcttaccc gctgtggctg ctccctcagt gcttctacct ggtgcctgac   1800
```

-continued

```
ctttcagtct tcctaataaa tctgcctgag cttcggtgcc tcctcaggtg tcacgagggg   1860
agtttgtaga ccctttggga gctgatgtca aatgctcaac aaatgttctg ttaagttagt   1920
gctgcagtag tctggaaagg agaagattaa aggaataaaa tatgcccccca acagttttgg  1980
agaacactag ccagtgggga ctctgctctg tcatctaagg tgaccatatg gttggctgat   2040
aaatgataac aatttttctgt aacacgtggg cttttcatct tcccaacagt ctggaggaaa  2100
aatattagat atgatgacag gagcagtttt taccatgtcg ttaagggccc aaatgtagtt   2160
ttagattcca tagacactaa atccagcaat gccacaagaa tgcctgtgca aacaggatct   2220
gtgttgcagt taaaattttt tttttatttc tgatatatac aaagaaaact cacttcatct   2280
agcttaaaca aataaggtta ttttgttagg aggtacaaag tatcagcaga atccaagaga   2340
gcaggtgttg ctgggtctct cagggacctg ccaccaggtt cccacagggc atcggccacc   2400
aaggaagaag ctccctctcc catctttcgc ttcctgcatt tatttgcttt attcttccct   2460
ccatacagcc tgcctttctc tgcctctcct gggcttcaca tgctcagttc cagacctgag   2520
caatgattga cttgctcttg gtccctgtta taaattccaa gggaaaataa tagaactggc   2580
ctggggaggt atgtagggtg gcctagagca tctggcttca gagagggacg taattctggg   2640
tgggagttaa taatctagag gagattgtgg atgatacaga caccaatagc ctctgggacc   2700
tctctgatct atgacagagc gatttctgtc agggcacaat tgctttgcat tacaggctag   2760
gaatctgcaa gtcagtgttt ctgctttttt ggaggtttac ttcatatctt cactgggtac   2820
tattgaagag gtgaacactg ggtataaata ctgttcttat tactgtgtta cgcacgcacc   2880
tgagaagttc taagaggcga ttctatccag gtttaaataa ggagctttgc agaggtagta   2940
tatctcatga tcatatttga gatatctggc agaaaaaatg ggtgtgttct tgactgtccc   3000
tagtccttga gtttggaggc acttctcttc tatccttcca aggctctctg ctattcaccc   3060
atgccctctt gtcaacttta gtgtccacaa gtacctgata gggacctcac cctgcctaaa   3120
gcaggatttt tggatttgcc ttggtttctg cccatgctgt tccccatact tgagattctt   3180
ttaattcctt ccgtgtctct aactcataca tatcatttaa ggtcaagttc tgtacctttt   3240
gtcatggttc actgggcttc cttactttag aactcattca gtagtgattc actgaacagt   3300
tacttataca gcagagtgct ggctggttat gttgttcgct agggctaaac aaaaaaaattg  3360
atttcctcac agttatggag gttagaagtc caagatcaaa gtgtcagcag gtttgaattc   3420
ttctgaagcc cctcttgtca ttcctctctg tgcactcgtg tctctttgtg tgaccaattt   3480
tcctcacctc tttaaaggct ctatctccaa ataccatcac attctgaagt agggggcatc   3540
tggacattaa cttatgaatt ttggagggac acaattcagc cccaacacca gtggagacag   3600
gggtgaagaa gacgtgcatc atcttagagc tcctgtagtt tgacggtgtg gtagggaaca   3660
caggtattaa ctatttacat gactaggcca ttagttacca ctgtgggatg atgcaagaag   3720
tagaatacaa atgctggaaa aggtagtctg gggaagtgag actgaaagtg tgagatctga   3780
aagaagattg gatgggagcc agccagctgg aaagagagag agtcaagtat tccagacagg   3840
aagatctgtg aattccatac ccagggaatt gaaagaacca aagtcaaagg gccagattac   3900
acaggacctt atttactgac atcctcattt catgcttacc tcggactgtt gtcaaaaatc   3960
ttttaagggg agtgttggcg tgcacaattt gcttctcctg attcaaggga gaagacttca   4020
actccttttg tattctctct ccacatatgc aacatagggc tggacatata gtaggtgctc   4080
aagaaataaa tgtggatatg agaaatgaga tgaatagaag cactcttggg tgtgtttctc   4140
caggctctga aaggtgagga ctttgatact ataatgccac ctagtgttct tgttattaca   4200
```

acaacacagg ggagcagggt ggtgctagtc ttcaatccag aaaattggaa atcaatttgt 4260
ttcatcagca taaattgata tgtccgacca cccatccttt atccattcat ccatctgtgt 4320
tgatgccccc tgcatctctt ctatgagctg aacatgtcac gcgcctttct actccttgtg 4380
gttctttgat tgctcagttt tgggtctttt tgtcctccta taagtaaggt ctcagatacc 4440
agtatctaga ttctctgagc tcccattgtg ctttctgtta aaatggcata tactaaat 4498

<210> SEQ ID NO 83
<211> LENGTH: 1706
<212> TYPE: DNA
<213> ORGANISM: Homo sapiens

<400> SEQUENCE: 83
ggctaattaa ctcttagccg gcgggaccct cctcctccga ggttggccag gagcagcggc 60
atcccaggcg ttcctgtctg atgtcatagg ctgccggcga ttgcggagaa tcgccaccac 120
gcctttatga aggtcccaac tttgccatct gataccctt actactgaca ggcgctcagc 180
caatcaggag cggcgagcgg ggtctgggga cccggagccg ccgaagccgt ctcgggaacc 240
ggctcttaac tctttgcggc gcagccgccg aggcagcagg gccaggcggg aatctgggaa 300
ggggcgccta aagagcggat gcccgagggc tgcgacgccg cggggcttgc aggtggcgcg 360
gggctgcggc aggggagctc ctcctgggga tggtctccca tattgaagga gagaagatta 420
tccaagggga tagctcattg agaggtcacc tttcaattct gccttccata gctgtggtcc 480
tcagccttca gccacaatgg aagtgattat gtccataggt gtgagttcaa agtacagtgc 540
agagtcacca ccttaaatct tgacccttac acatctcctt tcctaggagc accatgaggt 600
cagctgctgg gtcacagaca ggggtagtgt ggtcagctca cctatgttgt tccaggacct 660
gtggtcctct cttagcaaat cccctcccac caaggtcatt attgtgtgag tggatctcat 720
ggtcttcttg aagagttctt gtctctagta tcacctcttg tccattttct ctttttattc 780
tctcacacat cggagcattt attcatcttt agaaaatgca tttagggatg tgagcaagtc 840
actgtgacct tgaagtctct caactcccag ttactcccag cacccacaag gcccatacaa 900
gtgtgtgtgg gcactatgag gaagatggtt tttacacttt gggctcacat cacgagattc 960
attttaaatt gtgggaagac atgagttgac ccagtaactc ccactgtgtg aacaccactg 1020
tgtctgtgag gaaggccctt gcaaatcctc aagtctctca gactcgcaga aatgcatttg 1080
gaaatatggc cctcgagagt gggtggcccg tgggaaaggg ctgtgagccg ctgagtctcc 1140
agggcttccg aagttgcttg gcataggcat tgcctaatat ccatgagctt aaatgctact 1200
gggaactcaa tcataatgta tttacattct tataaatcca aattactgct tggaaaccat 1260
ccagcaaatt catttctgag taagacaaat acatgaaaat cttgcattat gtggatatgt 1320
gtccaaaata ttacaataaa tatcagtgaa tttgcattca aatattaggc tatttttccc 1380
aaatatggca gtgctgtgat tatgtgataa acatgaaaaa ggcaaaatgc ttgtttacat 1440
tttgtcttca attttctatt agcagggttt aagtgtagtg agtttgtatt ttctcttatt 1500
taactggcca ttattctctc tgaaaatcat attataaata acctacacag cagaaagaat 1560
gcttgatact gttaaattat tctttttctt tttaattaat accttcaccc ttgtgtcttg 1620
aatagaataa tctaagcaca gacaagatgt gttggatcat agttaaaaca tttaaattta 1680
ttactggaat aaagagccag agtccc 1706

<210> SEQ ID NO 84

<211> LENGTH: 2000
<212> TYPE: DNA
<213> ORGANISM: Homo sapiens

<400> SEQUENCE: 84
cgtcacgtgg ccgtctagac accctgtcgc tttaaaaaaa aaaaaaagcg attgtgtttc 60
gcaaacaaca gatcgggttt ctaaaagcta tttctccccc cccccccgcc accgccaccc 120
cctcccgggt ctgtagaggg gtaccgatgg aggggagagg tggggggcag agaagctccc 180
agaatggatt gagccccggc cggagcatgg agaaattgga aaagcaggga gcaccgagcg 240
ggcgagtttg gagctgagcg agcgggagat cctatattgt agtaggatgc caacagtgca 300
gaaccctact ggacggacag aaaaggccac ataagctgca gttgtataac atcataattt 360
tgttgtaaat taaaatatgg cttattgaaa ccttgtgtga acattctaaa gcaacctgtg 420
aagacagcag ctgagaaagc acaggagaga atggagaagg agtgatccca gcactttggg 480
taggcaaggg aagacgaaag agacagaagt gggattgatt ccaggctggg gcgttgccgc 540
ggttaagaac tagggccaac agcaatcccc acgttaggcg agcacttggc agagtttata 600
agattttctg ggcaagtttc cgctctctag ggtcccattc ctctccctaa atgagagtgg 660
tcagaccagg cttcaagcaa cagaaaggat taaataagca gaaagtagag gtcataattc 720
taattcagtt tcttggctaa atggagaatc tgaagaattt tggagatctg agtagtgcta 780
aggctctgta atgagaggcc ggagcacaca cagggcaggt aggtttcatg ggtgtttcaa 840
gagtggagtc tgacgtcacg gtttgtctgg gtggaacatg catgtacttg cagagatatg 900
ttcccgtata gtgtaattgt aggtgtatta attcaggtgt cacccctctc tacacggctt 960
tcctcttcca ttttgctacc ctaggtagaa gtgggtgcgg tgctgagcaa gtagctacaa 1020
tgattggtgc tttatagctc cctggcatcc cctgaatcag ttaacatccc agctttcctg 1080
atagccccac cccatcacat tcttatccct ctcctctcca agaaagaagc cagaagcctg 1140
gcagtagagt cccagcaggc tggtgtgcct agaaaggtag tttctttctt tcccttcaca 1200
ggcacaaagg aggccaacaa acaccagttt cagactattc tgacccttaa gaaaaaagtt 1260
taagagtcca aactatttcg ctttggtgat agtaatcaaa ccctaatcat ggtgccgcca 1320
caagtcacag agaccaaaat agcagagtta tgacaaacaa ggatggaatc agctaaagac 1380
ctggctatta atcaccggcc actctcttga ccggctgctg gaccataaag gaaaaatctg 1440
gagaatgcag taaaatgagg ttcaagccag aagggattat aaacgttaca tagcccagag 1500
agtctccatc ttcagtccat cttatttggt acttttttctt tgcttttttct attttattga 1560 tttttggcaa tgcatgcaca atggtacaca attcaagaat acaaaagggg aggaagaaaa 1620
agatagcttc ctggctgcca gcacccatgc ctctggcagc caccattaca gccaaagagg 1680
cagaacatga acattaggtc tctgctttgc tctccagtcc cacttgcctg gtcaatatct 1740
caaaggcacc ctagctctta ggtcccagat agccaaacag gcttttcctc cagagctact 1800
cctcaccata tcacaaccag aaaccaagga caacctctcc cttacccctt atcctaccac 1860
ccaaagccta tcatctccaa aatgcctctc cacttatctg cttttctcca gtctcaccca 1920
ccacaaccac ccagcatctg tccgggactg gtccacacct tacctctggt cttcctcaga 1980
cccacccagt ccctctcccc 2000

<210> SEQ ID NO 85
<211> LENGTH: 4772
<212> TYPE: DNA
<213> ORGANISM: Homo sapiens

<400> SEQUENCE: 85

```
cattccttta tgagcctgcc aaatcaaaga agcctttaca actggctgcc taagaatacc     60
agggcacaac aggaaacatg ttgaaatatt attgaaaaca atattggaat taaaattaaa    120
aggtatcctt tgttataatt gggacccata gcatttttttc attatgcttg ctgccttacc  180
ggctttatga agtttggaaa actagttact gaattttaat atgtgaaatc cacacctaaa    240
aagagcagac catgacccca tagaagtcta aaaataccct ctgatgcctt cagaccttga    300
ttctgttata atattcttag gttgccaaat taagaattcc tgctaatgca gaccataatg    360
taaaggaggt tcggtttgtc cacccatgaa ccttatgtaa aacttatcac atttctgctt    420
cctttctgct gaatgagagc atctatttat aggctacata acatgaaaag catgggaggg    480
ttttctttca ggcaataaaa atgtgatcta agtcttccct tgtaatgaaa aacaaacagt    540
ttgacgtgta attctgtaac tgcttaaaag agtcacttat caaaacagat cttttagtct    600
tctaacagag tgtgtaaatt tgggtaatga gttaccaaga cttgaaaggt gtgttgtaac    660
atattcaata aatggttagt gctagtgtga gaggaaggaa gaaagggtca aacttccaga    720
aaacattagg tgggtggcag ggtgactctc ccaggaccct gaattcctga tttcagcagt    780
gggcacatga ttctgactcc acaaatcata atgagctatc tctatgggaa cagtgatcgt    840
acttccttga gttggaagtt gagaagcctg aagctcctgg gctgatcatg catttgcaag    900
attaagtatt tccaatattt attattataa accacatatt atttgttact atcgctgtag    960
tatatgacct ggaacgctag actaaggtat atgcatattt ttaaaaaaca acttactgag   1020
atgtaattct atatcatacg gttaatctac ttaaagtaca cattcaatgg ttgttagtat   1080
atttatagtt gtgcaactat cactacagaa tagtttagaa ctttttatca ccccaaaaaa   1140
tattctatgc ccattagcag tcactcccca ttccaacccc agtccttggc aaccactaat   1200
ttctttgtca ctgtagattt gtctattctg gacatttcat ataaacgaaa tcataatgtg   1260
tttttttttg tggtggtttc tttcacttag cgcaatgcta tcaaggttga tctatgttgg   1320
agaatttcat cctttcttat tgctaagttt attttaatag tgtaacgaat aagataaagt   1380
ggctgtgatg aaggtctgga aagcatctgc ctaaaggcaa atatagtgat tactctttac   1440
atataacctg aaatccagaa caatatagca tctgaggata aaataattta ttgtagggcc   1500
taaggtttgc atcctgatgt atctgaaatg tgttccatat taccttggct ttcaatttct   1560
ctaattttct atttgattag aagttattca ttttgggggc aatgatgaaa ttccaattcg   1620
aactgtctta tatcttttaa tcagaatttt cccaaagcac aaaagtgaaa atgtagaagt   1680
tgctgtgttt cattagtttc attcttttga atgttgctac actgaaagcg ctgtgtgaaa   1740
ttattacaag ttttcaaatg gttgtaaaag aagatgcata tatggggact cactcaaagg   1800
gcattattta aaaaagaaat ttccagccac ccagatctca gggtagctat gtccattcaa   1860
ggatagagaa tccaccatct gtatgattat ttttacgtct gaactttttt atacaccaga   1920
gagactcaaa actttcaggg tcatttgctc agcatgtagt ggaatgtcct gcgcaataga   1980
ttccaattaa tatgaccatg ttcaatggcc ctttaccacc aatgatatct aactgctttc   2040
cacttggctt tatatggtac ttctttgtta cagctgcaac caggtctatc gcccctttga   2100
taaaaatttc agttacccca gggagaagct ttcaacttta ttaagtattg aagtctgtac   2160
atttgttctt ctttggaaga gcagatcaaa agcacgcttt ctaagtaagt aatctgataa   2220
attaggatag catttgcaga cttgggcaat atgtttttcc gtaattgaaa cctgagaacc   2280
```

-continued

```
tgtgtcaact gactatacta ttataaactt cttagcattt aacaagagtt tcttttattt   2340
tttgaaagta aatagaattc cttgattcga tttaaccaat tctttagcat gctgtttcct   2400
ttttgttgtg gttaggaaaa cctcaatgta ggtttagaga tagaaaactg acaatcaaga   2460
aaaaaagcaa ttagatgatc aagttgtgca gacaaaagcc cgtgttgtcg tcttatctct   2520
ggcattaatt actgtaaaaa cttgagcaag ccacttaatt tttctcatct ttgaaaaggg   2580
ataattggct aaattatgtg taagacttct gctgattctg aaattctctg attctaagtc   2640
ttaggcagaa tgaggctaga cacagaatac ccggccattt ttactttggc ctgcttcaat   2700
tccaggtttg gtttggcaat ggaataatat ggtgctattt ggtaggaatg agatatatct   2760
ggatcactta aaactggagt agtaatacct tccaaaggag actagacggt tgtatttctc   2820
ccacagtccc aagctactag aatgttgaaa acgcaccaga tttgaaaatt ggctcttctt   2880
cgcatacatt tacaataaaa atacaaataa attcagattt ctccatagct gatgggacaa   2940
attttgcctt ctgtgttcgt ctgaatctga gggttacctc tgtattttca aagatttaga   3000
ttgcgacctt tgaattccaa ttcgtgggat ttggatgctt aaaaaggaaa ctatataaat   3060
aaattttagg tatgtggttg tgttaaaatc ctcttatttg ttttgaactt agaatgggtt   3120
ttttatcatg catgattttg taacatcatt caatgataaa aatattagtt cactgactta   3180
ctcagatttt ctgaatcttg acccatttcc ttatacaatt gttaatatca ccactaatct   3240
catcagaaaa gaagtgttga aaaactatca agttcatagc agtagattca agatttctaa   3300
aattttaatt ttctcttgaa agctcacatt ttgatcatag gcaataaata ccatctttgt   3360
ttttcttgaa acgacaggct tactttgtcc attaaaatta aagtctgcaa tctgaaaatt   3420
catcatttgt cagtcttttt tttcaagtaa aaatgatgtt ttatgaaaat gtatgctggt   3480
atgagtttct tttcctagag acaactatca tatttcaaga aatgctatat gcacttccat   3540
tttgtaatac ggttttattg tgagtgcgtg atggtgaaga atgactaggg ttcaatattg   3600
ttacagtctt gaatttcccc ttcgccagct tcttactgct ccatttccca tgaagttaaa   3660
acaccaaaag taagaaacta ttaacactga ggcccactca ttagcaggga cccgcttctt   3720
aatgactaga ttttcttgtc ttgtgtctcc cattttctaa tattgtcata aaggttgtaa   3780
aaattcaagc caaaacactt tatatggtat ataatttttt aataaagtta aaacataagc   3840
taatattaca ttgataatta caaatatgtc ctttgacagg aatatctgta atccttcacc   3900
atgtgtgatg cacttggtgc ttgaagattc tttaggaact gcatatatgc agatgaaatg   3960
aagttcttta ctattatcct tatcaacata aatttcttga gaatgtaaag attccctgtg   4020
agaacccaag aacataaatg ctaacaattt attcactaaa actgaaacta agatttgaaa   4080
atttaaagaa gataatcttt gagtgctagg aaaagctaat cattttcttt aatcgctctt   4140
aagcttcatt cttcctgaaa atttaaagtc ttcctaatca gcaaatacta caacgtgtaa   4200
aaatcataca ggtgtacagc aaatgtgtct ttaaaatttt atgtcctact gatttgaaaa   4260
ttaaatcata ttttaaatgt attaagagaa atcccatata aaagaatgct aggatgaatc   4320
tttcagtgag gaattctatt gttagaaaat tctctctaat tatattttga gtgtctggat   4380
ttgtgtattt catgtatttt aagtcaagat atgttttagt agaagctatt acaaaagcat   4440
ttcttttcat ttacaagtta gaataatacc aagtcattct agtaaagtat cctgaaggaa   4500
aaaaacaact atgagtcatg gctgagtttg ctaccagtaa tagaattaat tttagtatgc   4560
attttccttg acctcacacc aatagagcta tttaacaatc ctgggctgtt ctgttttaca   4620
cagttagact tcatggatcc aaatcctggt tacagggctt gaacaggcaa gccttaaact   4680
```

ctgtgtgtct acttcctaaa atataaaaga gaataatgtc actacttcat gggataattg 4740
tgaggattaa atgaatacat ttaaagaatt ta 4772

<210> SEQ ID NO 86
<211> LENGTH: 3625
<212> TYPE: DNA
<213> ORGANISM: Homo sapiens

<400> SEQUENCE: 86
ataagctagg attcgctcct gagaacagca catcaggctt gggtgtgtgc gatgccactg 60
gagacgccac aggagaggct gctgggcagc tctgactgtg gccgaccaca tcaaagctct 120
ttgtaaagca ccaccccgtg ttgagtagtc cctccaggtt ctgcaggggc ttgctcaacc 180
cgtgtttatc cagcagagac accattaaca ttcacataca gaaaacaagc tgtgagcgct 240
tctgcattgg ctggggaaat ggccatgtac atttcatcct gacagatatt gtagtaaaga 300
gtgcccccat ctagcagaaa gttggtcgag gcaacacagc atttcctgca tcatcacccc 360
acgtgcaacc ctgtgctcag ccgtggaaca tcaatcataa caagttgctg ttcagatcat 420
ttcctgtggg actaaccatt aaggacacct tttcttcaac aaaaccacat ctgttgcatg 480
attaataacc acagctaaca attatttagt cttattttgt gtcaggcact ggcttaggta 540
ctttataaac gtgccttctt cacagccacg gtatgagatg taggtactgc tagctttccc 600
ttacatgtga gatagcaccc cacattcaca ggccaaatgc cagatggcat ggggtgctag 660
ctctgagaac acccaaacct ggggcctctg gcaccacccc agccaggata tggggctgag 720
aattgaacta gaaagctctt cccagcagca caccaggagt tcgacctgca gggtgtcggc 780
cctgtggagc tgtccgggca cactttgaac cctggttctg ctgttaacta gctgtgtggc 840
cccgctcatt tgttttcact ggtaaatggg agtaaattaa taacccaccc acagaactgt 900
tattagggac agttgaaaaa atgcatctaa agcagaatag acaaaaatgg atgcaatttt 960
tagtgctagg cctttaagaa gtggccctgt cctagaagca cattaatctc gggctgaaaa 1020
tgatatttta actgaaaatt atgtaatctt catgaatttt ttaaaaaaga ctataaagct 1080
cctcacaatg acttttccag cattgtgctt tgtgggattg gggaggaaac ccaactccag 1140
cctcttcgat tttcatgtgg ctttgatgaa cccatgtgct tttgcttggc tttagtgtgt 1200
gctcctgagg gcctgcttag cgccaggtgg cagtgagccc tgggctgaag cagctcacga 1260
caccctcctc ccctgagcag ctgcccagac agctgtccaa gatggcccca cgagactcaa 1320
ctttgccaaa agagcaagtc aggtagctca gcatactcaa taaaacctga ggggctaatc 1380
ccattctaca gcagtttccc tggtgactca cagtccccccg accttgccta tgcaatgagc 1440
acgtaggagc caagcgtagg agctggaaac actttttcct gcttccatgc aaacccggag 1500
gtggctgcca tcatcgtgtt gtgagcgtat tccccaaaat agtaaccaca ctattctaca 1560
atatcccata tggcgtggtg catgcctgct gagacacgtt ttacagcacc tgtcagggag 1620
gggagtgggt gggcaacagt tagaaagcca ggtcagggag agggattcct gagaactgca 1680
gacccatgag gatggagggg aagcagaaac taggtttaac cccaaggtca tcatttgaag 1740
accacagtta atggcagcca aggctcagga atagggaaga tgcagtaatc aagacaggct 1800
ctctggcagc cttgcacctt ggggtatagg tgaggaggct ggcaagggca agggcaggga 1860
cacatttcca ttacagaaac aaaattgctg gttggagctt tcaagggcac cagaacaagg 1920
tgcacaggga cccaggagct gagggtggga cccagtggga gttgcacaca gccctgaagg 1980

-continued

```
atttgtgccc ccaggggctg agatggggac ctcccaggag catcgtctga gccccatttg   2040

tgcagcatgg ggagcaagtg gagccagaga ccagggtgag acagcctcct ccaatgcctc   2100

gaggctggga tgtgcctccc tgcacctgat gccatttggg acagagaaat gagccggctg   2160

ctcggaagac actctgatag tagagtgtct gcagtctgtg ccttaaagag cctggtaaaa   2220

cctaaaggag aggttcaaac tgagcacaga aactggggag cttcatggta aatttgattt   2280

cctatcaaga caagattagt cagaaaataa aatcctgtgg gagttccagg ttcctttggt   2340

ctgttctctg gggaacccca tttatgaacg ggaacttccc aggatgcaat ttgaatcagc   2400

cctggctact gaggtctctg gctcctggga acaaacagct tttgccaaac aagcactgcc   2460

aggaatcgtg agttcataaa tgaatcctta ggagcaccat taattgccca atgagcgatt   2520

tcaggcaaag aggtctctga tgtctcctag atggcaagtg agtgttggaa cttgccccca   2580

agatttggag ctctcgtgca gctagtcaag gggatgatgg tggtgaattt ccagcgacac   2640

tgccaaggag tgtttgcatc cacccctgac tccattgctt ttgttgcaga gctttgttct   2700

ggcctgcaga ggcacagtgg gtcttcttgc ttggggaggg acactgctac tgtcacatga   2760

gaacacgtcc aggccaaata catatgaggt acagccaact gcgtgctgaa aggtaggaga   2820

gcaatgcctt gggtgcagca agacacatca gcccagcgtt tataaatggt tttttggaaa   2880

catttataaa gtcaccacac ccttttcatg taaaactgta atttgtgtat tatttaacca   2940

ttatttaaga atgtctgctc atggtgaaat gtttgtcttt ccaatattta attaaatttc   3000

atttcatggt ttaaagattc ctttgctttg acttgtcttt atgcaaaaac gatcagcctc   3060

atttttgtgt tctaactgag tggaactatg caaatgtttt gattaaatga taaactattt   3120

tgccagaagc agctatttcc acaggaggct atgctactga attatccaag caaaatggaa   3180

tgatgccagt cgctggcaga tgtagggaaa ctgatagaag cttctaaatg tgtctattat   3240

caagcaatca aaataaattt aaaacaaaaa caaacaaaaa aactcaaaac cttaagataa   3300

agttggtaga catggtcaca cgtagtggtg ggccagtttg cttggtatct tccacctaaa   3360

ctttttggca ctcaatttac acattctgaa actttccaag tttgttcctt ttcatttgga   3420

attcccttcc tatagaaaca gtgttaaagt tggttgtgtc tcaggccagc ccatgagaaa   3480

cttttcaata catagtatat taaaacacgc atctgcaatg aaaagtgtgg aaaacaaaac   3540

gcaacaatat caatcattca aataggaaaa cagtaaaaaa aatttaaaaa attatcttat   3600

ttctgaggtt ggttctgtga aaatc                                         3625
```

<210> SEQ ID NO 87
<211> LENGTH: 2068
<212> TYPE: DNA
<213> ORGANISM: Homo sapiens

<400> SEQUENCE: 87

```
agtggctata ggcacggagg gatcagggag catttcaaat gctgtcacat cagcagcacg     60

cttcccacac aaaccccagg ctcctgcaga ctggccaggg caccagatgc taccagttca    120

ctggaaagta cactgacctt ggagtcgggt tggagtctcc cctctgccat tgcccatctt    180

gagacaggta gttaataaat atatagaatt ccagagtcca ccctgtatcc ccagagcagg    240

tgtatgtccc cccggagcag atggaaaccg tttgtatgct gagagagtct gcagatttaa    300

gatgacagtt gctcttagcc tgcacctgag tatattccag ctctgcaatt cggagttggg    360

cattgaaaag ctaggcctgc ccttgctgag gaaggggaaa gccatatcca acattgctgc    420

cactgtatac cgagccctgt gccccagcaa actcttccag tgtacttcct aactcagtgt    480
```

```
gacctcaggc aagtcgcttg ccctctctga gcctccatct cctcatttcc acccgttgca    540
attccccaaa ccacactgcc ttccattatt atgaagcttt gttattaaga catgagcgag    600
agagaaacat tcctagttgc tgaggaagac attagtaaaa ataaaccagg aagcagaaaa    660
attcaaaatc cccccacgaa aacctgcacc tgctttgtag ggaaggaatt ggctacagga    720
aaagaagggt gaaaaagcca acaacccact tagcaactac cactaaagat caatactgga    780
ccaaaataga atcccatgta ggaagcgatc ttgcttcaca gccccagaaa gaaaaaaaaa    840
aagttaacat agagaagcca tttaaagcag aaaaaatatt tgtatgtaaa aggaaatatt    900
ttaggtagga gttgaatacc aaatgatttt gggtctctgt ggggagtaat gaggcgcaaa    960
cacacaattc tatatgcatg taatattatc cacgctcgga aagcttttaa atcacagaaa   1020
tgcagttagg gaccattgta caaaataaac atcccacttg gtgtcttgct tgccctaagt   1080
tccttgatct agagcggcac tgccagattt ttacagcccc gtaaattaac gtggtgctga   1140
tttgattgag ctaaattaat aagacttgtg ctttgttgca aaataactat tacagtatgt   1200
tgtggggacg cactgccgat aaggaaattg gtgcctttaa caatcccact gaagtttcat   1260
ggaggatttc aaaaccaatt ttaattaaaa caaaagccaa tgtgtggcaa taatgtgggt   1320
gttaaggaga gaaaatgcaa aatgtctttt taaatccatt ttaatatgtc ttaaggactg   1380
gatgatcgat gtggtgagag ccagcggctg acactgagct gggaggctgc ctgtgcgcct   1440
ctctccagtg acaatggcac caggctcacc cggtgggcct ctgcgctggc tctcgatttc   1500
cagacctggg gtcatctccc aggttgaagc tccggggaag gaccccttt ctcagtccag   1560
gggactgtgg cacttcgtcc tccacacagg ctggagcaga ggtagacaga gcctcagcct   1620
ccaggcggct ccagcctcaa agcaggttct ccccagctcc cttaaggcac ctctgggaag   1680
cctggggatg gggattgaat aagaaacatc tggagtgcac tagcaagagg aaggtggtgc   1740
cctgaggcag agcagtgagg atggaaaacc tgcagaccag gcagaggcct agacctgcag   1800
tgaggagggc cccgaggctc gaagctggag ccgctggggg cctggggcca gagaagtccc   1860
cagagccggg gcaggagtgt gagactcact ctaagtctca acctccctca cctcggtttc   1920
ctcagctgta aaatggaaac agtgatagaa tttacatcac atagctgctg tgaggattaa   1980
atgaggttgg tacctgacac acaaatgcct aagatagtta ttgatataaa aagaaccata   2040
atatgacctt ctttttacct gtcatgtt                                      2068
```

<210> SEQ ID NO 88
<211> LENGTH: 1279
<212> TYPE: DNA
<213> ORGANISM: Homo sapiens

<400> SEQUENCE: 88

```
atgcctactg ataaggcccc gtgccactct ctgtatctgg ggctggacct ctctggagcc     60
aagagacatt ggtgagctca cggtgctgcc ctggtttgga cagagagaag tgtcagtgct    120
ccacgggagg gctttgccgc tggggtttct cagaggccag cggtttgacc acggcagctt    180
ccaggaactg ggatggcctg tctggggcag gagcagggag aatggagccg acaggcagga    240
gcaactagaa tcccttgaaa gaattcaagt tcctttaatg tagactgttc ctaatacaca    300
acggggtgat cagagccagt gaaacagtaa gcagaggaac tcgaagttcc gcccagtgct    360
gagattctat ggtttgcagg atattacagc tgtaatattt taaatacttt aaaatcatga    420
atacgtatca gttttaattg atccaggcct aatcttagct agaaggaaga aggcccggcc    480
```

-continued

```
actatctgag ctctgttatt tgacaggctt gcctgtcctc ttggcactgc ttctttcttt    540
cattgtttaa tttattgctg ccacaagatc cttaaagcaa ctcattgagt gtccaggatt    600
aaattagctc ttggatgggt aactatatcg gcctttaggg tgaccaacat cctggtttgc    660
atgggctgag ggatttcttg agtgtggagc ttctaggggt aaaactggga aacctaaata    720
aatcagtcaa cccaaccact tcagcaattg ggcaactggg ttttttccat tcaaatgcct    780
aaaatttttg agactgcacc tctggtgtac ttactaagaa actgttgtgc ctaacgtctc    840
cagatcttgg ttgttgatgc aacaagcaca caacccctgt cacagacatg ccattttaag    900
gccctggtgt tgcatccaag aaccactcag agccttacat aaacatatct tctaatgtcc    960
ccaaagcact ttaatgatga gtgtgcctct tgccagcaag cacattacat gctggctgtg   1020
gagtattctt aggattctca ctgctggctg ccacacgacc ctgcttagtg cttgggagcc   1080
acagctgtgt atctctgaac ccttctttct caaatgctag tgctctgtga cttccagttt   1140
tctggcaaat tcaccgttgc ccggcatgag ccctccaagt gcccttcttg tggttagctc   1200
caaagctgaa tgtctgtgtg caagcccctt aatagaatct agacaagatc aggcctcccc   1260
tctgccaaac ccctttctg                                                1279
```

<210> SEQ ID NO 89
<211> LENGTH: 3490
<212> TYPE: DNA
<213> ORGANISM: Homo sapiens

<400> SEQUENCE: 89

```
aaggttttac tttatcacat taccaccaaa acatctatca aactatagtt acttagaaat     60
agatatattt taagaaccca cacaacacac ccaaggacat cagaaagagc gttccccata    120
tattatctct gggctatgcc ttcccatgca gcgaaaatgc cactcaaatt aggctgttca    180
gaaaacagaa gtgtaagagt ttaaattccc ttcttctttt acagaccaac tgtaaaacaa    240
acaacctgta gtatcaacaa taaaaaagta attgcttgag cttctcattc tagaaagaca    300
gagaaagagg gaaggaagga aagaaaagga aggagggagg gaagaaggaa ggaaggaagg    360
aaagaaagaa aaaagaaact ctcaatggct ccccactgcc cacagaaaaa ggccacgctc    420
tttggcatag cacatgttcc tccataatct tgagaaccct cattcctaga attgccttct    480
cctttatctg tcctctgacc tcttatccct taggattctg ttcaaatatt atctcttttc    540
taataattta tcatgctgca tatgtgtctc atgatgcatt taatgatttg tttgcctgtc    600
cctgccaata tgttgtgatc ttaacaacca agagcttggt gtttgctaat acctctatct    660
agcattggat attgaaagga cagtttaagc accacttttc tgtaaaatgg gaaaaaatac    720
tacccgtcag cattttcatg agattaatat tatacgcaga agggcctagc atactgccta    780
gaatgtgtac ctatccatta gcatcataat accaacaata tttaagtgaa tgcttaaatc    840
ttgctttata aaattatagt cacagttatg caaaatatac ttcattagat ttgggcaaag    900
ctggcaaggt aaaaggcagt ttggaggctg agctgcgggt gacttctgga atgctcattg    960
ctgactcact tagccgtcta tggctcagct tccaagactc gccagtgagt attaaacacc   1020
agccagccca caaggtaatc agtccaggag agcagctgat aacattcctg gagttctatc   1080
aaaacactga aggcttacta tgaggcaatg acagtggtgg atacaaaata aatcaggtgt   1140
tttcctggct ctcagctcaa gcttcatgcg ggcagcagag acatatacaa gggacaacaa   1200
gacaagctgg aattggcaga tgttatagta gagatacaag caaatacatt gatggtgcaa   1260
aagagagatg aattttattt gagggaatgg gaagcaggaa cgcaggttta ttctgtaccc   1320
```

atgctgggcc gggggtagct catttggtct tctaatatgg tgagatagag aatgttagat 1380
gagcacccta aggcccagag aggtgagata acttagctaa atcacactga tagtacactg 1440
gcctttctgg ttttgactgc accagctaat ccccaaggga gctgaaatgg ccacatggaa 1500
gcagagcgcc aagtagggag aattgagtgc cccagataga agggtgtaga caaaaccata 1560
gaaagcaagg gaactgtata tttaaacgtt tcaatacaca tacacattgt gaaatgatca 1620
ccgcaatcaa gctaacatat tcacctcaca tgctttttat ttttattttt tgtggtgaga 1680
acctactctc tcagaatcca gtctttacct atagtcactg tattgtatct tagatctcca 1740
ttacttattc atctgcttag ctgaaacttt gtgccctttg accaacaccc atggcaacca 1800
ccattctact ctgctgattc tacctacaag tgagatcata cggtatttgt ctttgtgtct 1860
ggcctaagtc acctcacata ctgtcctcaa ggcacaccaa tgttattaca atataatgcc 1920
cttctttgac caacttaagg tatttcgtat ctatgatgcc catttcctgc cgacatttgc 1980
cccagtttat ggatcggatc actgagacaa gcacttgttt cagtaacttg tgcaaagtca 2040
tgacacaaga cagagcagac ccttaaacac ctggtgctaa caatctactg tgctctagac 2100
aaagtgaaga agatgtggac cctgagcctc agtttcctca tctgcaagat ggacataata 2160
ccttgtctca aagagatttt gcaacttcac aagaccgcac ggcgggggta tctactgata 2220
gggagataag caaatatttc ctgtaaccct ggaaatgtca ttagggccct tagcaaaaga 2280
gttctaatgt tcagagagac tatctggaag agagaaatct acaactgaaa gagatgggca 2340
ctcaagagga aaccaccacc tttgcacatc tgagccacta acaatgactt gttgctgaat 2400
atgcttctta gctcctacta gtaaagtctt gtcaaacagg aaacaggttt ttaaggcaac 2460
ggggtccctg tgagttcaaa cttctgcttt caaatgttct tacaagatgc acaattggca 2520
ctgacttaca ggaaatattt aattggaatc ggaaggcgct ggctccacgg gcctggtttt 2580
atattgtcta caggcttctg ctgaaatgat tttggtgtgt aagcaccagt ccgtcactta 2640
tttattttgc caagggggag taaaaccaaa acatagccca aggggtttct ggggcacaag 2700
tgcaatctgc acagggttag gaaaagagtg ggggagaaaa catgcaaaaa ttcctcttaa 2760
aaaggaaagg gctgggactt ttatgagctc agtatcagtt gcttgagctg ataagcactg 2820
gtcattaaag gaaggaaaag tcacctttgt gtatataaaa tatacaagat tcgtagtctg 2880
aaaagactga acaggaaagc attgggtaaa tagcggatat cccttaaagt ataatgtgaa 2940
aatcaaataa cttcaagaag gttttaacaa caatatgaca gtctagcgca ccttggtagg 3000
agggtggggt gcggacagaa gaagagcatt tcctggaaat cctataatga tttcattttc 3060
taatccccaa atgaccttgg tccatgggga ggccctccct ccctcacccc aggccttggt 3120
tttttgagtc ttcatctgtg tgtcatcatg gcccttagat taggcctccc agggtagaca 3180
acaatcctcc tgtctctcag agaccactaa ctcttcctta tcccttattt ctacttcctc 3240
tcggaacctg cagattccgg tctgataagc atatctgcat tagaagccag atttgcatat 3300
ctcaggactc acccttggaa tattcaacta actggcctgt ccccattcgg tcacaattgt 3360
aggttcctgc aaaatgatgg tttatgacaa gtgttcttcc ctcaggctag gttagaaaag 3420
attttctcca gtagaaaaca gacagaaaaa taccttattt ttgtagaatt tctaccatgc 3480
aggataaact 3490

<210> SEQ ID NO 90
<211> LENGTH: 674
<212> TYPE: DNA

<213> ORGANISM: Homo sapiens

<400> SEQUENCE: 90

```
tggacaagag acgcttctgc cttaggtggt gagagaggag cgctggcggg gtggaggagg     60
cctctaatag agagcgggaa gagttatgtt gctttcccag ttagaatcac aggataataa    120
agccagcaga ctccaagccc ttagcacaga gcgtccttaa tgaacagtcc cctcattctg    180
ggggagcaca gccctgagca cagcctcaga cgtcaacatc ccgaaagagt gagagtccca    240
gtgccgtgag tcagtgtctc actgagcttt ccccacatgt tcctccttaa aatgaatcaa    300
gaaaaagaaa gagacaaacc agagaacagc ctgatgtctt tggccagatc tcagcatact    360
ctggacagca aagcaagagg agtctcaggt tcatcgtgga aaacgtgtgg tttctggctt    420
ctggaattta aatgattgtg tatcttcttg tcttatcaat tatccccttt acgtaaaacc    480
atctcagact atgtgactga acgctaaacc atataatctc taattcagta ttcctctttg    540
tagacccaga agaagatacg agacaatgtg gaaatgcaag aacaagaagg attcttaact    600
tttacttgtt tctaaattgt tagttgtatt gaaactagtc agttgaatgt gtcccattca    660
cactcttacc tcac                                                     674
```

<210> SEQ ID NO 91
<211> LENGTH: 4676
<212> TYPE: DNA
<213> ORGANISM: Homo sapiens

<400> SEQUENCE: 91

```
aaaatttatg ttagcatgaa cactgactcc ttggaaatta taccaatgct caacaagcaa     60
atttttagaa agaaaaatag aggaggacaa agaaggaaga aggcaagctg caactataaa    120
tttctaaaga gcagcttgtt aaataaatgg tttctctttg gaaggcagat gtttatcagt    180
aaatgctcct ctgaagtgca gcttgttaat ctgcagggag atgtctgggc acttttgttc    240
caaaggtcgg gatgagataa agggggaaag cttgacagct gctctgggat ctgtattcat    300
gaagcaaccc ggaatcaggt ttatgctcac agctaatcac agactttcct tctaacatac    360
agaatggtgt gcccacattt gtgagtacac aaacgtgcgt gcacgcacgc gcacacacac    420
acacacctta cctgattctg gcatagcaat aaggagatta atattcagaa agagttctgt    480
accagaactt tgtaccagtg tttccaacag tggtgtacag cacactggtt tgaaaccagg    540
cttgaagtct aaaacaagag agctacctac tgtttaaaat cttgggaaag acttttaaag    600
aatgttattc tccatgaggg cggggaattt tactttctta gcattgtatg tcagccctgg    660
cacaggatct agcccaatac atatttgatg aatgaacaga taaatgaatg aatgcacaaa    720
tgccatatta cagcaaatat ttcacctctt ggggatctta gaggaaattt gtccagccag    780
catttcctct ctctaatatc ataccactat ttgagctcat tggaagagaa gcttaaaagg    840
cagacataaa tgtttattcc tctatcgctc agccttgata accaaatacc aatcaactct    900
acaaaaaagc acacccatcc ctctggatgg aatgggacat ccatttccct acagaaggca    960
tgttttatcc ctaatgttgg taggaaaatg gttgggtaaa gtcctttccc tctccccatt   1020
ttgggggcag tcatgtcctc attactgttt cctctctctc ccaaatatat ccacaaatgt   1080
ttgctactta tattacaaaa cctttagaaa attctctctt cccaccttcc agagttctca   1140
actttcccgt cttcaaccct aagtaaaatt tcaaaggtgg catccaaagc caaaccgcac   1200
ttttcacttg acaaaaccca ataattactc tttcttaagt cagatgctcc tgctaatctg   1260
atacaaacca tccaaaatta gcgccttcct tccccttcaa tgccaatggt attaaatgac   1320
```

tcaactctgc ctcacaccag ccccttgtca ggacacactc tcttgttctg tagcatcttt 1380
tccattcacc atgataaacc atcttcttca cttcagcacc cctctctata gcttaaataa 1440
agtcaggctt ggctctttcg acacagggtt atagcagcag cagatgctct gctatctggc 1500
atagttggga aaaatgttgc ttaatctata ttccagttaa aggacagggg tcacatttat 1560
caaacttggg tggtcaacct tcaaatacag tgattcacat ggtaaagtgt acttagtact 1620
gaagtgacac tgaattttga tgagtctttg atgattcaga aggtactgca ggaatattgc 1680
aacacttatg agtcatcatt attatcagcg atcactggat tgtaggtttt gaaaggccgc 1740
tgatggatgg accagatttg cttctgtgca ctgggacaca gcacatcctg aacttgcctg 1800
gaaaatctgg agggcactag ctggcatctt ggcgtctgtt caacaaatat ttaagttcct 1860
actatgtgcc tggcagaatt gctagatttt tggttctgac atatctactg catatgatga 1920
tcttccttga gtgccttagc aaatagaatg ggtaccatgc ctccctgtct cttttaggaa 1980
aaggtttgtt ctatttttcc cagtgttaat tttaacaaat ggagaaattt cacagggtct 2040
ttctcttgat tttatctgat ctgttgggaa tatggagtgt aaagcataac taggtttctg 2100
aattattttc agttgacaat tttctaactg caaaagagaa caaactcatt tctatgccaa 2160
acaggactaa aaaacattca tggatgtgtc cacttccttg taactcacca atttattttg 2220
gttggggggg gggcggtaag tccactgatt gatatttgat ccctaacttt attcaagaca 2280
agatttaatt tgaaggccca gtggagagaa atggtcctgc agaccaggaa gcagtcctgg 2340
ctctgctggg gaccgctgtc tgtacttcag cattcccaat ggttttaaac tggatgttag 2400
tacttgccca tagcaatggg aaatatctga tggtgactgg aaggctttat atgagccatt 2460
gtctgaaaag agctgcatta atctatcata tcaggtattt ttaattaatg gtatttggca 2520
ctatatacca actcgatttt atatatttta ttgaaaatat gcacaaaata aataaaacaa 2580
tgtcacatga ttaaaggtaa gcattgaaat tctttcagat aacctggagt ttctctttgc 2640
cgagtttctc tctgggtgaa gaaacaagat tgtgagagtt cagagttcct tcctcacctg 2700
ctgcaagttc acactcagca ggtcgccaga ctataataat acttaaaagc aagggatgag 2760
gcaaaaggca tctttgaaaa ttacatttga agaatgcagt gtaaatggaa ttagatattc 2820
cagtctagtc acatcgaatc tttccaaaac tcatcatttc tcccatctct tagcaaatgg 2880
tccagccatc cctcattccc caaactggta tctgggcact gctagcagca aggatgcacc 2940
actcttgccc ctcacctttc tagctgctgt ttaccctaag atgttccttt ccttaaaaac 3000
tgtatttgac atatacaaac attacctaca aaatcaccat accagatttt aggttatcat 3060
tccactttgc ctttattttt tataatatat taagtaaaca tatttaatat gtaaaaaact 3120
gttgcatata gtaaacactt gtaagcctac caggaggaac cagaacagct acttggcatc 3180
tacctatgtg ctcctgtccc ttccacttcc tccttctgtg ggtaattact atgctcaatt 3240
ttggtttatc agttaccttc ttttttttta gtatacgtat gcttagacta catattcttt 3300
ggttttgctt gtttttgggc tcaataaaaa tagtacgccc catgtggtct cttcaaactt 3360
gctttttttcc tattttctga gattcattct tattgtgagg tatagctgta gttcactcat 3420
ttccactact gaataatatc ccgtagaact attttcctgt agacagaatt tcactttttc 3480
cagttattaa cttaaatatg taactatgaa caacatgcaa gagtttgctg gacatactgg 3540
gagttctgca aatgttcaag tctgtaaggg ataattgttt tttagcagtg gtatgttgta 3600
caagtcccta cagatctaac actgtagacc caacctttgc aaatcttatg gatataaaat 3660

```
ggaatctcac cctgaccaat gctacagaac atctatttat ttaaaaggta gtcttcacta   3720
tttttctatt tttttaaata ggaattctct atatttgtga ttatgaatcc ttcatcagtt   3780
atttgtatta taaatgtctt ctcatgtgga tcactcactt gcttaatata agccttgagt   3840
tttaacagaa ttgacttaac catcttgtcc tttatgatta ctactttatg tctcaagaga   3900
ttctttcctg ccctaaggct tttttcatcc aaacactgac aatttttgct ttttgtatta   3960
agaaatgagt gactttatgc tgcccacttg tccaactccg cacgggatat cagagcccag   4020
ctgagaacct gctcaatcct ggaaacaata gatgttaaca cccttaacag taactttctc   4080
tcctcatttc ctttttgggg tacggaaata tgaaattatg ggagacgaaa atgcccagaa   4140
agcatggctg cttgaccaca ctggggcaaa tggcttcagt gtttctgaca agcaagcagt   4200
gagcttttgc caaagagttc tgcagccatt tagtccagcc ttgaaaacga ggtcttccga   4260
agagaacaga gctacacctt ccccgtcaga atccactgtt ataaccactt agattaaaat   4320
gccccatttc tcacagtatc attttgtcac agggtcacac ttctctattc aactcagttt   4380
caggcttttc ttctaagagg aaaaaaagac gactaagtgg cctcctagat tccactgtaa   4440
aaacagaaaa aagcaggttg acttgctttg aaatcaaacg atgtcttcag tctgtcccca   4500
tctcgaggga ccagggaaac cacgaaccct gctcactgct cttcacgcaa ggtcccaaaa   4560
aaagcgcctg ttttccaggc actgcaggcc tgctcctcta caaggtccac taaatagtct   4620
tcgaaaacca gaagcaggta agtgtcagcc agatgcactg ttgttgttat ttttaa       4676
```

<210> SEQ ID NO 92
<211> LENGTH: 11241
<212> TYPE: DNA
<213> ORGANISM: Homo sapiens

<400> SEQUENCE: 92

```
ttagattgtg accatggaaa tgattgttag aactttaaag gtcatttcct ctttgcagaa     60
agaatggctg ggattagacc tttatgttct ctttttggtg acccagtccc tgagccacat    120
gggatttgga acatttgaag agaatactca atgaacacag aagcagtttc ctaatgctga    180
gaccactgaa gagcattgtg tctcagtgct aagaaaaaaa aattaatcaa agtggacaca    240
gttttctaga tagctatgtg atctttgaca agttacatta tttctctgaa cctattttct    300
catcataaga ctggcaaaat gtctcaagac atcatctgct cactaaagtg tatgcatcct    360
tcttcctggg tacgccactt tcgggaagtg gtatttcctt ccacagttta tccagtcctt    420
tctacaggat gatgcacata gtgacctgac agttcccatc ggtatcccac catatctctt    480
ccttgcaaaa gggcagctac actttctgct gtccaactta ctcaccaata aagactgcca    540
gatgtagaaa aaaagaaccg aggaaaatgg gcagaaaaga aacctcttga cgtttgtttg    600
aaattaaccc attgggtgac cacagtaatg aactacttct cccactttca ctggattggc    660
agctttgatc cggaaatccc aggtgcctga gtgaggacag agctatgaaa attcaagcgg    720
gatgacattt tccaaggaga gttggattag tgcaggggaa aatgctgcca agctgaaaac    780
cttttagtat ggggaacgag aaactgcata agcaacatca tacctgcaac atgagtttat    840
tcacagtgaa gagctgtgac ctttgtgtga aggaaacttg ggctccgcag ccgacgtttt    900
tctaatgcta atgttcccct tcccagctgc aaaactcatc tgcactcttc tcatgctttt    960
cttctccttc ctgctctggt tatttttccg ggcacacttc ttacactgtc agaacttaat   1020
attattttac aaccctgagc caaaccttgg gagcttgaag aatagctgag aggcagacac   1080
aagcatgaac tgacccctt tacacacacg tggctcttaa gatagggaa cccaggactc   1140
```

tgctggtgtt gtgggaaatg gtttgtcctt atctgaactc agtttgtgtt ggggggggctt 1200 cttaaattct gaggatgaga aagtgggttc agaaagtttt actgctctag tgtcacagac 1260
ttagcaatga taaagtcagg atttgtatct agatttactt acaccatgat ggcaataatg 1320
gccatttact gagcatcgaa catactctaa ggacttcatg tctatttctc tcattattct 1380
ttgtaattct atcatcatac caattttaag gttaaaaacc ttagtgaggt tttattactt 1440
gttcatgtct actgggatga gactttatga taaagaaaaa gcgcaaagca aatgagagct 1500
aaatgttcct cttgcccatg ccacaggtgt tccaatagca catcttcaat tactagtttg 1560
atcttaagaa tttcataata agaacctaat aattaggatg caattgaggt gcaattctaa 1620
gcactttcag atcatcagca atccttctgc caacaaaaga ttgtggtgtg gggctaacga 1680
cactttacag ttatcaaagg atcacaccca agacagacgg atttttctaa ttgtaattgt 1740
ccctcttgtc acacctcact cagcttcaag gagtgaatgc atgaaagctg ctgagaaggt 1800
gaataattat tccaggggac atgtatgcat ttcatacgtt tgagttcagc tcacagagag 1860
tgaatcaccg aatactggac cataggcatt gtgtctatgt ttccaaaaat atcacaatta 1920
tttatggtat attattgttc cctctctttc tgataagaaa acctttcctc tagtgtattt 1980
ttatcttctc tcaggattgt ccacagaact tggactgcag attcgttagc agggactggg 2040
gctgctttaa gtcacataaa attctgtcaa ttgtctgctc attacgtctt ctataacata 2100
ttgtagtctt ttggttttca aatatactac catgctattt ttcagcaggc aagcctgggc 2160
agatattttc tccattggtc tacagataat gctattttcc attttctgcc ttggaaaaaa 2220
ccaacatttt tacaaatgtc tattgttttc ccgattcaaa gagctatcag catttatttg 2280
atataacttc caaaagagat cattttagga gtacttacta catatgagaa ttgtcttcac 2340
acaccctgat ttccatgagc atgagaccag agaggtactt ttcccctaca gtggttacag 2400
gaggttgtac catatgaaaa tgttttaaac catctaatgt caacaatttc gtacggttcg 2460
atctaatacc acatgtggaa catagcaagt aaataaatat ttgttgattg gatggtatgc 2520
atttagccaa ctaaaactta aaggaggtga aactatttac ccagcagaga aaatcactct 2580
cttcatatcg gcagcaagtg ggctcttgtc tttgagacaa aaacaaatct ttttgctgct 2640
tcaattcatt cacttgttca ttcattgacc tttcagtaat tatttagcat cttatgtgac 2700
ggcaccatgc cagctgagaa aatgcaagcc cactgtcaaa tgttgcaaac acctagaggt 2760
gccacttcct ggtgataaga ctgaggaggc aggagccagg ccaggaaact cttttaagga 2820
gtttgtattt tatcttgagg gaaatgggga ggcgtaaaag gtattaaaca aggcagtgac 2880
ctattcagct ttatgtatta gtacagatca tctgaaaaat gatttgagga tgtttttcaa 2940
ctaaaaagtg aactaatggg agtttttgct tatggaatca aatttgtagt tttggtatct 3000
ttccatcttt attatattgg tcttttcatt atgtcaatta tatctctaat cattttggag 3060
tggctttatg ttcctaagga tggattgtcc tgggtggagg agtgagttca gatcacctat 3120
aattgctgaa aatagaaatt ccctttacca ggacttcagc aatagacaga catgagcaca 3180
ggacctagga agatgtatct tgagttgctt acaatttgca ctgaaaataa aaaaatcttc 3240
ccttccctcc aacaagagcc tgaacaatgc tctagaagag ctattttcca gcacacactc 3300
atgtctcttc tccaacactc aaagatttaa aagagtcgct gaaaagcttt taaactgaaa 3360
gacagaaaat aatactttca ttgcattatt ttaagcattt atttttttct tgttgtatca 3420
tttaattttt gtctttgttt tttatgaaat atttacatct gtctcattat aaaagtgaat 3480

-continued

```
taagttagca tatttagtaa atacctacta ggtagacaga ataatgcaga catgttagga   3540
tggcctggag tagagaagtt ggaagggaag tatgtatttt gctgacttga atgagttaca   3600
ataaaatcag tgagtaagca ggaaaacaat tccttcacta agaattggca ggtcaaccat   3660
tacttccaga taagtacaca gtcttgtgaa gatttgttca acaagtaatt actgatcatt   3720
tgccatgtgc aaggtattgt gccatgtgct ggggggttag aaaagaatca gaaatgaata   3780
tactcaagga acaatgccat ttctatgaag actataaact gtgaaatgat ctttatcagt   3840
caagaataaa caaaacaaaa cattgactac aatcacatcg ctccagcagc gtcatcattt   3900
caacatctat ttggcttctt tgcttctgta actgtgtggc tacaatttat ggttgtaaat   3960
atggatgaaa aatttaaaat gttccttctg gaaatgtctg gtccaaggac ttaggatcca   4020
acctgagttc tttgcatggg agatttgggg gaatttgcaa tcgtgactca aggaaagggc   4080
tcaatttttt tcctgaaatc aaacttctct tacaagatgc atttgagtac attaaaggta   4140
aatagcacgg aaacatatgg tttgaatttc ccatgaaatg tgaaagtttt gataagcaca   4200
tacttcagaa agataatttg gcctctgtaa aaccagaaca tttaagaaat ccttctagag   4260
actttgccaa aacccagtgg actgtttttg cctacagctt ccacttcagc cagaccccta   4320
gtgacccggc caagtgaaac agagaactca gcatcttctg aggggatgtc tgccaatctc   4380
aaccctggta tatgttcaag ggcttccagc tcatcctgtg agccaagaga acaatttgaa   4440
aacgctggac tcttagcata tctgcttcgg gttactttga gagacagtgt gtgtgagaac   4500
aggatccatg ctggaaacta tttgcaaaag ccccacttcc ttctgccagg ccagcttctc   4560
cgcaacccag acagtccgag aacaaaaaaa caaggactat tgtcaaatta atagcactcc   4620
ctaaaaaagt atggcaggtg gtgagattct tggccattga gttccagcca aaacatttca   4680
catttttttc tcctgaggga ggcactggag cttgctgtga gtcagaagtg gggggctgca   4740
gcagagaggg ccgcttgagc atcttgcctg ttcctgatga gaattagtca attcttggaa   4800
agagggaaga gctcgccttg ctctgctacc cacttccaga ttctctgctc agccttgggt   4860
tggagagtga gtaatctaat gtgattctgt ttattccact caatacatat acattactga   4920
gtttttattc agcatcaggc cttggctctg tctctagctt attttctcac atggctatta   4980
cccacagcaa ctttagaaat aacagcccag tacaaagagc caaacttatc ctttcgggag   5040
acaaagacga tatttaaaga taaccacaaa gtatggagtt agcacagagg acagtggaat   5100
cagaagactt tgaagagatg gattctaagt aggttttgat agaagaatga agttttgaaa   5160
acacagggat gacccttcca ggcaaagaga aacatgtgca aggacatgtt gttttcccga   5220
atgaagctct ctcccatttg taggaaagtg gatgggagga cagcagagga tgccgagaaa   5280
ggctagaaca tctcaagctt gttccactgt tttcagctgt aggtaaatat taaaatatgg   5340
aaaacatctt tctcctagtt caagtacctg gtgtttaacc caatgtacct tcttcatgca   5400
ttgtgtgatg tgctcttttc tactgcattc aatcaaagcc atcaagccca attttctata   5460
aaatgaaggc ctctgaagaa agggaagaat ggctctgctg ttcgggagca ctcacccagg   5520
aggtacctag gtgcctggga ctgtgcaaac aaacttgaga gtatattatg atgggaatgc   5580
tgaggaatga ggcagattgg ggttgagatt ccaatgggtg agctggaaat tgtctgggaa   5640
ggaatgaaat cctgaactaa gcaaaatttg gtgctgtttg ccctatggca caaggtcaga   5700
aagtgcagga gtcagggaga ctggggtctc gttccagctg aacacaactt gctgtgcaat   5760
catggcagat ggctttccct gaaagtgaaa tggattagac catgaaactc aaagaacatt   5820
tcagctccaa tatactataa tctatccatt gtcagcaaat gctcaacatt aagttaaaat   5880
```

taaaacaaat tatgttcaaa tgtatacatt cgaaagatca gtgaaaaagg gaatattagt 5940
acaatgtgct agacacatgc tatgttctta ataactgtgt aaaagtttct ttcatcccta 6000
ttttgcatat gagtggatga aggctcagaa aagttttccg aagttctctc aactcccaaa 6060
tgagagaggc agggtttggt agcaagtcag tgtgggtgca aagcccctgc tcctttttttt 6120
tgcaccatca tcctgaaaca aagtttatta agcactttga gtggacgagc agagtggtct 6180
gccttccaaa gtcaagagga tgctgttaat ggaacaggga aatgccaagg ctgtttccta 6240
atcttggcat agaagtgtgg catcatacag aggctgctct gcacaaagtc ttgtggagtc 6300
cgccactggg gcaaagttac aggggtaacc aggcaaactg gagcccactc actggaaaca 6360
gcttccccac tcccccgcct ctttatccag gtcagtgggg ctagctttgc ttcaacatgg 6420
ccaataaaac ctcaccccag aaaccttccc cagtgtaacc ccaattggag aaaagccatg 6480
tgaattgaag cccagtggcc aattcggatt cagtctgagc aaggtcatga aaacactgca 6540
ttgctggctg gttggttgca ggcctcctgt aaccaaataa tcacaaacct tgtggttaac 6600
acagaaattg atttctcaca aatatgaaaa agttactttc acatgtggaa gctagatgtc 6660
taagatcaag gcatcagcag gttgaggttg ttcgaggcct ctgccctttc tccctctctt 6720
cttctaagga caccaattgc attggactag ggtccatctg tgacttcatt taaccttagt 6780
catctccaag gccttaactc caaatacaca ctggggatga agatgccaac atacacattt 6840
tgagagtgca caggtcagga aagaaggtgt tctagtgaaa ttttcattgc aaatatattc 6900
atggaaaaac atgagggcag ttagcaatgg gatttagaaa cacttagaat agtagttgca 6960
aatagatgac cacattgctc atggagaaag tgattctttt caagtgactc attcaaaatg 7020
gctgctgcat agcacatgat gaaatgctgt gacagatgag gcagaagaat gacctcttta 7080
gcgatggtta cttgaactca ggagaaccag gaacactttg tttggtggtg acttcatctt 7140
gaaatctttg gcctagcagc ctacagatgc tgagtgattg ttaaatggac aagtgtattt 7200
gcaggaaatt caattcctgt tttaaaatta cttattcctc cttccaaagg ttttgtcaat 7260
taatgtgaca cttaaaagcc ctttgatgtc ttagactcag gaagctgagt gtgcaccaga 7320
atgcacaatc ttctccagaa acgctggaaa gcatctttca aagcctctgc ccttaacccc 7380
aaccctgggg atctctttct ctttttgtgt aggtgacgga gctgagggct ttcttgctga 7440
ggtcctcagc gttcttccct catcagtcca atcctgctct gaaggggcca gtgcctctca 7500
aggtgcttcc caacatgaag gacacttgtt atcctgtctc tggcgatcct agctcctgcc 7560
cagtctgctc actggaatga ttcgccaagg accatagata gtcacactgg aggatctttg 7620
aaaacactca tttcaacccc ttcattgata aaataagcaa ataagaccct agaggaaggg 7680
actgttttag gagaatcagc aatttagaac ccaggcttcc tgattaccat ccaatgtctt 7740
ttgaatacgc cacatgtgtt tctctgagtt taatttcaag gcactctgtt aaacctcctt 7800
gctaagtgtt ctgatttttt caccacgtgc tcatttataa ttattactcc ctcagcattg 7860
tagtaaactg tatctctgtt ccctgaatgc actgtgcatt ttgcaatgaa cctgttcatc 7920
ttgttctttc aggacttatc attcatactc tcttcttctc aagtgttact attctcttct 7980
cctagggcac aaatcaactc aagcattgaa ttgctttatc attccaggta ctaaaagttt 8040
aatttcagaa gtttcaaggc atgggcattt cccacttctg gcagcatctg ctgcatcgtt 8100
cctttcccat cattctttcc ccccttcatc ctttcccgtc tcaacttaga gccacattca 8160
actaaaaatt ttcaagcaga tgccatgtca gatgcttaat atgtgtgagg tcatttcatt 8220

```
ctgacaataa ttcagggtaa acattattat ccccactttt caagggagaa aactgaggct   8280
caggagggtg acgaactggg accaggtagt gaagaaatag gtggtccaca tgtgaacaaa   8340
ggttctttcc tgctcactgg gctttaggct acattgttac ttaggtttga tgggagttct   8400
acttgatagt aaaatcaggt gaaattatcg ctgtattcca tttctctggc aatagatgtg   8460
gtgacgtgct gtctgccagc attatgcatc gagttacatc tcttcccggt tcccacatcc   8520
tgtggataac tcaagcgcca gccagccgtt aaaatcattt cttccaaatg agggtggtgg   8580
gacctgacat gtggatgttt cctgcttcca aatccaagaa atgaaggtaa ctgactccaa   8640
gctaaaagag aatcatcctc atctgtggca tcacttagca gtgttctagc tgcggctctg   8700
cagtcagcaa ggataagaaa gctgtggggt cagagctgtg gaaggagggg agcttgaatg   8760
ggaggaggta ggagcaccct gcctggagat gcagcccaga ggaataatat gtgaatctca   8820
catgactcag cccctgtgca ggtaataaaa tctcaacgag acatgagctt atttaagaaa   8880
acacgcagga agaattcatc attgatgtgg ctattttggg agatgaaagg gagcgtgaaa   8940
cggaggaaca tgtgaaaagc attcaagctg agtgagtgtg atagaaaact aagatttccc   9000
ttcataattg aacagtaaaa atcaagtgtg tccccatctt tcaagtcttc ggattggaag   9060
agtgaggttt gggtgcagat gttggcagtt ctttactccc tggataaaca gattgtggtt   9120
ttgatttgga agggattgct tttttatttt attgttgcta agagaaacca ggtctcaaat   9180
gcaatctctt gggctgggaa tggagattcc ccacgccccc ttgaacgtgc cagcatccct   9240
gtgaaaagag gcactgctgt tagatgctgc tattacctca tagtgagagc agaaatcctt   9300
tttctatcac ttgcaggaga ctctcagtta aacacgatca gctacgaaga tgacgggaca   9360
caggggagag tcttctgcct ttgatgagat gtgccagatg tggatgttcc cagctactct   9420
attctctccg ggttctcac agcagccttg tttatcttcc agacatccat ccagccttat   9480
atcccaagta ggaaaggggt ctccaacctt gattcctttc attgtttttc ctatctctga   9540
ttctgtgtct tcctacttct gacttctgac atcaattgtt cattcagtcc cacatattta   9600
tgaagtccta ggtctctgtt ctcccgtcta agccccctcc cttcactttt tctgatgctc   9660
agcccatgga aacacttgtt caccatttgg attttcttcc tggttaagcc acccagggca   9720
aacatccctc aaaccctact gccctgtgac tctggcatcc gaaatactct cagggttgcc   9780
agaccccttt agaaaaccta cacattcacc ctgcagtcta ccttacgaat gccacagttg   9840
ctctgatatt gtctctcttg gcctagaaaa catcaatgac tttctactgg tccaaaccaa   9900
tcccaaaagt gtctcctgag gatgaatcag tggagattga ttctaataca agattcaaag   9960
cagtgtcttt ctgctctttg taaatattta ttgaatccct ctctgtgtag gaccttaata  10020
gattctgtgg atacagtgat gacaaattag atgtgtgtgc ctcgtgatag ttaccatttg  10080
tcatggaaga catcaaacaa ctaacactgt gaagatagtt tgaagaaagg caaagggtgt  10140
tatataaatg caaaaggggg aatgggtctg gcaaacatag tctgaaaaat cagagaagat  10200
tgagacctag agtgtgagga gggattcatt aggccaggtc cagggacaat agtggcaggt  10260
ggcaggaacc atatatgtca agaccatatt gctggaaaca gcagatgtgt tcaggaccca  10320
gaaggaaggt ggaatggctt gaggacatgt gatgctttca agcaatgatt cttgagggac  10380
tttgtataat catctggaac acacactaaa tatctgattc tcatccccaa ttgttgaata  10440
agagtctctg tggatgaaac tctggtagat aggatacaaa aatggttgtg tttttcactc  10500
tctcctaagc ccatgacatg tgtgatgtaa cttcgcagct cttggaggtg gggtctcttt  10560
ctttgatctg ggctggtggc caacagaata aaaagaagta ttgccaacta tgaccaagac  10620
```

tcaagaagta gtgtgtgctt ctgaccctct ctcagaacct gcccccctcc ccaaaacaag 10680
agcagactag cctggtgcag aatgagagac cacatggagg accagcctat tatccctctg 10740
agaccatcct agatcagcct atagcaagcc agtccctgac aagcaagtcc acccagatca 10800
gcagagccgc ttaccctagg acatcagtaa atccagagac caatggctta aacaataatc 10860
attgcaacaa taataattaa gtcactgagt ggttatttat tctgttacta gagacaacaa 10920
ttagtgagat aggcagagga ggtcagcttg agtaggactt tgtaggcatg atgtgaattt 10980
ggtgttttgt cccaggagtt atgtgaaatt actgaaatgt tttgagcatg aagtggcaca 11040
attaggtttg tgttatagaa aaatgaactt ggctattctg tggagtataa atggtgggag 11100
cagggattta gaatgaatca taggaatcaa cttggtatag tttagttttc ctttaaatat 11160
ctatattggg ctttagcaat gtatgcgatt acaaggagga aggctcatat cctgtcttta 11220
aatctagtga gaacagaaag a 11241

<210> SEQ ID NO 93
<211> LENGTH: 1397
<212> TYPE: DNA
<213> ORGANISM: Homo sapiens

<400> SEQUENCE: 93
cttagtcgca ggtccccact agtgataaag gaagcgatgc tgctgcataa tagagaattt 60
gtctgacttt gcccagggtt tctggcacag accttatatt gttatccatg agacccttag 120
accacacttg agtttatgaa ctcacgatca gctcctagat agcttcagga tgagagctgc 180
tcaccagaaa gaccagctgc atcattcgag ggctgggact ttgaaccagg ctgacctcca 240
gaagaggctg gagagtgaga ctttatatgt caaatgagaa aattggtatg atttatacaa 300
gcattttgcc cagaagagca tgccatgctg agtaatccca agtgaggaca taataaactt 360
ttggaaagtg ttttaggtcc ttctcttaac ctgcctctgt actttttgag tgaagaggtt 420
actacagatt ccatcacact gttgtcttct gacattttgt tggtttcagt aaggtcagga 480
tatttttcat cctggatttc cttgaaggca gagtccaaga atagggttcg tgttcaggta 540
gttttataag tgataatagg aagcaggagt gtaaatctga gctttctaag aagaaaacag 600
actatgcctc agcattgtcc accagaaggt aaaatggaga agcaattcac tattgtctcc 660
agcccccaag ggctattgat tgcccacatt tatttgttac ttgaatgagt gctgagcaga 720
gtgtggagta taaaagaggg aagagcagca gacacgtgag ttgaggcact gccagcctga 780
aacaggccaa aacctacata gaattgttca gtaaggacaa gggtacatga gttggtgtac 840
aacaggttgc atatactgtg tatttattcc cttgagtccc tccttgcaag gccaccgcag 900
gtgatttata tcaccctacc taaggctaca gctcctgttg ggtggcccat gaacctcgga 960
tctgagccaa ccaacttctg gctccgacaa gagacccagg taccaaaatg aaacctggtt 1020
ctgaattgga gaatccaatg ctctagggga tagcaatgta aatctgccaa acccaaaagg 1080
ctaagcatca tgagattggg aaactgtaag aaacatctac tcaggtgaat ctaaaaagaa 1140
aaattacaaa gtatgtggtc aaaatattta tcagaaaata ttttgtacaa acaaacagga 1200
gaatttatta ctgaggaact gtaagtttta gaaccatatt ttaaagtaga ctttacacca 1260
tgtggtaaaa tccccaaaga atataagaaa atgtagtatc catgaagaaa gaacaagaaa 1320
ttataaaata aaaacaggtg gatatgagtc aagaacagaa agatttttgg agggagttgt 1380
ctttttaaaa caagctt 1397

<210> SEQ ID NO 94
<211> LENGTH: 5008
<212> TYPE: DNA
<213> ORGANISM: Homo sapiens

<400> SEQUENCE: 94
gtggcagttt tgctaagaag aaaagcaggt gaaagtggga gattccaaaa gagaccagag 60
agaaggcagt gtgtcctgcc caatctgccg ctagggtcag agaccagctc cctagtcaca 120
ctcggccaag gcaggctgcc ggctgactcc aactctaaac aaagccaggc agccgcccag 180
gtgggtgaag gctgcagatt gcgctcaggc gtgacgccgg ggtgcaggtg ggagcgacgc 240
ccgggtgcgt gggtgcagcg ctcgcccgcc cgcggttagg cgcaccgcgg gaaccggtca 300
ggtgcgccgt gtggggcggg gcgggcgccc ccaggctggt gcctggggca gaggattcgc 360
ctgcttgacg cgctgatgcc ttgatttggt ctgacaagtg gaggctgctt tgagaagcgg 420
cctgtatttt tgacattcag gaagctagaa ataaccagct gggctcctgg cgctctggcc 480
gcaaatgtct tgcgctttcc aggcaactgc cagattgaag ggcttttcc ccatgtagac 540 ctgtgctctg tgtgctagga ggccgaggtt ccagtccagg ctcggcttct gactccctac 600
tttaggctct cccacaagcc tcgggggggg taaacaaaag tgagaggtga agctgctgca 660
gcgaagtacc ccttcaaaat cttcagtacc cttcagacag cgctctatca cataaactgt 720
acaactccag tcaaccagca gccgcctggc tggcacagga agagccaatg caattttgca 780
cagtcttgct tgaaggtatt gcctggcaaa tgggcaatgg ggaaccacag ggagggcctc 840
gagctcgctt tggcactctc acgaagtcca ctcttcattt aaaacgttgc tcagccttaa 900
gggggcctga aaaccacagc ccccaaggga gccaggtctg ttcaaggcat tgcttccaag 960
tgagactctt cacaagcctt ttttcttgga gaccaatgga gcagcgttaa tctggcacag 1020
atgagcactc ccataatgct caacatctct ttccaagagt ggagagagat gatgcagaga 1080
tagtcaatca tcccaatata aaaattagtg gacaattggc aaataggaag gaaatattta 1140
ataattgtgt tgttcatgca tctatcccag aaatgaattc aatcaaacac tgcattatga 1200
gcatgaattt gtgttacatg atagactcag ggatggcaac aaaaatattt gagtgctact 1260
ctttgctcga aactctgctt tacttttgct cattcaccat gtctcatgaa ttcccctgtc 1320
ctttgatttc tggttcttta atattctggg attcaatctt tctccccatc cccactgcct 1380
tgattcacaa cctccatcat ctgtcagtag atttattata aagctctctg ttatggacct 1440
cccacacctc agaatgtgac tgttttggga gacagggcct ttaaatgggt aactaaggca 1500
aaattaggtc atatggctgg gccctaatct gatgtcctta taagaagaaa gtaggacaca 1560
gatgcacaga gagggaagac catgagacag ggagaaaccg gccatctgca aacctaggaa 1620
ggagtcctat cctacgttga tctcacaagt ccagattcca ggattgtgag acaatccact 1680
gttgttcaag ctccagtctg tggcacttag tcatggcagc cctcttaaaa taacacagcc 1740
ttctgcctgg gctctgtgct tgttccccag ttaaattcag aaaagtctaa aaattattgt 1800
tgtttatctg aaattcggtt caactgggtg tcctgttttt tatctggcaa ccctgtacag 1860
gaccctttgt gactgctagt gaacagactg aaccaaaatg aatttgataa gaattgtttc 1920
ccccagttaa cacaatagaa aaagatagtc aagattgatt cttggctttc aatattcttt 1980
caatttacca ccaacccttg ttcacagttt agaattatct gaggagcatt taaaaatatc 2040
cataccccat ccctaaccaa ttagaatggg agttactaaa tggggagtta gaaaggcagg 2100
gcagggagag aggccaggca agtgtatggc cactctcagg agccaaccct gcacttgcac 2160

-continued

```
agccctgaga gtgagaacct ccttaaatct tatgccctat acacctgttg tagtcaggcc   2220
ctatttaaag ataaagaaaa agaagggttg tgcagaagag cttccagggg atttctgagc   2280
agtcctgggt cccagctctg tgtttcattg ctttagaagg aacatcgacc tttccgagca   2340
atgaacatca gctccagctc ataggcatga gtcagggcag gcttcaccag gccaggttcc   2400
tgaaatgtaa actcacagca ggctctggtt tcctctagaa gaccactcct aaaaggcttt   2460
aaatgcttag gttccttgtt ctttttcagt tcaggctggt gattgagtag ctttagtcat   2520
tggcatccta aagattctgt ttcacattca agcatggttt taaattacta caagatgtaa   2580
tgaaagtata ggtttcactc ttctctccaa ggttttaaag actctcaccc ctgttctcct   2640
tcctccctct ctgccttctg cccttttctt gctggtgatt ttctgcccca tcactggcag   2700
cctggtcagg agcacctcat taatccaccc actggtacag tgtgcccaga acagccaagg   2760
ccaaccttgg aaggccaact ctctgaacag tcccttcctt tacctctaag ttccgtgatg   2820
tcatcagcat tctgccctgg ctggcggcca gatccttaac tactgattcc cagatctctc   2880
cacgttttaa aattctagga aaagaaactg tacttttcca gtgctaaaaa aggatgggaa   2940
tggttggtgg aagctcccag cacagctaaa attaacttct ttcttttgtg ataattgaat   3000
gattttcaat gatgttcttc ctataatagg attcaaaaag ttttcctcag ggaaaaattt   3060
ggaagagaaa aatacaaggg aaagggttct ctcagtagca atttccttgc aatatgaagc   3120
tcatgaaatt acatgggtgt atctcactta gcttaataga catgtccctg taaatttcat   3180
ataaatggaa tgtttaaaaa attaaatcac tgtaagtgca gctaaataaa ggaagcccgg   3240
ggtgactcac tttataaagt gaattatctt tatgtaatgt acatcatcct cccccacaca   3300
ctgatttata ttataatttt gaatttttca gaggctggat tctcataagg taagggtgcc   3360
tcttacgatg acaactggac tgaggtcaca gctgttctca tactctgaag ctgaactttt   3420
ttaacgttct ctggggagtg tgtagatgcc agggttctgc ggggatttaa gctcttacac   3480
tgacccagac tcctcctggc ctatccctgg agtgatgtgg gaaattgtca atgactggac   3540
agtggaagaa gtcatggtag acaagctgag gctagaagca tgatctgtgg ccagaagact   3600
acggccctgc gtctgtcctc tagctgggga ttctctgagc ctcggtatca ccccagccag   3660
ttgttaggat ttagatatga aaactgtgct gttgaattct taagcaaaaa aatgactaac   3720
tttgaggaag acttcaaaag agaggtgaca tttgaaagtt acaagtatta tcttatttaa   3780
ttccttagta ttggtgagat gtccagctgg ttgcccacct agtatttaaa aggcactttt   3840
taatttacat ggccaggcag tgtggctggc taaaagtctc tattttccag tctccctggc   3900
aggcagctat ggcccataag atggaaacag atcattgggt cagacttaaa agcttcttaa   3960
aaggggtata ggctatttac ttggagtttc taagctcttt cctcttcttc ctggttcttg   4020
cctgaaatga agacaagacg gctaaggctc tagcaccaac ttgtgacctt gagaaaggca   4080
aggggagtct ggtccctggt gaccgtgact gcttagcaac cttggactgc cgagctccag   4140
acttgcttgt ttaaatgaaa gaaaaataaa ctatcttact taagcctgtg ttatttttgg   4200
caattgttat tagcatctga cccaatccct aactggcata agctcctgag gccattaggc   4260
agaggtgcgt tcccactacc ctacactgtt ggggcaagcc tgtggctcca gggcacccga   4320
agagcctaga gtgtttcctt taaattgcaa ttcctttttt gtcaggccct ggcatcaagc   4380
acacagcctg gtcagtagca ctcaatatat gttgaaagaa tacaatgaat aactgccgct   4440
cgaccatttc ccaaggagct gtttttctga ggggttttca cttctcggat ttccacagga   4500
```

```
cagcatcagt acgaagcttg tgggacatcc aaagtgcttt gagatttaaa aaaaagaata   4560
aatcggaaat gataaacatt taaacaatga agatatacat aaagcctcat ttaagtagta   4620
tgttttaaaa ggtgaagcaa aattgtgtat tttttgtaga ttttaaaaat ataattaaat   4680
gggatgaaac tgctatccca aatccctttt aaaaaattat ttttgagtga ttgcaaaata   4740
acaaatataa ctttgtaaaa gaatcgaaat tatttagaaa ggttaaatat tgaaagccct   4800
ttcatagaac agtttggtaa atatcctttt aactcttctg tacataaaaa tcatgcaaat   4860
agatgcgtat aaataagctc atgatgtgta tattattttg caacctttgc tttttttcact   4920
taacatccta tcttgggcat ttccccacgt ctgtgcattt agattaacct ggttctctgt   4980
aaggtaatag agcatccttt atcccaat                                      5008
```

<210> SEQ ID NO 95
<211> LENGTH: 3639
<212> TYPE: DNA
<213> ORGANISM: Homo sapiens

<400> SEQUENCE: 95

```
cacagaggaa gattcaacta tcccttcttg aagaagttga gaagaaacaa ctatgttcac     60
cagtctaccc taacacaaaa ctgagatttc actgtttcaa gaaaaaggct gaaatacagg    120
ctagggaaaa aaagctcttt tggttaactt tcagtaaggt agaactttcc aacactagaa    180
cttaggcagc agctgccttt gaggcttctc tgcaaagatg ggttctgaat tcaaaatgat    240
gaacttgaga tcatcggccc ttcatctttg actccaataa caggacagaa ttcacctgag    300
tcaggtgaat aactgcagac tatggacatc ttggtatgga agggcttgaa agggatccac    360
tacaggcaca gaatcacagt cctggaggcc accccatcag acagccctca tcttccactc    420
cgtactctcc tgaggggaca ggactcatcc aggctctcat caagtctgca acttgtgatt    480
tgtctcttcc aagcagagtt tggtggtgag aattctgact gattttgtgt ctattgctac    540
ttcaacagtt attgatcatg gatacattgt ttaaattgtc taaaccttgg attcctcttc    600
tgcaaaatga ggaaatgata acttcagaaa gcagagagcc cctttttggg tgtcttggtc    660
ttggataagc ctttgatgga cttttgggtt atacaaaagt gatgcccagc tcctgttttc    720
aaatagtgag gttgagatga tgagaagata aactgctttg cctgggaaat gcttcctaca    780
tgtgttaaga ggaagcatgg tgttggaagg agggagaaca tacctacctt ataaatgatg    840
agaggcagat gtgggttaaa acataaacca gcctgaagtt gattcctgac tgctacttac    900
cagttgtatg tccttgagca tcttaatatt tctggtacct ggtgtcccca tctgtgaatg    960
gggggaataa caatattaac tttgtttttt atttgactga atctcattgt tgtaagctca   1020
ctgttttatc tttggaggga aaattatcac tagatatcct gaaagtgaat gggagttgtc   1080
agtgggagga gagttggttc tgggcatggg ctacttttca gagatgatat aaatttagag   1140
ggaaaaatgg ggccagtgat ttactctccg gttgagaata taagttgcta atgtagagtg   1200
tgtgacccta gctcttctaa actttcagtg tcgttttagc aatcctcggc ctctcctgaa   1260
tgtctggaga cagggcctgt ctctcttgcc cccactccgc cccccttat gaaatggcag    1320
cccctggtgc agagcctttg ccaatgggag gctgggctca ggttgcccgc ttacttagca   1380
caggacaagg caagaggcca aggcgatttc ctctctttta ctgcatcata aaaaagcatc   1440
tcattcttca gacacctctt agtgctcatg tccaggccat gattagcaga taatctccta   1500
ggtctgtggt ccatgcacgc ctgcatccca gctgccaaga cccacctgag aggaaagaaa   1560
aggtctgtgt tgaagacccc ttcccacggc cttgagggcc cacctccttg aagttgctcc   1620
```

```
tttctgtctg gggggtaatc ccagccctct cctccttgct gacttggctc cccggctgct   1680

atataccttc tcaaagagaa ccccgccacc aaccacccag acttcctgag ggtcacacca   1740

caaagagacg gcagaagacg gatggaatcc agatctctat ggtctacact cacctggcca   1800

ttttgggact atttctgggt gtttcctagt aaatgcttgc tgagatgggg cctgagatcc   1860

caggggactg gccctggatc taccctggga aatcatcaga gctgccatgt tgcctgttca   1920

gctcagcagg gacatctagg aggggacagg aagaggtggt cagcatggcc actcctcttc   1980

cagcctggtg agagcatagt agagagagca gcatgggctt gagtctgaga cagacctgag   2040

ttctagtcct ggcatgccac tttctagctg tgggacattt gacaatataa gtcatctctc   2100

tggaccacat tttaaaaata aataaaaatg acaggcatta cactgtaatg gaccaagaga   2160

gattctccat agagtactca ctacattatt attattatca tcacaaaact aggcaaatca   2220

caacctatgt gagtctcaaa tttgtcctct aaaatagtgc ctagtgggtt ctccagttag   2280

cgttagtttt cttcacttca tattgcaagt ccaagaggga gttttggtag cagaaagaaa   2340

tgcaagttaa ccgaaggtta aggctcaagt tctatcactt ccaacatgtg cctaacacat   2400

ctatatctac atcaatatct tgacatatat gttcccagtc atttttttc cttttttaa   2460

aacaaagact gaccattcta ctatatttga aaaaagtatg ctcatgaaaa ataattaata   2520

gaaaaaagtt gaaacatgaa tgtagtaaaa tcagaaatag ctctccttaa gaataaatac   2580

atcatcctat tgtttttgta ttcatacaca tacgtatcta aaaacacttt aataaaatga   2640

gatcataact gtaaatgcta tcttaaaata tgaagtatta actttaaatt tactggaata   2700

caacagaaaa aaatatacca aagtaaaact atagaaattg ttgaataaat ttttctttac   2760

tgtagcatag tattttttga aaaatcttct caggttaatt aaatgattat ctaaaacatc   2820

aaaaggtggc agtcatcatt tcttctgaaa ctacatggtt caattttagt atcagttgtg   2880

tttgggctgt gaaagataag ggcattagtg ctcagatttc ttccagctcc cttcccaaca   2940

aaacttaagt cttgttagtt accttgttat ttttacactg ttcagatgta tggctctgac   3000

tagaatagtt ttatttatgc attaatccca tcccccgatt aacttctatg gggcagaagc   3060

agatggagca gcttcataga gaggtattgt ttaattcagg aaatagattt gctaccacta   3120

atgatatttc attcctaagt ttatttcttt tctttatttc ttaactggct gaatattatt   3180

gtcacatagt tttgttcaag aagggctcat gggtgctgta ttcctggttt ttcatgtctg   3240

agaaagtatt gctttttat accattcttg tatgccataa tatcctgggt gcactttctt   3300

tcccttagac attgtgaaca ctgtcttttg gcatgaaatg ttgctgtggg agaggctagg   3360

gcaagcctga tttgaacccc tttgatgtgc ttttcctgac tgtatgaatg ttcaaagtgc   3420

cattatttaa ctaacttgta tcttgaactg tctgcatttt cctggaacat ggtatgtctt   3480

tcaacttgca tattcaattt ttttatttag atgattgtaa aattttactt ttggatttgc   3540

atacttcttt attaggtgtt ttaaaatcta ttatctttgt actttctcta atgtttttgt   3600

tttaatctac ctttacttta tctcagactc tcatccatg                          3639
```

<210> SEQ ID NO 96
<211> LENGTH: 1146
<212> TYPE: DNA
<213> ORGANISM: Homo sapiens

<400> SEQUENCE: 96

```
acttctactg agctgggttg aattttctta gccaacattc tgctctaatt gactagtgag     60
```

-continued

```
agagaaatga gcatgcaaat aaagccttca tagaaacagc tacacagctc caggctcctt    120

ctcctttttg aataactaag attgtttctg gcattgggga cagctcctcc aggcatttca    180

aaaccattag gcacagagga gggagagatt aatgtcaaca ggaggtacta ggaaggcctc    240

ctgcaggatc ctgcaggaaa acacactcct ctgctaaaac catggctcca aagtgcaagt    300

cttccaaagg cagaaatccc tcttcccttt agcacccaca tctgagtcac cagcaagtcc    360

tataagttat aactacaaat tttattccaa tatatacatt tttctgccta tttctactac    420

taccacccta atccaaggta catcatccag tgctggtttt tcctactaat gctccttgga    480

cctcttcttg ccaacccaaa ccattcccta cacagcagca tgagtaagct taaaatgcaa    540

accagaccat ggcactctct tactttttaa ataattatca attttgttta aaattaaatt    600

taaactcctt accatgggtc tctaaatatg catgatttgg tccctgctta tcttttcaac    660

ttcatcccat cgatttcttc ttcattattc tgcattcata aagacctcct ttattttgtc    720

caacacaaca catttttccc agctcatggc tttgtacttg ctgttttctc tgccaaggat    780

gcctgatatg aaagaagaaa aaaagaaaga ggaaaggaaa gaaagaaaag aaaggagaag    840

agggaaagcc tgagctaagg cacaaaggcc agaagtagaa ttagaaaaag ataagcactt    900

tggtggtgct taagtataaa cacaatgatg ataaaaggat gaagaaacaa cagaggctaa    960

gaccagatta agtaaatatg tattagctgt tattgctgca cccagaattt agcagtttaa   1020

aacaacagtt aatctcacac tttcaatgtc agcaacttgg gagtaacttc tggttcagaa   1080

ctttttatga ggtttcaatt aagacacagc ctggacttta gcatttaaag tcttgaatgg   1140

gactag                                                              1146
```

<210> SEQ ID NO 97
<211> LENGTH: 1820
<212> TYPE: DNA
<213> ORGANISM: Homo sapiens

<400> SEQUENCE: 97

```
atggatagtt accagtctgg tatgtattct cacttttctt cacaactcag tgaaggtact     60

gttattctta ttcccatttt acagatcggg aaattgatgt ataaggacaa caagctccag    120

gagggcaaga ccagcatctc tttcactcac ccctgtgcct ggaacatagt aggctcataa    180

atacctatga aatgaaattc agtatgactc ttagattgga ttctagtttc aagacaactc    240

cccaaacact tcaccacaga agagaacatt agaattatga gactggagtc aagaagatca    300

gacaggaggt tgttgtaatt caagcaagag atatgaattt cagctaaggc aacattatga    360

aaggatctgg taacttttac ttattattaa agctctattt aatccgcttg ctataaccta    420

gttaataaac ttggcagcat tagtgcactt ctcagatcat catctgagtg cctgcctcac    480

actgtgcaaa gagctttaca catatgctaa ttcttactgc agcactggaa ggtagatatc    540

attatctcca ttttacagat agaaacacca aatcaaagct cagggaaatt aagcagattt    600

gccaaggtca cacagataga aagcaggtaa gtgcatagcc agtctattta gccctagcta    660

gttcctatta atagtctatt gaatgaatct acaacaatat ctgttgatga ttatttaatg    720

gaatttctgg atcctaaggt agagttatgt tataggtatg tgttttatca tattacagaa    780

gtatccatca attcatttta ctgattgttc ttgacaccaa tgtcctttga tgttgccttt    840

tctgcatctg tggaaataat caaaattttg tagtgttgct ttattaacag gatgaactct    900

tgatgttttt tctaatatga aacccacttg ttcatacttc tttatgtacc aatggagtct    960

gttcattagt atttagtttt atttaagact attatccaaa attcatatga ctagtctgtt   1020
```

```
gtttcttttc tggtatagca tggtcagctt tggagatcaa tgtaatacct acttcataaa   1080

aataaattct ctttcatgat ttgaaataat ttaagtagca ttataattat gttattatta   1140

aagacttggt tcaatctggt tctctttatg ggggtgtatt cagttacttt ctctatttaa   1200

gatcatttgt ctctggggtc aattttagtc acctgcattt ttttctaaaa actcatctac   1260

attttcaaag ttatttccat agagctattg taagtagtct ttaagttatt ttaatttttt   1320

ctgtgtccat gattatttct cttttgtcct aattgtgtat atttaccatt tctccctcat   1380

tttttaaaat taggttggtt agtagcttat atataataca gtgttggatg ttgttttgtt   1440

taccaatcaa aaaaattaat agataataat cccattttat ttttttaaat gattgtttgc   1500

cttcaacact tatatattaa tttcttatat tttgtaacag atatagcact ttcccctttt   1560

ttggttattt tttatttggt tcttactatg agccatatta agaggtaata ccctcttttg   1620

ttcttttccc tgcatcactc tcaaataata cagtaagctt ttcctacttt tcgtgttttc   1680

cctactttcc cctaatattt tgatgtacta tccattacat attaatataa ttaccatcta   1740

gttgaaattc tacatgtaaa tattcagtac ttaccatgta aatttttctt cattctttat   1800

tgttgaagaa ttagcctgaa                                                1820
```

<210> SEQ ID NO 98
<211> LENGTH: 5410
<212> TYPE: DNA
<213> ORGANISM: Homo sapiens

<400> SEQUENCE: 98

```
gtagagaaag gacaagaaga gacaggaaaa gaactagatg catagcaaat cttcagggtg     60

agttgtcttg tgacactttt gtttcaggta cttgatacac acatacaagt atcttgggga    120

atccaattga ttgtataaat tacatagttt tgtgagaagt tgagcccctg gatggagcta    180

ggagagggga tcggagaaca gccttggttt aatctttcat gtaacttgtg tgcatggcaa    240

gtctttttcc gtctcagtcc tcatgttttc ttcctatgat aggagaatat ttgaataaat    300

taggagccct tgtattggtt tccatcactt gtgtgttcat gaactcagca gttgtaatta    360

ctttcataag ataattgctt aaactcaagt atttctaact tgcagtttct cacaattgca    420

tctaacctgt aaattactat atattttaag ctgaaatatt ttaaagtgaa ttgcaggccc    480

ccctaaatat ttccaaatgt atctctaaaa accattttct taaacagtcc taacctctat    540

tttgtgttca gtttctcctg acatccccac cggaacccaa tctgtgatcg tgcgttgcac    600

ctggcctgga tttttctggt cacttccctg acagtgtctc ctggcttgcc gctgtgtccc    660

ctgtttcttc cagtgcagtg tatgggtctt tggggtgcac tgaggtgatg gacgcttagt    720

ccagtctggg gccagaattt ccaggagatg ctccctgaga ttgtcttgag ggcagatga     780

gactcatgca gccatagagg gagggaaggg cattccaggc agggggaaca cccaggcagg    840

cattggggca gggagcaaca tgggtctcag ctctacaagc agctatgggt tcccctggag    900

tgtgactcgg catgaggctg gccatggagg agcagaatgt tccaccgagg aactgggact    960

ttacgttgtg agtgatgggg gctcactgag aggtgtcaag aaggggcagg caagtcaggt   1020

ctgtatgtca ggagctcagg tgagtggagt gcccgaggga ggtggggtga agggaggtgg   1080

gcacccaggt gagagctagt gcagggctgg ggaggccaag gcctgggcag tgggagagga   1140

ggggcagaga tggacagggt agaactgagg gcacctgcga ttggtagggg tgatgaggga   1200

gggagaaaag gccattgcca ggtttctggc ctggttgcca ctgcccatta acacagggag   1260
```

gtgaaactgc ctaaggaaga accctggagg atcaggattg gttctggaaa gtgttggagt 1320
taaggtgcct ggagtgcctg gatcgtgttc cacttattag gggtgggccg acccaggcgg 1380
cgatgctaag caggtgctct ggcgtgcttg tctaagctct gaggagaggt ggtgggtatg 1440
gtgttgtcag cagatgcaca gcagctggca tggtgagaat ggatgatacc accaggtcat 1500
agacagaaaa ttgcagtggg ccgaggtggc cgaatggtcg gagaaggggg aggagaaacg 1560
aggagcatgt ggatgatgcc aaggagggtt cgaagaacag cagagaaatg tatagcgttc 1620
cacaccccag gtccagagag acaaatggaa aaagtgccgt gcgctgggaa acagggcgga 1680
cacggtgtcc cttgccagtg cagtttggag taggaggagg agaggaacaa tacagtggct 1740
taaccttcca gtacaggcat ttggccccag gaggaaagag gagggaggat gagataaaaa 1800
tgacagtcga agtactggag tcaaacaggt gccgcatcac ctctgttaac ccagccacat 1860
gttcatcctg gaacccaagt tcctcatcca ggcctcggtg gtcccaggaa ctggccaagc 1920
ctgcattctt tctcccataa gcctccacag attagagcat ggccactccc ctgccttgca 1980
cttctgctat tcctcatcct ggccccccttc ccagacttct ttgtcccgcc aagtcccgtc 2040
ctttcaaact gagcgtttgg gaggtcttct ctgtctacca gcagaaacca tctcacctca 2100
gtaatggtga gcccagccca cttttttctc ccacacaatt gagatgtctc cgaccagcct 2160
cttcagtgct ggatacttct tgcattctat gaatttagga tctctacgtg tttctcaaca 2220
cacatgcata cacaaggaca cacgcagaca cacacattag cacacagaca tacacacaca 2280
gtgacacatg catacaggga cacacacatg gacacatgca catatgtgca catacactga 2340
catgctctga cacacacttg acacacacgt gtgcccacac gcgcgcacac acacacgcac 2400
aaacacacac acacaggtaa cattgacagc tgtggctgta gaagtgcttc caagggcctt 2460
tctttttgt ccttgtctgg agtttacagc acttggaaaa tgtcaggcgt gggaggcctt 2520
ttggtcttgg gttagggtaa actccctcca catatttgga gagcctccag gccctgcaaa 2580
ccgctcacga agcagataac agtgaccttg ctgtgaggga ggacggcccg ccgaggccag 2640
ggagctgtgc tggcagctga ggttacctct cctccccgct gcacctgggt cggctctgat 2700
gtcaagacct cccccgctcc atccccggtt gggctcccgg ccctctttgt gccggaaaca 2760
aggcccagct gggaggaggg gagggcagag cactgctctg tagttccagg tggagaacag 2820
cccagctctc ccctaggggc tgcaggctga gtgtccgact ccaacccccct tgccttttttg 2880
caggcccaaa gcggcttctc caggatggcg acagattttc caagactcat cccaggctgg 2940
agggggccca gctgcaactt cactggtgtg tgtatgtgtg ggtgagctga ccctgagagt 3000
ctggtgctag agggctggag gtcatgtcat cacagaaccc tctctgctgg cccccttcaag 3060
catcctgttc agggagctca ctgctaccag gggctggagc ctctccaggt ttctgtctct 3120
gtcacttcct taactcttga gctactcaga ttaggactag cccttcttcc acatatgtga 3180
aaacagctgc attcatacat tcagctacat atagctttga atgcaaggcc tggctgggag 3240
ctggggatag acacatggtt tgctacatag ttggtggcct agtggaggag gcagacggca 3300
ggccctggtc agcgtgctga gtctggggga ggagcaagcc tgcaggagga agttactctg 3360
ctggggagcg gggccttaag gtgctccaga cagaggggac aggatgcgca aagctgtgtg 3420
ggtctttgcc ttaggcaggg gtgggagtca gcatttagtt ggagaagggg ttcaggggcg 3480
tccagtggtg tgggcagagc acagggggct gcagtggctc tggcgagagg tggtggtacc 3540
taaagttgtg gcagtggcca cggggctggg agctgtaggt ggagttgggc agaccaagct 3600
ctcctctgca tggagctcca gagtccacac agatgtctac ggatagctcg aagccctccc 3660
tgatcagcca gctccctctc tttggccccc atttgcaagg aaagttcaaa tgcggtgctc 3720
aggatggaag cagacttcta atgtgactta ccgtagttcc atctgcttat aaaaacataa 3780
gtcatgccct ttttcacgcc gaaaagtgtg aaaaaagaat tttatatttg caaaagtttt 3840
ccctagaagt tgctgcctgg gctccagtgt tccatggtca ggtcctctgg agccgctgcc 3900
gcccgggcct gagggcccag gcctgtgact tcctcctcct gtctgtctgc ccgggagccg 3960
gcaccggcac ccaaagccga agccgcctcc ctcttatcct ctgcgagatc agcccagcca 4020
ggaaggggcc ccagccgtct ggctgtctga gccgggaccg gttggcgggt gctctggcct 4080
tcctcattag cggggtctcc actgcccttc ctctcgcagg ctaggctgtg gctcctatta 4140
tagctactgg agggtttttt agtcaaagag caccatgcat catttattat tttaccattc 4200
actcagacgt tccctgagca cttcctatgc tgctgctgga cccagggatc agccaactag 4260
ccccaaacgg cagatcctct gtggagagtg aggaggttgc tgggctgaat caaagtgctc 4320
tcacgcacgg tggaagttgc tacgtgcaaa gagatgcggg caaccaagtg ctctgaggtg 4380
cagaggaggc agaggccatg ccaaggagag cttacggctc tcagcccttc tccgtgccag 4440
gcgctgggct gagcacttca catgctaatc ctggaggtaa tccatggggt aggtacgatg 4500
actatttcca gatgaagaga ctgaagctta gagttaagtg atcccagtga gtacaatgcc 4560
tggattcata gccagaggct gtgctttgaa gccccagttc agttgccctc ctaccatctc 4620
tacccactcc cccagcccct tggggctgca gagcgacagc aagctacttc gtcatattgc 4680
atctcagttt tcctgtctcc taagcttgtt gtgggtttta aaggaacaaa gcctctagtg 4740
tgctcagcag tgactggcac agaatacatg ctccataaac gttagccatg tttatttttg 4800
taattgtcac tactaggtgc tttgtaggag gcccctctcg ggctggtgca tcctctgcca 4860
tttctgtctc agggtcagcc cgtctcccca gtgctcacaa tctgttcatt aagatcatct 4920
ggagtctgag tcccttctta ttaaaattgt aaaaatatac agaaccacaa gttaccattg 4980
taactatttt taaggattca gttgagtggc attaagaata actgttatgc aaccatcacc 5040
accaagaatt ttttgctatc ctcgactaaa actctatcca taaaacacgg agtcccattt 5100
ctcctccccc cagcccctgg caacctctac ttcgcatctc tatgtatttg actcctctgg 5160
gtgccccata taaacgaatc atacaatgtt tgtctctctg tgactggctt atttcactta 5220
gcatgatgtc ctcaaggttc acccatgtgt cagaatttcc ttgtttttga ggctgaataa 5280
taatccattt gatggtttta tttatccata tggccacctg ggttgcttac acattttggc 5340
tattgagaat aatgctatat atatatacat acccaaatgt acccaatata tacttcaacg 5400
tccacaacta 5410

<210> SEQ ID NO 99
<211> LENGTH: 2690
<212> TYPE: DNA
<213> ORGANISM: Homo sapiens

<400> SEQUENCE: 99
cagtgtgtag aagactggag tgggagttga ggtggtatct gattacatct tgatatccac 60
actaatgagc atacatcact ttgtaacaaa cgggctgttt ctgagccaag accatgagct 120
gatagtgtgg atggtggctg ggacagggga gagagcccat cctgagggac ggtcaaatcg 180
taataaagta gcaacaaata gctaaagctg gagtgtaaca gacaggtaga actgattgag 240
gttcaaatga agacagagga gaaggaacta aagatgattt gggggttctc tgcttgatgg 300

-continued

```
aagtggggta gaggtgtcat gacttgcagg acacagaagg gttgaggatt agatagcagt    360
aaatacatgc atgagggagg aagggcatgg tttgggacat gttgagatcc tatgttgaag    420
atcaccatcc agtggggaca caggcaattt cagtgcagtg tgattagtga ctggatgagg    480
aagcttagag aaggttccaa aatggaggac acacagaatt tggttctaga ctacaggttc    540
ttaatcattt tttttccagt aaatggcagt gtggtttaaa aaatcagatt caagtttgac    600
aacttgttca aatgaagctg tattggttct aaatagaatt tatatgaaag cacaataaca    660
tattaccttg ctgaagtaca cacacacaca cacacacaca cacacacaca cacacacact    720
actctcacct ctaaatttct ttctcccgcc agatggcact atgcttcaat atttaaagct    780
acagatatgg tgaactcagt tgtctttatt cttctcgcta tgtggacctt aataaatggg    840
cttaatgaca tatgctgaac taacatccta actgctactc ctgtaaaata aaaagcagcc    900
gagctatatt atgctttatg aaatatttat aactgccaaa cacaaaggca gtaagaacat    960
tggtttatac agcaaaagcc gaaactctat ttaagtgaag attaatgtgg aaatgttatc   1020
acattctcac actgcaaaac taaattgata tagaggtgat aaatgtggat agacgtggaa   1080
tatacatata ggcacacatt atacatttta cctgataaaa tataccagct gaatttgcct   1140
aaggaagctg ctaaagtcag atttgatgac gatttgtgga agttaccttg tggggcagcc   1200
caactgctag aacatttcag gaagttctat attgatggaa gagaaatttt aattatttct   1260
cctaaataag gagagagcca ttaggtgtgg gattttgtgt tctctttcaa atttgaatag   1320
acagaaggta tgtagaaatc aacatgatct tttcctttat tcacatataa ttgtaaataa   1380
catgggtaat acaatttcca aatctattta ctatgttgtt aaagtagttg gaatggttcc   1440
tagatttata acatattcca caggcagcaa tttgaaaatc tttgagaagt ttaaaaaata   1500
tctggcttac aatcatctca ttaaggtata aaatcagggc ttatatttta tctgattgtt   1560
attctcagat ctacagtttt ttaaaagaca agtcttggtt ccttatagat ctatcagctt   1620
ccctccatgc acatttggct catgaatgta tgaaatactt tggacgtatt tctattaaat   1680
tgctttcctg gggaaataca ttatagttct cttttattta gattaatgag ttttaggtta   1740
atctgtcgtg aatcctctgt aaatcagatt cttgatagtt aatatttcat ctttgtatat   1800
ttaaaatcag ttcacatgtt aagttaaaga tgaaaaagag aactaaatca gcaatattgt   1860
tatgtgcata aattaatgtg catgtatgtc tgctttaagt ttagtttata gaagttttaa   1920
aaaatgaaaa ttggcatttt tctacaaaga atgatgcctt ttgtcttcct acctgcctaa   1980
tttcccaaga agagatctag atgtcagaac atgctgattg actatatttt ctaagaaaaa   2040
ttttagaatt attaatatat ctatactaac taaacacatc cacttacctg tttttctggt   2100
actcttggat atagtctttt ataggatttg agctgtgaat agacaaagaa gatcatttgt   2160
ccagctttgg ttttagtttt tctaggactg cattgcacaa gccttttccc agggtgcatc   2220
ctagcagctt agtcttcaaa tctcagcatt ggtatgtggg gctgcgttca gcaaataata   2280
aaaatttagt tgttttgtca tctggacctg cattatgttt gtgcatgcac ccatatatat   2340
atatatttat taaatataca tatatattat atacacatta tatccattta tataaatata   2400
cagatgttta tatacaaaga aaagttcaaa acattgatca ttgtaatcta tggtaataac   2460
attatagata tcttggtata ctgttttatg tttcctaaat ttcaatgata tattttattt   2520
tgaatcagaa aaaagttaaa attatagaaa tttaaataat acataattta aaattctgaa   2580
tactataggg aaagagtaaa cttaacattt ttctaggtag ttatctaatt tctcagaatt   2640
atttttgaaa aaagccatca tttctctata taaaatttat tatagactaa              2690
```

<210> SEQ ID NO 100
<211> LENGTH: 579
<212> TYPE: DNA
<213> ORGANISM: Homo sapiens

<400> SEQUENCE: 100
gtgtgtttct cggcgcgcaa agctataaat aatggcacag atcattaaac cccgagagca 60
ggcccagccg ccccgcaaac aagatgaagt acaaaccacc acgtgaggag gagagaggga 120
ggtacaaggc agagccccag acccagcctg tacctctcag ctgggtccca gtgaacttgg 180
gcctccaagg caccaccagc aggacctggt gtgactgcac atgatcagca gacccttcgt 240
tttggggcca gttgtcaggt agcaacccct gaaaaaatca tacagcagct gaagtgaaat 300
acaacaatgt cttcagagca cttttaccca cttccttcta aaaagatctg agatggccta 360
ccgtataaga cacacccatg aaagaacaag aacagataaa gaagtggatt ttaaaatgtc 420
ctgggaaaag aaacccaaga atggacagtt actgcagagg aacccaaaac ttagccctca 480
gcttcctaga tgaaaccagg tagtagctta aaagcctctt cgcctacacc agaaataaac 540
tgagcaccta ctattagtca tgcatcaaag acatgatca 579

<210> SEQ ID NO 101
<211> LENGTH: 3793
<212> TYPE: DNA
<213> ORGANISM: Homo sapiens

<400> SEQUENCE: 101
agcaatgaaa aggggacgga gtgctgtggg gttcagccag tgaaatgtga agaaactcca 60
ggtcctagaa tgtggaatcc aggagagcca caggcttgca gtcacgaggg ccaggccgac 120
taagaactgg agaggctggg attcaccggg aggcatggga tggaaggggt tgtcaccaca 180
caggagccag gaacccagag acaggcagct gcaatgcaga aagaggaaaa gacatctttt 240
gaggaatgtt cgcagcgtga agcatttggc gtgatcttca ggacccgggg ctcagcctgg 300
gtggtgctga aagtgacccg gggctcagcg ttgttgcctt tgcttcttta actcctgagc 360
tgcctctgtg gtccccttgg gctcccagag ctgctttgcc tggagggtca gagagaagaa 420
gcgccttgga ctcacttgtg tgtcaaaaag gagtgtttgc aggccctagc agttttttat 480
gattggccat atggctctat taagttcaga atcaaagata tattttttga cttatccata 540
agaagcataa gagaaattta aataatctta ggtgtttttc tgtccatttt gcataaaatc 600
acctgagtgt tttatcaaaa tgaagatgag gaaacggcct gcatttctag ggtttattt 660 gcttttttttt taaatcattg ctggttctag ttggaattgc cctttgggac tctcaggtct 720
ggatagttct ctgaggctga tgagcgtggc agcgtgcccc tggtgcaggc agccaaagaa 780
ctggaatctg actcaggggc agagaaatgg gttaggggtg aacccaacat ctctgctcac 840
ttggtccttg aagcttttct tggcaaggat ggtggtgggg gacctgagtg ccatcgtgtt 900
caaacaccca cagtggtgac atcatctctg catctgtaca gtgcacaggg tgtggttaga 960
gcaggagttg gaaggagaac agtcatagct tccagtccca tctgcttctt gtctctatgc 1020
ccagaacctg accctggaac aggactggtg cacagaagac cttgtgtgag tcctttggta 1080
ccacgtttgc tgcacgaatg tctgagacac ctcacagtcg cttgttcagc ctctccctcc 1140
tctctccgct ggggaacatc atccctcatc actggaagaa attacaagga ttgtgtaaac 1200
aattacaagt attctacaaa cagtgagcat gctggtttgg cccatctatt tgtaagaaaa 1260

```
aacatggggt tttatggcaa tgagttacag ctctaactcc tggcacaatc acaaatatca   1320
gcacaaaaca ccaagttatg tctcccttct gtcctaaaag ggtaactact tcattcctaa   1380
tattactgca caccaagtct ctcaatccgt taccaatttt atccttgact cctgatgaaa   1440
cacaaatctc tttgatcagg ttatcacatg gcataggatg gtggttgctt cagggaaata   1500
atttaaagta ctttgcagtt tgctaggtgc cctggggcat agtattcttt gggcctccta   1560
aggttctgat ggtgatactg atttaacgta tagaatagtt tttaaatgtg aagtgctaca   1620
gggaccacta tgcagggagc tgaagggcta ttgagctgga cacttgagca ttggctgcat   1680
tgaatgataa atattgttct cttcctcaaa atagaaaatg acaatggaaa acttttaata   1740
atgtcaacat tggtgactag aaaacatatg tgcctcctta tgaaagcagg ggtggtgact   1800
gaatagaatt gttttgtttt tagagaacga ttttcttttt gtttttttctt cttttatagt   1860
attttactta aaaatccaag taatagtatt ctactgtatt gcgaaaagtc agaacactta   1920
tgtattttta tttaaaaacg aacgttttag tcagcaccca atgcaacaaa agcaaactag   1980
aaattgctca gcaataaaac aggttgattc tcacctttgc tgatttagcc gcatggaacc   2040
taattaatgg gtagattata catttgctca acaagtatta atgggttcta ctcccgcgag   2100
accctcatga agtcctgagg ttgcctctcg ttcacaggga gctccatgag gctggaggac   2160
ttcatcagtc ccaagaaaca cgtgggcctc tcagtaggat gctgcagggc agagacctgg   2220
ttctgtagct gactccacct ggctaaggag cctctgggct gtggatacac cacctacagc   2280
tgctcatcag gtgcagggca ccagattccc aaattctgct gaggttttta ctctggtctg   2340
tcactgactg gtcctgaaca aagtcactgt tttactttgt caaggatatt ttcatgcgaa   2400
atgagctcag gtgcacttca aatcttctcc cacagccact gtccccagga cacggggctg   2460
gatacccagg ttgagagagg ctccagcacg cccacaccac ggacccaaag ccatcctact   2520
tcaactacaa tactcattgg aggagatctt tcagatctga cacagccact aggtcaggct   2580
ttttgaaaaa ctgaactggg gaacacactg gattggaacc cagcactgta tgactagaaa   2640
ctatagcatg ttttccttgt gagcataaat tctaggatta caggcacaat tttaaaagac   2700
atctatcaat attggactgg catgatcctc catgtttcag tttactccat atcctgttat   2760
tagtaatggt atatatcaaa attacagtgg cctcataggt atccagccat tttcagaagt   2820
ctttggaaat tcttggatga tttctaagat ttaatttatt tttaaatgct ttttccttct   2880
atgcatataa atatatataa atatttacat atacatgcgt gtatatatgt gtgcatattt   2940
gtttttatgt acaaacttat agacacacac atataccttta acttgagaga atggagattt   3000
cagcagagaa aattgtagag acatggccat gagacgtgtt tatttgtaat tgatcccttc   3060
aaatgtagag aaacaaggac atttgatggc catagacttg gaaagatttt ttttaaatac   3120
aatcatcttg ctatattttg aaagtcaatt ttagcacaat ggagaaacat atttggaaga   3180
catttaggtg tgaaagctga gttttgttga tatttatggg cagagaaaac ttccttttttg   3240
actattctgc agggccagag acagattgat cagttctagt gtttttgaag aaaaattact   3300
ctctgtggct gacgagcttc tgggaggcag gaattgtccc agtcaccagc acccaaagga   3360
atgcccaccg tttaataaac atcccatatc ttgaatgaat aaaaaaatgt taccgatata   3420
tggtactatc agtttctagg catggttcat gccccaatta aatcagtttc aggaagtagc   3480
ctttttttgaa acacacaaaa tcttgaaaaa tgctggtgaa aacataaaaa ttatctggga   3540
aagtcagaga aatggctcag agtccgtgat tttatggaga gcataggcta ccaggagatg   3600
acagtgctct tcatgtaatg agtgtggctc tgccatatga gccaggctct gtgactggac   3660
```

caaccagtga aattataagg attataattt agatataaac agaccctgat atttattttc 3720
caacattaga acaggctatc acgtgagata ggaaacatta cggaagcatt ctaagaaagt 3780
tagataaaaa ttt 3793

<210> SEQ ID NO 102
<211> LENGTH: 4515
<212> TYPE: DNA
<213> ORGANISM: Homo sapiens

<400> SEQUENCE: 102
cactagaagt ttagaaattt gaaagagaga atctattttt ggataggctt tacccaccaa 60
atgatatcag gtttcctgaa gatttttaaa ttactgaaga aacaagttac taccagtaaa 120
gggtttagat actcacagga atcccatttg gtaagcttgc tgcaagccca ctatgtgaga 180
ggtgctagtg ctagaagtag ctcaagggtc taaaactctc cacactaatg gattgagctc 240
ccagtgtatt gctacattat tttatttttg gtccagatat atctgcccta attgtagcta 300
caaatacctt tttacgtaca ggctttttca ttatctctct catttctact tctgagtctg 360
ccctgaggta ctgttctttc accatcgcat ctttcctctg atggacactt attatgccac 420
cttgtgggaa cctagaactt attctcccag atgctgtgag tgctgctggc agacagccct 480
tagatcttag ctccattcag aaatccttag ctgaagaaag aaaaaatcca cactcaataa 540
tggaagtgaa gacataaggg tctggccttc ggcccagttg gaacatctgt aaaggcctgc 600
tccatttgca gtgcatctca tagatttaca gtgagactgt cttacctctc agcttggctt 660
cgcctcctac ccacttttgt ttccttttct tctttcttcc agtattgatt ccaaaaacat 720
atcatagtaa acttcctgta tctccttctc agttctacat cctaggaaat ccaactcaca 780
gcctttctct tttctgctcc tctaaaaaac tgccacttat gcctgttctc tgagaaactc 840
ctatcaagac tgggtgaaac accatttctc acacaaagcc ctctctgcta cttcaggtga 900
caccccaaac tgagttttag tgtctttttc ctatgatgat aatagggaaa agaggaggta 960
attacaatta ttagtattat ataacttagt ggctatttga tccattgata ttaacattta 1020
aggttttatc tttcaaaata catgtagatg gttaacacat atttctgtga agccacagaa 1080
aagcacggaa tattactttt ttcaaagtaa aaaatacagt gctatctaca ttgtaggaaa 1140
ggcacttgct gtttaatagg gaactaaaaa accactggct attgagtttc aaatctgaaa 1200
catccttcag gcttctccgc atgtgaaact agatcaagaa gagaaagtct ttgctcttgg 1260
tgaactctga atcccattgc ttcttctttg tccttaatct ctcccttcct gaactttgtt 1320
cctccagcct tgctctaatt ctctattcta aatccctcat aattggcatt tctaaagtgc 1380
ttctgagttt gtttttactg aatcctaact aataaccagt gtacactaca ctcaccatga 1440
tcatctttac cacacagaaa gtttgtaatc ccatttgttt ccttttaaat ctgctactat 1500
ttcaacattg gcaaacattt cttatcaact ataaaaaaaa aaatggcact ccacagttca 1560
acacatatga aatagaattt gaaaaaatgc attaatggct acaaagcaaa aaattaaagg 1620
caatggtttt aaatgttgag atctacttca tgtagataca gaacaaagaa taacctacat 1680
tataactgct cataaaaaat gccgtgcagc aacatgggtt tccaacacat ttgataacct 1740
gtttctgtct ccccccttcct ccattaaatt gaactctctg aattattcat gaaggctatt 1800
ttaatgggat aattttttct ggcgaacgct gacactgata ccaaagaata tctctaggta 1860
ttcatcttgg ataaataagg ctcctggtaa ctagttttct tgatgcttca ccttattcaa 1920

-continued

```
atgaacatat atggaagtaa ctaatgtaaa ccatttttta accccttaatg ttttcaatat   1980
gtttctctcc atgtatgtat agtcaaacat atgtttacac aggaattagc cagggtgttg   2040
aattaaatga aagtaaagca gaaagttaag caattctcag gtgaacttgg gcaggacatt   2100
aagaagaaat ttaaagtcca cagtttccag ctgtgatgac agttcggcat tgctgtggga   2160
atagcccatc tctccacagt actttggcca tagtcagaac caatcattca cttgaatgtg   2220
tacattaagg gttcttagcc caggatagta ggattttagg gagttgatga atcctttgaa   2280
atggaatatc aaattttctg tgtattattt ttcttctgaa aataaagttt atgacattca   2340
tcagcttctc agaggtgttc ttgactacca ccatacttct aaatggcaag aattcttatt   2400
tcacacagaa aagaccttcg gcagccagga ttctctggat ttccctgttc atgtgtgtgt   2460
cagaggtatt tgtccctcat taaatttagt attataaaaa ttcacatgca aacctttcaa   2520
cttggaaaaa attgtacttt gggttaatta tatatcaact tttacagttt aatttttaca   2580
aatatctttg agtttttcct aggtatctac aagtctgctc atattttttta aatattaccg   2640
caataatttt tgatttttat actaatgcac aataagaact taagttagat actggaattt   2700
attttagtca caatgtaaaa taaggattta tattaccttt aaagaagcaa aattctcaga   2760
aatacagctt tccaacattt ctaatcattc tgtaataaat cttttaagac actgaggtga   2820
ctgtcactgc tggatgtgtc ctgggggctt ttctgtcaga ggagatagtg actcttccca   2880
tgcagattaa gctggtgttt acagatttgc cctgggtgtg catttttatc ccgctgtgat   2940
caagtaacac cacctgacga gtgccagaca gatctctgga taagaaagtt cactatgccc   3000
tcactttgca caagatgcag ccctaatctg gagaagagtc tgtttcttgt tcttttctca   3060
gtgatactgt tatgtacact ttacctttag gtgaagcatt aggaatgaat ctgtctgtgc   3120
tgaaacttag atcatgaatt gaaatcaatg tacaaaccaa cattagggtt tctggagaca   3180
tgagaggagg cctgtgtgac aagtggaaaa catctaaaaa tatttgagtc cttagtaatt   3240
tcaaatttgt gtggagagtt ttcacagaca aaactagtga cataagaaat cttattcgca   3300
aaagctaatc aggctccaga tgctgtgagt gcaaaccact cagccccagg tccttttacc   3360
ttttcaccat ttggtcttaa agcattttta atatccatga aacaaaactg gctgttttct   3420
tcagatactg aaactcagct ctccatattt cgatttctta cttcattagc caagttatga   3480
ggtaaatgat tagctaacta gagtttgtca caattaggaa gtgagaatga aattcaattt   3540
gtgtttagaa gtttattttg cattaagctc ttctatctag ggttttaaac cacacagaaa   3600
aagcttacac ttgttaggtg gtagagttat tttttagttg catacattga tataagtaat   3660
tcatctttga ataagctcaa aacttgggtt cacattttcc ttccttatat ctcttatttg   3720
agacttacct aatgaggaac ctgacattta gagggtatta attcaccaaa agccactttc   3780
atgcactgtt ttgatcagta atggaaaagt cacactccat ctatttggat agtgttttgg   3840
agtatacaga tcaatatgat tcaaaaagta atgtataact aacaacaaaa tatcagtgaa   3900
tgcactaaat atttgacatg agaattcaaa tccaatctca caggtgtttt ttaagccttg   3960
gcttgagtca ggtctgctaa tatcccattg gtcaaagcaa gaatgagcca agccaagaat   4020
caaaagaagg gagaagtgag ggtgatgact atattgaaca aaatcccaca caggaaatgc   4080
agaagaaata tgtaactgtt ttcttgtttc cttttaaaat aaattttgtc tattaaggga   4140
atatatatga attgtcatta attttattta taattaacta attattaatt taaatccttt   4200
tccactgcaa ggtctactat aaaaagaaat tcagagagac ctgggattct agtatgtatt   4260
tgttatcctt gttctccaaa aggttaaagg ggggtggtag tgtataatca taactaataa   4320
```

taattagaac ataagaatct gaaaatcaat attgaggggg atctaattat gcccatggca 4380
tttattttct tagtttgaga atggtgtgac aggtacggat gaatccaaac attccataag 4440
ctcctcaaca tttcagcttc cctgcagtta agctatgact tactctagcc aatgaaatga 4500
ctgtagaagt ggtat 4515

<210> SEQ ID NO 103
<211> LENGTH: 470
<212> TYPE: DNA
<213> ORGANISM: Homo sapiens

<400> SEQUENCE: 103
tgagtcacaa gaggctgaaa gtgacctctg ggtgtctata attaggccct gcctgacgtc 60
agggcaacgg attttctggc ttggccaagt tcaccgtgcc aggcactgag ttaagtccat 120
tatgcattcc ctgacacttg cagcaacccc actaggcccc cattctccaa ggagaaaact 180
gaggcccagg agggtcatgc cctgctgagg ttactcagat caaggaggtt tcaactgagc 240
cagcaggaca gaggtgtgct gaggcttggg gccattcttc tgaccacttc tgctcctttt 300
tccctttctc taattttttc cccacatggc cctttgcctg aaatgccctt catatctatc 360
aggtttctgt gtaattgtca cctcctccag gaagtcttcc ctgacctttt cttctttgaa 420
ctgatctctg aaatgatctc tacctgttta ttgcttgttg atgtgaactc 470

<210> SEQ ID NO 104
<211> LENGTH: 1086
<212> TYPE: DNA
<213> ORGANISM: Homo sapiens

<400> SEQUENCE: 104
gaatcatctc agactgatga gactcttttc acatcagaat ataaaccagc caaggtactc 60
tatttgaaaa tgcagagcct gggtcttgta atgaagtgcc tgggtaaaaa gagtctaaat 120
gtcattgact ttgagttctg gagactggaa gttcaagatg tcagcatagt tggtttctgg 180
tgagggctct ctccttgggt tgcagatgac tgccttctgc tgtgccctca caggacagag 240
agagatagca aactctgttg tttcttctta taagggcact aattccatca taaggccacc 300
taacctcatc taacaaattg cctaccaaag cccatcctca aataccatca aattagagtt 360
atgtaattat aaaattctgt gctcaataat aagaaaaaca attaaaaaaa tcaaaagaat 420
caaacaaaca tgggtgacaa ataagcaaag aagaagatgc tcagcatcat tagtcattag 480
gaaaatgcaa attaaaacca taactactga atggctaaaa ttaaaaagac tgaccatacc 540
aggtgttggt gaggaggtag aggaacttga actcttatac cttgctgggg aaagtataaa 600
acagtacaac cactctggaa aacagtttgt cagtttctta gaaagttaaa cataaaccta 660
ccattttatc cagccattca ctcttaggta taagagaaaa aacatgcatc tatatagaat 720
tatgcataaa tgttcataga atcttcattg gtaatagccc caaactgaaa caacccaaat 780
gtccatgtac aggtgaacaa accggtatat cagaaaaaga gtatgcagta tgagttcatt 840
tatataacat gctaggaaac gcaaactaac gtatagtgtt agtggtttct ggtggatgag 900
gagatgtgaa agaacaggaa gaaagtgtta caaaagcaaa gaaacttttt gaggtatttt 960
cactatatta attgtggtta tggtttcata gttgcatatt tatgtcaaaa cctatcgagt 1020
tgtacatttc aactatatgt tatttattgt aagtcagtta taccccaata aagctgtaaa 1080
tattag 1086

<210> SEQ ID NO 105
<211> LENGTH: 15
<212> TYPE: DNA
<213> ORGANISM: Homo sapiens

<400> SEQUENCE: 105
tacaacctgc ttact 15

<210> SEQ ID NO 106
<211> LENGTH: 16
<212> TYPE: DNA
<213> ORGANISM: Homo sapiens

<400> SEQUENCE: 106
tcatactata tgacag 16

<210> SEQ ID NO 107
<211> LENGTH: 20
<212> TYPE: DNA
<213> ORGANISM: Homo sapiens

<400> SEQUENCE: 107
gtggggaggt cagctacaaa 20

<210> SEQ ID NO 108
<211> LENGTH: 20
<212> TYPE: DNA
<213> ORGANISM: Homo sapiens

<400> SEQUENCE: 108
cggaaatggt ttgaaatgct 20

<210> SEQ ID NO 109
<211> LENGTH: 20
<212> TYPE: DNA
<213> ORGANISM: Homo sapiens

<400> SEQUENCE: 109
acagacctgc agcagtgaga 20

<210> SEQ ID NO 110
<211> LENGTH: 20
<212> TYPE: DNA
<213> ORGANISM: Homo sapiens

<400> SEQUENCE: 110
gctagggaac gcagaacaag 20

<210> SEQ ID NO 111
<211> LENGTH: 20
<212> TYPE: DNA
<213> ORGANISM: Homo sapiens

<400> SEQUENCE: 111
aaggcttccc agagaaggag 20

<210> SEQ ID NO 112
<211> LENGTH: 20
<212> TYPE: DNA
<213> ORGANISM: Homo sapiens

<400> SEQUENCE: 112
actgggtgag tctcgctgtt 20

<210> SEQ ID NO 113
<211> LENGTH: 20
<212> TYPE: DNA
<213> ORGANISM: Homo sapiens

<400> SEQUENCE: 113
tgggacagca gagctaaggt 20

<210> SEQ ID NO 114
<211> LENGTH: 20
<212> TYPE: DNA
<213> ORGANISM: Homo sapiens

<400> SEQUENCE: 114
agattccagc acgcacttct 20

<210> SEQ ID NO 115
<211> LENGTH: 20
<212> TYPE: DNA
<213> ORGANISM: Homo sapiens

<400> SEQUENCE: 115
aaagggaaga gggaaaacga 20

<210> SEQ ID NO 116
<211> LENGTH: 20
<212> TYPE: DNA
<213> ORGANISM: Homo sapiens

<400> SEQUENCE: 116
cgtctagaac cagcccagag 20

<210> SEQ ID NO 117
<211> LENGTH: 20
<212> TYPE: DNA
<213> ORGANISM: Homo sapiens

<400> SEQUENCE: 117
cagccctgct ttagttcctg 20

<210> SEQ ID NO 118
<211> LENGTH: 20
<212> TYPE: DNA
<213> ORGANISM: Homo sapiens

<400> SEQUENCE: 118
ttcgttgggg attttactgc 20

<210> SEQ ID NO 119
<211> LENGTH: 20
<212> TYPE: DNA
<213> ORGANISM: Homo sapiens

<400> SEQUENCE: 119
tttggagatg gaacctggag 20

<210> SEQ ID NO 120
<211> LENGTH: 20
<212> TYPE: DNA
<213> ORGANISM: Homo sapiens

<400> SEQUENCE: 120
tctggtatgg gggagacttg 20

<210> SEQ ID NO 121
<211> LENGTH: 20
<212> TYPE: DNA
<213> ORGANISM: Homo sapiens

<400> SEQUENCE: 121
agctctgggt tggactgaga 20

<210> SEQ ID NO 122
<211> LENGTH: 20
<212> TYPE: DNA
<213> ORGANISM: Homo sapiens

<400> SEQUENCE: 122
tgcatacatt ctggcagagc 20

<210> SEQ ID NO 123
<211> LENGTH: 20
<212> TYPE: DNA
<213> ORGANISM: Homo sapiens

<400> SEQUENCE: 123
ggttgggtgc ctattaaacg 20

<210> SEQ ID NO 124
<211> LENGTH: 20
<212> TYPE: DNA
<213> ORGANISM: Homo sapiens

<400> SEQUENCE: 124
ggttcatgag cctttggaag 20

<210> SEQ ID NO 125
<211> LENGTH: 20
<212> TYPE: DNA
<213> ORGANISM: Homo sapiens

<400> SEQUENCE: 125
tgttaattca ggggcacaca 20

<210> SEQ ID NO 126
<211> LENGTH: 20
<212> TYPE: DNA
<213> ORGANISM: Homo sapiens

<400> SEQUENCE: 126
ggtggagagc cactgaagag 20

<210> SEQ ID NO 127
<211> LENGTH: 20
<212> TYPE: DNA
<213> ORGANISM: Homo sapiens

<400> SEQUENCE: 127
tctctgtccc ttgtgtgtgc 20

<210> SEQ ID NO 128
<211> LENGTH: 20
<212> TYPE: DNA
<213> ORGANISM: Homo sapiens

<400> SEQUENCE: 128
cttggaggtg tgggcatagt 20

<210> SEQ ID NO 129
<211> LENGTH: 20
<212> TYPE: DNA
<213> ORGANISM: Homo sapiens

<400> SEQUENCE: 129
gagccaagtg cacacagaaa 20

<210> SEQ ID NO 130
<211> LENGTH: 20
<212> TYPE: DNA
<213> ORGANISM: Homo sapiens

<400> SEQUENCE: 130
tggtctgttc ctggccttag 20

<210> SEQ ID NO 131
<211> LENGTH: 20
<212> TYPE: DNA
<213> ORGANISM: Homo sapiens

<400> SEQUENCE: 131
gtggacgaca agggaggtta 20

<210> SEQ ID NO 132
<211> LENGTH: 20
<212> TYPE: DNA
<213> ORGANISM: Homo sapiens

<400> SEQUENCE: 132
cggaatggct cctacaacat 20

<210> SEQ ID NO 133
<211> LENGTH: 20
<212> TYPE: DNA
<213> ORGANISM: Homo sapiens

<400> SEQUENCE: 133
gaggctcctg gatctctgtg 20

<210> SEQ ID NO 134
<211> LENGTH: 20
<212> TYPE: DNA
<213> ORGANISM: Homo sapiens

<400> SEQUENCE: 134
ttgggaggca aaggtagatg 20

<210> SEQ ID NO 135
<211> LENGTH: 20
<212> TYPE: DNA
<213> ORGANISM: Homo sapiens

<400> SEQUENCE: 135
gaaatgagtg gtggcagtga 20

<210> SEQ ID NO 136
<211> LENGTH: 20
<212> TYPE: DNA
<213> ORGANISM: Homo sapiens

<400> SEQUENCE: 136
cttaggtctg cgcctaatgg 20

<210> SEQ ID NO 137
<211> LENGTH: 20
<212> TYPE: DNA
<213> ORGANISM: Homo sapiens

<400> SEQUENCE: 137
gcacagatgc atagcctcaa 20

<210> SEQ ID NO 138
<211> LENGTH: 20
<212> TYPE: DNA
<213> ORGANISM: Homo sapiens

<400> SEQUENCE: 138
gcagcctgga cttttctcac 20

<210> SEQ ID NO 139
<211> LENGTH: 20
<212> TYPE: DNA
<213> ORGANISM: Homo sapiens

<400> SEQUENCE: 139
tcacctccaa gtgggtcttc 20

<210> SEQ ID NO 140
<211> LENGTH: 20
<212> TYPE: DNA
<213> ORGANISM: Homo sapiens

<400> SEQUENCE: 140
agctcggtct gtcgtgagtt 20

<210> SEQ ID NO 141
<211> LENGTH: 21
<212> TYPE: DNA
<213> ORGANISM: Homo sapiens

<400> SEQUENCE: 141
caaggcttaa taccgccact g 21

<210> SEQ ID NO 142
<211> LENGTH: 22
<212> TYPE: DNA
<213> ORGANISM: Homo sapiens

<400> SEQUENCE: 142
aatgtgcata gtaaccaggc tg 22

<210> SEQ ID NO 143
<211> LENGTH: 19
<212> TYPE: DNA
<213> ORGANISM: Homo sapiens

<400> SEQUENCE: 143
atggggtctc tggttctgc 19

<210> SEQ ID NO 144
<211> LENGTH: 22
<212> TYPE: DNA
<213> ORGANISM: Homo sapiens

```
<400> SEQUENCE: 144

caataccatc ttgctccgtg aa                                                22


<210> SEQ ID NO 145
<211> LENGTH: 22
<212> TYPE: DNA
<213> ORGANISM: Homo sapiens

<400> SEQUENCE: 145

aagagatacc gctatgccta cc                                                22


<210> SEQ ID NO 146
<211> LENGTH: 19
<212> TYPE: DNA
<213> ORGANISM: Homo sapiens

<400> SEQUENCE: 146

gctgctcgcc agtaaaggg                                                    19


<210> SEQ ID NO 147
<211> LENGTH: 16
<212> TYPE: DNA
<213> ORGANISM: Homo sapiens

<400> SEQUENCE: 147

tgcttgctag tgtggt                                                       16


<210> SEQ ID NO 148
<211> LENGTH: 15
<212> TYPE: DNA
<213> ORGANISM: Homo sapiens

<400> SEQUENCE: 148

aggtgtgcga tagag                                                        15
```